United States Patent
Gotoh et al.

(10) Patent No.: US 9,708,534 B2
(45) Date of Patent: Jul. 18, 2017

(54) POLYMERIZABLE COMPOUND HAVING TRIPLE BOND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Kazuo Okumura, Chiba (JP); Mayumi Goto, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/751,822

(22) Filed: Jun. 26, 2015

(65) Prior Publication Data

US 2015/0376505 A1 Dec. 31, 2015

(30) Foreign Application Priority Data

Jun. 27, 2014 (JP) ................. 2014-132903

(51) Int. Cl.
| | | |
|---|---|---|
| *G02F 1/1333* | (2006.01) | |
| *C09K 19/54* | (2006.01) | |
| *C09K 19/34* | (2006.01) | |
| *C09K 19/30* | (2006.01) | |
| *C07C 43/215* | (2006.01) | |
| *C07D 303/04* | (2006.01) | |
| *C07D 303/16* | (2006.01) | |
| *C08F 22/10* | (2006.01) | |

(Continued)

(52) U.S. Cl.
CPC .......... *C09K 19/542* (2013.01); *C07C 43/215* (2013.01); *C07C 45/40* (2013.01); *C07C 51/34* (2013.01); *C07D 303/04* (2013.01); *C07D 303/16* (2013.01); *C08F 22/10* (2013.01); *C08F 38/00* (2013.01); *C08F 214/18* (2013.01); *C09K 19/18* (2013.01); *C09K 19/3001* (2013.01); *C09K 19/3066* (2013.01); *C09K 19/3068* (2013.01); *C09K 19/32* (2013.01); *C09K 19/3402* (2013.01); *C09K 19/3458* (2013.01); *C09K 2019/0448* (2013.01); *C09K 2019/0466* (2013.01); *C09K 2019/123* (2013.01); *C09K 2019/183* (2013.01); *C09K 2019/301* (2013.01); *C09K 2019/3004* (2013.01); *C09K 2019/308* (2013.01); *C09K 2019/3009* (2013.01); *C09K 2019/3016* (2013.01); *C09K 2019/3019* (2013.01); *C09K 2019/3027* (2013.01); *C09K 2019/3071* (2013.01); *C09K 2019/3077* (2013.01); *C09K 2019/3078* (2013.01); *C09K 2019/3083* (2013.01); *C09K 2019/3422* (2013.01); *C09K 2019/3425* (2013.01)

(58) Field of Classification Search
CPC .............. C09K 19/653; C09K 19/3458; C09K 19/3068; C09K 19/3402; C09K 19/3001; C09K 19/3066; C09K 19/18; C09K 19/32; C09K 2019/3077; C09K 2019/308; C09K 2019/3083; C09K 2019/3422; C09K 2019/3078; C09K 2019/3425; C09K 2019/3071; C09K 2019/0448; C09K 2019/0466; C09K 2019/123; C09K 2019/183; C09K 2019/3004; C09K 2019/3009; C09K 2019/301; C09K 2019/3016; C09K 2019/3019; C09K 2019/3027; C07C 43/215; C07C 45/40; C07C 51/34; C07D 303/04; C07D 303/16; C08F 214/18; C08F 38/00
USPC ..... 252/299.01, 299.6, 299.61; 349/182, 183
See application file for complete search history.

(56) References Cited

U.S. PATENT DOCUMENTS

| | | | |
|---|---|---|---|
| 2012/0182516 A1* | 7/2012 | Taugerbeck ....... | C09K 19/0403 349/183 |
| 2013/0093975 A1 | 4/2013 | Taugerbeck et al. | |

OTHER PUBLICATIONS

English Abstract of CN 101671252 issued Mar. 2010.

* cited by examiner

*Primary Examiner* — Geraldina Visconti
(74) *Attorney, Agent, or Firm* — Wenderoth, Lind & Ponack, L.L.P.

(57) ABSTRACT

To provide a liquid crystal compound having high polymerization reactivity, a high conversion ratio and high solubility in a liquid crystal composition, a polymerizable composition containing the compound, a liquid crystal composite prepared using the composition, and a liquid crystal display device including the composite.
The liquid crystal display device prepared using the polymerizable composition containing the compound represented by formula (1):

(1)

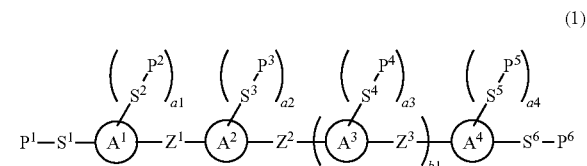

wherein, in formula (1), $P^1$ to $P^6$ are a polymerizable group; $S^1$ to $S^6$ are a single bond, alkylene or the like; a1, a3 and a4 are an integer from 0 to 4, a2 is an integer from 1 to 4; ring $A^1$ to ring $A^4$ are a divalent group derived from benzene, naphthalene, anthracene, pyrimidine, pyridine or the like; $Z^1$ (Continued)

to $Z^3$ are a single bond, alkylene or the like, and at least one of $Z^1$, $Z^2$ and $Z^3$ is —C≡C—; and b1 is 0 or 1.

15 Claims, No Drawings

(51) Int. Cl.
*C08F 214/18* (2006.01)
*C09K 19/18* (2006.01)
*C09K 19/32* (2006.01)
*C07C 45/40* (2006.01)
*C07C 51/34* (2006.01)
*C08F 38/00* (2006.01)
*C09K 19/04* (2006.01)
*C09K 19/12* (2006.01)

POLYMERIZABLE COMPOUND HAVING TRIPLE BOND, LIQUID CRYSTAL COMPOSITION AND LIQUID CRYSTAL DISPLAY DEVICE

TECHNICAL FIELD

The invention relates to a polymerizable compound, a polymerizable composition containing the polymerizable compound and a liquid crystal composition, a liquid crystal composite prepared from the polymerizable composition and a liquid crystal display device.

BACKGROUND ART

A liquid crystal display device utilizes optical anisotropy, dielectric anisotropy and so forth of a liquid crystal molecule in a liquid crystal composition. A classification based on an operating mode for the liquid crystal molecules includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode and a vertical alignment (VA) mode.

A liquid crystal display device having a mode in which a polymer is combined with the liquid crystal composition is known. Examples of the modes include a polymer sustained alignment (PSA) mode or a polymer stabilized (PS) mode. In the liquid crystal display device having the mode, the liquid crystal composition to which a polymerizable compound is added is injected into a display device. The display device is irradiated with ultraviolet light in a state of applying voltage between electrodes to polymerize the polymerizable compound, and thus the polymer is formed in the liquid crystal composition. According to the method, a liquid crystal display device in which a response time is shortened and image persistence is improved is obtained.

The method can be applied to liquid crystal display devices having various operating modes, and such modes are known as a PS-TN mode, a PS-IPS mode, a PS-FFS mode, a PSA-VA mode and a PSA-OCB mode. The polymerizable compound to be used in the device having such a mode is considered to have high capacity for aligning the liquid crystal molecules, but solubility in the liquid crystal composition is far from high. An attempt has been so far made on improving the solubility in the liquid crystal composition, but as the solubility is improved, polymerization reactivity tends to decrease. Therefore, development has been desired for a polymerizable compound having a suitable balance between the solubility and the polymerization reactivity.

CITATION LIST

Patent Literature

Patent literature No. 1: WO 2011/160765 A.
Patent literature No. 2: JP 2011-225665 A.
Patent literature No. 3: CN 101671252 A.

SUMMARY OF INVENTION

Technical Problem

A first object of the invention is to provide a polymerizable compound having high polymerization reactivity, a high conversion ratio and high solubility in a liquid crystal composition. A second object is to provide a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and suitable pretilt. The object is to provide a liquid crystal composite having a suitable balance regarding at least two of the physical properties. A third object is to provide a liquid crystal display device having a wide temperature range in which the device can be used, a short response time, a high voltage holding ratio, a low threshold voltage, a large contrast ratio and a long service life.

Solution to Problem

The invention concerns a polymerizable compound having a triple bond, a polymerizable composition containing the compound and a liquid crystal composition, a liquid crystal composite prepared from the polymerizable composition and a liquid crystal display device including the liquid crystal composite. The polymerizable composition contains at least one compound represented by formula (1) and at least one compound selected from the group of compounds represented by formulas (2) to (15). The above compounds are described later.

The invention also concerns an optically anisotropic body, formed by polymerization of the polymerizable composition.

Advantageous Effects of Invention

With regard to a first advantage of the invention, a polymerizable compound has high polymerization reactivity, a high conversion ratio and high solubility in the liquid crystal composition. With regard to a second advantage, a liquid crystal composite satisfies at least one of physical properties such as a high maximum temperature of a nematic phase, a low minimum temperature of the nematic phase, small viscosity, suitable optical anisotropy, large dielectric anisotropy, a suitable elastic constant, large specific resistance and suitable pretilt. With regard to the advantage, the liquid crystal composite has a suitable balance regarding at least two of the physical properties. With regard to a third advantage, a liquid crystal display device has a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal compound" is a generic term for a non-polymerizable compound having a liquid crystal phase such as a nematic phase and a smectic phase, and a non-polymerizable compound having no liquid crystal phase but being mixed for the purpose of adjusting physical properties of a liquid crystal composition, such as a maximum temperature, a minimum temperature, viscosity and dielectric anisotropy. The compound has a six-membered ring such as 1,4-cyclohexylene and 1,4-phenylene, and rod like molecular structure. "Liquid crystal composition" is a mixture of the liquid crystal compounds. "Polymerizable compound" includes a compound to be added to the composition for the purpose of forming a polymer. "Polymerizable composition" is a mixture of the polymerizable compound, the liquid crystal composition, an additive and so forth. "Liquid crystal composite" includes a composite to be formed by polymerization of the polymerizable composition. "Liquid crystal display device" is a generic term for a liquid crystal display panel and a liquid crystal display module. "Maximum temperature of the nematic phase" is a phase transition temperature between the nematic phase and an isotropic phase in the liquid crystal composition, the polymerizable composition or the liquid crystal composite, and may be occasionally abbreviated as "maximum temperature." "Minimum temperature of the nematic phase" may be occasionally abbreviated as "minimum temperature." "Polymerization reactivity" means a degree of ease when a reactant is polymerized. "Conversion ratio" is expressed in terms of a weight ratio of a reactant consumed by a chemical reaction to a total reactant.

The liquid crystal composition is prepared by mixing the liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a light stabilizer, a heat stabilizer, an antifoaming agent, a polymerization initiator and a polymerization inhibitor is added to the composition, when necessary. A ratio (amount of addition) of the additive is expressed in terms of weight percent (% by weight) based on the weight of the liquid crystal composition in a manner similar to the ratio of the liquid crystal compounds. Weight parts per million (ppm) may be occasionally used. A ratio of the polymerization initiator and the polymerization inhibitor is exceptionally expressed based on the weight of the polymerizable compound.

A compound represented by formula (1) may be occasionally abbreviated as "compound (1)." The abbreviation is also applied to a compound represented by formula (2) or the like. Compound (1) means one compound, a mixture of two compounds or a mixture of three or more kinds of compounds represented by formula (1). A circle surrounding $A^1$ in compound (1) means a six-membered ring, a condensed ring or the like. An oblique line crossing ring $A^1$ means that a bonding position on the ring $A^1$ can be arbitrarily selected for a $P^1$-$Sp^1$ group (-$S^1$-$P^1$) A same rule is also applied to a symbol such as $A^2$.

In formulas (2) to (15), a symbol $B^1$, $C^1$ or the like surrounded by a hexagonal shape each corresponds to ring $B^1$, ring $C^1$ or the like. A symbol of $R^{11}$ is used for a plurality of formulas such as formula (2) and formula (3). In the compounds, two terminal groups represented by two of arbitrary $R^{11}$ may be identical or different. In formula (8), when i is 2, two of $D^1$ exists in one formula. In the compound, two rings represented by two of $D^1$ may be identical or different. A same rule is also applied to $D^1$ when j is larger than 2. A same rule is also applied to any other symbol. A same rule is also applied to formula (1) or the like.

An expression "at least one of "A" may be replaced by "B"" means that a position of "A" is arbitrary when the number of "A" is 1, and the positions thereof can be freely selected without restriction also when the number of "A" is 2 or more. An expression "at least one of A may be replaced by B, C or D" means inclusion of a case where at least one of A is replaced by B, a case where at least one of A is replaced by C, and a case where at least one of A is replaced by D, and also a case where a plurality of A are replaced by at least two of B, C and D. Specific examples of alkyl in which at least one of —$CH_2$— (or —$CH_2CH_2$—) may be replaced by —O— (or —CH=CH—) include alkyl, alkenyl, alkoxy, alkoxyalkyl, alkoxyalkenyl and alkenyloxyalkyl. In addition, a case where two of consecutive —$CH_2$— is replaced by —O— to form —O—O— is not preferred. A case where —$CH_2$— in a methyl moiety (—$CH_2$—H) is replaced by —O— to form —O—H in alkyl or the like is not preferred, either.

Then, 2-fluoro-1,4-phenylene means two divalent groups described below. In a chemical formula, fluorine may be leftward (L) or rightward (R). A same rule is also applied to an asymmetrical divalent group derived from a ring such as tetrahydropyran-2,5-diyl.

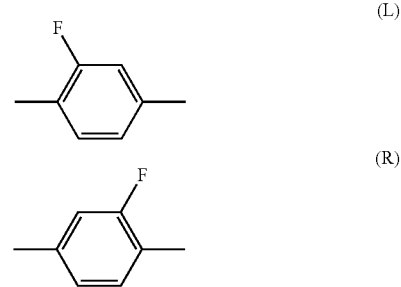

The invention includes items as described below.

Item 1. A polymerizable composition containing at least one compound selected from the group of compounds represented by formula (1) and at least one compound selected from the group of compounds represented by formulas (2) to (4):

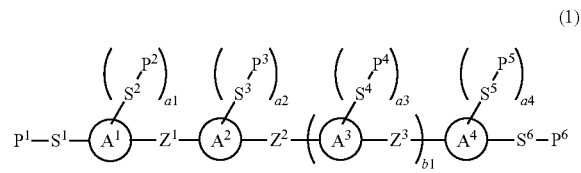

wherein, in formula (1), $P^1$, $P^2$, $P^3$, $P^4$, $P^5$ and $P^6$ are independently a polymerizable group;

$S^1$, $S^2$, $S^3$, $S^4$, $S^5$ and $S^6$ are independently a single bond or alkylene having 1 to 12 carbons, and in the alkylene, at least one of —$CH_2$— may be replaced by —O—, —COO— or —OCO—, at least one of —$CH_2CH_2$— may be replaced by —CH=CH— or —C≡C—, and in the groups, at least one of hydrogen may be replaced by halogen;

a1, a3 and a4 are independently 0, 1, 2, 3 or 4, a2 is 1, 2, 3 or 4, a sum of a1, a2, a3 and a4 is 3 to 10, in which either or both of -$S^1$-$P^1$ and -$S^6$-$P^6$ may be hydrogen;

ring $A^1$, ring $A^2$, ring $A^3$ and ring $A^4$ are independently a divalent group derived from benzene, naphthalene, anthracene, pyrimidine or pyridine, and in the divalent group, at least one of hydrogen may be replaced by halogen, alkyl having 1 to 12 carbons, or alkyl having 1 to 12 carbons in which at least one of hydrogen is replaced by halogen, and ring $A^2$ and ring $A^3$ may be independently a divalent group derived from cyclohexane, cyclohexene, tetrahydropyran or dioxane;

$Z^1$, $Z^2$ and $Z^3$ are independently a single bond or alkylene having 1 to 12 carbons, and in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$), —C(CH$_3$)=C(CH$_3$)— or —C≡C—, and in the groups, at least one of hydrogen may be replaced by halogen, and at least one of Z$^1$, Z$^2$ and Z$^3$ is —C≡C—; and b1 is 0 or 1;

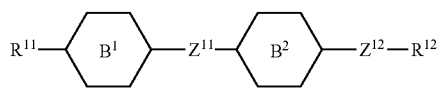
(2)

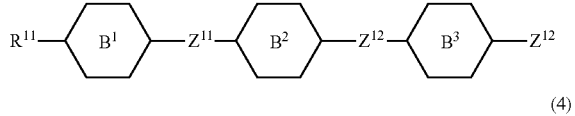
(3)

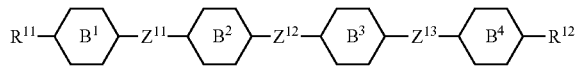
(4)

wherein, in formulas (2) to (4),

R$^{11}$ and R$^{12}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;

ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and Z$^{11}$, Z$^{12}$ and Z$^{13}$ are independently a single bond, —CH$_2$CH$_2$—, —CH=CH—, —C≡C— or —COO—.

Item 2. The polymerizable composition according to item 1, further containing at least one compound selected from the group of compounds represented by formulas (5) to (7):

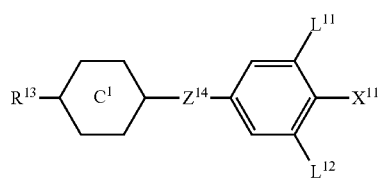
(5)

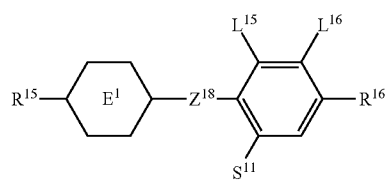
(6)

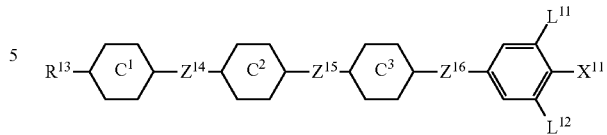
(7)

wherein, in formulas (5) to (7),

R$^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring C$^1$, ring C$^2$ and ring C$^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

Z$^{14}$, Z$^{15}$ and Z$^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and L$^{11}$ and L$^{12}$ are independently hydrogen or fluorine.

Item 3. The polymerizable composition according to item 1 or 2, further containing at least one compound selected from the group of compounds represented by formula (8):

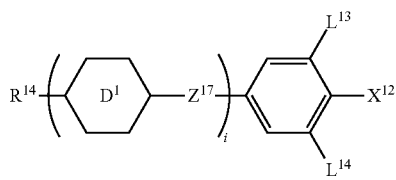
(8)

wherein, in formula (8),

R$^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

X$^{12}$ is —C≡N or —C≡C—C≡N;

ring D$^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

Z$^{17}$ is a single bond, —CH$_2$CH$_2$—, —C≡C—, —COO—, —CF$_2$O—, —OCF$_2$— or —CH$_2$O—;

L$^{13}$ and L$^{14}$ are independently hydrogen or fluorine; and i is 1, 2, 3 or 4.

Item 4. The polymerizable composition according to any one of items 1 to 3, further containing at least one compound selected from the group of compounds represented by formulas (9) to (15):

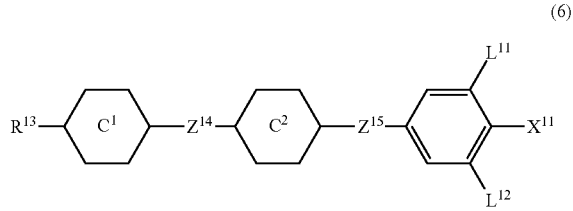
(9)

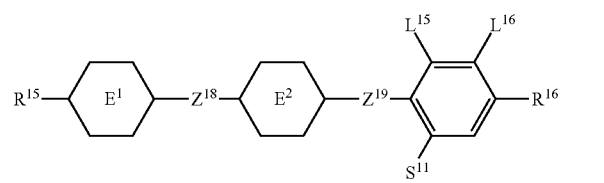
(10)

-continued

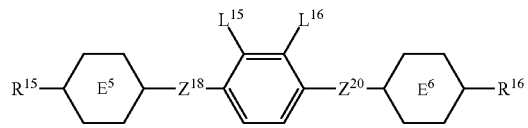
(11)

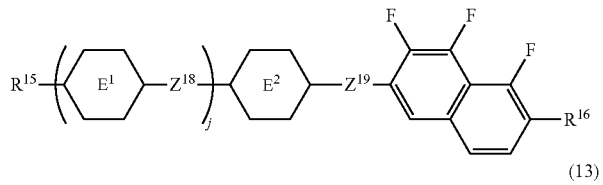
(12)

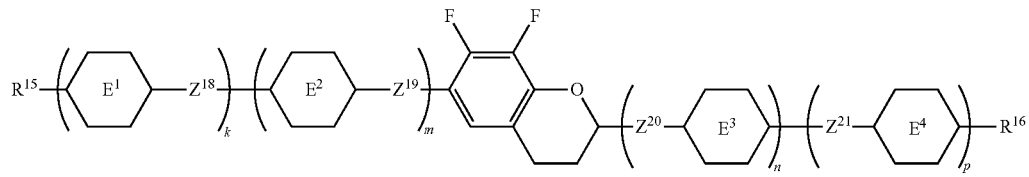
(13)

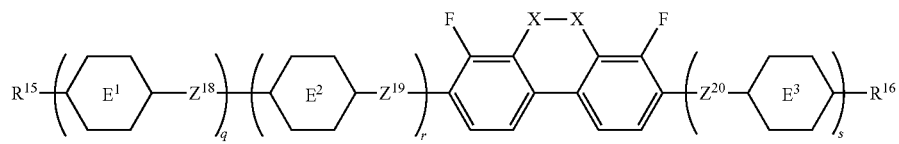
(14)

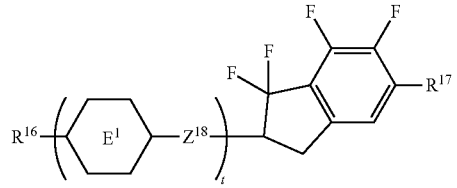
(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 5. A liquid crystal composite, formed by polymerization of the polymerizable composition according to any one of items 1 to 4.

Item 6. A liquid crystal display device, including the polymerizable composition according to any one of items 1 to 4 or the liquid crystal composite according to item 5.

Item 7. A polymerizable compound represented by formula (1-1):

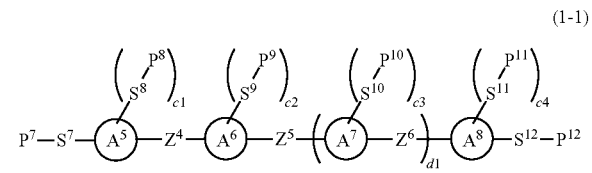
(1-1)

wherein in formula (1-1), $P^7$, $P^8$, $P^9$, $P^{10}$, $P^{11}$ and $P^{12}$ are independently a polymerizable group;

$S^7$, $S^8$, $S^9$, $S^{10}$, $S^{11}$ and $S^{12}$ are independently a single bond or alkylene having 1 to 6 carbons, and in the alkylene, one or two of —$CH_2$— may be replaced by —O—, —COO— or —OCO—, one or two of —$CH_2$—$CH_2$— may be replaced by —CH=CH— or —C≡C—, and in the groups, at least one of hydrogen may be replaced by fluorine or chlorine;

c1, c3, and c4 are independently 0, 1 or 2, c2 is 1 or 2, and a sum of c1, c2, c3 and c4 is 3 to 6;

ring $A^5$, ring $A^6$, ring $A^7$ and ring $A^8$ are independently 1,4-phenylene, pyrimidine-2,5-diyl or pyridine-2,5-diyl, and in the rings, at least one of hydrogen may be replaced by fluorine, chlorine, alkyl having 1 to 12 carbons, or alkyl having 1 to 12 carbons in which at least one of hydrogen is replaced by fluorine or chlorine, ring $A^6$ and ring $A^7$ may be independently 1,4-cyclohexylene, 1,4-cyclohexenylene, tetrahydropyran-2,5-diyl or 1,3-dioxane-2,5-diyl;

$Z^4$, $Z^5$ and $Z^6$ are independently a single bond or alkylene having 1 to 6 carbons, and in the alkylene, one or two of —$CH_2$— may be replaced by —O—, —CO—, —COO— or —OCO—, one or two of —CH$_2$—CH$_2$— may be replaced by —CH=CH—, —C(CH$_3$)=CH—, —CH=C(CH$_3$)—, —C(CH$_3$)=C(CH$_3$)— or —C≡C—, and in the groups, at least one of hydrogen may be replaced by fluorine or chlorine, in which at least one of Z$^4$, Z$^5$ and Z$^6$ is —C≡C—; and d1 is 0 or 1.

Item 8. The polymerizable compound according to item 7, represented by formula (1-2) or (1-3):

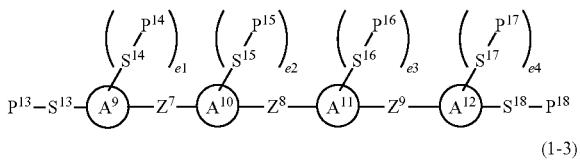

(1-2)

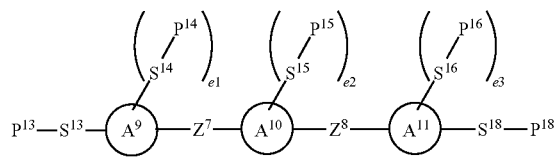

(1-3)

wherein in formula (1-2) and formula (1-3),

P$^{13}$, P$^{14}$, P$^{15}$, P$^{16}$, P$^{17}$ and P$^{18}$ are independently —OCO-(M$^1$)C=CH(M$^2$), vinyloxy or oxiranyl, in which M$^1$ and M$^2$ are independently hydrogen, fluorine, methyl or trifluoromethyl;

S$^{13}$, S$^{14}$, S$^{15}$, S$^{16}$, S$^{17}$ and S$^{18}$ are independently a single bond or alkylene having 1 to 6 carbons, and in the alkylene, one of —CH$_2$— may be replaced by —O—, —COO— or —OCO—, one of —CH$_2$—CH$_2$— may be replaced by —CH=CH—, and in the groups, at least one of hydrogen may be replaced by fluorine or chlorine;

e1, e3 and e4 are independently 0, 1 or 2, e2 is 1 or 2, and a sum of e1, e2, e3 and e4 is 3 to 6;

ring A$^9$, ring A$^{10}$, ring A$^{11}$ and ring A$^{12}$ are independently 1,4-phenylene, pyrimidine-2,5-diyl or pyridine-2,5-diyl, and in the rings, at least one of hydrogen may be replaced by fluorine, chlorine, alkyl having 1 to 6 carbons, or alkyl having 1 to 6 carbons in which at least one of hydrogen is replaced by fluorine or chlorine;

Z$^7$, Z$^8$ and Z$^9$ are independently a single bond, alkylene having 1 to 6 carbons, —CO—, —CH$_2$O—, —OCH$_2$—, —COO—, —OCO—, —CH=CH—, —C(CH$_3$)=CH—, —CH=C(CH$_3$)—, —C(CH$_3$)=C(CH$_3$)—, —C≡C—, —CO—CH=CH—, —CH=CH—CO—, —CH=CH—CH$_2$O—, —OCH$_2$—CH=CH—, —CH=CH—OCH$_2$—, —CH$_2$O—CH=CH—, —CH=CH—COO—, —OCO—CH=CH—, —CH=CH—OCO—, —COO—CH=CH—, —C(CH$_3$)=CH—COO—, —OCO—CH=C(CH$_3$)—, —C(CH$_3$)=CH—OCO—, —COO—CH=C(CH$_3$)—, —CH=C(CH$_3$)—COO—, —OCO—(CH$_3$) C=CH—, —CH=C(CH$_3$)—OCO—, —COO—(CH$_3$) C=CH—, —C(CH$_3$)=C(CH$_3$)—COO— or —OCO—C(CH$_3$)=C(CH$_3$)—, and in the groups, at least one of hydrogen may be replaced by fluorine or chlorine, in which, in formula (1-2), at least one of Z$^7$, Z$^8$ and Z$^9$ is —C≡C—, and in formula (1-3), at least one of Z$^7$ and Z$^8$ is —C≡C—.

Item 9. The polymerizable compound according to item 7 or 8, represented by formulas (1-4) to (1-10):

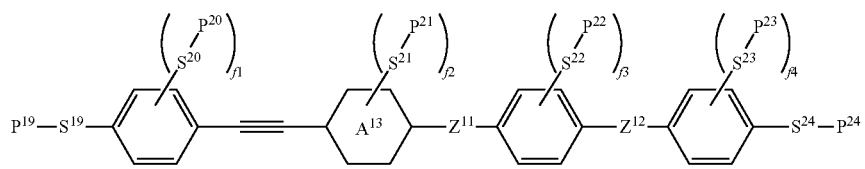

(1-4)

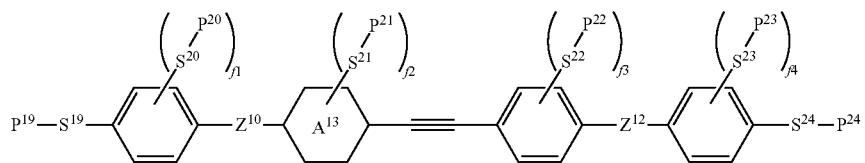

(1-5)

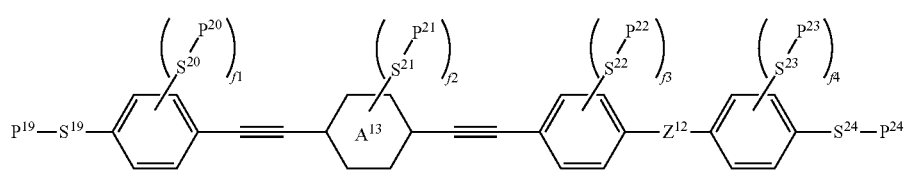

(1-6)

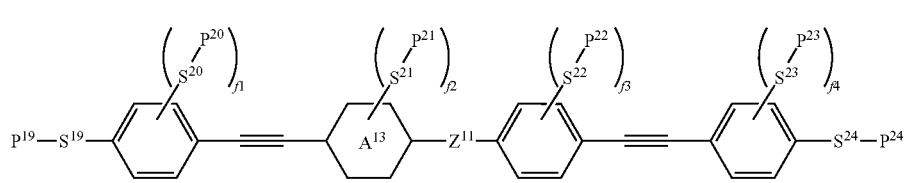

(1-7)

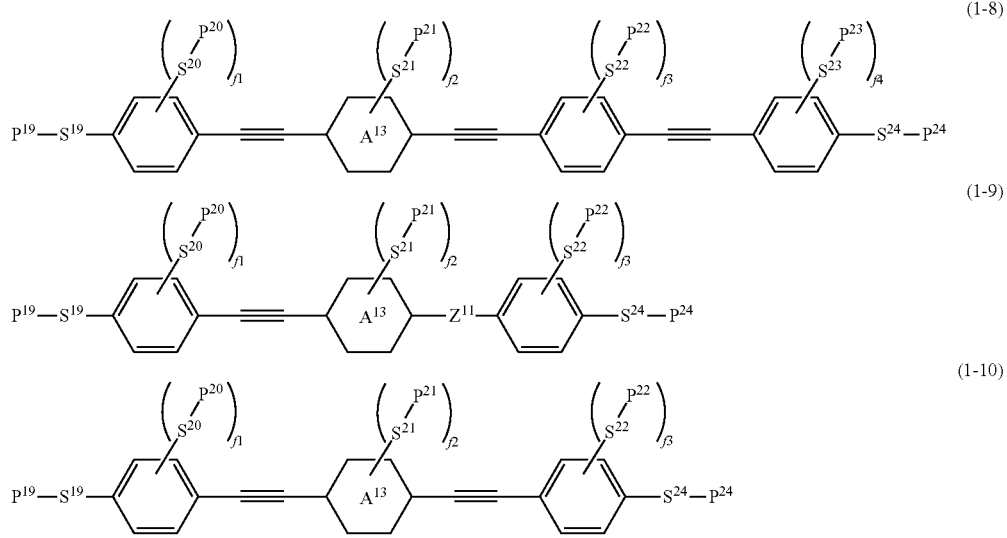

(1-8)

(1-9)

(1-10)

wherein, in formulas (1-4) to (1-10), $P^{19}$, $P^{20}$, $P^{21}$, $P^{22}$, $P^{23}$ and $P^{24}$ are independently a single bond, —$CH_2$—, —$CH_2O$—, —$OCH_2$—, —COO—, —OCO—, —$CH_2CH_2$—, —CH=CH—, —CF=CH—, —CH=CF—, —CF=CF—, —C≡C—, —$CH_2CH_2O$—, —$OCH_2CH_2$—, —CH=CH—O—, —O—CH=CH—, —C≡C—O—, —O—C≡C—, —$(CH_2)_3$—, —$(CH_2)_3$—O—, —O—$(CH_2)_3$—, —$(CH_2)_4$—, —$(CH_2)_4$O— or —O$(CH_2)_4$—;

$S^{19}$, $S^{20}$, $S^{21}$, $S^{22}$, $S^{22}$ and $S^{24}$ are independently a single bond or alkylene having 1 to 5 carbons, and in the alkylene, one of —$CH_2$— may be replaced by —O—, —COO— or —OCO—, and one of —$CH_2$—$CH_2$— may be replaced by —CH=CH—;

f1, f3, and f4 are independently 0, 1 or 2, f2 is 1 or 2, and a sum of f1, f2, f3 and f4 is 3 to 6;

ring $A^{13}$ is 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-chloro-3-fluoro-1,4-phenylene, 2-methyl-1,4-phenylene, 2-difluoromethyl-1,4-phenylene, 2-trifluoromethyl-1,4-phenylene, 2-ethyl-1,4-phenylene, 2-pentafluoroethyl 1,4-phenylene or 2-propyl-1,4-phenylene; and $Z^{10}$, $Z^{11}$ and $Z^{12}$ are independently a single bond, alkylene having 1 to 5 carbons, —CO—, —$CH_2O$—, —$OCH_2$—, —COO—, —OCO—, —CH=CH—, —C≡C—, —CH=CH—$CH_2O$—, —$OCH_2$—CH=CH—, —CH=CH—$OCH_2$—, —$CH_2O$—CH=CH—, —CH=CH—COO—, —OCO—CH=CH—, —CH=CH—OCO— or —COO—CH=CH—, and in the groups, at least one of hydrogen may be replaced by fluorine.

Item 10. The polymerizable compound according to any one of items 7 to 9, represented by formulas (1-11) to (1-17):

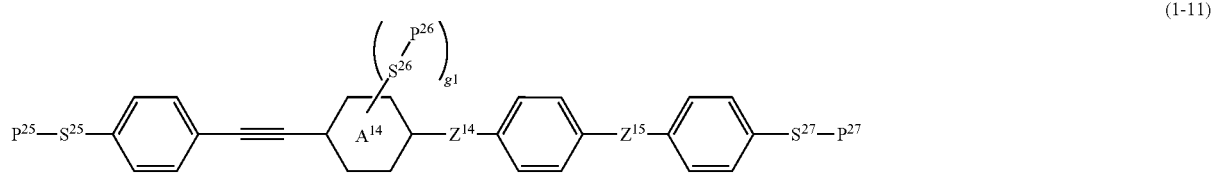

(1-11)

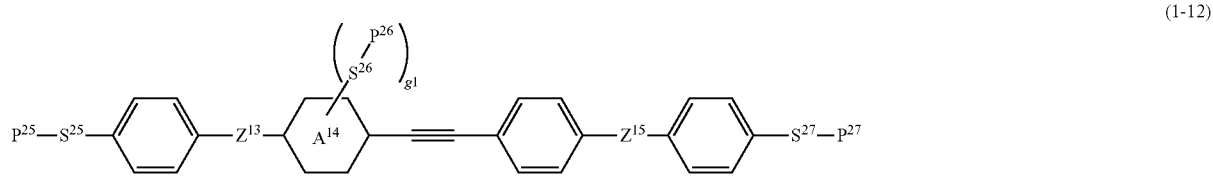

(1-12)

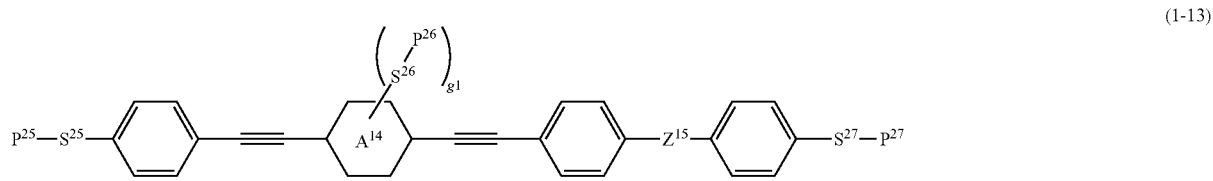

(1-13)

(1-14)
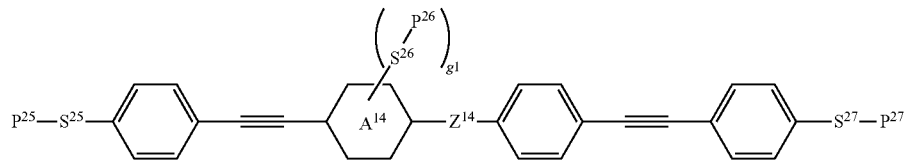

(1-15)
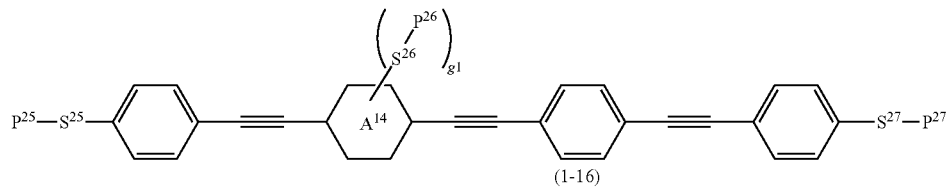

(1-16)
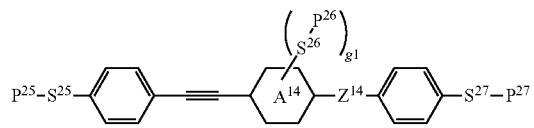

(1-17)
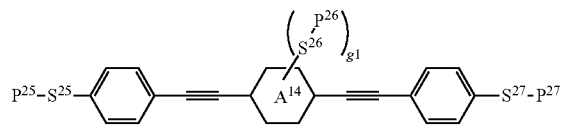

wherein in formulas (1-11) to (1-17), $P^{25}$, $P^{26}$ and $P^{27}$ are independently acryloyloxy or methacryloyloxy;

$S^{25}$, $S^{26}$ and $S^{27}$ are independently a single bond, —$CH_2$—, —$CH_2O$—, —$OCH_2$—, —COO—, —OCO—, —CH=CH—, —C≡C—, —$CH_2CH_2O$—, —$OCH_2CH_2$—, —CH=CH—O— or —O—CH=CH—;

g1 is 1 or 2;

ring $A^{14}$ is 1,4-phenylene, 2-fluoro-1,4-phenylene, 2,5-difluoro-1,4-phenylene, 2,6-difluoro-1,4-phenylene, 2-chloro-1,4-phenylene, 2-methyl-1,4-phenylene, 2-ethyl-1,4-phenylene, 2-difluoromethyl-1,4-phenylene or 2-trifluoromethyl-1,4-phenylene; and $Z^{13}$, $Z^{14}$ and $Z^{15}$ are independently a single bond, —CO—, —COO—, —OCO— or —CH=CH—.

Item 11. The polymerizable compound according to any one of items 7 to 10, represented by formulas (1-18) or (1-24):

(1-18)
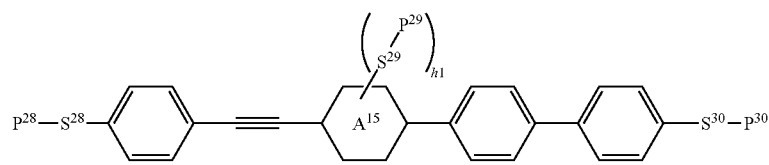

(1-19)
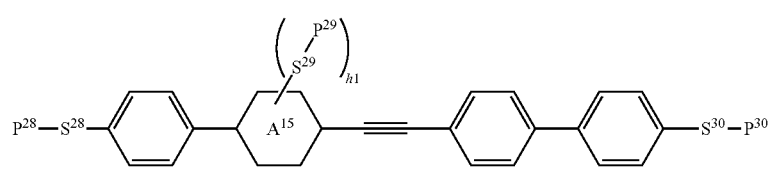

(1-20)
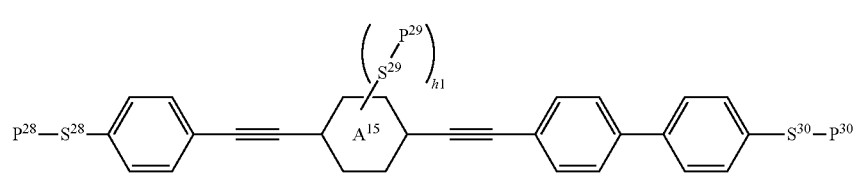

(1-21)
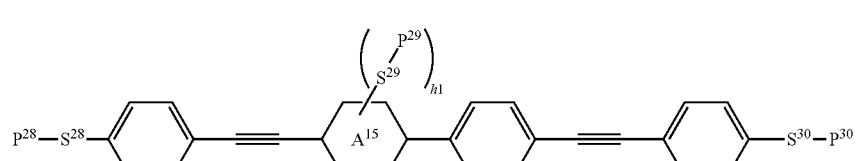

-continued (1-22)
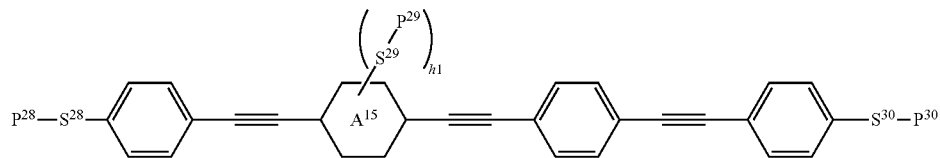

(1-23)
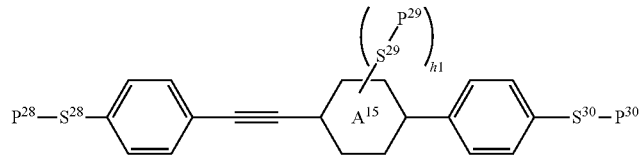

(1-24)
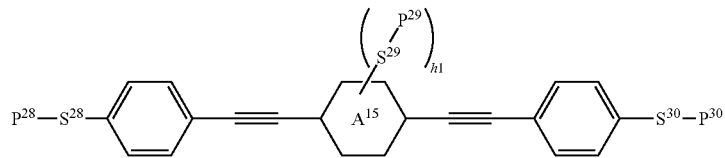

wherein in formulas (1-18) to (1-24), $P^{28}$, $P^{29}$ and $P^{30}$ are independently acryloyloxy or methacryloyloxy;

$S^{28}$, $S^{29}$ and $S^{30}$ are independently a single bond, —CH$_2$—, —CH$_2$O—, —OCH$_2$—, —COO—, —OCO—, —CH=CH—, —C≡C—, —CH$_2$CH$_2$O—, —OCH$_2$CH$_2$—, —CH=CH—O— or —O—CH=CH—;

h1 is 1 or 2; and ring $A^{15}$ is 1,4-phenylene, 2-fluoro-1,4-phenylene, 2,5-difluoro-1,4-phenylene, 2-methyl-1,4-phenylene, 2-difluoromethyl-1,4-phenylene or 2-trifluoromethyl-1,4-phenylene.

Item 12. The polymerizable compound according to any one of items 7 to 11, represented by formulas (1-25) or (1-26):

(1-25)

![formula 1-25]

(1-26)

![formula 1-26]

wherein, in formulas (1-25) and (1-26), $P^{31}$, $P^{32}$ and $P^{33}$ are independently acryloyloxy or methacryloyloxy; i1 is 1 or 2; and ring $A^{16}$ is 1,4-phenylene, 2-fluoro-1,4-phenylene, 2-methyl-1,4-phenylene or 2-trifluoromethyl-1,4-phenylene.

Item 13. The polymerizable compound according to any one of items 7 to 12, represented by formulas (1-27) or (1-28):

(1-27)

![formula 1-27]

(1-28)

![formula 1-28]

wherein, in formulas (1-27) and (1-28), $P^{34}$, $P^{35}$ and $P^{36}$ are independently acryloyloxy or methacryloyloxy; and j1 is 1 or 2.

Item 14. A polymerizable composition, containing at least one compound selected from the group of compounds according to any one of items 7 to 13.

Item 15. An optically anisotropic body, formed by polymerization of the polymerizable composition according to item 14.

The invention also includes the following items: (a) the polymerizable composition, further containing at least one additive such as an optically active compound, an antioxidant, an ultraviolet light absorber, a light stabilizer, a heat stabilizer, an antifoaming agent, a polymerization initiator and a polymerization inhibitor; (b) the polymerizable composition, further containing a polymerizable compound different from compound (1); (c) an AM device including the liquid crystal composite prepared from the polymerizable composition; (d) a device, including the liquid crystal composite prepared from the polymerizable composition and having a PS-TN mode, a PS-IPS mode, a PS-FFS mode, a PSA-VA mode or a PSA-OCB mode; (e) a transmissive device including the polymerizable composition; (f) use of the polymerizable composition as a composition having a nematic phase; (g) use as an optically active composition by adding an optically active compound to the composition.

The invention also includes the following items: (h) in a liquid crystal display device having a PSA mode, use of a polymerizable composition containing at least one compound selected from the group of compounds represented by formula (1), at least one compound selected from the group of compounds represented by formulas (2) to (4), and at least one compound selected from the group of compounds represented by formulas (5) to (7); (i) in the liquid crystal display device having the PSA mode, use of a polymerizable composition containing at least one compound selected from the group of compounds represented by formula (1), at least one compound selected from the group of compounds represented by formulas (2) to (4), and at least one compound selected from the group of compounds represented by formula (8); and (j) in the liquid crystal display device having the PSA mode, use of a polymerizable composition containing at least one compound selected from the group of compounds represented by formula (1), at least one compound selected from the group of compounds represented by formulas (2) to (4), and at least one compound selected from the group of compounds represented by formulas (9) to (15).

Compound (1) will be first described, and then a synthesis method, the polymerizable composition, the liquid crystal composite and the liquid crystal display device will be described in the order.

1. Compound (1)

Polymerizable compound (1) according to the invention has a feature of having at least one triple bond. Compound (1) has a polymerizable group such as acryloyloxy ($-OCO-HC=CH_2$) and methacryloyloxy ($-OCO-(CH_3)C=CH_2$), and therefore polymerization reactivity is high. Such high reactivity is presumably due to an effect of the triple bond existing in compound (1), and a conversion ratio in a polymerization reaction is high. Compound (1) has a rod like molecular structure similar to the structure of a liquid crystal compound, and therefore solubility to a liquid crystal composition is high. Compound (1) has a suitable balance regarding at least two of the polymerization reactivity, the conversion ratio and the solubility. Compound (1) having such properties are described. Preferred examples of polymerizable group P, connecting group S, ring A and bonding group Z in compound (1) are also applied to a subordinate formula of a formula for compound (1). Physical properties of compound (1) can be arbitrarily adjusted by suitably combining types of the groups. No significant difference exists in the physical properties of the compound, and therefore compound (1) may contain an isotope such as $^2H$ (deuterium) and $^{13}C$ in an amount higher than an amount of natural abundance.

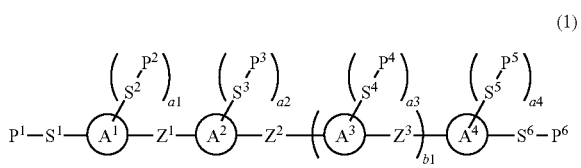

(1)

In formula (1), $P^1$, $P^2$, $P^3$, $P^4$, $P^5$ and $P^6$ are independently a polymerizable group. A preferred polymerizable group is acryloyloxy, methacryloyloxy, acrylamide, methacrylamide, vinyloxy, vinyl carbonyl, oxiranyl, oxetanyl, 3,4-epoxycyclohexyl and maleimide. In the groups, at least one of hydrogen may be replaced by fluorine, methyl or trifluoromethyl. A further preferred polymerizable group is an acryloyloxy group (P-1), a vinyloxy group (P-2) and an oxiranyl group (P-3), in which $M^1$ and $M^2$ are independently hydrogen, fluorine, methyl or trifluoromethyl. A most preferred polymerizable group is an acryloyloxy group (P-1), in which $M^1$ is hydrogen or methyl, and $M^2$ is hydrogen. More specifically, the most preferred polymerizable group is acryloyloxy or methacryloyloxy.

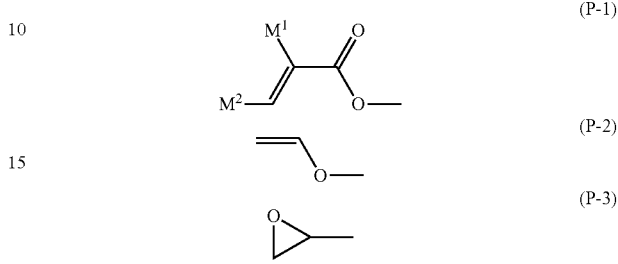

In formula (1), $S^1$, $S^2$, $S^3$, $S^4$, $S^5$ and $S^6$ are independently a single bond or alkylene having 1 to 12 carbons, and in the alkylene, at least one of $-CH_2-$ may be replaced by $-O-$, $-COO-$ or $-OCO-$, at least one of $-CH_2CH_2-$ may be replaced by $-CH=CH-$ or $-C\equiv C-$, and in the groups, at least one of hydrogen may be replaced by halogen. The halogen means fluorine, chlorine, bromine and iodine. Preferred halogen is fluorine and chlorine. Further preferred halogen is fluorine.

Specific examples of $S^1$ to $S^6$ include a single bond or alkylene having 1 to 6 carbons, and in the alkylene, one or two of $-CH_2-$ may be replaced by $-O-$, $-COO-$ or $-OCO-$, one or two of $-CH_2-CH_2-$ may be replaced by $-CH=CH-$ or $-C\equiv C-$, and in the groups, at least one of hydrogen may be replaced by fluorine or chlorine.

Preferred $S^1$ to $S^6$ are a single bond, $-CH_2-$, $-CH_2O-$, $-OCH_2-$, $-COO-$, $-OCO-$, $-CH_2CH_2-$, $-CH=CH-$, $-CF=CH-$, $-CH=CF-$, $-CF=CF-$, $-C\equiv C-$, $-CH_2CH_2O-$, $-OCH_2CH_2-$, $-CH=CH-O-$, $-O-CH=CH-$, $-C\equiv C-O-$, $-O-C\equiv C-$, $-(CH_2)_3-$, $-(CH_2)_3-O-$, $-O-(CH_2)_3-$, $-(CH_2)_4-$, $-(CH_2)_4O-$ or $-O(CH_2)_4-$. Further preferred $S^1$ to $S^6$ are a single bond, $-CH_2-$, $-CH_2O-$, $-OCH_2-$, $-COO-$, $-OCO-$, $-CH=CH-$, $-C\equiv C-$, $-CH_2CH_2O-$, $-OCH_2CH_2-$, $-CH=CH-O-$ or $-O-CH=CH-$. Particularly preferred $S^1$ to $S^6$ are a single bond, $-CH_2-$, $-CH=CH-$, $-CH=CH-O-$, $-O-CH=CH-$, $-CH_2CH_2O-$ or $-OCH_2CH_2-$. Most preferred examples include a single bond. A configuration of a double bond ($-CH=CH-$) in the groups may be a cis form or a trans form, and the trans form is preferred to the cis form.

In formula (1), a1, a3 and a4 are independently 0, 1, 2, 3 or 4, a2 is 1, 2, 3 or 4, and a sum of a1, a2, a3 and a4 is 3 to 10, in which either or both of $-S^1-P^1$ and $-S^6-P^6$ may be hydrogen. More specifically, the number of polymerizable groups is 12 (10+2) at a maximum. Preferred a1, a3 or a4 is 0, 1 or 2. Preferred a2 is 1, 2 or 3. The sum of a1, a2, a3 and a4 is preferably 3 to 6, further preferably 3 or 4, and still further preferably 4 or 5. A total of the polymerizable groups ($-S^1-P^1$ to $-S^6-P^6$) may be preferably 3 to 6, further preferably 3 or 4, and still further preferably 4 or 5.

In formula (1), ring $A^1$, ring $A^2$, ring $A^3$ and ring $A^4$ are independently a divalent group derived from benzene, naphthalene, anthracene, pyrimidine or pyridine, and in the divalent groups, at least one of hydrogen may be replaced by halogen, alkyl having 1 to 12 carbons, or alkyl having 1 to 12 carbons in which at least one of hydrogen is replaced by halogen, and ring $A^2$ and ring $A^3$ may be independently a divalent group derived from cyclohexane, cyclohexene, tetrahydropyran or dioxane. Ring A is a group (divalent group) derived from a six-membered ring or a condensed ring, such as benzene, naphthalene or cyclohexane, by removing any two hydrogen atoms on carbon. Ring $A^1$ is a divalent group bonded with $S^1$-$P^1$ and $Z^1$. Here, $S^1$-$P^1$ may be hydrogen. A same rule is also applied to ring $A^4$ and $S^6$-$P^6$, which is as described in paragraph 0040.

Halogen means fluorine, chlorine, bromine and iodine. Preferred halogen is fluorine and chlorine. Further preferred halogen is fluorine. Preferred alkyl is methyl, ethyl, propyl or butyl. Further preferred alkyl is methyl. Preferred examples of alkyl in which at least one of hydrogen is replaced by halogen include alkyl in which at least one of hydrogen is replaced by fluorine or chlorine, and the examples also include perfluoroalkyl and perchloroalkyl. Further preferred examples include —$CH_2F$, —$CHF_2$, —$CF_3$, —$CHClF$, —$CH_2CF_3$ or —$CF_2CF_3$. Most preferred examples include —$CF_3$.

Preferred ring $A^1$ to ring $A^4$ are independently a divalent group derived from benzene, naphthalene, pyrimidine or pyridine, and in the divalent groups, at least one of hydrogen may be replaced by fluorine, chlorine, alkyl having 1 to 6 carbons, or alkyl having 1 to 6 carbons in which at least one of hydrogen is replaced by fluorine or chlorine. Ring $A^2$ and ring $A^3$ may be independently a divalent group derived from cyclohexane, tetrahydropyran or dioxane.

Further preferred ring $A^1$ to ring $A^4$ are 1,4-phenylene, 1,3-phenylene, 1,2-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, anthracen-1,4-diyl, anthracen-1,6-diyl, anthracen-2,7-diyl, pyrimidine-2,5-diyl or pyridine-2,5-diyl. In the divalent groups, at least one of hydrogen may be replaced by fluorine, methyl, difluoromethyl or trifluoromethyl, and ring $A^2$ or ring $A^3$ may be 1,4-cyclohexylene, tetrahydropyran-2,5-diyl or 1,3-dioxane-2,5-diyl.

Particularly preferred ring $A^1$ to ring $A^4$ are 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-chloro-3-fluoro-1,4-phenylene, 2-methyl-1,4-phenylene, 2-difluoromethyl-1,4-phenylene, 2-trifluoromethyl-1,4-phenylene, 2-ethyl-1,4-phenylene, 2-pentafluoroethyl-1,4-phenylene or 2-propyl-1,4-phenylene. Most preferred ring $A^1$ to ring $A^4$ are 1,4-phenylene. Most preferred ring $A^1$ to ring $A^4$ are also 2-fluoro-1,4-phenylene.

In formula (1), $Z^1$, $Z^2$ and $Z^3$ are independently a single bond or alkylene having 1 to 12 carbons, and in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$)—, —C($CH_3$)=C($CH_3$)— or —C≡C—, and in the groups, at least one of hydrogen may be replaced by halogen, in which at least one of $Z^1$, $Z^2$ and $Z^3$ is —C≡C—. More specifically, when b1 is 1, at least one of $Z^1$, $Z^2$ and $Z^3$ is —C≡C—, and when b1 is 0 (zero), at least one of $Z^1$ and $Z^2$ is —C≡C—.

Examples of $Z^1$, $Z^2$ or $Z^3$ include a single bond or alkylene having 1 to 6 carbons, and in the alkylene, one or two of —$CH_2$— may be replaced by —O—, —CO—, —COO— or —OCO—, one or two of —$CH_2$—$CH_2$— may be replaced by —CH=CH—, —C($CH_3$)=CH—, —CH=C($CH_3$)—, —C($CH_3$)=C($CH_3$)— or —C≡C—, and in the groups, at least one of hydrogen may be replaced by fluorine or chlorine, and at least one of $Z^1$, $Z^2$ and $Z^3$ is —C≡C—.

Preferred $Z^1$, $Z^2$ or $Z^3$ is a single bond, alkylene having 1 to 6 carbons, —CO—, —$CH_2O$—, —$OCH_2$—, —COO—, —OCO—, —CH=CH—, —C($CH_3$)=CH—, —CH=C($CH_3$)—, —C($CH_3$)=C($CH_3$)—, —C≡C—, —CO—CH=CH—, —CH=CH—CO—, —CH=CH—$CH_2O$—, —$OCH_2$—CH=CH—, —CH=CH—$OCH_2$—, —$CH_2O$—CH=CH—, —CH=CH—COO—, —OCO—CH=CH—, —CH=CH—OCO—, —COO—CH=CH—, —C($CH_3$)=CH—COO—, —OCO—CH=C($CH_3$)—, —C($CH_3$)=CH—OCO—, —COO—CH=C($CH_3$)—, —CH=C($CH_3$)—COO—, —OCO—($CH_3$) C=CH—, —CH=C($CH_3$)—OCO—, —COO—($CH_3$) C=CH—, —C($CH_3$)=C($CH_3$)—COO— or —OCO—C($CH_3$)=C($CH_3$)—, and in the groups, at least one of hydrogen may be replaced by fluorine.

Further preferred $Z^1$, $Z^2$ or $Z^3$ is a single bond, alkylene having 1 to 5 carbons, —CO—, —$CH_2O$—, —$OCH_2$—, —COO—, —OCO—, —CH=CH—, —C≡C—, —CH=CH—$CH_2O$—, —$OCH_2$—CH=CH—, —CH=CH—$OCH_2$—, —$CH_2O$—CH=CH—, —CH=CH—COO—, —OCO—CH=CH—, —CH=CH—OCO— or —COO—CH=CH—, and in the groups, at least one of hydrogen may be replaced by fluorine. Particularly preferred $Z^1$, $Z^2$ or $Z^3$ is a single bond, —CO—, —COO—, —OCO—, —CH=CH— or —C≡C—. Most preferred $Z^1$, $Z^2$ or $Z^3$ is a single bond.

In formula (1), b1 is 0 or 1. A compound in which b1 is 0 has three rings. The compound is preferred from a viewpoint of ease of synthesis. A compound in which b1 is 1 has four rings. The compound is preferred from a viewpoint of ease of handling.

A polymerizable compound having objective physical properties can be obtained by suitably selecting a combination of polymerizable group P, connecting group S, ring A and bonding group Z with referring to the preferred examples described above. Preferred examples of compound (1) include compound (1-1), and also compound (1-2) and compound (1-3). Further preferred examples include compound (1-4) to compound (1-10), and also compound (1-11) to compound (1-17). Particularly preferred examples include compound (1-18) to compound (1-24). Most preferred examples include compound (1-25) and compound (1-26), and also compound (1-27) and compound (1-28). Such a polymerizable compound is useful as a component of the liquid crystal composition used for a liquid crystal display device having a mode such as PS-TN, PS-IPS, PS-FFS, PSA-VA and PSA-OCB.

2. Synthesis Method

A synthesis method of compound (1) will be described. Compound (1) can be prepared by suitably combining techniques in synthetic organic chemistry. A method for introducing an objective polymerizable group, connecting group, ring and bonding group into a starting material is described in books such as Houben-Wyle (Houben-Wyle, Methoden der Organische Chemie, Georg-Thieme Verlag, Stuttgart), Organic Syntheses (John Wily & Sons, Inc.), Organic Reactions (John Wily & Sons, Inc.), Comprehensive Organic Synthesis (Pergamon Press) and New Experimental Chemistry Course (Shin Jikken Kagaku Koza in Japanese) (Maruzen Co., Ltd.).

2-1. Formation of Bonding Group Z

An example of a method of forming bonding group $Z^1$, $Z^2$ or $Z^3$ in compound (1) is as shown in a scheme below. In the scheme, $MSG^1$ (or $MSG^2$) is a monovalent organic group having at least one ring. Monovalent organic groups represented by a plurality of MSG¹ (or MSG²) may be identical or different. Compound (1A) to compound (1I) correspond to compound (1). In formation of ester, a method of synthesis a compound having —COO— is shown. A compound having —OCO— can also be prepared by the synthesis method. Other asymmetrical bonding groups can be also formed in a similar manner. Formation of a triple bond is shown in section (10).

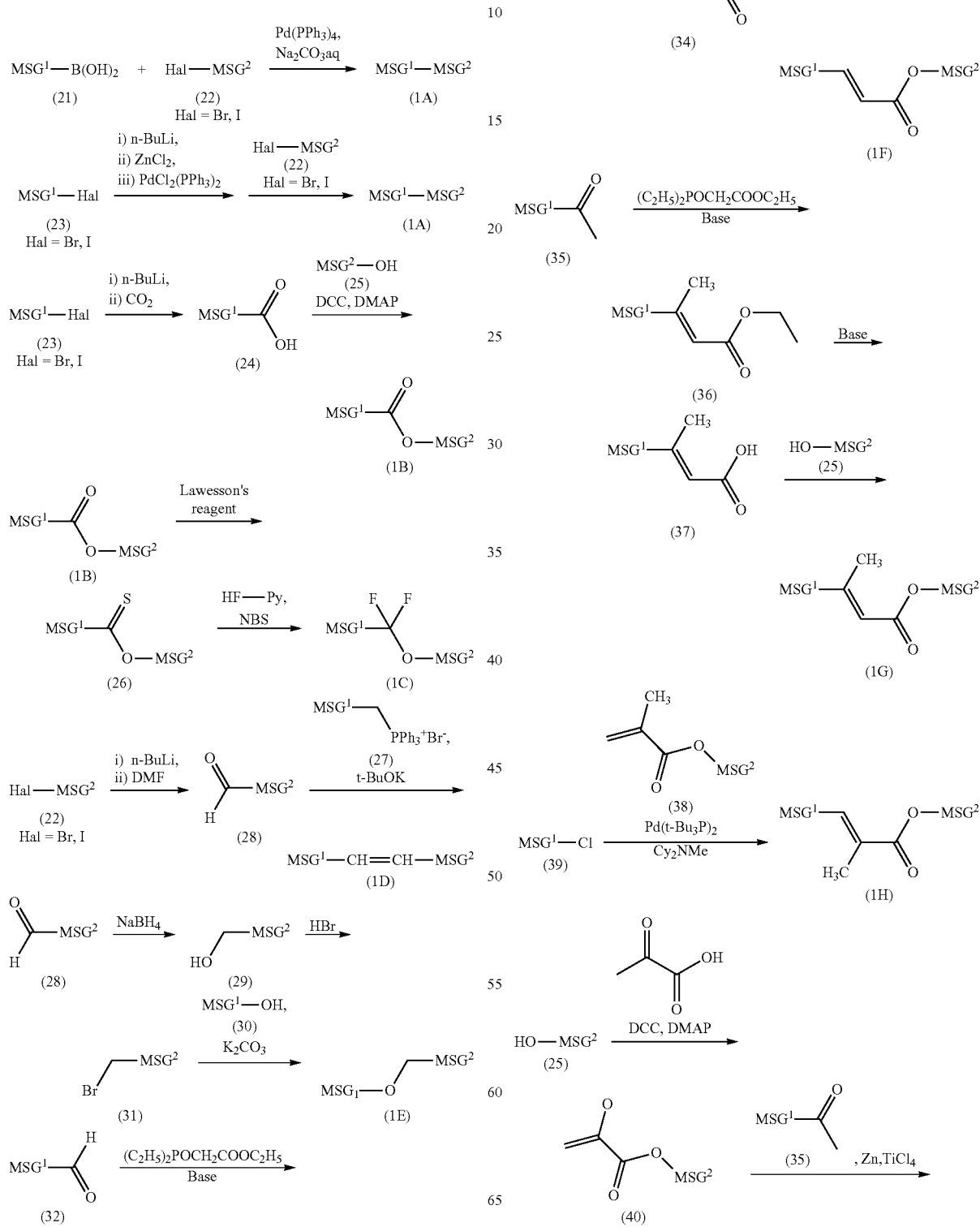

-continued

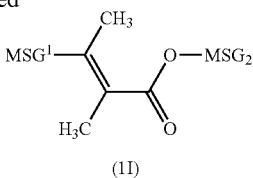

(1) Formation of a Single Bond

Compound (1A) is prepared by allowing aryl boronic acid (21) to react, in the presence of a catalyst such as tetrakis (triphenylphosphine)palladium in an aqueous solution of carbonate, with compound (22) to be prepared according to a publicly known method. Compound (1A) is also prepared by allowing compound (23) to be prepared according to a publicly known method to react with n-butyllithium and subsequently with zinc chloride, and further with compound (22) in the presence of a catalyst such as dichlorobis (triphenylphosphine)palladium.

(2) Formation of —COO—

Carboxylic acid (24) is obtained by allowing compound (23) to react with n-butyllithium, and subsequently with carbon dioxide. Compound (1B) is prepared by allowing dehydrating condensation of compound (24) and phenol (25) to be prepared according to a publicly known method, in the presence of 1,3-dicyclohexylcarbodiimide (DCC) and N,N-dimethyl-4-aminopyridine (DMAP).

(3) Formation of —CF$_2$O—

Compound (26) is obtained by treating compound (1B) with a thiation reagent such as Lawesson's reagent. Compound (1C) is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. The bonding group can be also formed according to the method described in Peer. Kirsch et al., Angew. Chem. Int. Ed. 2001, 40, 1480.

(4) Formation of —CH═CH—

Aldehyde (28) is obtained by treating compound (22) with n-butyllithium and then allowing the treated compound to react with formamide such as N,N-dimethylformamide (DMF). Compound (1D) is prepared by allowing aldehyde (28) to react with phosphorus ylide generated by treating phosphonium salt (27) to be prepared according to a publicly known method with a base such as potassium tert-butoxide. Because a cis isomer is formed depending on reaction conditions, the cis isomer is isomerized into a trans isomer according to a publicly known method, when necessary.

(5) Formation of —CH$_2$O—

Compound (29) is obtained by reducing compound (28) with a reducing agent such as sodium borohydride. Compound (31) is obtained by halogenating the obtained compound with hydrobromic acid or the like. Compound (1E) is prepared by allowing compound (31) to react with compound (30) in the presence of potassium carbonate or the like.

(6) Formation of —CH═CH—COO—

Phosphorus ylide is prepared by allowing a base such as sodium hydride to act on ethyl diethylphosphoacetate, and ester (33) is obtained by allowing the phosphorus ylide to react with aldehyde (32). Carboxylic acid (34) is obtained by hydrolyzing ester (33) in the presence of a base such as sodium hydroxide. Compound (1F) is prepared by allowing dehydrating condensation of the obtained compound with compound (25).

(7) Formation of —C(CH$_3$)═CH—COO—

Phosphorus ylide is prepared by allowing a base such as sodium hydride to act on ethyl diethylphosphoacetate, and ester (36) is obtained by allowing the phosphorus ylide to react with methyl ketone (35). Next, carboxylic acid (37) is obtained by hydrolyzing ester (33) in the presence of a base such as sodium hydroxide, and then compound (1G) is prepared by dehydrating condensation of the obtained compound with compound (25).

(8) Formation of —CH═C(CH$_3$)—COO—

Compound (1H) is prepared by allowing compound (38) to be prepared according to a publicly known method to react with compound (39) to be prepared according to a publicly known method, in the presence of a base such as N,N-dicyclohexyl methylamine (Cy$_2$NMe) and a catalyst such as bis(tri-tert-butyl phosphine) palladium.

(9) Formation of —C(CH$_3$)═C(CH$_3$)—COO—

Compound (40) is obtained by dehydrating condensation of compound (25) with pyruvic acid. Compound (1I) is prepared by allowing compound (40) to react with compound (35) in the presence of zinc and titanium tetrachloride.

(10) Formation of —C≡C—

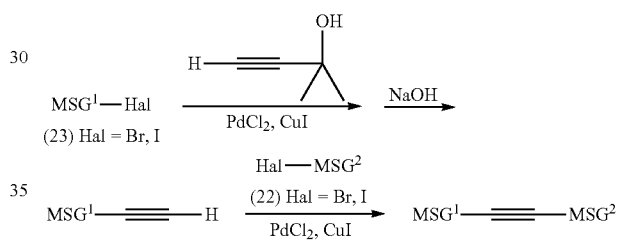

Alkyne is obtained by allowing 2-methyl-3-butyn-2-ol to react with compound (23) in the presence of a catalyst including dichloropalladium and copper halide, and then deprotecting the resulting product under basic conditions. A compound having a triple bond is prepared by allowing the alkyne to react with compound (22) in the presence of a catalyst including dichloropalladium and copper halide.

2-2. Formation of Connecting Group S

P$^1$ or P$^2$ is a polymerizable group. Further preferred examples of the polymerizable group include an acryloyloxy group (P-1), a vinyloxy group (P-2), and an oxiranyl group (P-3), in which M$^1$ and M$^2$ are independently hydrogen, fluorine, methyl or trifluoromethyl.

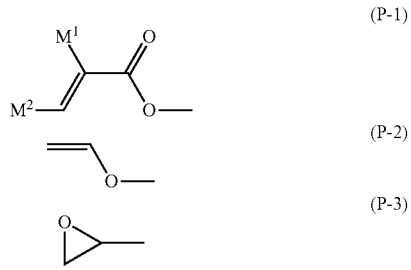

A method for preparing a compound in which acryloyloxy group (P-1) is bonded with a ring by connecting group S will be described.

(1) Single Bond

When a connecting group is a single bond, the method is as shown in a scheme below. In the scheme, MSG¹ is a monovalent organic group having at least one ring. Compound (1J) to compound (1M) correspond to compound (1).

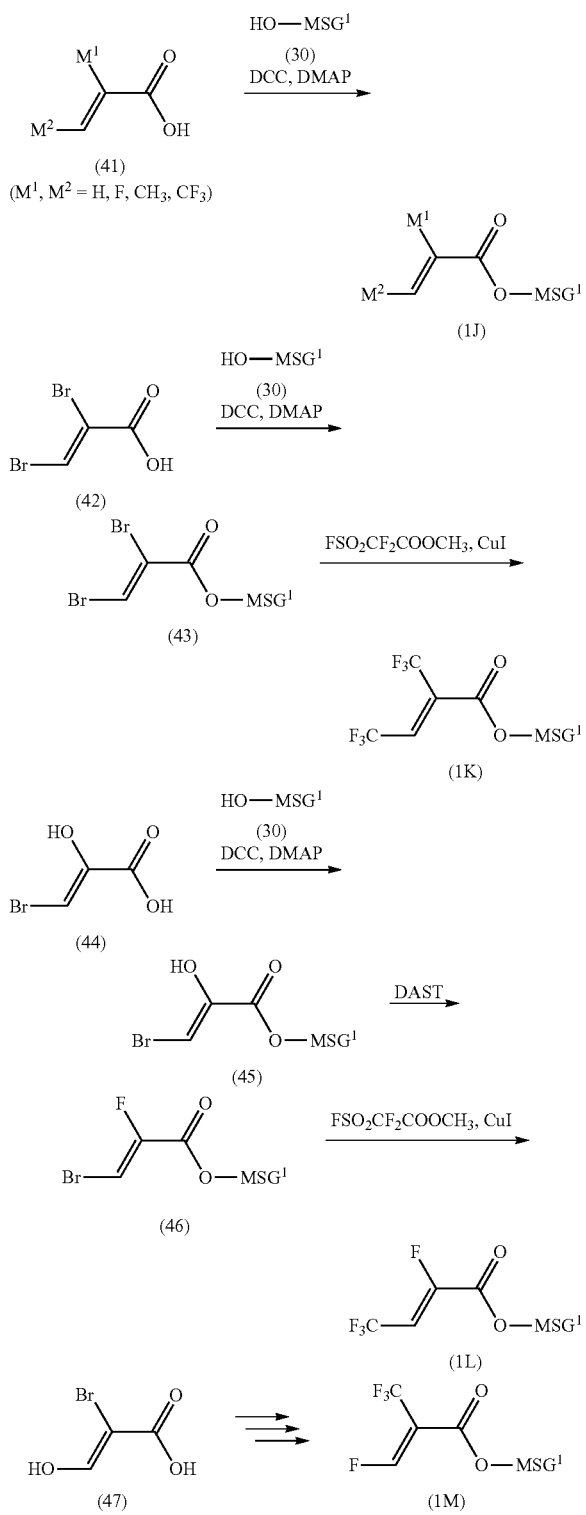

When neither $M^1$ nor $M^2$ is —$CF_3$, when $M^1$ is fluorine and $M^2$ is not —$CF_3$, or when $M^1$ is —$CF_3$ and $M^2$ is not fluorine, carboxylic acid (41) shown in the scheme above is commercially available. Compound (1J) is prepared by allowing dehydrating condensation of carboxylic acid (41) and compound (30) in the presence of DCC and DMAP.

When both $M^1$ and $M^2$ are —$CF_3$, compound (43) is obtained by allowing dehydrating condensation of carboxylic acid (42) and compound (30) in the presence of DCC and DMAP. Compound (1K) is prepared by allowing compound (43) to react with 2,2-difluoro-2-(fluorosulfonyl)methyl acetate in the presence of a catalyst of copper iodide.

When $M^1$ is fluorine and $M^2$ is —$CF_3$, compound (45) is obtained by allowing dehydrating condensation of carboxylic acid (44) and compound (30) in the presence of DCC and DMAP. Compound (46) is obtained by fluorinating compound (45) with a fluorinating agent such as DST. Compound (1L) is prepared by allowing compound (46) to react with 2,2-difluoro-2-(fluorosulfonyl)methyl acetate in the presence of a catalyst of copper iodide.

When $M^1$ is —$CF_3$ and $M^2$ is fluorine, compound (1M) is prepared using carboxylic acid (47) as a starting material according to the method described above.

Other Connecting Groups

A case where the connecting group of acryloyloxy group (P-1) is the single bond is described above. In a scheme shown below, a method of synthesis of a compound in which acryloyloxy group (P-1) is bonded with a ring by any other connecting group (S is not equal to a single bond) will be shown. In the scheme, MSG¹ is a monovalent organic group having at least one ring. Compounds (1N) to (1Q) correspond compound (1).

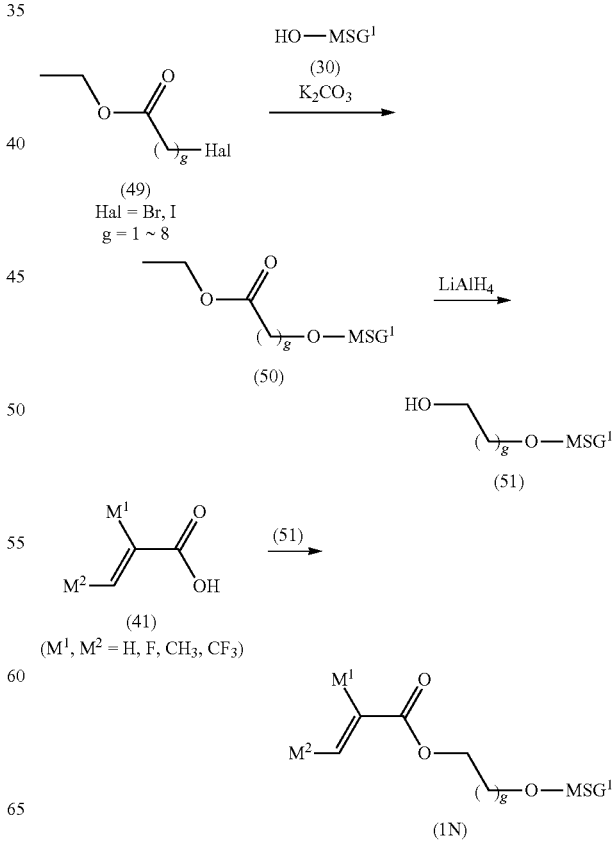

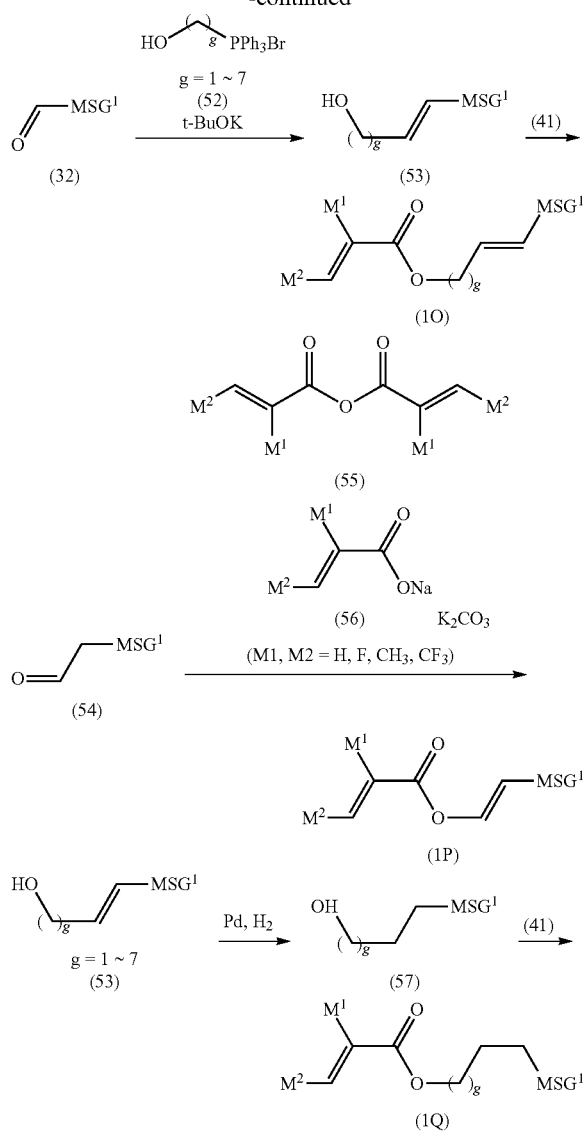

(2) Formation of —(CH$_2$)$_g$—O—

Compound (50) is obtained by allowing compound (49) to be prepared according to a publicly known method to react with compound (30) in the presence of potassium carbonate or the like. Compound (51) is obtained by reducing compound (50) with a reducing agent such as lithium hydride aluminum or the like. Compound (1N) is obtained by dehydrating condensation of compound (51) and carboxylic acid (41).

(3) Formation of —(CH$_2$)$_g$—CH═CH—

Compound (53) is obtained by allowing phosphorus ylide generated by treating phosphonium salt (52) to be prepared according to a publicly known method with a base such as potassium tert-butoxide to react with aldehyde (32). Compound (10) is obtained by dehydrating condensation of compound (53) and carboxylic acid (41).

(4) Formation of —CH═CH—

Compound (1P) is obtained by allowing aldehyde (54) to be prepared according to a publicly known method to react with acid anhydride (55) and sodium carboxylate (56) in the presence of potassium carbonate or the like.

(5) Formation of —(CH$_2$)$_g$—CH$_2$CH$_2$—

Alcohol (57) is prepared by hydrogenating compound (53) in the presence of a catalyst such as palladium on carbon. Compound (1Q) is obtained by allowing dehydrating condensation of the obtained alcohol and carboxylic acid (41).

Vinyloxy Group (P-2)

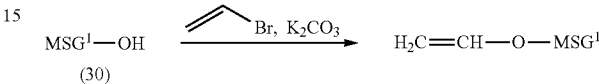

H$_2$C═CH—O-MSG$^1$ is prepared by allowing MSG$^1$-OH (30) to react with vinyl bromide in the presence of potassium carbonate.

Oxiranyl Group (P-3)

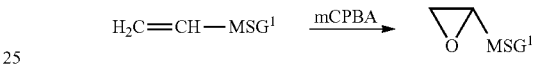

A corresponding epoxide is prepared by oxidizing H$_2$C═CH-MSG$^1$ to be prepared by a publicly known method with meta-chloroperbenzoic acid.

Compound (1) has higher polymerization reactivity, a higher conversion ratio and higher solubility in the liquid crystal composition in comparison with a similar compound. Compound (1) has a suitable balance with regard to at least two of the physical properties. Accordingly, compound (1) can be added to a liquid crystal composition for the PSA mode.

3. Polymerizable Composition

A polymerizable composition contains at least one of compound (1) as a first component. A component of the composition may include only the first component. The composition may also contain any other component such as a second component and a third component. A kind of the second component or the like depends on an application of an objective polymer. The polymerizable composition may further contain any other polymerizable compound different from compound (1) as the second component. Preferred examples of any other polymerizable compound include an acrylate, a methacrylate, a vinyl compound, a vinyloxy compound, a propenyl ether, an epoxy compound (oxirane, oxetane) and a vinyl ketone. Further preferred examples include a compound having at least one acryloyloxy or a compound having at least one methacryloyloxy. Specific still preferred examples include a compound having both acryloyloxy and methacryloyloxy.

Additional examples of any other polymerizable compound include compounds (M-1) to (M-12). In compounds (M-1) to (M-12), R$^{25}$, R$^{26}$ and R$^{27}$ are independently hydrogen or methyl; u, x and y are independently 0 or 1; v and w are independently an integer from 1 to 10; and L$^{21}$, L$^{22}$, L$^{23}$, L$^{24}$, L$^{25}$ and L$^{26}$ are independently hydrogen or fluorine.

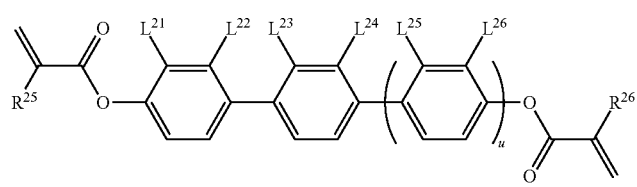

(M-1)

-continued
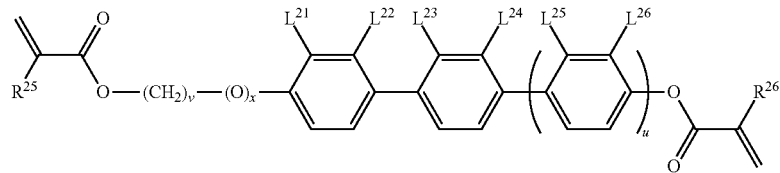 (M-2)
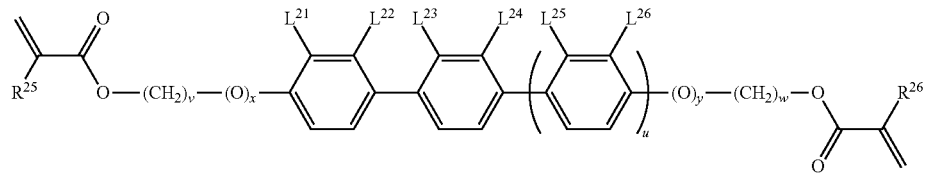 (M-3)
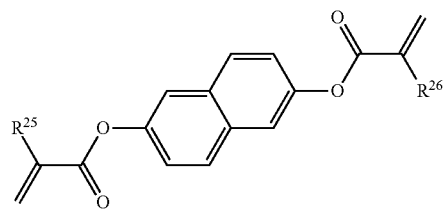 (M-4)
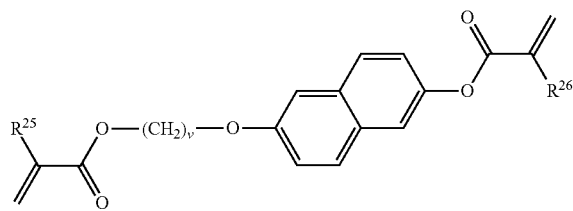 (M-5)
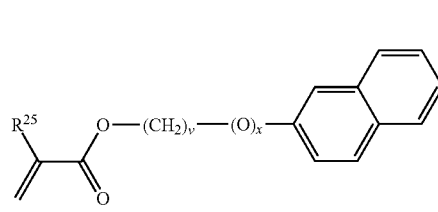 (M-6)
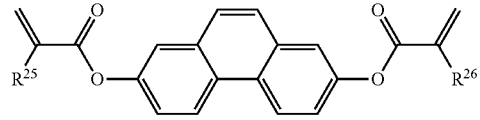 (M-7)
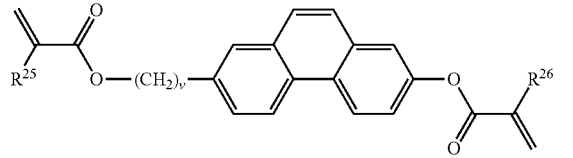 (M-8)
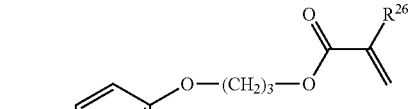 (M-9)
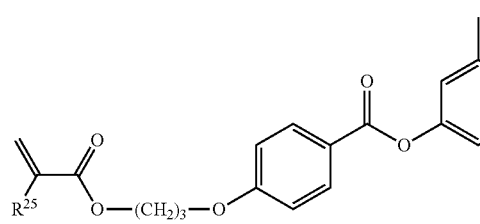 
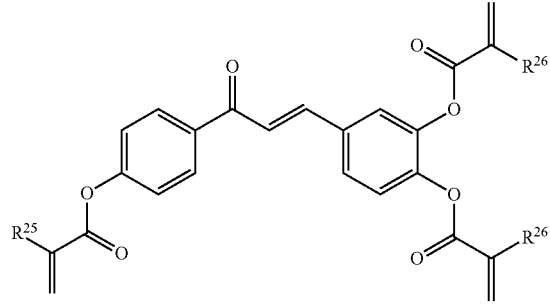 (M-10)

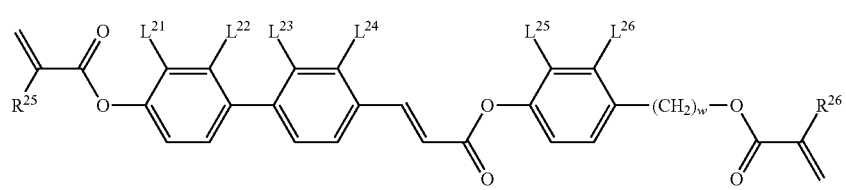

(M-11)

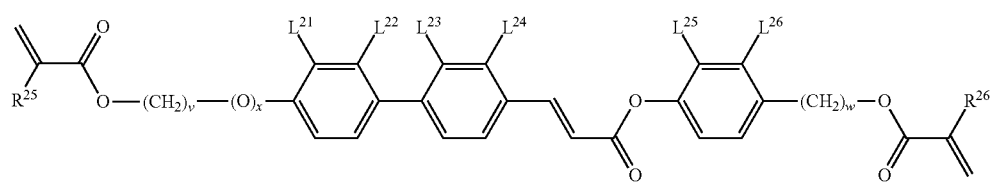

(M-12)

When the second component of the polymerizable composition is a polymerizable compound having the liquid crystal phase, an optical anisotropic body is formed by allowing polymerization while controlling alignment of liquid crystal molecules. The optical anisotropic body can be used for a phase difference film, a polarized light device, a circularly polarized light device, an elliptically polarized light device, an antireflection film, a selective reflection film, a color compensation film, a viewing angle compensation film or the like. An additive such as a polymerization initiator may be added to the polymerizable composition for the purpose of adjusting physical properties of the optical anisotropic body.

The polymerizable composition may also contain a liquid crystal composition as the second component. When a liquid crystal display device for the mode such as PS-TN, PS-IPS, PS-FFS, PSA-VA and PSA-OCB is targeted, the polymerizable composition contains compound (1) as component A, and preferably further contains a compound selected from components B, C, D and E shown below. Component B includes compounds (2) to (4). Component C includes compounds (5) to (7). Component D includes compound (8). Component E includes compounds (9) to (15). Upon preparing such a polymerizable composition, components B, C, D and E are preferably selected in taking positive or negative dielectric anisotropy, magnitude of dielectric anisotropy, or the like into consideration. The polymerizable composition prepared by suitably selecting the component has a high maximum temperature, a low minimum temperature, small viscosity, suitable optical anisotropy (namely, large optical anisotropy or small optical anisotropy), large positive or negative dielectric anisotropy, a suitable elastic constant (namely, a large elastic constant or a small elastic constant), large specific resistance and suitable pretilt.

The polymerizable composition is prepared by adding compound (1) to the liquid crystal composition. An additive may be added in the composition, when necessary. In such a composition, an amount of addition of compound (1), namely component A, is in the range from approximately 0.05% by weight to approximately 20% by weight based on the weight of the liquid crystal composition. A further preferred amount of addition is in the range from approximately 0.1% by weight to approximately 10% by weight. A most preferred amount of addition is in the range from approximately 0.2% by weight to approximately 1% by weight. At least one of other polymerizable compounds different from compound (1) may be further added thereto. In the above case, an amount of addition of compound (1) and any other polymerizable compound in total is preferably within the range described above. Physical properties of the polymer to be formed can be adjusted by suitably selecting any other polymerizable compound. Examples of other polymerizable compounds include acrylate and methacrylate, as previously described. The examples also include compounds (M-1) to (M-12).

Component B is a compound in which two terminal groups are alkyl or the like. Preferred examples of component B include compounds (2-1) to (2-11), compounds (3-1) to (3-19) and compounds (4-1) to (4-7). In the compounds of component B, $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine.

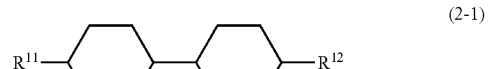

(2-1)

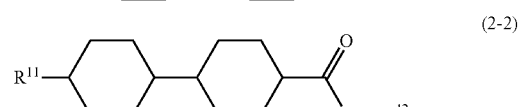

(2-2)

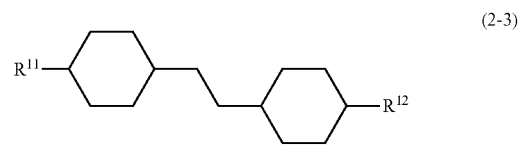

(2-3)

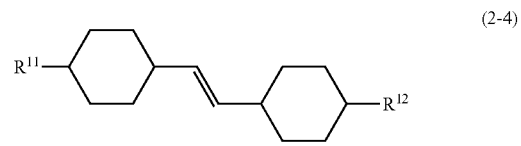

(2-4)

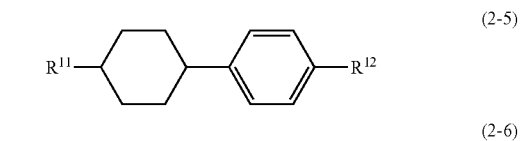

(2-5)

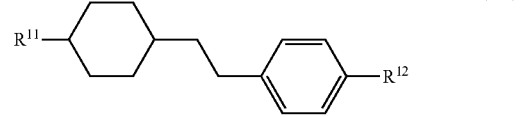

(2-6)

-continued (2-7) (3-8) (2-8) (3-9) (2-9) (3-10) (2-10) (3-11) (2-11) (3-12) (3-1) (3-13) (3-2) (3-14) (3-3) (3-15) (3-4) (3-16) (3-5) (3-17) (3-6) (3-7) (3-18)

-continued

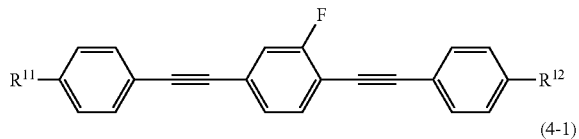
(3-19)

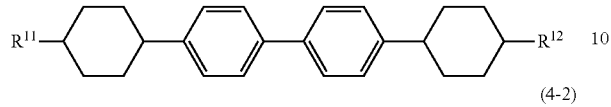
(4-1)

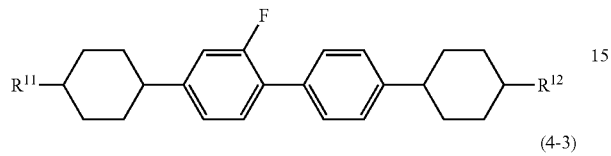
(4-2)

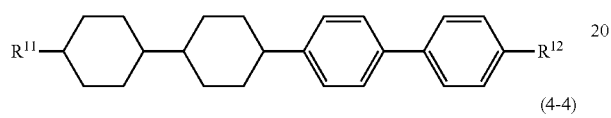
(4-3)

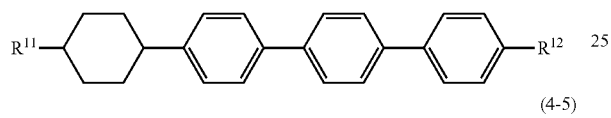
(4-4)

(4-5)

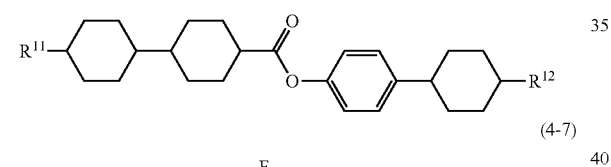
(4-6)

(4-7)

An absolute value of dielectric anisotropy is small, therefore component B is a compound close to neutrality. Compound (2) is effective mainly in adjusting the viscosity or the optical anisotropy. Compounds (3) and (4) are effective in extending the temperature range of the nematic phase by increasing the maximum temperature, or effective in adjusting the optical anisotropy.

As a content of component B is increased, the viscosity of the composition decreases, but the dielectric anisotropy decreases. Thus, the content is preferably as large as possible, as long as a required value of threshold voltage of the device is satisfied. Accordingly, when a composition for the mode such as PS-IPS and PSA-VA is prepared, the content of component B is preferably in the range of approximately 30% by weight or more, and further preferably in the range of approximately 40% by weight or more, based on the weight of liquid crystal composition.

Component C is a compound having a halogen-containing or fluorine-containing group at a right terminal. Specific preferred examples of component C include compounds (5-1) to (5-16), compounds (6-1) to (6-113) and compounds (7-1) to (7-57). In the compounds of component C, $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

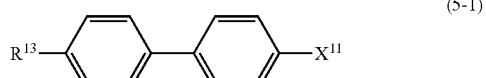
(5-1)

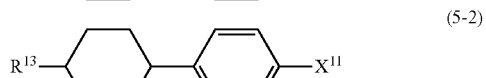
(5-2)

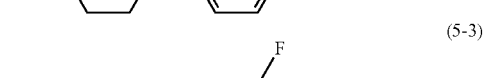
(5-3)

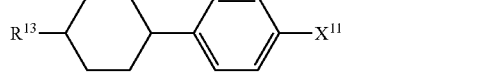
(5-4)

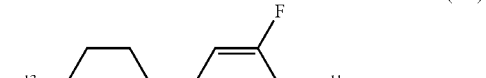
(5-5)

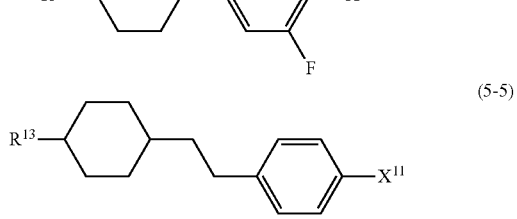
(5-6)

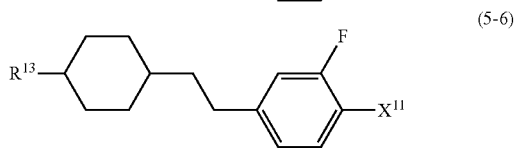
(5-7)

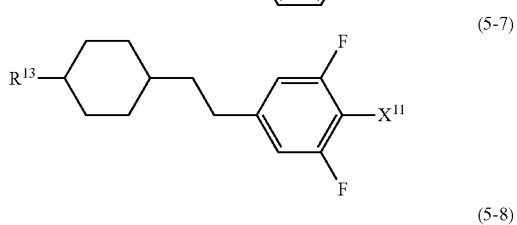
(5-8)

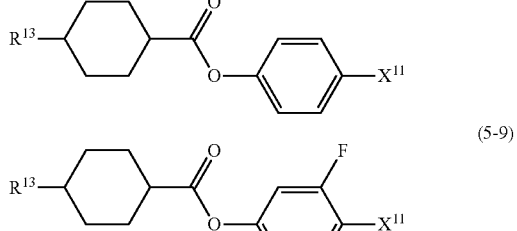
(5-9)

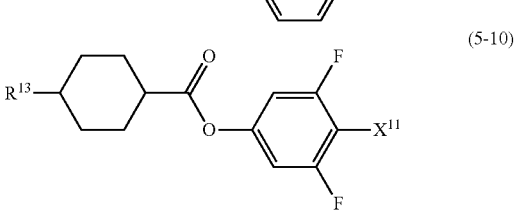
(5-10)

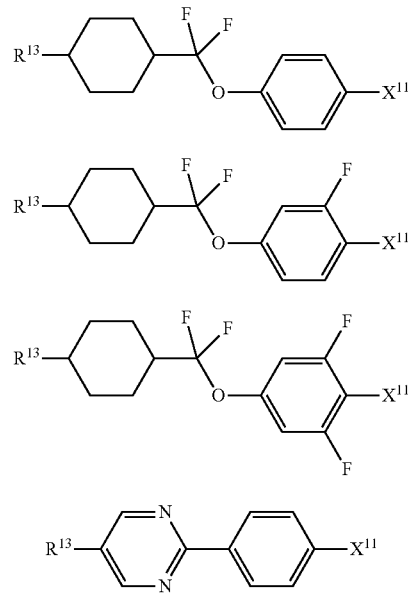
(5-11)
(5-12)
(5-13)
(5-14)
(5-15)
(5-16)
(6-1)
(6-2)
(6-3)
(6-4)
(6-5)
(6-6)
(6-7)
(6-8)
(6-9)
(6-10)
(6-11)
(6-12)
(6-13)
(6-14)

(6-15) 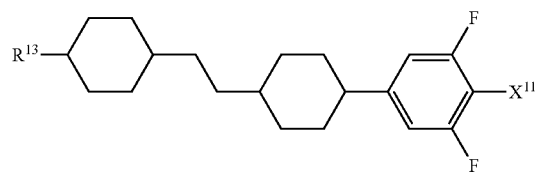
(6-16) 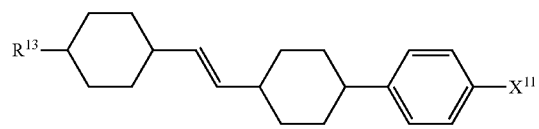
(6-17) 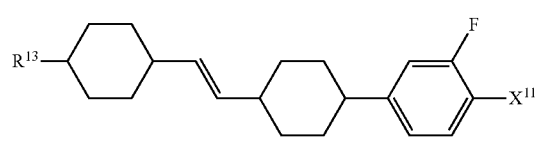
(6-18) 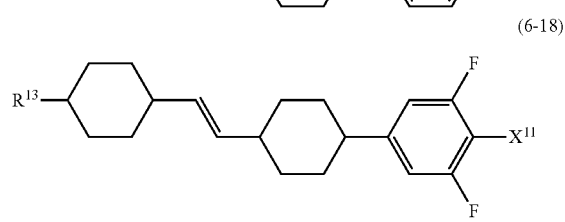
(6-19) 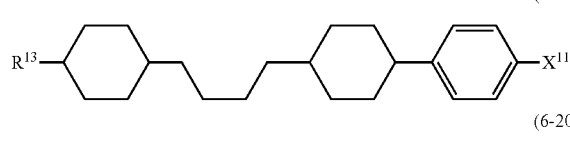
(6-20) 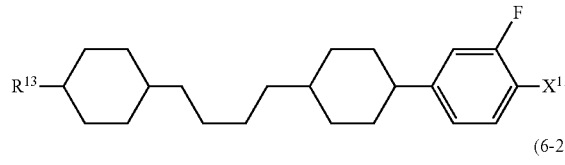
(6-21) 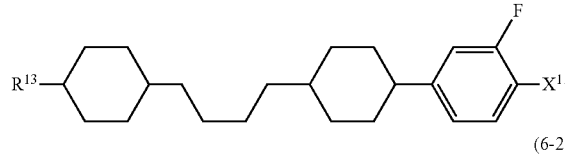
(6-22) 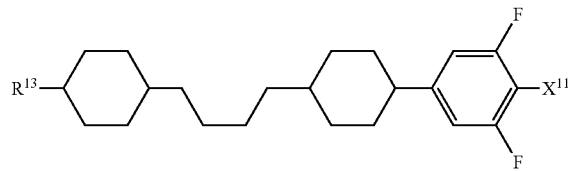
(6-23) 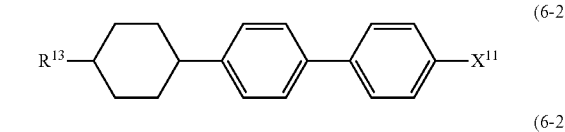
(6-24) 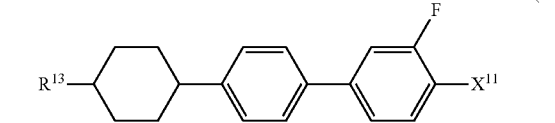
(6-25) 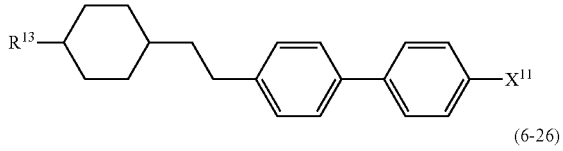
(6-26) 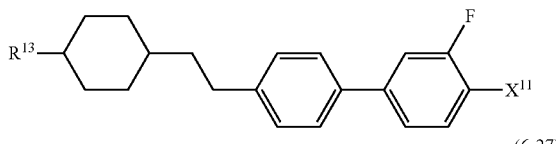
(6-27) 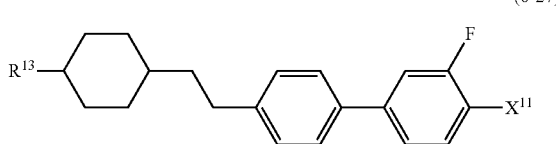
(6-28) 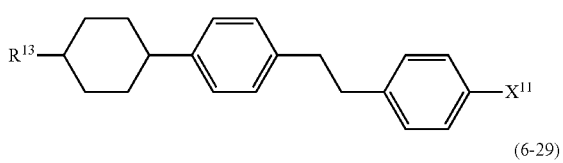
(6-29) 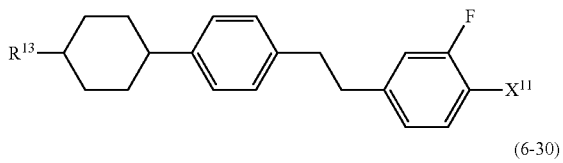
(6-30) 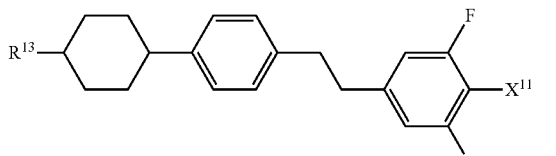
(6-31) 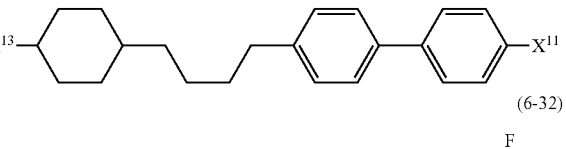
(6-32) 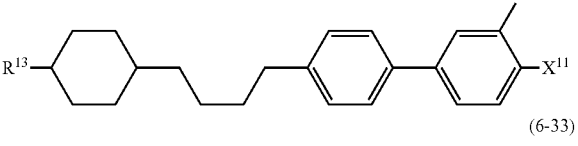
(6-33) 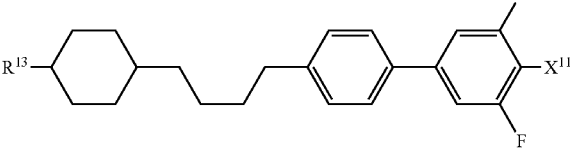
(6-34) 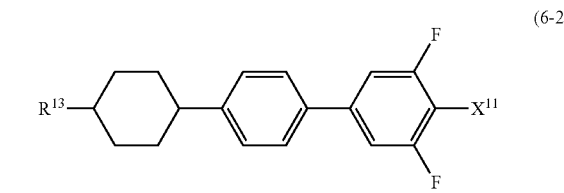

(6-35) 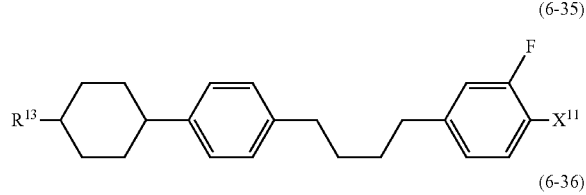
(6-36) 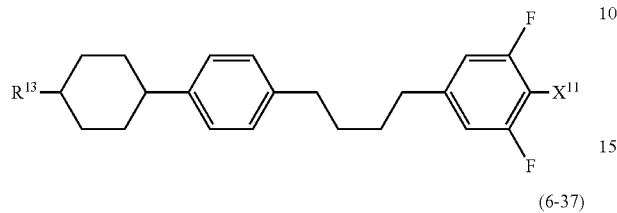
(6-37) 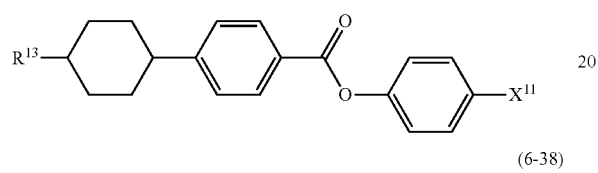
(6-38) 
(6-39) 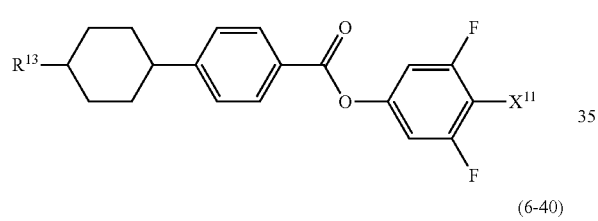
(6-40) 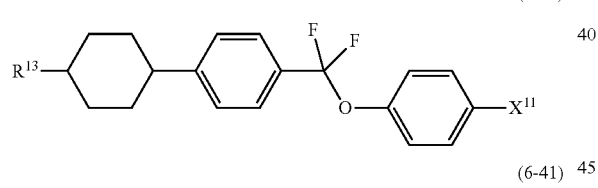
(6-41) 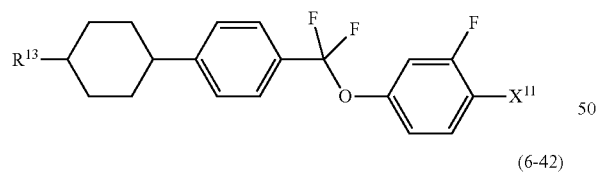
(6-42) 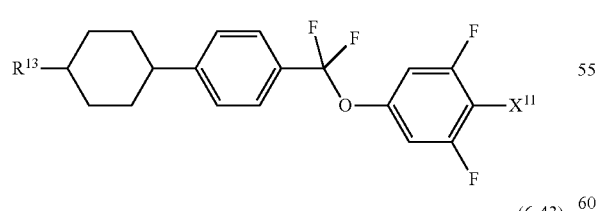
(6-43) 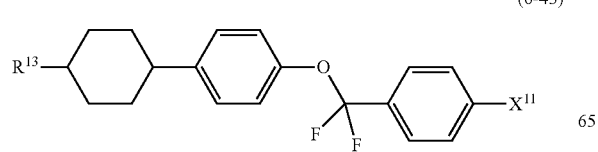
(6-44) 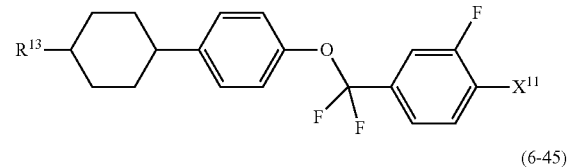
(6-45) 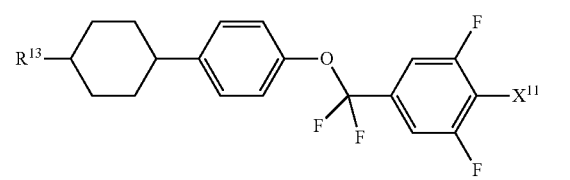
(6-46) 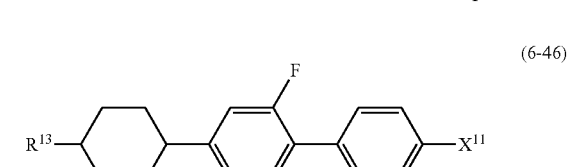
(6-47) 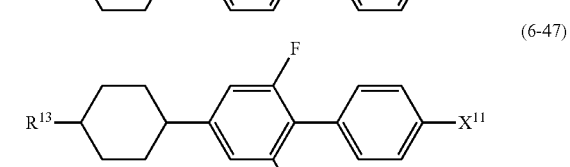
(6-48) 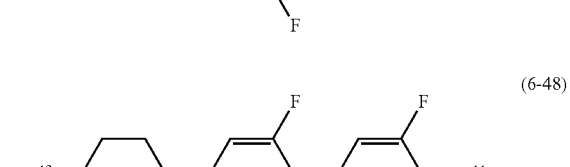
(6-49) 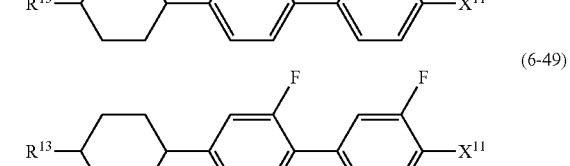
(6-50) 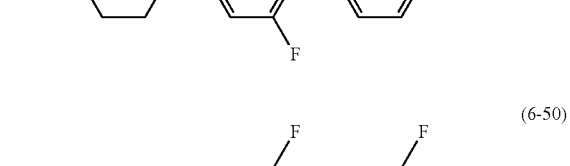
(6-51) 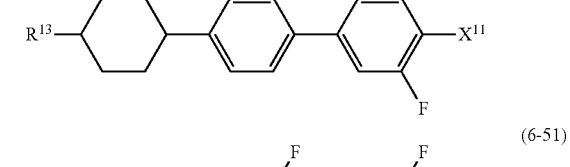
(6-52) 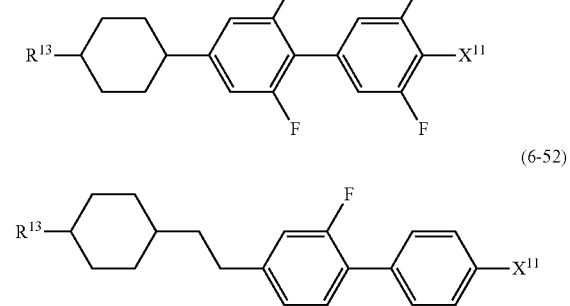

(6-53) 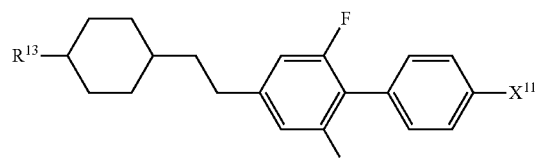
(6-54) 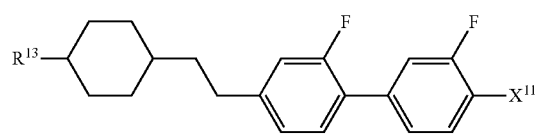
(6-55) 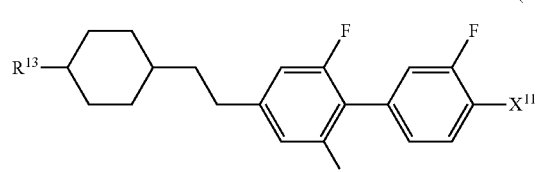
(6-56) 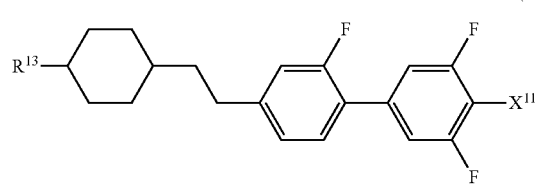
(6-57) 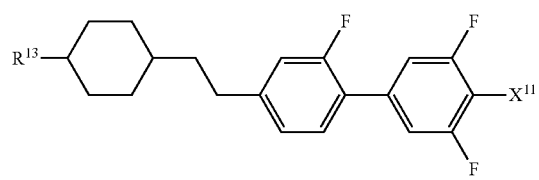
(6-58) 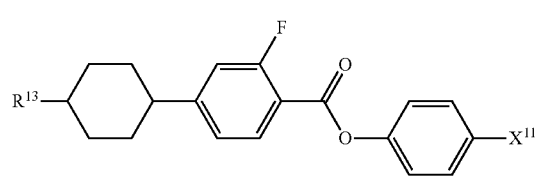
(6-59) 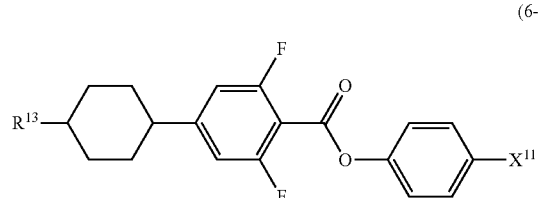
(6-60) 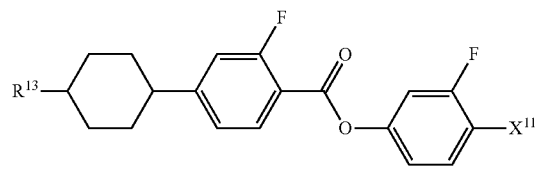
(6-61) 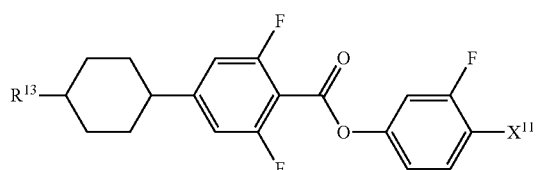
(6-62) 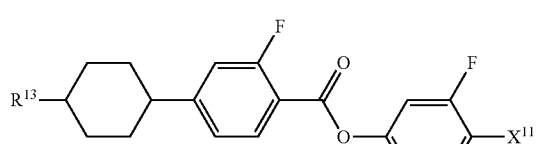
(6-63) 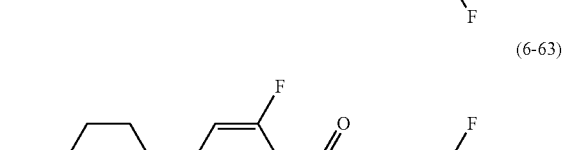
(6-64) 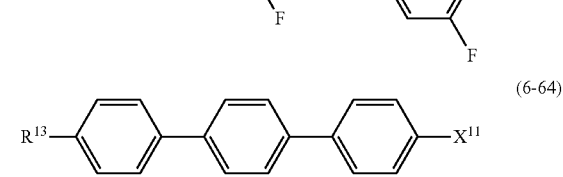
(6-65) 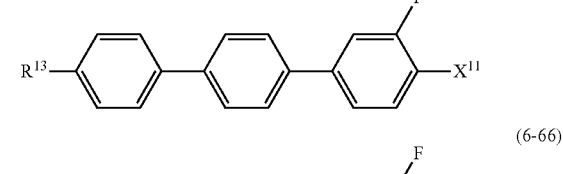
(6-66) 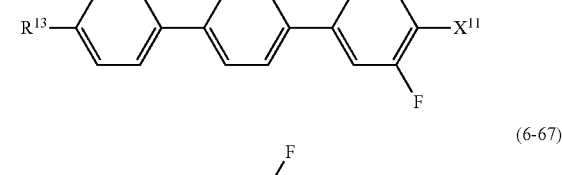
(6-67) 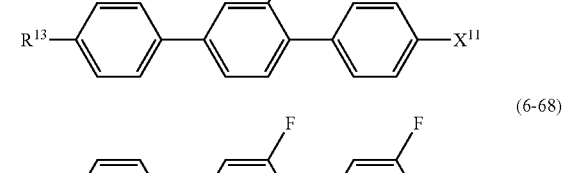
(6-68) 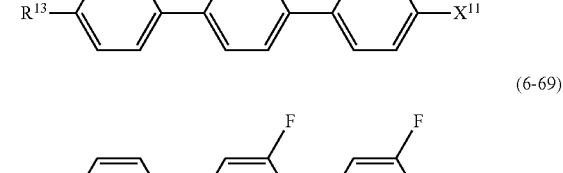
(6-69)

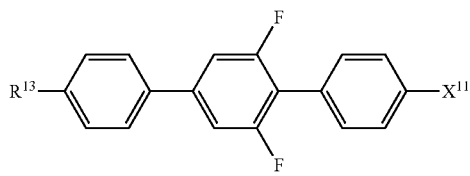 (6-70)
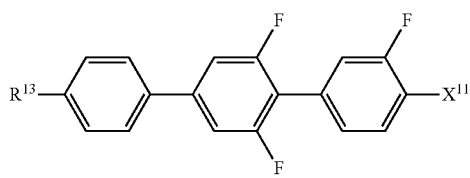 (6-71)
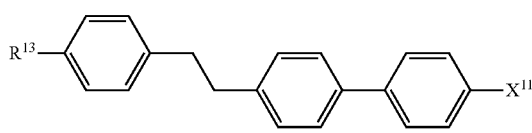 (6-72)
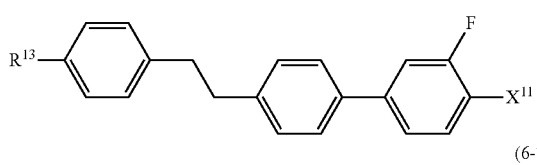 (6-73)
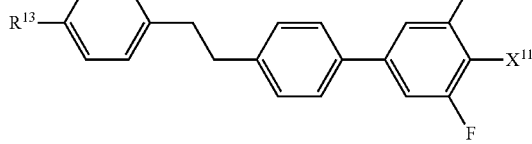 (6-74)
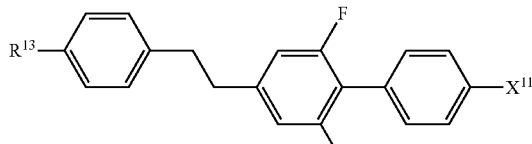 (6-75)
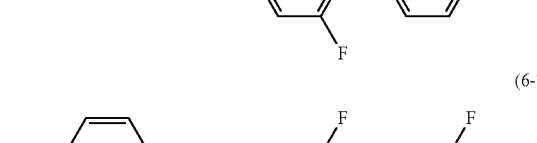 (6-76)
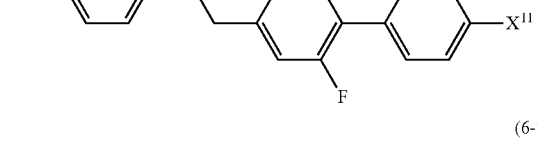 (6-77)
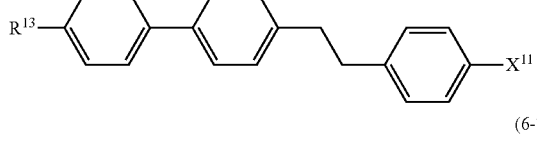 (6-78)
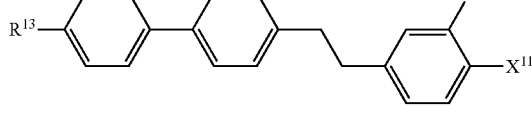
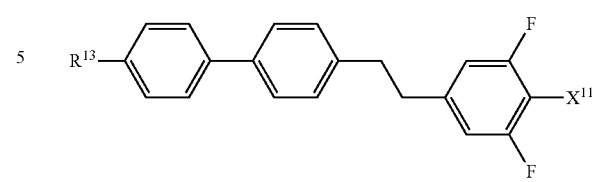 (6-79)
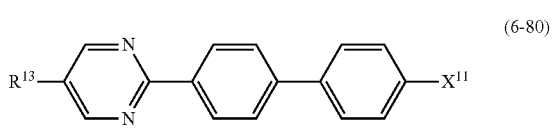 (6-80)
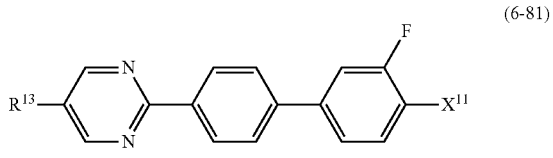 (6-81)
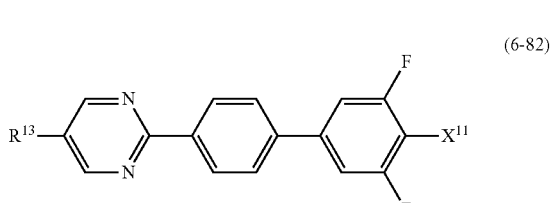 (6-82)
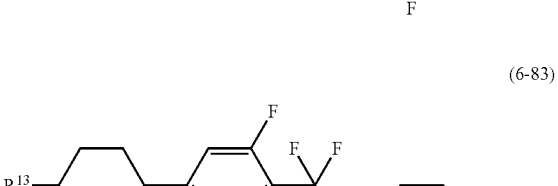 (6-83)
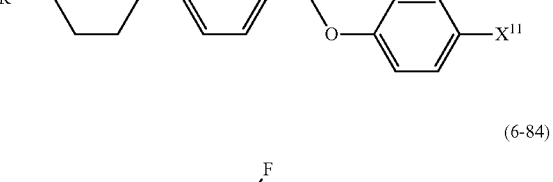 (6-84)
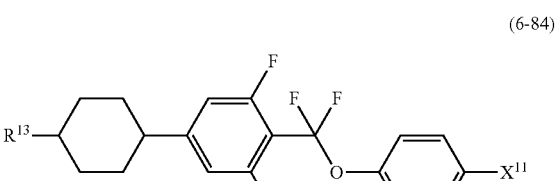 (6-85)
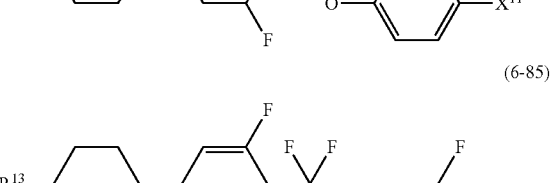
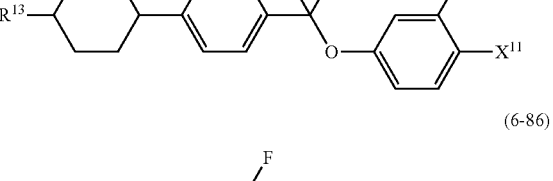 (6-86)
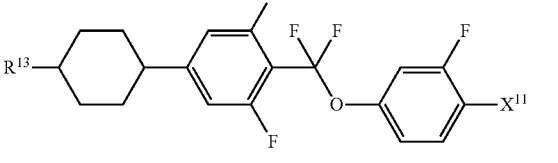

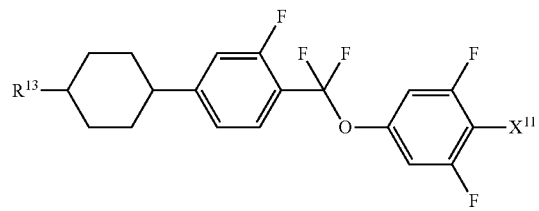
(6-87)
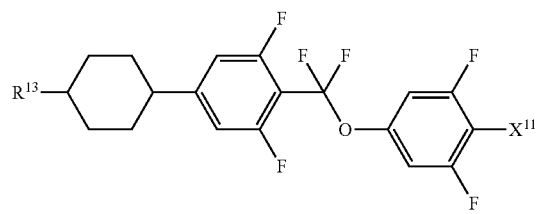
(6-88)
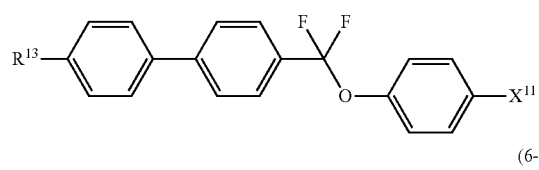
(6-89)
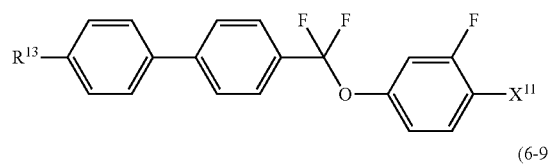
(6-90)
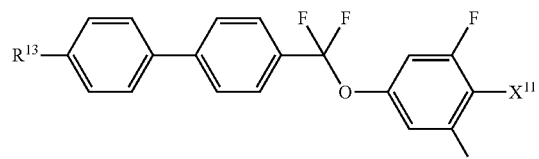
(6-91)
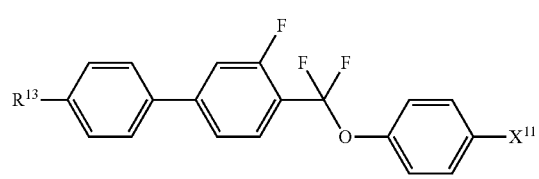
(6-92)
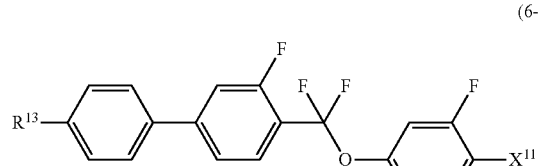
(6-93)
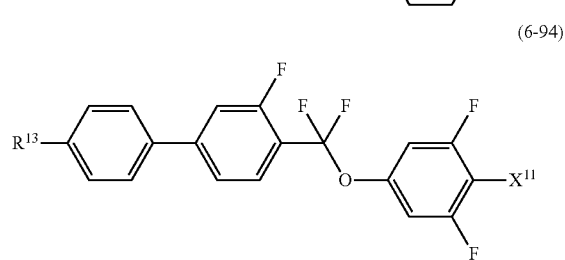
(6-94)
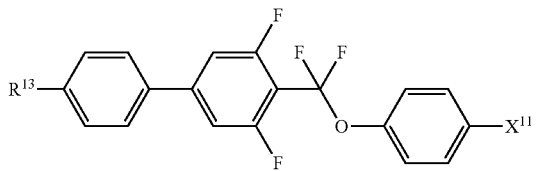
(6-95)
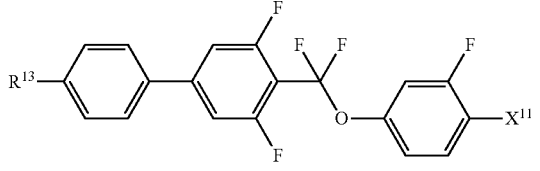
(6-96)
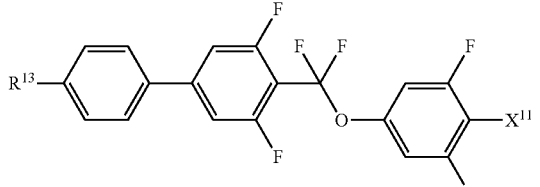
(6-97)
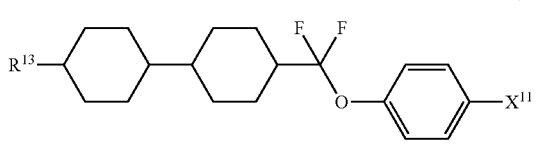
(6-98)
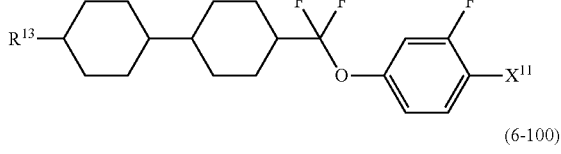
(6-99)
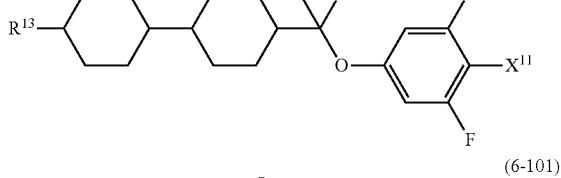
(6-100)
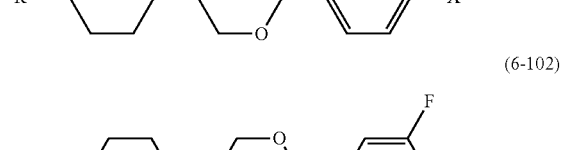
(6-101)
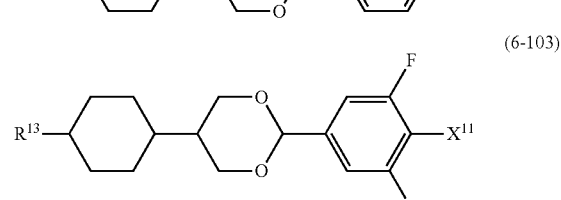
(6-102)
(6-103)

(6-104)
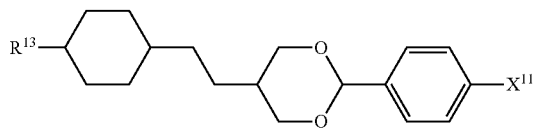
(6-105)
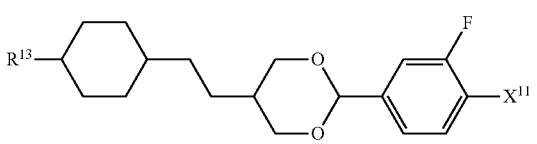
(6-106)
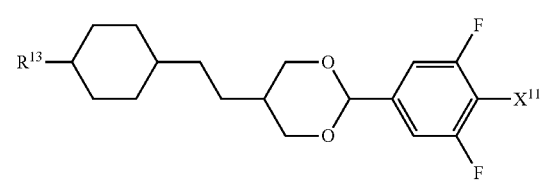
(6-107)
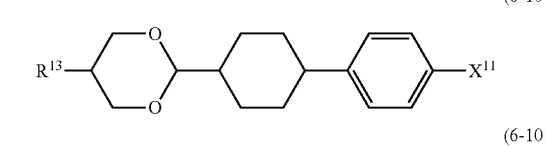
(6-108)
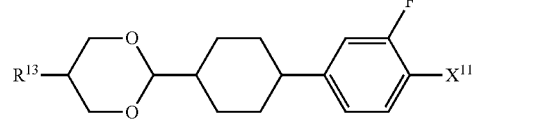
(6-109)
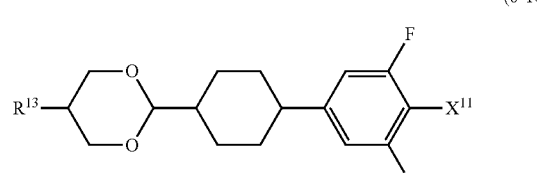
(6-110)
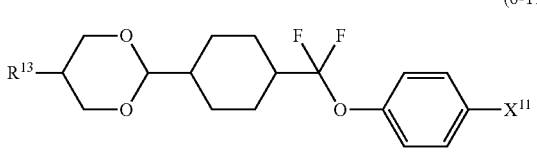
(6-111)
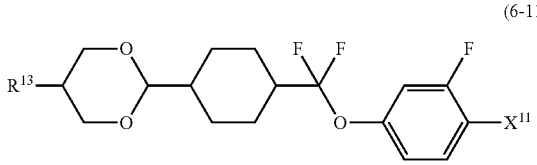
(6-112)
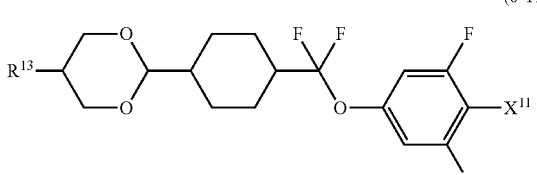
(6-113)
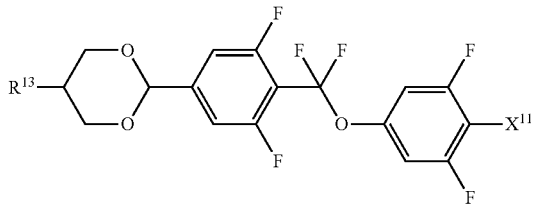
(7-1)
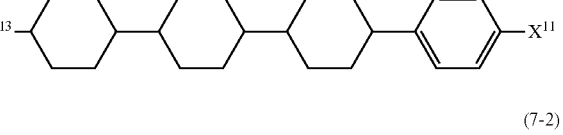
(7-2)
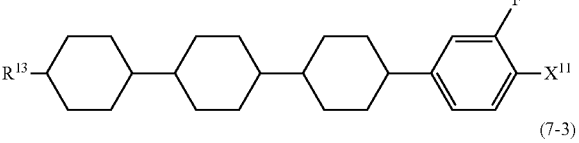
(7-3)
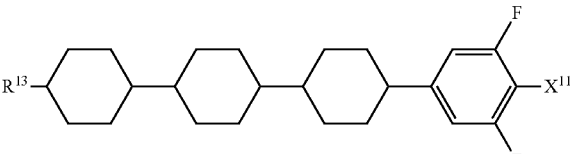
(7-4)
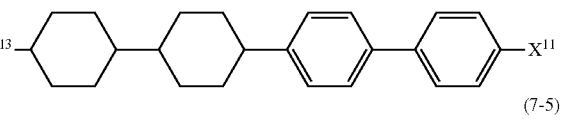
(7-5)
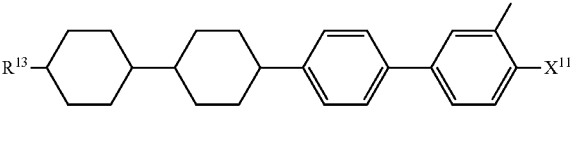
(7-6)
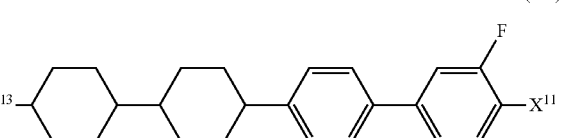
(7-7)
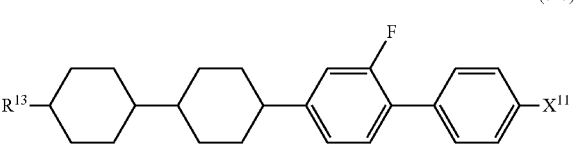
(7-8)
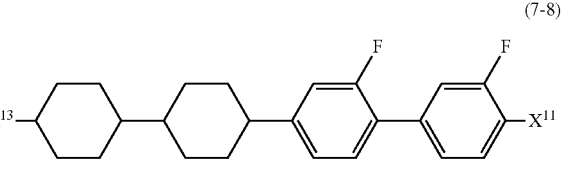

(7-9) 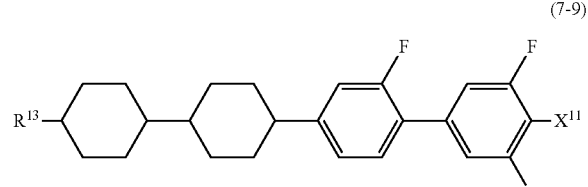
(7-10) 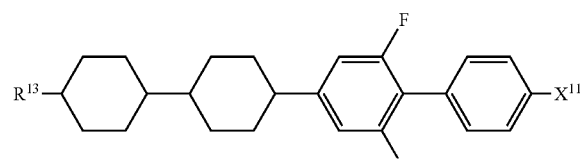
(7-11) 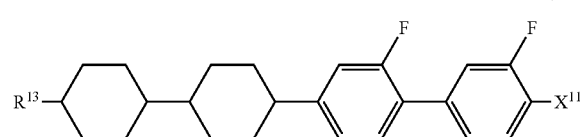
(7-12) 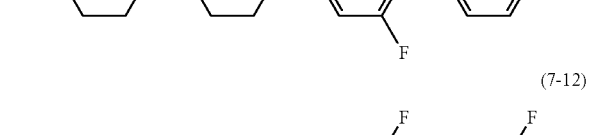
(7-13) 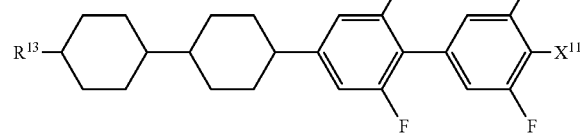
(7-14) 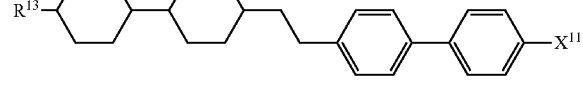
(7-15) 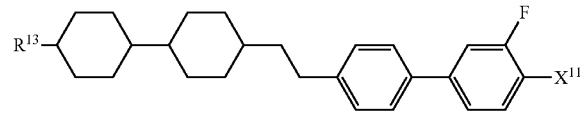
(7-16) 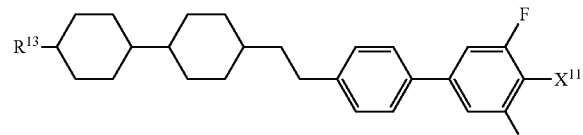
(7-17) 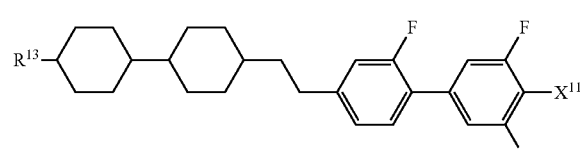
(7-18) 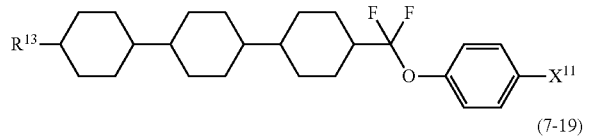
(7-19) 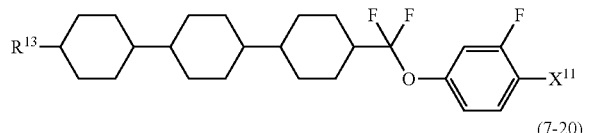
(7-20) 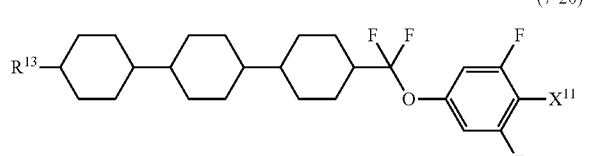
(7-21) 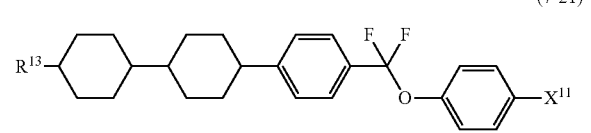
(7-22) 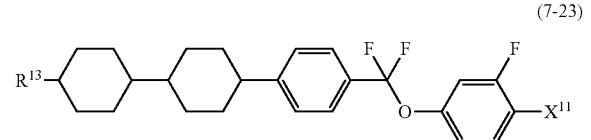
(7-23) 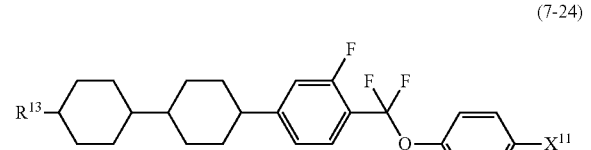
(7-24) 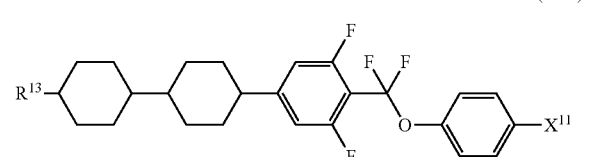
(7-25) 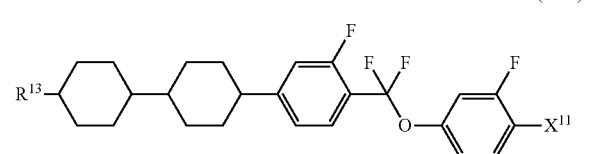
(7-26) 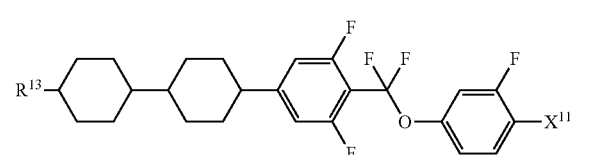
(7-27) 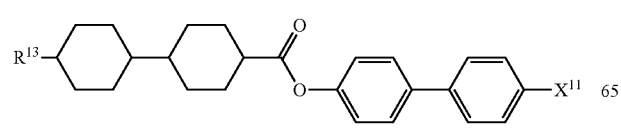

(7-28)
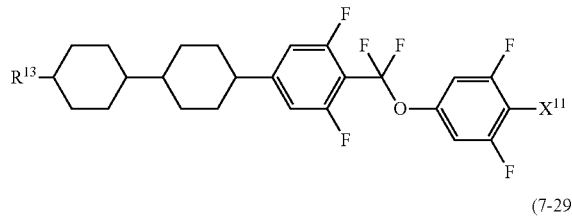
(7-29)
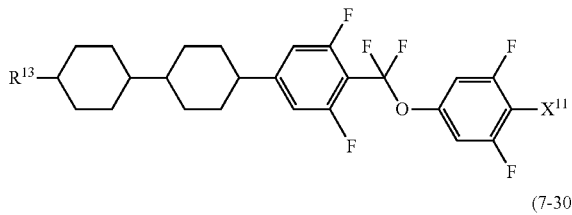
(7-30)
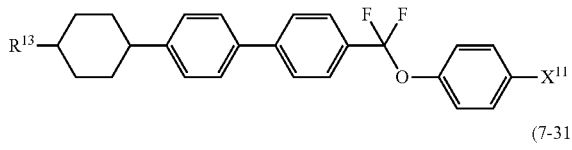
(7-31)
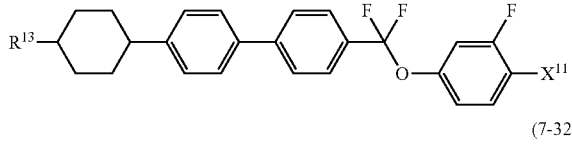
(7-32)
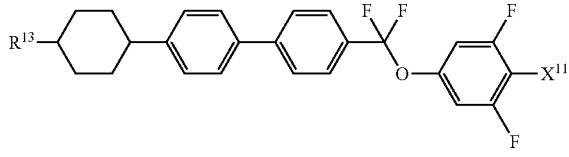
(7-33)
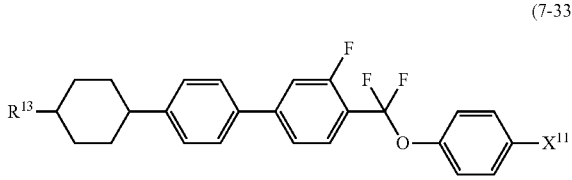
(7-34)

(7-35)
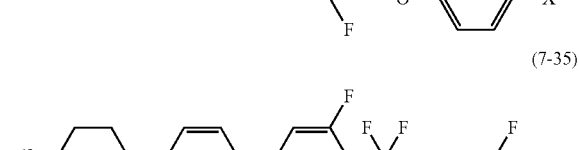
(7-36)
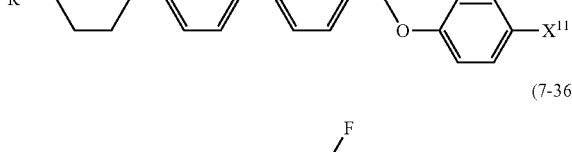
(7-37)
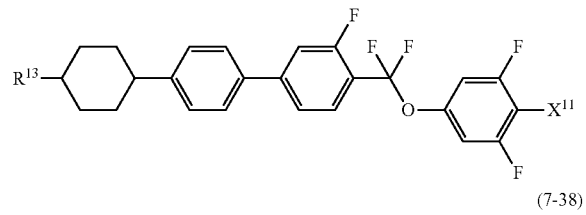
(7-38)
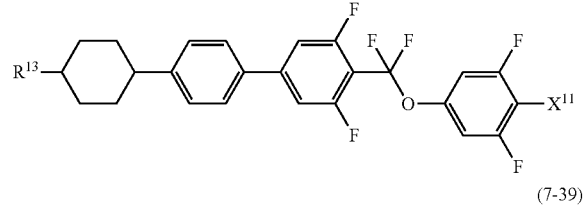
(7-39)
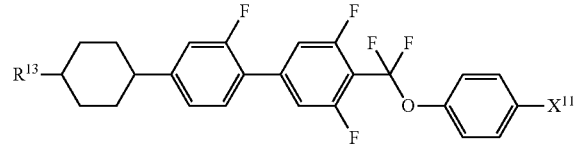
(7-40)
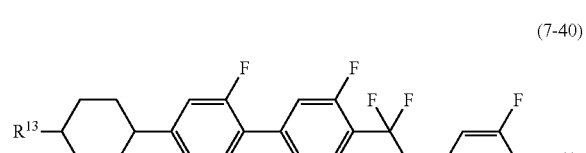
(7-41)
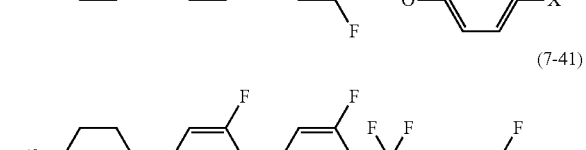
(7-42)
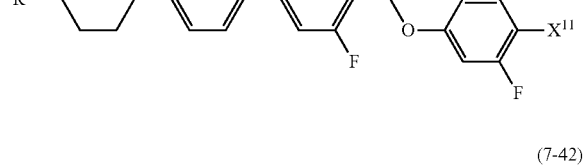
(7-43)
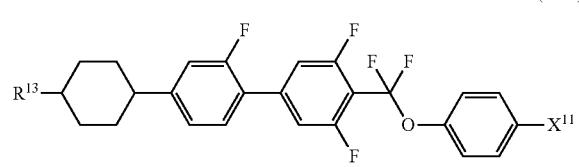
(7-44)
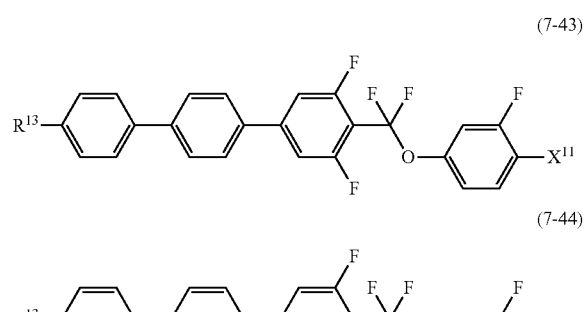

(7-45)
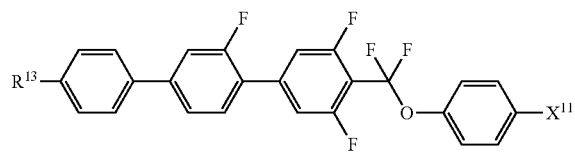

(7-46)
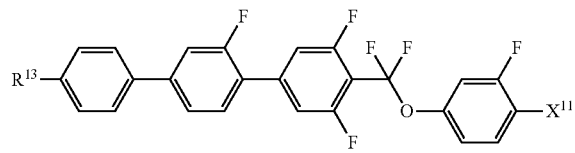

(7-47)
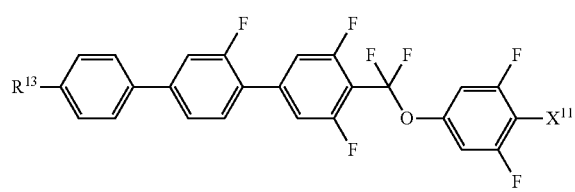

(7-48)
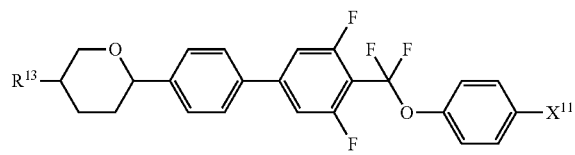

(7-49)
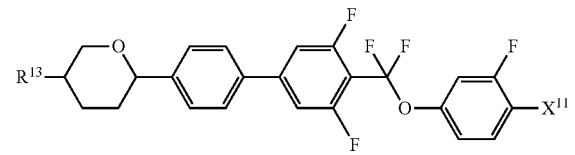

(7-50)
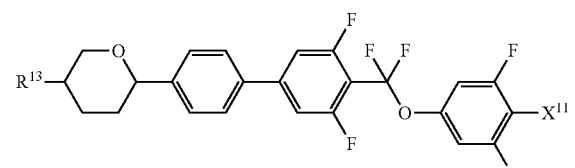

(7-51)
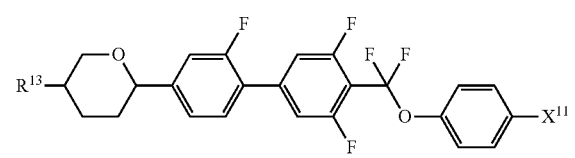

(7-52)
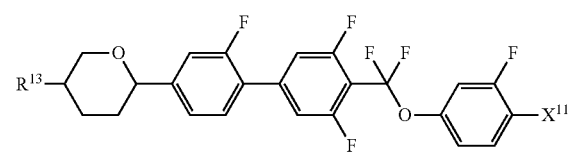

(7-53)
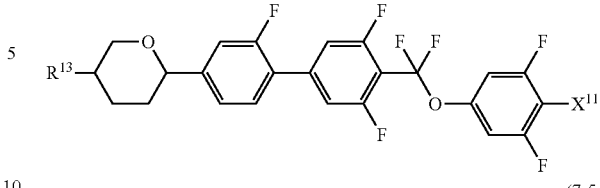

(7-54)
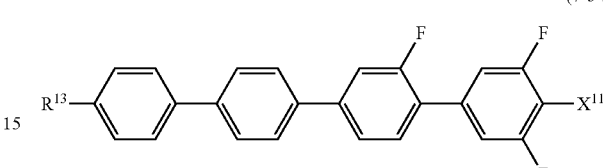

(7-55)
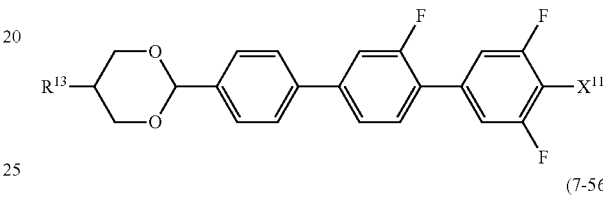

(7-56)
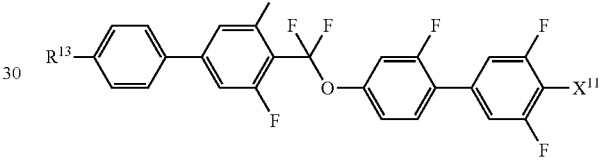

(7-57)
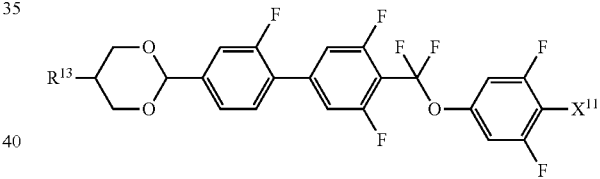

Component C has positive dielectric anisotropy and superb stability to heat, light or the like, and therefore is used when a composition for the mode such as PS-IPS, PS-FFS and PSA-OCB is prepared. A content of component C is suitably in the range from approximately 1% by weight to approximately 99% by weight, preferably in the range from approximately 10% by weight to approximately 97% by weight, and further preferably in the range from approximately 40% by weight to approximately 95% by weight, based on the weight of liquid crystal composition. When component C is added to a composition having negative dielectric anisotropy, a content of component C is preferably in the range of approximately 30% by weight or less based on the weight of liquid crystal composition. Addition of component C allows adjustment of the elastic constant of the composition and adjustment of a voltage-transmittance curve of the device.

Component D is compound (8) in which a right-terminal group is —C≡N or —C≡C—C≡N. Specific preferred examples of component D include compounds (8-1) to (8-64). In the compounds of component D, $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{12}$ is —C≡N or —C≡C—C≡N.
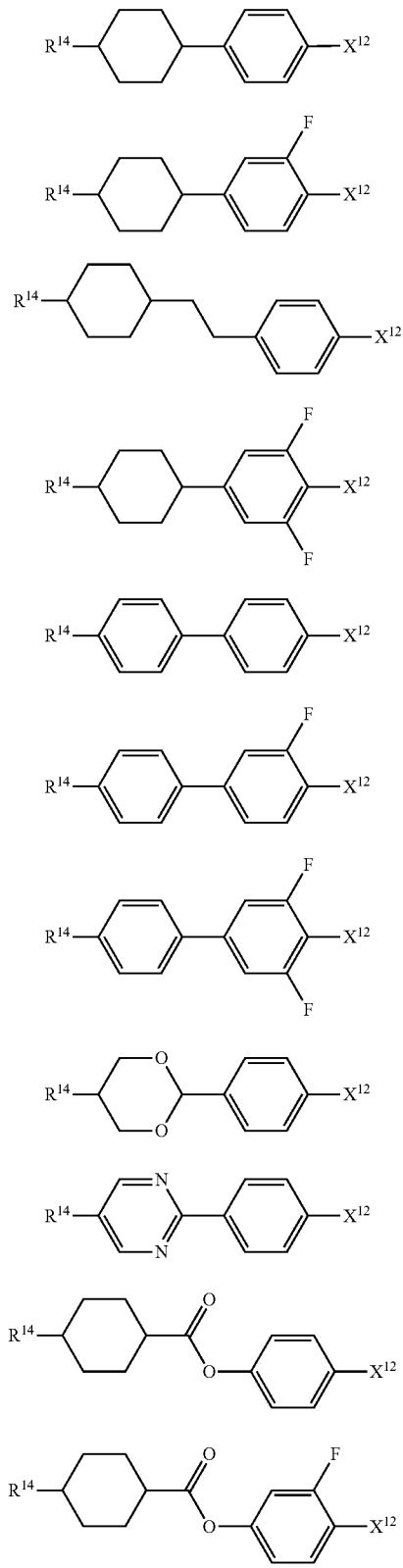
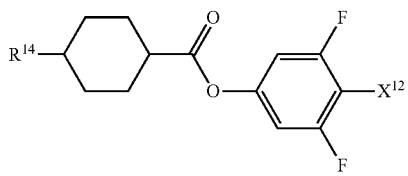
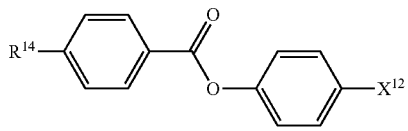
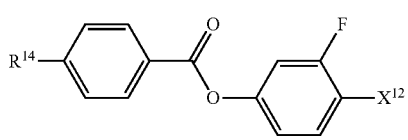
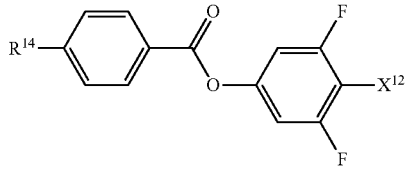
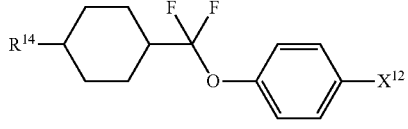
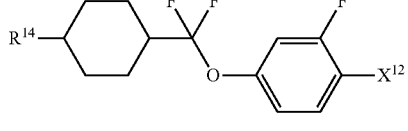
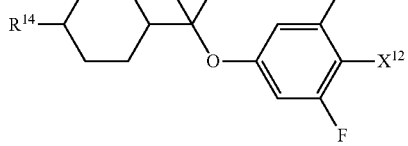
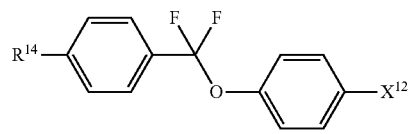
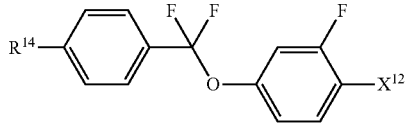
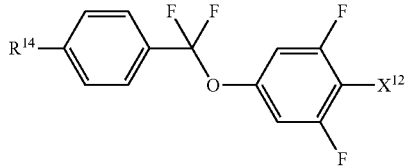

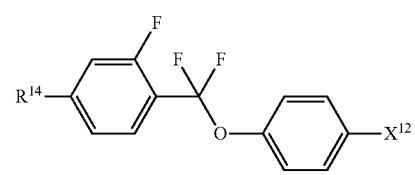 (8-22)
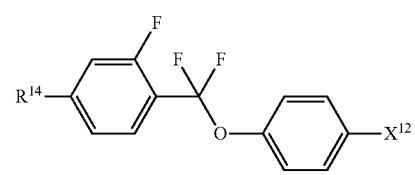 (8-23)
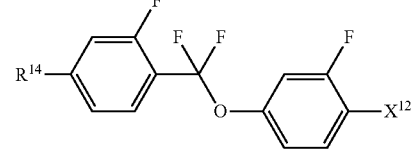 (8-24)
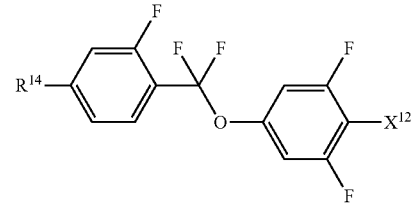 (8-25)
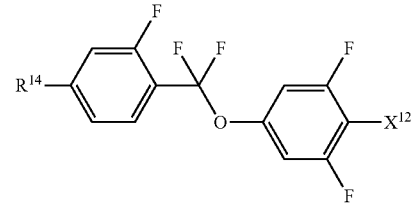 (8-26)
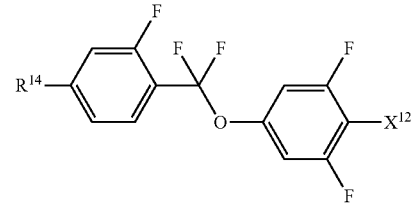 (8-27)
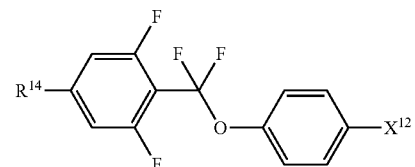 (8-28)
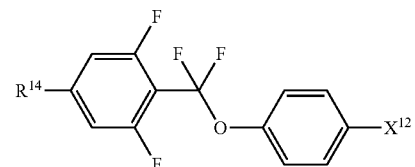 (8-29)
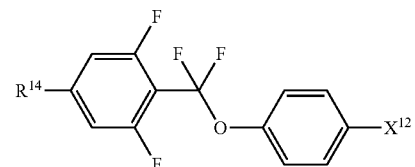 (8-30)
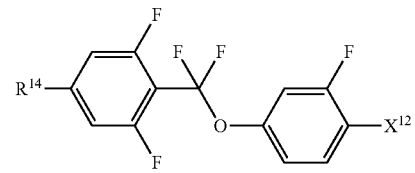 (8-31)
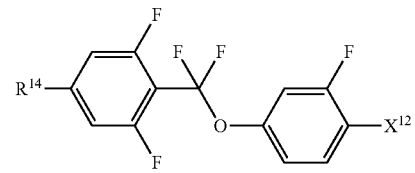 (8-32)
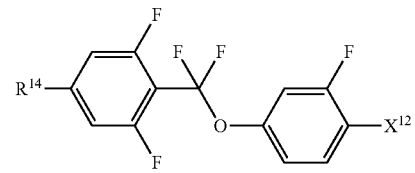 (8-33)
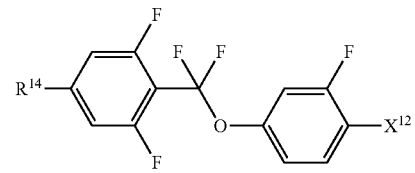 (8-34)
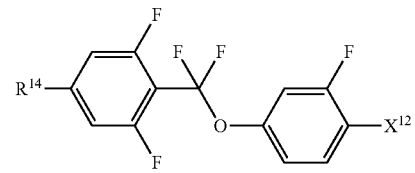 (8-35)
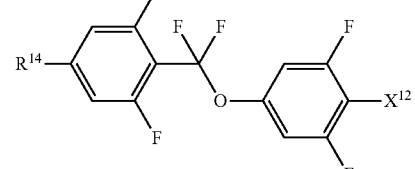 (8-36)
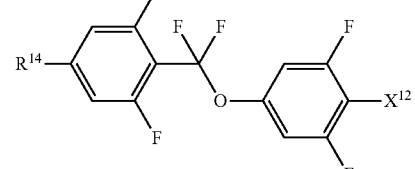 (8-37)
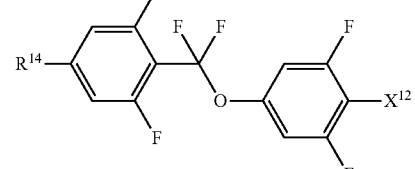 (8-38)
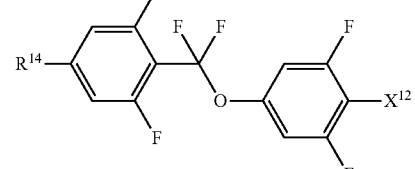 (8-39)
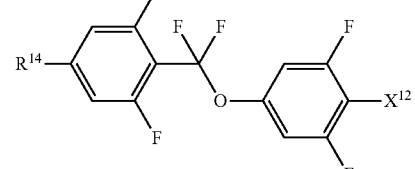 (8-40)

-continued
(8-41)
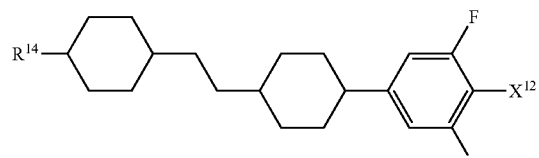
(8-42)
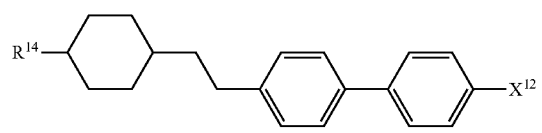
(8-43)
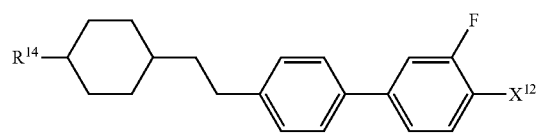
(8-44)
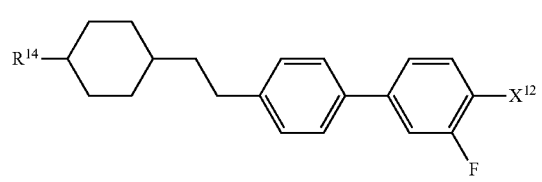
(8-45)
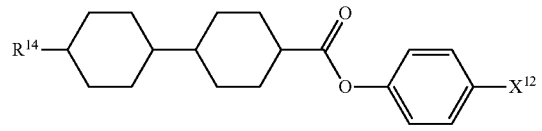
(8-46)
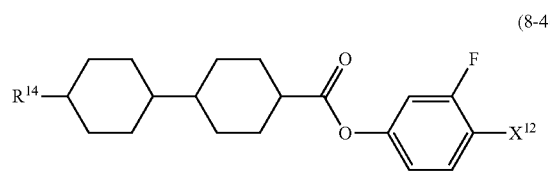
(8-47)
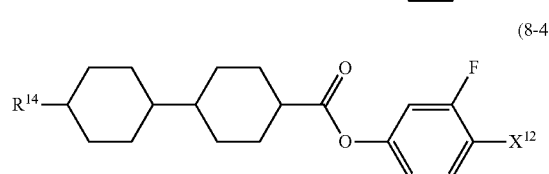
(8-48)
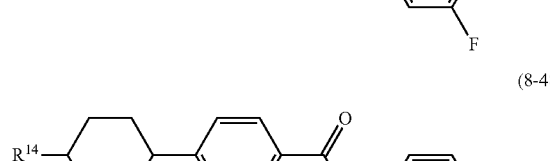
(8-49)
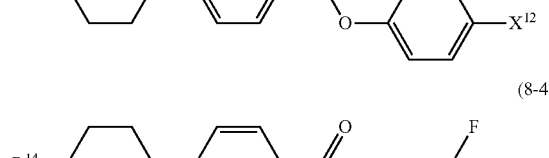
-continued
(8-50)
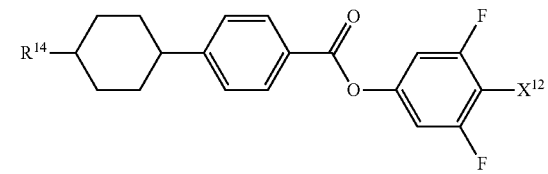
(8-51)
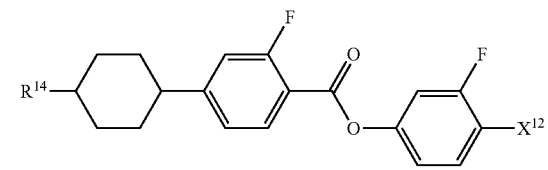
(8-52)
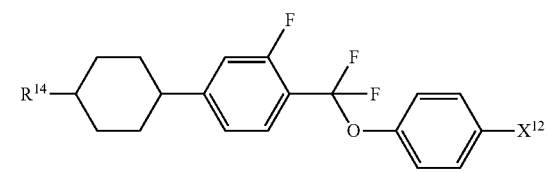
(8-53)
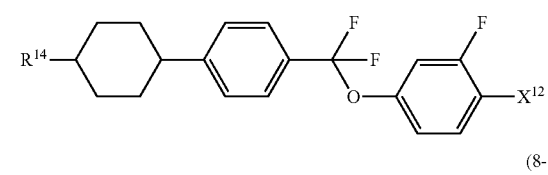
(8-54)
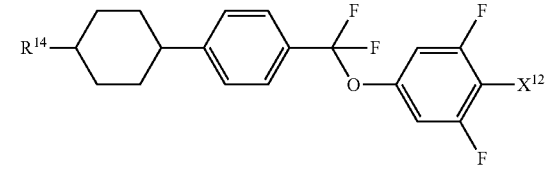
(8-55)
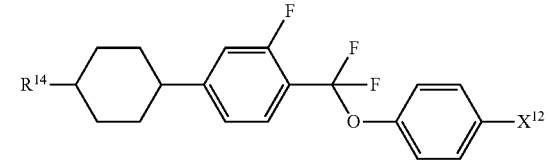
(8-56)
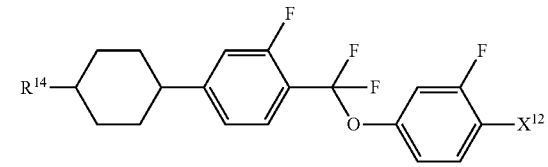
(8-57)
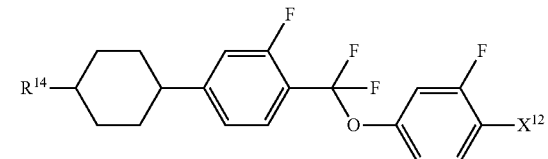

-continued

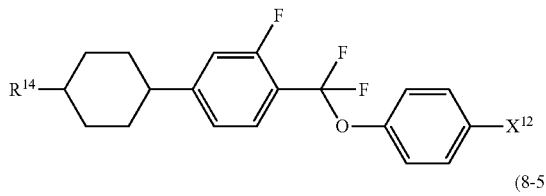
(8-58)

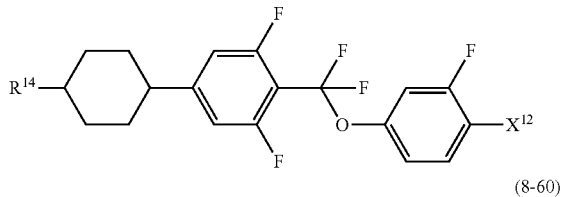
(8-59)

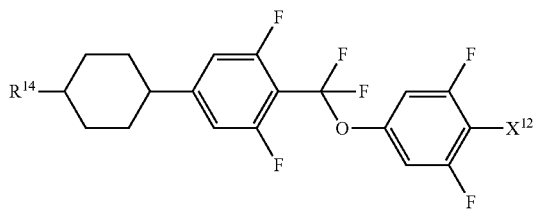
(8-60)

(8-61)

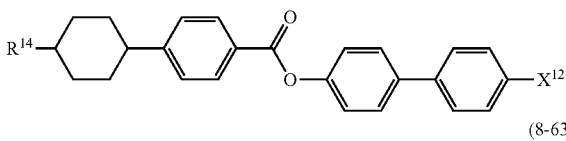
(8-62)

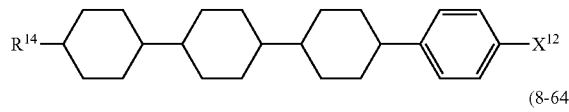
(8-63)

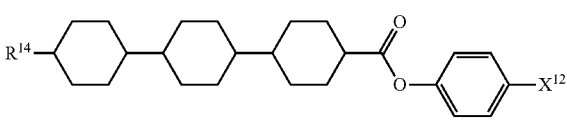
(8-64)

Component D has positive dielectric anisotropy and a large value thereof, and therefore is mainly used when a composition for the mode such as PS-TN is prepared. The dielectric anisotropy of the composition can be increased by adding component D. Component D is effective in extending the temperature range of the liquid crystal phase, adjusting the viscosity or adjusting the optical anisotropy. Component D is also useful for adjusting the voltage-transmittance curve of the device.

When a composition for the mode such as PS-TN or the like is prepared, a content of component D is suitably in the range from approximately 1% by weight to approximately 99% by weight, preferably in the range from approximately 10% by weight to approximately 97% by weight, and further preferably in the range from approximately 40% by weight to approximately 95% by weight, based on the weight of the liquid crystal composition. When component D is added to the composition having negative dielectric anisotropy, a content of component D is preferably in the range of approximately 30% by weight or less based on the weight of the liquid crystal composition. Addition of component D allows adjustment of the elastic constant of the composition and adjustment of the voltage-transmittance curve of the device.

Component E includes compounds (9) to (15). The compounds have a benzene ring in which hydrogen in lateral positions are replaced by two of halogen, such as 2,3-difluoro-1,4-phenylene. Preferred examples of component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds of component E, $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, at least one of hydrogen may be replaced by fluorine; and $R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine.

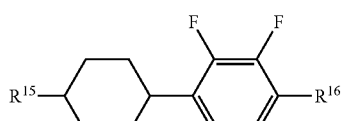
(9-1)

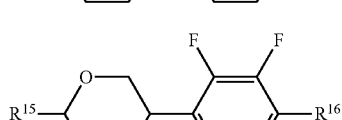
(9-2)

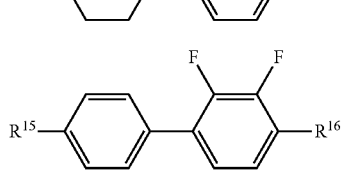
(9-3)

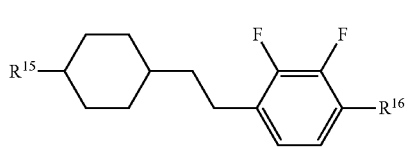
(9-4)

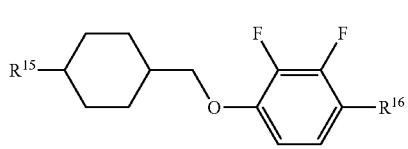
(9-5)

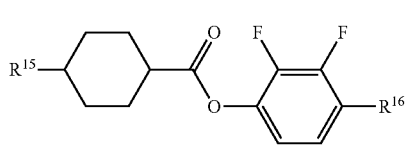
(9-6)

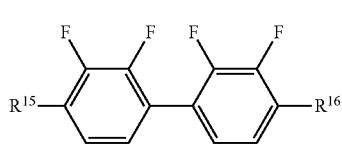
(9-7)

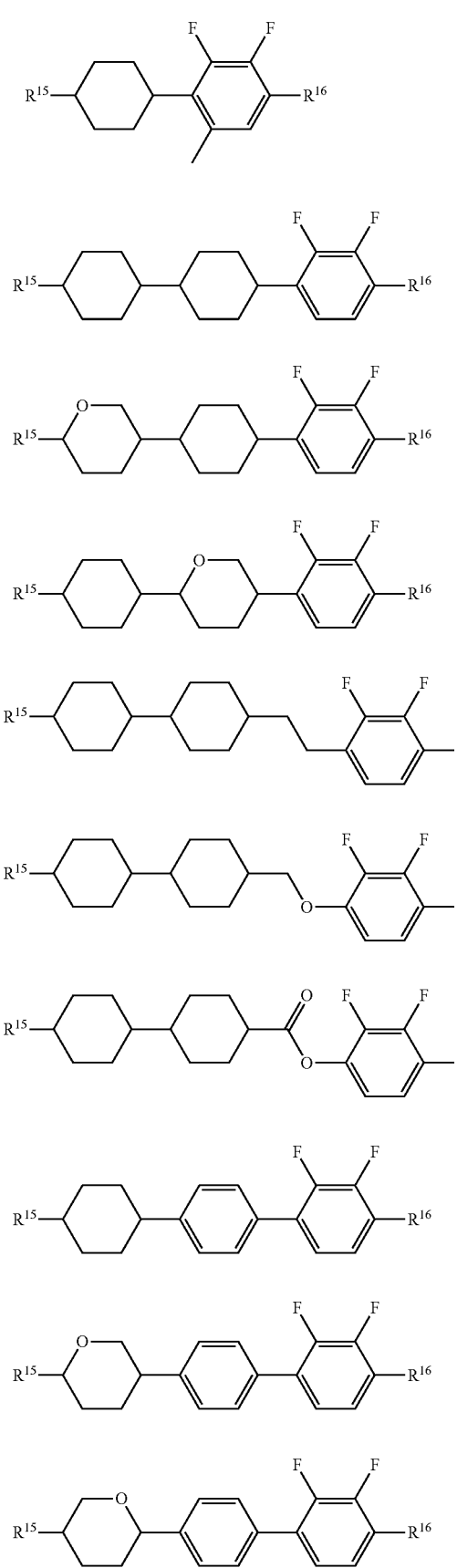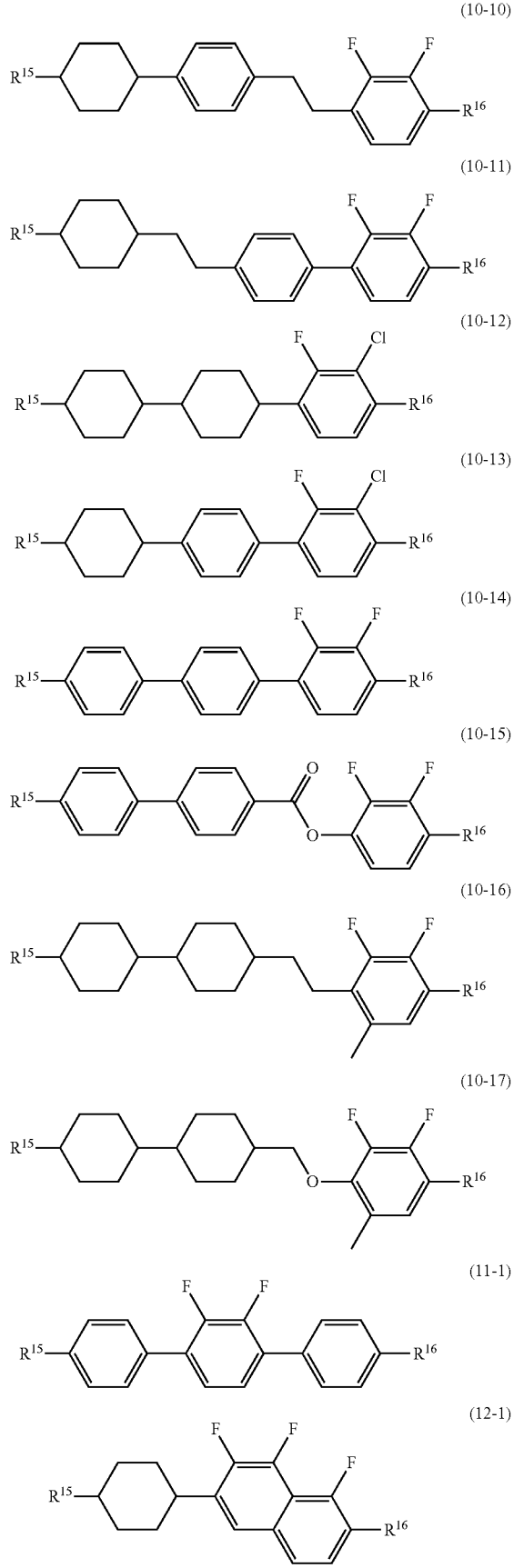

(12-2)
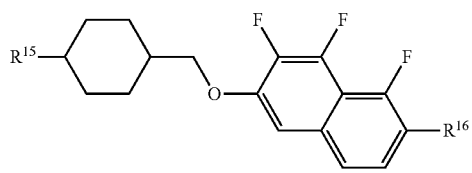
(12-3)
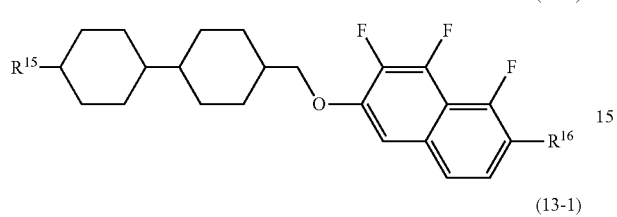
(13-1)
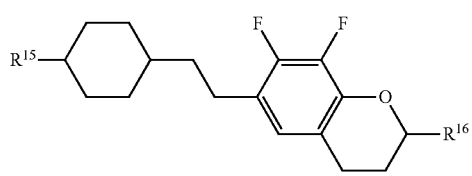
(13-2)
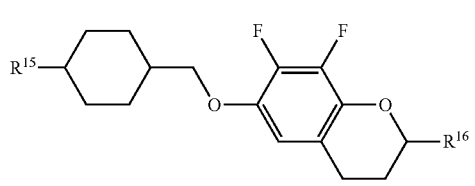
(13-3)
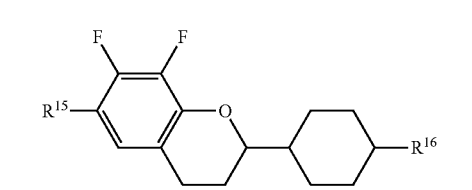
(13-4)

(13-5)
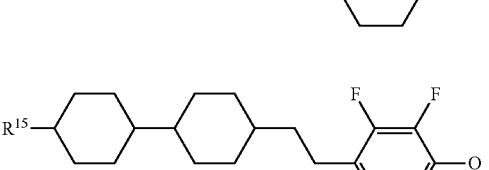
(13-6)
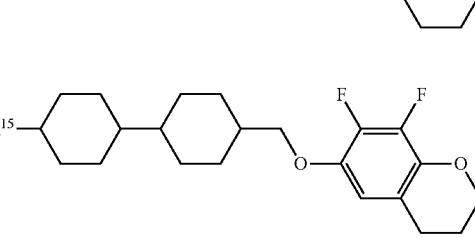
(13-7)
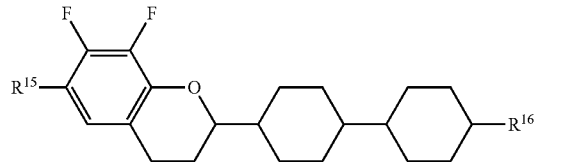
(13-8)
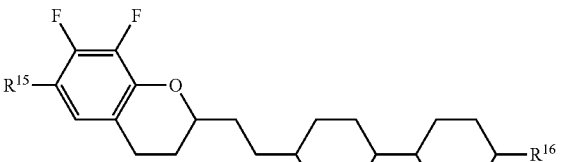
(13-9)
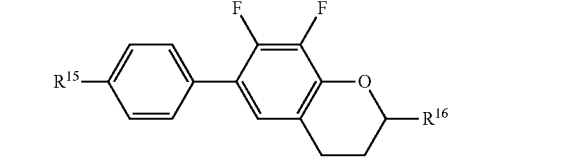
(13-10)
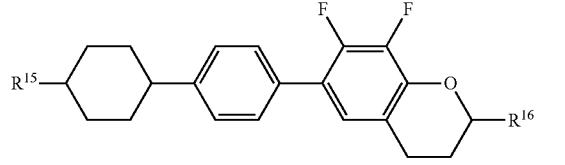
(13-11)
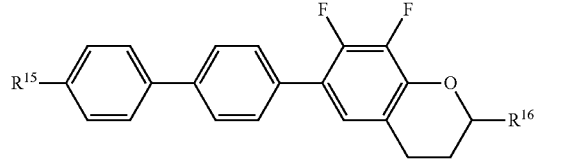
(14-1)
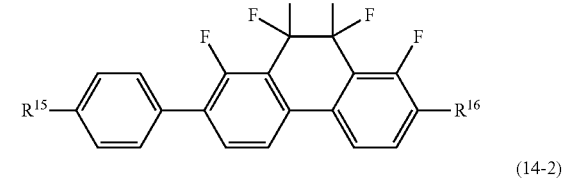
(14-2)
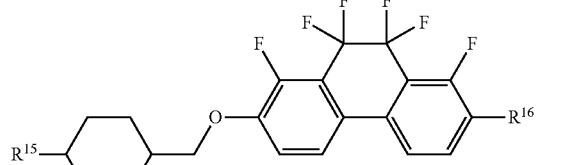
(14-3)
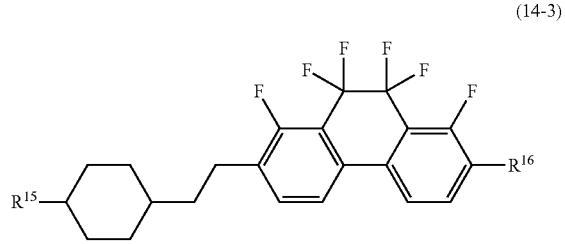

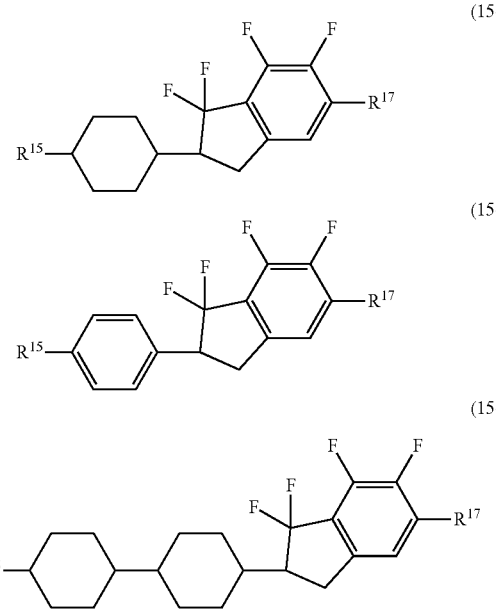

Component E is a compound having negative dielectric anisotropy. Component E is used when a composition for the mode such as PS-IPS, PS-FFS and PSA-VA is prepared. As a content of component E is increased, the dielectric anisotropy of the composition is negatively increased, but the viscosity increases. Thus, the content is preferably as small as possible, as long as a required value of threshold voltage of the device is satisfied. Accordingly, in consideration of approximately 5 in an absolute value of dielectric anisotropy, the content is preferably in the range of approximately 40% by weight or more in order to allow sufficient voltage driving.

Among types of compound E, compound (9) is a bicyclic compound, and therefore effective mainly in adjusting the viscosity, the optical anisotropy or the dielectric anisotropy. Compounds (10) and (11) are a tricyclic compound, and therefore effective in increasing the maximum temperature, the optical anisotropy or the dielectric anisotropy. Compounds (12) to (15) are effective in increasing the dielectric anisotropy.

When a composition for the mode such as PS-IPS, PS-FFS and PSA-VA is prepared, the content of component E is preferably in the range of approximately 40% by weight or more, and further preferably in the range from approximately 50% by weight to approximately 95% by weight, based on the weight of the liquid crystal composition. When component E is added to a composition having positive dielectric anisotropy, the content of component E is preferably in the range of approximately 30% by weight or less based on the weight of the liquid crystal composition. Addition of component E allows adjustment of the elastic constant of the composition and adjustment of the voltage-transmittance curve of the device.

The polymerizable composition is prepared according to a method for dissolving required components at temperature higher than room temperature, or the like. According to an application, an additive may be added to the composition. Examples of the additives include an optically active compound, an antioxidant, an ultraviolet light absorber, a light stabilizer, a heat stabilizer, an antifoaming agent, a polymerization initiator and a polymerization inhibitor. Such additives are well known to those skilled in the art, and are described in literature.

The optically active compound is effective in inducing helical structure to provide liquid crystal molecules with a required twist angle, thereby preventing inverted twist. Addition of the optically active compound allows adjustment of a helical pitch. Two or more optically active compounds may be added thereto for the purpose of adjusting temperature dependence of the helical pitch. Preferred examples of the optically active compound include compounds (Op-1) to (Op-18) as described below. In compound (Op-18), ring J is 1,4-cyclohexylene or 1,4-phenylene, and $R^{28}$ is alkyl having 1 to 10 carbons.

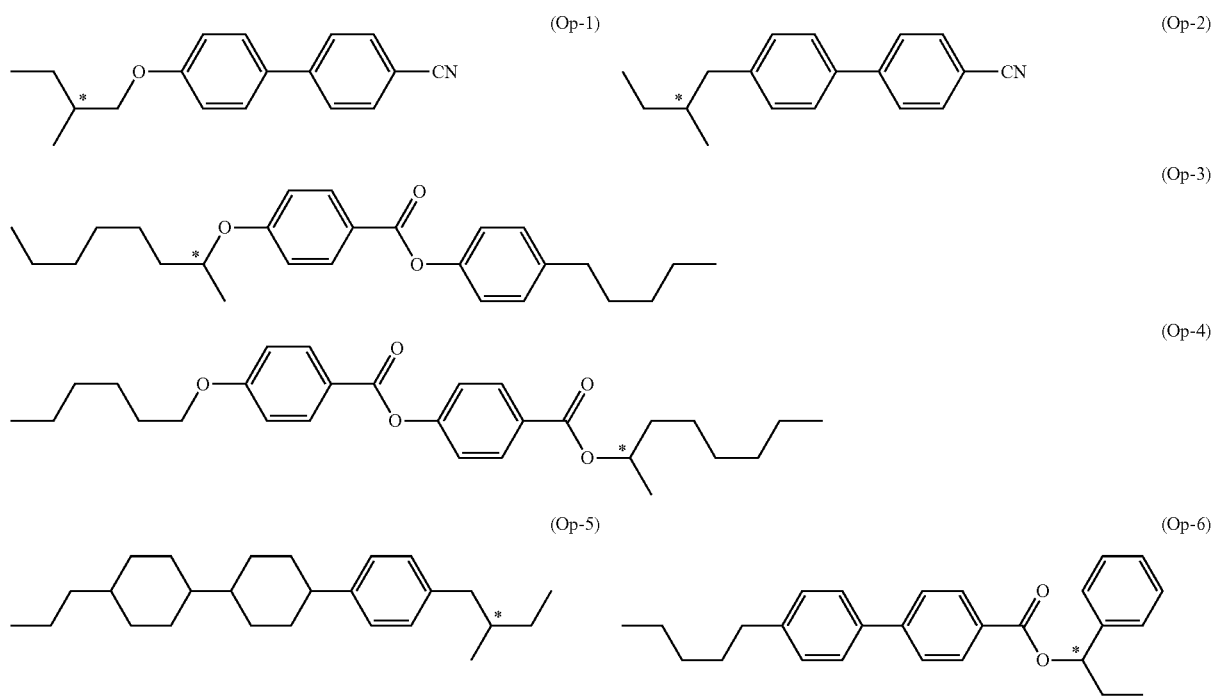

-continued
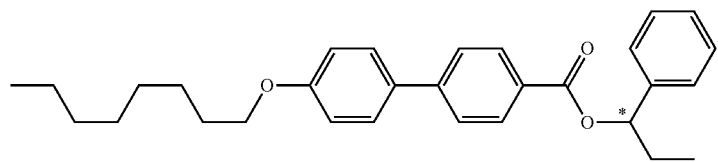
(Op-7)
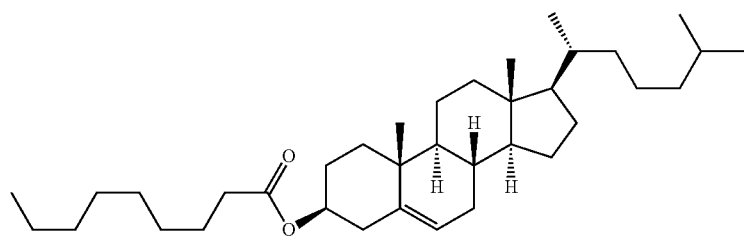
(Op-8)
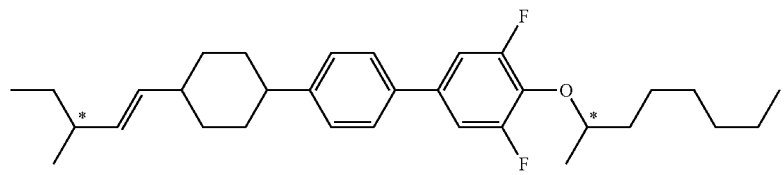
(Op-9)
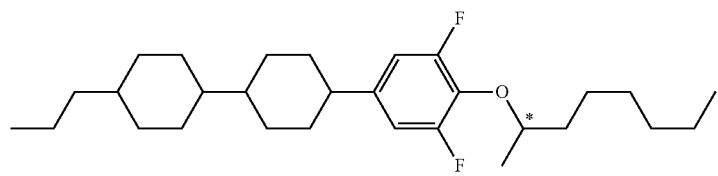
(Op-10)
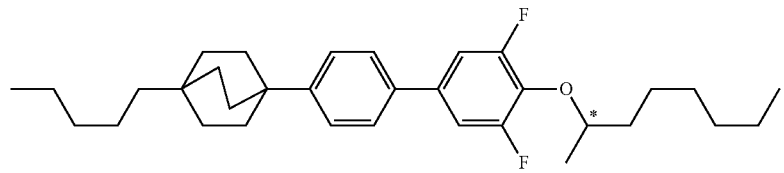
(Op-11)
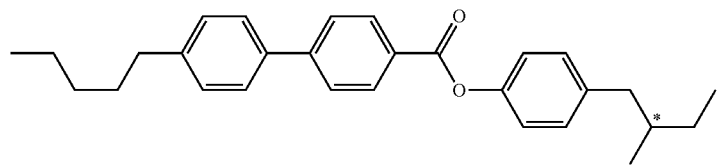
(Op-12)
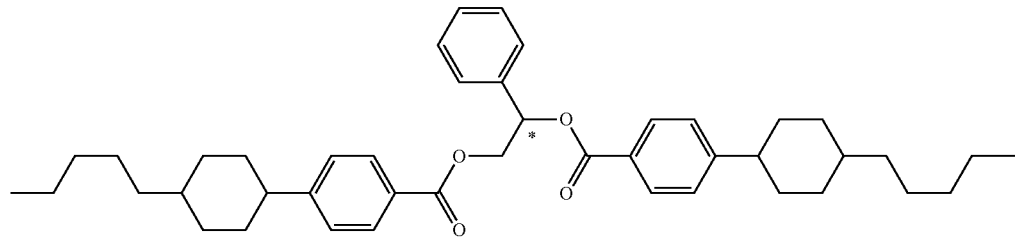
(Op-13)
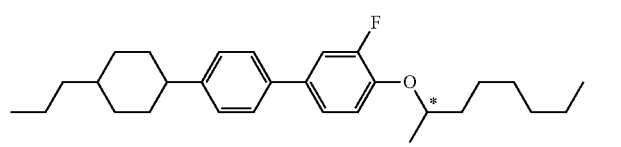
(Op-14)
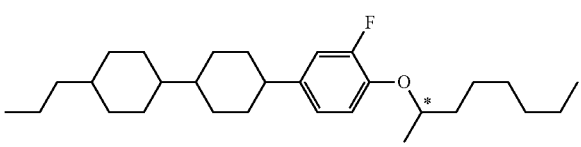
(Op-15)

-continued (Op-16)
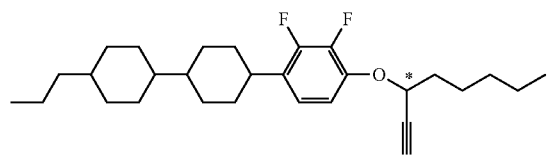

(Op-17)
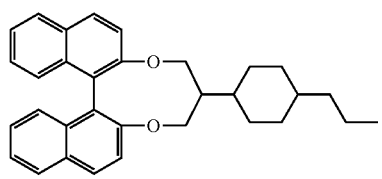

(Op-18)
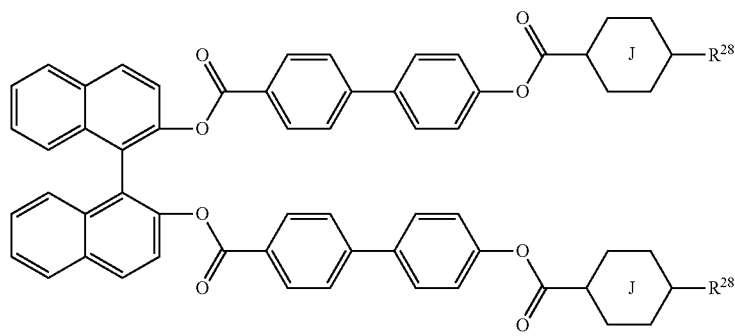

The antioxidant is effective in order to maintain a large voltage holding ratio. Preferred examples of the antioxidant include compounds (AO-1) and (AO-2) described below; IRGANOX 415, IRGANOX 565, IRGANOX 1010, IRGANOX 1035, IRGANOX 3114 and IRGANOX 1098 (trade names: BASF SE). The ultraviolet light absorber is effective in preventing a decrease in the maximum temperature. Preferred examples of the ultraviolet light absorber include a benzophenone derivative, a benzoate derivative and a triazole derivative. Specific examples include compounds (AO-3) and (AO-4) described below; TINUVIN329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

Alight stabilizer such as an amine having steric hindrance is also preferred in order to maintain a large voltage holding ratio. Preferred examples of the light stabilizer include compounds (AO-5) and (AO-6) described below; TINUVIN 144, TINUVIN 765 and TINUVIN 770DF (trade name: BASF SE). The heat stabilizer is also effective in order to maintain a large voltage holding ratio, and preferred examples include IRGAFOS 168 (trade name: BASF SE). The antifoaming agent is effective in order to prevent foam formation. Preferred examples of the antifoaming agent include dimethyl silicone oil and methylphenyl silicone oil.

(AO-1)
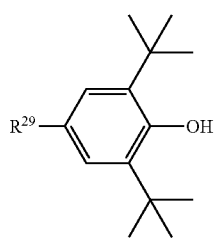

(AO-2)
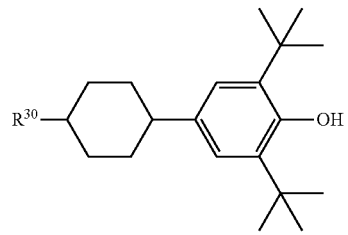

(AO-3)
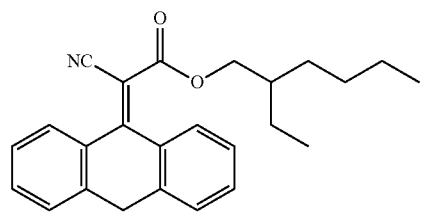

(AO-4)
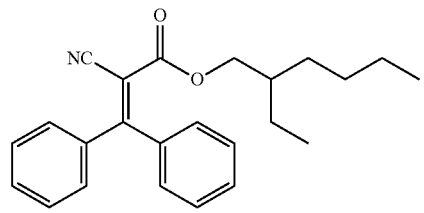

(AO-5)
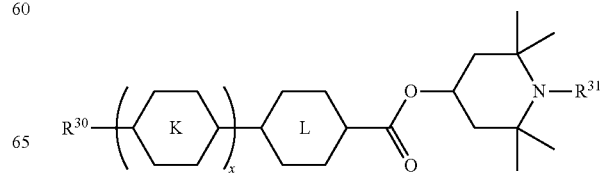

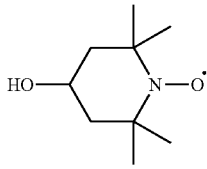
(AO-6)

In compound (AO-1), $R^{29}$ is alkyl having 1 to 20 carbons, alkoxy having 1 to 20 carbons, —COOR$^{32}$ or —CH$_2$CH$_2$COOR$^{32}$, and $R^{32}$ is alkyl having 1 to 20 carbons, in which, in compounds (AO-2) and (AO-5), $R^{30}$ is alkyl having 1 to 20 carbons. In compound (AO-5), $R^{31}$ is hydrogen, methyl or O. (oxygen radical), ring K and ring L are 1,4-cyclohexylene or 1,4-phenylene, and x is 0, 1 or 2.

4. Liquid Crystal Composite

Compound (1) has high polymerization reactivity, a high conversion ratio and high solubility in the liquid crystal composition. A liquid crystal composite is formed by polymerizing the polymerizable composition containing compound (1) and the liquid crystal composition. Compound (1) forms a polymer in the liquid crystal composition by polymerization of the composition. The polymer is effective in generating pretilt in the liquid crystal molecules. The polymerization is preferably performed at temperature at which the polymerizable composition exhibits the liquid crystal phase. The polymerization is generated by heat, light or the like. A preferred reaction includes photopolymerization. The photopolymerization is preferably performed at 100° C. or lower in order to prevent simultaneous occurrence of thermopolymerization. The polymerization may be allowed in a state in which an electric field or a magnetic field is applied.

The polymerization reactivity and the conversion ratio of compound (1) can be adjusted. Compound (1) is suitable for radical polymerization. Compound (1) can be rapidly polymerized by adding the polymerization initiator. An amount of remaining compound (1) can be reduced by optimizing reaction temperature. Examples of a photoradical polymerization initiator include TPO, 1173 and 4265 from Darocur series, and 184, 369, 500, 651, 784, 819, 907, 1300, 1700, 1800, 1850 and 2959 from Irgacure series in BASF SE.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyldimethylketal, 2-methyl-1-[4-(methylthio)phenyl]-2-morpholinopropane-1-one, a 2,4-diethylxanthone-methyl p-dimethylaminobenzoate mixture and a benzophenone-methyltriethanolamine mixture.

The polymerization can be performed by adding the photoradical polymerization initiator to the polymerizable composition, and then irradiating the resulting mixture with ultraviolet light in a state in which the electric field is applied. However, an unreacted polymerization initiator or a decomposition product of the polymerization initiator might cause poor display to the device, such as image persistence. In order to avoid such a poor display, photopolymerization may be performed without adding the polymerization initiator. A preferred wavelength of irradiating light is in the range from approximately 150 nanometers to approximately 500 nanometers. A further preferred wavelength is in the range from approximately 250 nm to approximately 450 nm, and a most preferred wavelength is in the range from approximately 300 nm to approximately 400 nm.

When the polymerizable compound is stored, the polymerization inhibitor may be added thereto in order to inhibit the polymerization. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

5. Liquid Crystal Display Device

An effect of the polymer in the liquid crystal display device is interpreted as described below. The polymerizable composition is a mixture of the liquid crystal compound, the polymerizable compound and so forth. Application of the electric field to the composition causes alignment of the liquid crystal molecules in the direction of the electric field. Molecules of the polymerizable compound are also aligned in an identical direction according to the alignment. The composition is irradiated with ultraviolet light in the above state, and the polymerizable compound is polymerized. As a result, a network of polymer is formed in the polymerizable composition. The liquid crystal molecules are stabilized in a state of being aligned in the direction of the electric field by the effect of the network. Even when the electric field is removed, the effect is maintained. Accordingly, a response time of the device is to be shortened.

The polymerizable composition is preferably polymerized in the display device. One example is as described below. A display device having two glass substrates provided with transparent electrodes and an alignment film is arranged. A polymerizable composition containing compound (1), the liquid crystal composition, the additive and so forth as a component is prepared. The composition is injected into the display device. The display device is irradiated with ultraviolet light while applying the electric field to polymerize compound (1). The liquid crystal composite is formed by the polymerization. The liquid crystal display device including the liquid crystal composite can be easily produced by the method. Rubbing treatment to the alignment film may be omitted in the method. In addition, a method for stabilizing the liquid crystal molecules in a state without the electric field may be employed.

When an amount of adding the polymerizable compound is in the range from approximately 0.1% by weight to approximately 2% by weight based on the weight of the liquid crystal composition, a liquid crystal display device having the PSA mode can be prepared. The device having the PSA mode can be operated in a driving mode such as an active matrix (AM) or a passive matrix (PM). Such a device can be applied to any of a reflective type, a transmissive type and a transflective type. A device having a polymer dispersed mode can also be prepared by increasing an amount of adding the polymerizable compound.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail byway of Examples. The invention is not restricted by the Examples.

The invention includes a mixture of a composition in Example 2 and a composition in Example 3. The invention also includes a mixture in which at least two compositions in Examples were mixed. Physical properties of the compound, the composition and a device were measured by methods described below.

1. Example of Compound (1)

Compound (1) was prepared according to a method shown in Example 1, or the like. The compound prepared was identified by a method such as an NMR analysis. Physical properties of the compound were measured according to methods described below.
NMR Analysis For measurement, DRX-500 made by Bruker BioSpin Corporation was used. In measurement of $^1$H-NMR, a sample was dissolved into a deuterated solvent such as $CDCl_3$, and measurement was carried out under conditions of room temperature, 500 MHz and 16 times of accumulation. Tetramethylsilane was used as an internal standard. In measurement of $^{19}$F-NMR, $CFCl_3$ was used as an internal standard, and measurement was carried out under conditions of 24 times of accumulation. In the explanation of a nuclear magnetic resonance spectrum, s, d, t, q, quin, sex, m and br stand for a singlet, a doublet, a triplet, a quartet, a quintet, a sextet, a multiplet and being broad, respectively.
HPLC Analysis For measurement, Prominence (LC-20AD; SPD-20A) made by Shimadzu Corporation was used. As a column, YMC-Pack ODS-A made by YMC Co., Ltd. (length 150 mm, bore 4.6 mm, particle diameter 5 μm) was used. As an eluate, acetonitrile and water were appropriately mixed and used. As a detector, a UV detector, an RI detector, a CORONA detector or the like was appropriately used. When the UV detector was used, a detection wavelength was adjusted to 254 nanometers. A sample was dissolved in acetonitrile and prepared to be a solution of 0.1% by weight, and 1 microliter of the solution obtained was introduced into a sample injector. As a recorder, C-R7Aplus made by Shimadzu Corporation was used.
Ultraviolet-Visible Spectrophotometry For measurement, PharmaSpec UV-1700 made by Shimadzu Corporation was used. A detection wavelength was adjusted in the range from 190 nanometers to 700 nanometers. A sample was dissolved in acetonitrile, and prepared to be a solution of 0.01 millimole per liter, and measurement was carried out by putting the solution in a quartz cell (optical path length 1 cm).
Sample for Measurement When measuring phase structure and transition temperature (a clearing point, a melting point, a polymerization starting temperature, or the like), a compound itself was used as a sample. When measuring physical properties such as a maximum temperature of a nematic phase, viscosity, optical anisotropy and dielectric anisotropy, a mixture of a compound and a base liquid crystal was used as a sample.
Measuring Methods Physical properties were measured according to the methods described below. Most of the measuring methods are applied as described in the Standard of the Japan Electronics and Information Technology Industries Association (JEITA ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified. A state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high-sensitivity differential scanning calorimeter, X-DSC7000, made by SII NanoTechnology Inc. were used. A sample was heated and then cooled at a rate of 3° C. per minute. A starting point of an endothermic peak or an exothermic peak caused by a phase change of the sample was determined by extrapolation, and thus a transition temperature was determined. A melting point and a polymerization starting temperature of the compound were also measured using the apparatus. Temperature at which a compound undergoes transition from a solid to a liquid crystal phase such as a smectic phase and a nematic phase may be occasionally abbreviated as "minimum temperature of the liquid crystal phase." Temperature at which a compound undergoes transition from the liquid crystal phase to a liquid may be occasionally abbreviated as "clearing point."

The crystal was expressed as C. When kinds of the crystals were further distinguishable, each of the crystals was expressed as $C_1$ or $C_2$. The smectic phase was expressed as S and the nematic phase as N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed, for example, as "C 50.0 N 100.0 I." The expression indicates that a transition temperature from the crystal to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature." When the sample was a mixture of compound (1) and the base liquid crystal, the maximum temperature was expressed in terms of a symbol $T_{NI}$. When the sample was a mixture of compound (1) and the compound such as component B, C and D, the maximum temperature was expressed in terms of a symbol NI.

(4) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_c$ was expressed as $T_c \leq -20°$ C. A lower limit of the temperature range of the nematic phase may be occasionally abbreviated as "minimum temperature."

(5) Viscosity (Bulk Viscosity; η; Measured at 20° C.; mPa·s)

Viscosity was measured using a cone-plate (E type) rotational viscometer made by Tokyo Keiki, Inc.

(6) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(7) Specific Resistance (ρ; Measured at 25° C.; Ωcm)

Into a vessel provided with electrodes, 1.0 mL of sample was injected. Direct current voltage (10 V) was applied to the vessel, and a direct current after 10 seconds was measured. Specific resistance was calculated from the following equation: (Specific resistance)={(voltage)×(electric capacity of a vessel)}/{(direct current)×(dielectric constant of vacuum)}.

(8) Voltage Holding Ratio (VHR-1; Measured at 25° C.; %)

A TN device used for measurement had a polyimide alignment film, and a distance (cell gap) between two glass substrates was 5 micrometers. A sample was put in the device, and then the device was sealed with an ultraviolet-curable adhesive. The device was charged by applying pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(9) Voltage Holding Ratio (VHR-2; Measured at 80° C.; %)

A voltage holding ratio was measured according to the methods described above except that the voltage holding ratio was measured at 80° C. in place of 25° C. The thus obtained results were expressed in terms of VHR-2.

Methods for measuring physical properties may be occasionally different between a sample having positive dielectric anisotropy and a sample having negative dielectric anisotropy. The measuring methods when the dielectric anisotropy is positive were described in sections (10a) to (14a). The methods when the dielectric anisotropy is negative were described in sections (10b) to (14b).

(10a) Viscosity (Rotational Viscosity; γ1; Measured at 25° C.; mPa·s)

Positive dielectric anisotropy: Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range from 16 V to 19.5 V at an increment of 0.5 V. After a period of 0.2 second with no voltage application, application was repeated under conditions of only one of rectangular waves (rectangular pulse; 0.2 second) and no application (2 seconds). A peak current and a peak time of a transient current generated by the applied voltage were measured. A value of rotational viscosity was obtained from the measured values according to calculating equation (8) on page 40 of the paper presented by M. Imai et al. A value of dielectric anisotropy necessary for the calculation was determined by using the device used for measuring the rotational viscosity according to the method as described below.

(10b) Viscosity (Rotational Viscosity; γ1; Measured at 25° C.; mPa·s)

Negative dielectric anisotropy: Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range from 39 V to 50 V at an increment of 1 V. After a period of 0.2 second with no voltage application, application was repeated under conditions of only one of rectangular waves (rectangular pulse; 0.2 second) and no application (2 seconds). A peak current and a peak time of a transient current generated by the applied voltage were measured. A value of rotational viscosity was obtained from the measured values according to calculating equation (8) on page 40 of the paper presented by M. Imai et al. As dielectric anisotropy required for the calculation, a value measured in a section of dielectric anisotropy described below was used.

(11a) Dielectric Anisotropy (Δϵ; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ϵ∥) in the major axis direction of liquid crystal molecules was measured. Sine waves (0.5 V, 1 kHz) were applied to the device, and after 2 seconds, a dielectric constant (ϵ⊥) in the minor axis direction of the liquid crystal molecules was measured. A value of dielectric anisotropy was calculated from an equation: Δϵ=ϵ∥−ϵ⊥.

(11b) Dielectric Anisotropy (Δϵ; Measured at 25° C.)

Negative dielectric anisotropy: A value of dielectric anisotropy was calculated from an equation: Δϵ=ϵ∥−ϵ⊥. A dielectric constant (ϵ∥ and ϵ⊥) was measured as described below.

(1) Measurement of dielectric constant (ϵ∥): An ethanol (20 mL) solution of octadecyl triethoxysilane (0.16 mL) was applied to a well-washed glass substrate. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ϵ∥) in the major axis direction of liquid crystal molecules was measured.

(2) Measurement of dielectric constant (ϵ⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ϵ⊥) in the minor axis direction of the liquid crystal molecules was measured.

(12a) Elastic Constant (K; Measured at 25° C.; pN)

Positive dielectric anisotropy: HP4284A LCR Meter made by Yokogawa-Hewlett-Packard Co. was used for measurement. A sample was put in a horizontal alignment device in which a distance (cell gap) between two glass substrates was 20 micrometers. An electric charge from 0 V to 20 V was applied to the device, and electrostatic capacity and applied voltage were measured. Measured values of the electrostatic capacity (C) and the applied voltage (V) were fitted to equation (2.98) and equation (2.101) on page 75 of "Liquid Crystal Device Handbook" (Ekisho Debaisu Handobukku in Japanese) (The Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. An elastic constant K is expressed using a mean value of the thus determined $K_{11}$, $K_{22}$ and $K_{33}$.

(12b) Elastic Constant ($K_{11}$ and $K_{33}$; Measured at 25° C.; pN)

Negative dielectric anisotropy: Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(13a) Threshold Voltage (Vth; Measured at 25° C.; V)

Positive dielectric anisotropy: An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. Voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(13b) Threshold Voltage (Vth; Measured at 25° C.; V)

Negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. Voltage (60 Hz, rectangular waves) applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of a voltage at 10% transmittance.

(14a) Response Time (τ; Measured at 25° C.; ms)

Positive dielectric anisotropy: An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was approximately 5.0 micrometers and a twist angle was 80 degrees. Rectangular waves (60 Hz, 5 V, 0.5 sec) were applied to the device. On the occasion, the device was irradiated with light from a direction perpendicular to the device, and an amount of light transmitted through the device was measured. Transmittance at a maximum was regarded to be 100%, and transmittance at a minimum was regarded to be 0%. A rise time (τr: rise time; millisecond) is a period of time required for the change in transmittance from 90% to 10%. A fall time (τf: fall time; millisecond) is a period of time required for the change in transmittance from 10% to 90%. The response time was expressed in terms of a sum of the rise time and the fall time thus obtained.

(14b) Response Time (τ; Measured at 25° C.; ms)

Negative dielectric anisotropy: An LCD-5100 luminance meter made by Otsuka Electronics Co., Ltd. was used for measurement. A light source was a halogen lamp. A low-pass filter was set to 5 kHz. A sample was put in a normally black mode PVA device in which a distance (cell gap) between two glass substrates was 3.2 micrometers and a rubbing direction was anti-parallel. Then, the device was sealed with an ultraviolet-curable adhesive. A voltage having a degree a little over a threshold voltage was applied to the device for 1 minute, and then the device was irradiated with ultraviolet light of 23.5 mW/cm² for 8 minutes, while applying a voltage of 5.6 V. Rectangular waves (60 Hz, 10 V, 0.5 second) were applied to the device. On the occasion, the device was irradiated with light from a direction perpendicular to the device, and an amount of light transmitted through the device was measured. Transmittance at a maximum was regarded to be 100%, and transmittance at a minimum was regarded to be 0%. A response time was expressed in terms of a period of time required for the change in transmittance from 90% to 10% (fall time; millisecond).

Example 1

Compound (1-108) was prepared according to the scheme described below.

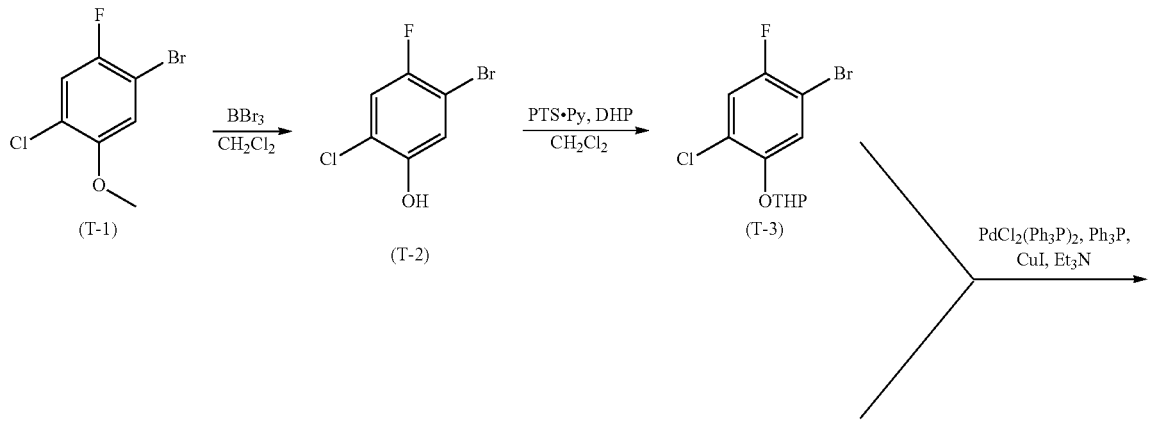

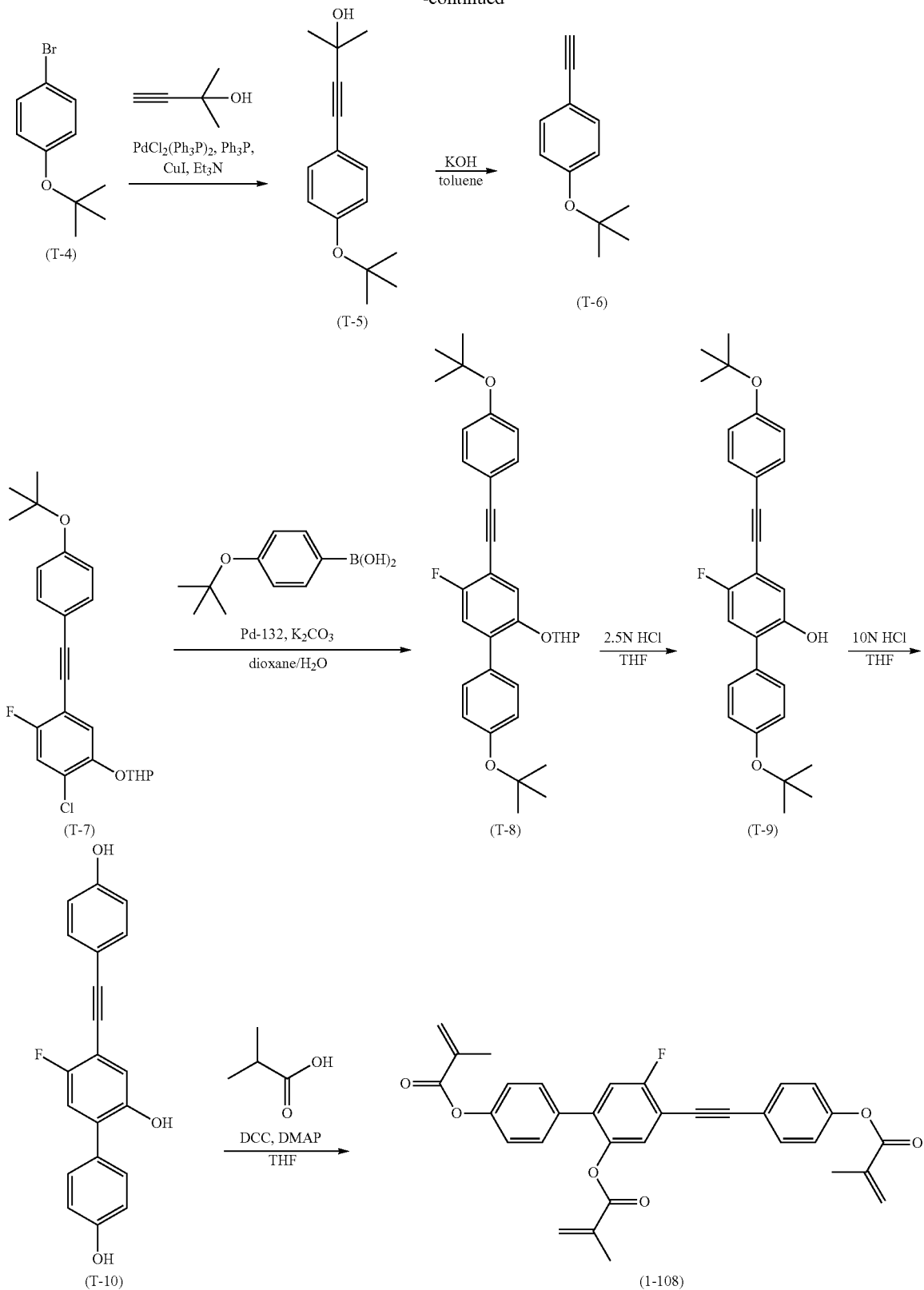
First Step: Synthesis of Compound (T-2)
Under an argon flow, compound (T-1) (59 g) was dissolved into methylene chloride (500 mL), and then boron tribromide (74 g) was added dropwise thereto at −50° C. in 30 minutes. The resulting mixture was stirred at 0° C. overnight, and then quenched with water at −10° C., and then subjected to extraction with methyl t-butyl ether (MTBE; 1000 mL). The resulting extract was concentrated under reduced pressure to give a colorless oily matter of crude product (36 g, yield: 65.1%) of compound (T-2).

Second Step: Synthesis of Compound (T-3)

Compound (T-2) (14 g) and pyridinium p-toluene sulfonate (1.6 g) were put in a 500 mL flask and dissolved into methylene chloride (100 mL), and then a methylene chloride (50 mL) solution of dihydropyran (6.26 g) was added dropwise thereto in the temperature range from 20° C. to 25° C. in 10 minutes. The resulting mixture was stirred for 15 hours, and then disappearance of compound (T-2) was confirmed using thin layer chromatography, and then the resulting reaction liquid was quenched with water (700 g). The combined organic layer was washed with aqueous solution of sodium hydroxide, and concentrated under reduced pressure. The resulting residue was purified by silica gel column chromatography (100 g) using hexane-ethyl acetate (10:1 in a volume ratio) as an eluent to give a colorless oily matter at a purity of 99% (HPLC) of compound (T-3; 13.6 g, yield: 710).

Third Step: Synthesis of Compound (T-5)

Then, 1-bromo-4-(t-butoxy)benzene (T-4) (114 g), 2-methyl-3-butyn-2-ol (92.4 g), triphenylphosphine (2.62 g), dichlorobis(triphenylphosphine)palladium (7.01 g), copper iodide (5.7 g), triethylamine (606 g) and 2,6-t-butyl-4-methyl phenol (0.2 g) were put in a 1000 mL flask, and then the resulting mixture was heated under reflux for 20 hours (85° C. to 90° C.). The resulting reaction mixture was cooled to room temperature, and then the reaction mixture was filtered, and then the filtrate was concentrated under reduced pressure to give a brown oily matter of a crude product (187.5 g) of compound (T-5).

Fourth Step: Synthesis of Compound (T-6)

Compound (T-5) (187.5 g), potassium hydroxide (92.5 g) and toluene (1200 mL) were put in a 2,000 mL flask, and the resulting mixture was heated and stirred at 105° C. for 2 hours. The resulting reaction liquid was cooled to room temperature and filtered, and then the resulting residue was washed with toluene (500 mL), and then the filtrate and the washed liquid were combined and concentrated under reduced pressure. The resulting residue was purified by silica gel column chromatography using hexane as an eluent to give a colorless oily matter at a purity of 98% (HPLC) of compound (T-6; 58.25 g, two-step yield: 66.70).

Fifth Step: Synthesis of Compound (T-7)

Compound (T-3) (8.6 g), compound (T-6) (5.4 g), triphenylphosphine (0.08 g), dichlorobis(triphenylphosphine) palladium (0.2 g), copper iodide (0.16 g), triethylamine (17 g) and 2,6-t-butyl-4-methylphenol (0.1 g) were put in a 250 mL flask, and the resulting mixture was heated under reflux for 17 hours (85° C. to 90° C.) under an argon flow. The resulting reaction mixture was cooled to room temperature and filtered, and then the filtrate was concentrated under reduced pressure. The resulting residue was purified by silica gel column chromatography using a mixture of hexane-ethyl acetate (50:1 in a volume ratio) as an eluent to give a colorless oily matter at a purity of 98% (HPLC) of compound (T-7; 8 g, yield: 71.40).

Sixth Step: Synthesis of Compound (T-8)

A mixture of compound (T-7) (7.7 g), (4-(t-butoxy)phenyl) boronic acid (7.4 g), Pd-132 (PdCl$_2$[(CH$_3$)$_2$)NC$_6$H$_4$P(t-C$_4$H$_9$)$_2$]; 0.06 g), potassium carbonate (5.3 g), dioxane (100 mL) and water (10 mL) was heated and stirred at 80° C. overnight under a nitrogen atmosphere. The resulting reaction mixture was filtered and the filtrate was concentrated under reduced pressure. The resulting residue was passed through a silica gel column using a mixture of hexane-ethyl acetate (20:1 in a volume ratio) as an eluent to give a crude product (6.6 g) of compound (T-8).

Seventh Step: Synthesis of Compound (T-9)

Compound (T-8) (6.6 g) was dissolved into THF (30 mL), and then 2.5 N hydrochloric acid (40 mL) was added thereto, and the resulting mixture was stirred under a nitrogen atmosphere. After 3 hours, the resulting reaction liquid was subjected to extraction with MTBE (200 mL), and the resulting extract was concentrated under reduced pressure. The resulting residue was passed through a silica gel column using a mixture of hexane-ethyl acetate (30:1 in a volume ratio) as an eluent to give a crude product (5 g) of compound (T-9).

Eighth Step: Synthesis of Compound (T-10)

Compound (T-9) (5 g) was dissolved into THF (80 mL), and then 10 N hydrochloric acid (30 mL) was added thereto, and the resulting mixture was stirred at −20° C. for 3 hours under a nitrogen atmosphere. The resulting reaction liquid was extracted with MTBE (200 mL). The resulting extract was washed with water (200 mL) and concentrated under reduced pressure. The resulting residue was passed through a silica gel column using a mixture of hexane-ethyl acetate (5:1 in a volume ratio) as an eluent to give a crude product (2.2 g) of compound (T-10).

Ninth Step: Synthesis of Compound (T-11)

Compound (T-10) (2.2 g), methacrylic acid (2.9 g), 4-dimethylaminopyridine (0.085 g) and 2,6-di-t-butyl-4-methylphenol (0.05 g) were put in a 250 mL flask, and the resulting mixture was dissolved into THF (50 mL) under an argon flow. A THF (30 mL) solution of DCC (7 g) was added dropwise thereto in 30 minutes while maintaining the temperature at 25° C. or lower. The resulting mixture was further stirred for 5 hours, and then the reactant was quenched with water (2 g) and filtered. The filtrate was extracted with MTBE (100 mL) and the resulting extract was concentrated under reduced pressure to give a yellow crystalline crude product (4.2 g). The crude product was purified by silica gel column chromatography using a mixture of hexane-ethyl acetate (1:5 in a volume ratio) as an eluent to give a colorless crystal at a purity of 96% (HPLC) of compound (1-108; 2.4 g, yield: 24%).

$^1$H-NMR (δ ppm; CDCl$_3$): 7.58 (d, J=8.7 Hz, 2H), 7.44 (d, J=8.7 Hz, 2H), 7.36 (d, J=6.2 Hz, 1H), 7.18 (d, J=9.4 Hz, 1H), 7.18 (d, J=8.7 Hz, 1H), 7.15 (d, J=8.7 Hz, 2H), 6.37 (s, 1H×2), 6.18 (s, 1H), 5.78 (s, 1H×2), 5.67 (s, 1H), 2.07 (s, 3H×2), 1.93 (s, 3H). $^{19}$F-NMR (δ ppm; CDCl$_3$): −113.94 (dd, J=9.4, 6.2 Hz, 1F).

Physical properties of compound (1-108) were as described below. Melting point: 147.5° C., polymerization starting temperature: 164° C.

Compounds (1-1) to (1-695) shown below can be prepared in a manner similar to the method described in Example 1.

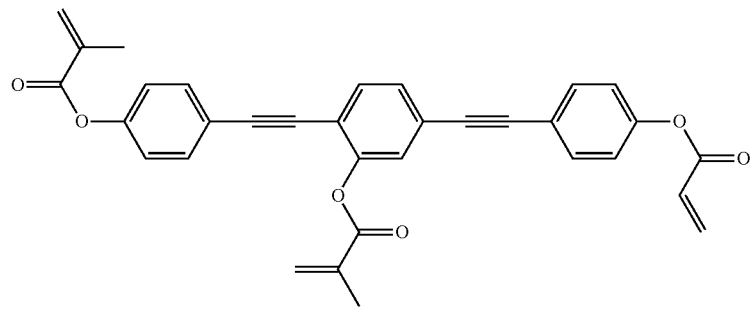
(1-1)
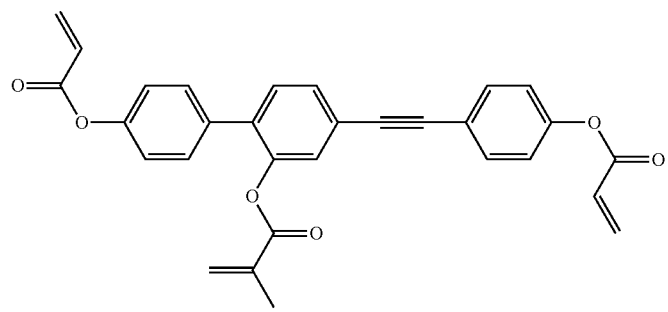
(1-2)
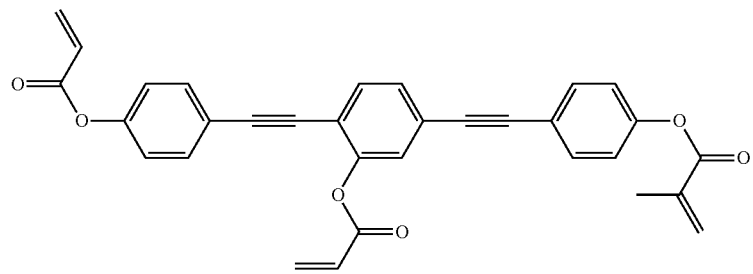
(1-3)
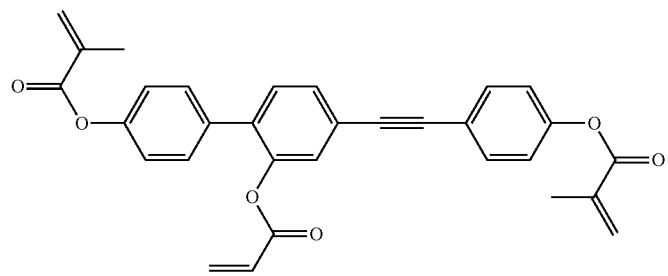
(1-4)
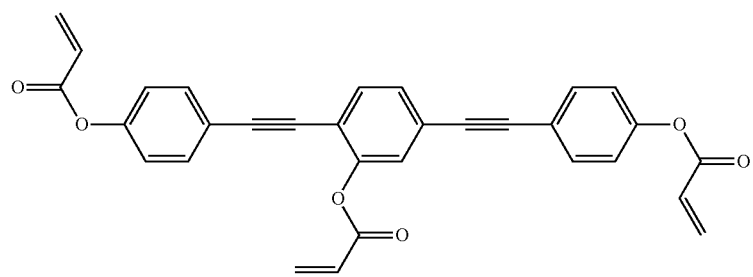
(1-5)

-continued
(1-6)
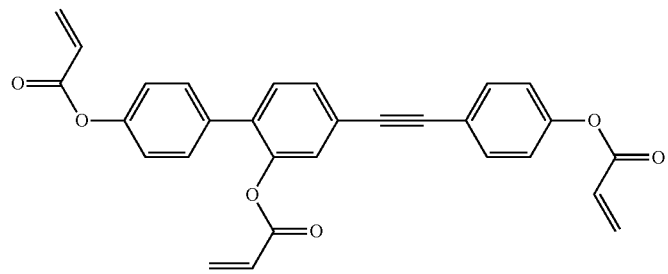
(1-7)
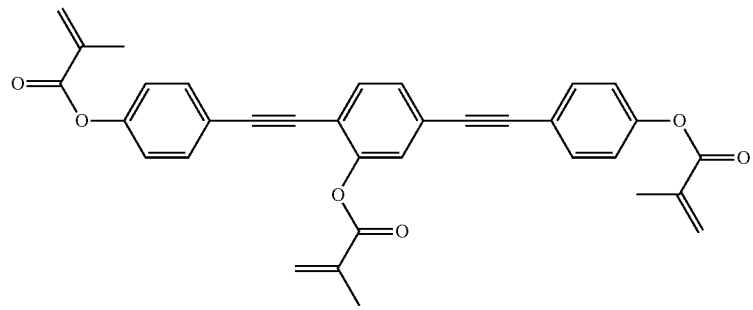
(1-8)
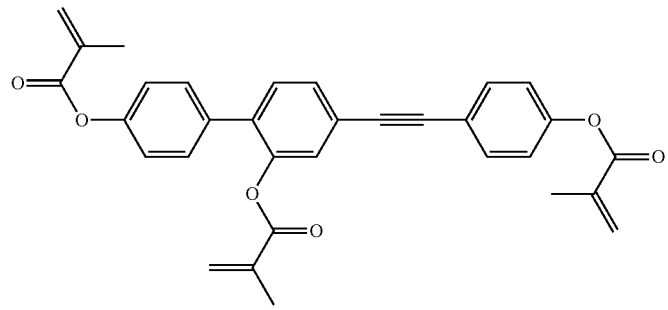
(1-9)
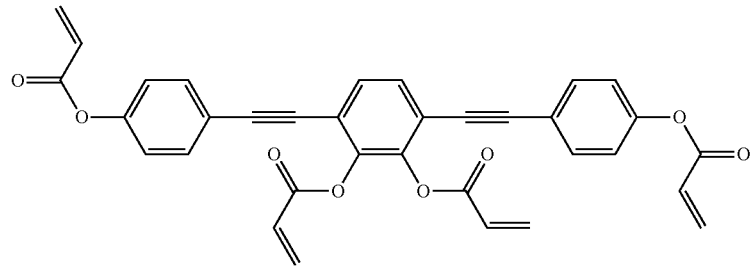
(1-10)
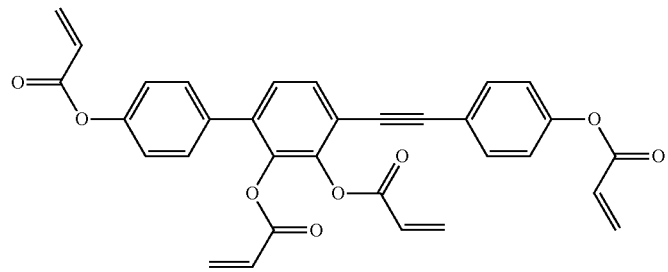

-continued
(1-11)
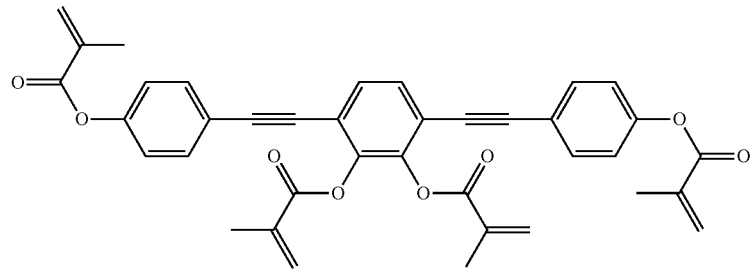
(1-12)
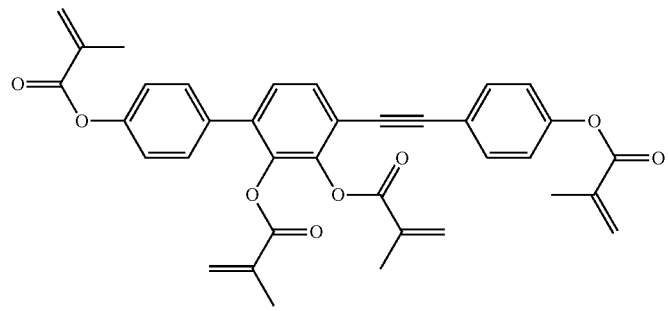
(1-13)
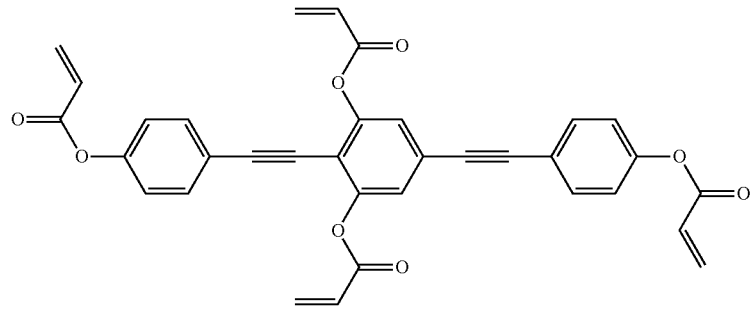
(1-14)
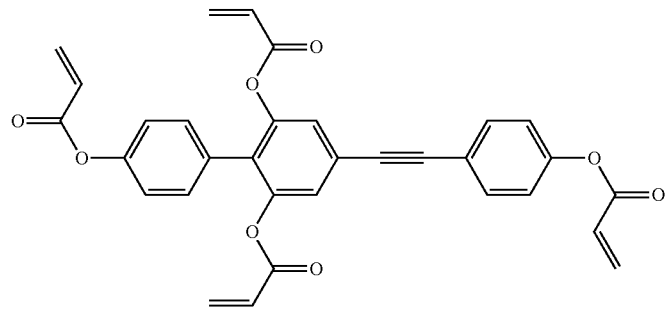
(1-15)
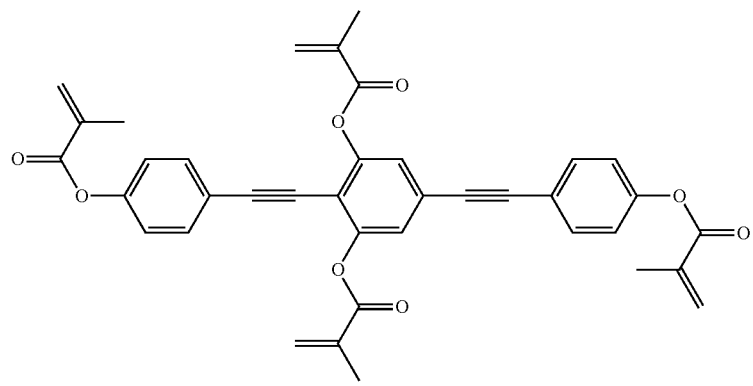

-continued
(1-16)
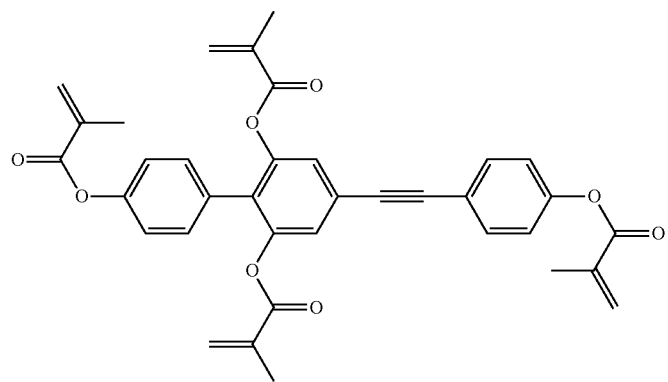
(1-17)
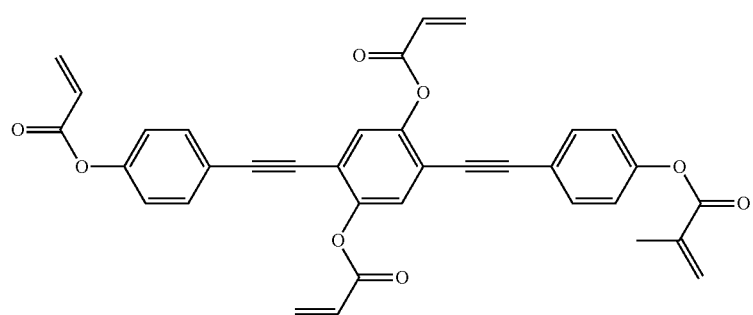
(1-18)
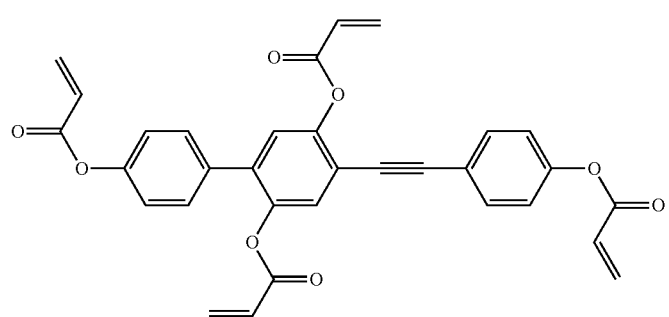
(1-19)
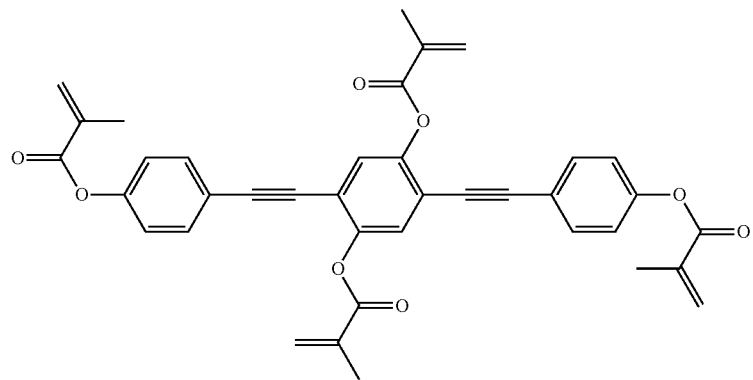

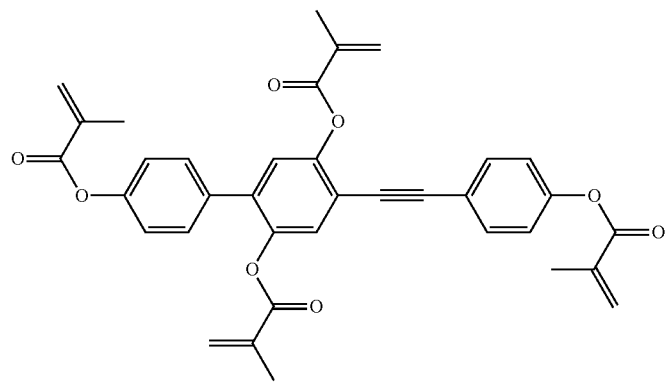
(1-20)
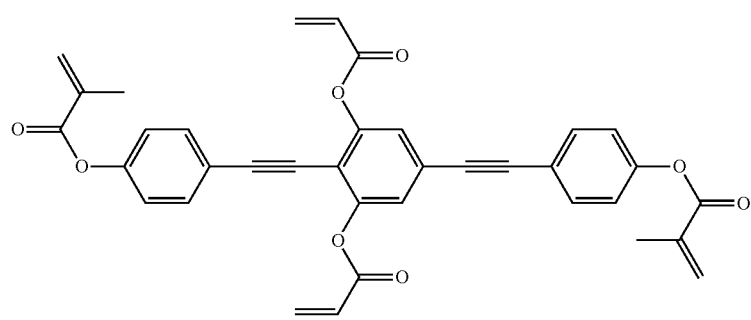
(1-21)
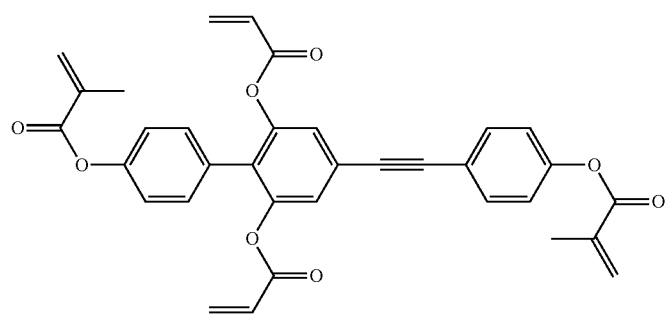
(1-22)
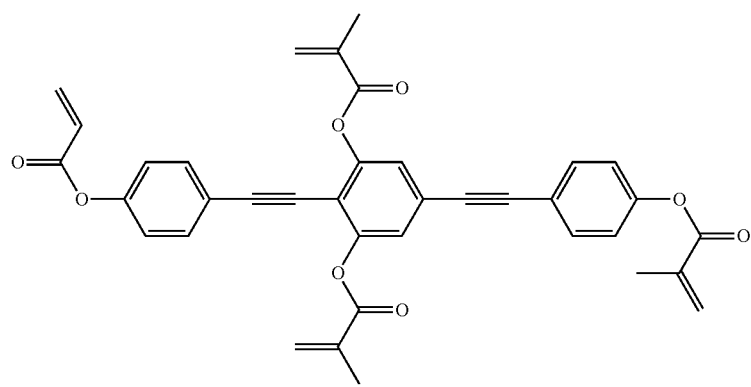
(1-23)

-continued
(1-24)
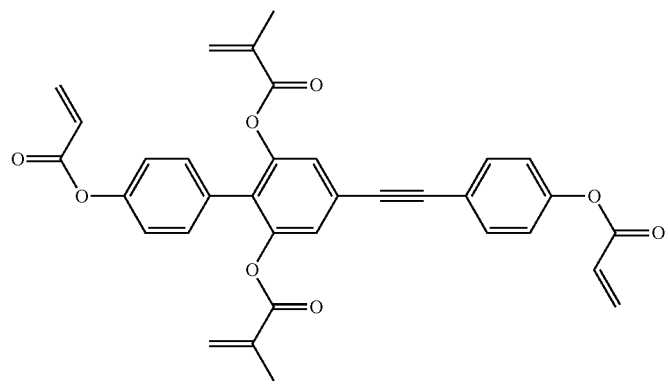
(1-25)
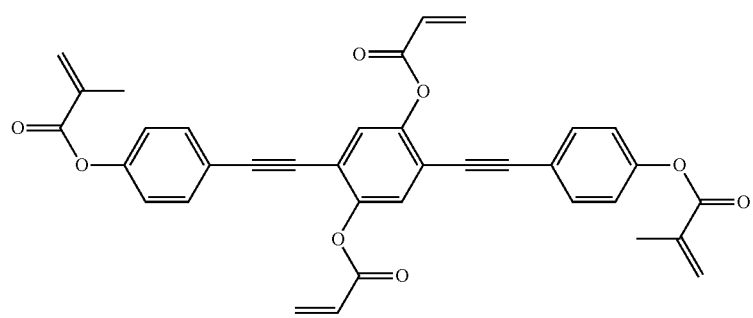
(1-26)
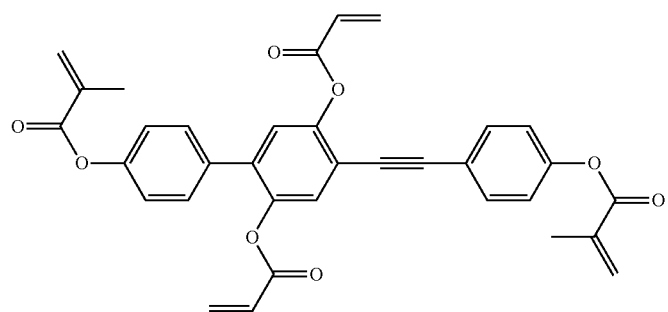
(1-27)
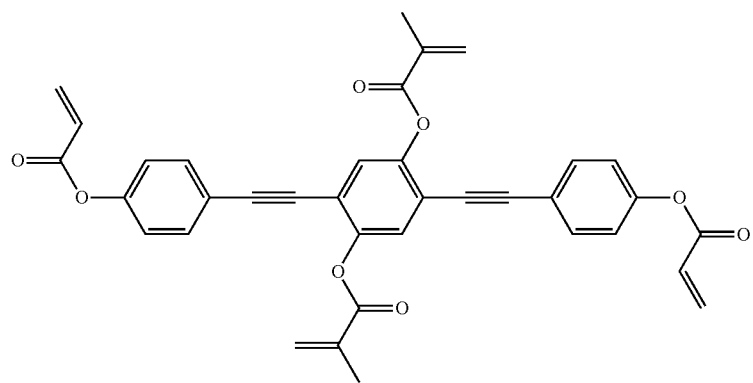

(1-28)
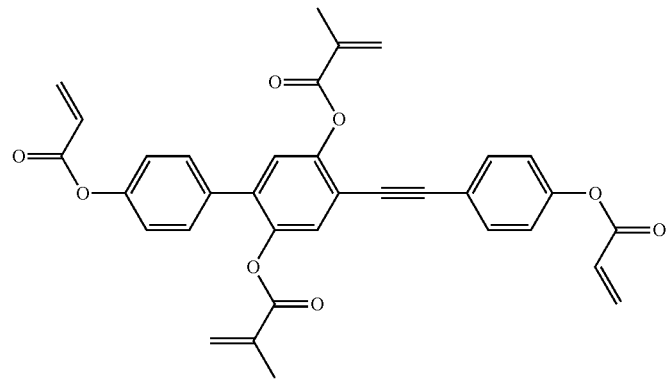
(1-29)
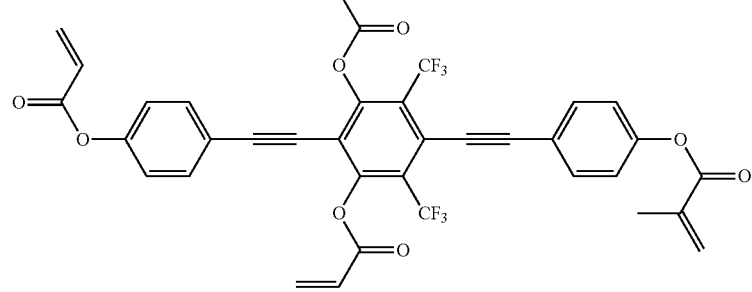
(1-30)
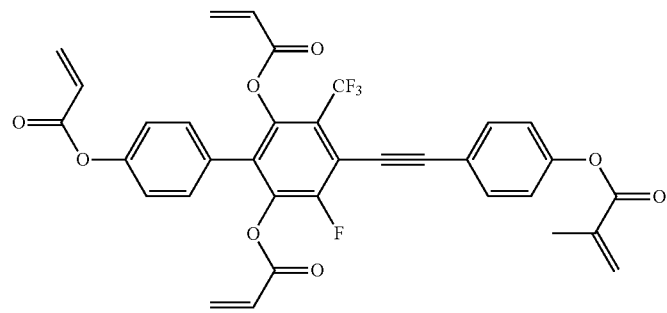
(1-31)
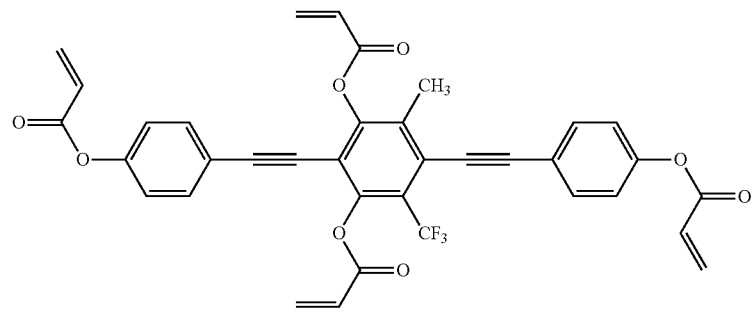
(1-32)
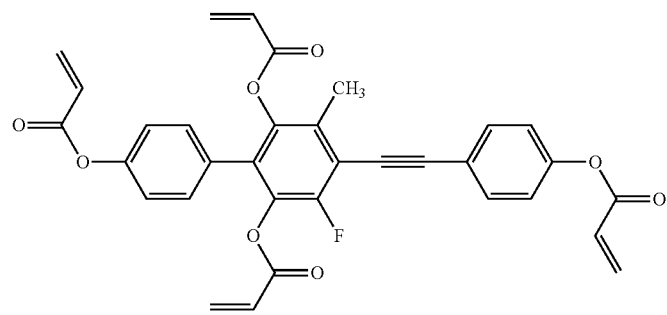

(1-33)
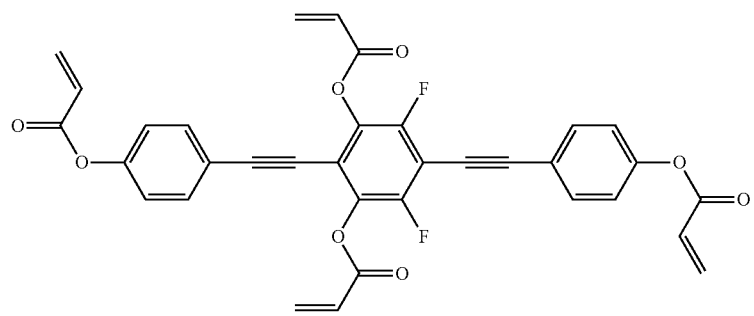
(1-34)
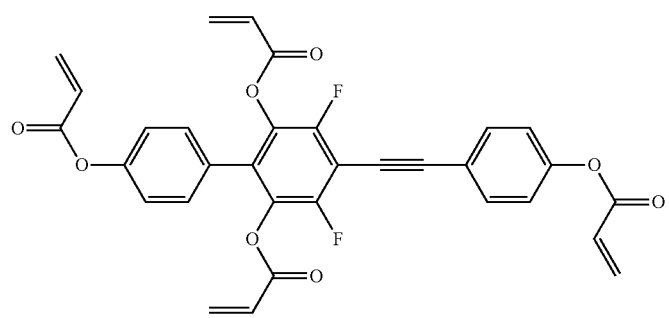
(1-35)
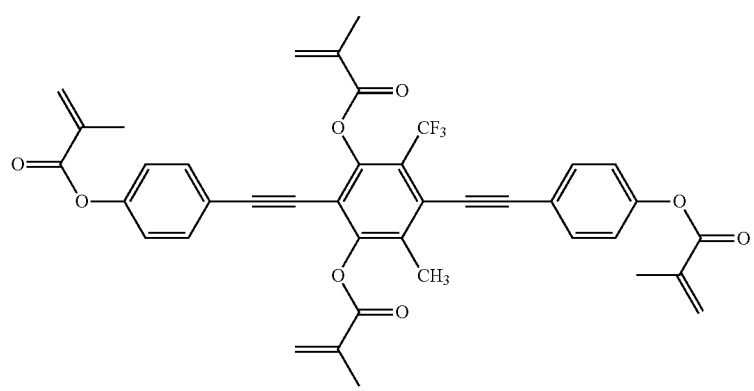
(1-36)
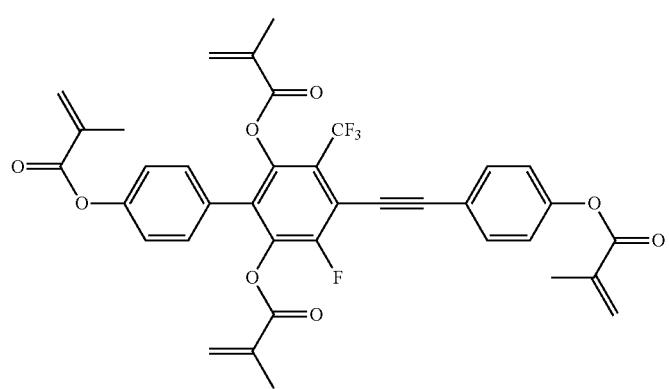

-continued
(1-37)
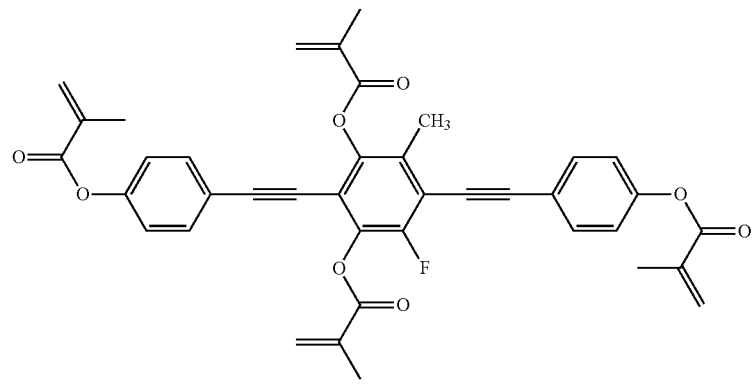
(1-38)
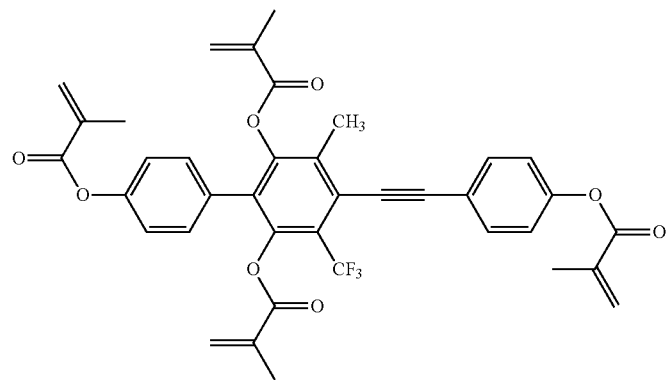
(1-39)
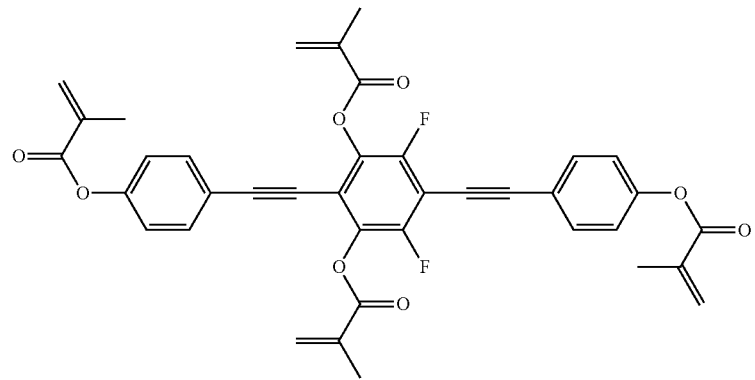
(1-40)
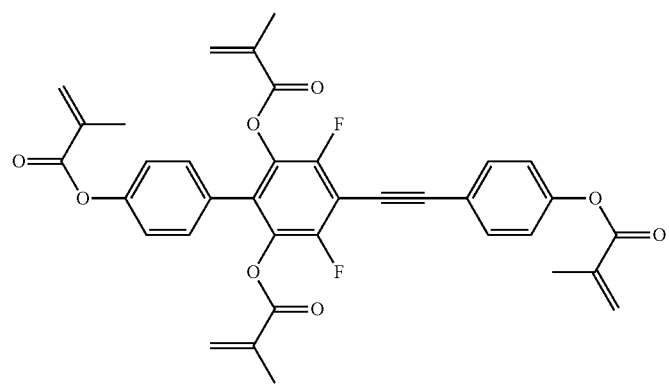

-continued
(1-41)
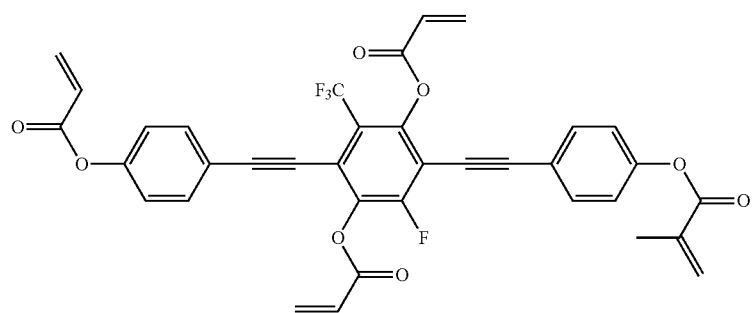
(1-42)
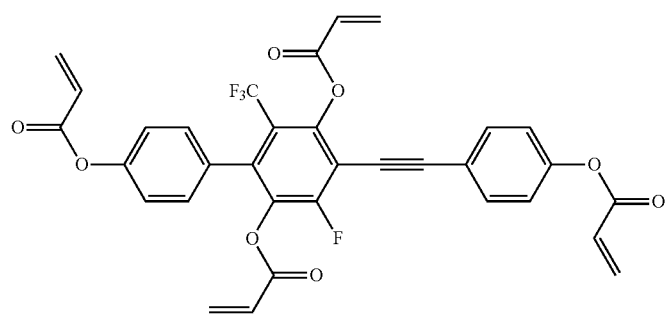
(1-43)
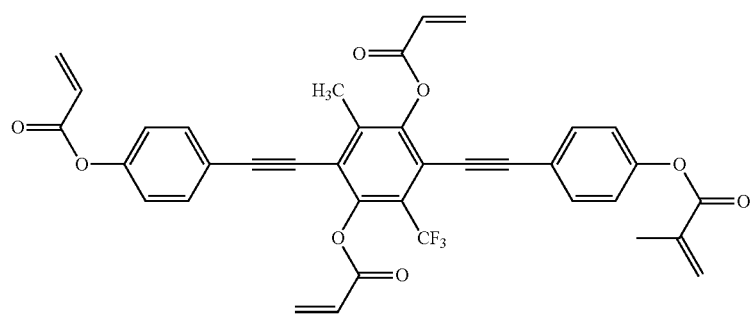
(1-44)
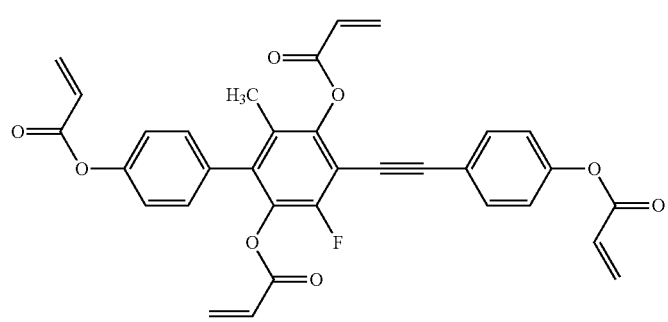
(1-45)
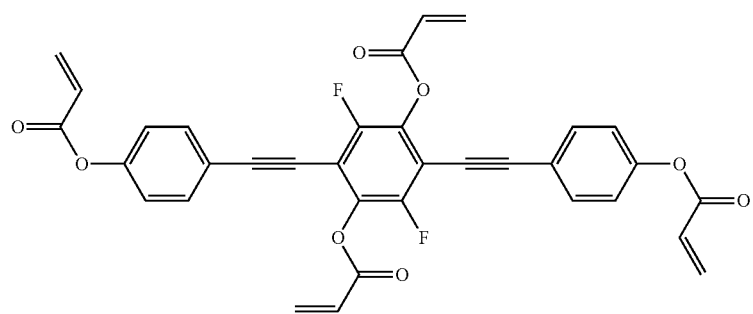

(1-46)
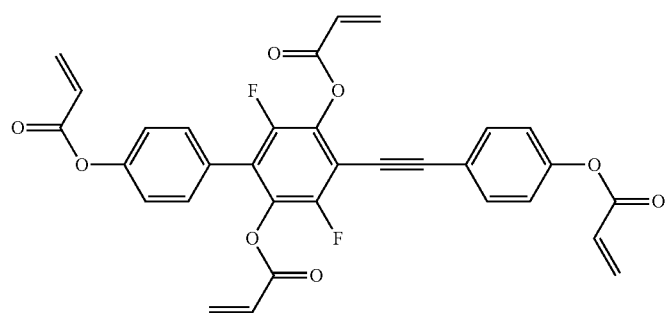
(1-47)
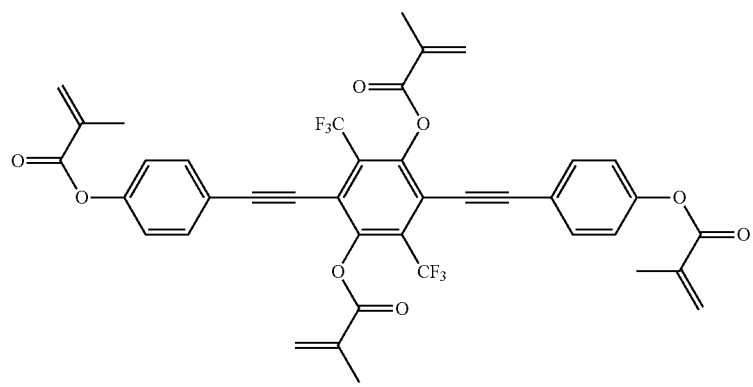
(1-48)
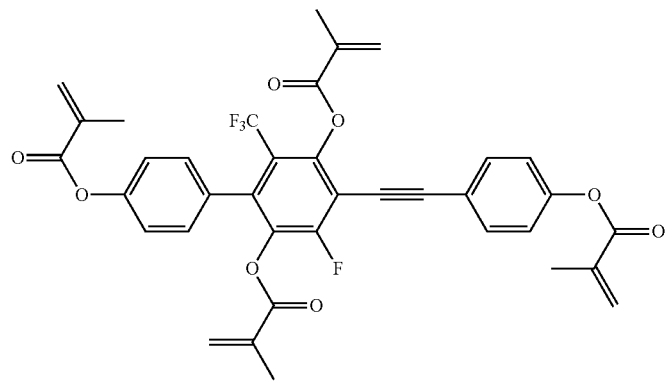
(1-49)
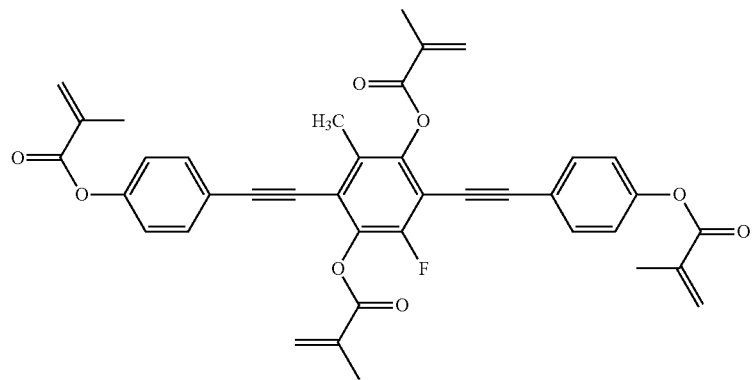

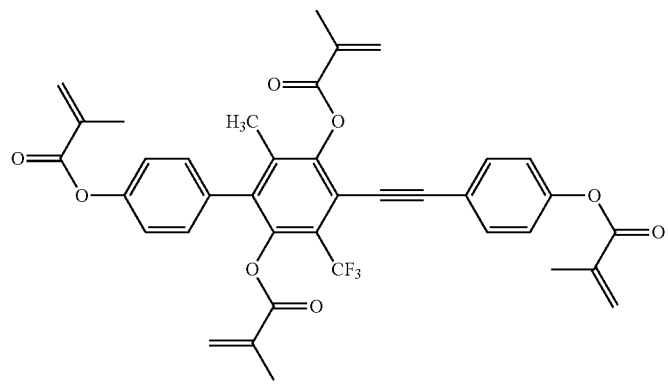
(1-50)
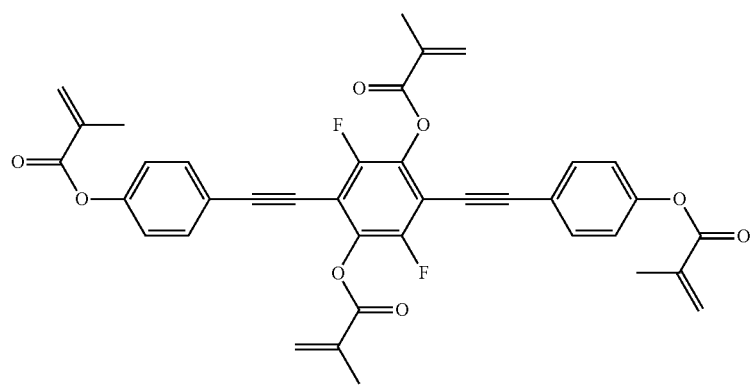
(1-51)
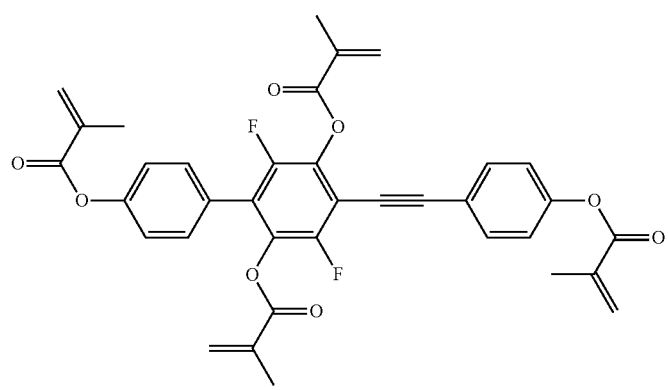
(1-52)
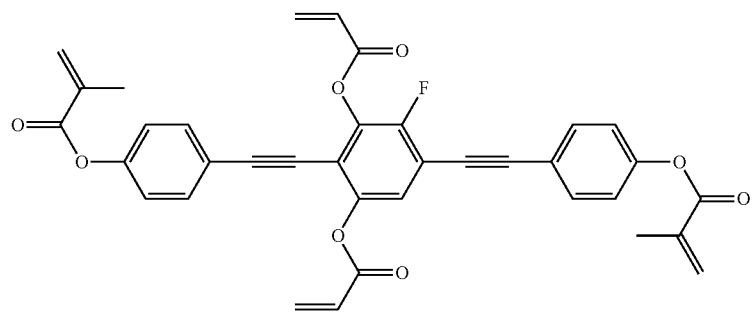
(1-53)

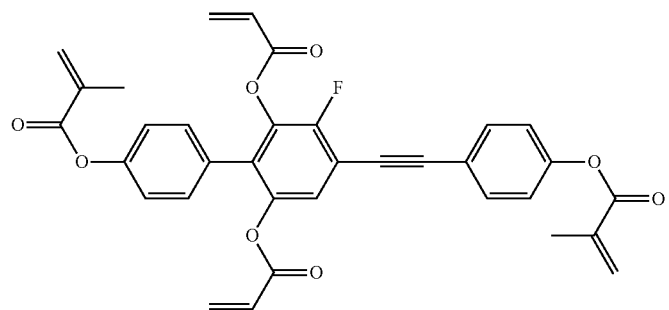
(1-54)
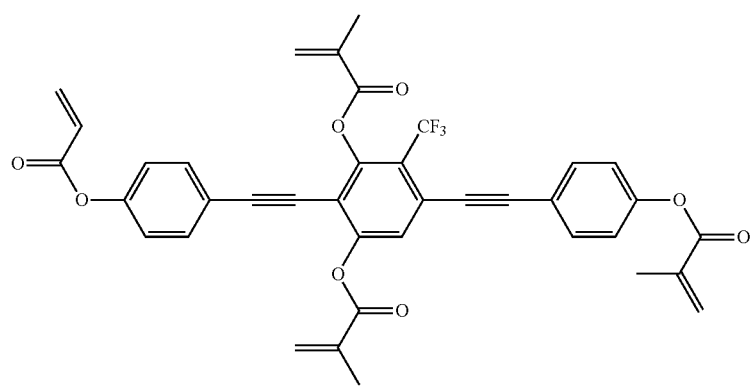
(1-55)
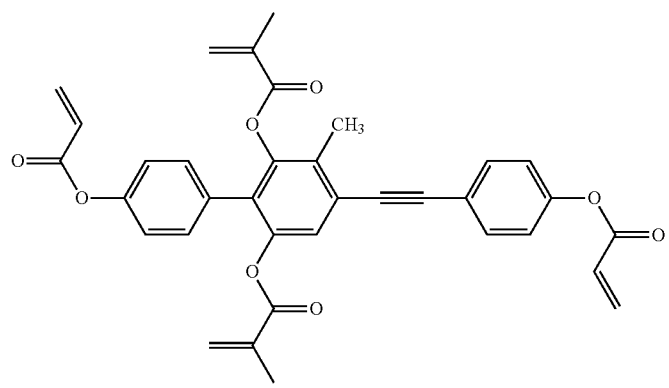
(1-56)
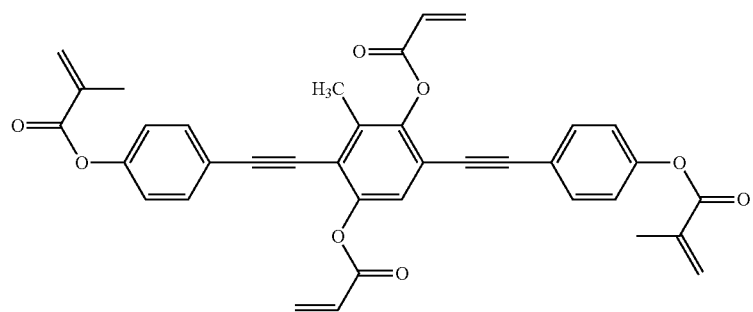
(1-57)

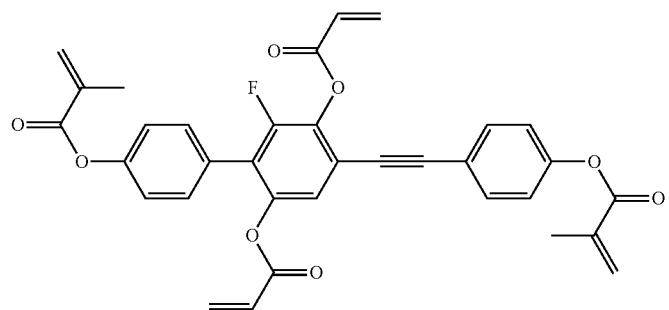
(1-58)
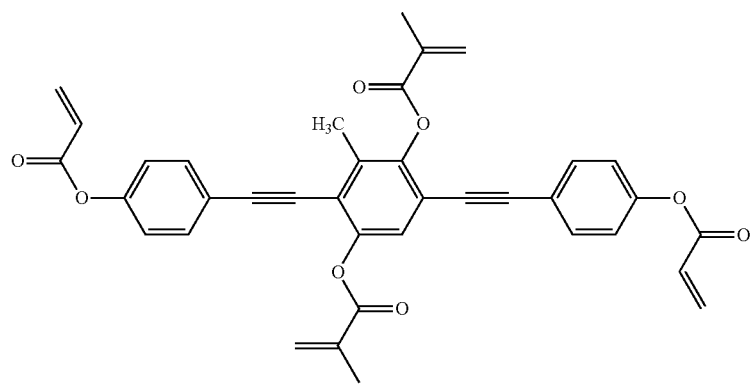
(1-59)
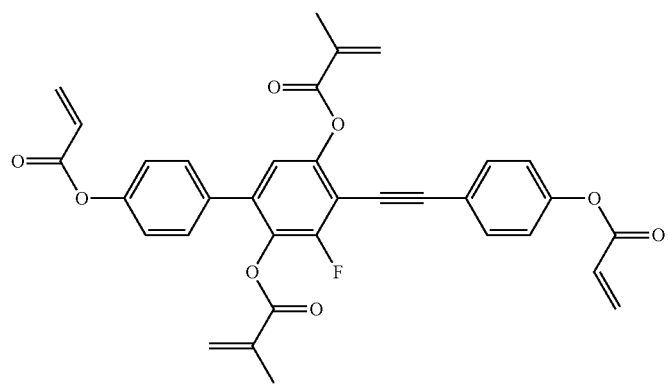
(1-60)
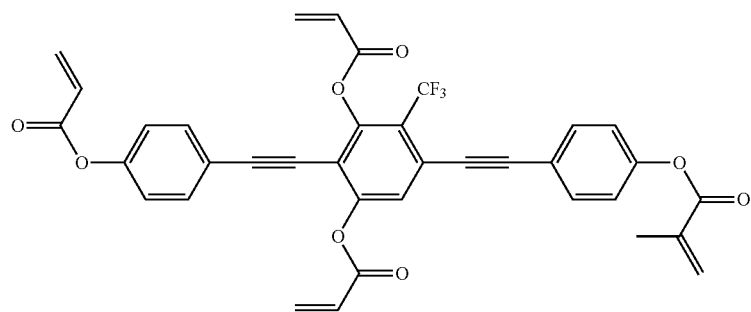
(1-61)

-continued
(1-62)
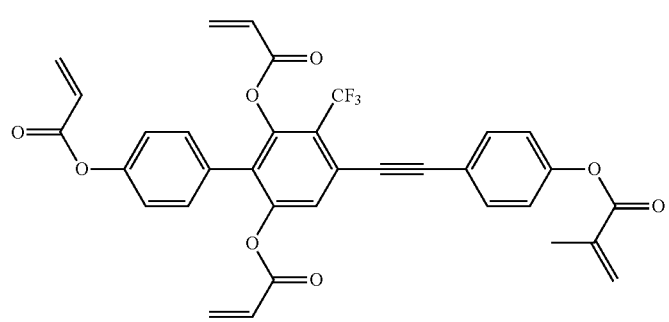
(1-63)
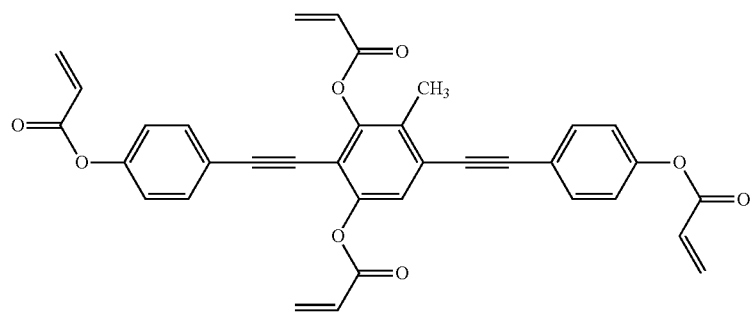
(1-64)
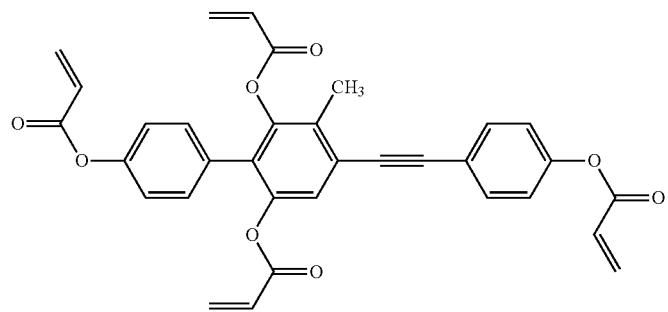
(1-65)
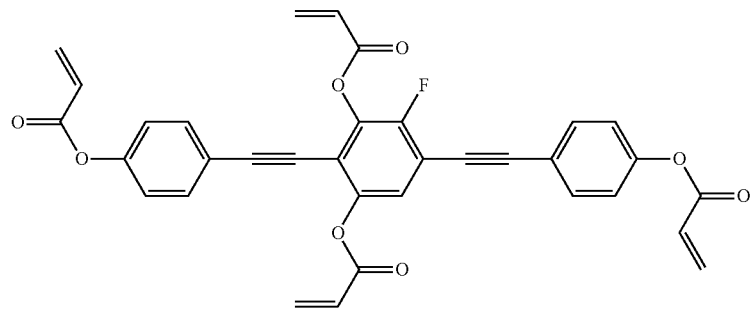
(1-66)
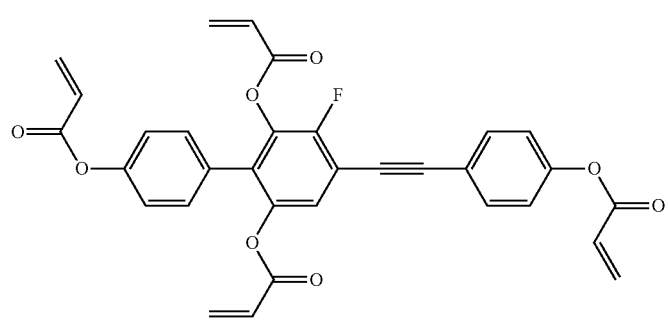

(1-67)
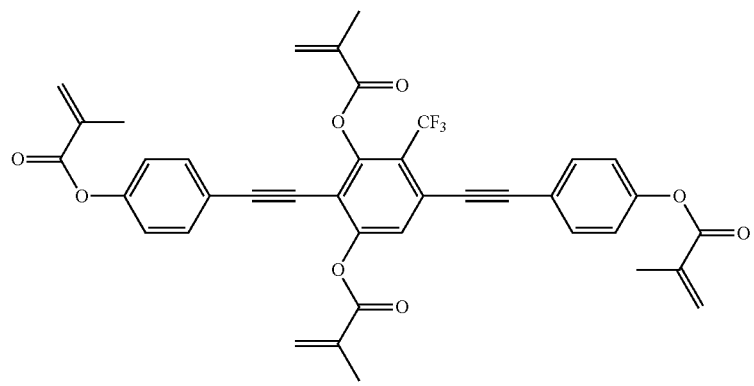
(1-68)
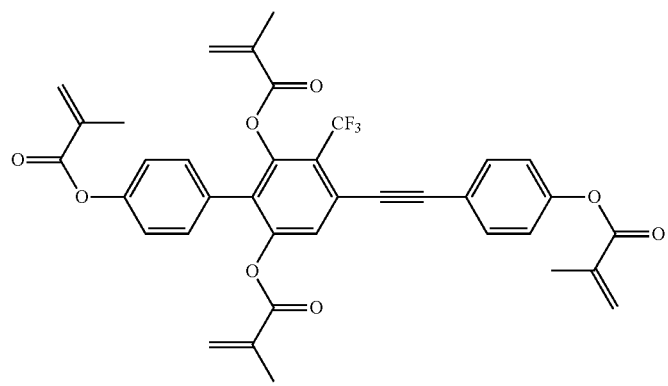
(1-69)
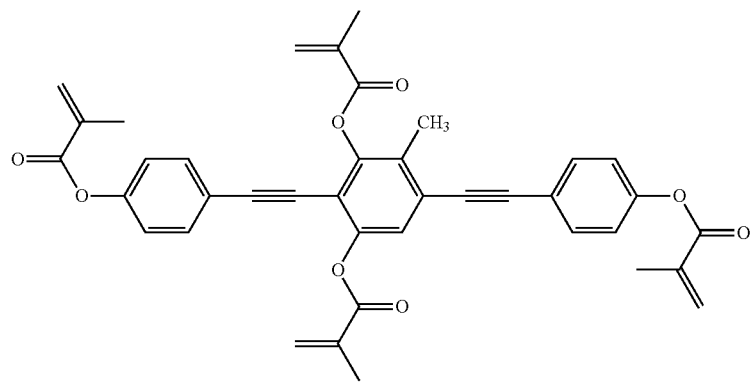
(1-70)
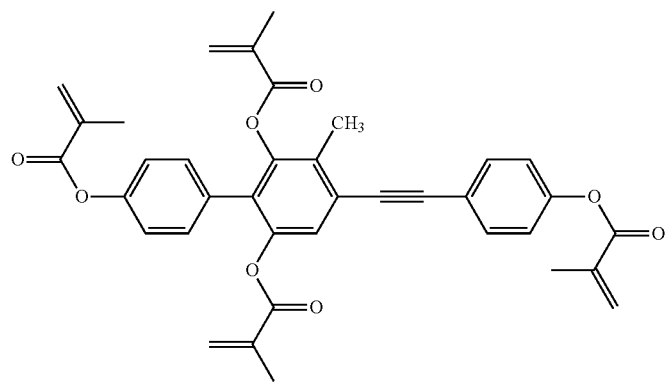

-continued
(1-71)
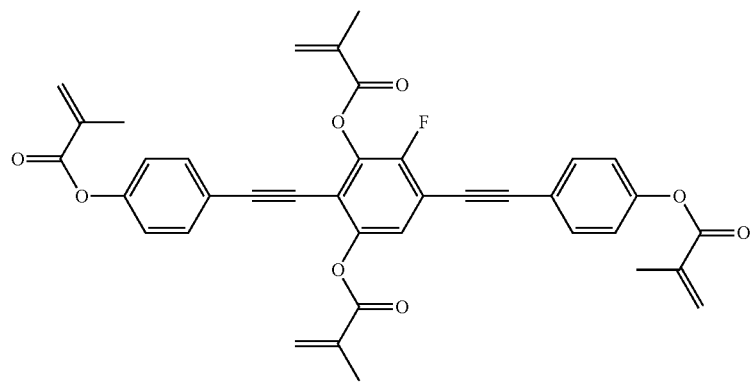
(1-72)
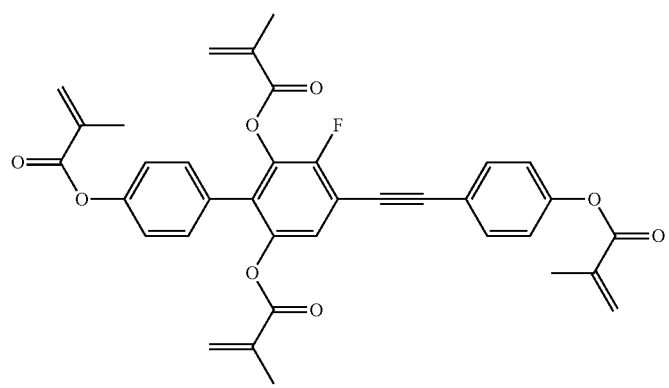
(1-73)
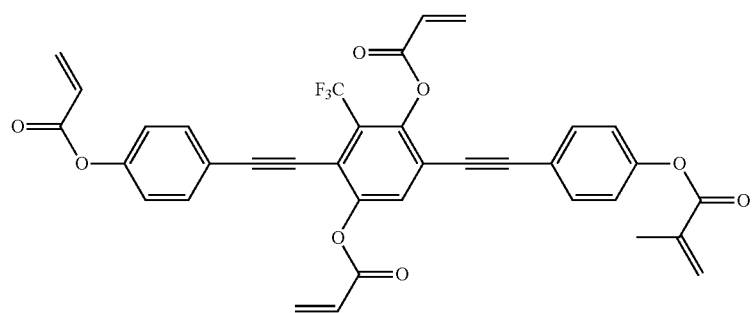
(1-74)
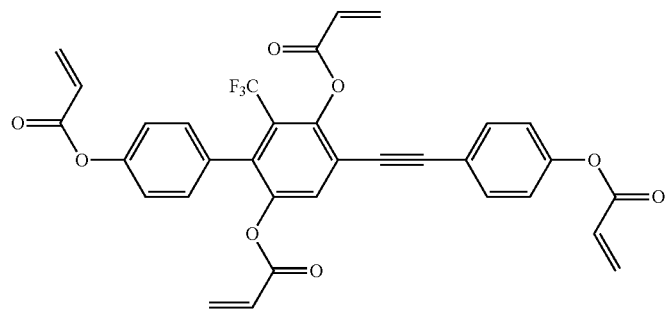

(1-75)
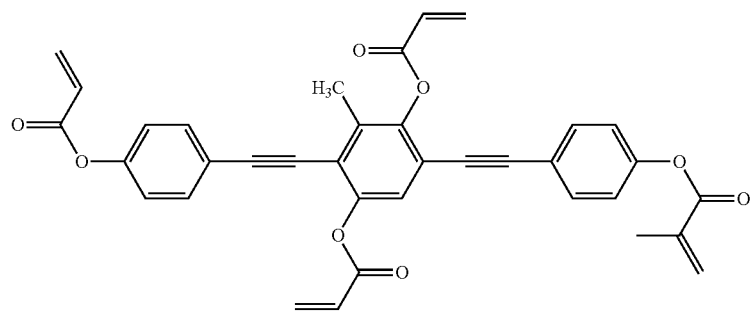
(1-76)
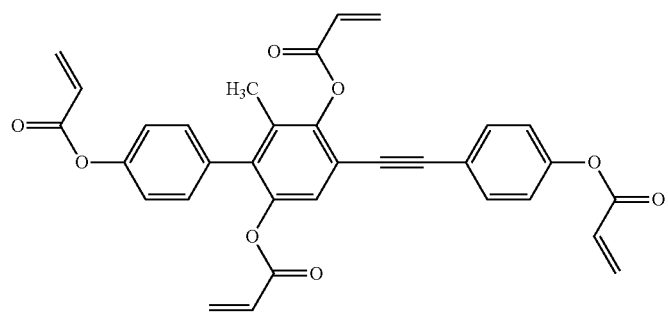
(1-77)
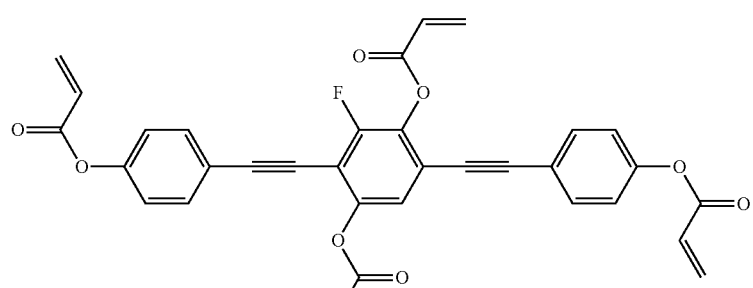
(1-78)
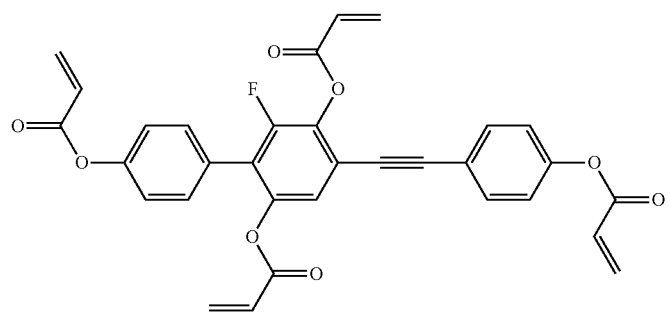
(1-79)
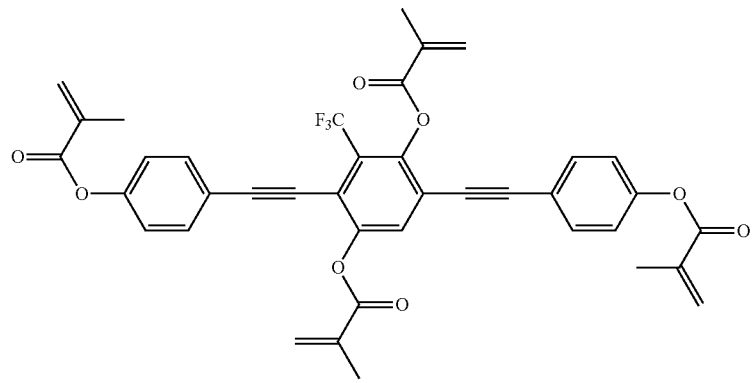

(1-80)
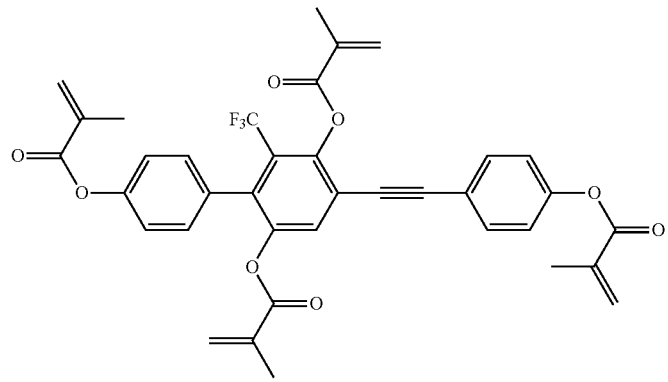
(1-81)
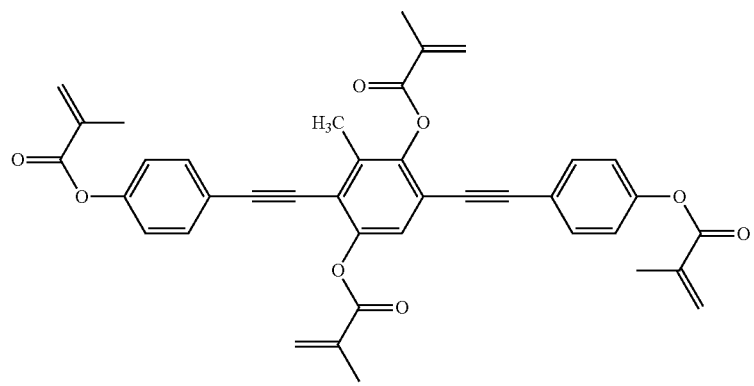
(1-82)
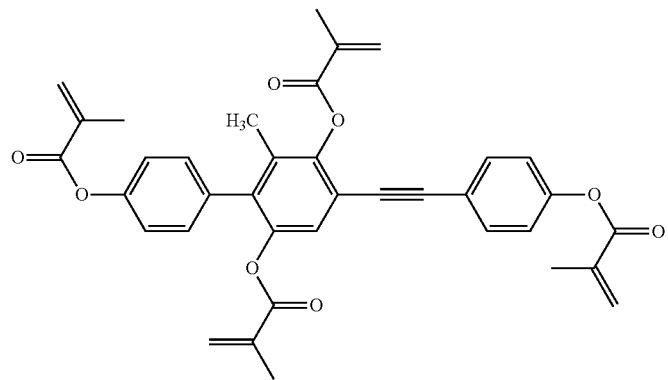
(1-83)
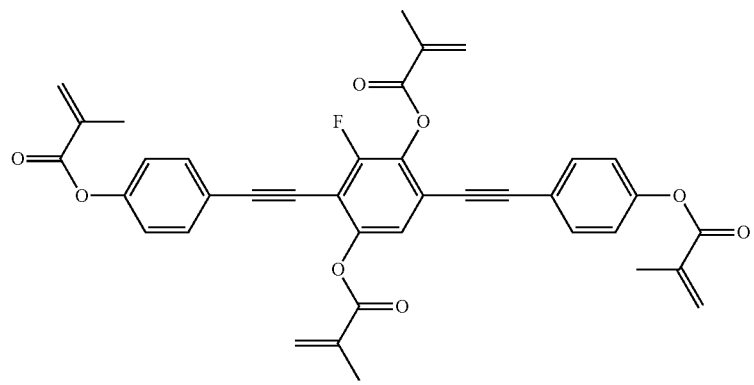

-continued
(1-84)
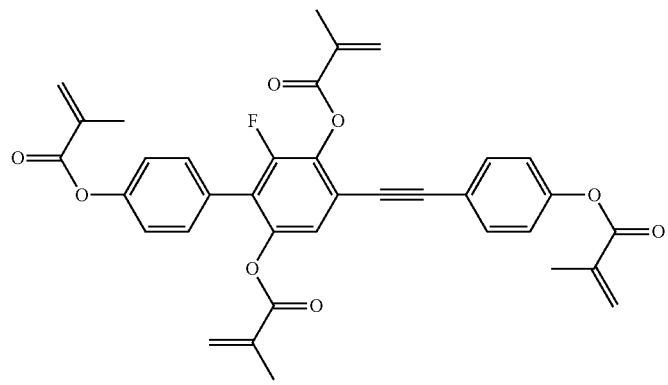
(1-85)
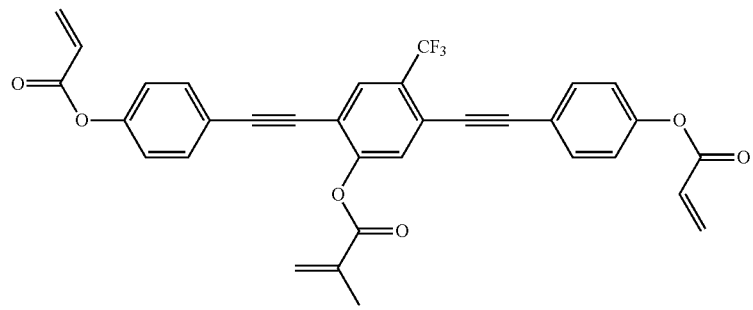
(1-86)
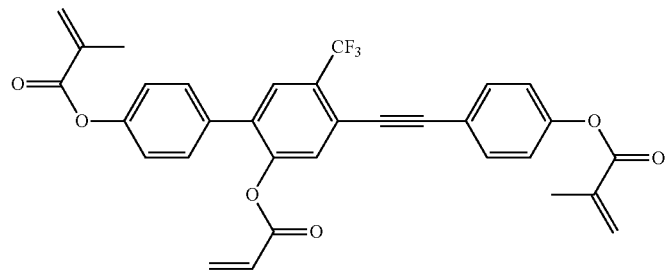
(1-87)
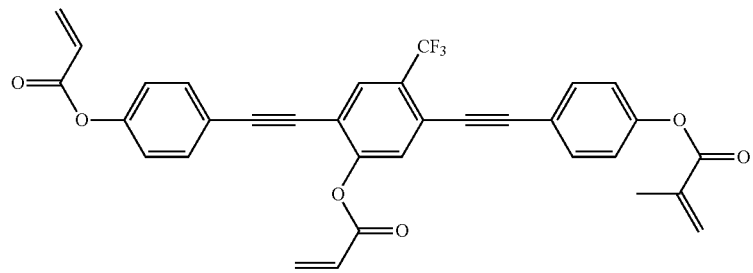
(1-88)
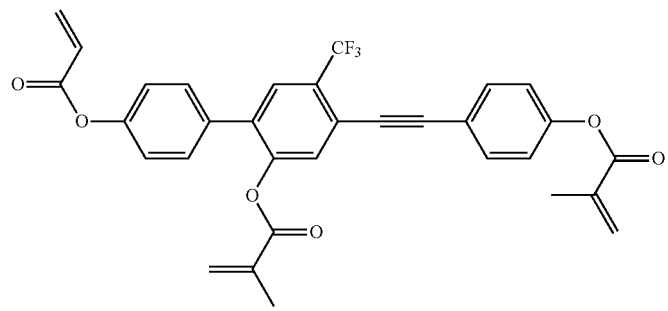

(1-89)
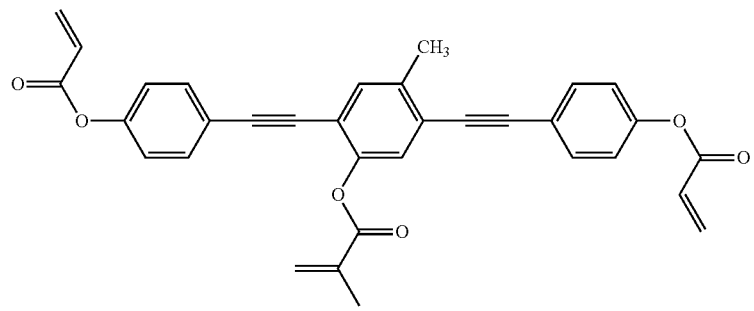
(1-90)
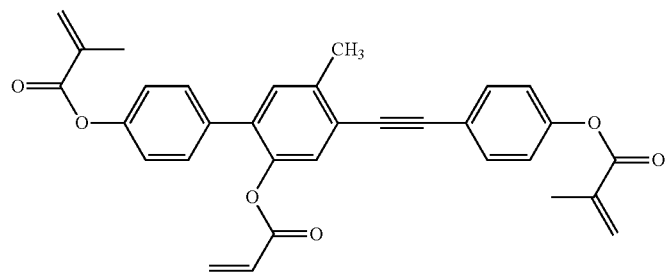
(1-91)
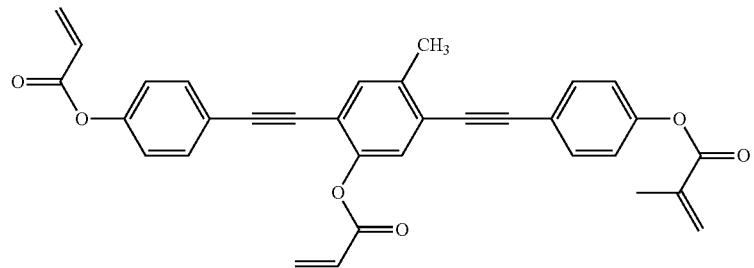
(1-92)
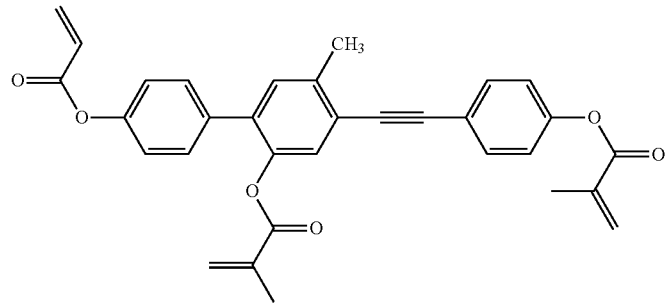
(1-93)
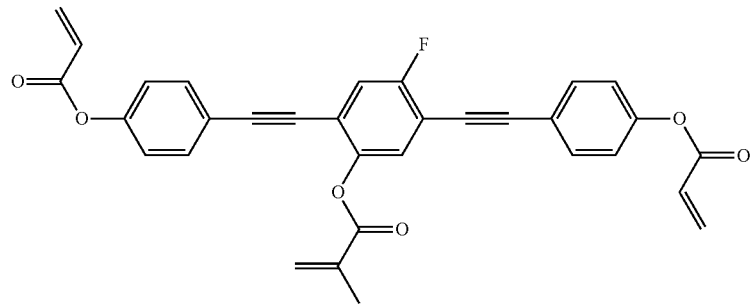

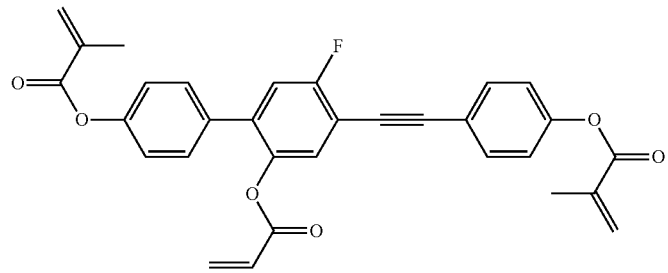
(1-94)
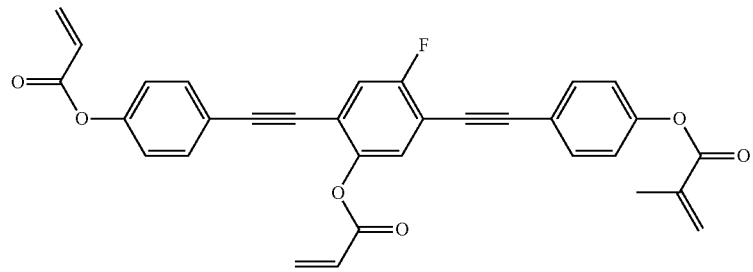
(1-95)
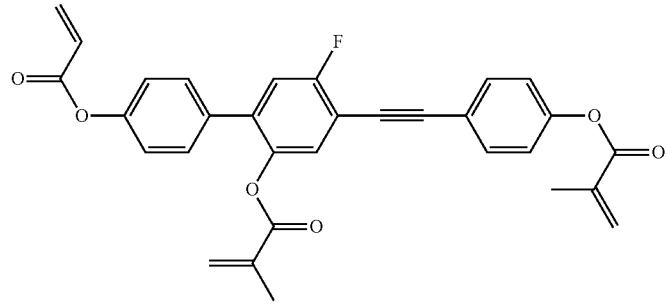
(1-96)
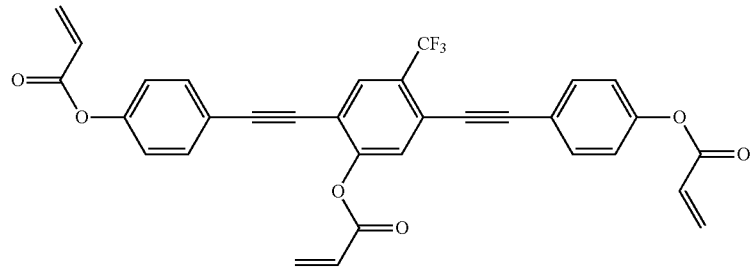
(1-97)
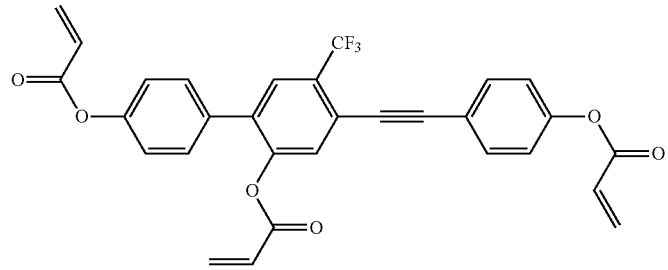
(1-98)

-continued
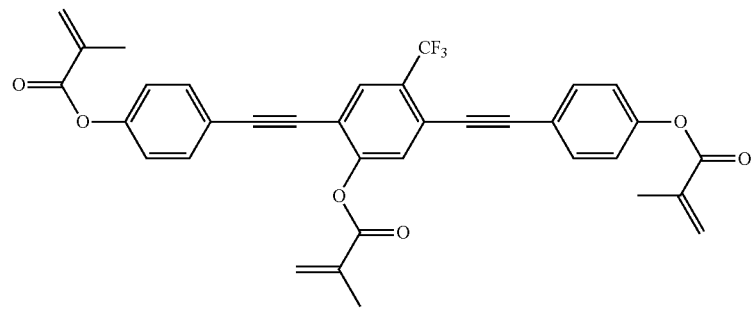
(1-99)
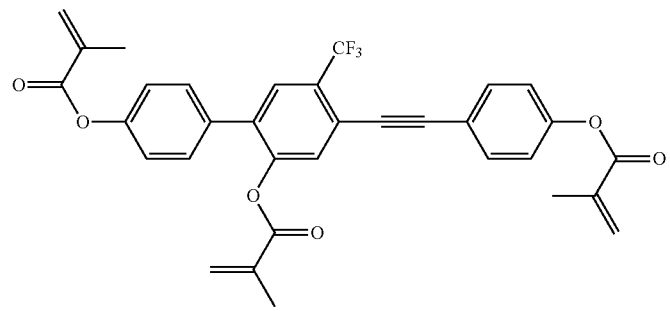 [SMILES: C=C(C)C(=O)Oc1ccc(C#CC2=C(F)C=C(c3ccc(OC(=O)C(=C)C)cc3)C(OC(=O)C(=C)C)C2)cc1]
(1-100)
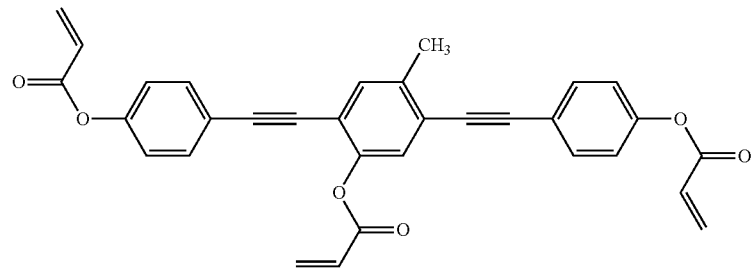
(1-101)
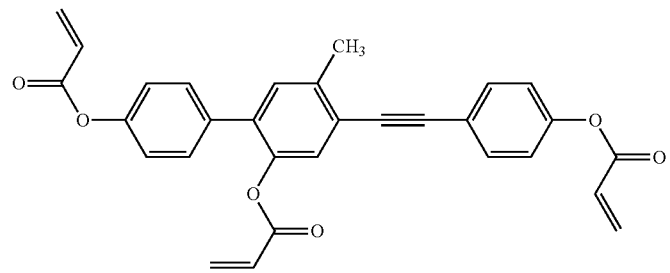
(1-102)
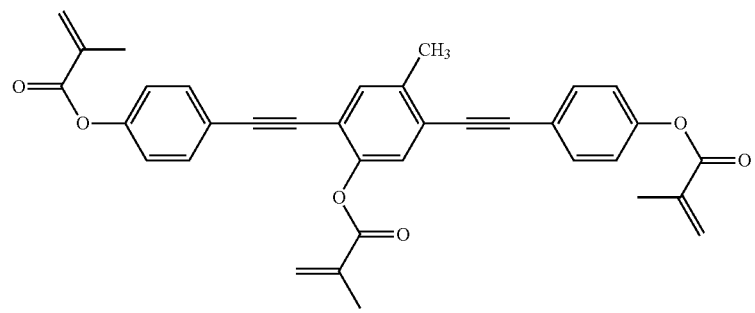
(1-103)

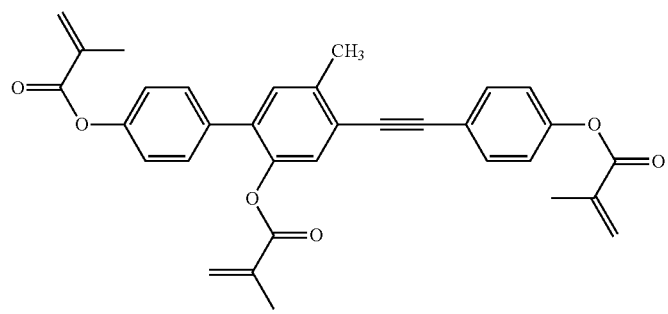
(1-104)
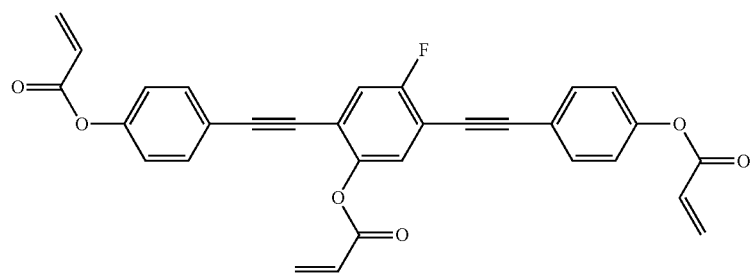
(1-105)
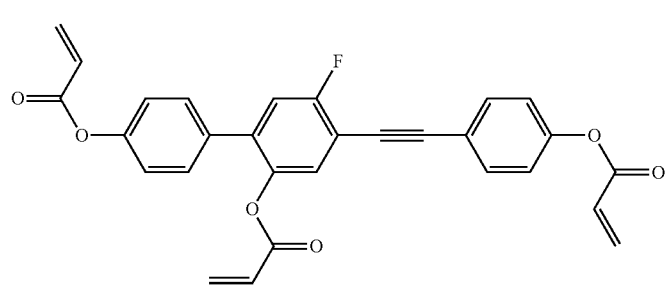
(1-106)
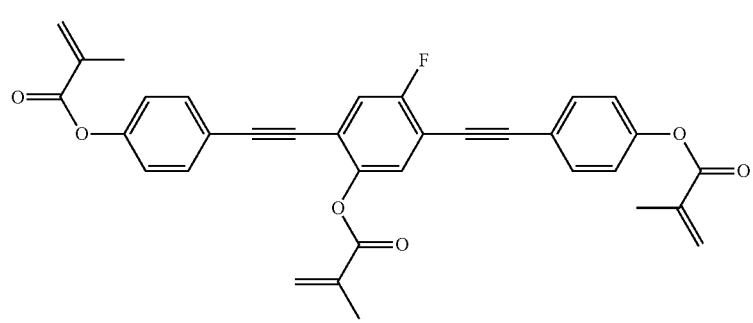
(1-107)
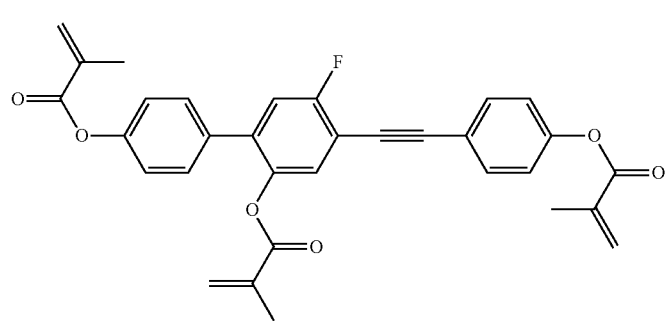
(1-108)

-continued
(1-109)
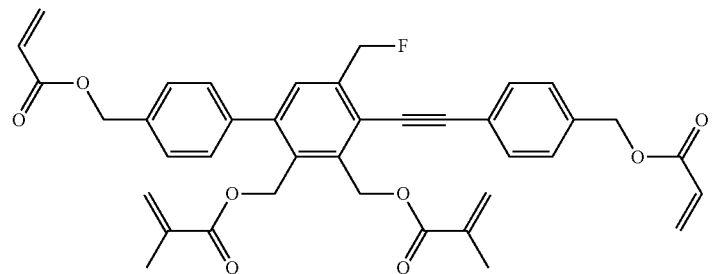
(1-110)
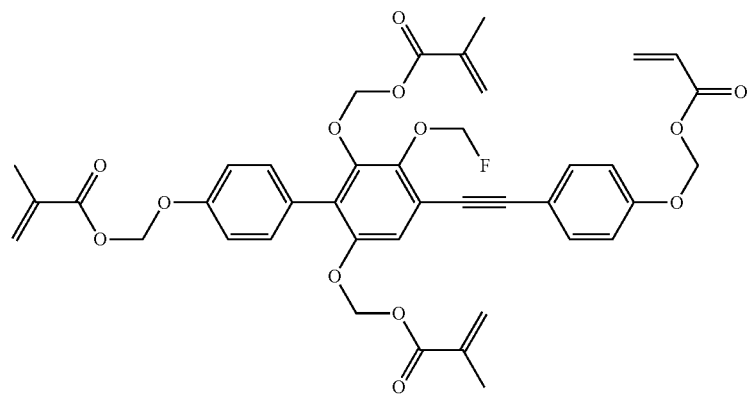
(1-111)
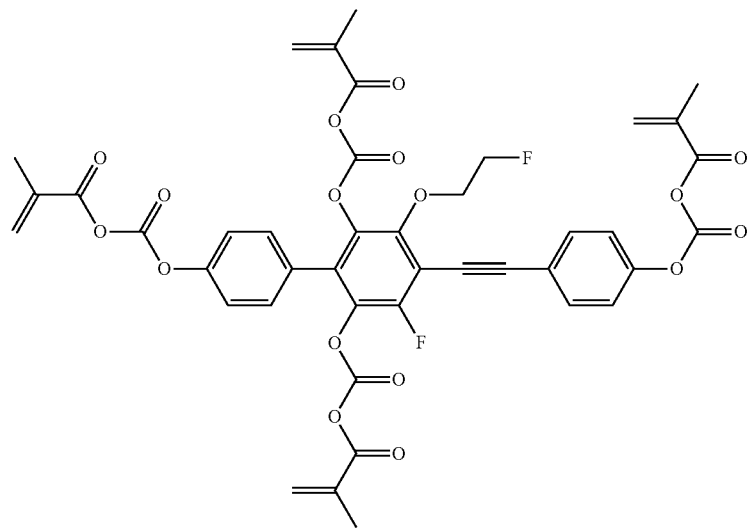
(1-112)
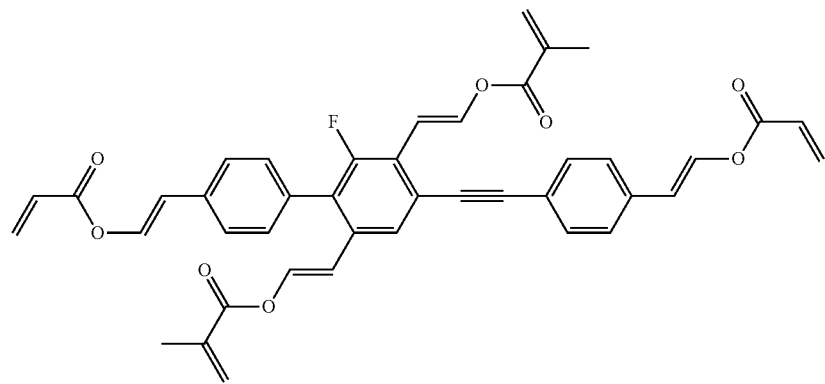

(1-113)
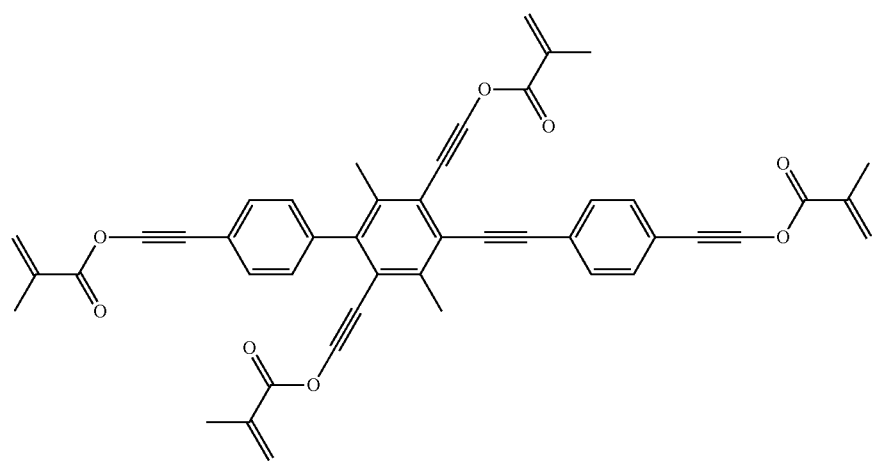
(1-114)
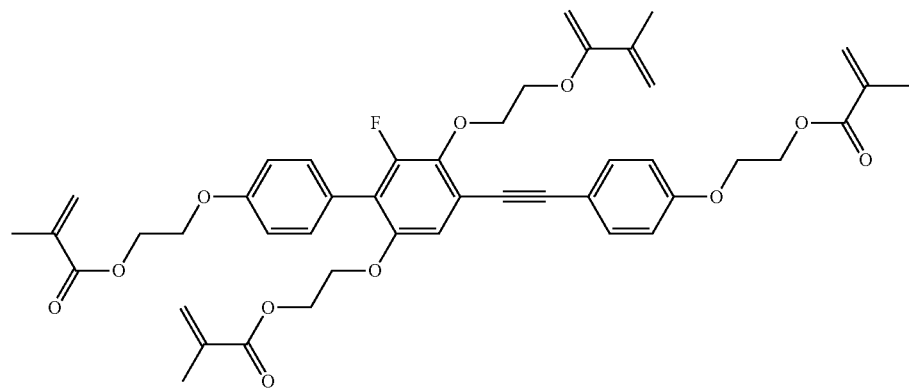
(1-115)
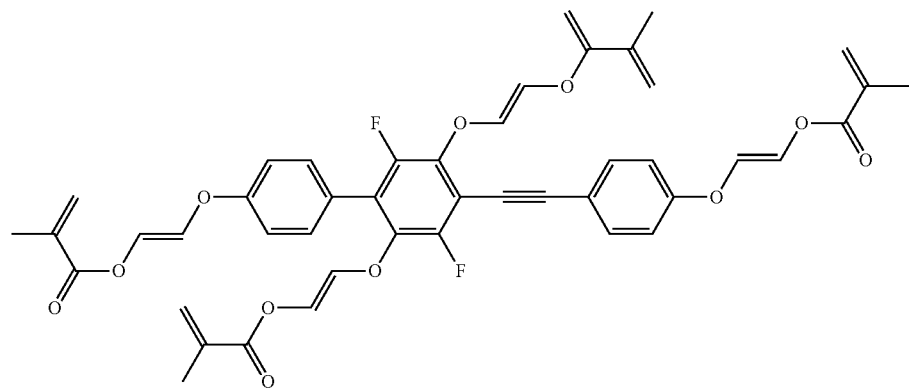
(1-116)
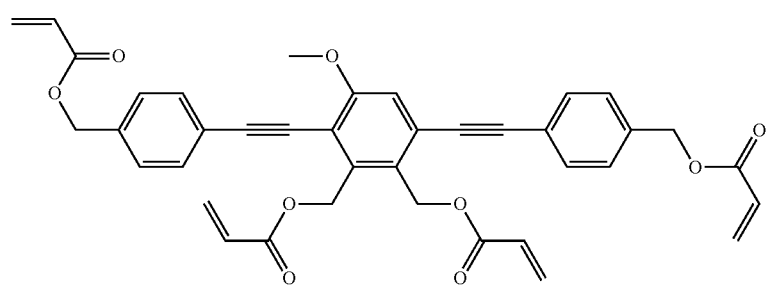

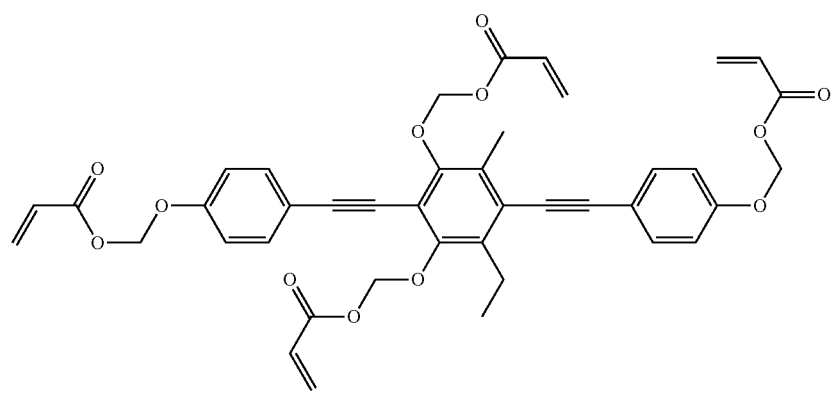
(1-117)
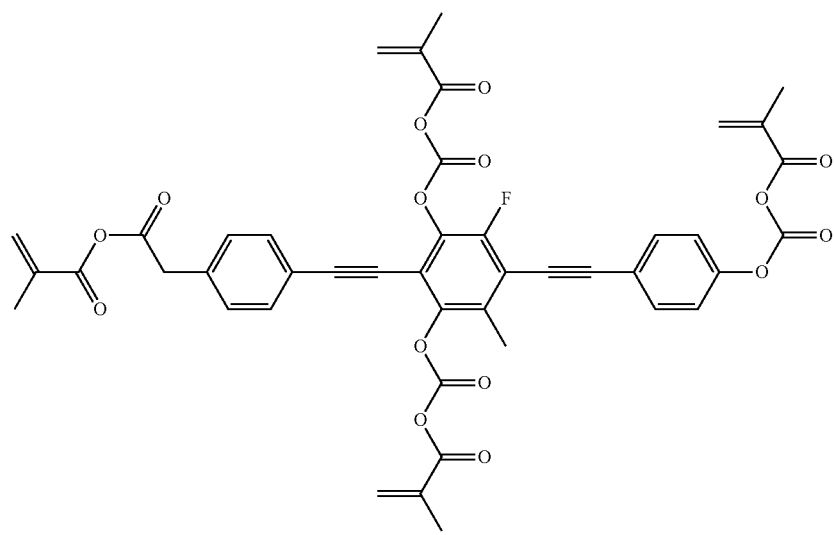
(1-118)
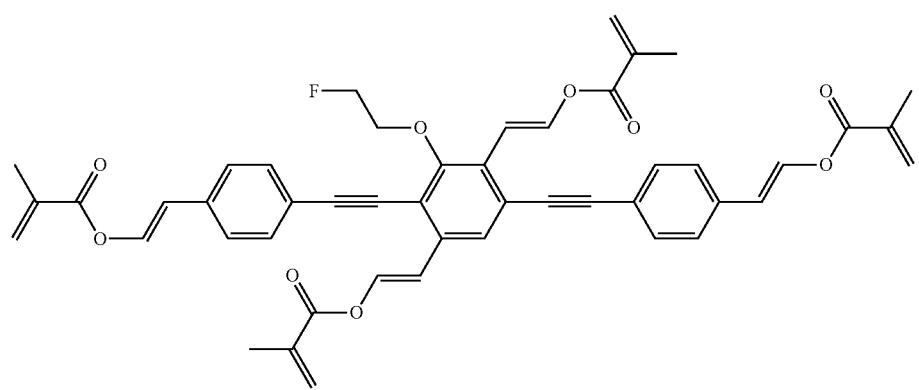
(1-119)

-continued
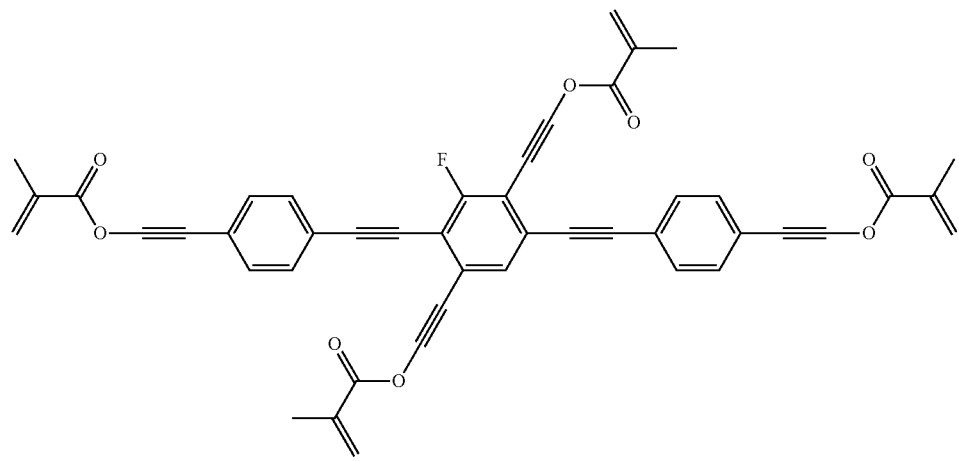
(1-120)
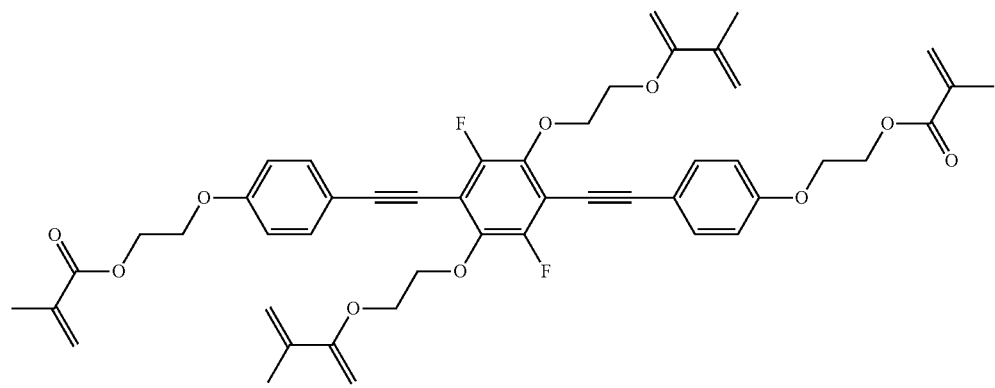
(1-121)
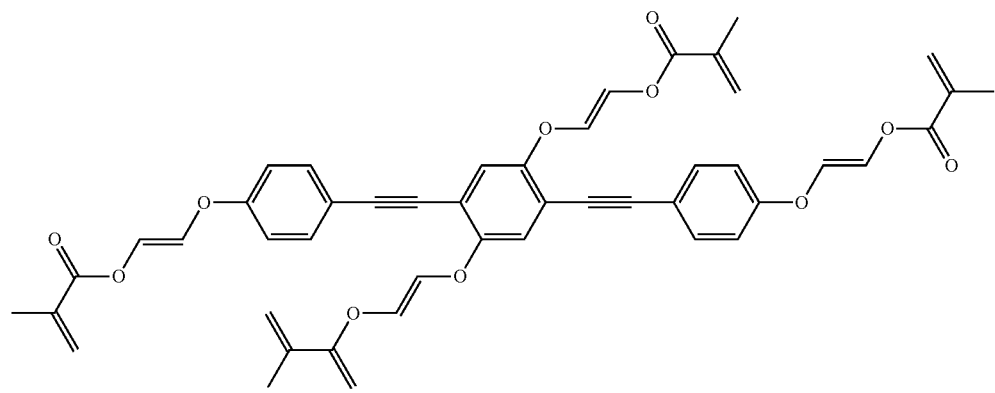
(1-122)
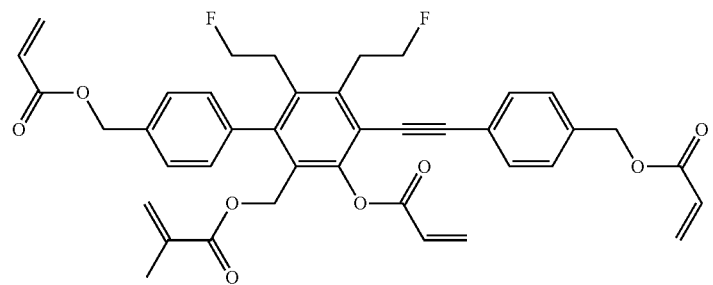
(1-123)

-continued
(1-124)
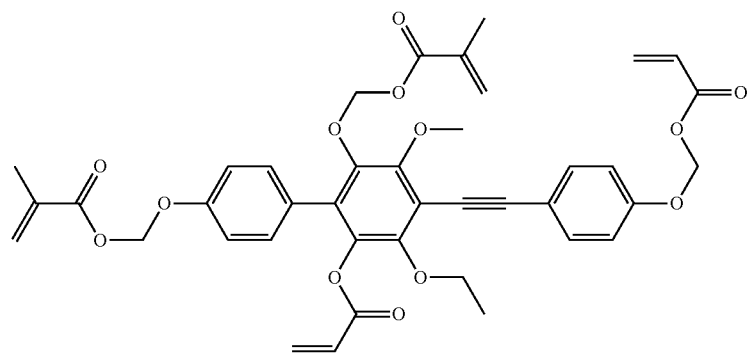
(1-125)
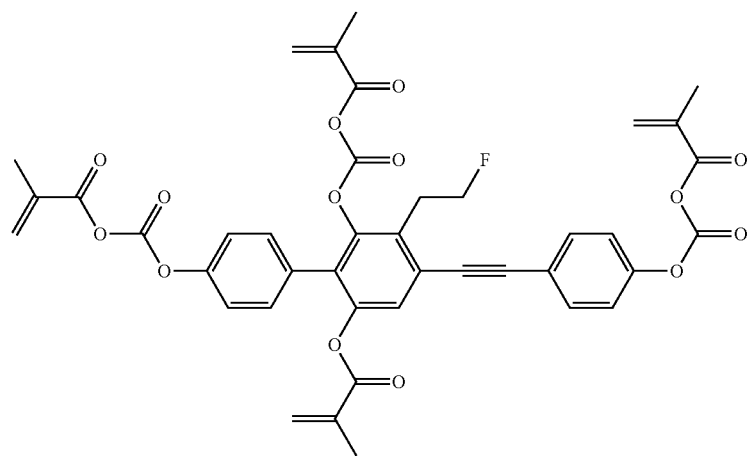
(1-126)
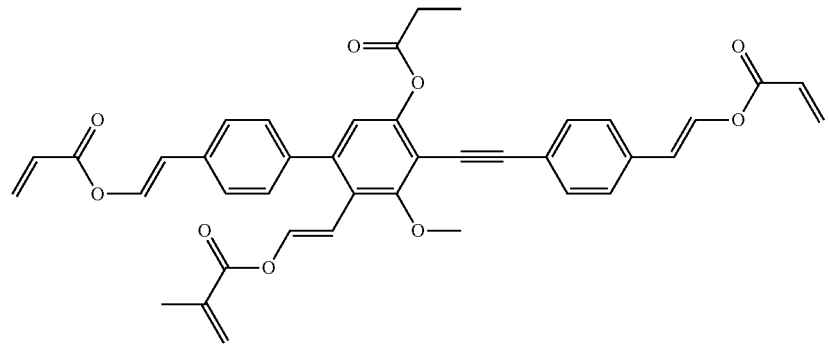
(1-127)
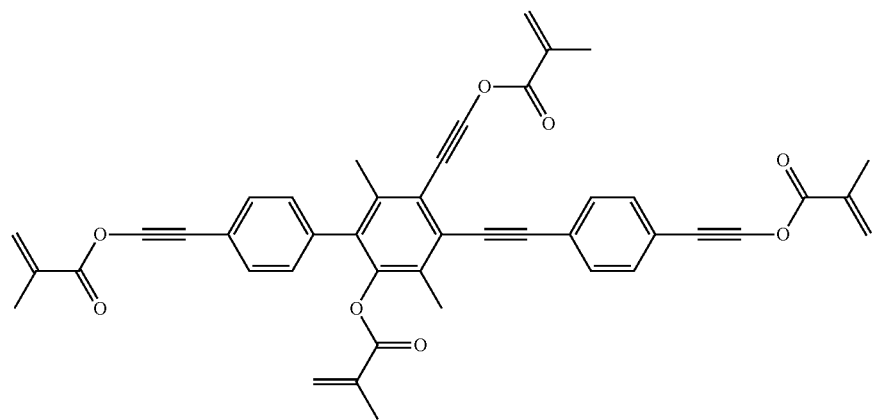

(1-128)
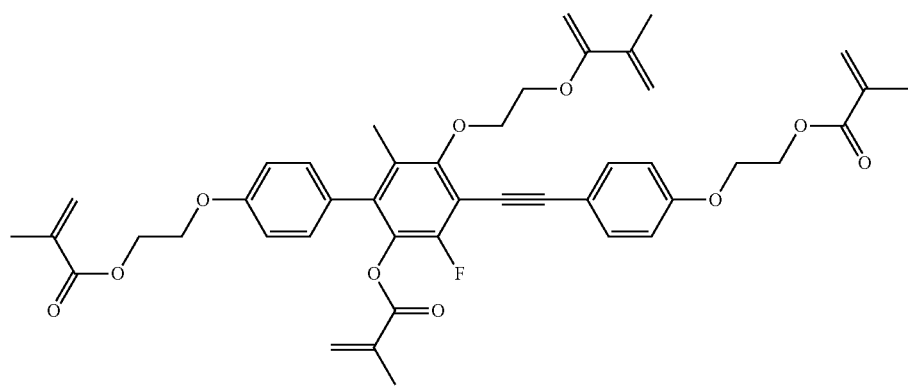
(1-129)
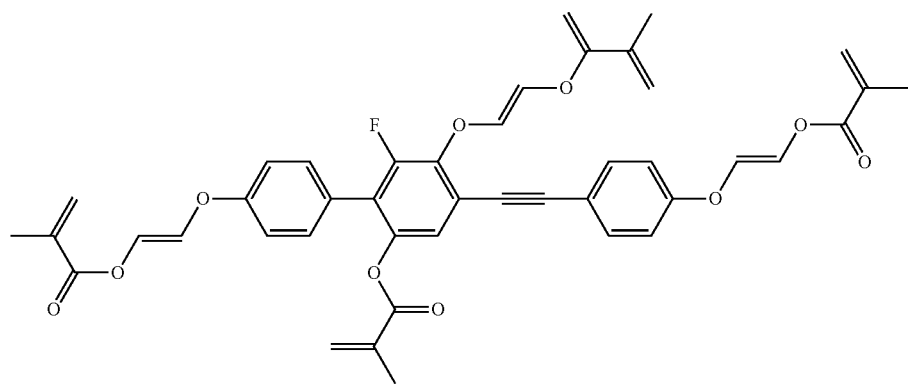
(1-130)
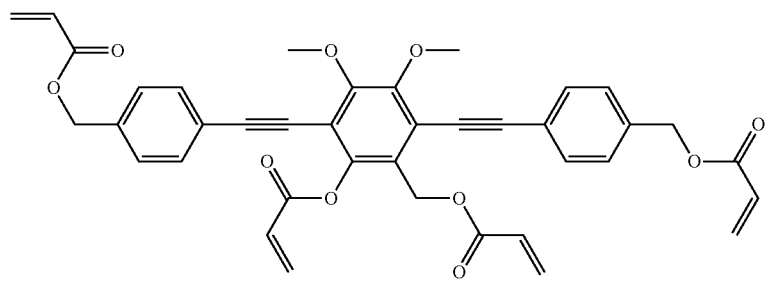
(1-131)
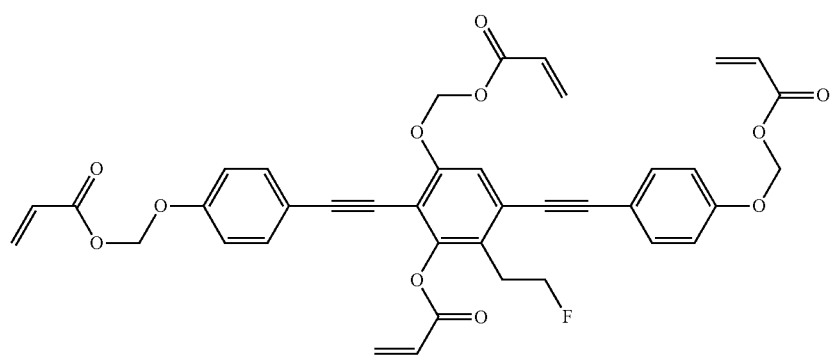

(1-132)
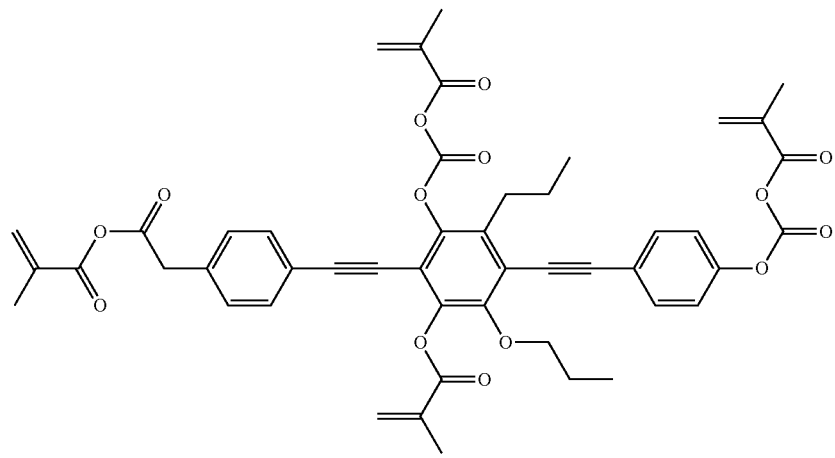
(1-133)
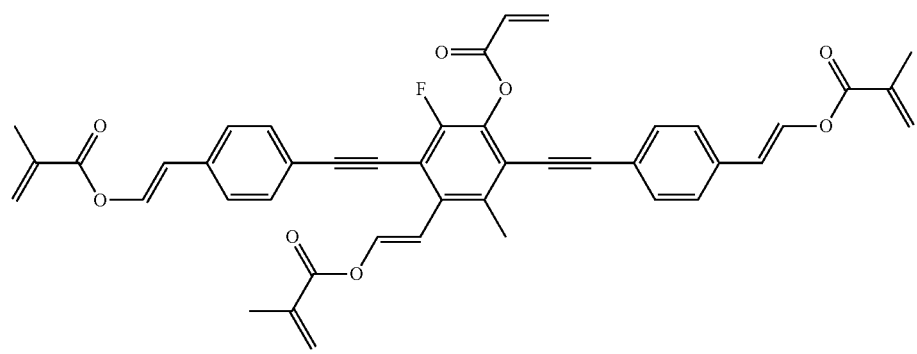
(1-134)
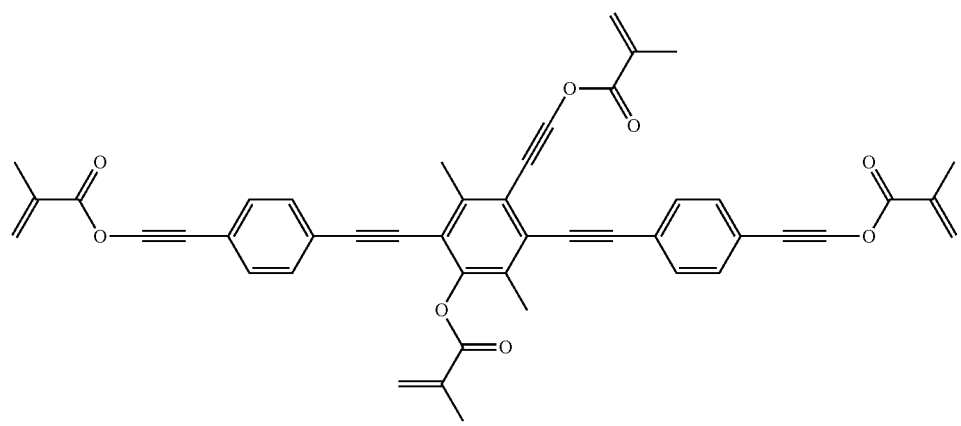
(1-135)
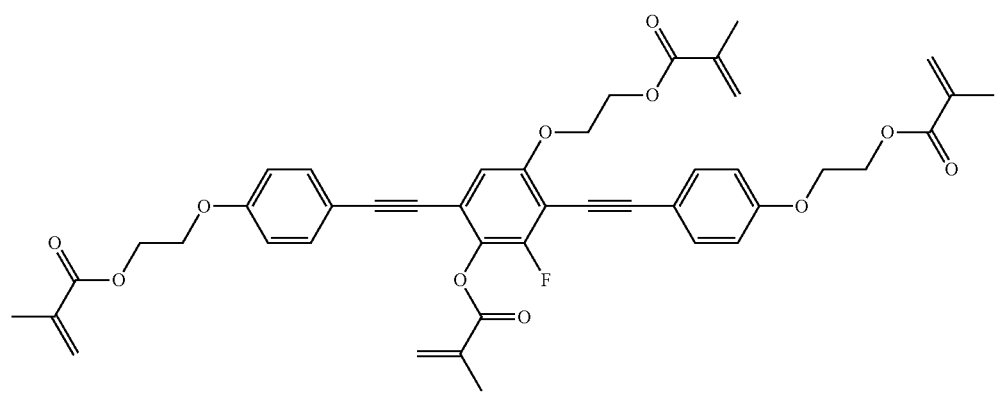

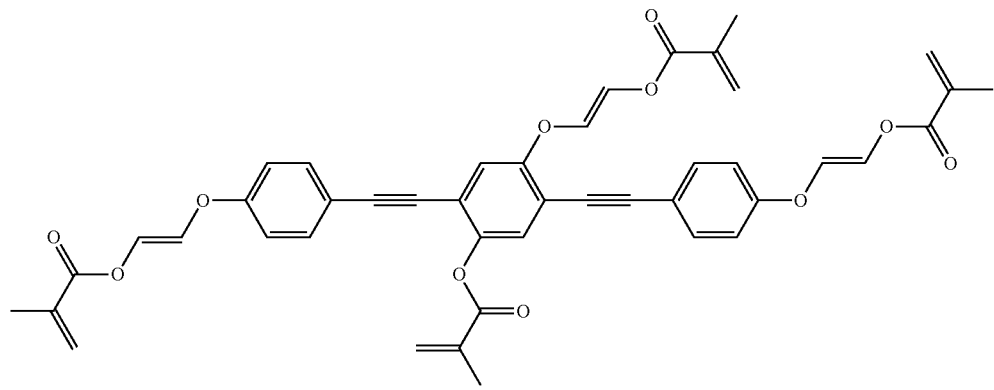
(1-136)
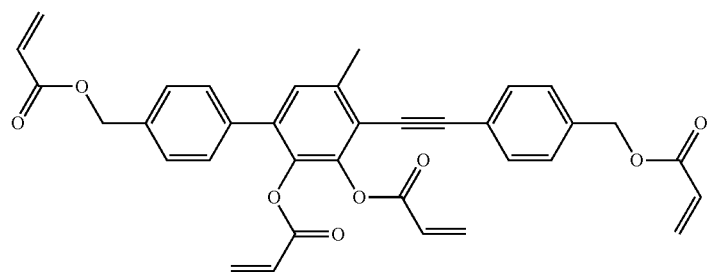
(1-137)
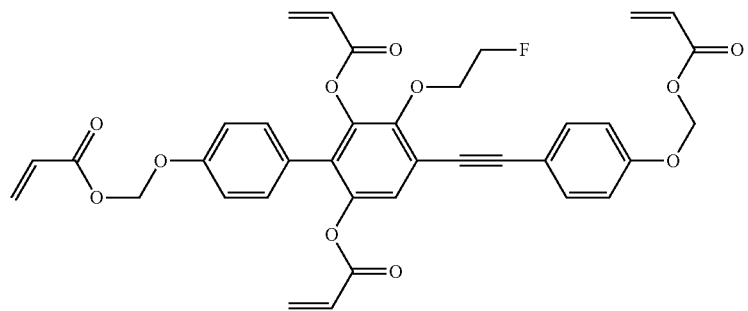
(1-138)
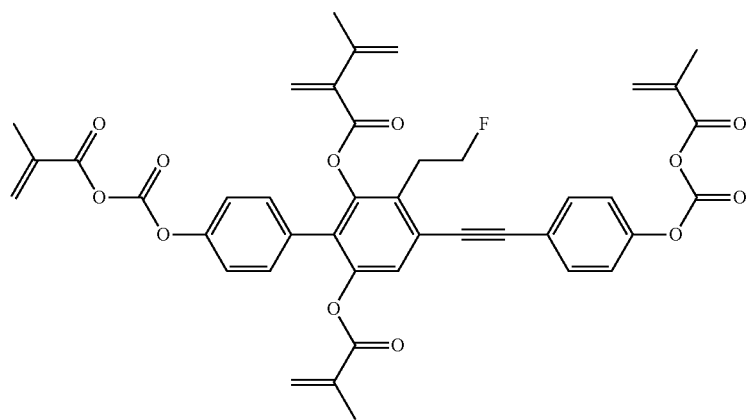
(1-139)

-continued
(1-140)
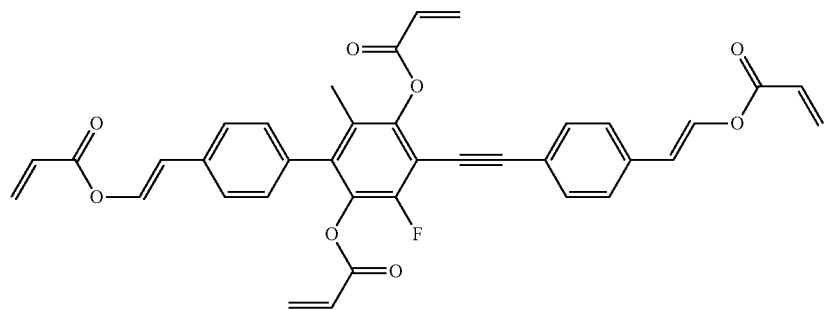
(1-141)
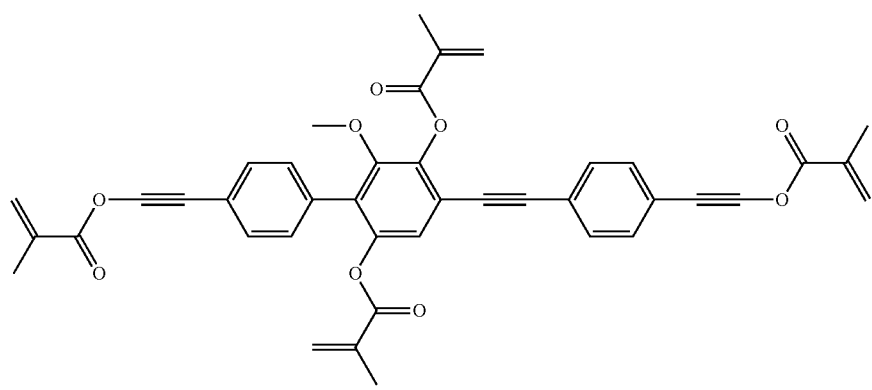
(1-142)
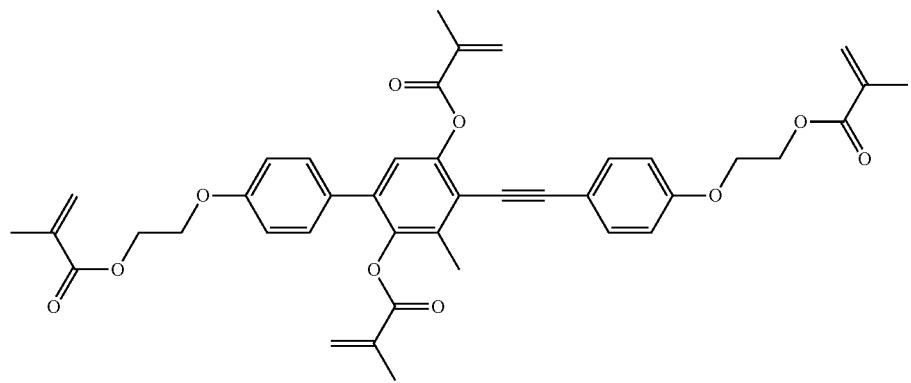
(1-143)
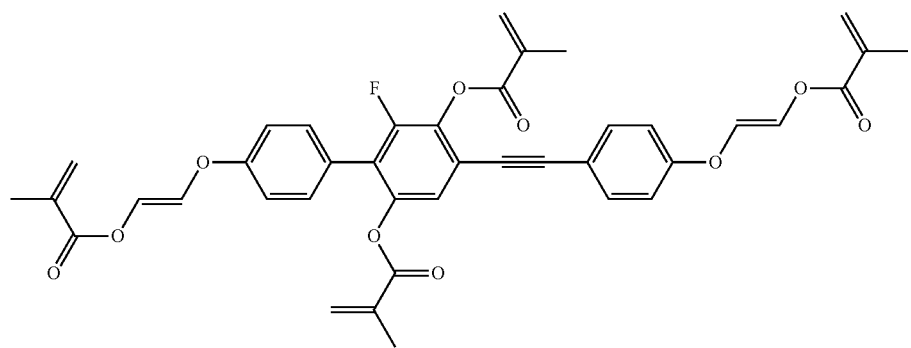

(1-144)
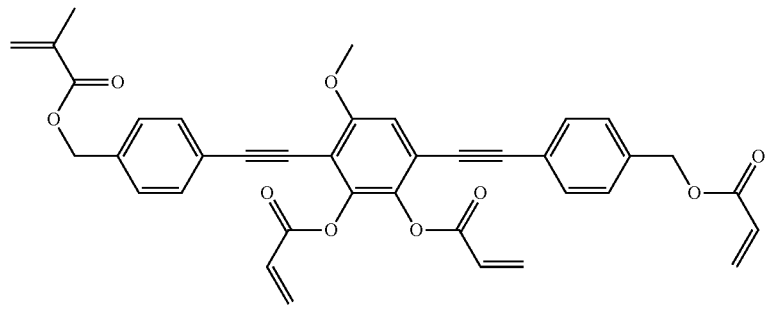
(1-145)
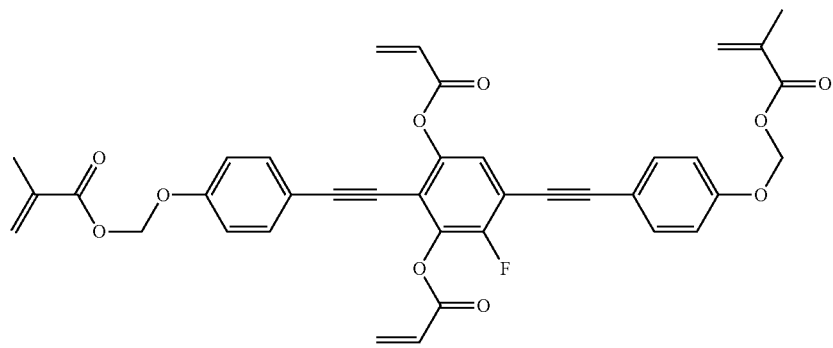
(1-146)
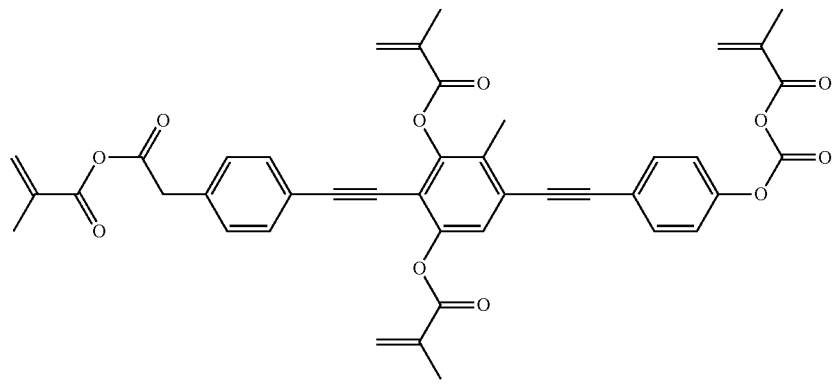
(1-147)
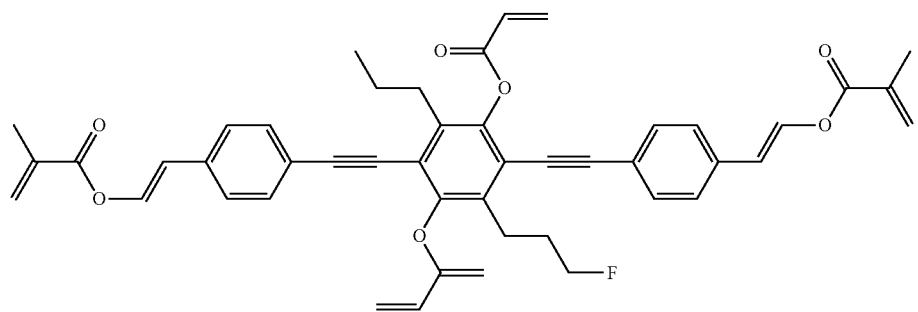

-continued
(1-148)
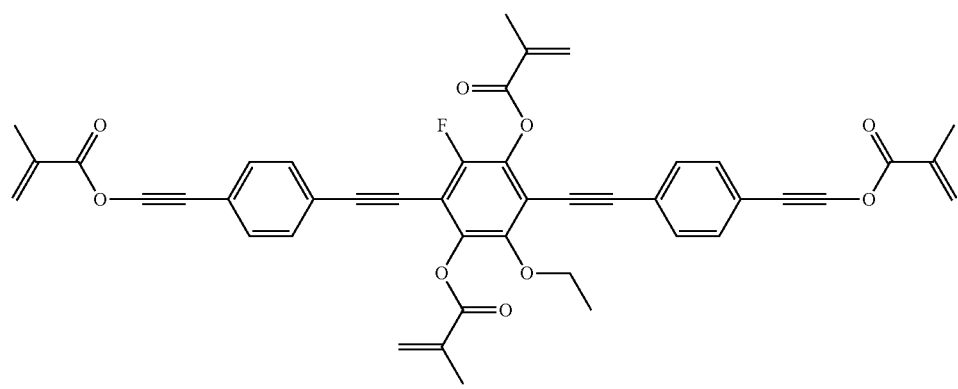
(1-149)
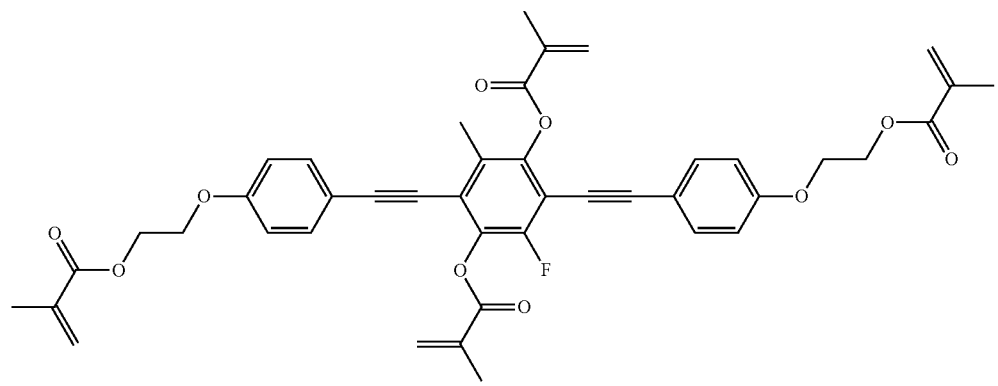
(1-150)
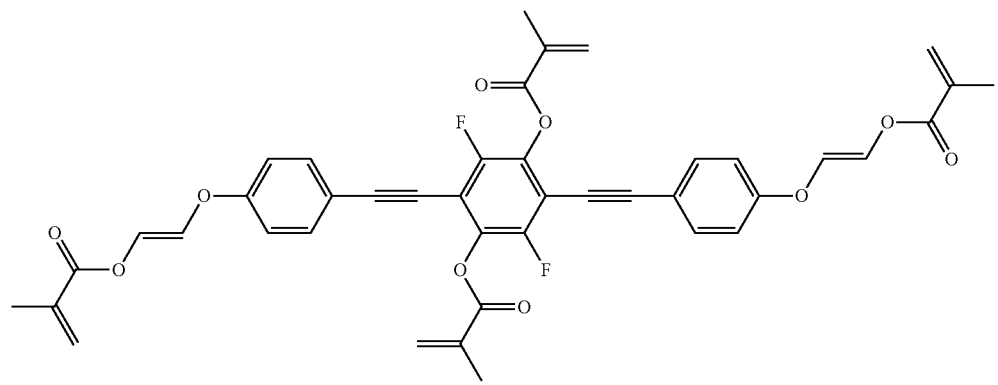
(1-151)
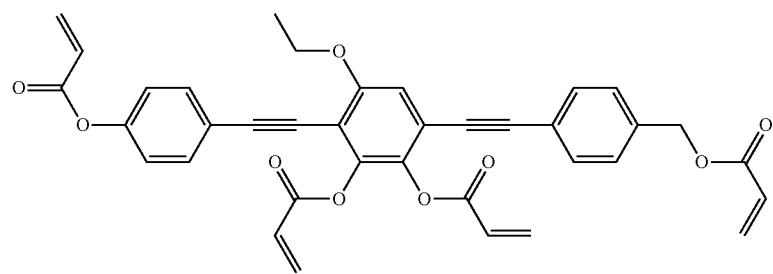

(1-152)
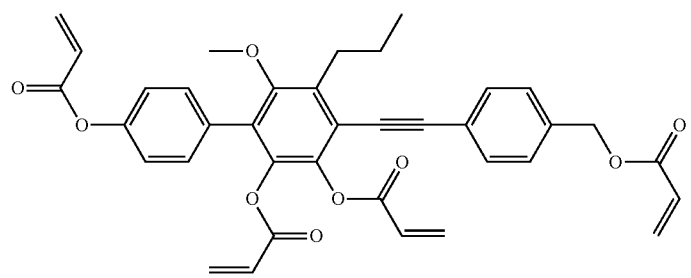
(1-153)
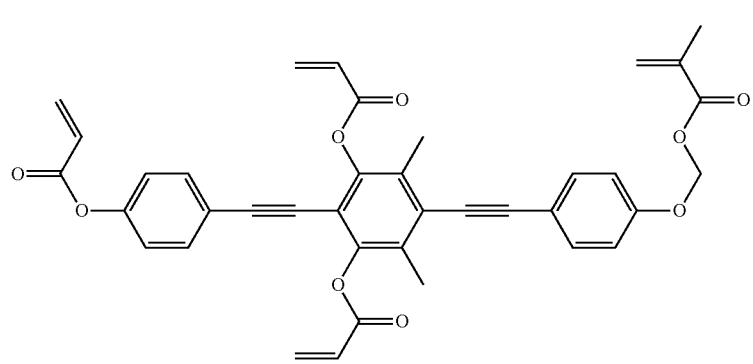
(1-154)
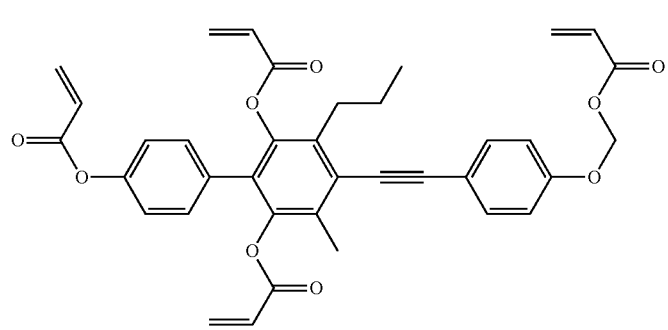
(1-155)
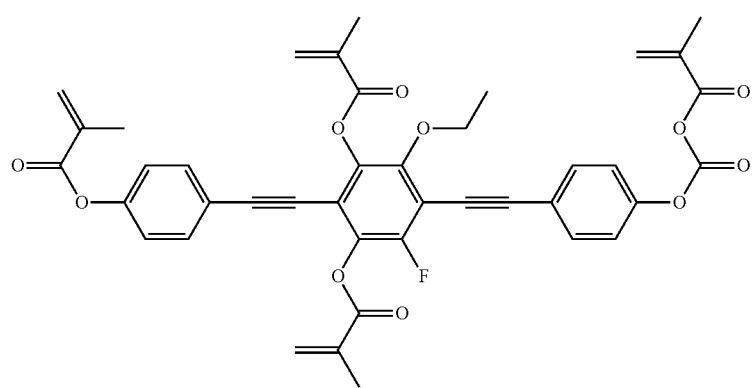

-continued
(1-156)
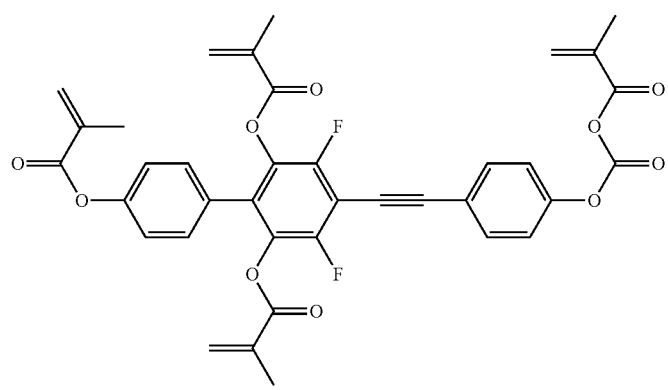
(1-157)
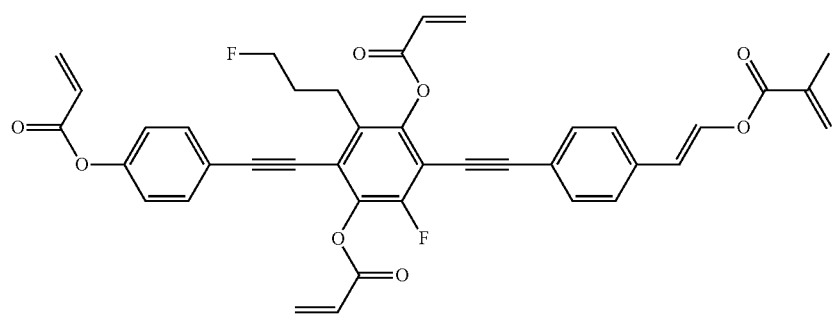
(1-158)
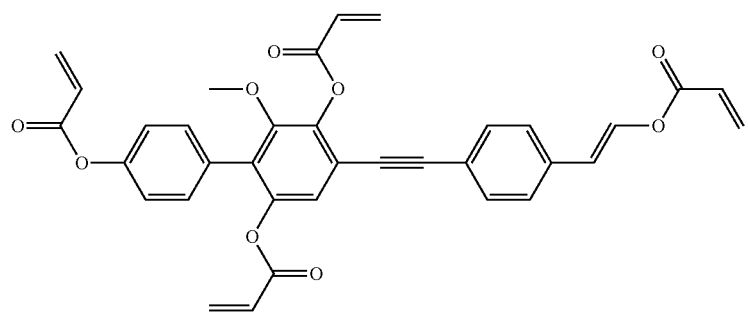
(1-159)
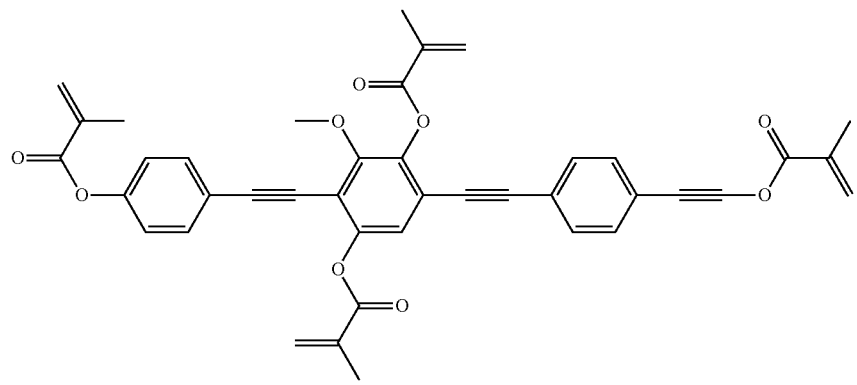

(1-160)
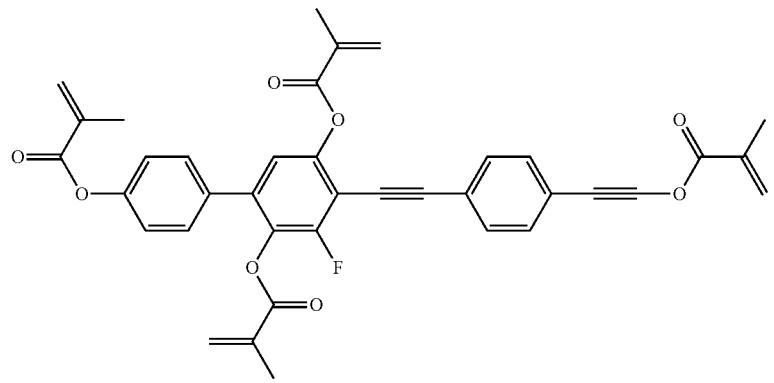
(1-161)
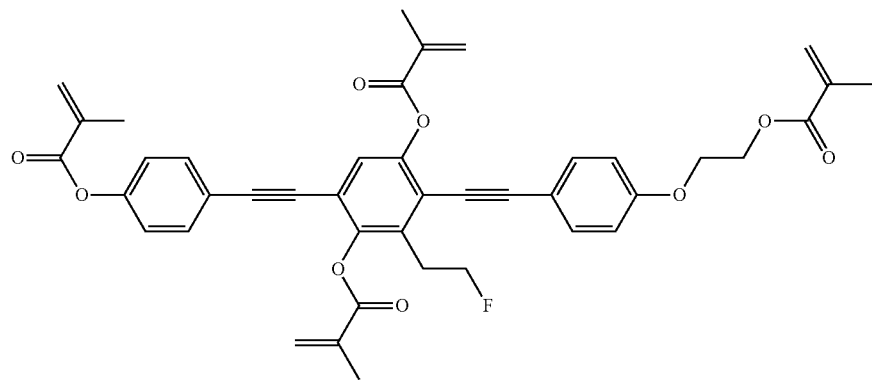
(1-162)
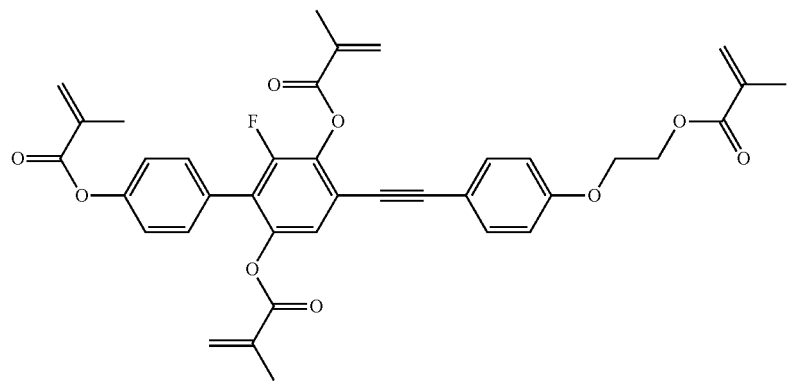
(1-163)
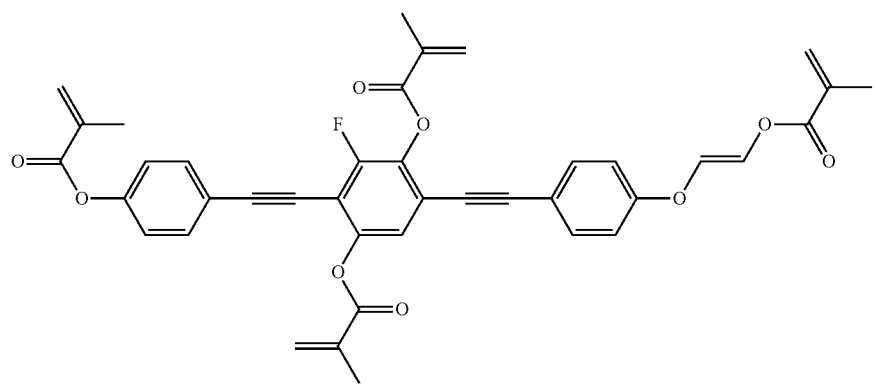

-continued
(1-164)
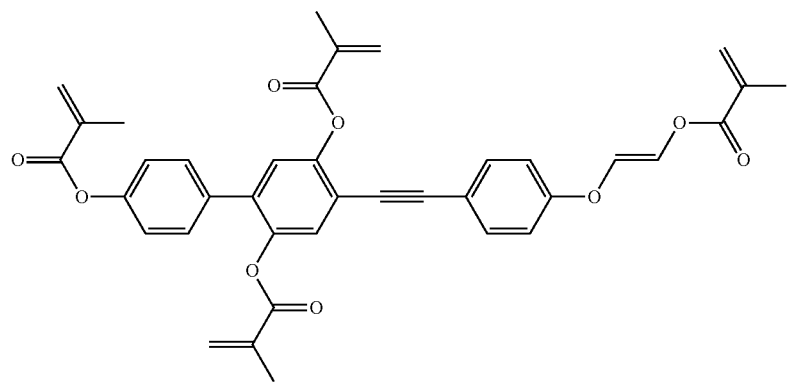
(1-165)
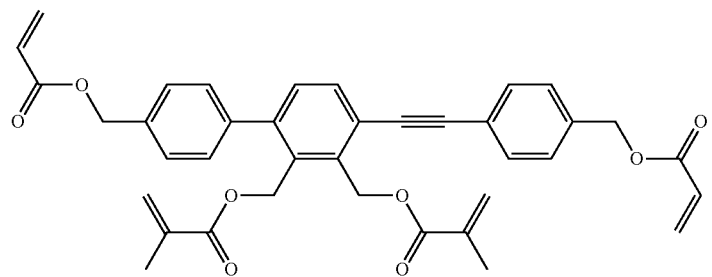
(1-166)
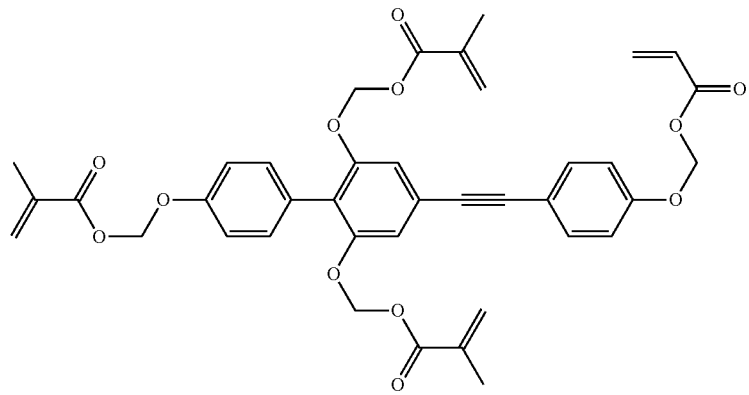
(1-167)
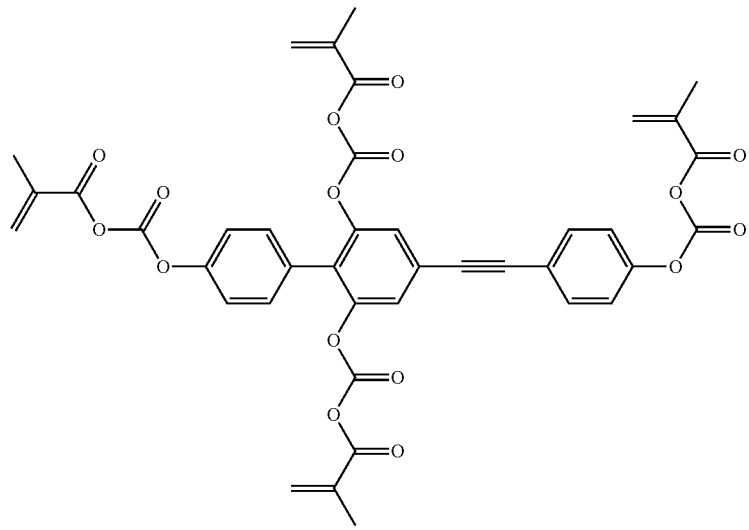

(1-168)
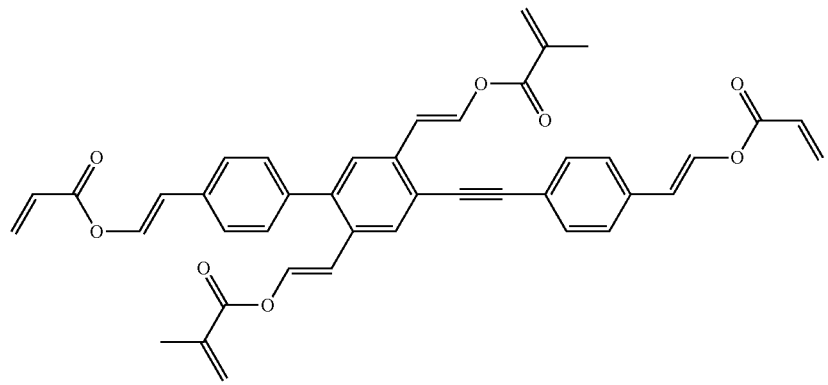
(1-169)
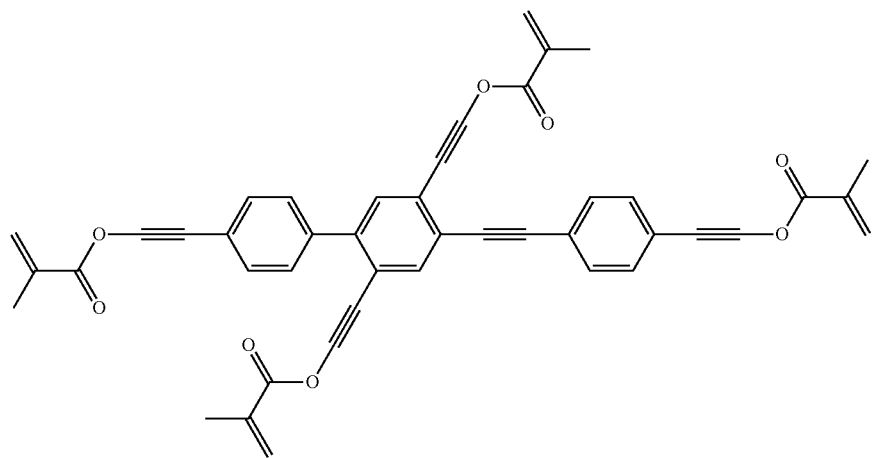
(1-170)
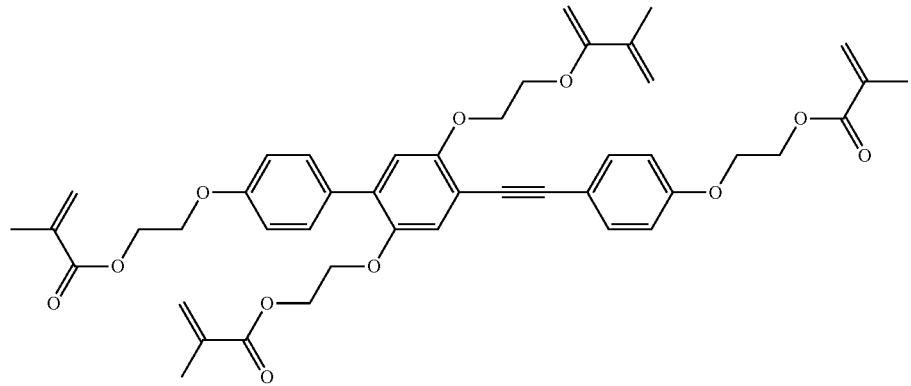
(1-171)
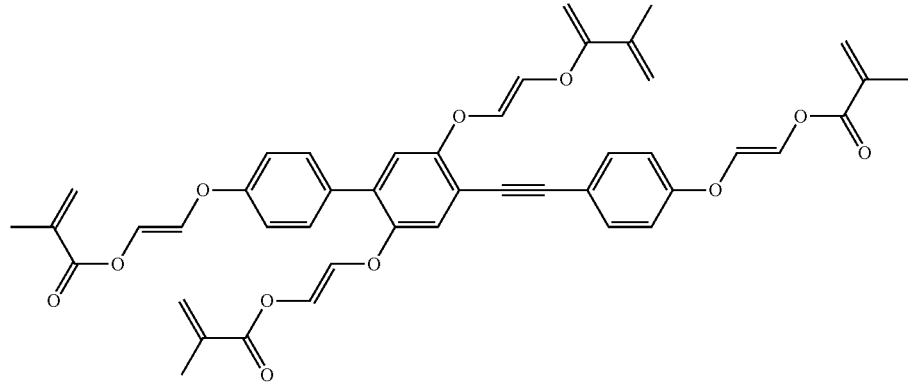

(1-172)
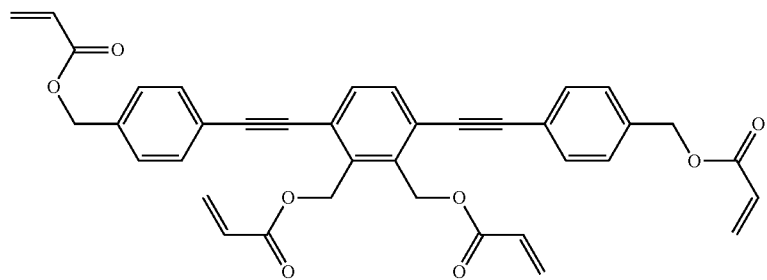
(1-173)
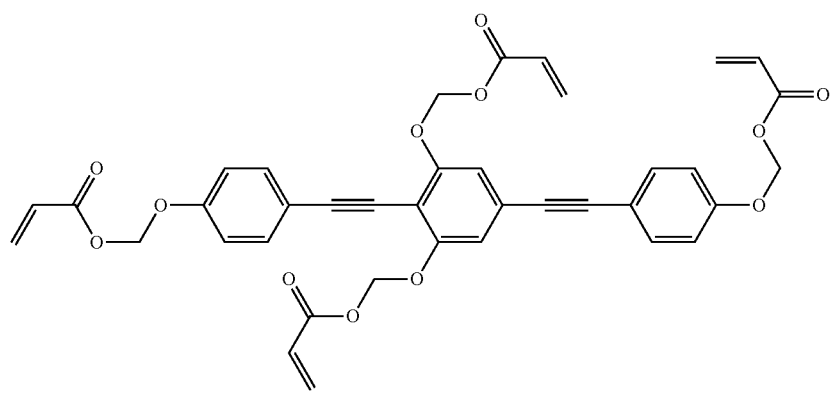
(1-174)
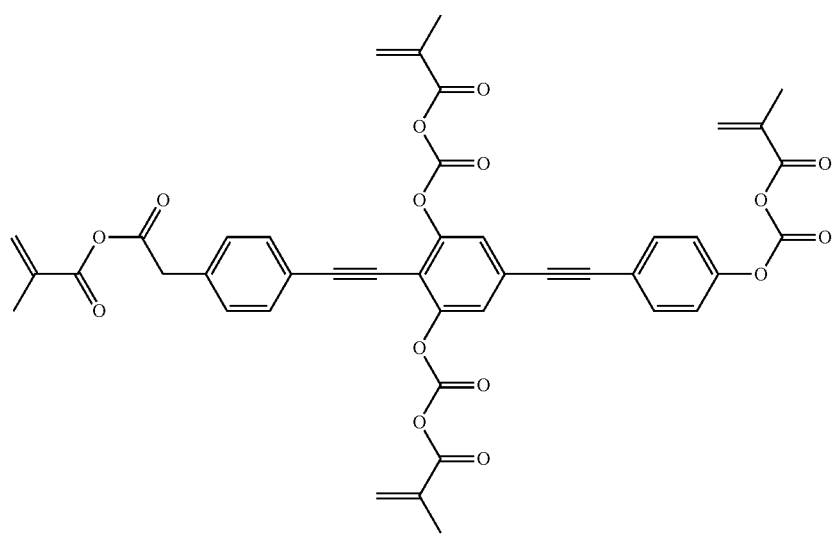
(1-175)
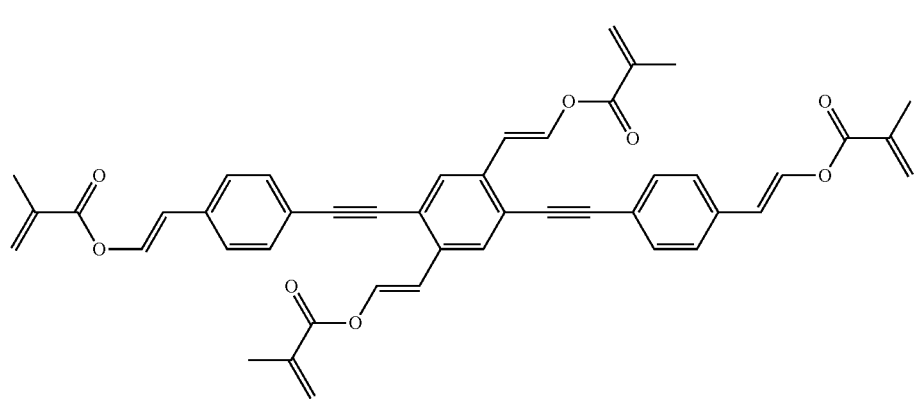

(1-176)
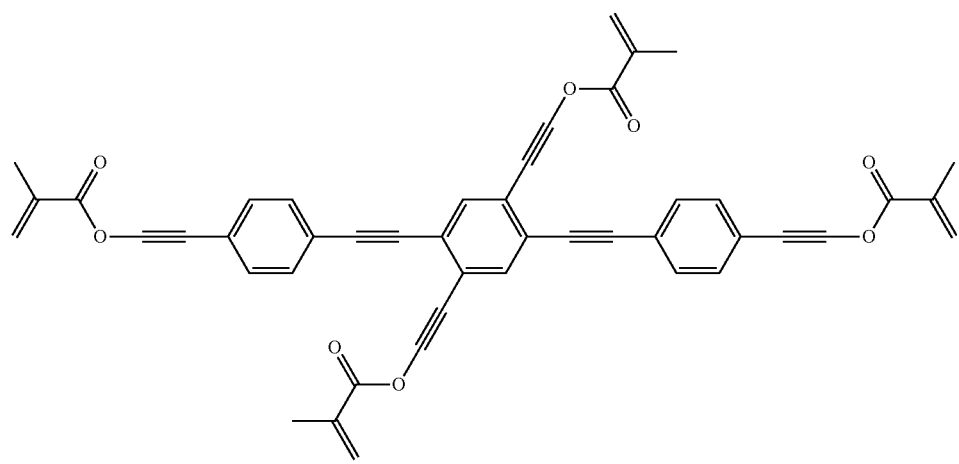
(1-177)
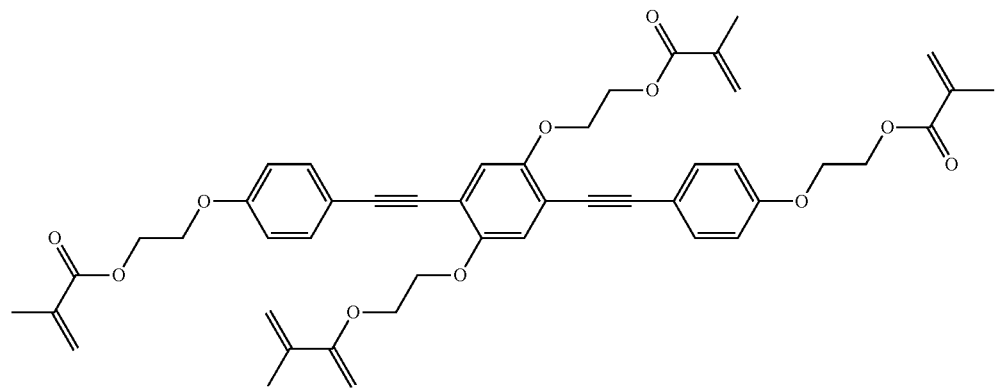
(1-178)
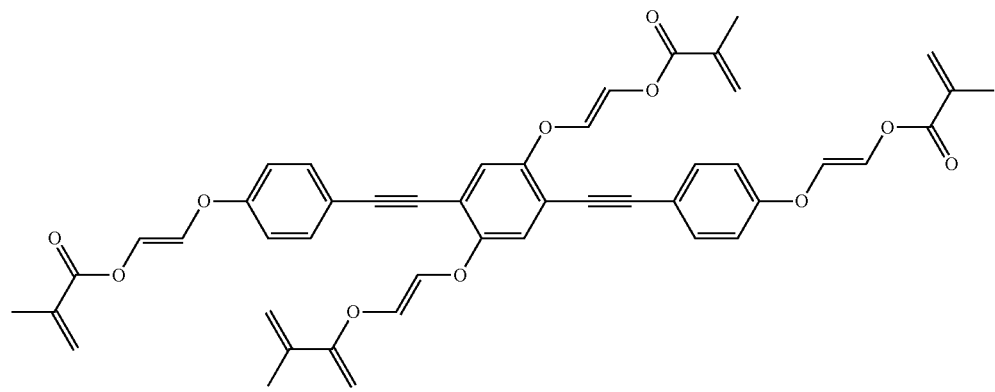
(1-179)
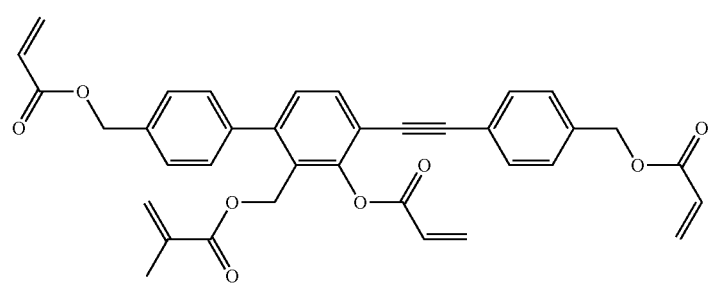

-continued
(1-180)
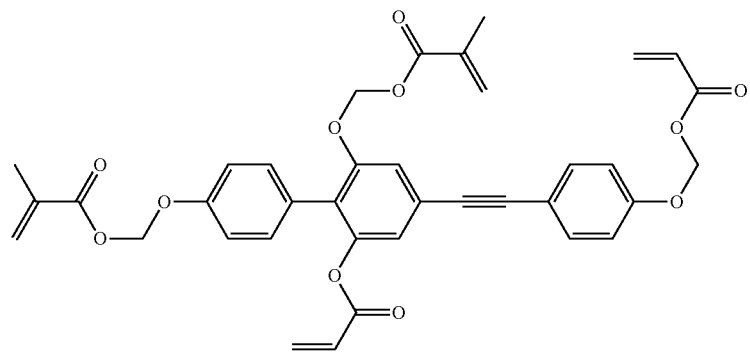
(1-181)
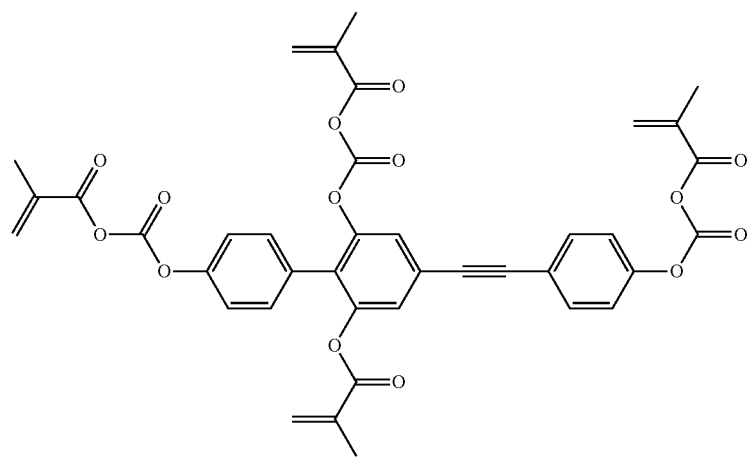
(1-182)
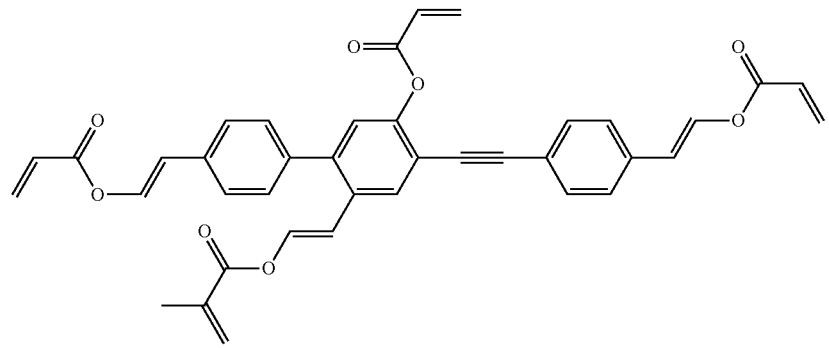
(1-183)
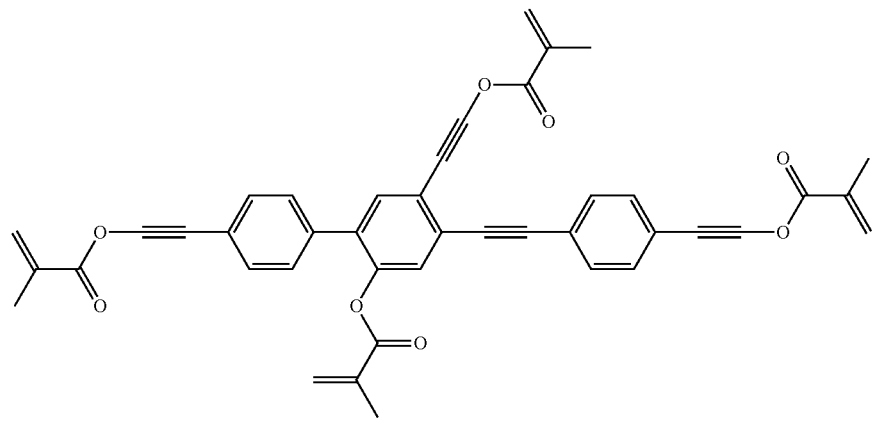

(1-184)
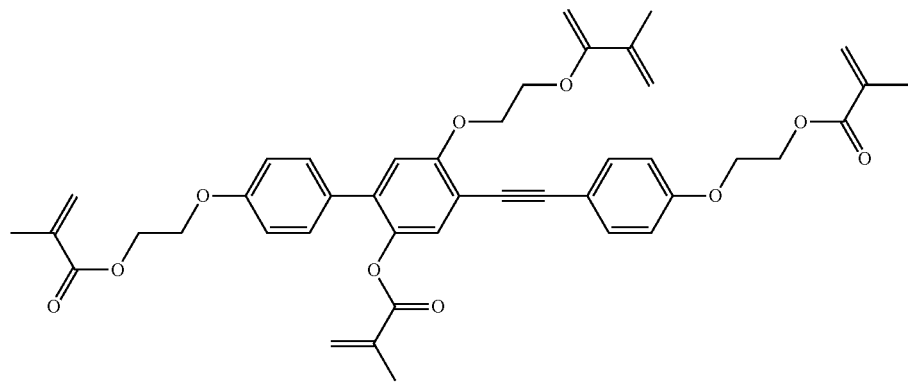
(1-185)
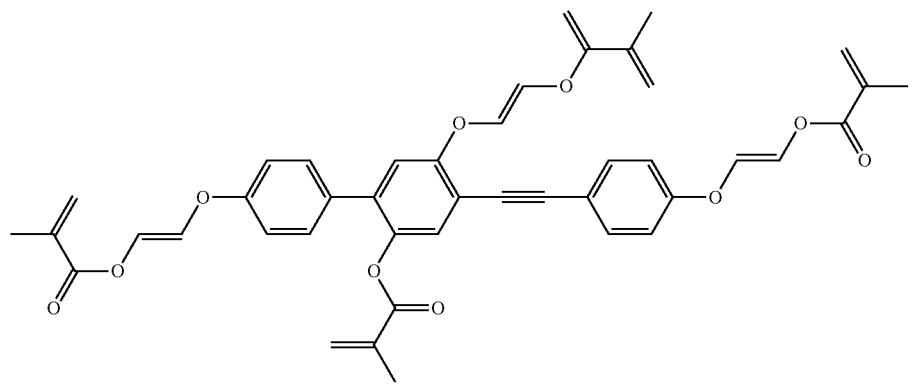
(1-186)
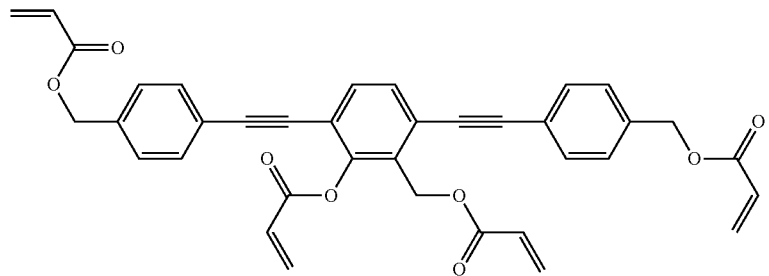
(1-187)
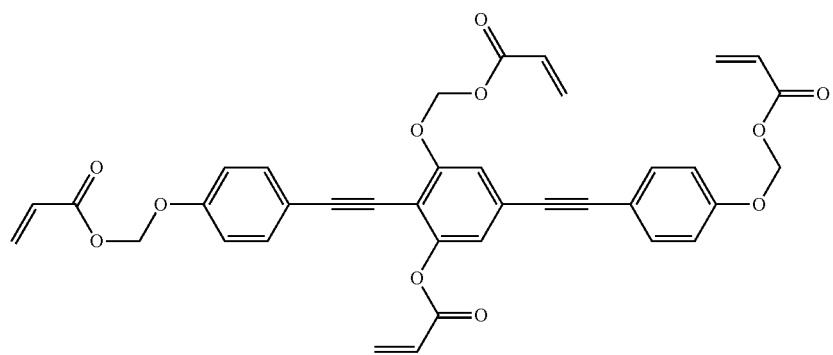

-continued
(1-188)
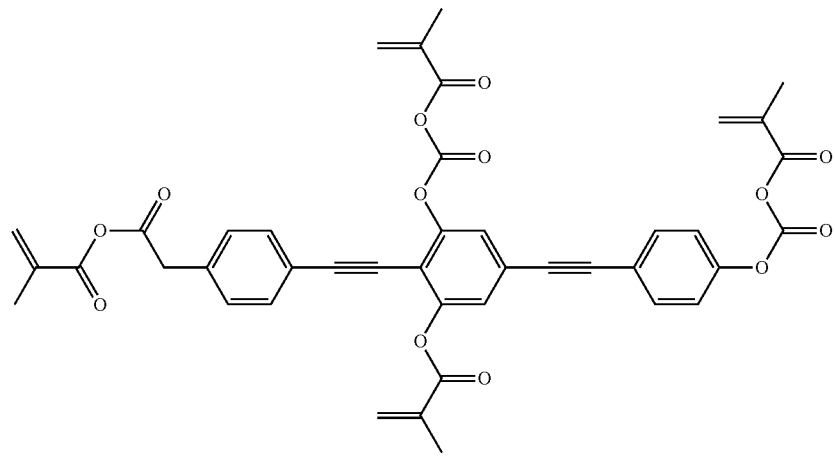
(1-189)
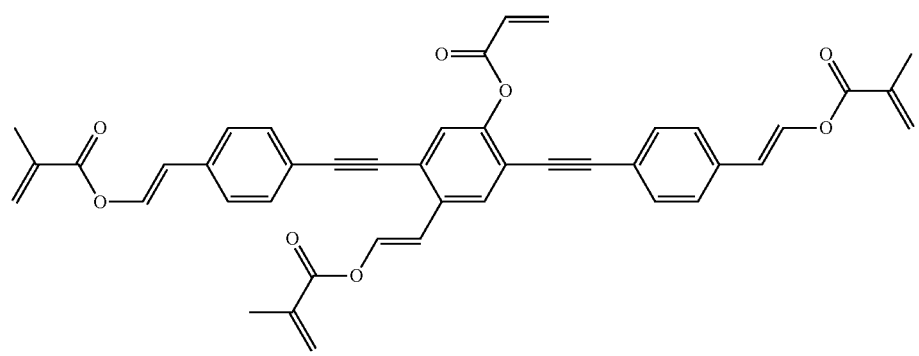
(1-190)
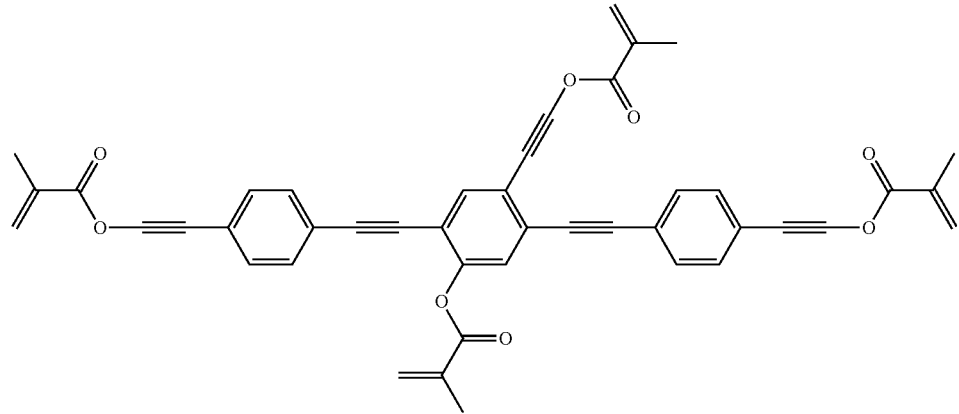
(1-191)
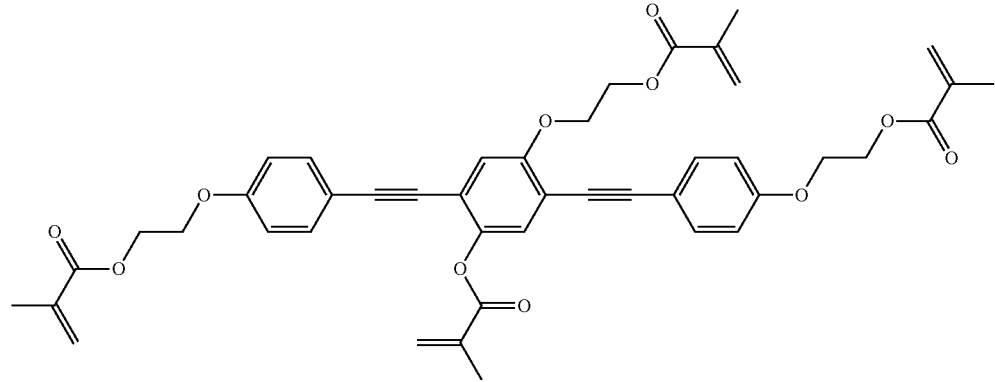

(1-192)
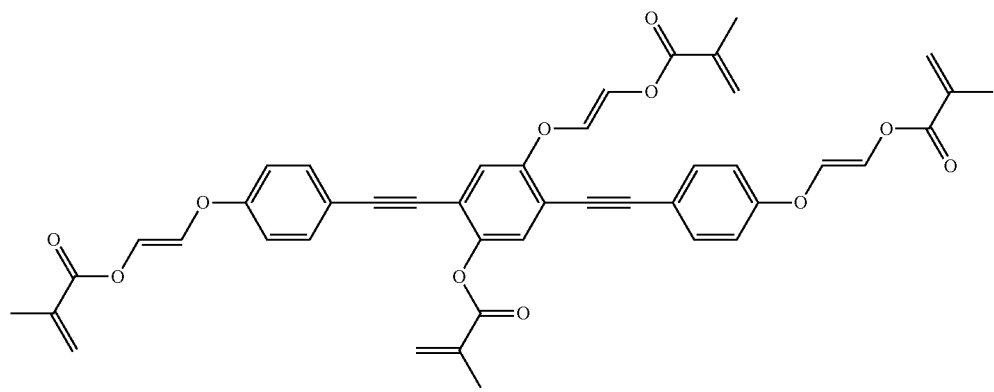
(1-193)
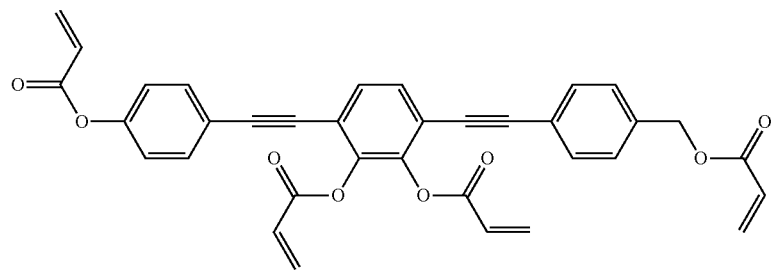
(1-194)
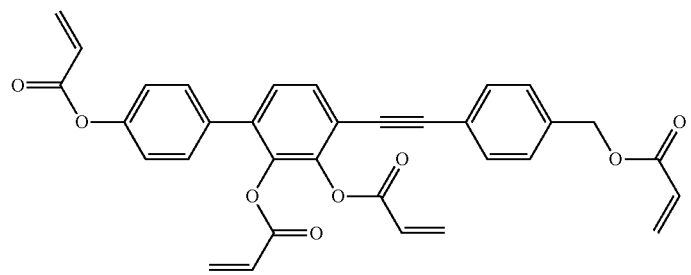
(1-195)
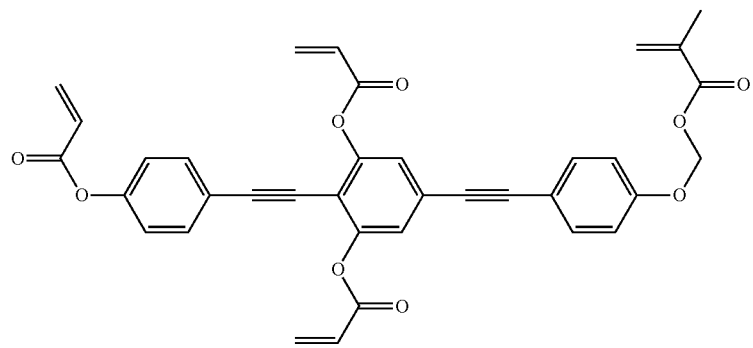
(1-196)
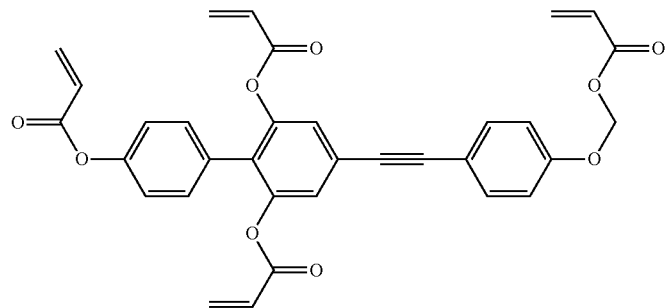

-continued
(1-197)
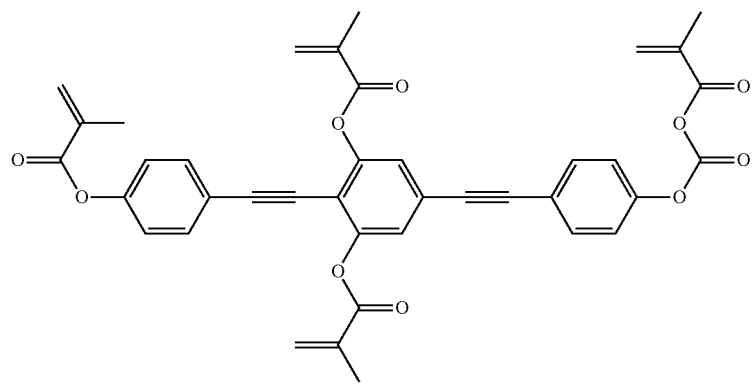
(1-198)
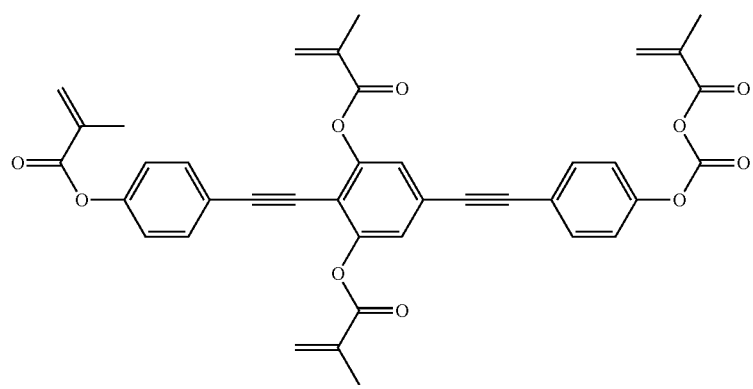
(1-199)
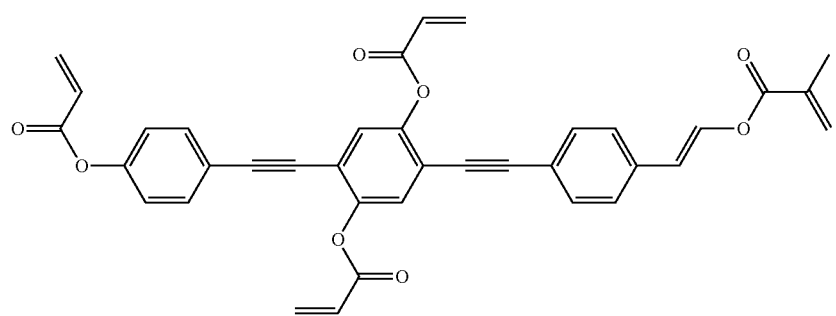
(1-200)
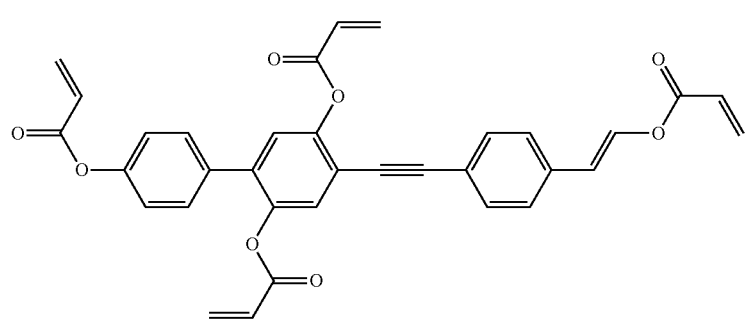

(1-201)
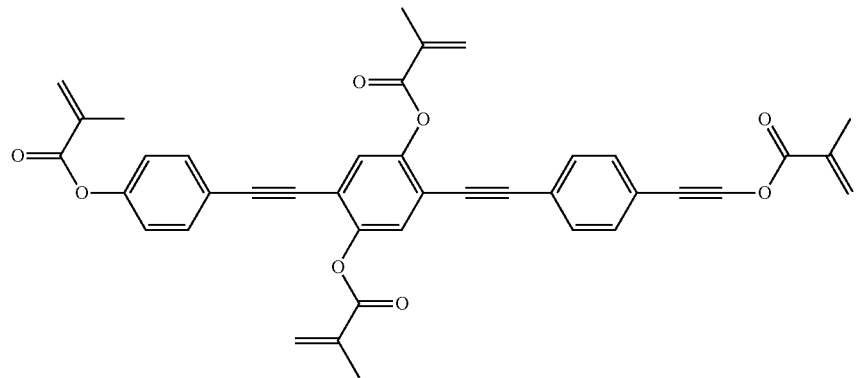
(1-202)
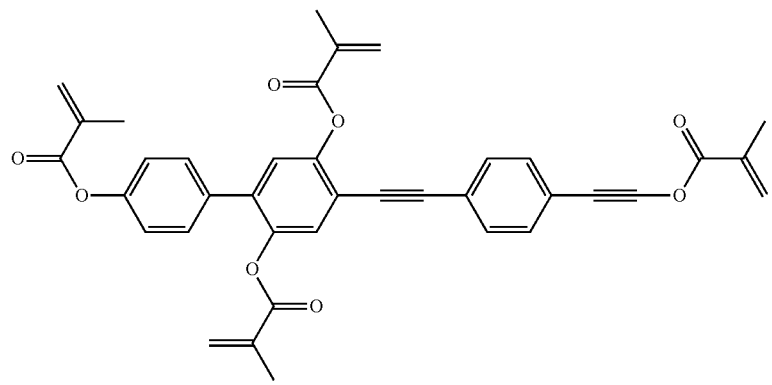
(1-203)
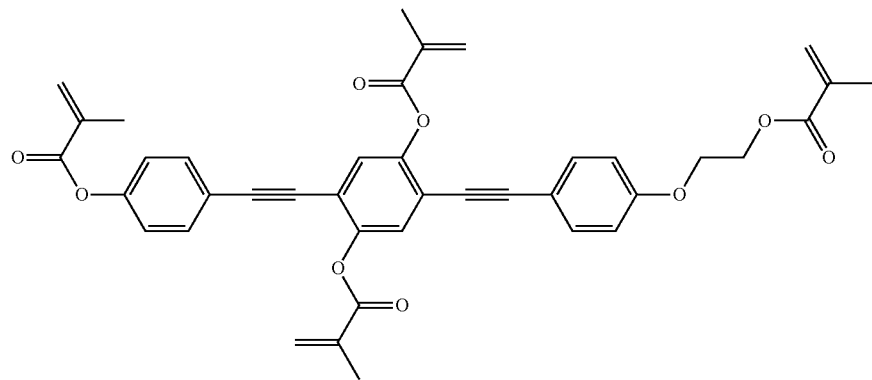
(1-204)
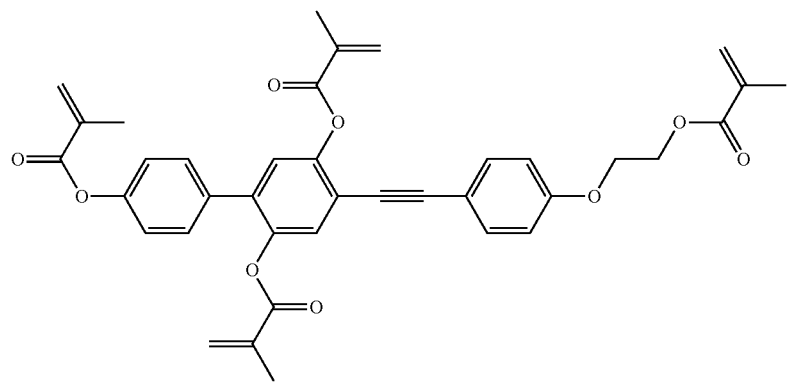

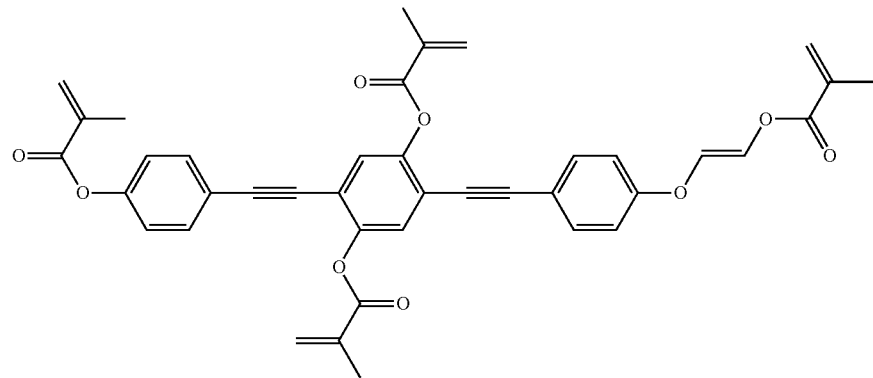
(1-205)
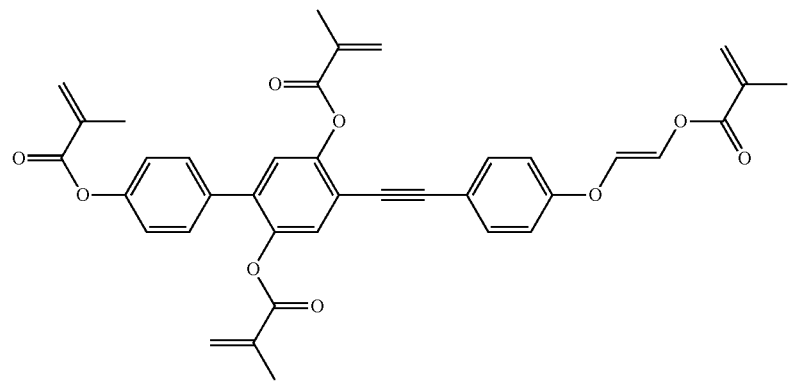
(1-206)
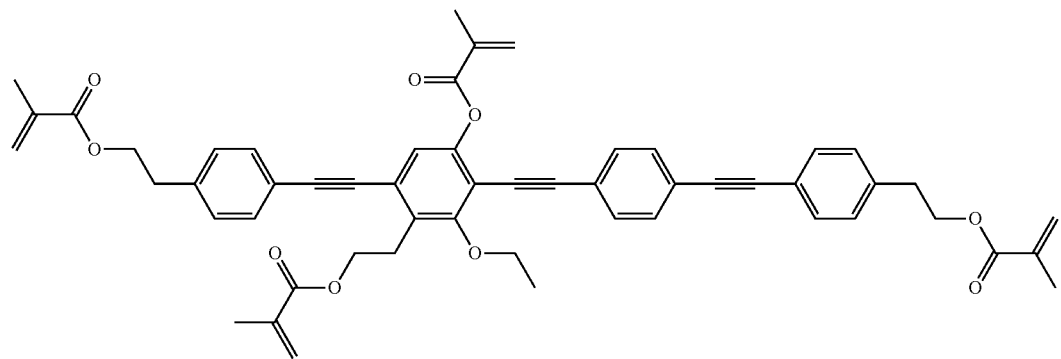
(1-207)
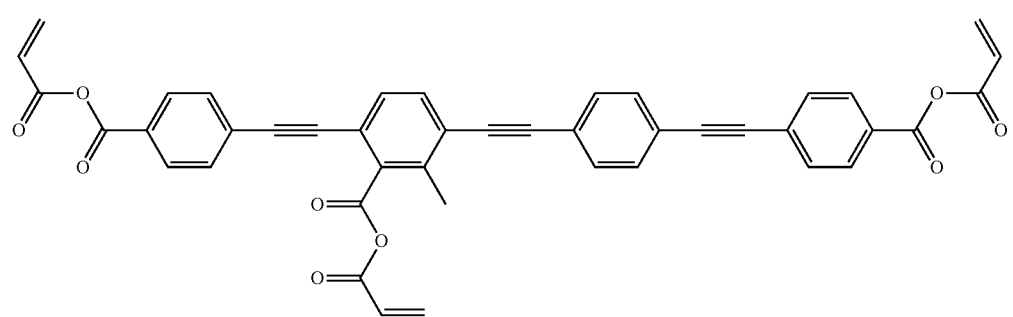
(1-208)

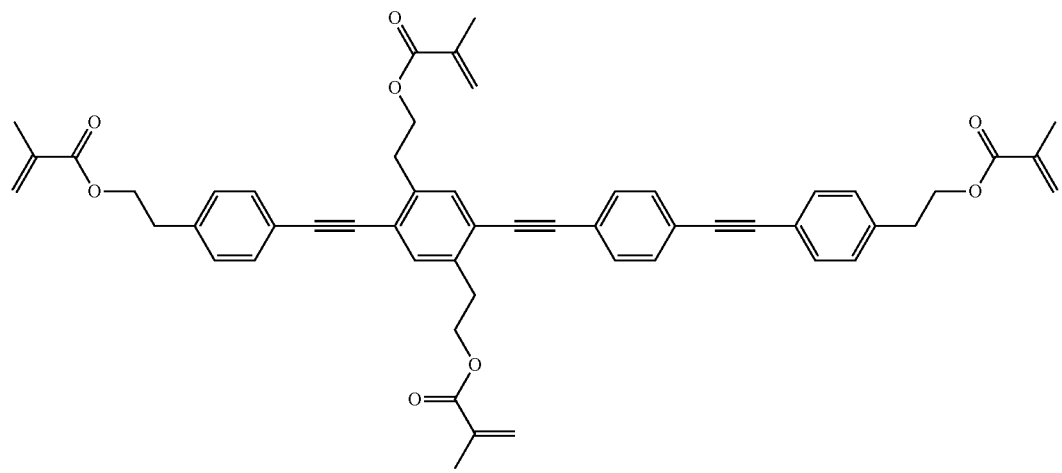
(1-209)
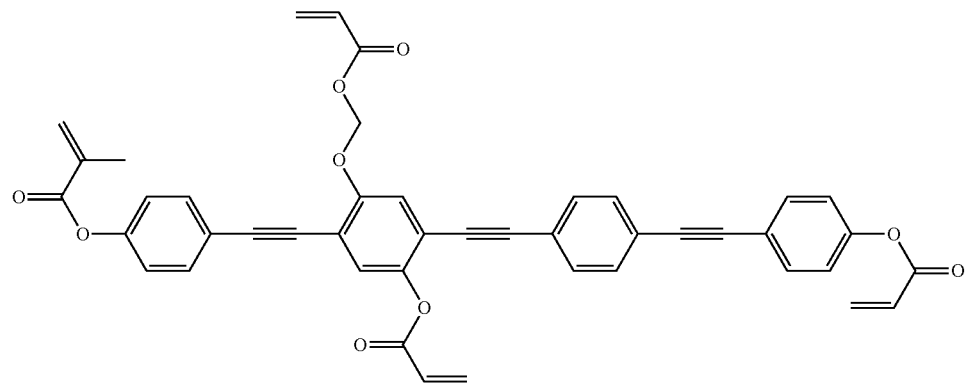
(1-210)
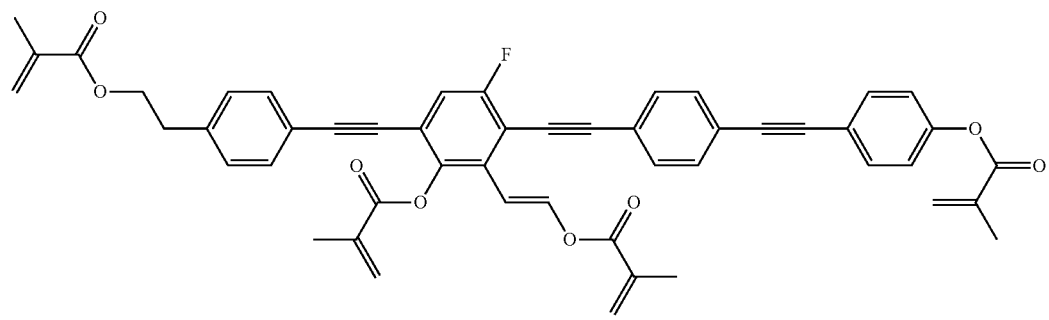
(1-211)
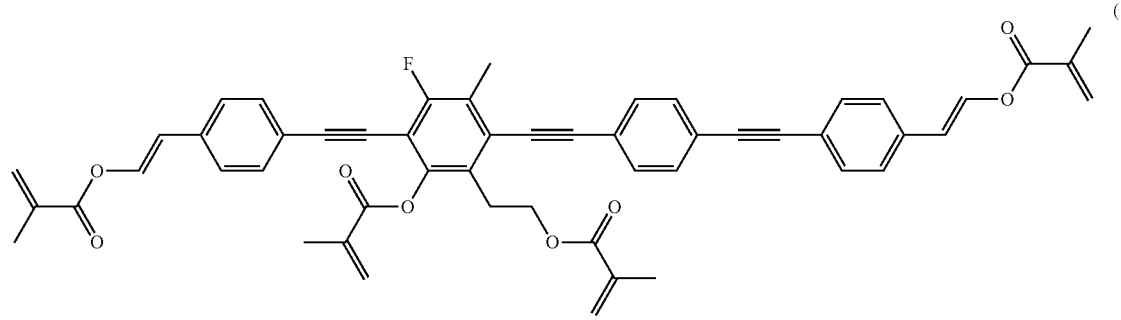
(1-212)

(1-213)
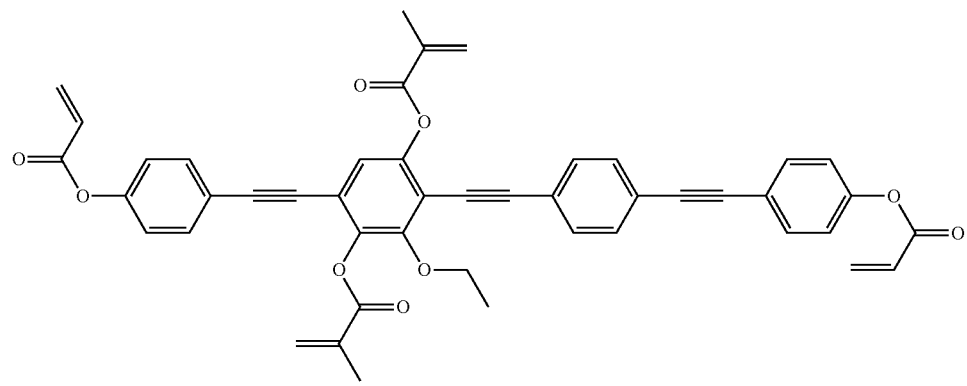
(1-214)
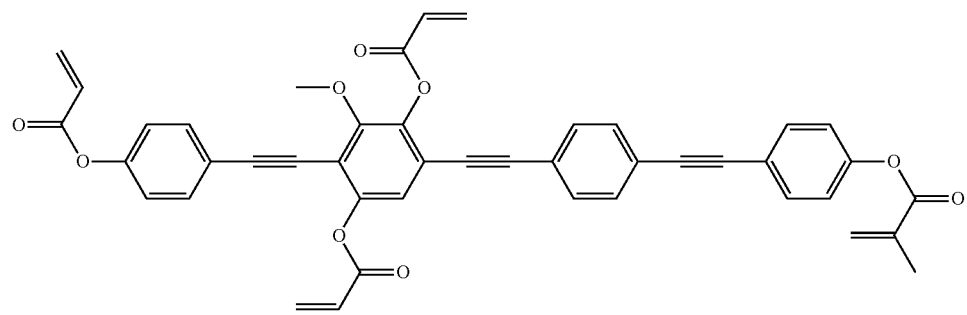
(1-215)
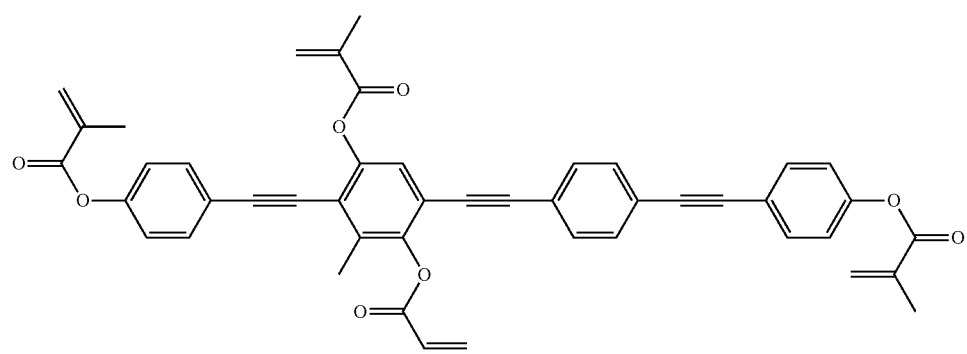
(1-216)
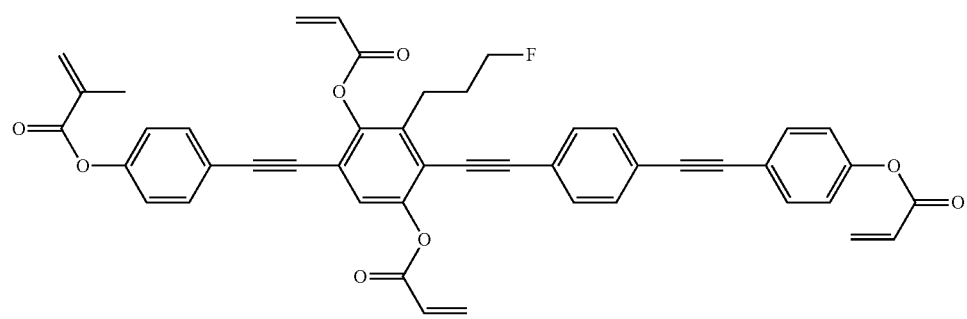
(1-217)
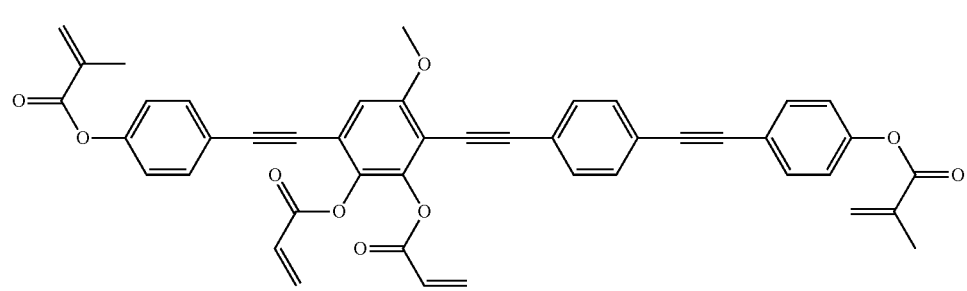

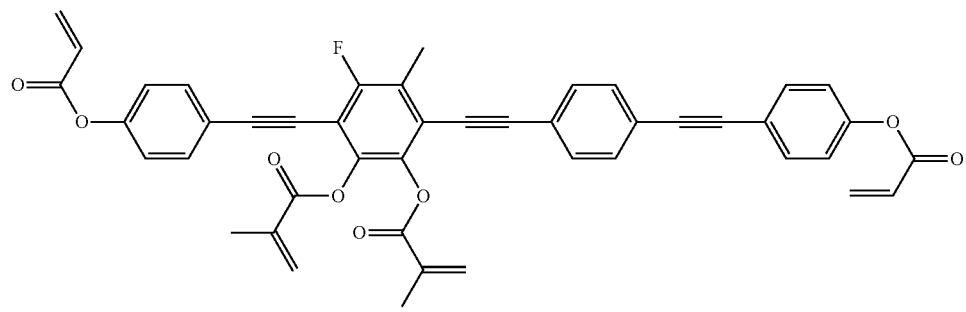
(1-218)
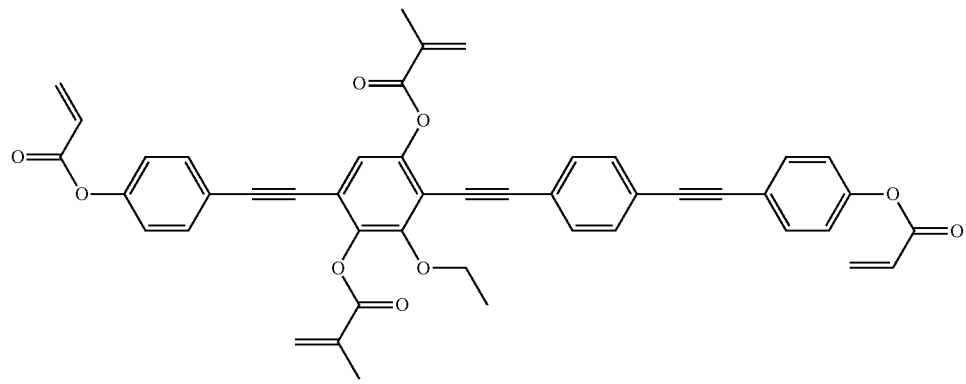
(1-213)
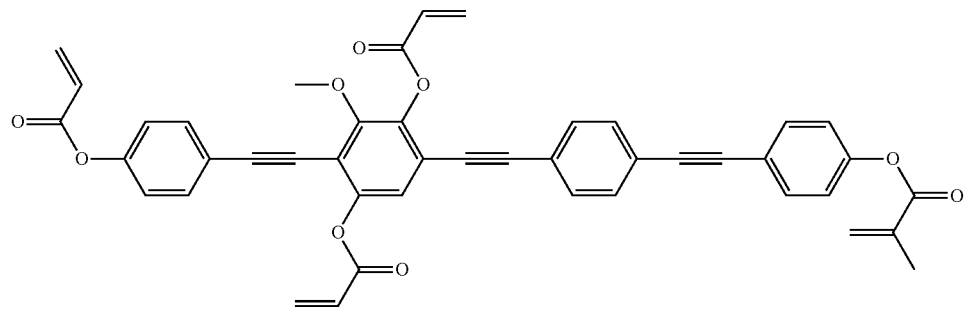
(1-214)
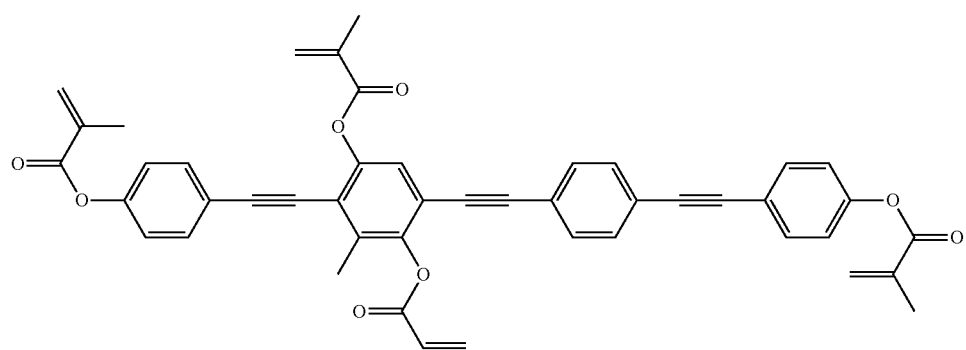
(1-215)

(1-216)
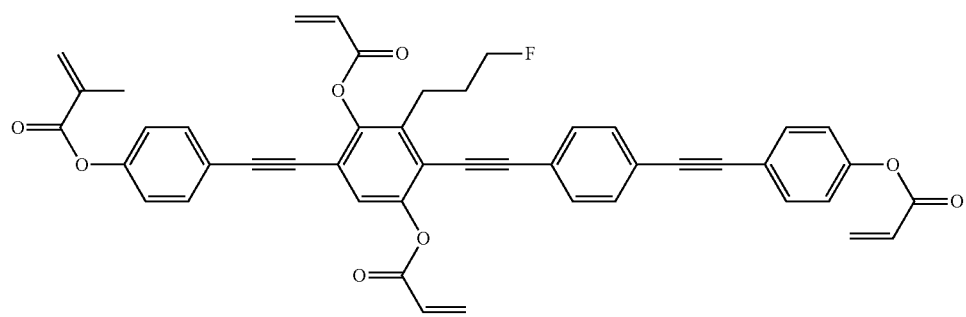
(1-217)
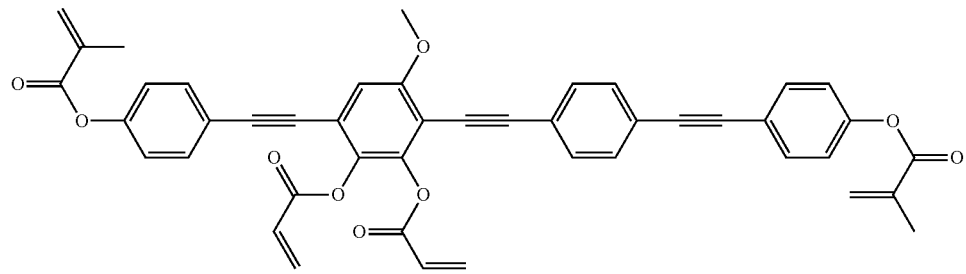
(1-218)
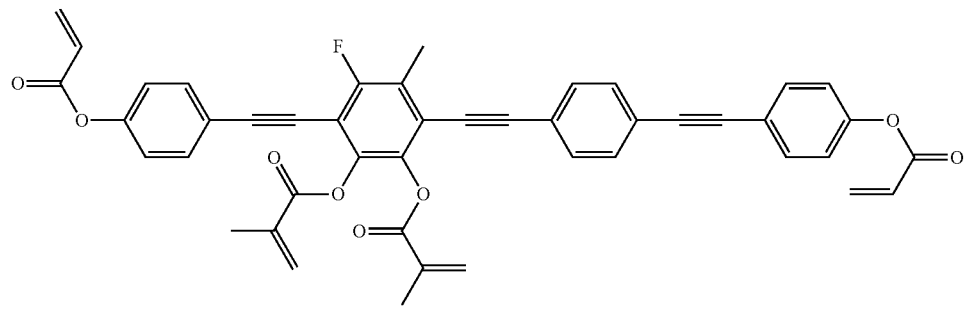
(1-225)
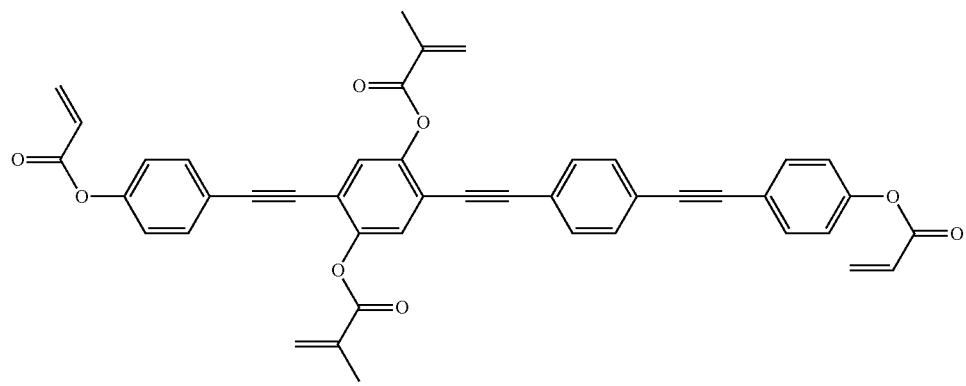
(1-226)
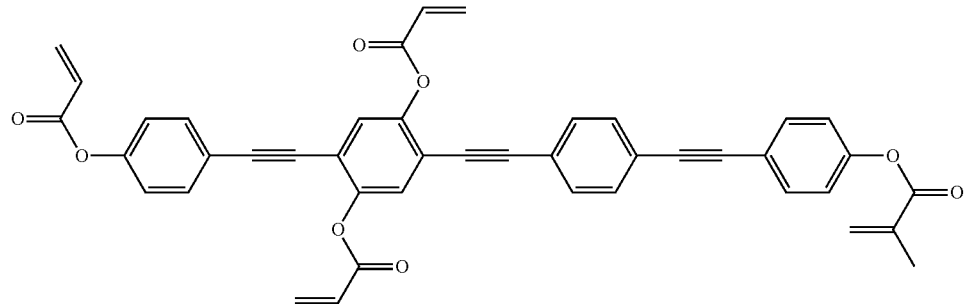

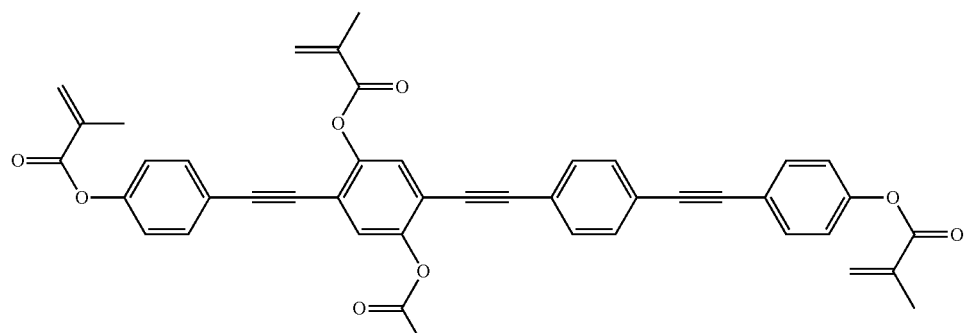
(1-227)
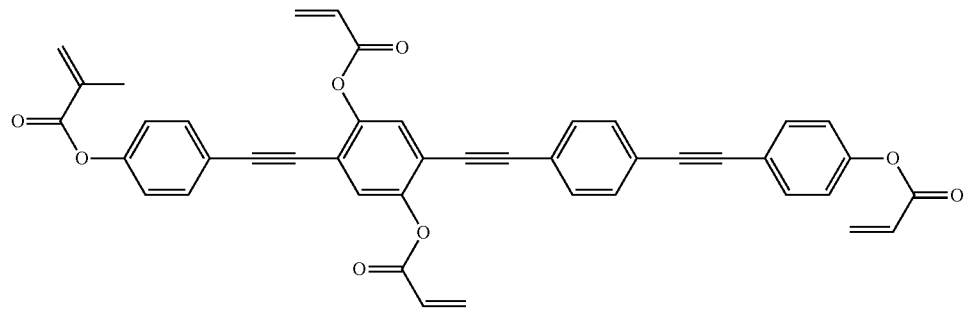
(1-228)
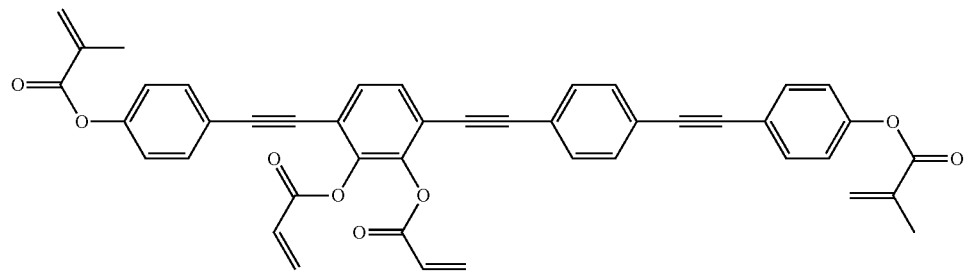
(1-229)
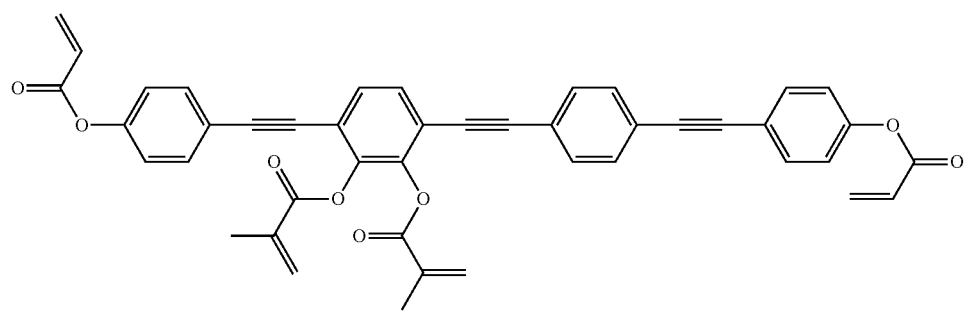
(1-230)
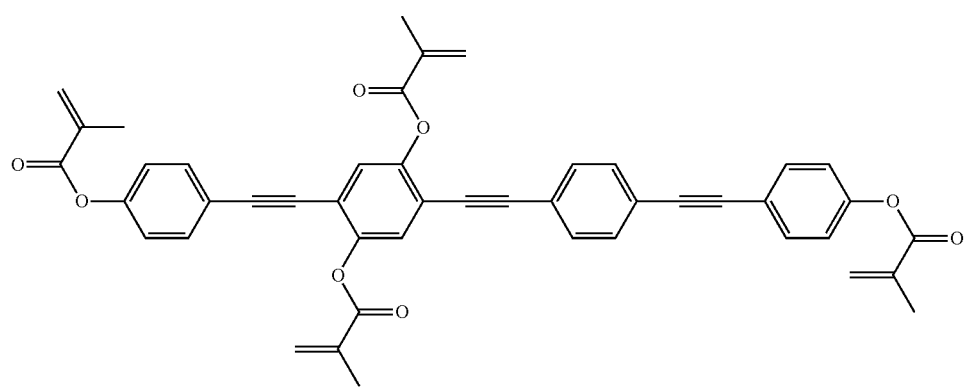
(1-231)

-continued
(1-232)
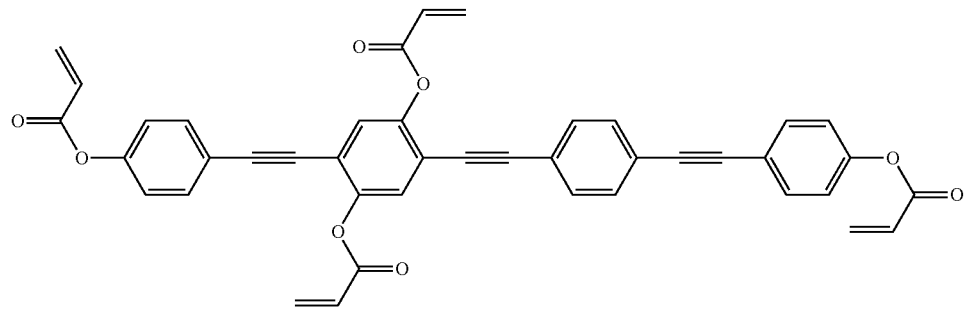
(1-233)
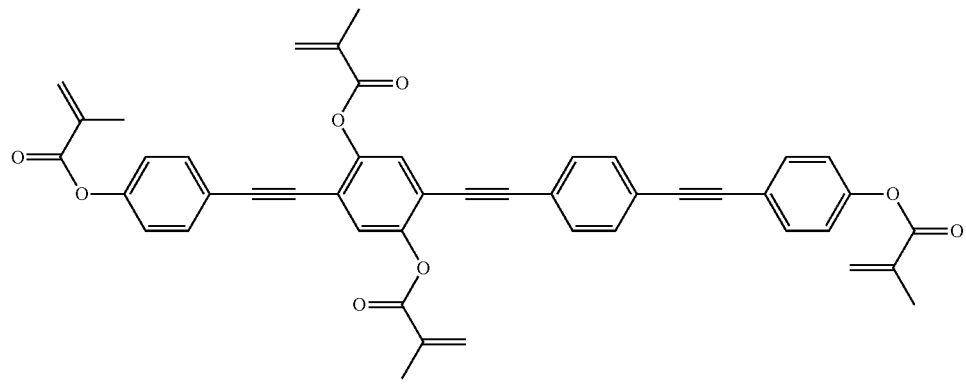
(1-234)
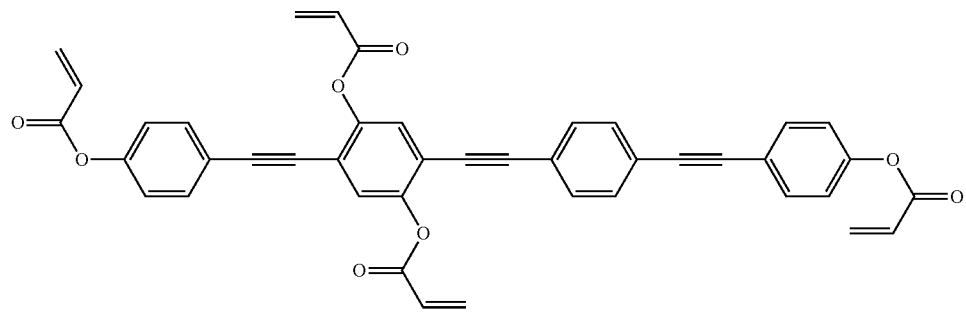
(1-235)
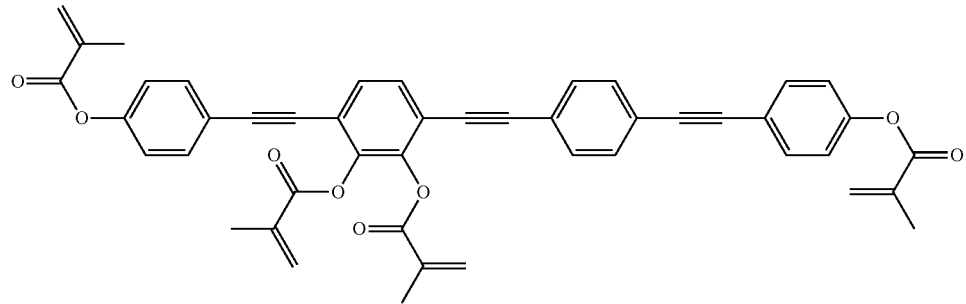
(1-236)
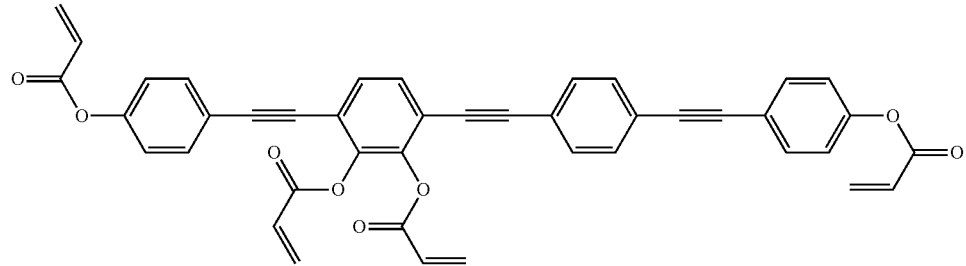

(1-237)
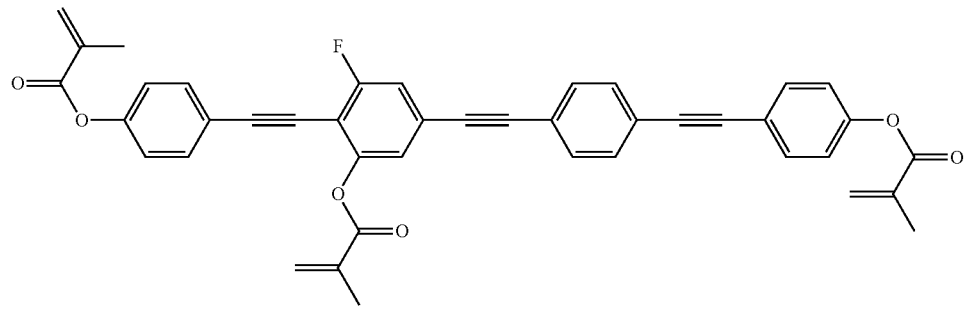
(1-238)
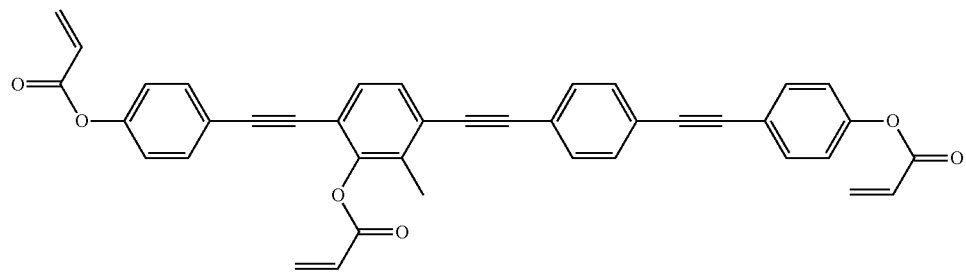
(1-239)
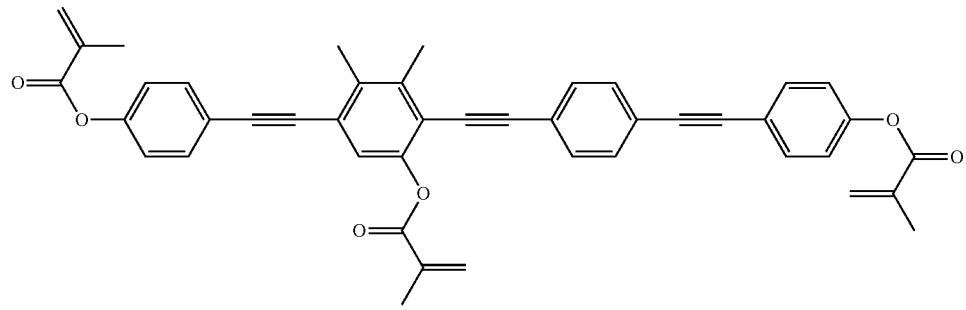
(1-240)
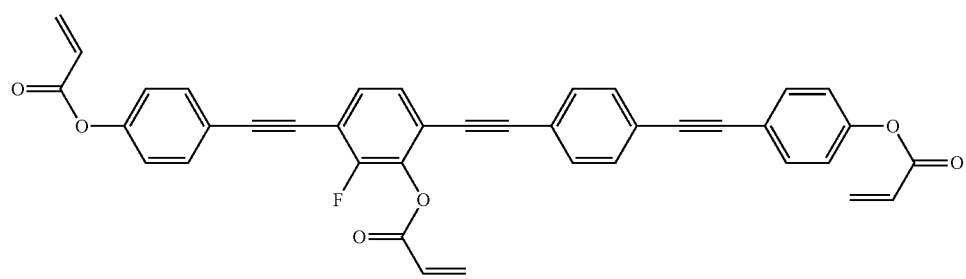
(1-241)
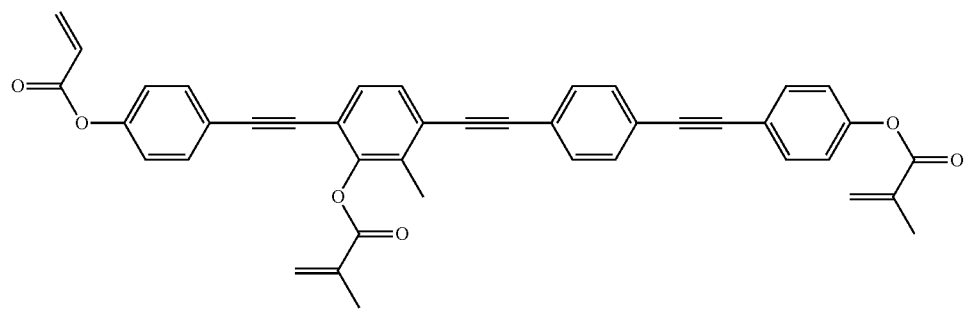

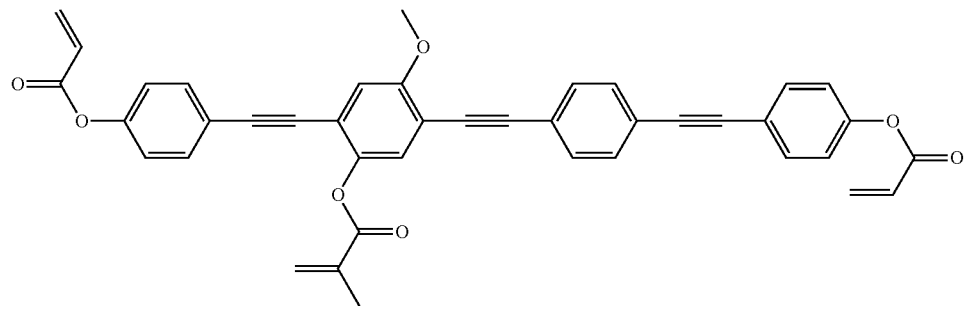
(1-242)
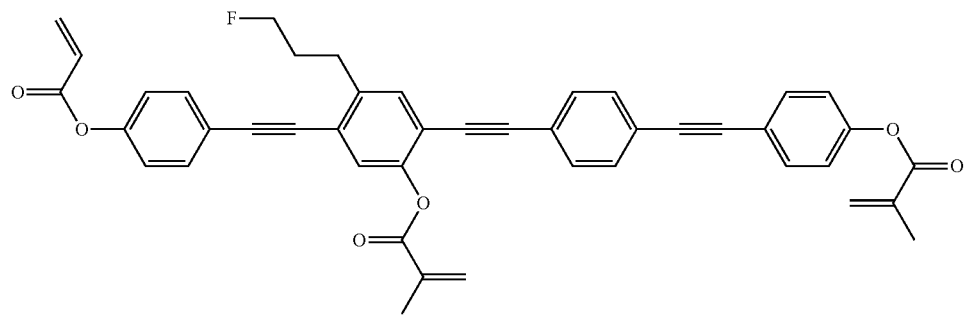
(1-243)
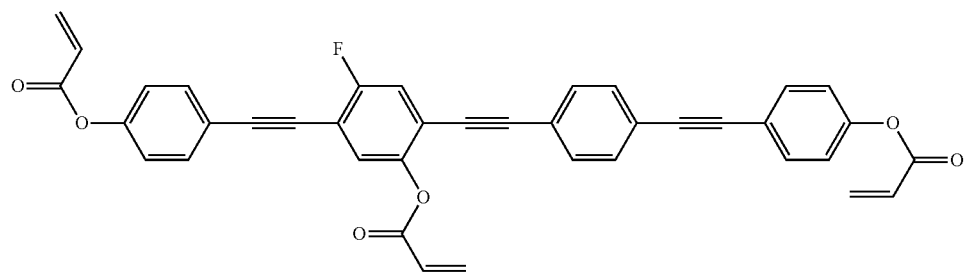
(1-244)
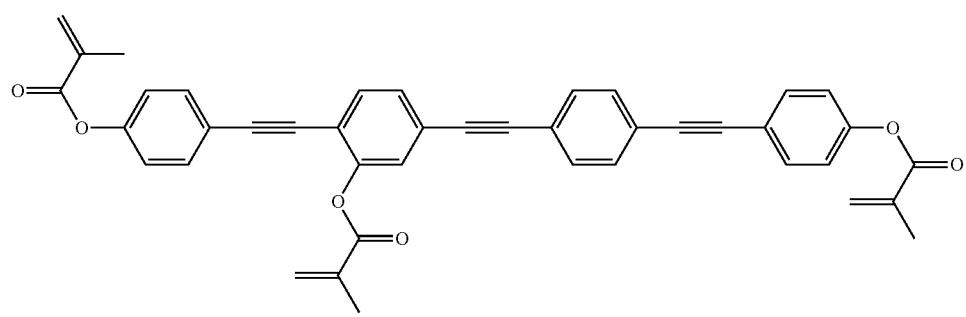
(1-245)
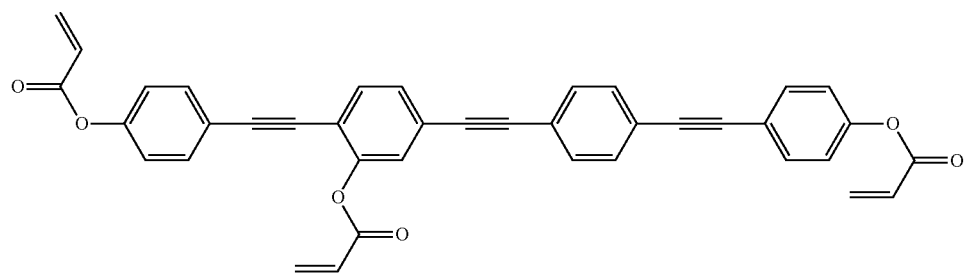
(1-246)

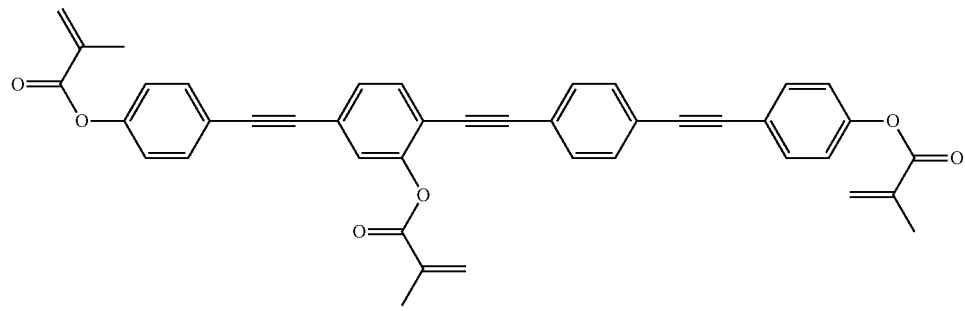
(1-247)
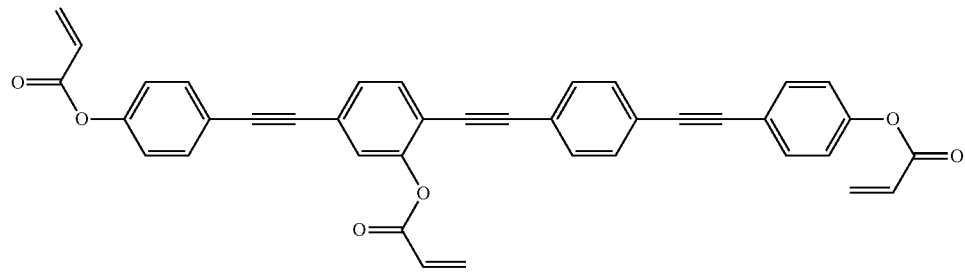
(1-248)
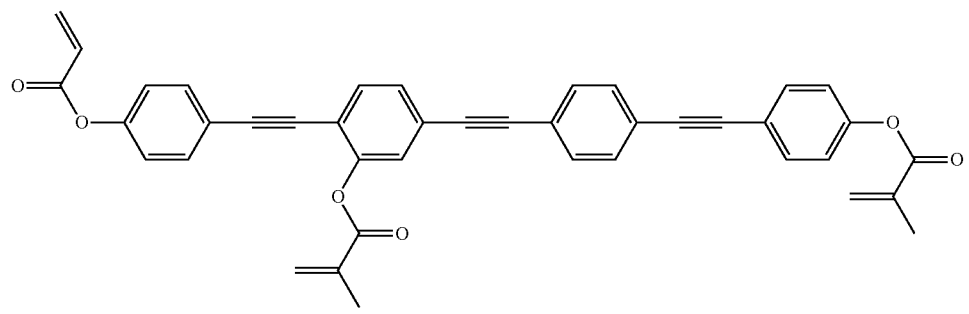
(1-249)
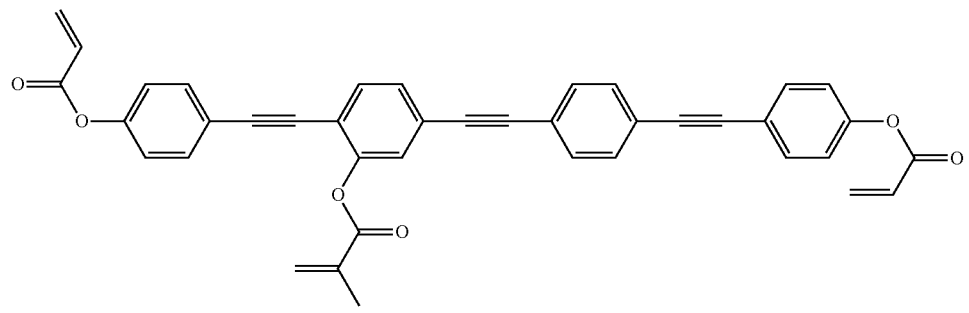
(1-250)
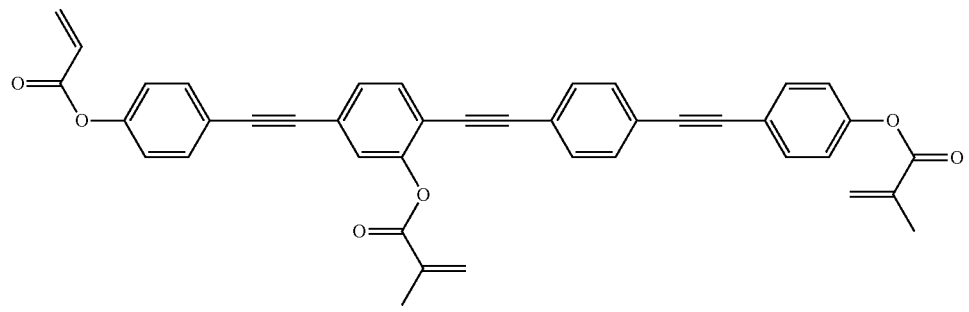
(1-251)

(1-252)
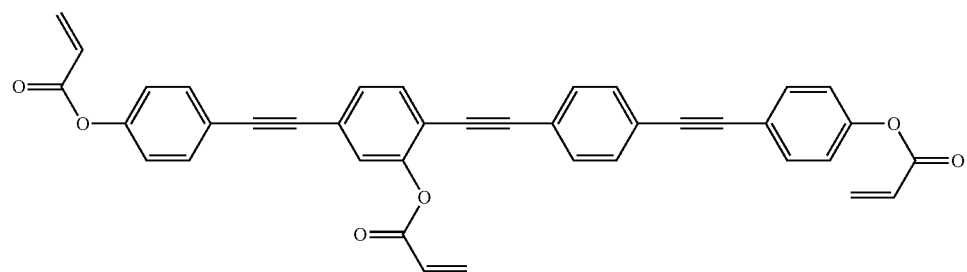
(1-253)
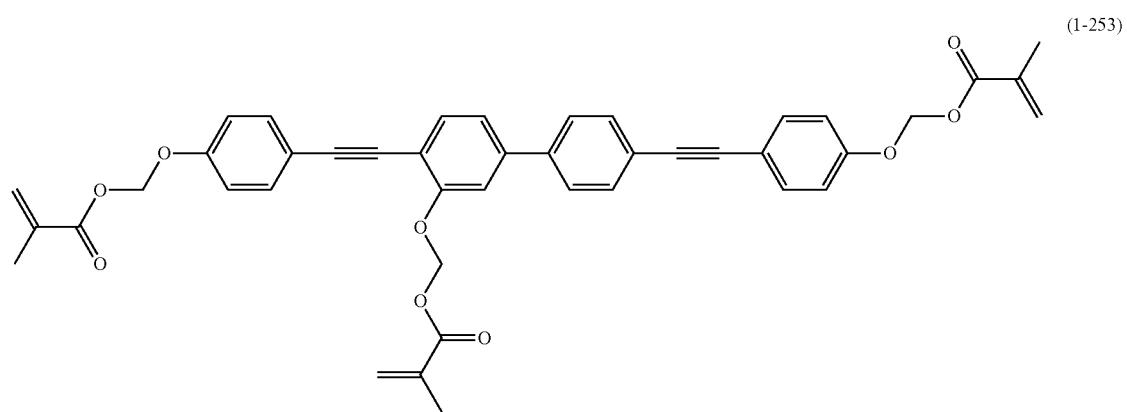
(1-254)
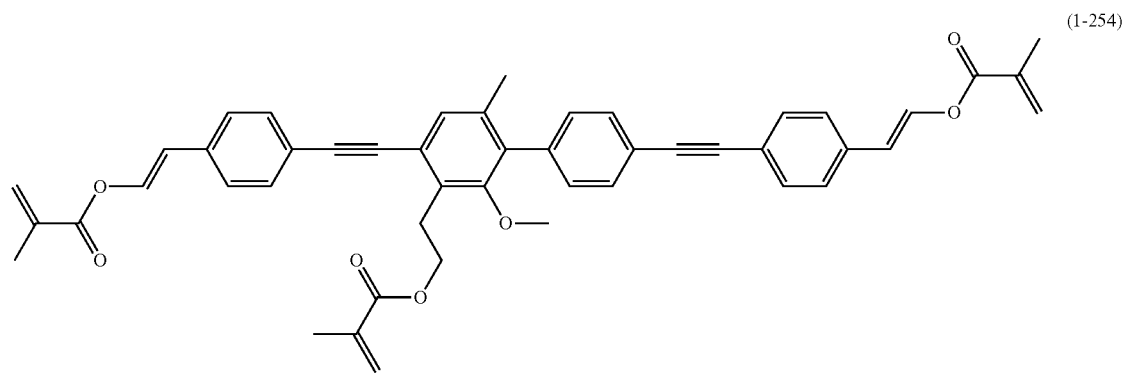
(1-255)
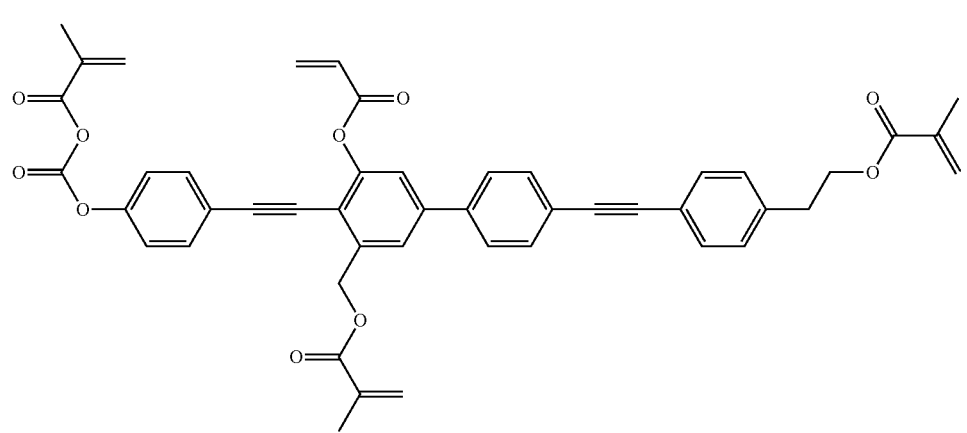

(1-256)
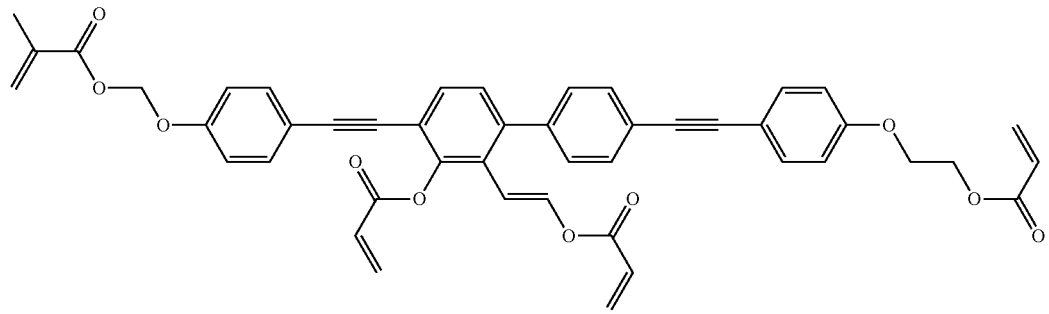
(1-257)
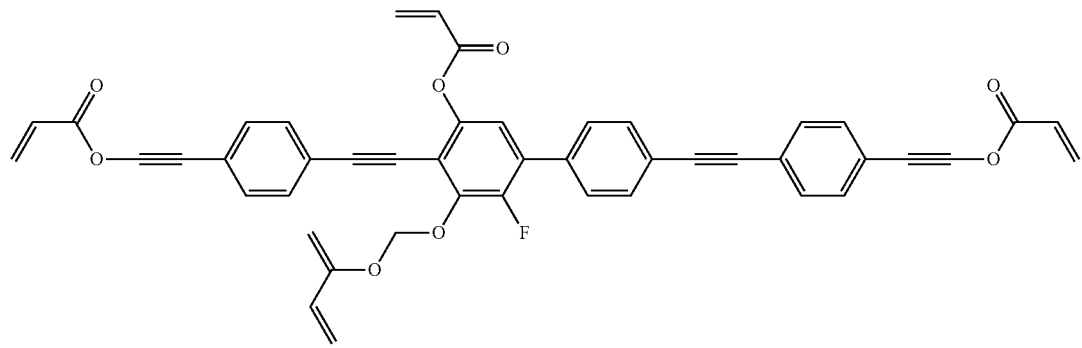
(1-258)
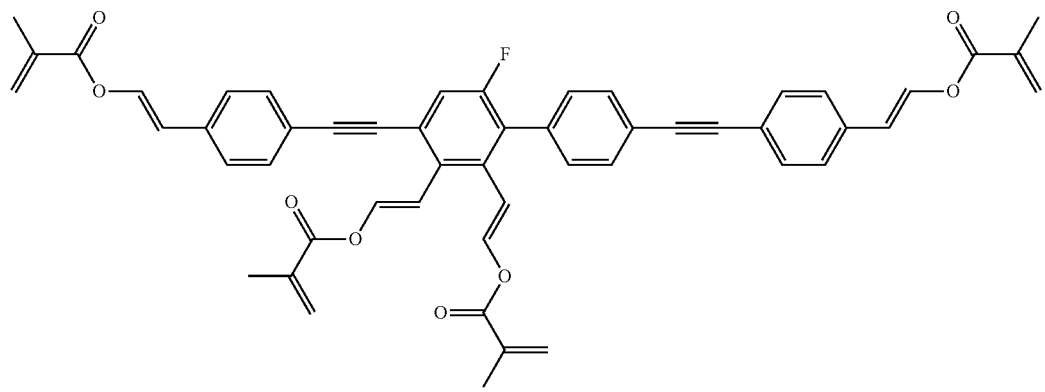
(1-259)
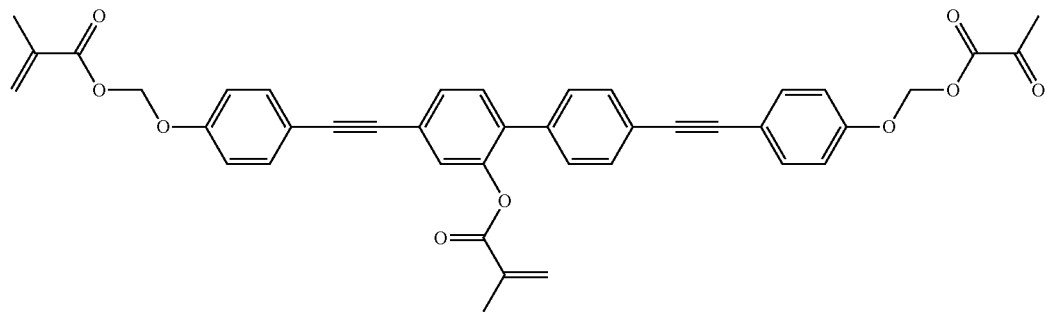
(1-260)
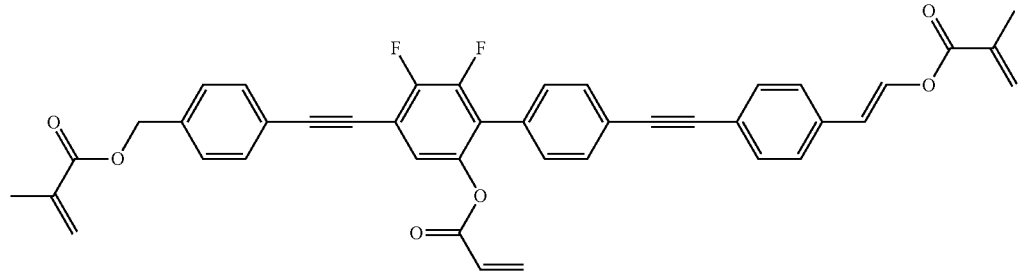

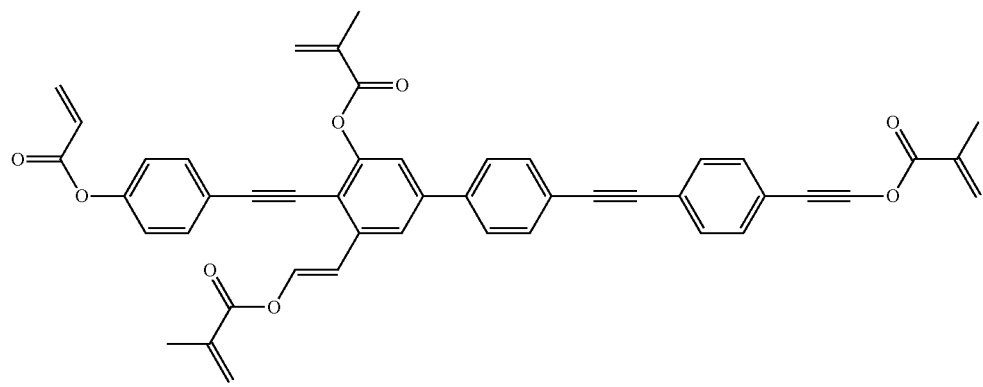
(1-261)
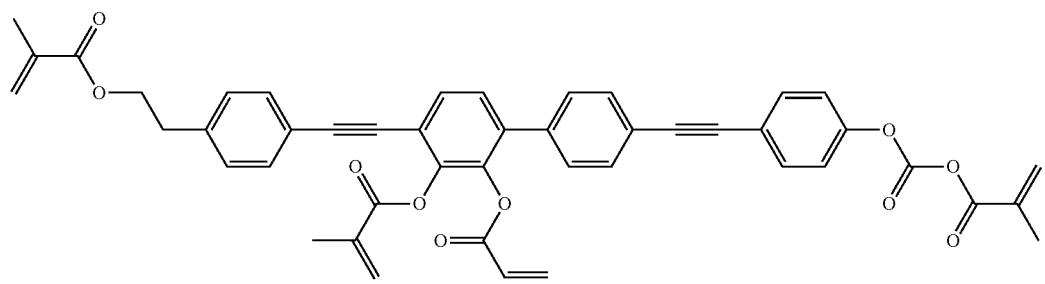
(1-262)
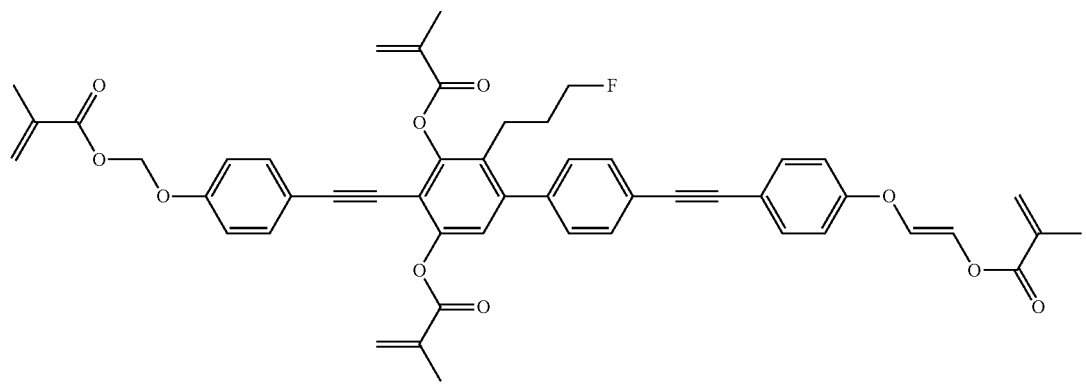
(1-263)
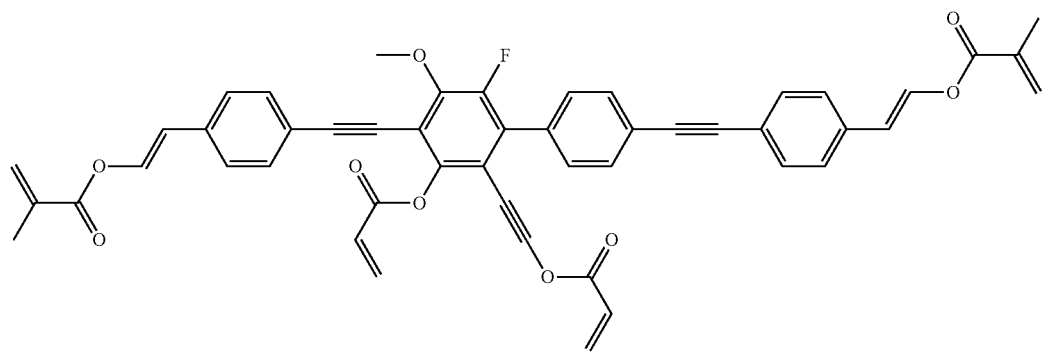
(1-264)

-continued
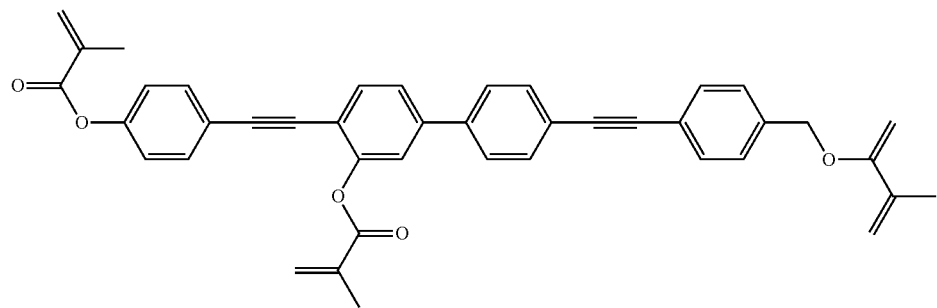
(1-265)
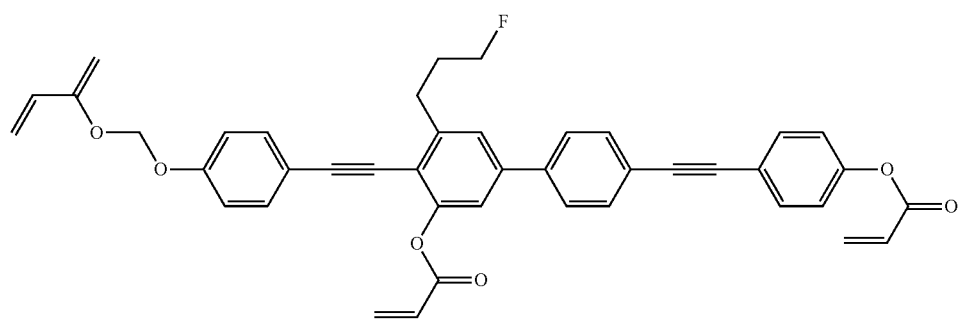
(1-266)
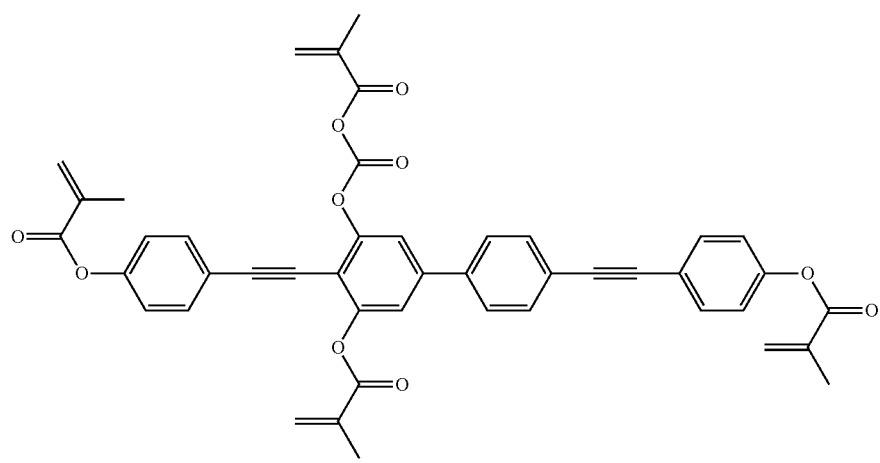
(1-267)
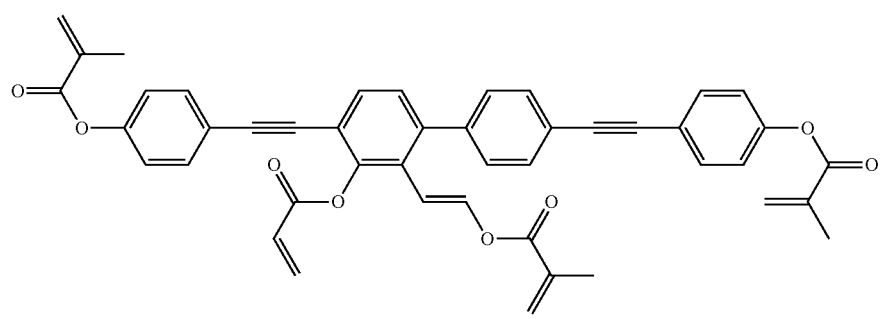
(1-268)

-continued
(1-269)
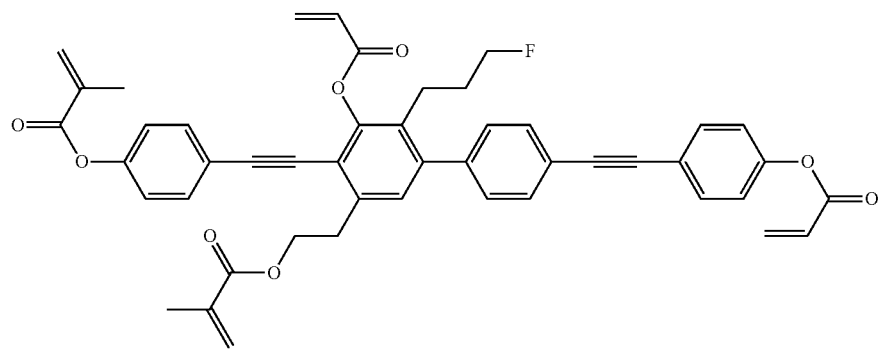
(1-270)
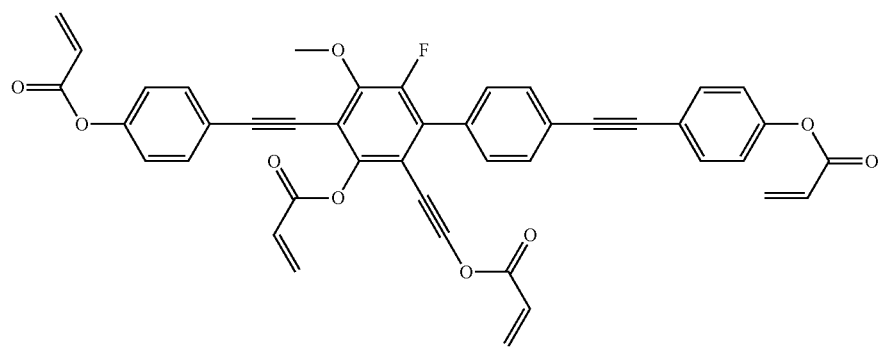
(1-271)
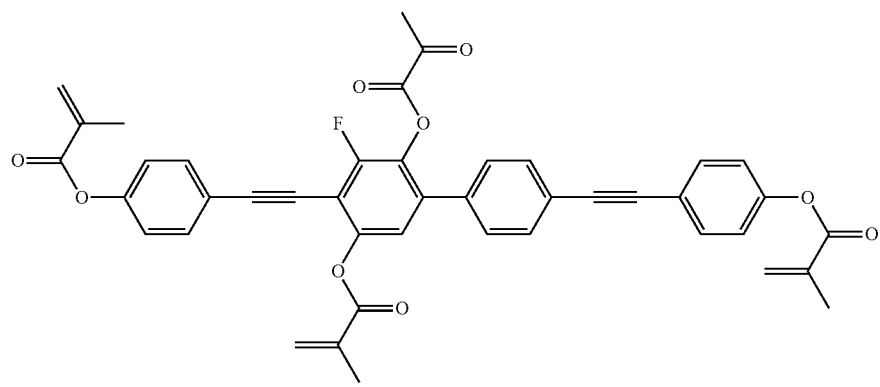
(1-272)
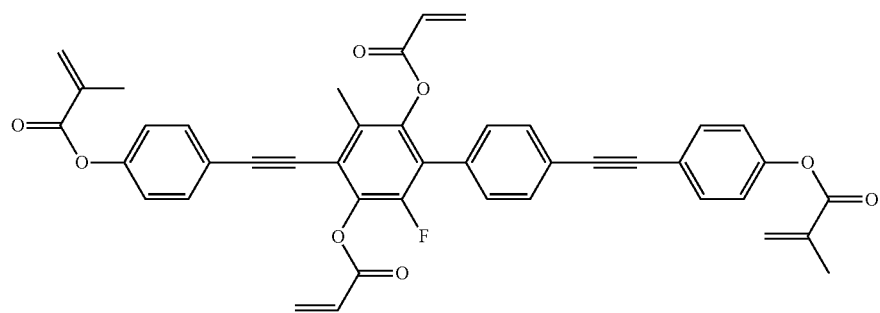

(1-273)
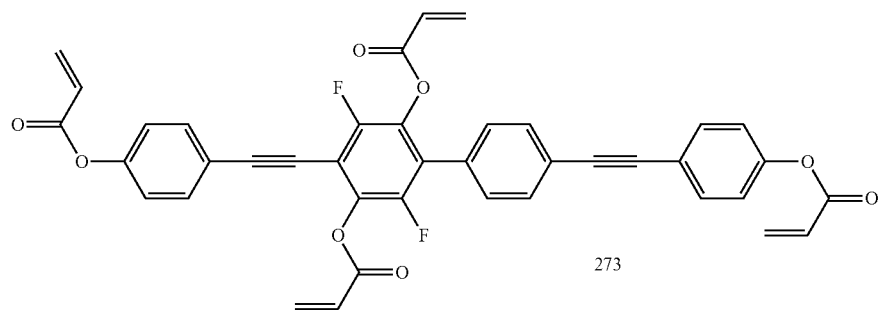
273
(1-274)
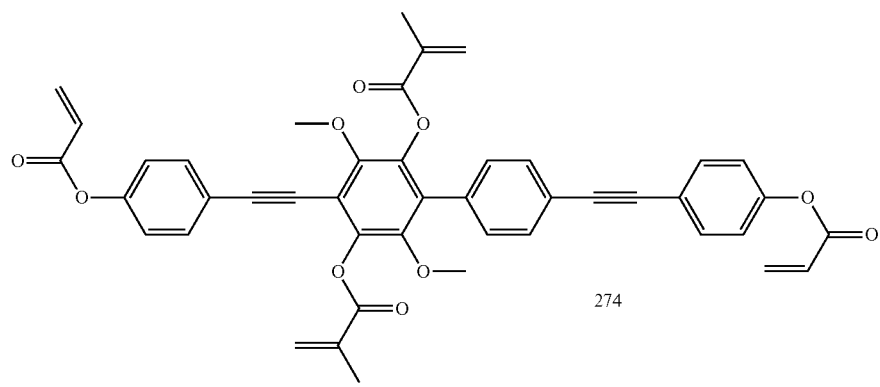
274
(1-275)
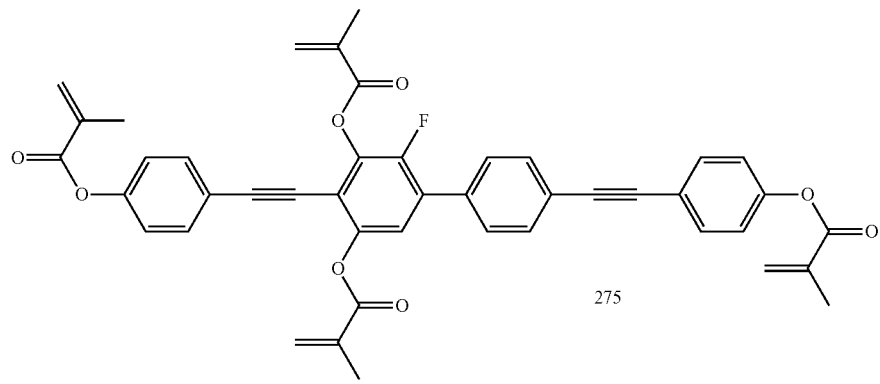
275
(1-276)
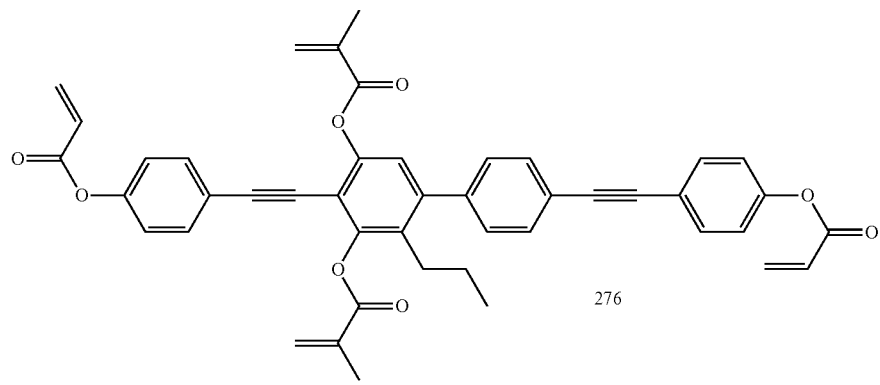
276

(1-277)
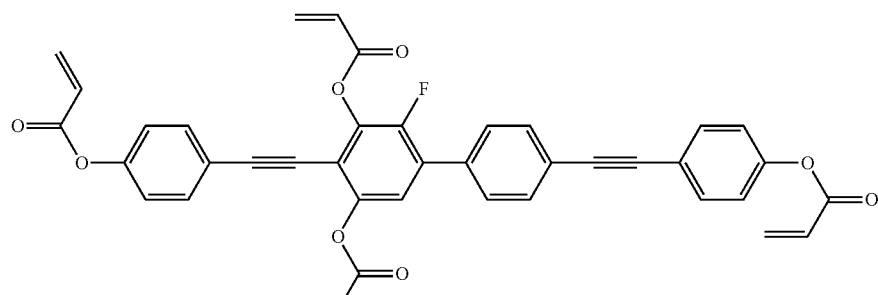
(1-278)
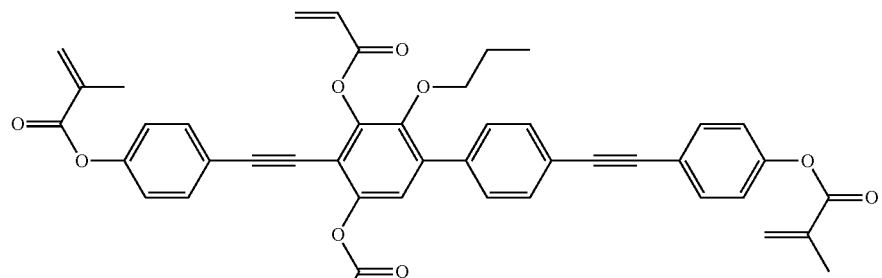
(1-279)
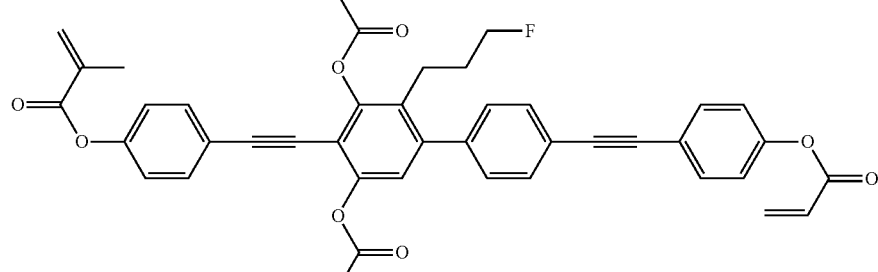
(1-280)
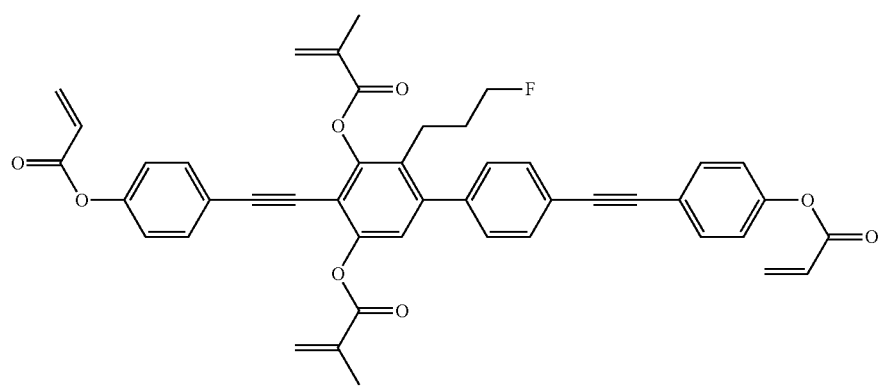
(1-281)
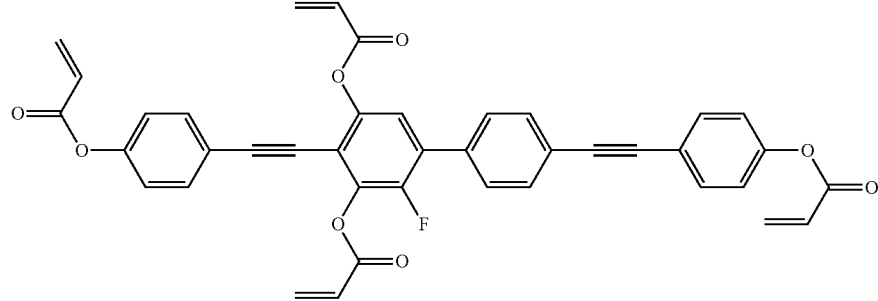

(1-282)
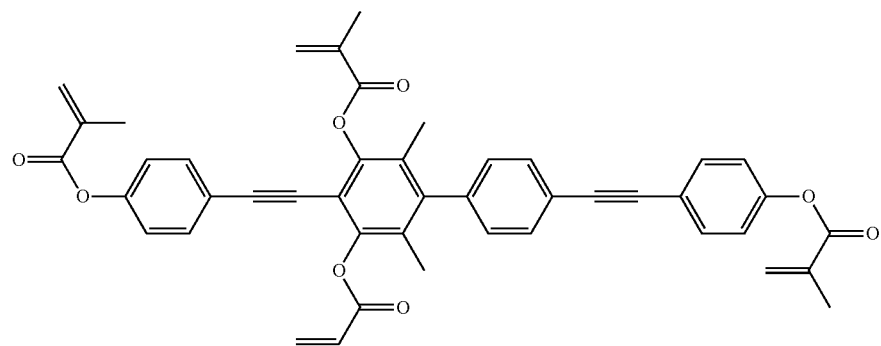
(1-283)
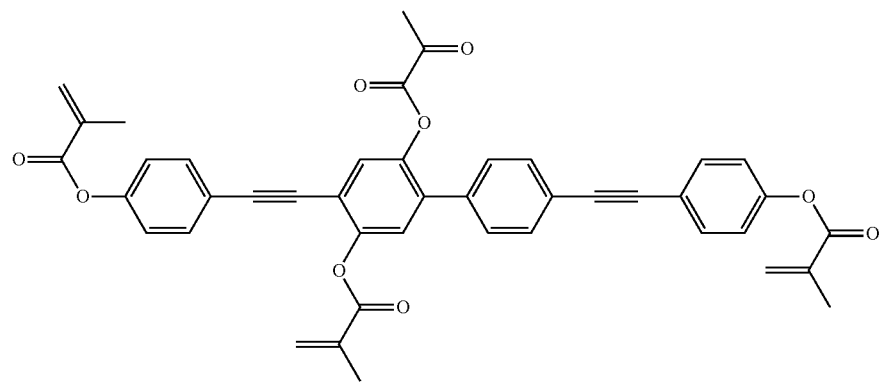
(1-284)
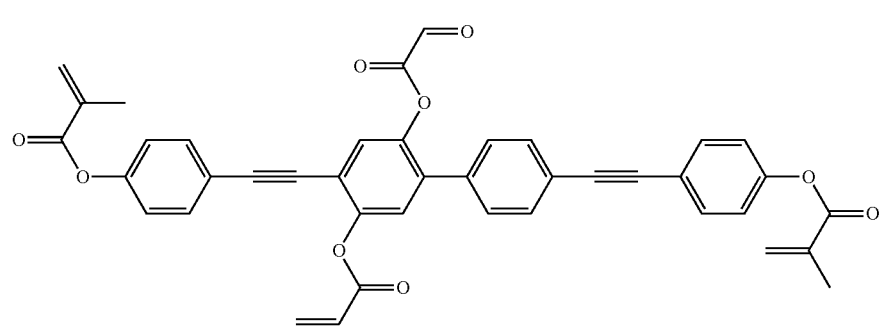
(1-285)
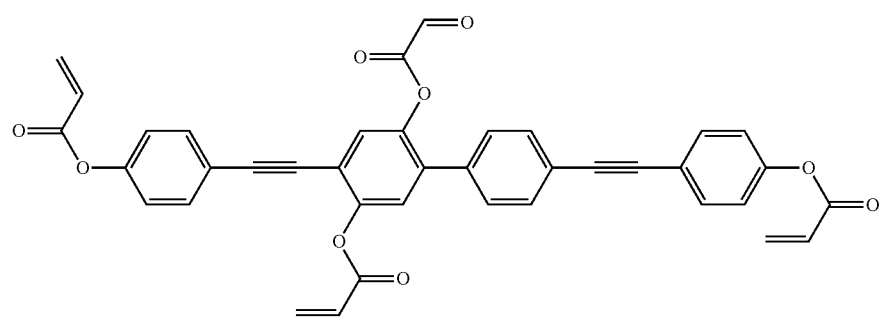

(1-286)
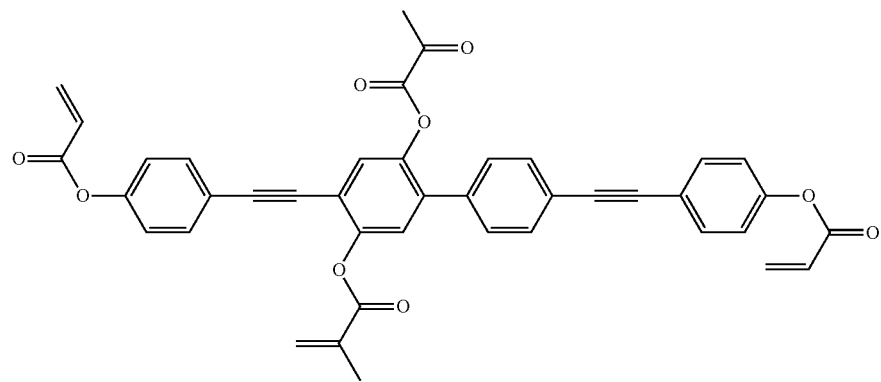
(1-287)
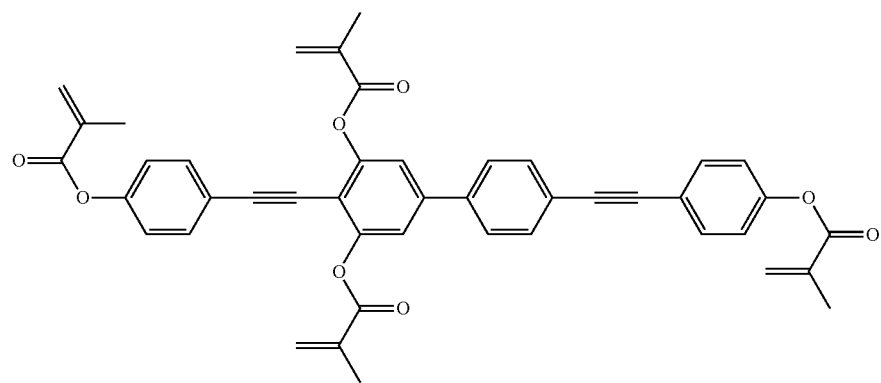
(1-288)
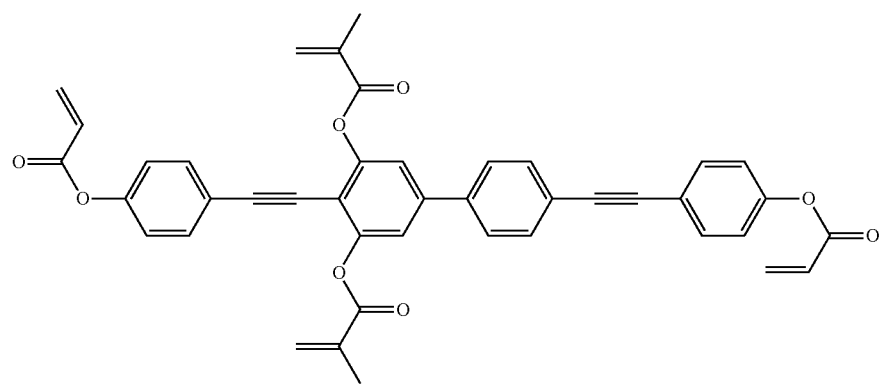
(1-289)
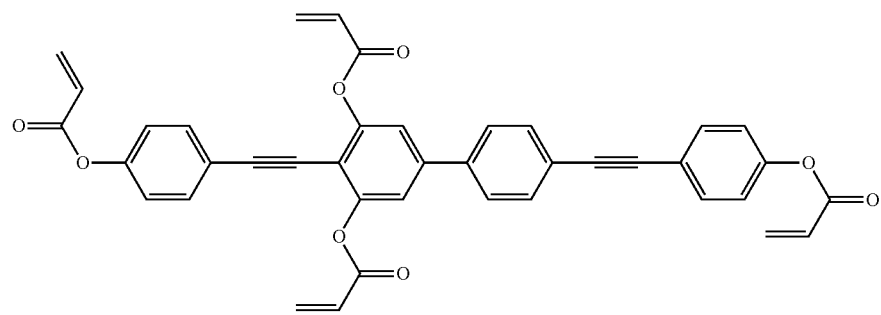

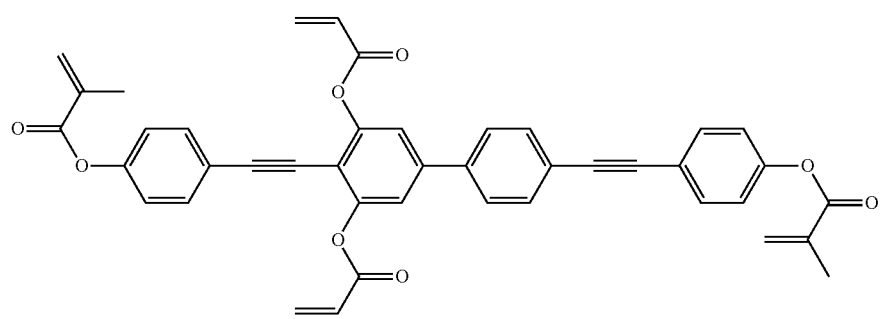
(1-290)
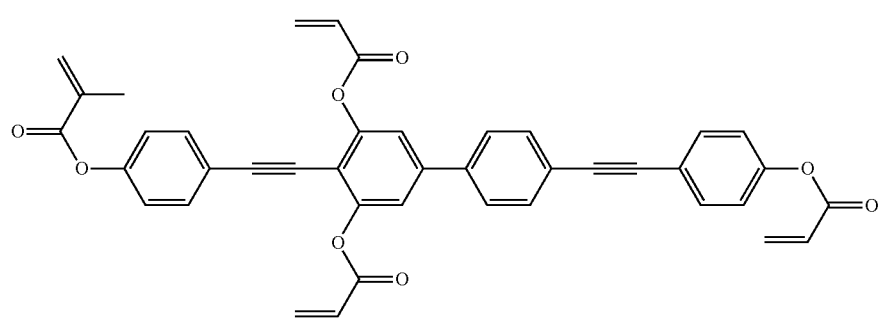
(1-291)
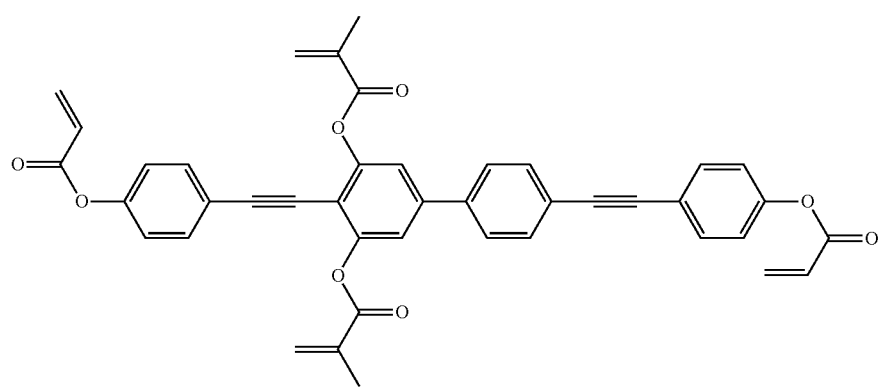
(1-292)
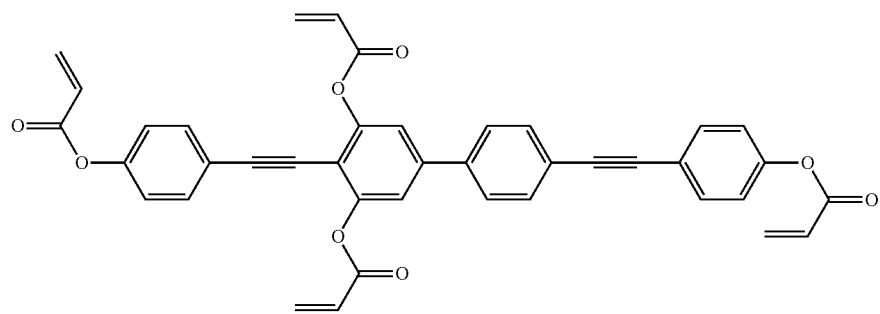
(1-293)

(1-294)
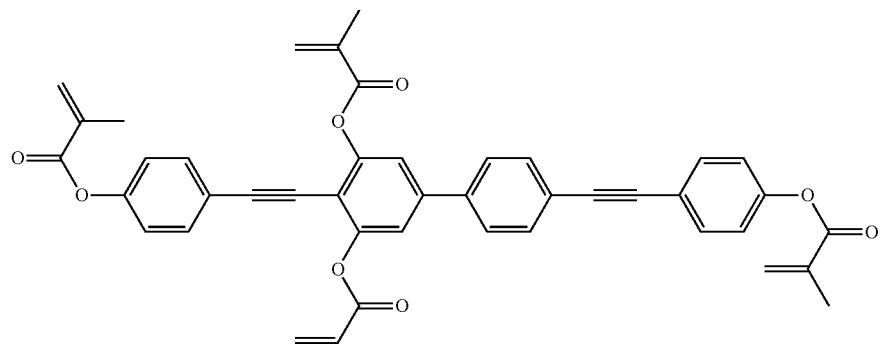
(1-295)
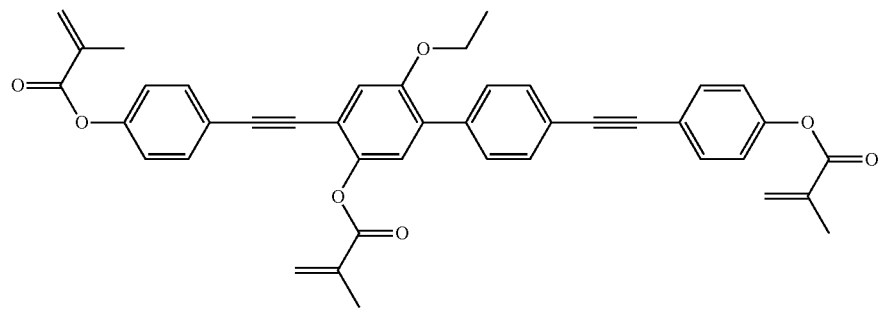
(1-296)
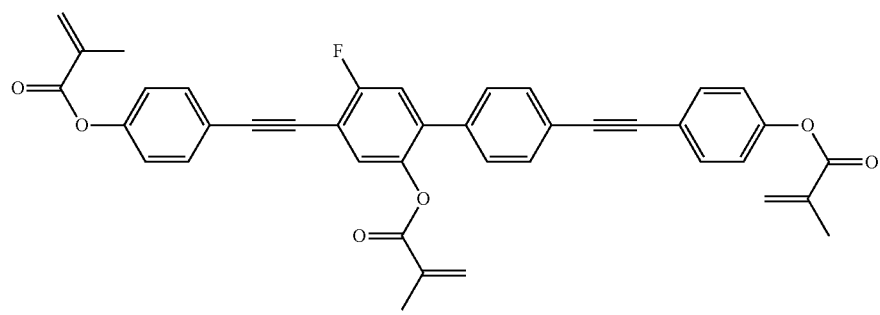
(1-297)
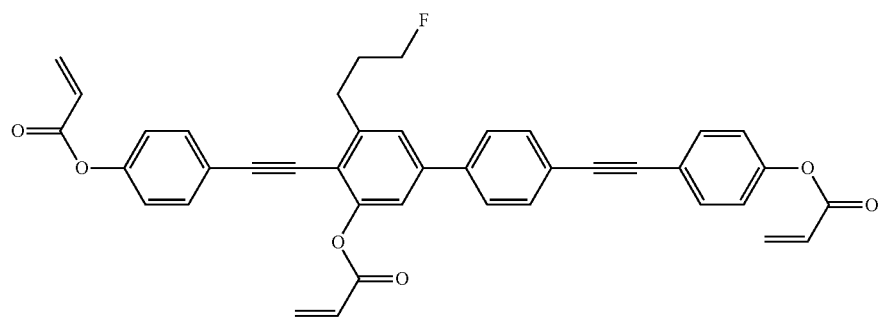
(1-298)
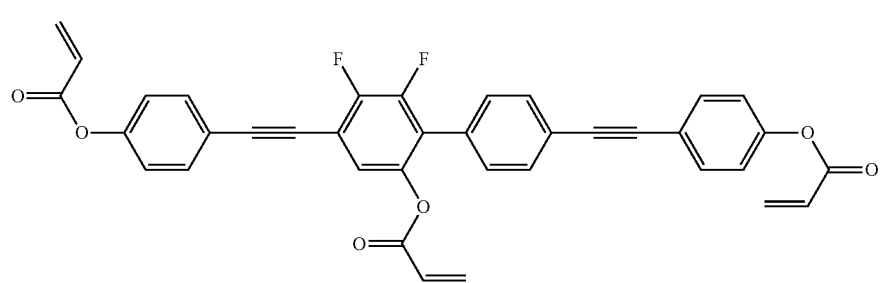

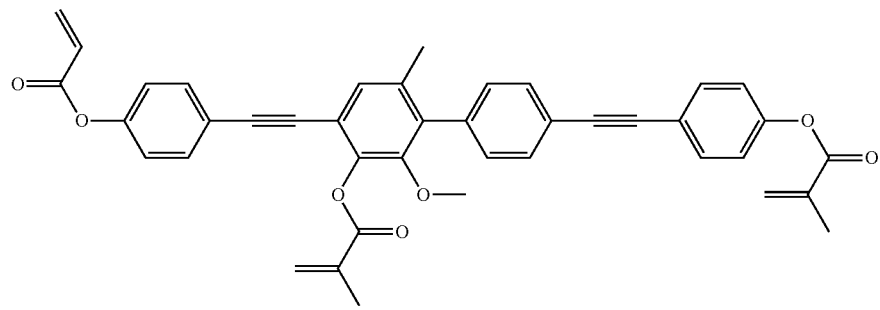
(1-299)
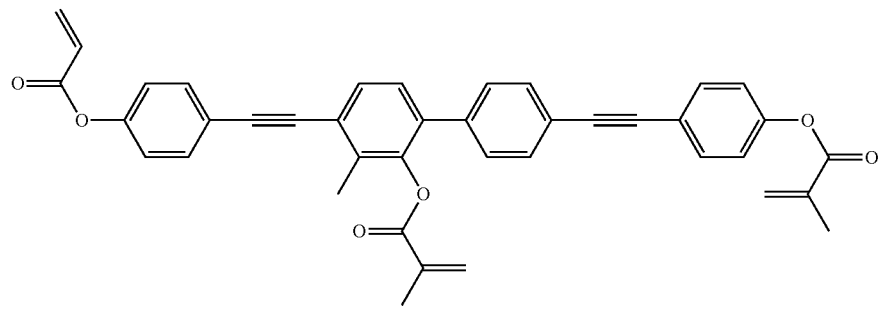
(1-300)
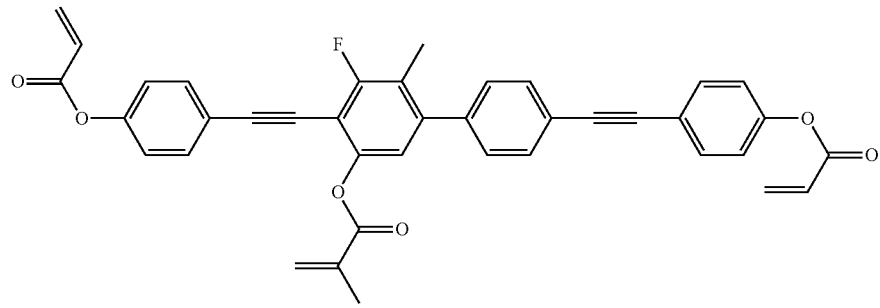
(1-301)
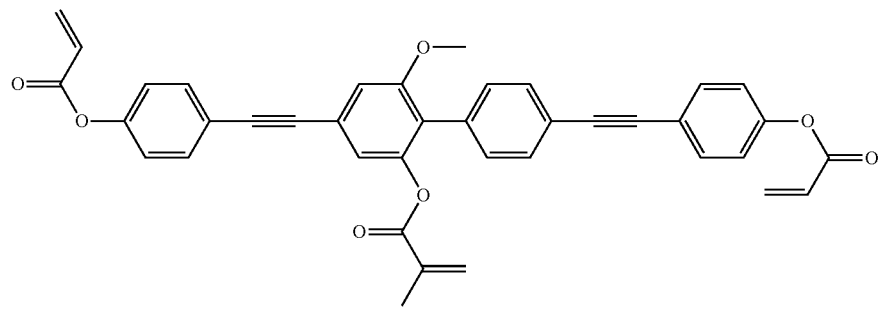
(1-302)
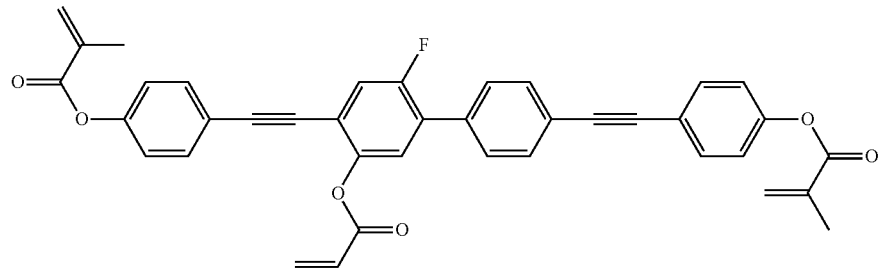
(1-303)

-continued
(1-304)
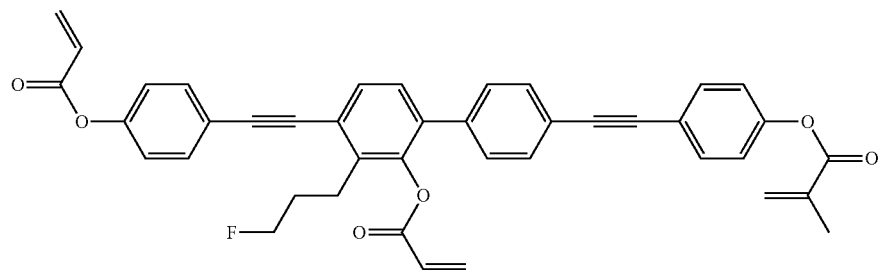
(1-305)
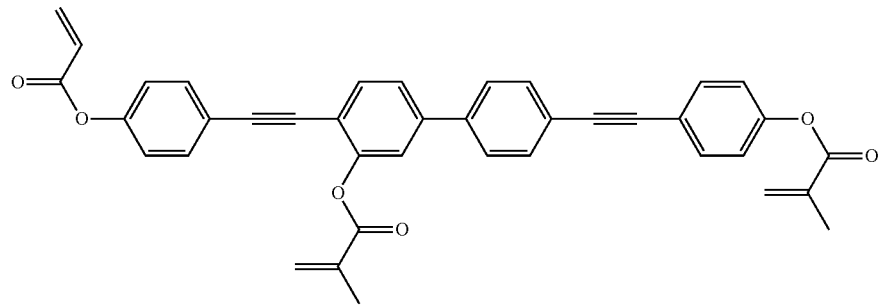
(1-306)
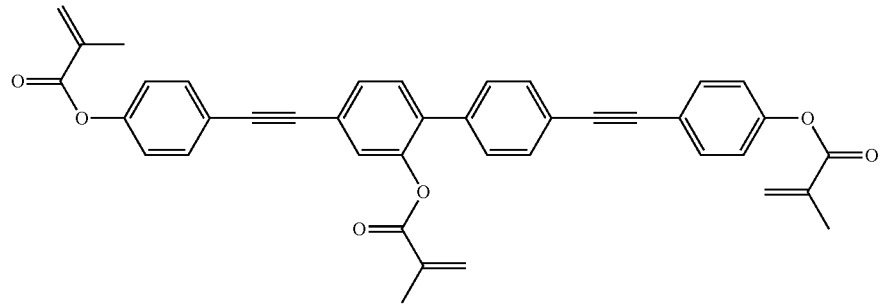
(1-307)
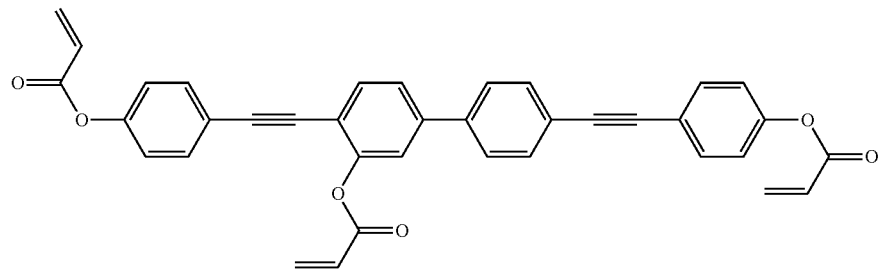
(1-308)
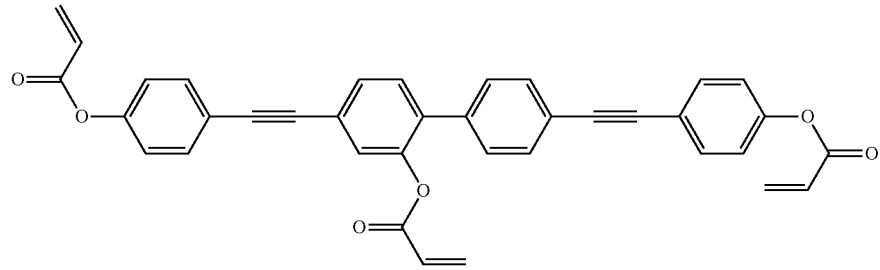

(1-309)
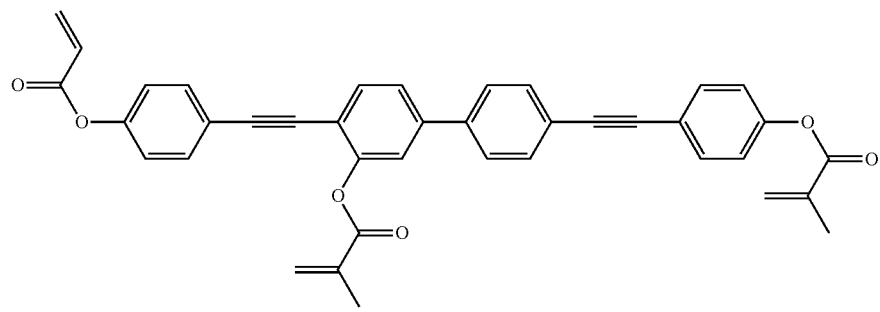
(1-310)
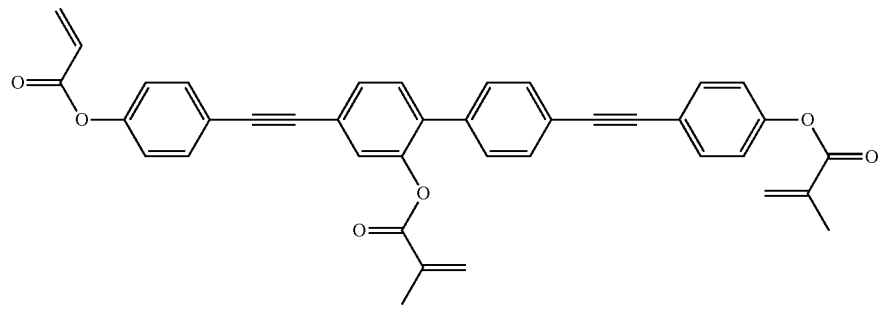
(1-311)
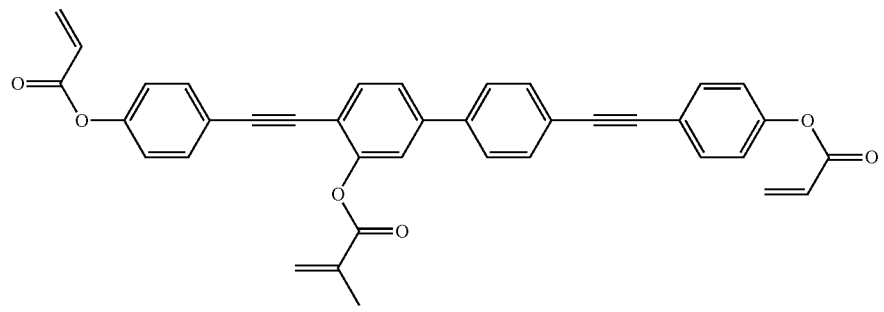
(1-312)
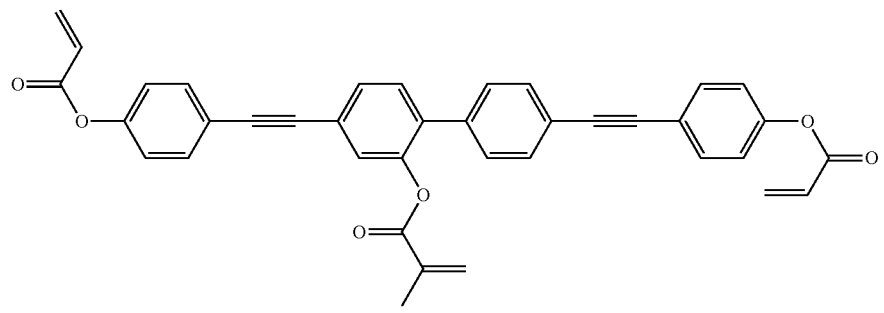
(1-313)
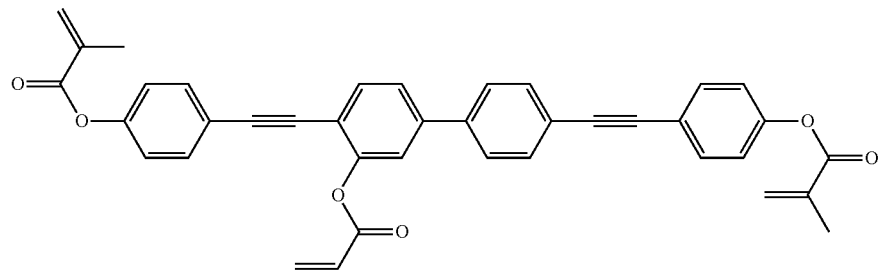

(1-314)
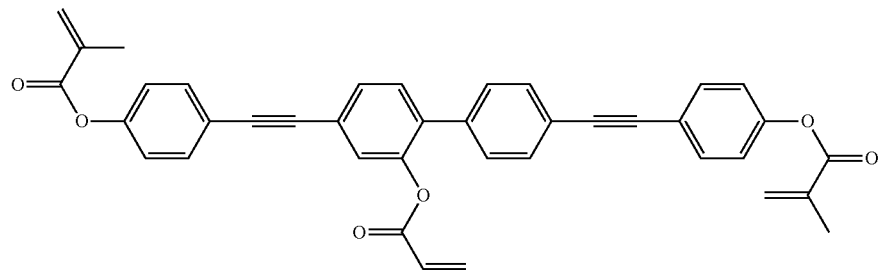
(1-315)
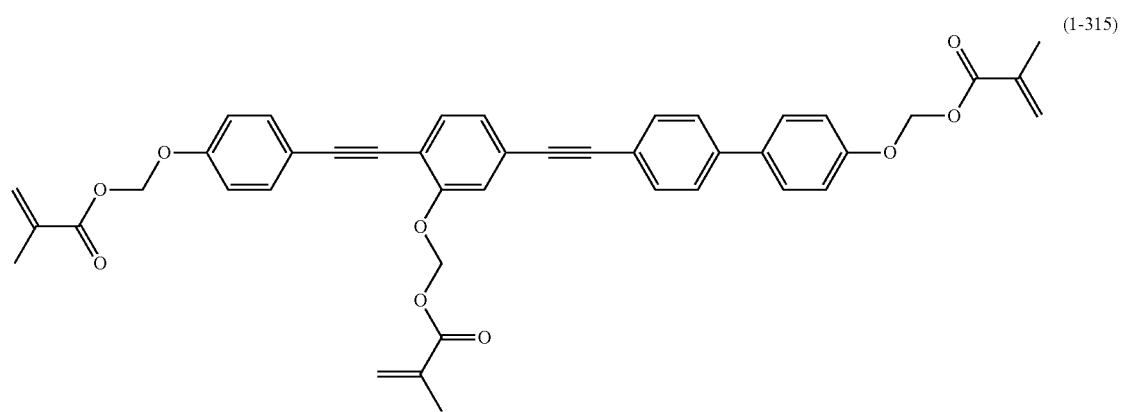
(1-316)
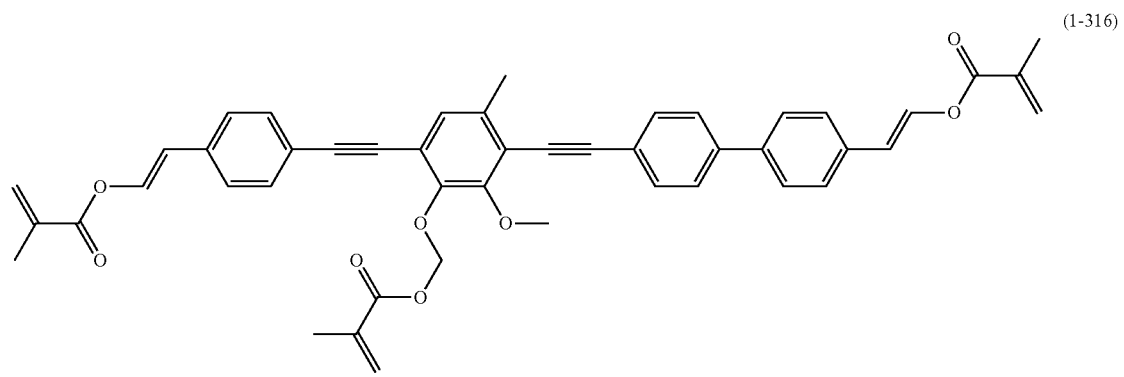
(1-317)
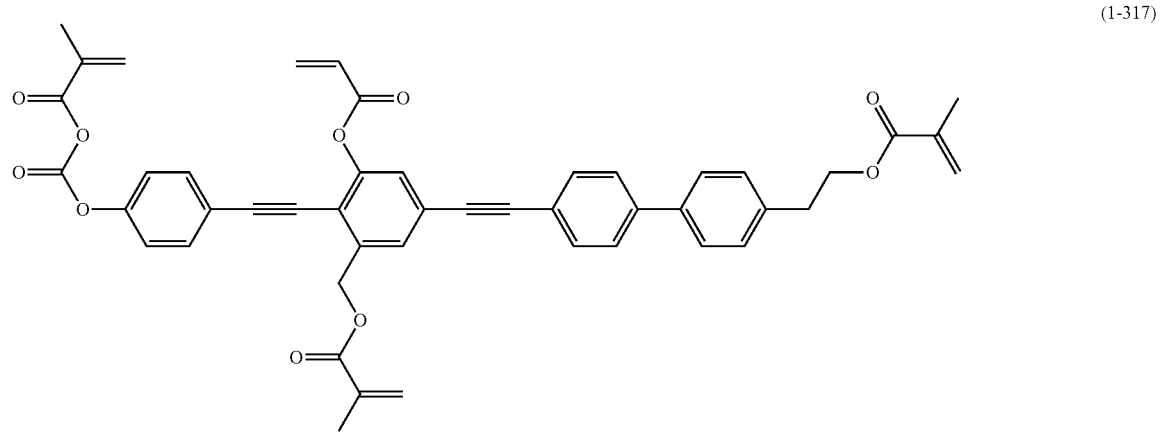

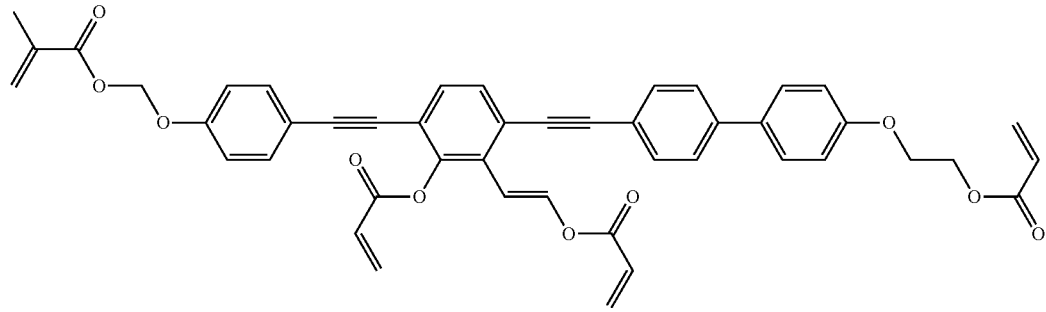
(1-318)
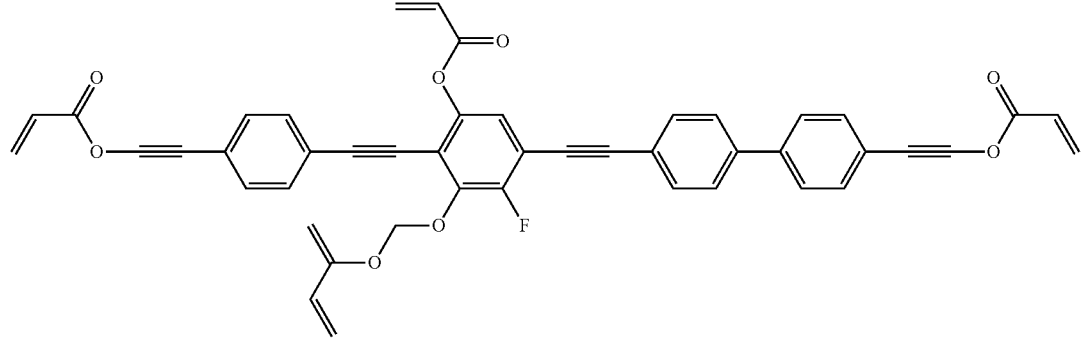
(1-319)
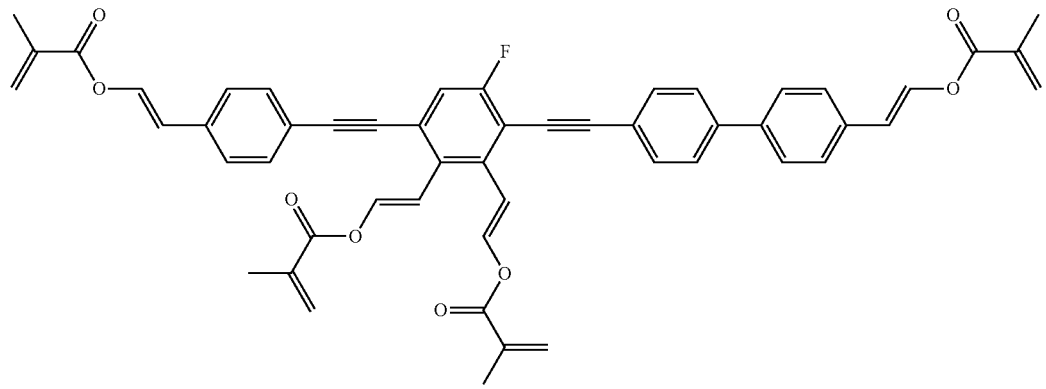
(1-320)
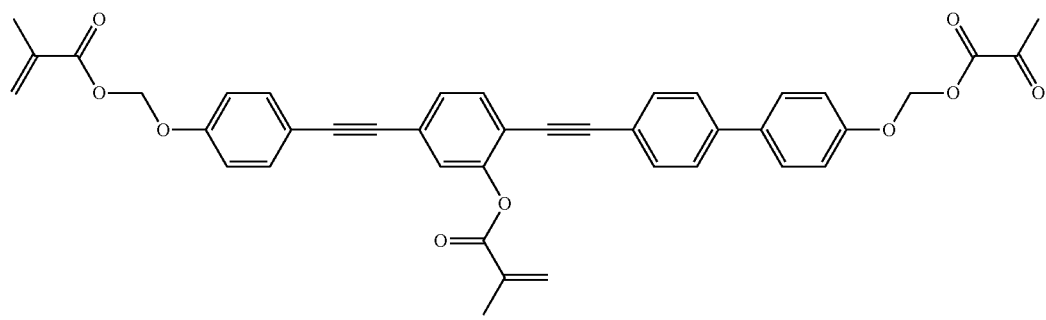
(1-321)
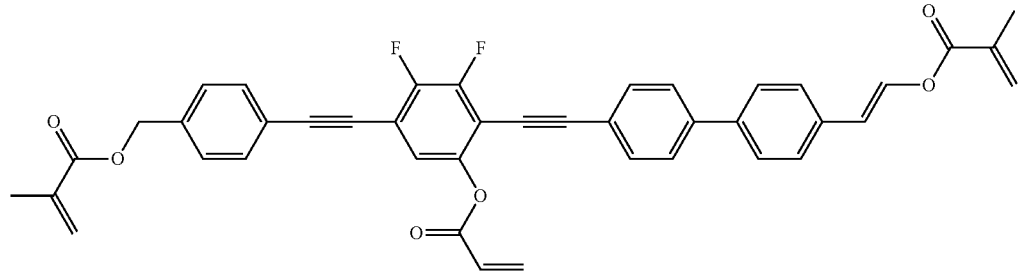
(1-322)

(1-323)
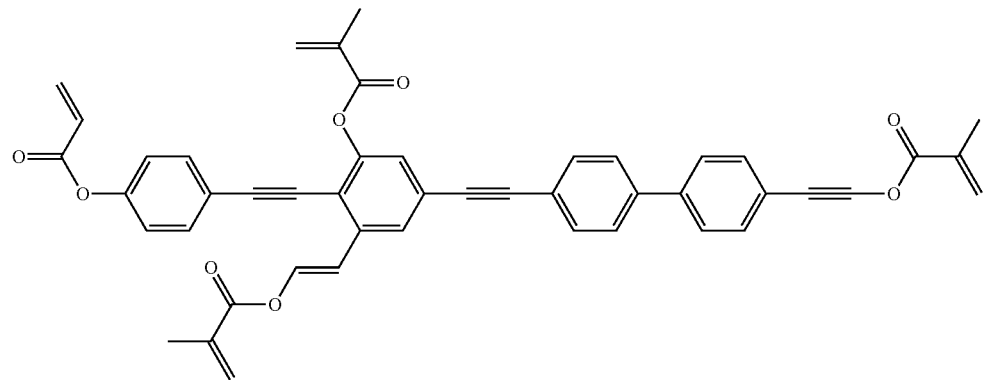
(1-324)
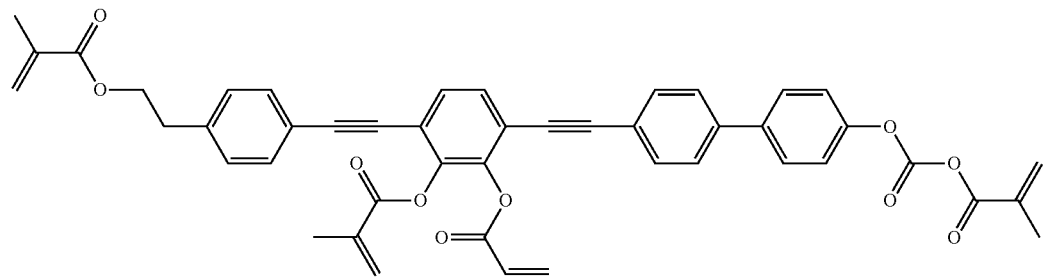
(1-325)
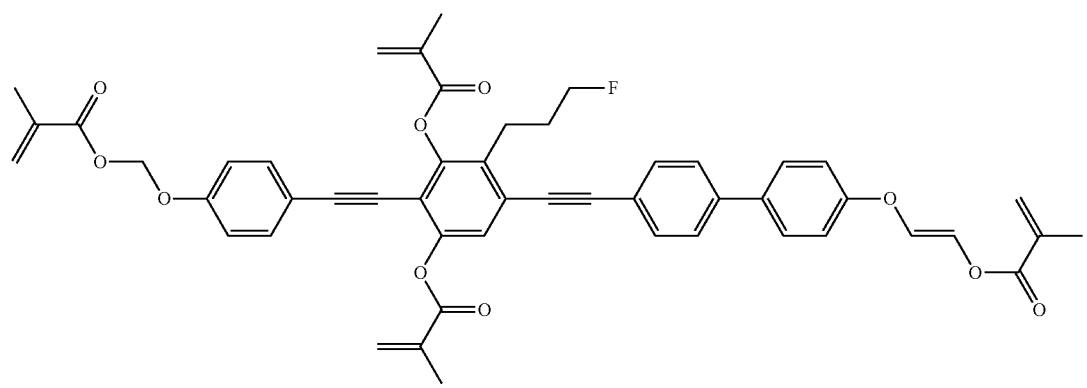
(1-326)
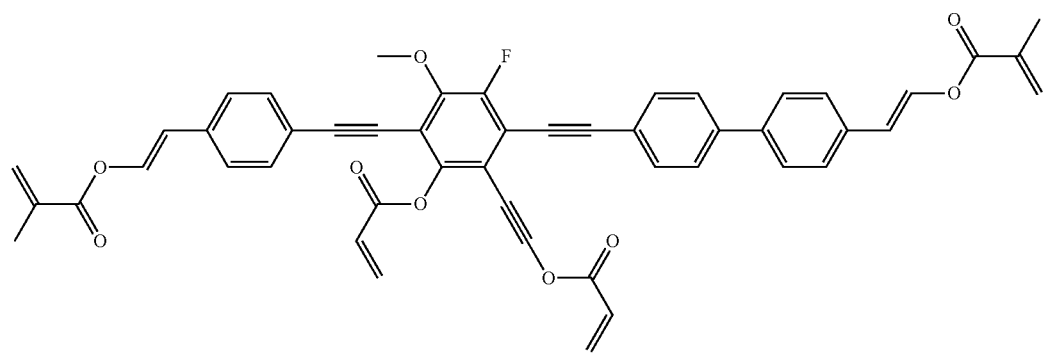

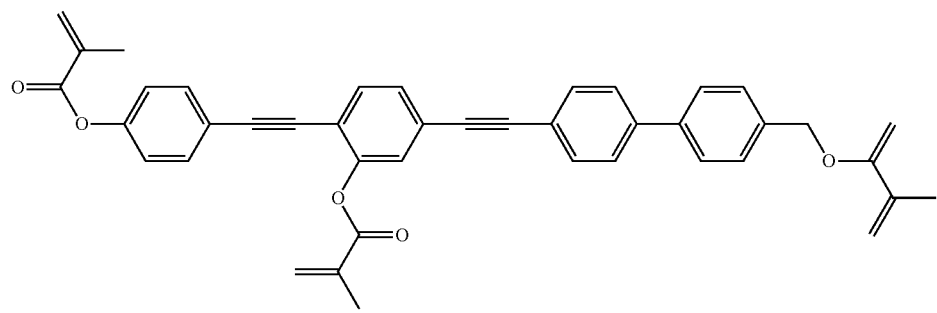
(1-397)
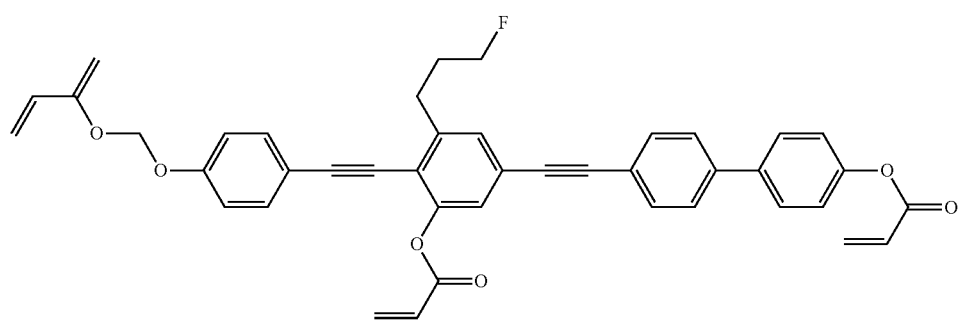
(1-328)
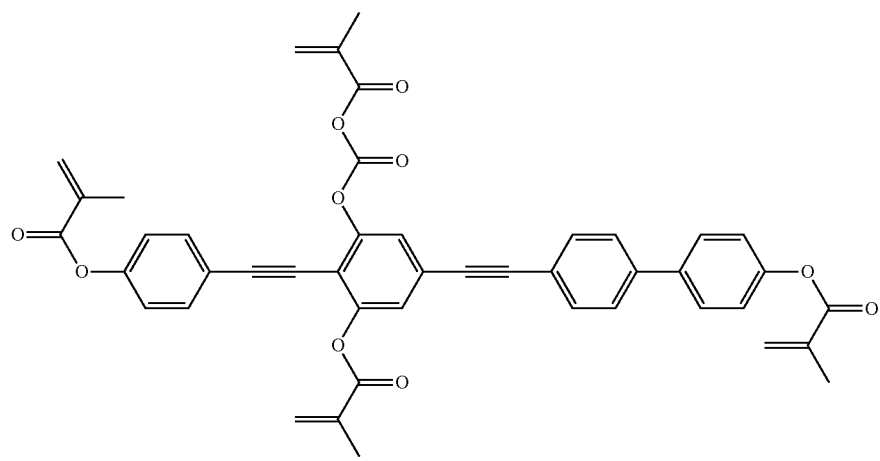
(1-329)
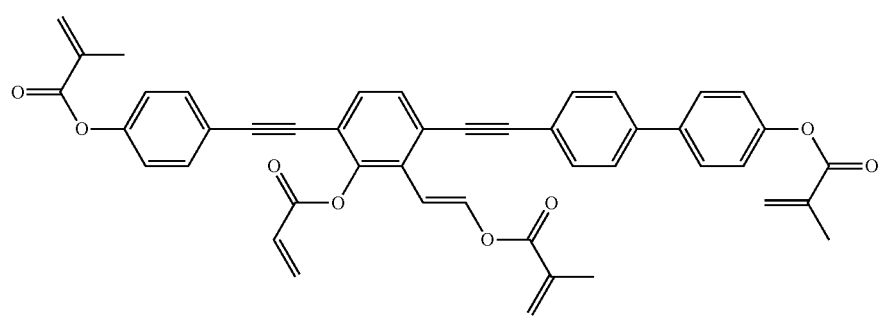
(1-330)

(1-331)
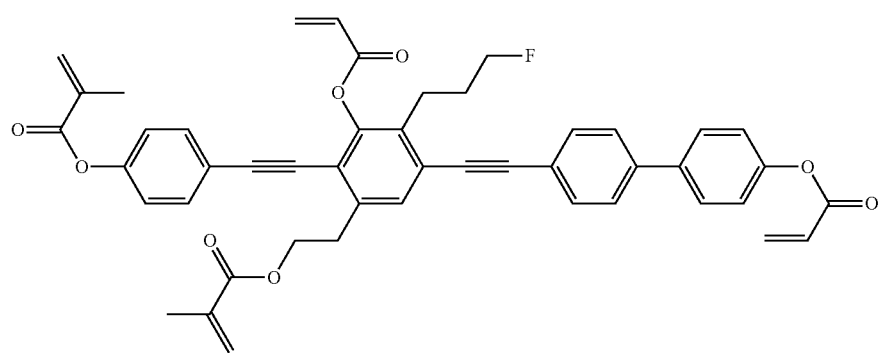
(1-332)
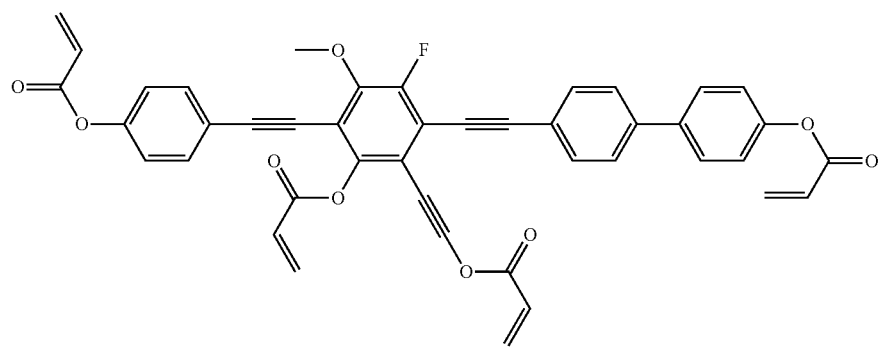
(1-333)
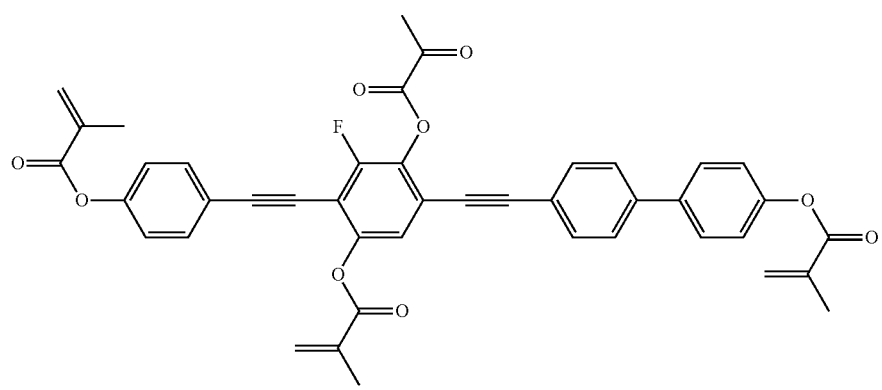
(1-334)
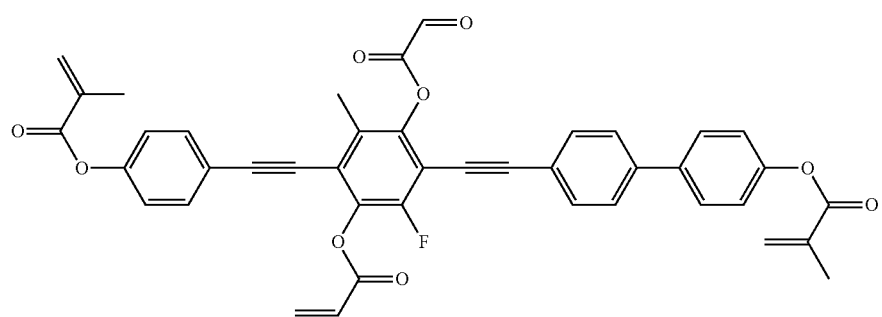

(1-335)
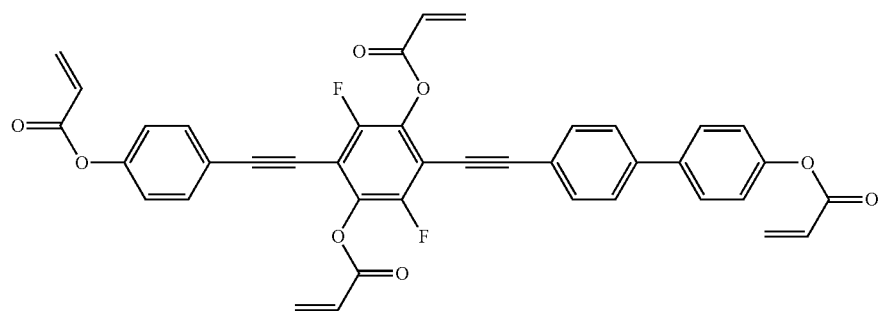
(1-336)
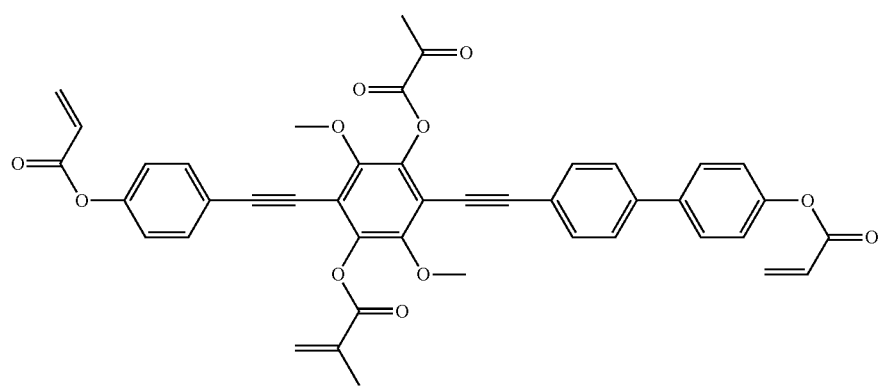
(1-337)
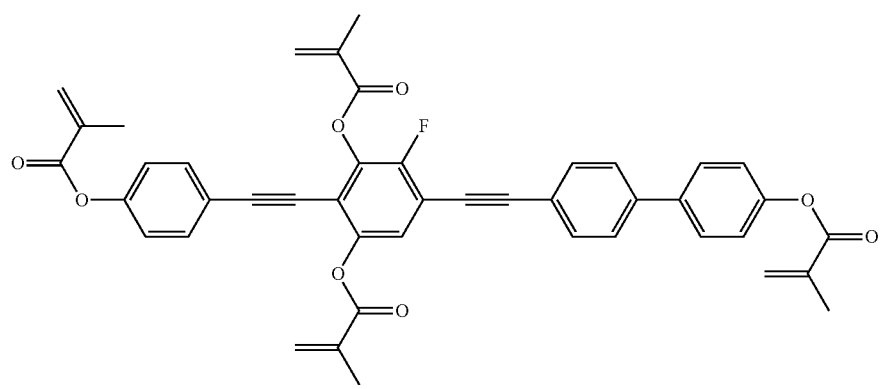
(1-338)
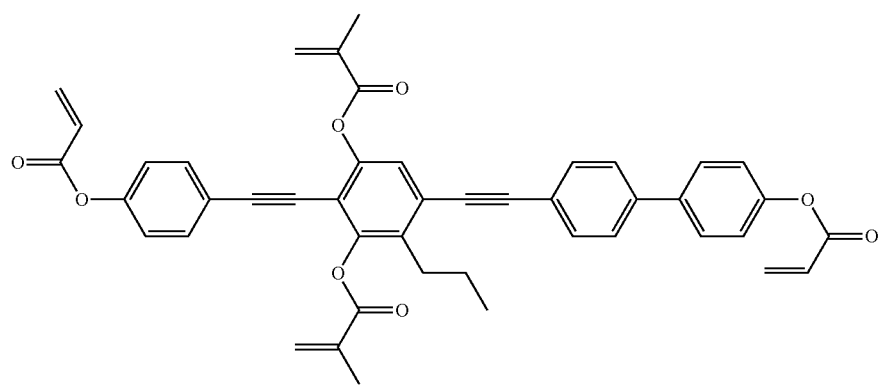

(1-339)
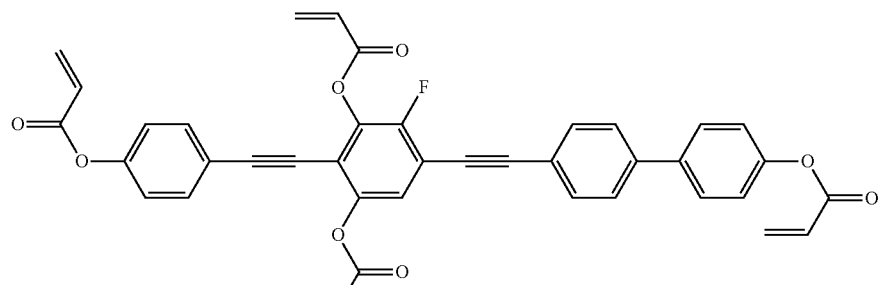
(1-340)
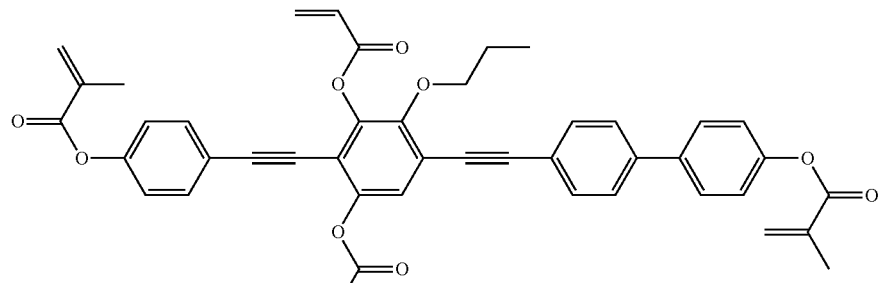
(1-341)
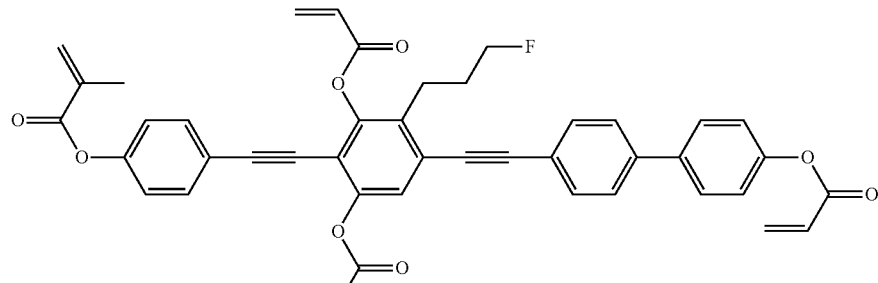
(1-342)
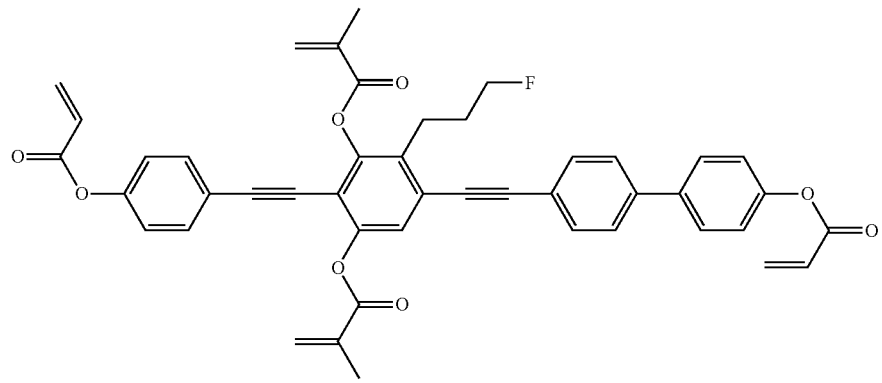
(1-343)
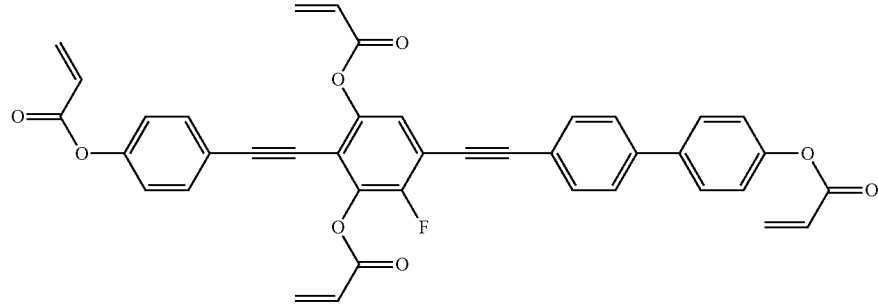

(1-344)
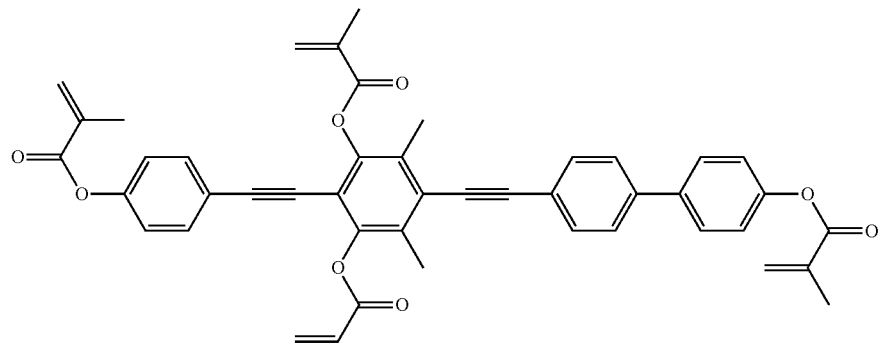
(1-345)
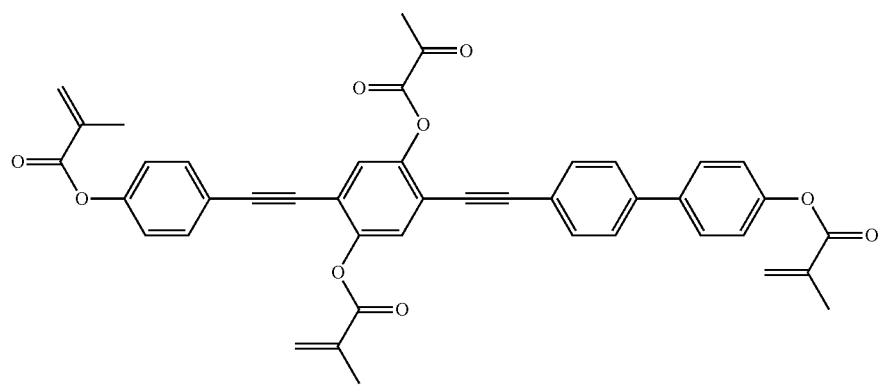
(1-346)
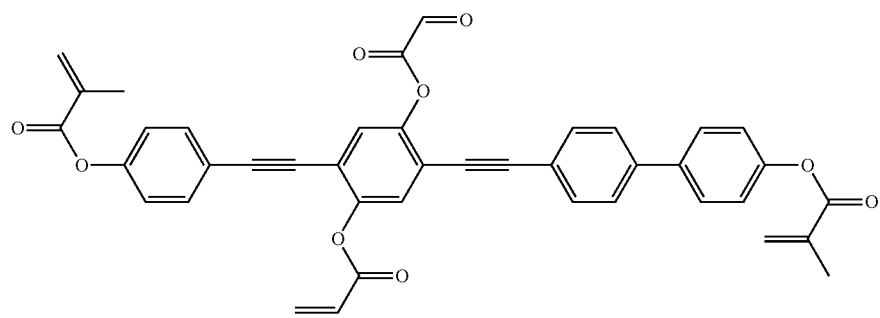
(1-347)
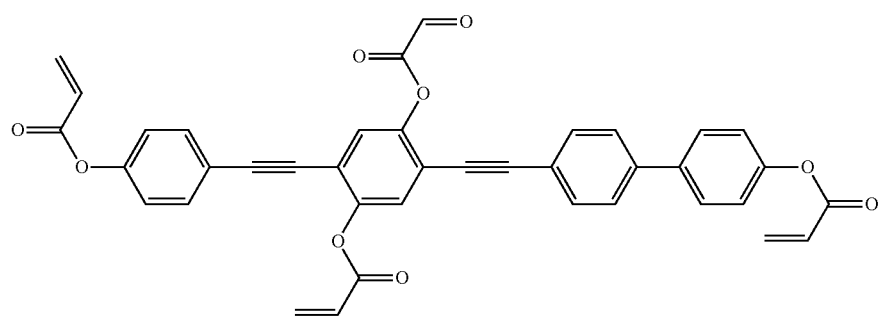

(1-348)
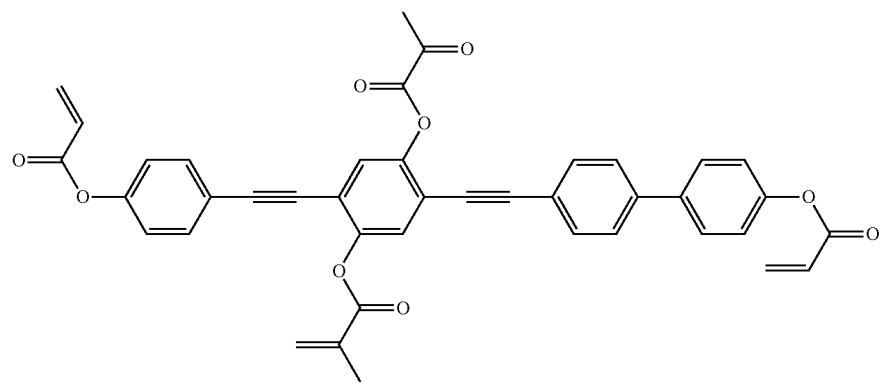
(1-349)
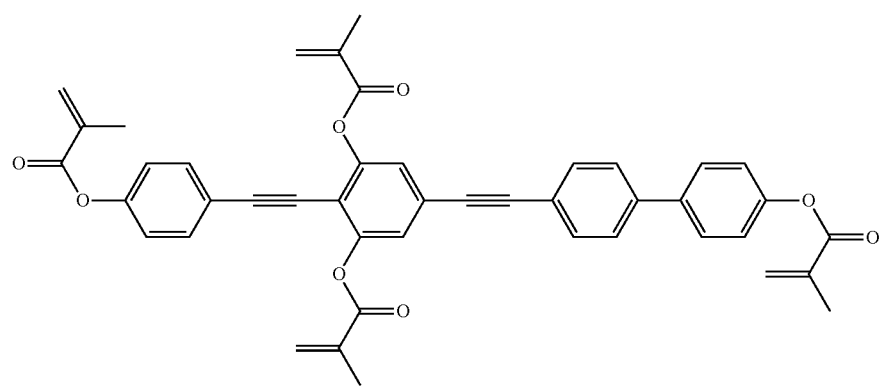
(1-350)
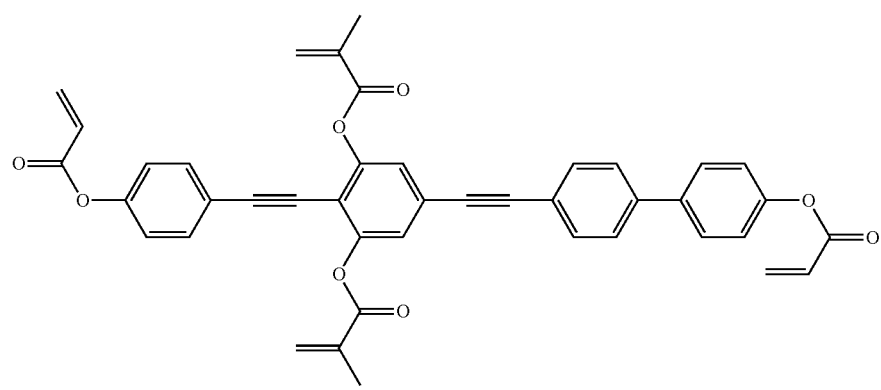
(1-351)
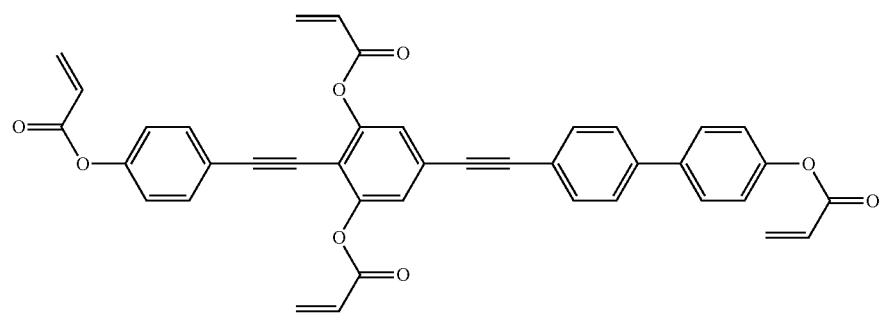

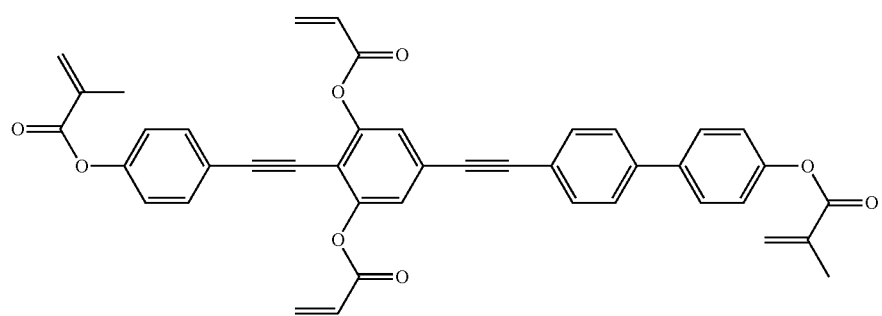
(1-352)
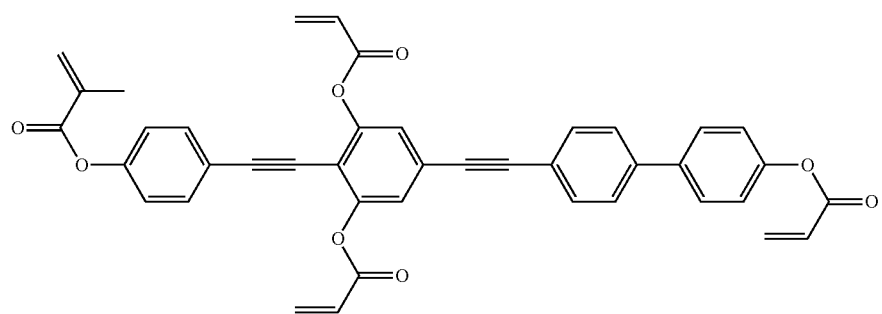
(1-353)
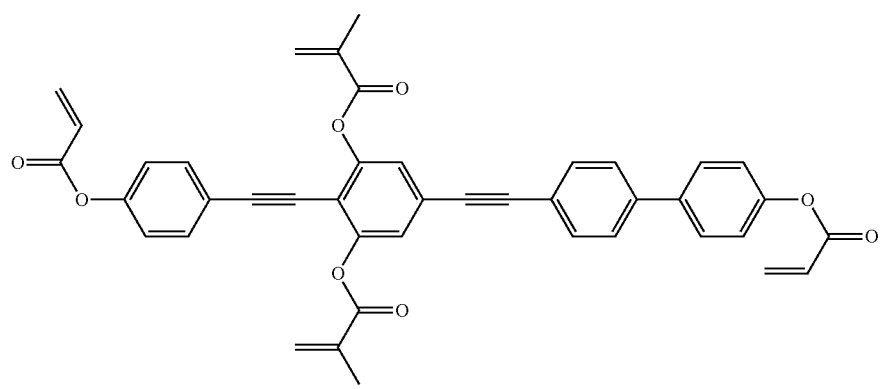
(1-354)
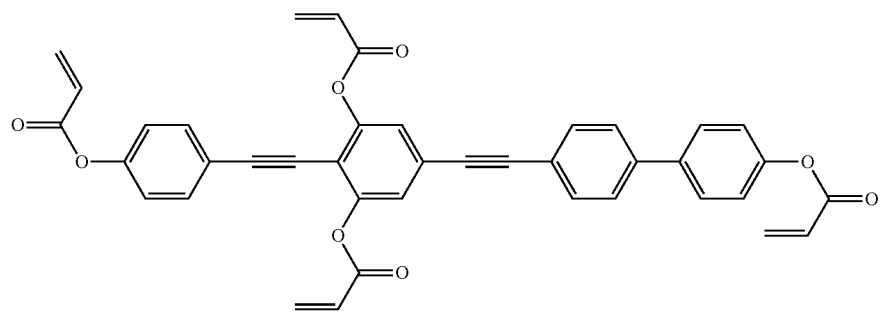
(1-355)

(1-356)
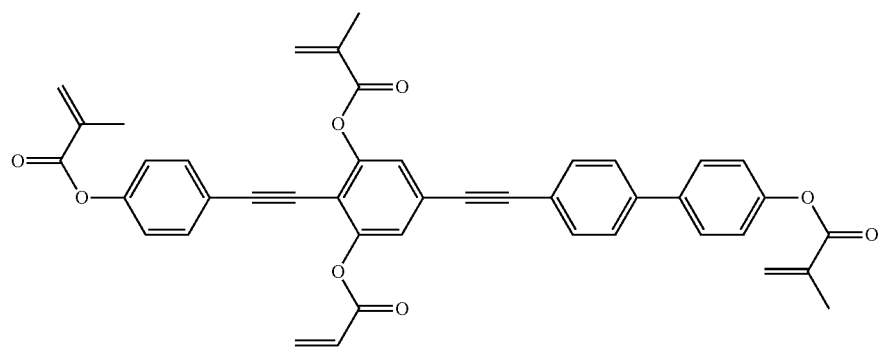
(1-357)
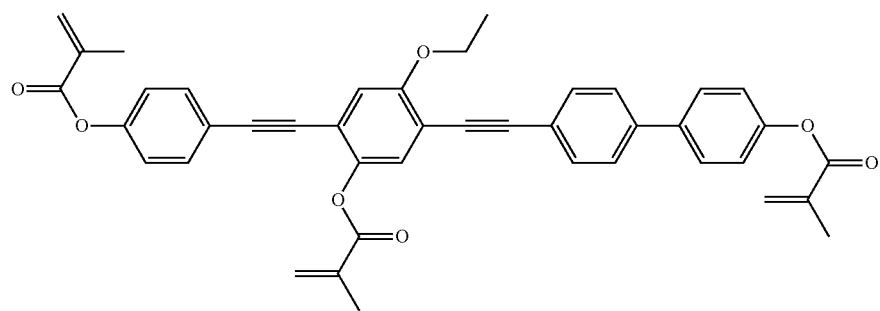
(1-358)
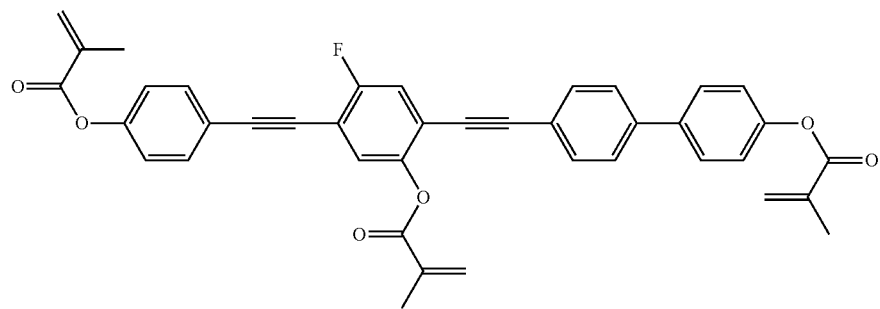
(1-359)
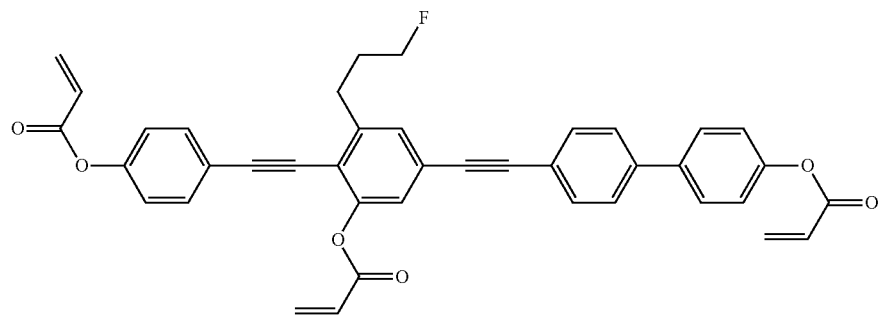
(1-360)
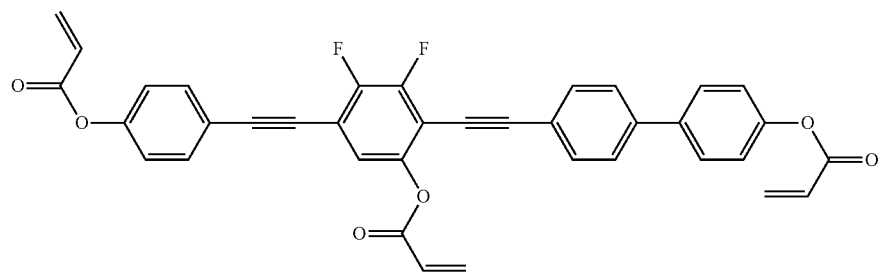

-continued
(1-361)
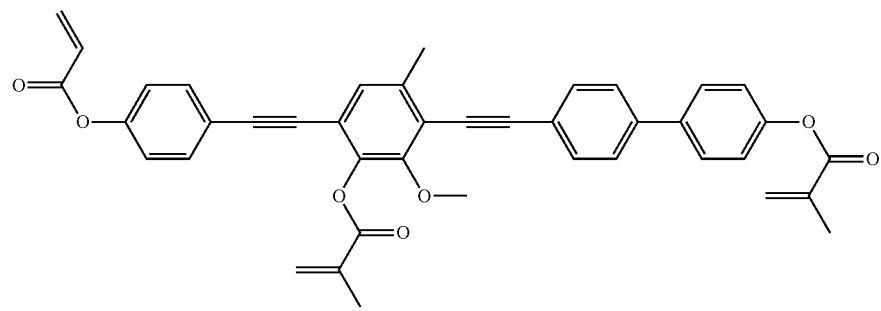
(1-362)
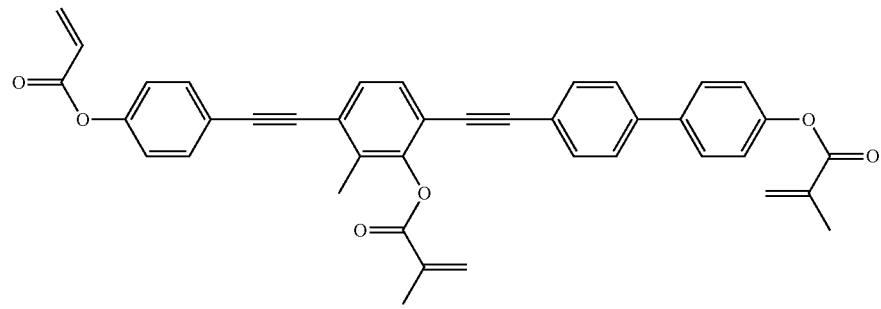
(1-363)
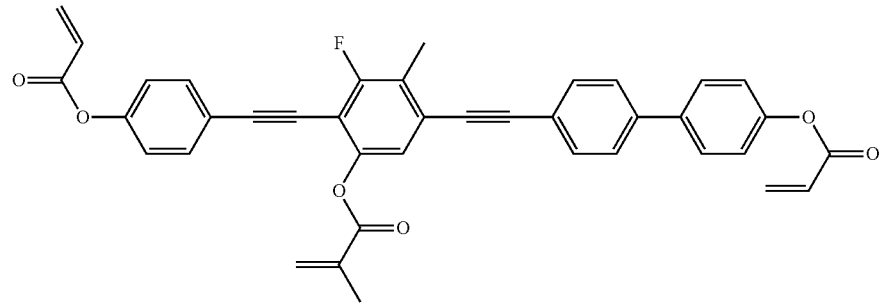
(1-364)
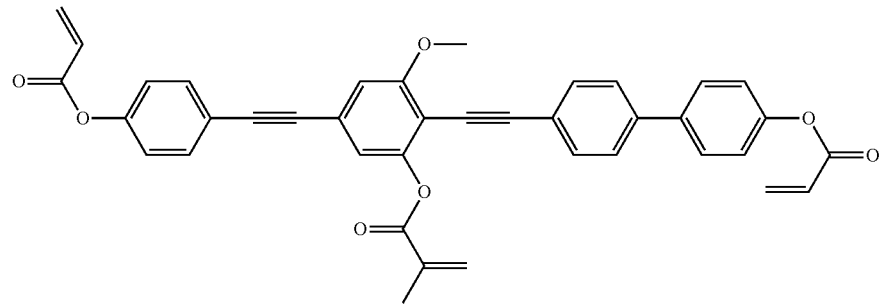
(1-365)
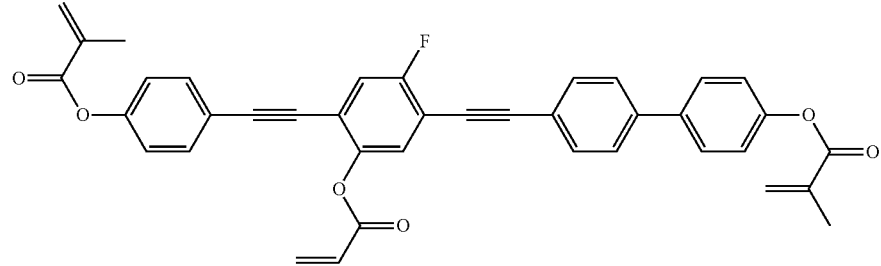

-continued
(1-366)
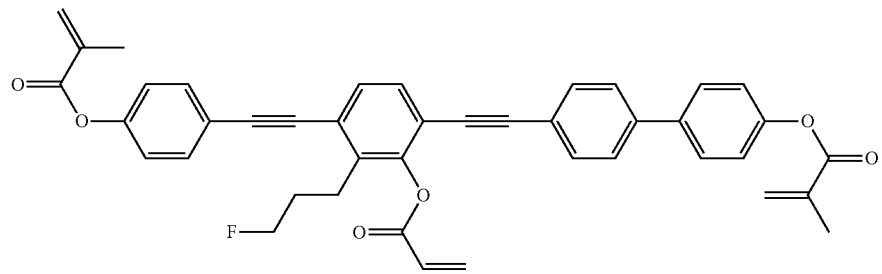
(1-367)
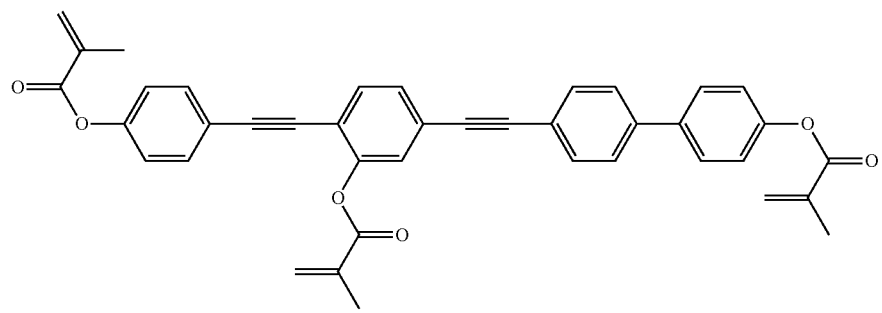
(1-368)
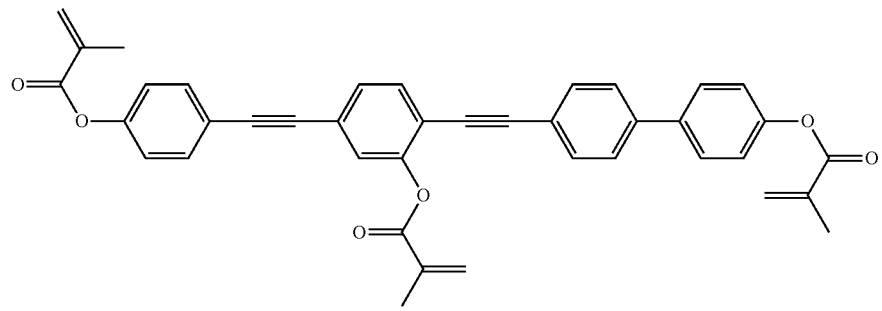
(1-369)
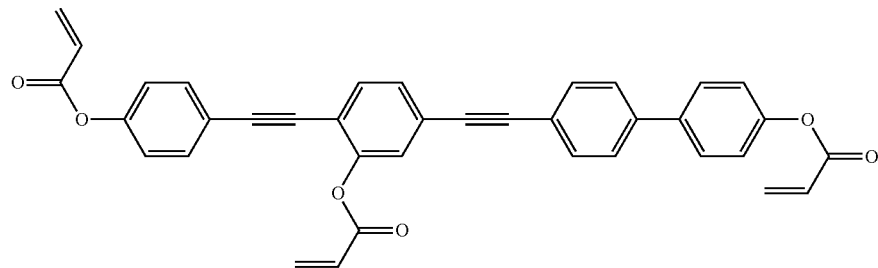
(1-370)
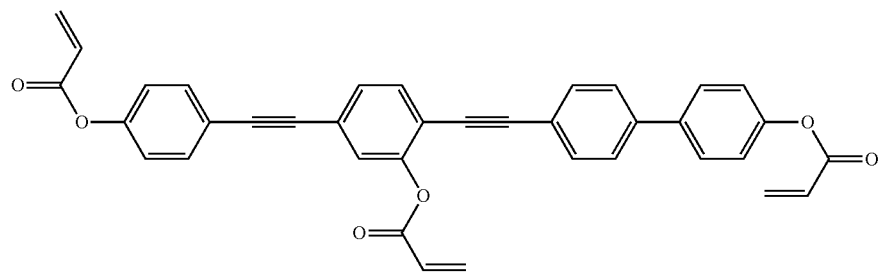

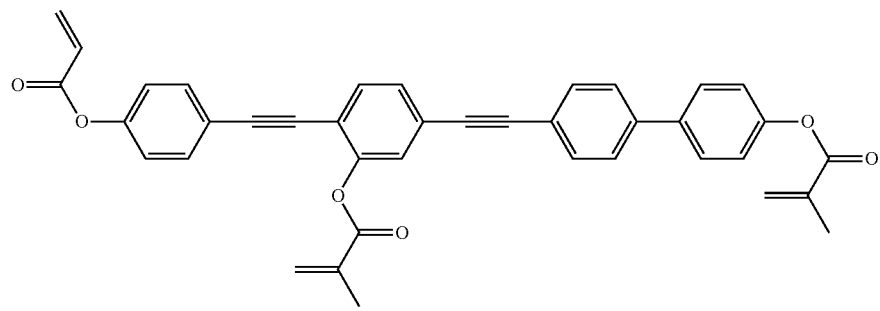
(1-371)
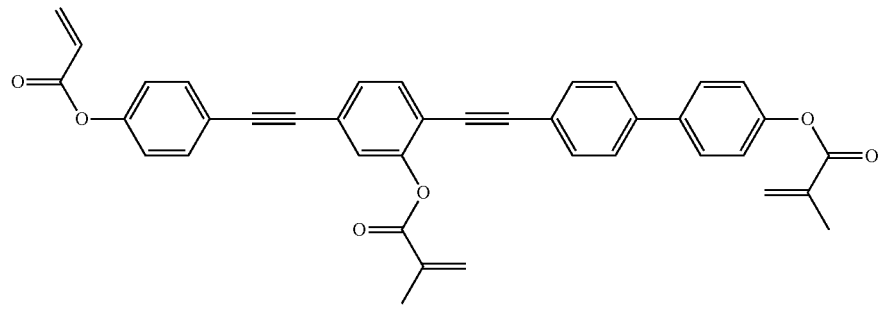
(1-372)
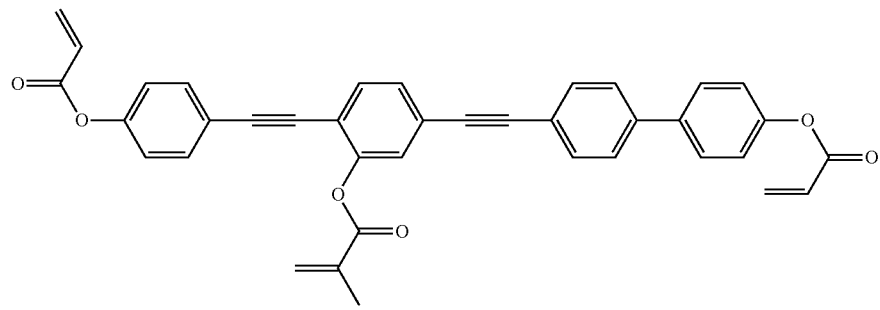
(1-373)
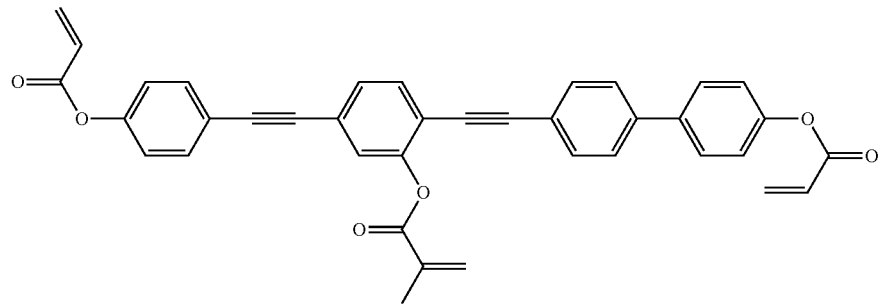
(1-374)
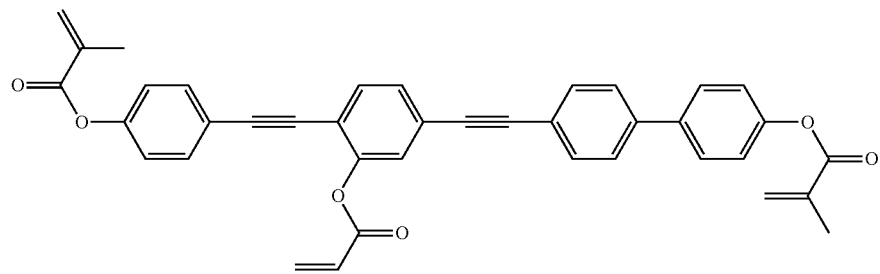
(1-375)

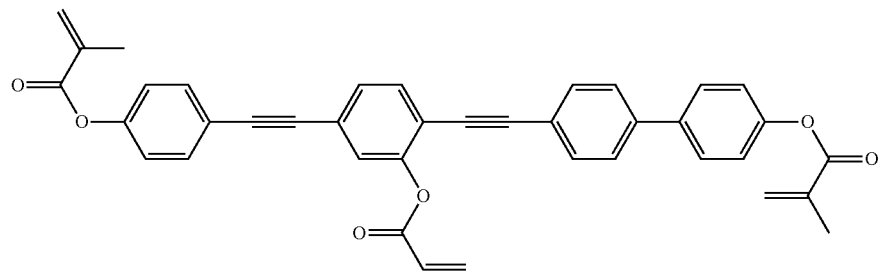
(1-376)
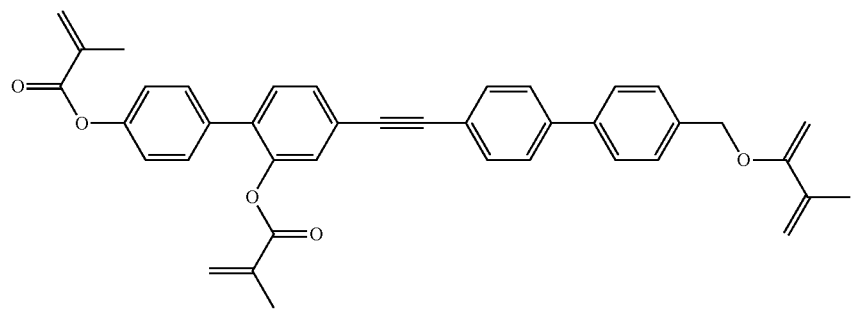
(1-377)
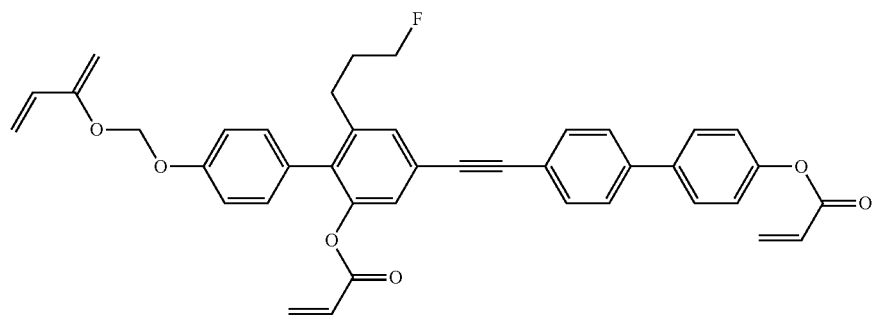
(1-378)
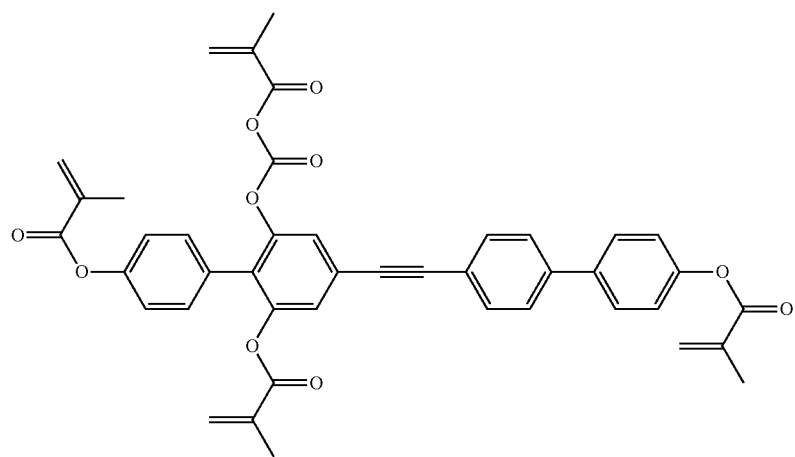
(1-379)

(1-380)
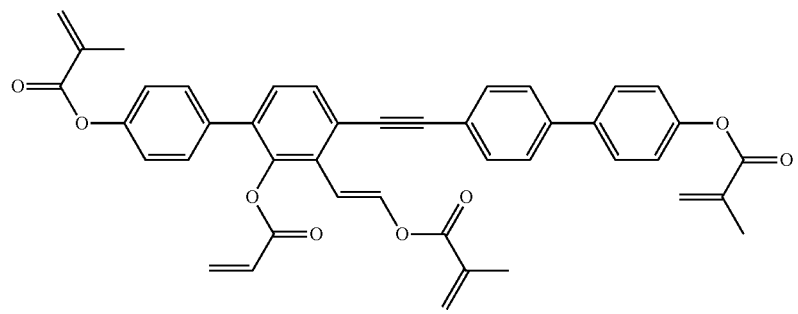
(1-381)
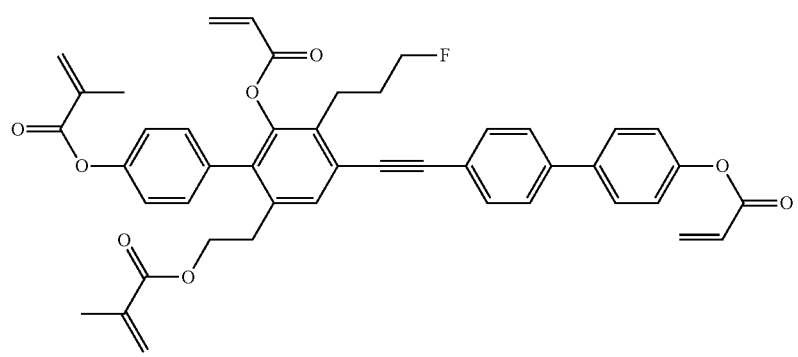
(1-382)
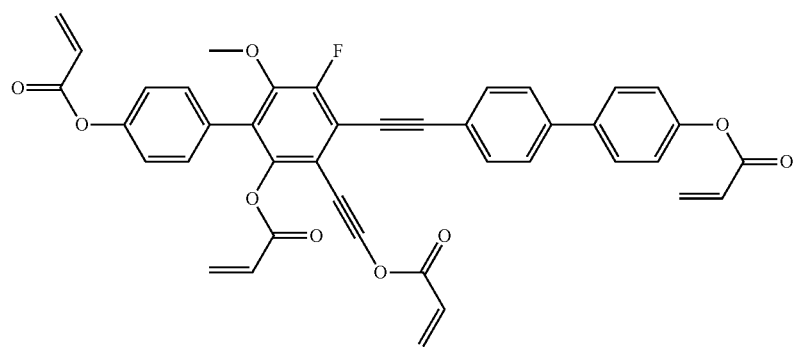
(1-383)
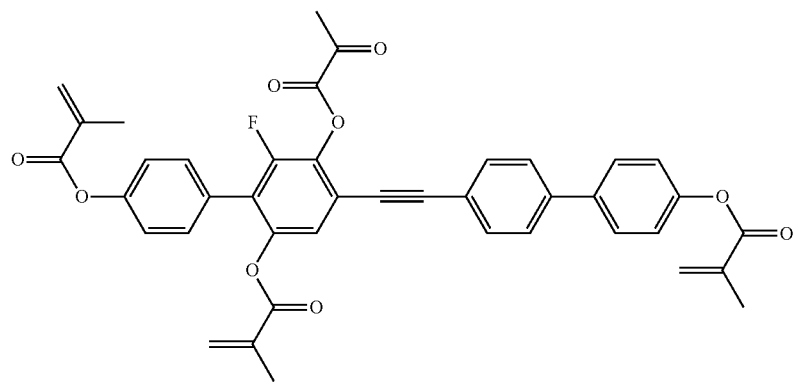

(1-384)
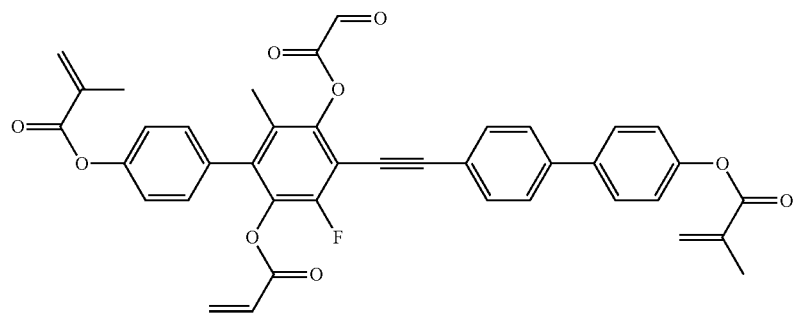
(1-385)
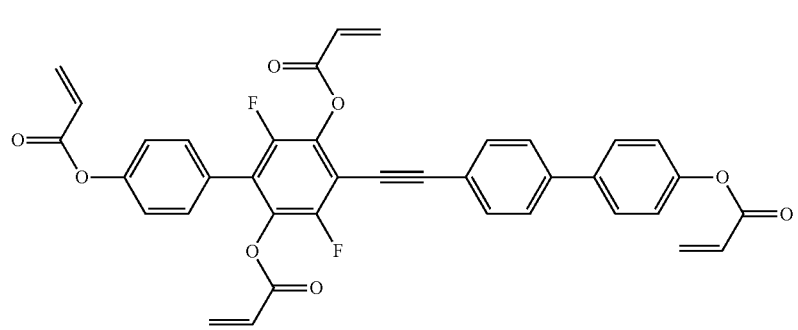
(1-386)
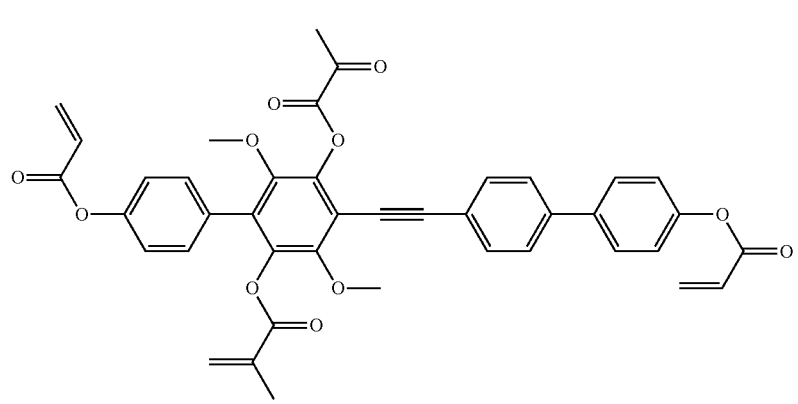
(1-387)
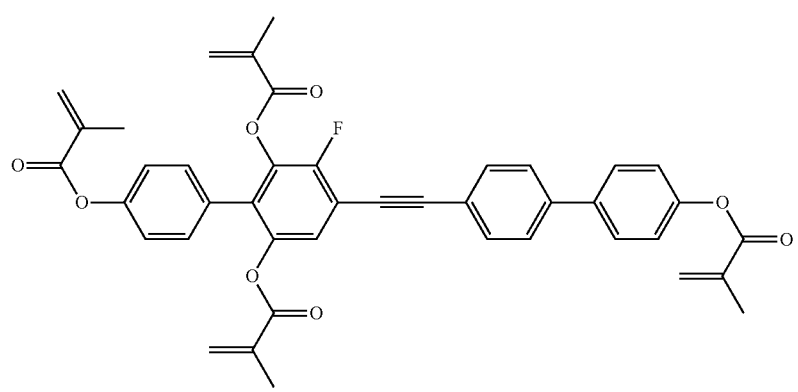

-continued
(1-388)
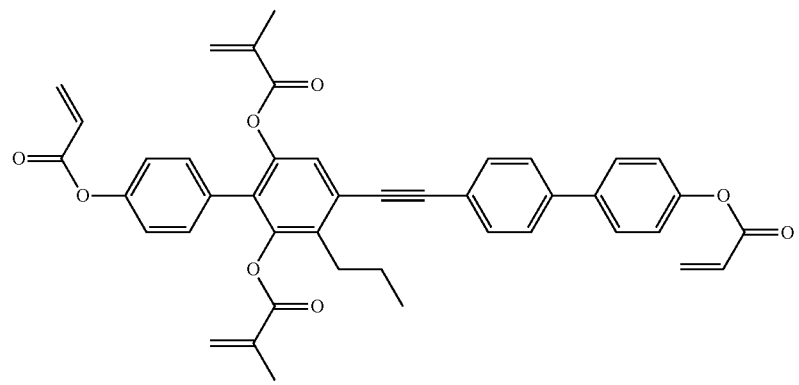
(1-389)
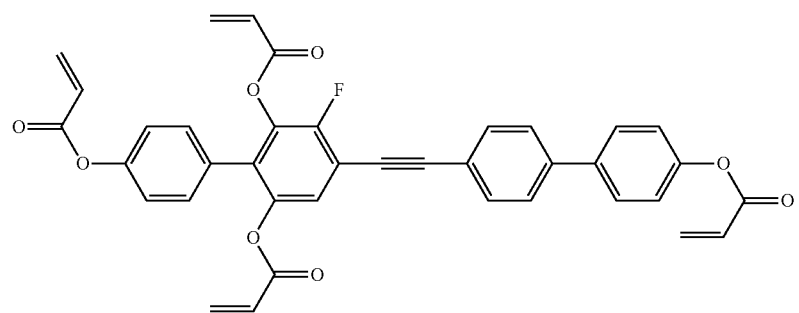
(1-390)
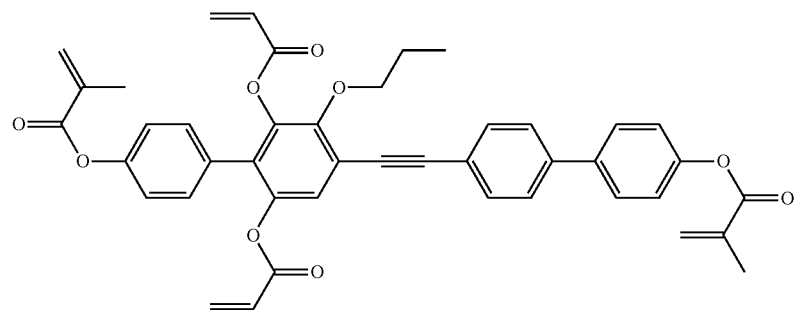
(1-391)
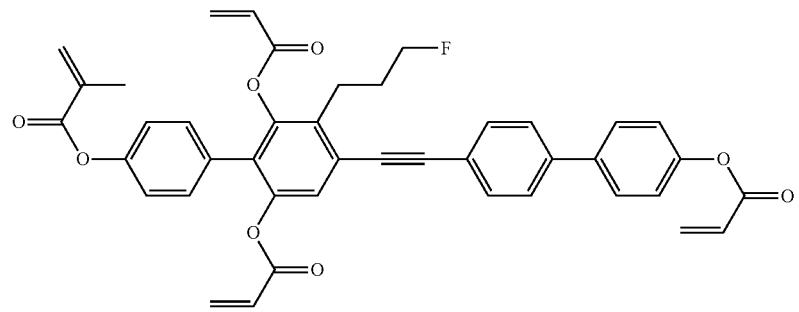

(1-392)
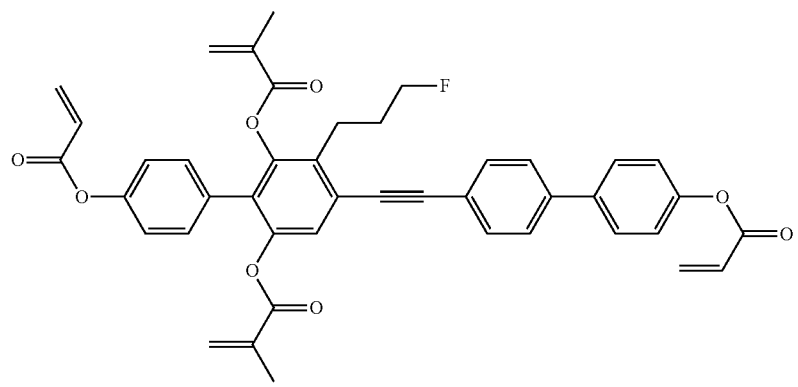
(1-393)
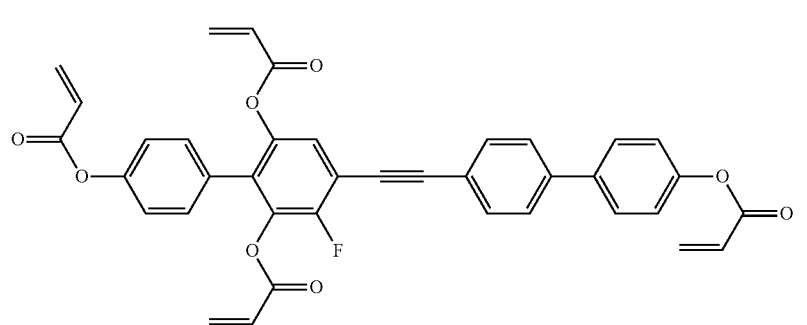
(1-394)
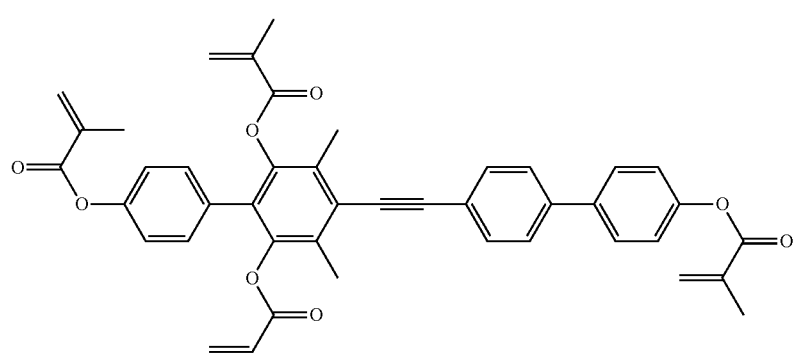
(1-395)
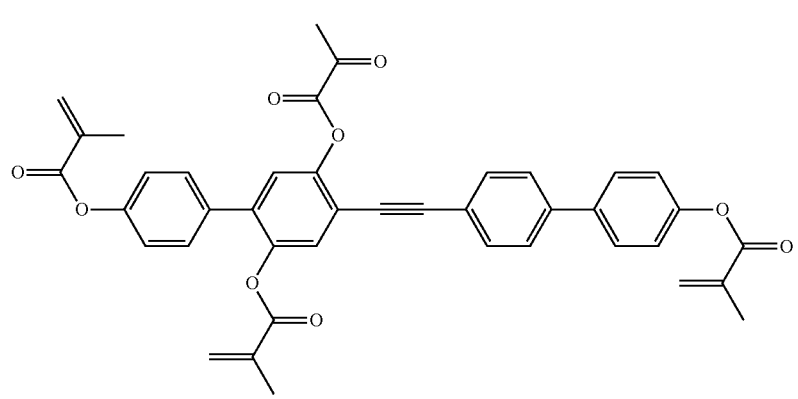

(1-396)
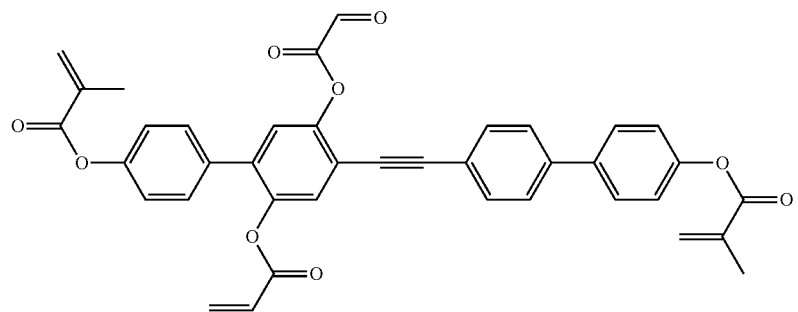
(1-397)
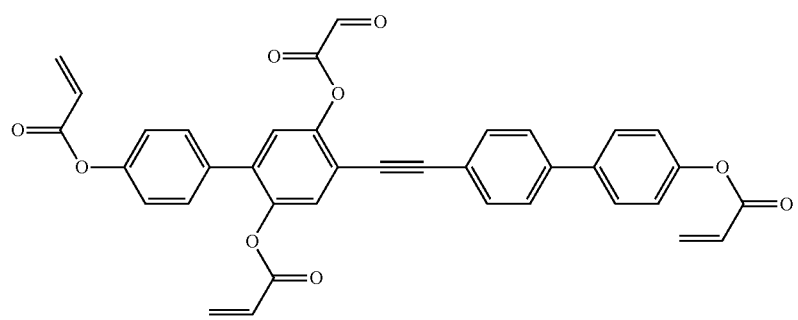
(1-398)
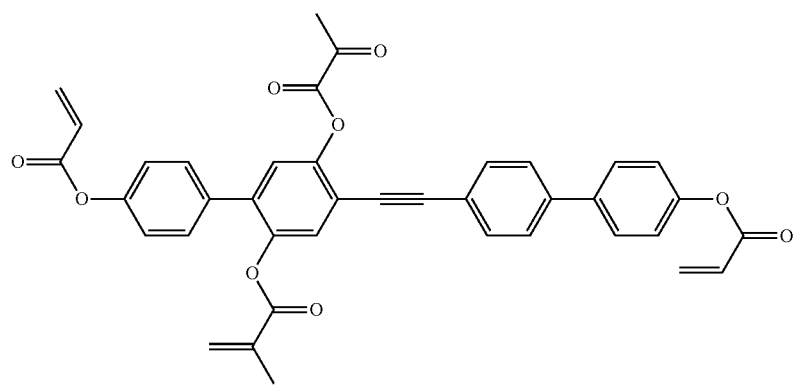
(1-399)
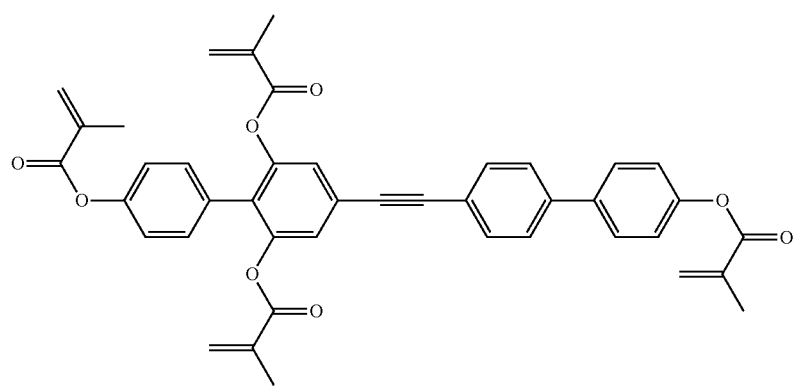

(1-400)
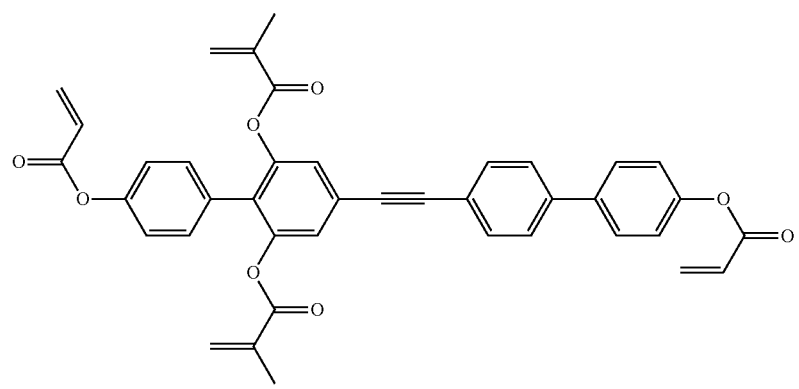
(1-401)
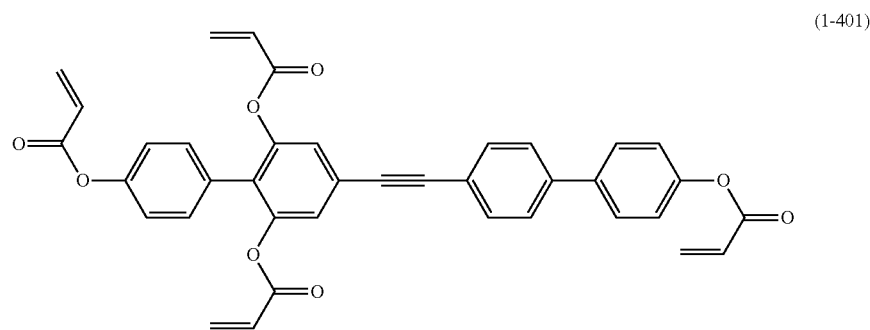
(1-402)
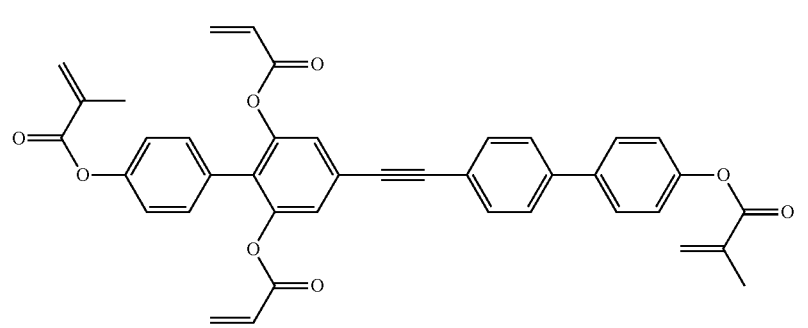
(1-403)
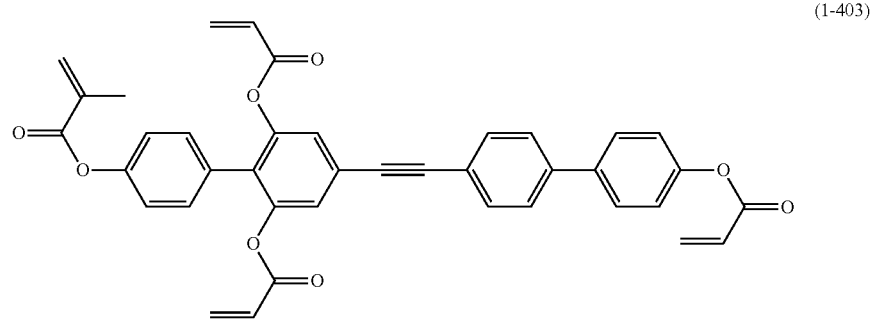

(1-404)
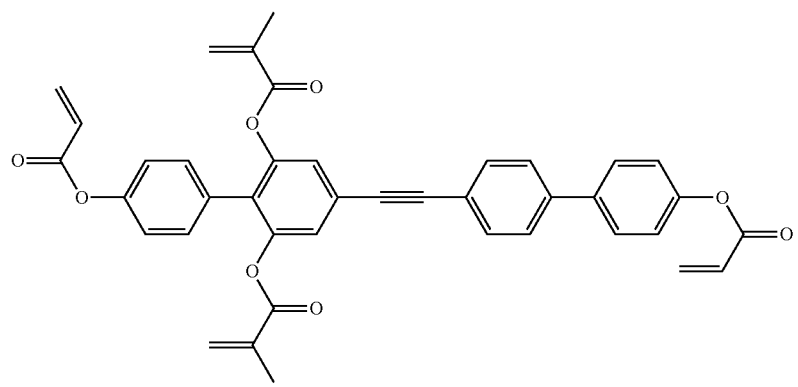
(1-405)
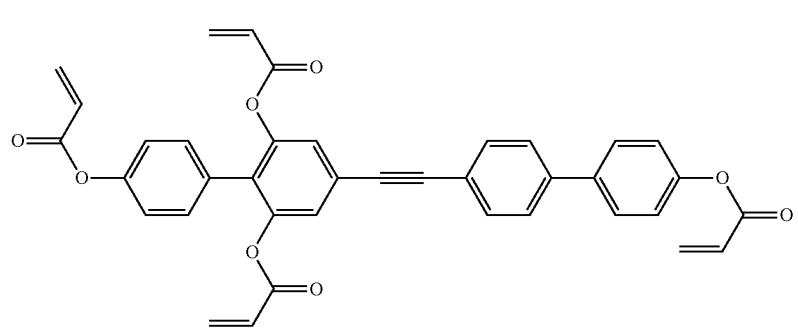
(1-406)
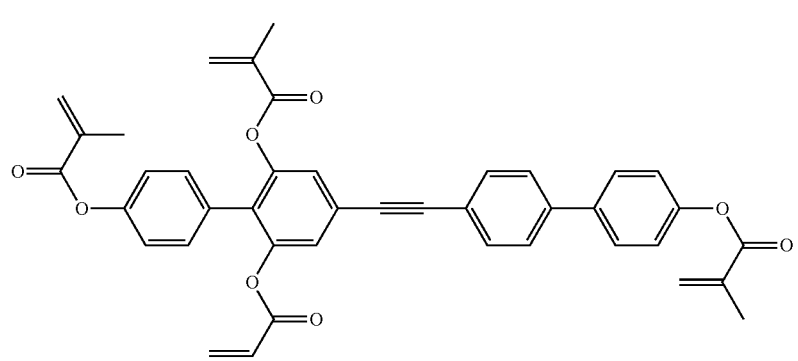
(1-407)
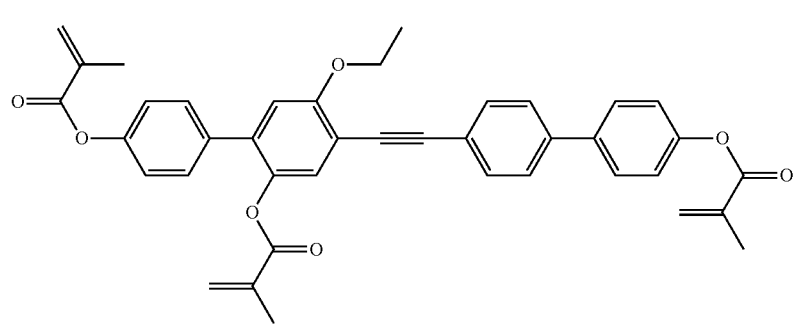

(1-408)
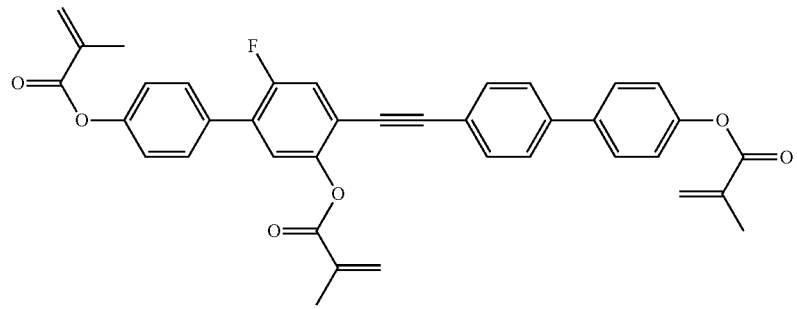
(1-409)
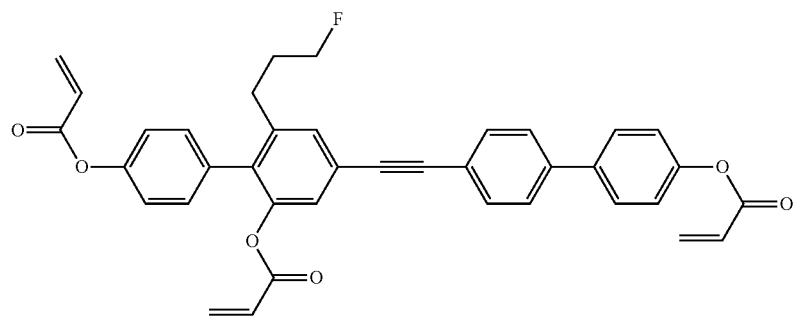
(1-410)
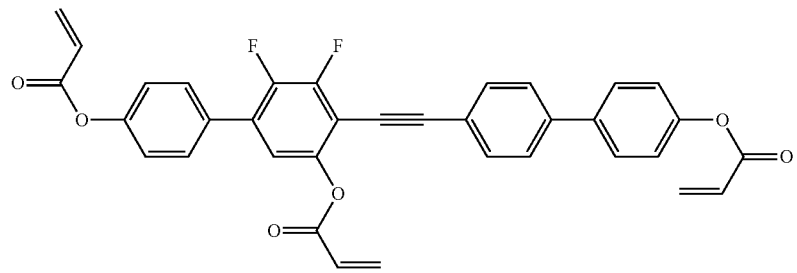
(1-411)
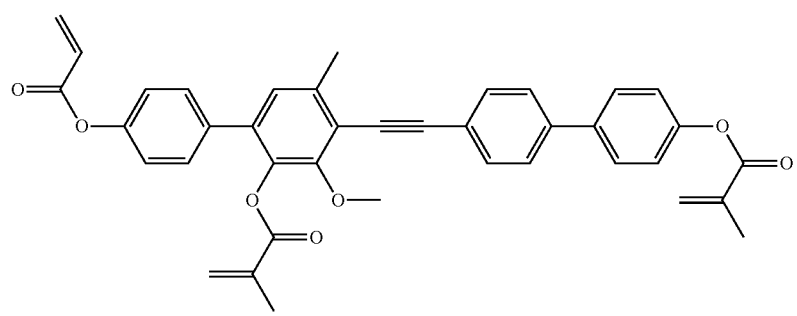
(1-412)
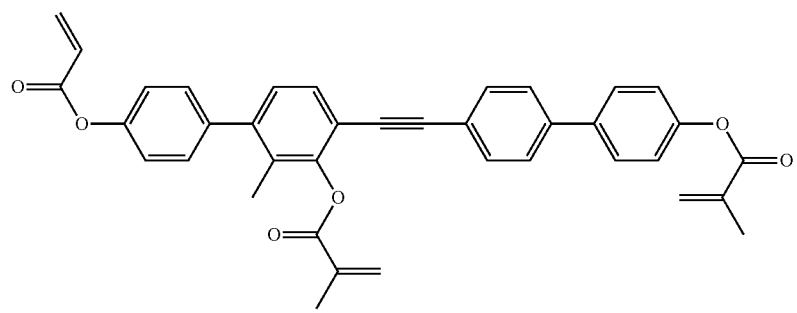

-continued
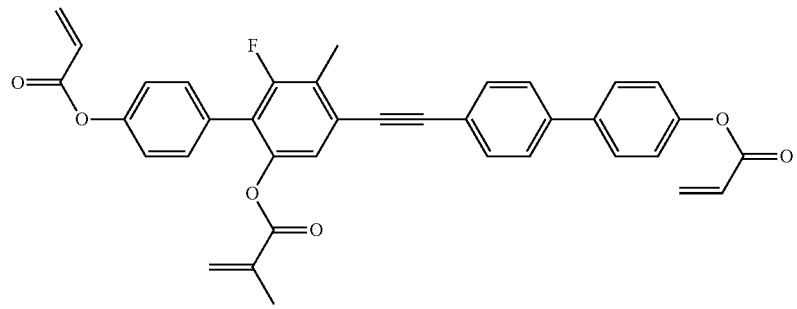
(1-413)
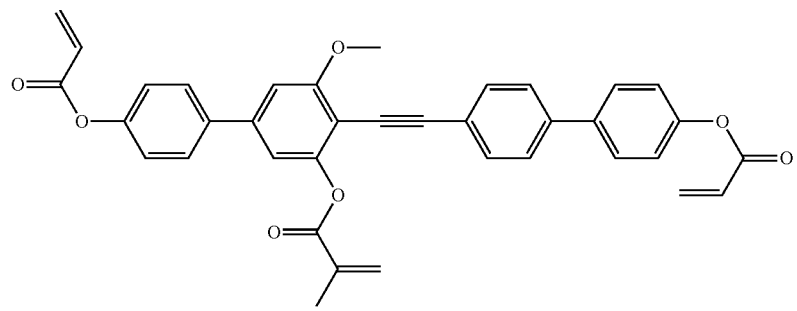
(1-414)
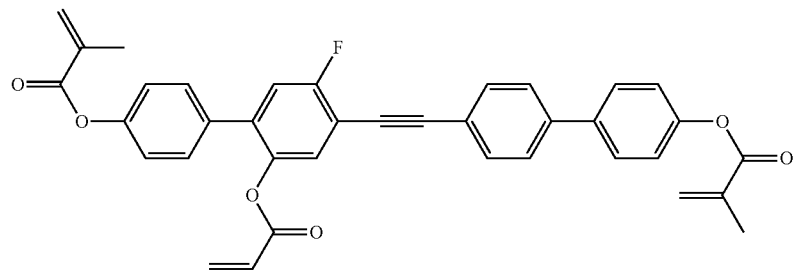
(1-415)
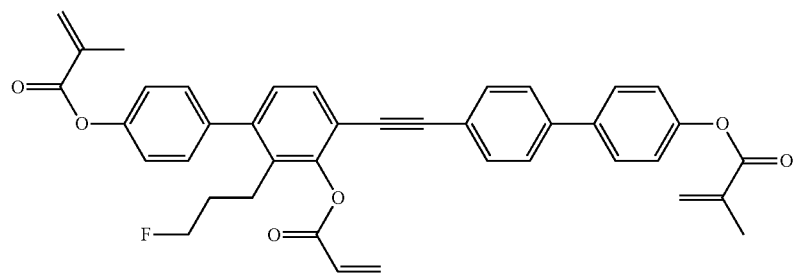
(1-416)
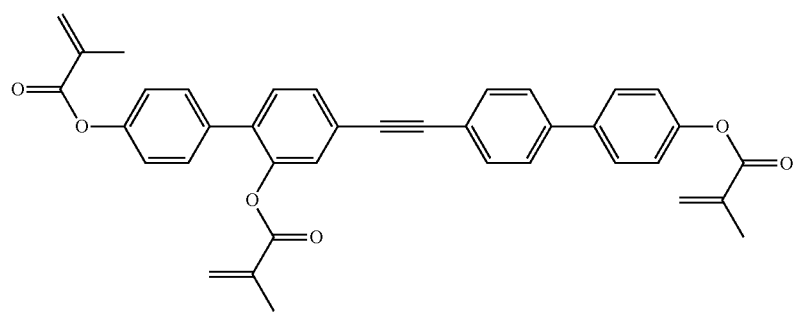
(1-417)

-continued
(1-418)
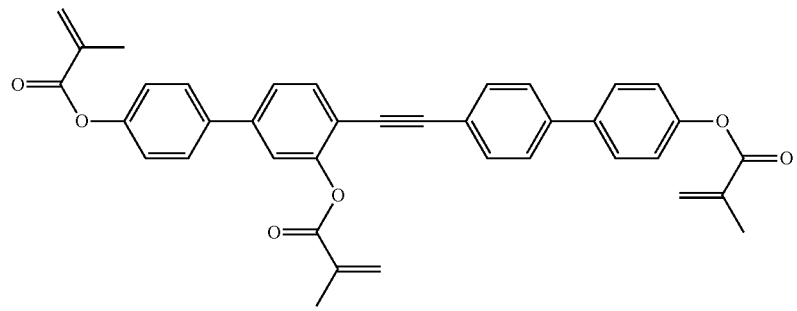
(1-419)
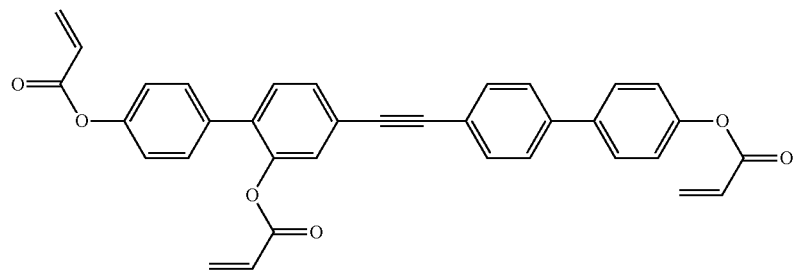
(1-420)
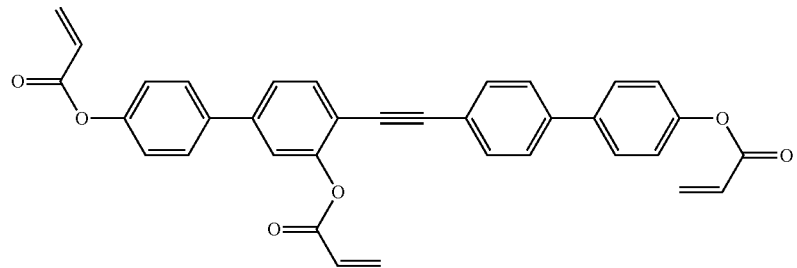
(1-421)
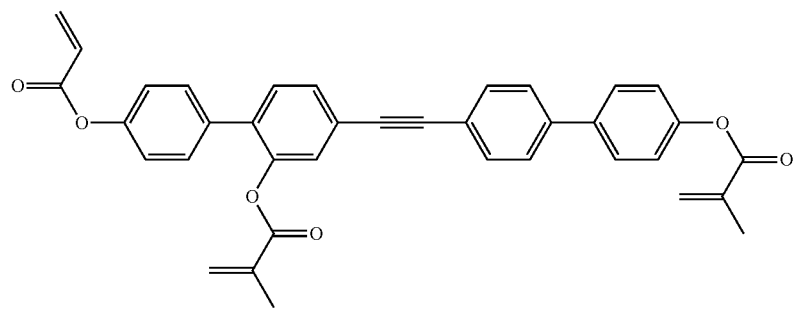
(1-422)
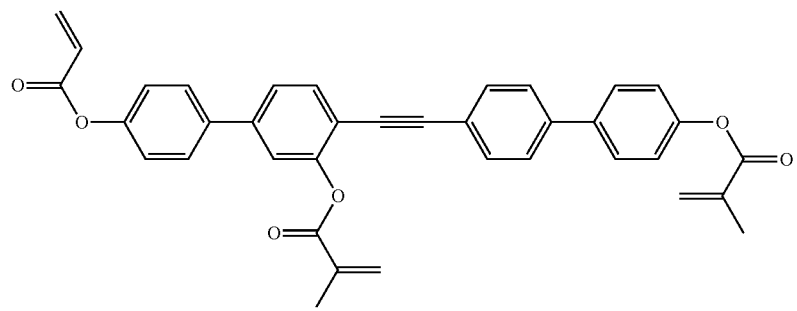

(1-423)
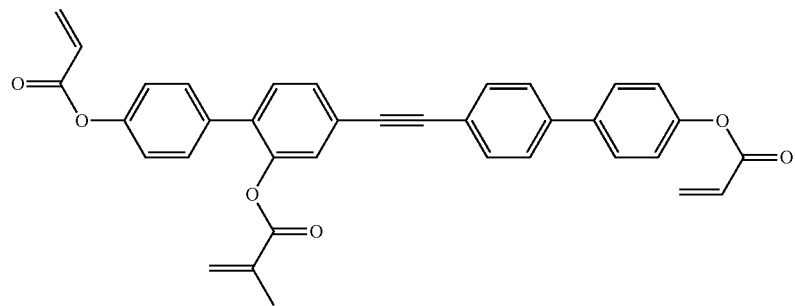
(1-424)
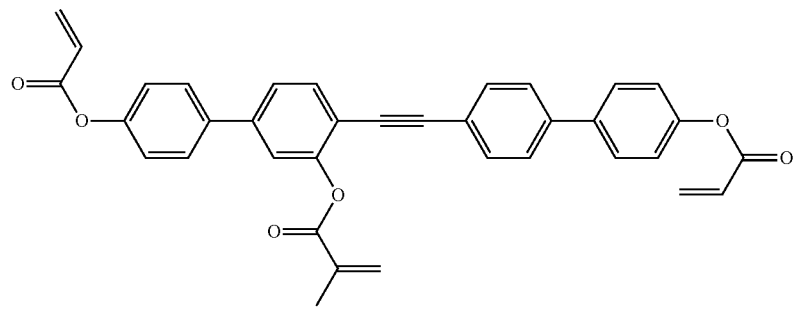
(1-425)
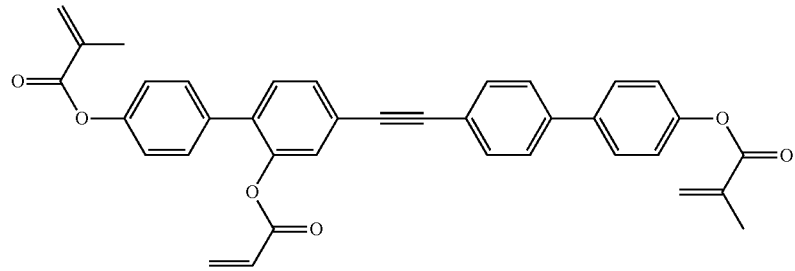
(1-426)
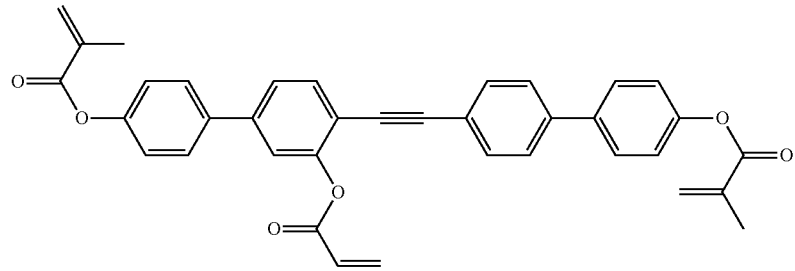
(1-427)
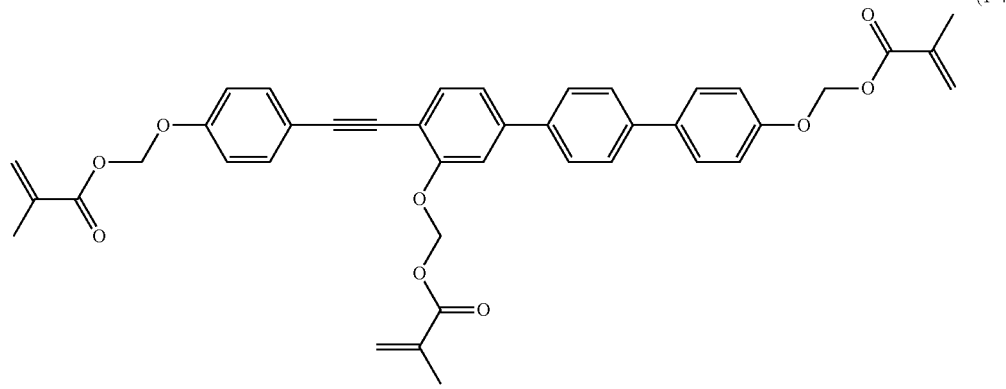

(1-428)
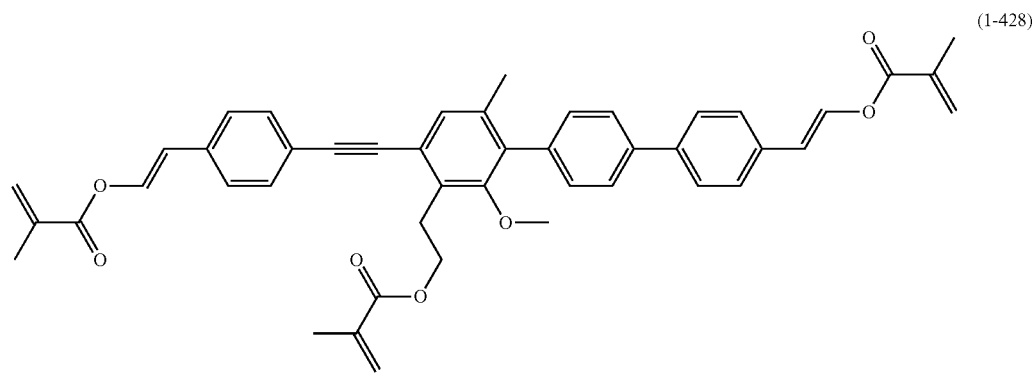
(1-429)
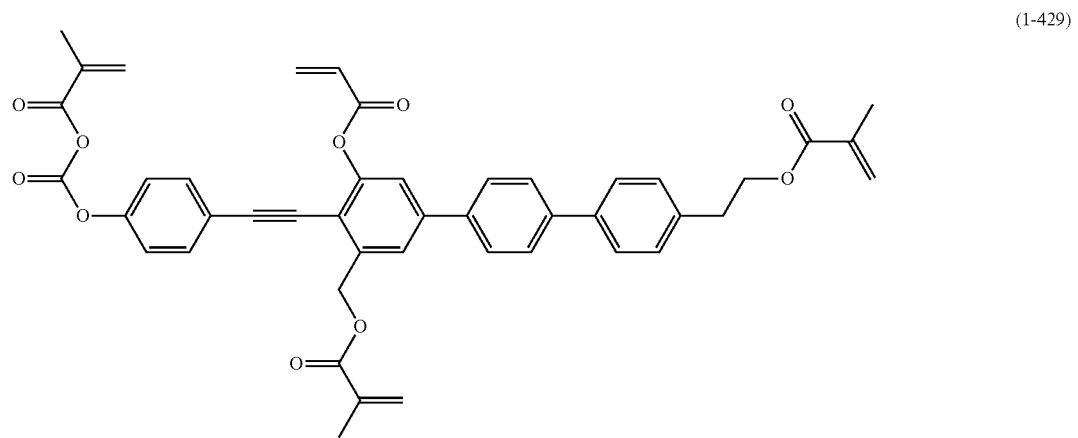
(1-430)
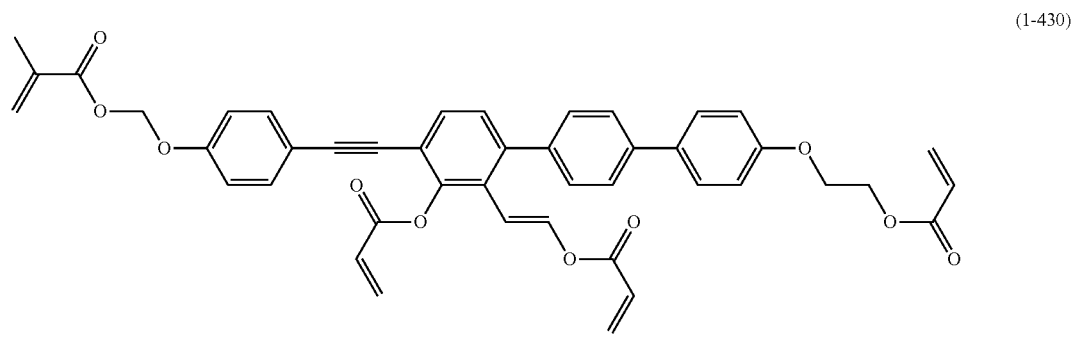
(1-431)
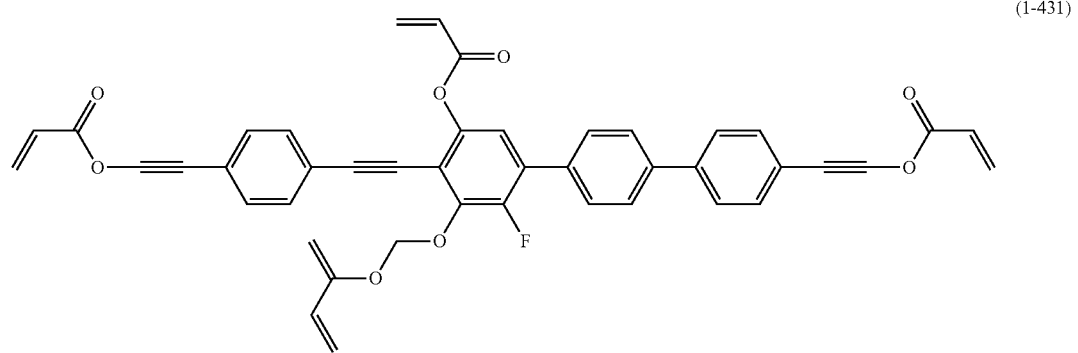

(1-432)
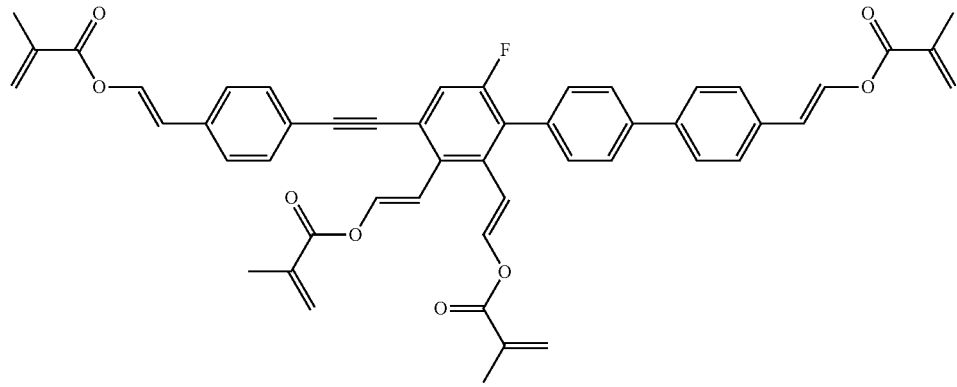
(1-433)
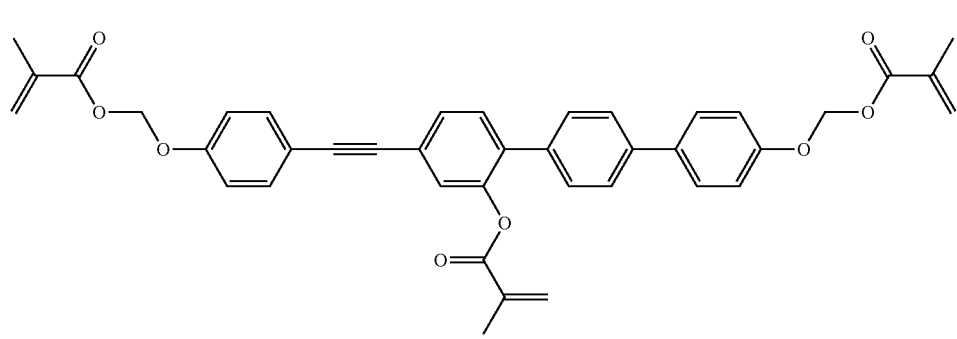
(1-434)
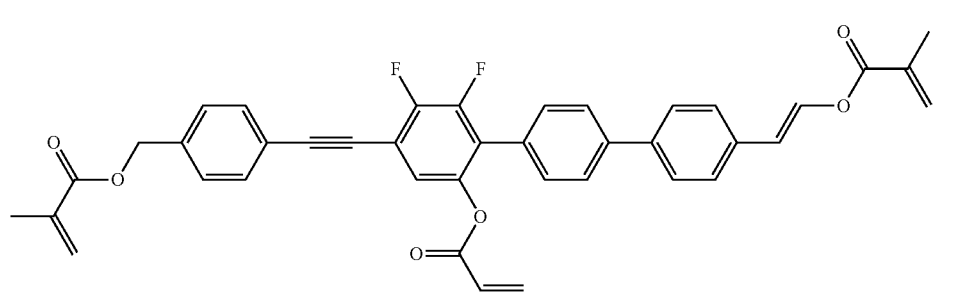
(1-435)
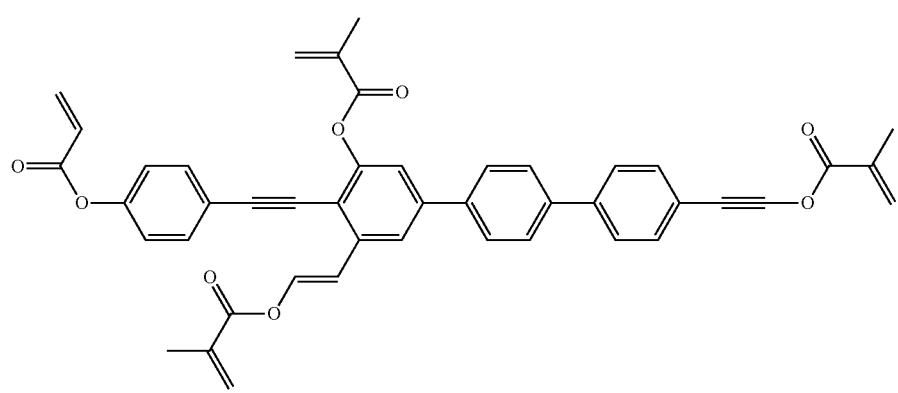
(1-436)
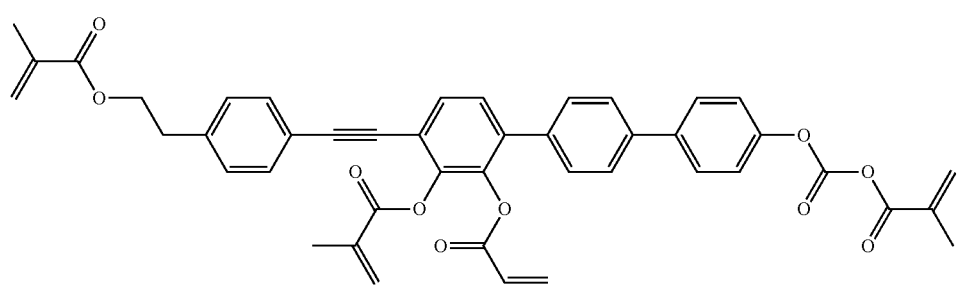

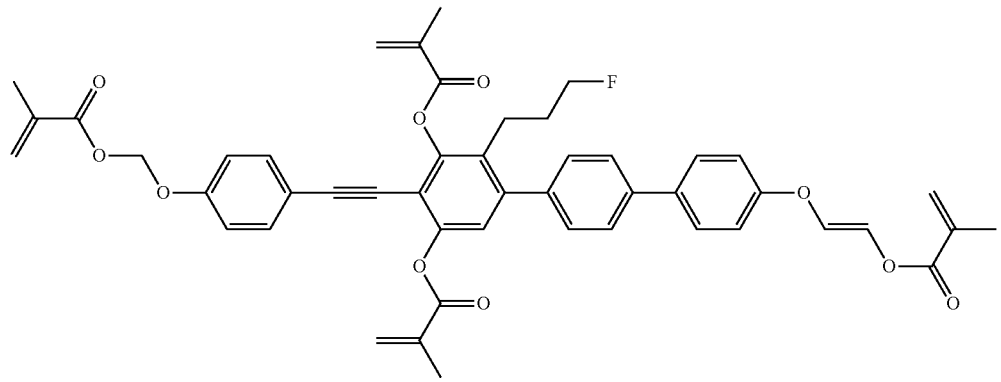
(1-437)
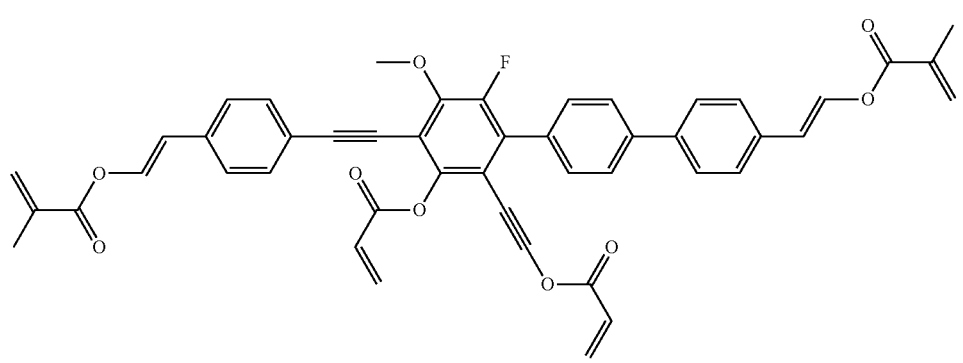
(1-438)
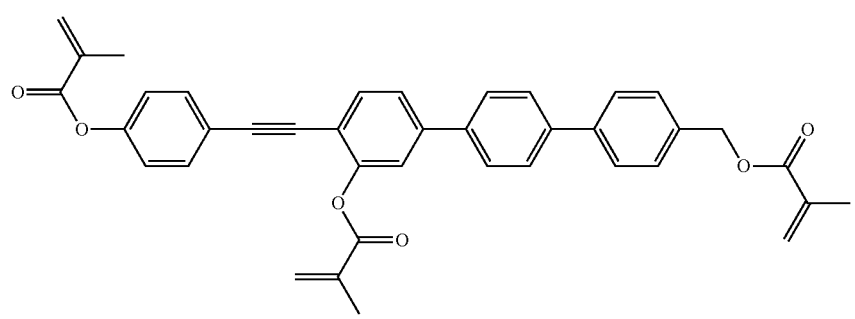
(1-439)
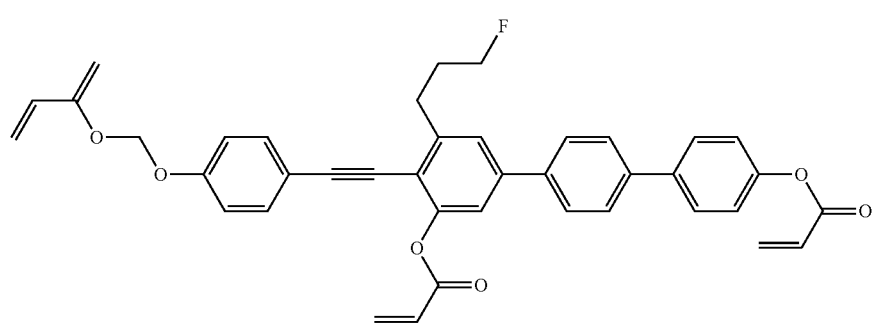
(1-440)

-continued
(1-441)
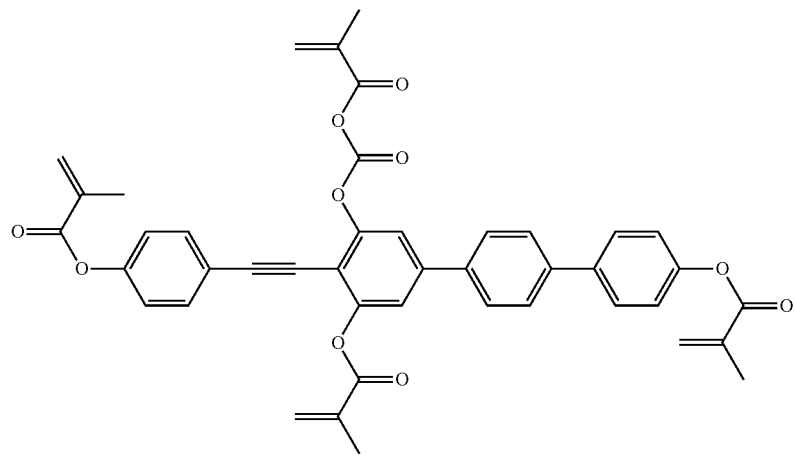
(1-442)
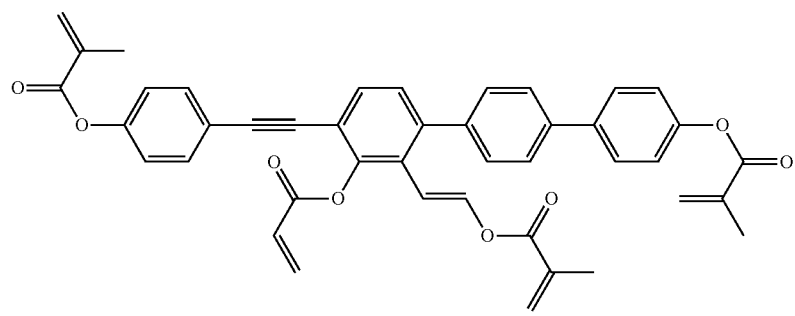
(1-443)
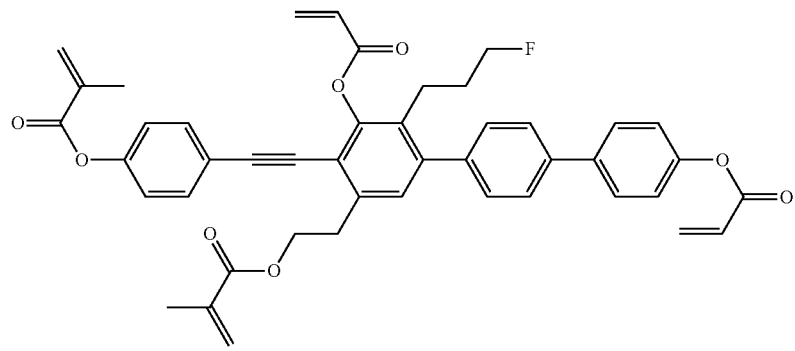
(1-444)
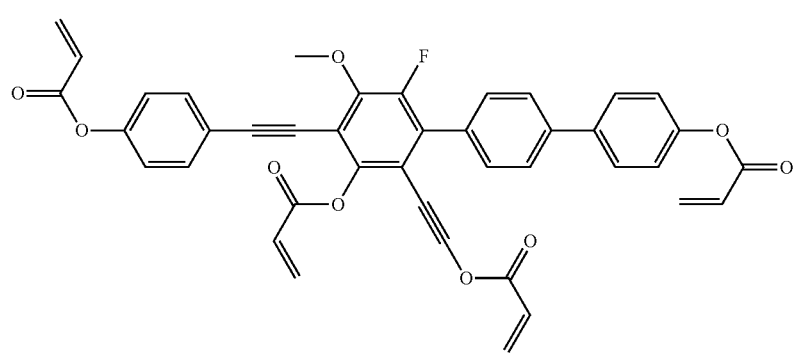

(1-445)
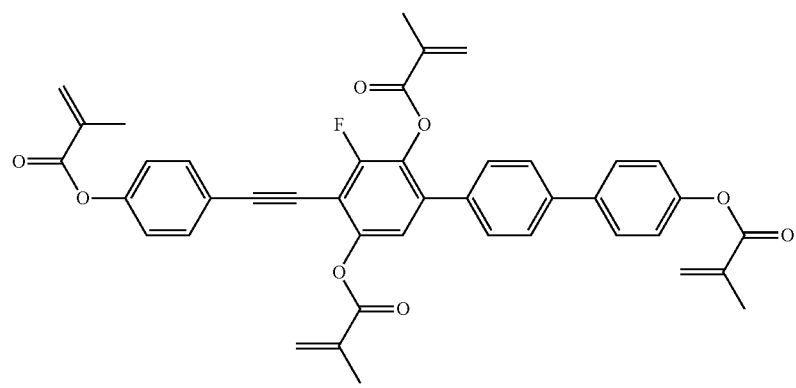
(1-446)
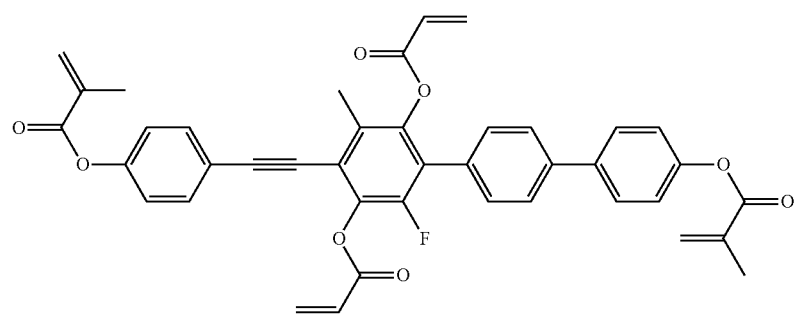
(1-447)
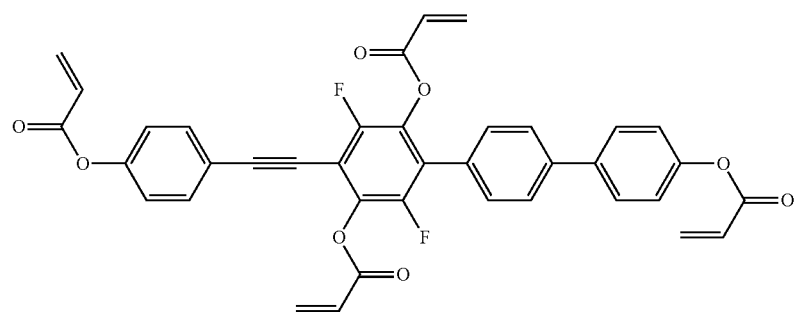
(1-448)
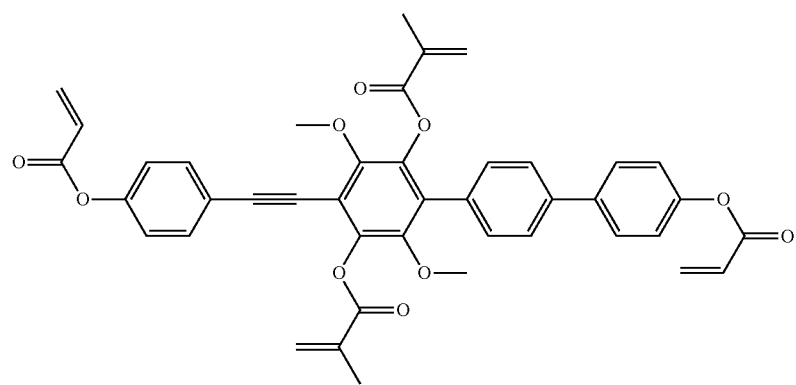

(1-449)
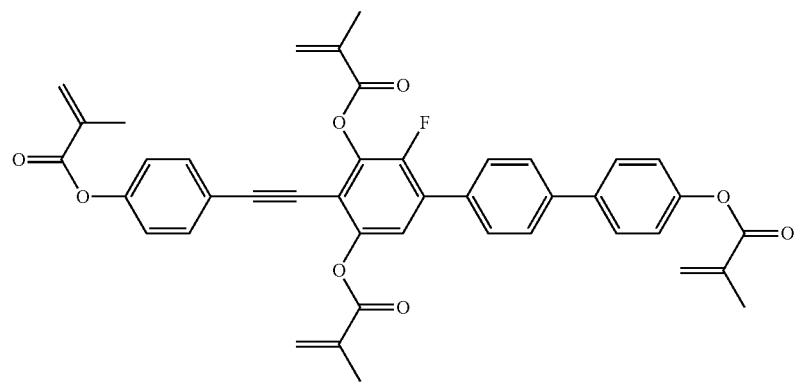
(1-450)
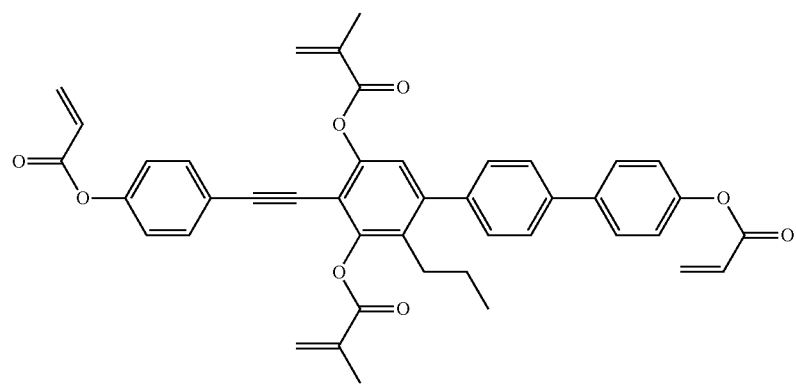
(1-451)
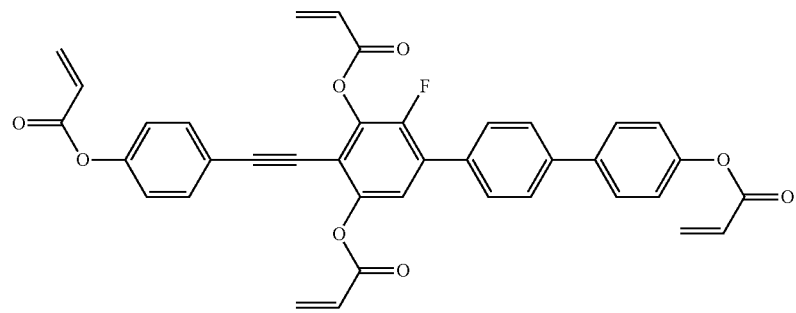
(1-452)
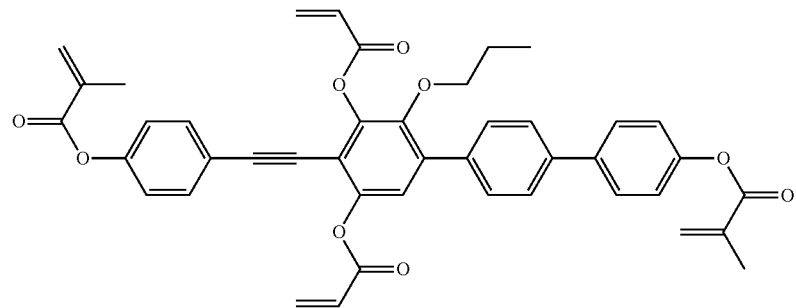

(1-453)
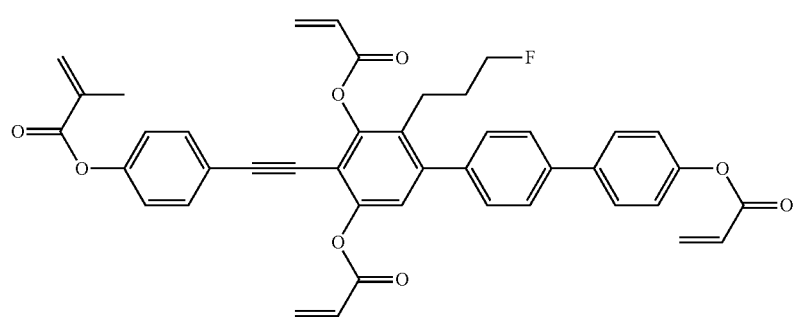
(1-454)
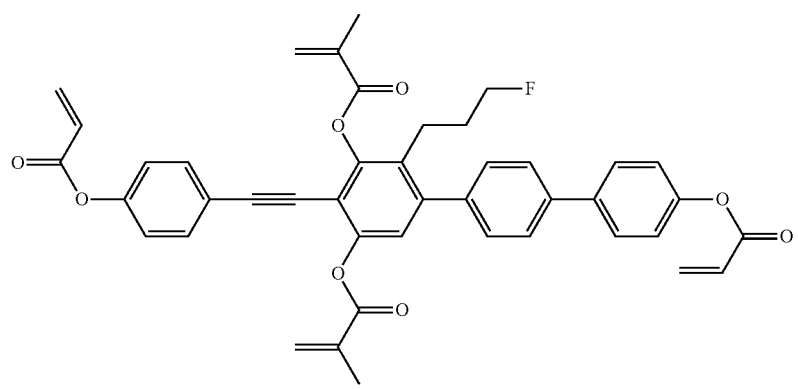
(1-455)
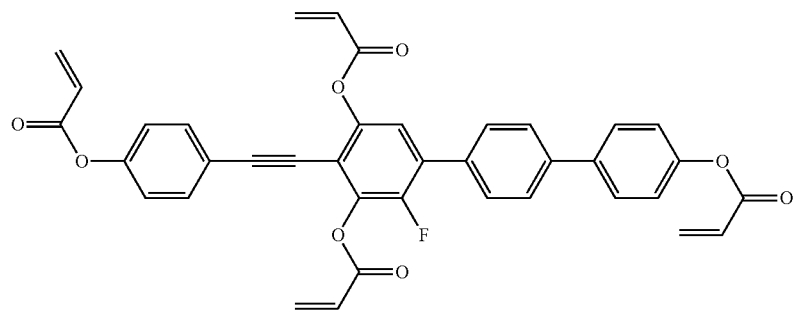
(1-456)
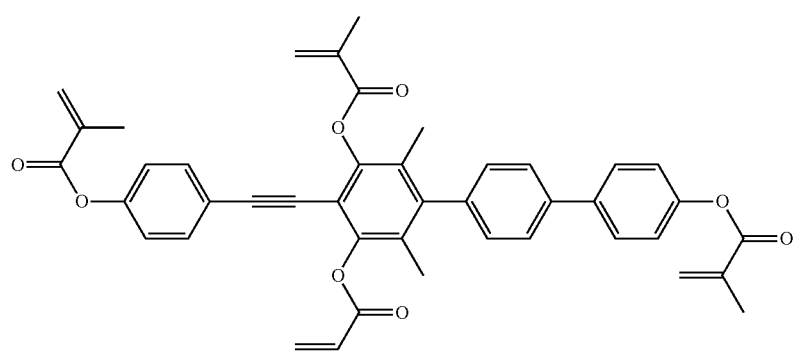

(1-457)
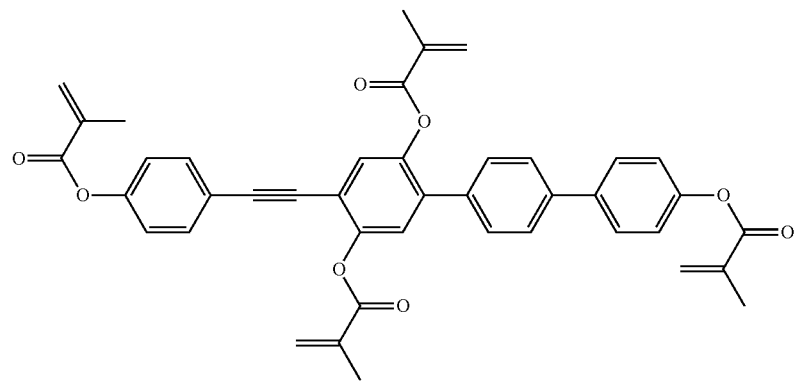
(1-458)
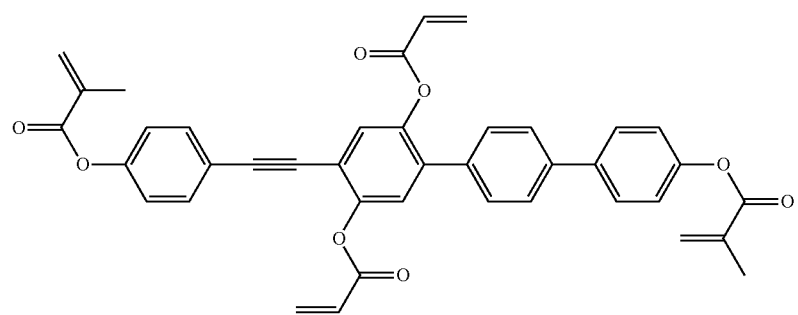
(1-459)
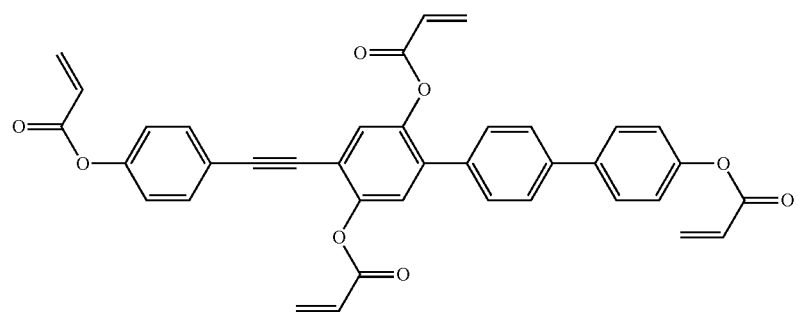
(1-460)
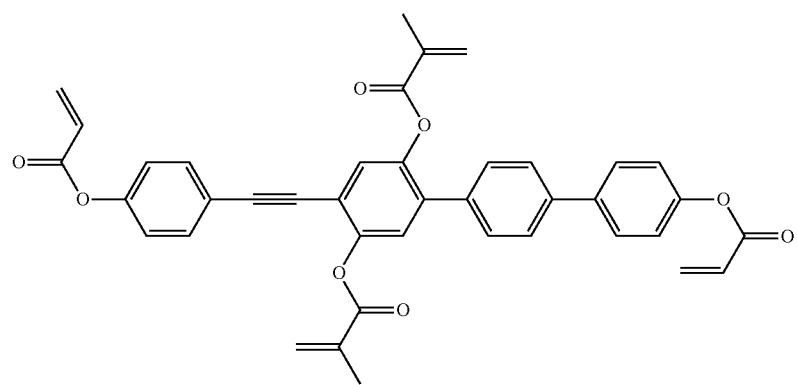

-continued
(1-461)
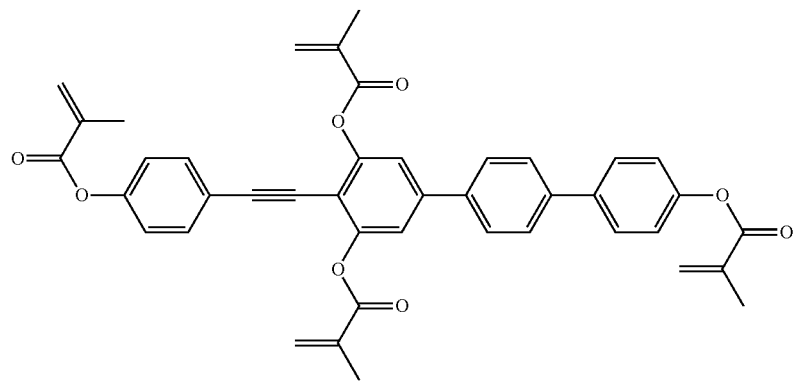
(1-462)
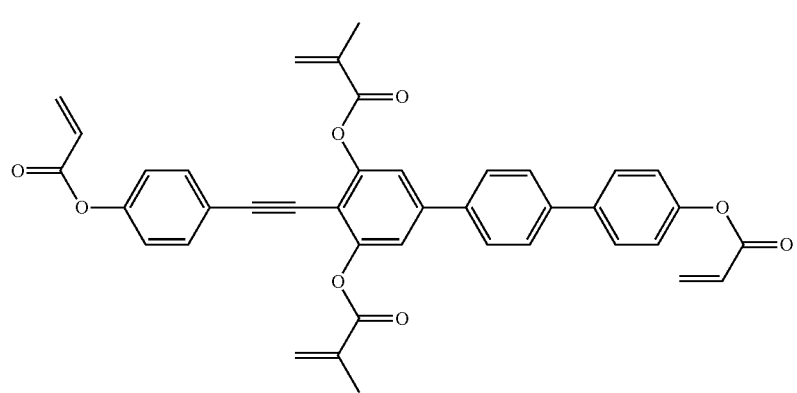
(1-463)
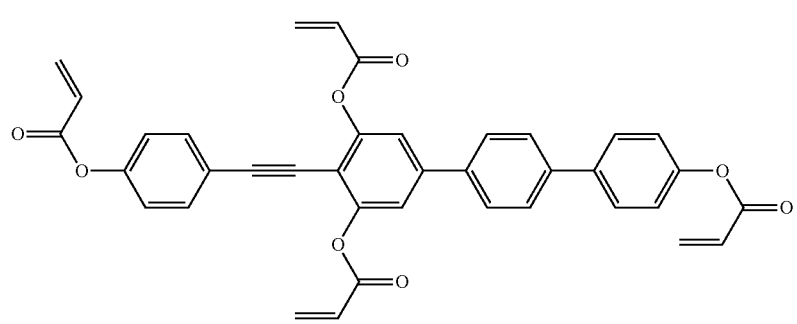
(1-464)
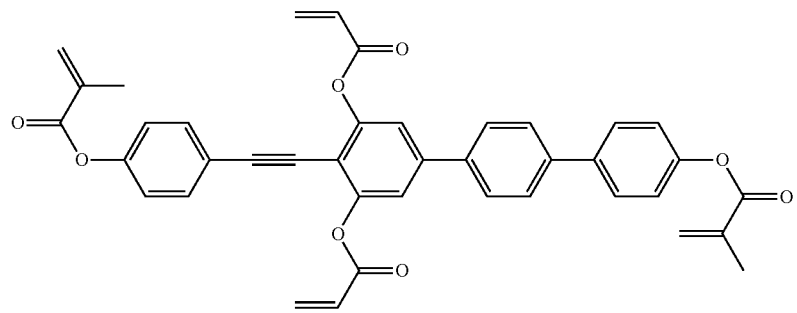

(1-465)
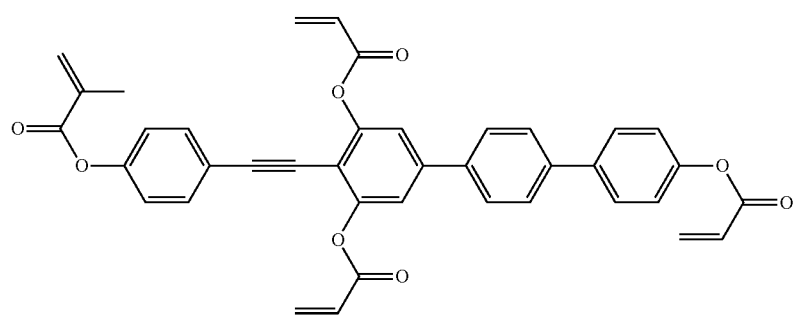
(1-466)
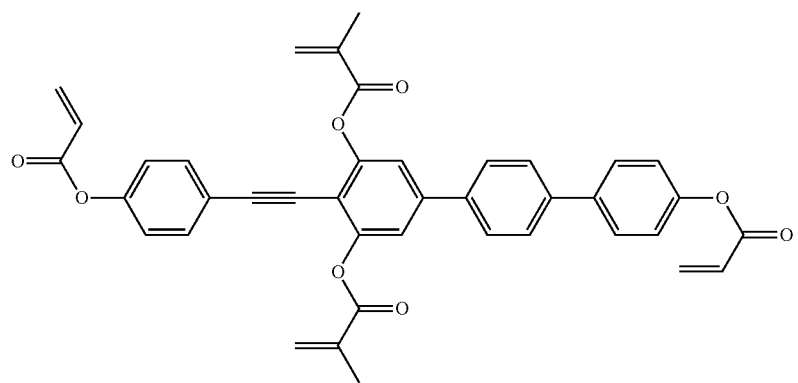
(1-467)
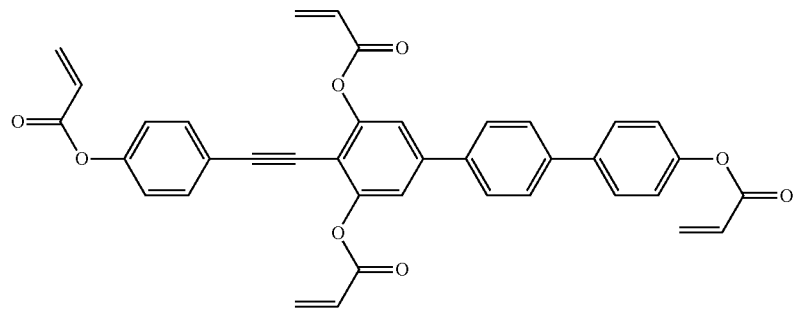
(1-468)
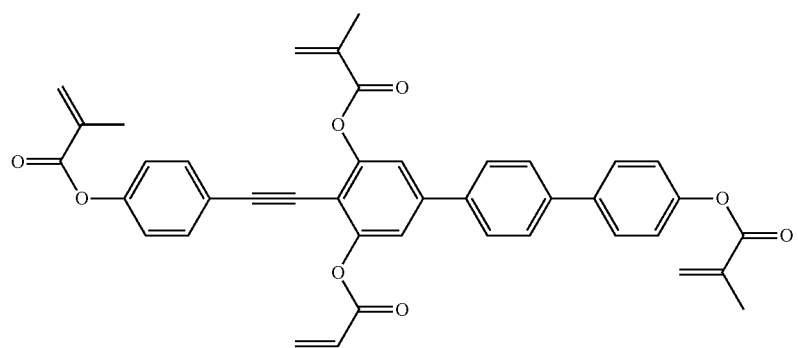

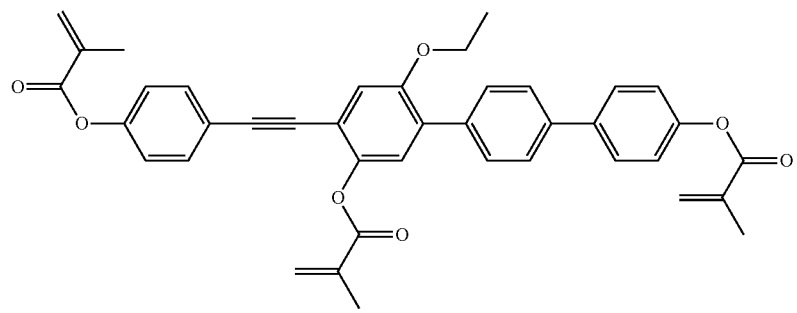
(1-469)
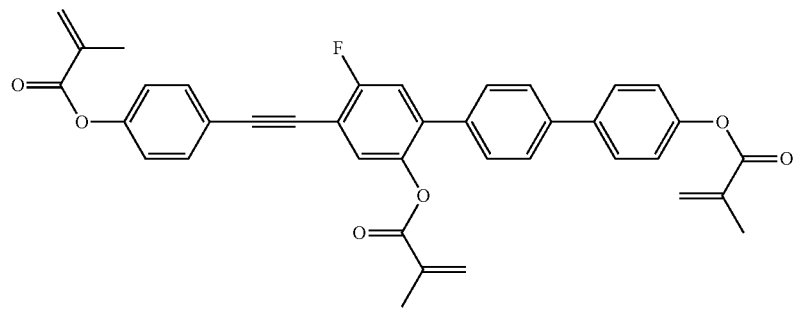
(1-470)
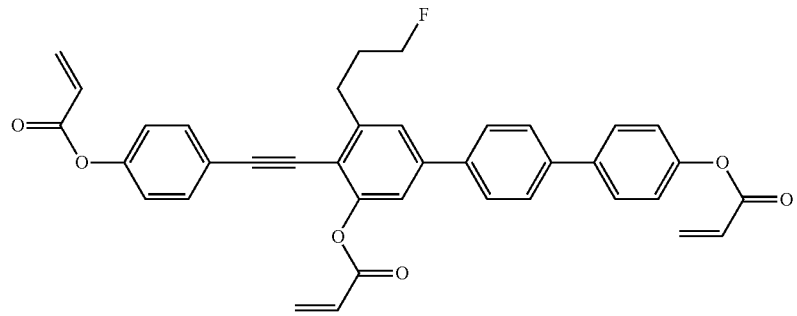
(1-471)
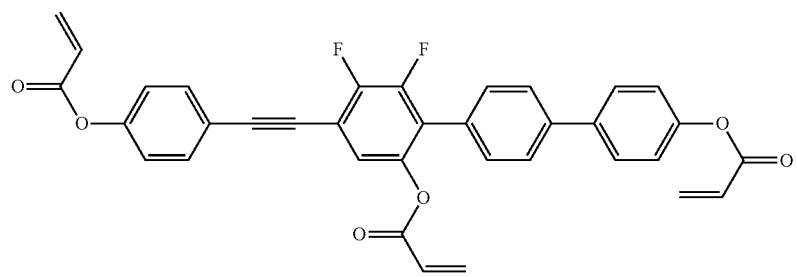
(1-472)
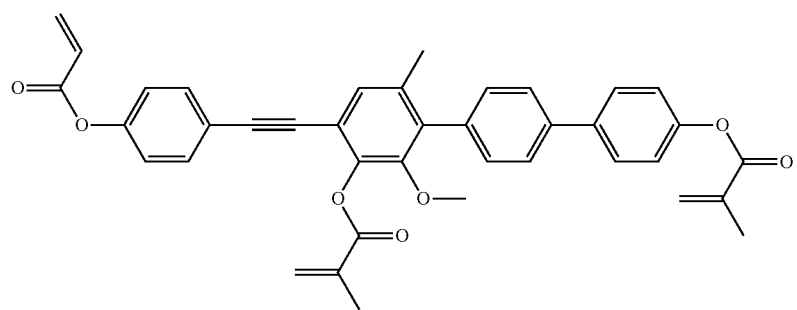
(1-473)

(1-474)
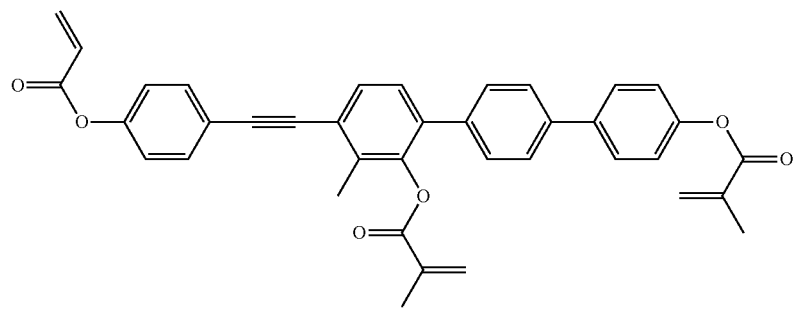
(1-475)
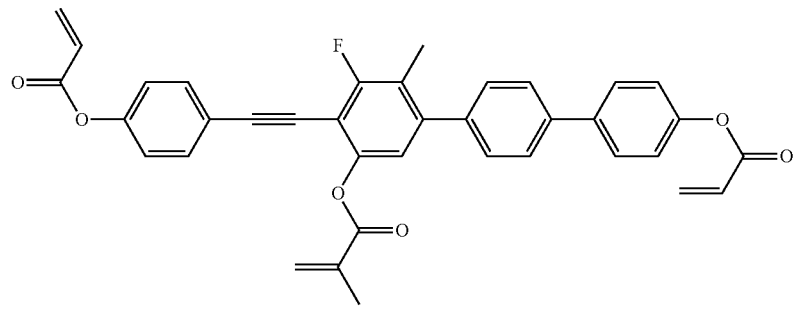
(1-476)
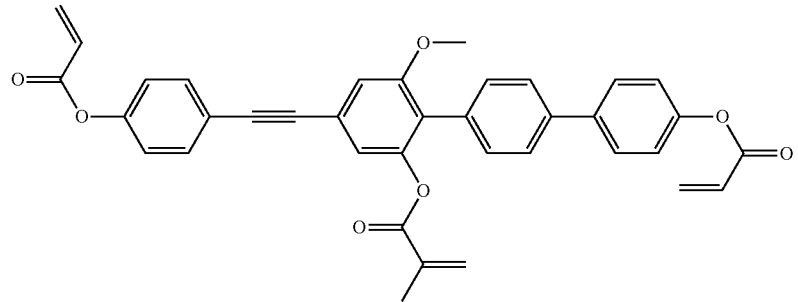
(1-477)
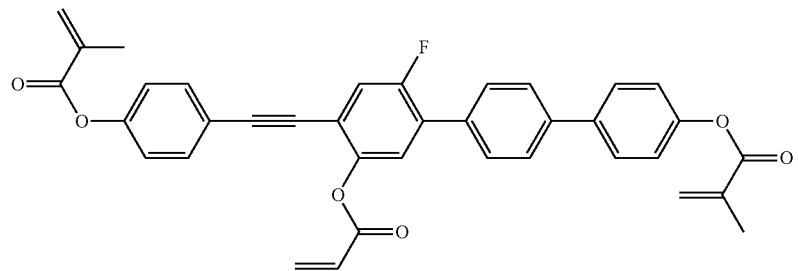
(1-478)
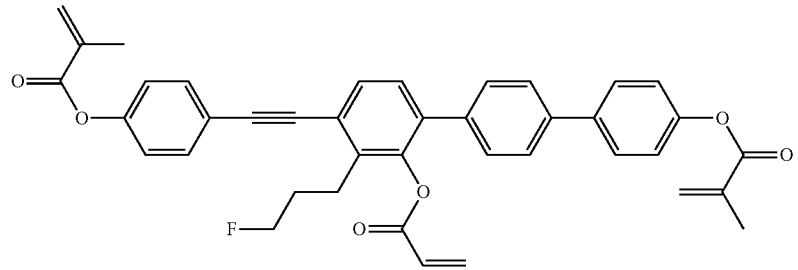

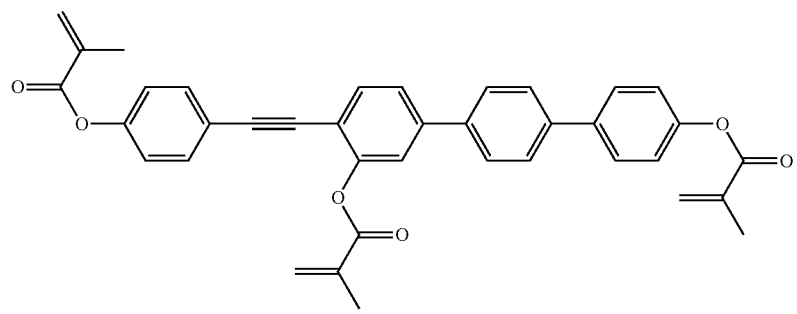
(1-479)
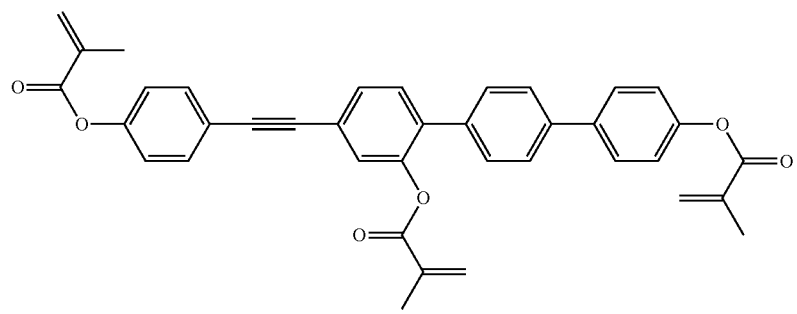
(1-480)
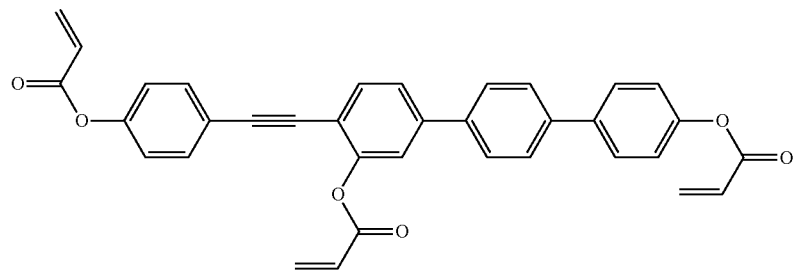
(1-481)
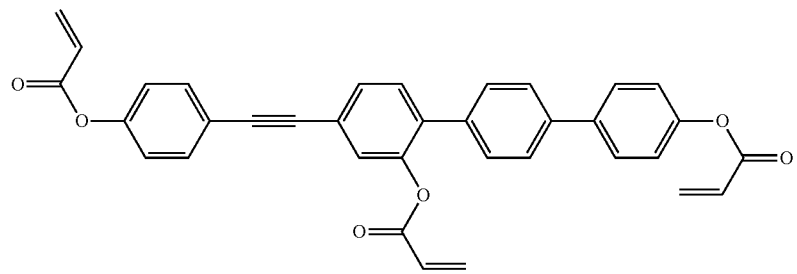
(1-482)
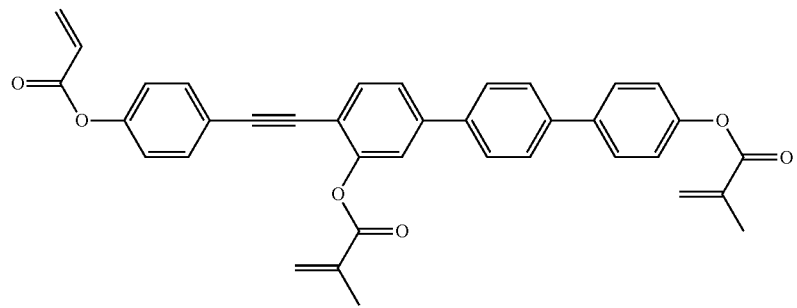
(1-483)

-continued
(1-484)
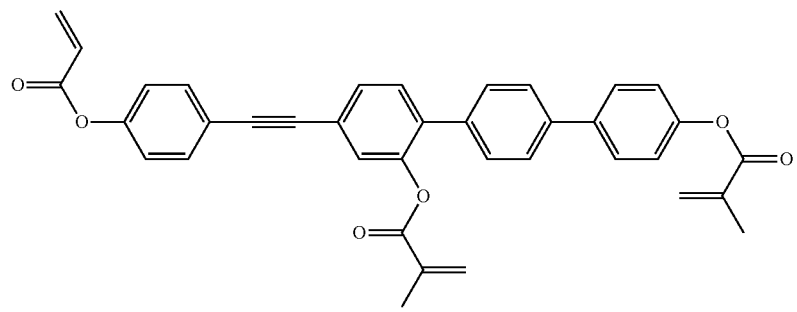
(1-485)
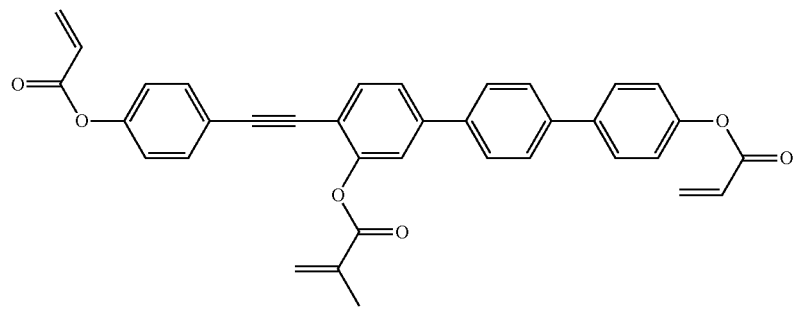
(1-486)
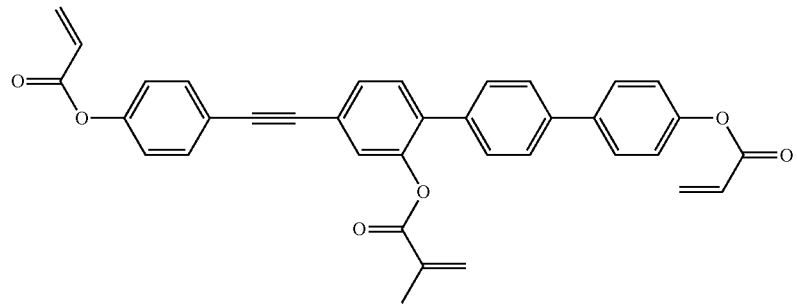
(1-487)
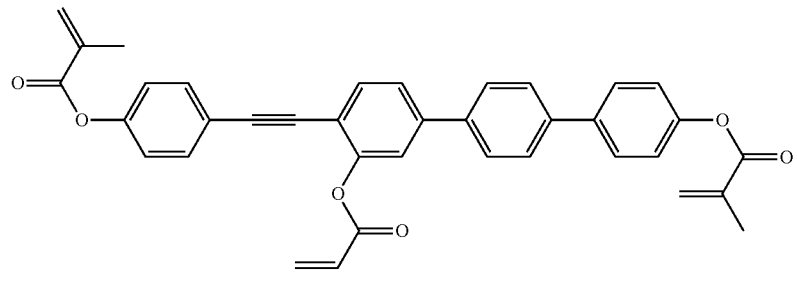
(1-488)
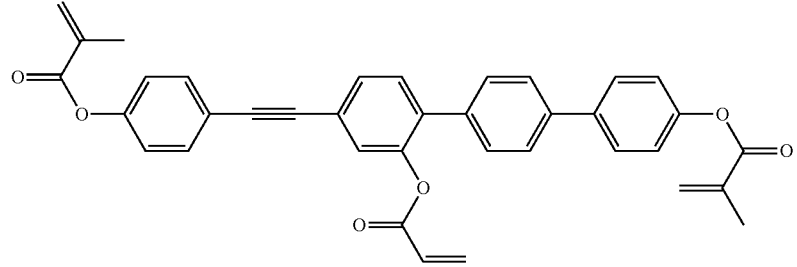

-continued
(1-489)
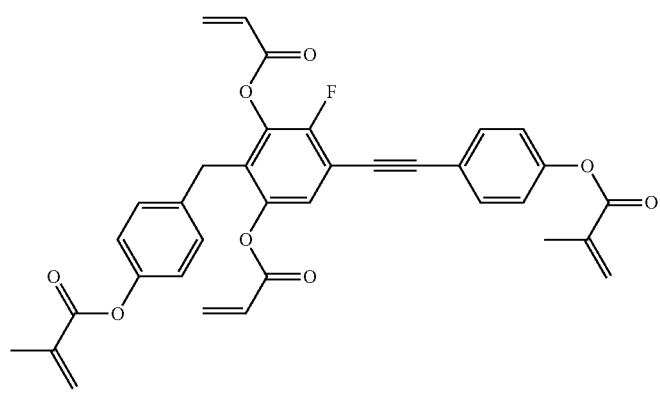
(1-490)
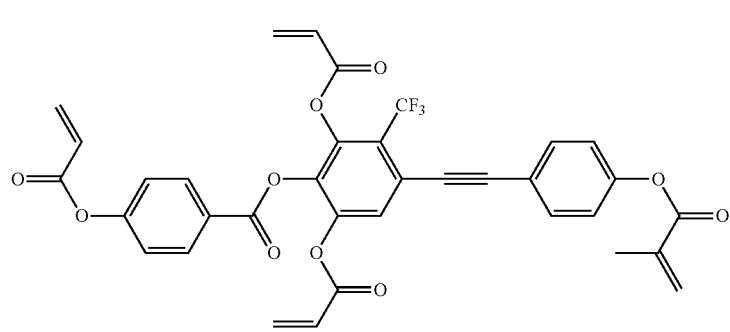
(1-491)
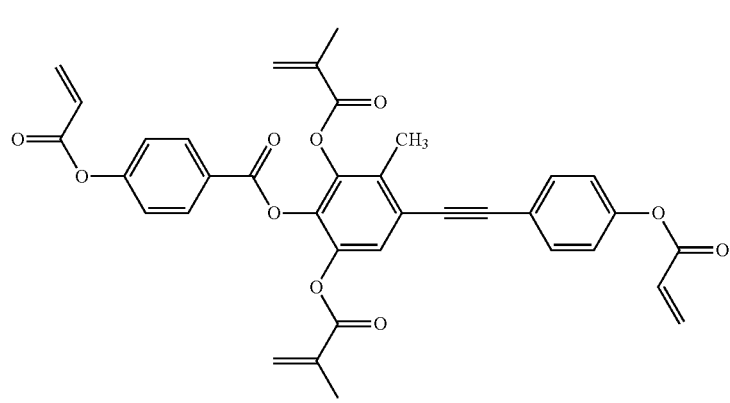
(1-492)
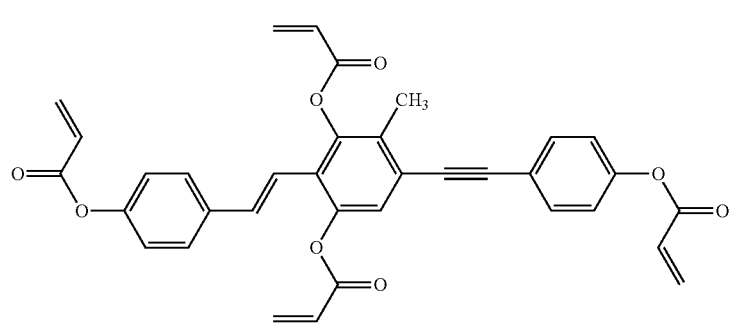

-continued
(1-493)
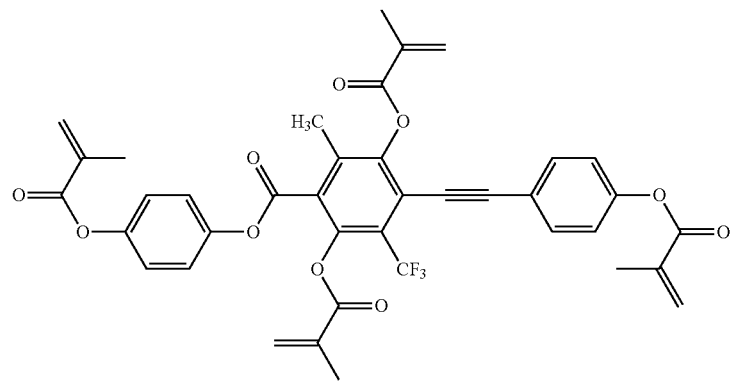
(1-494)
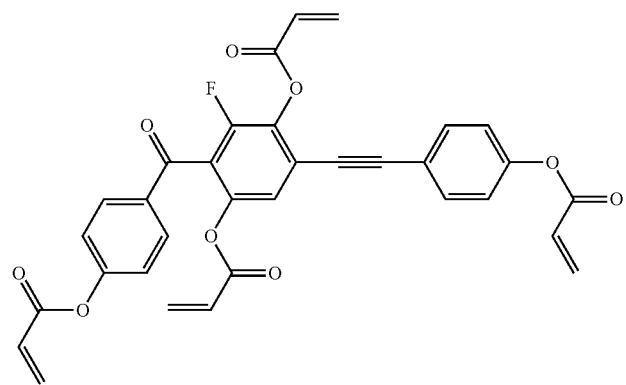
(1-495)
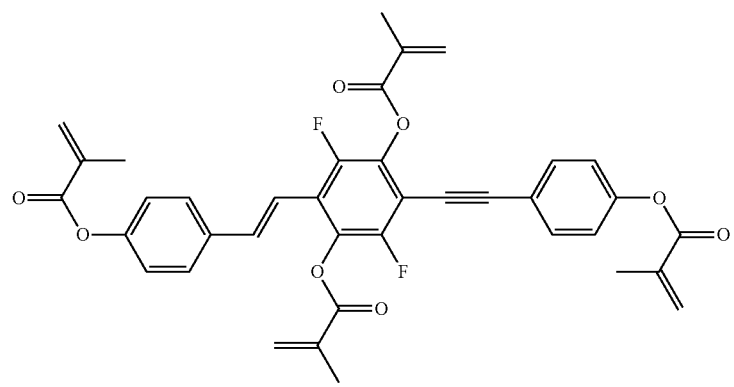
(1-496)
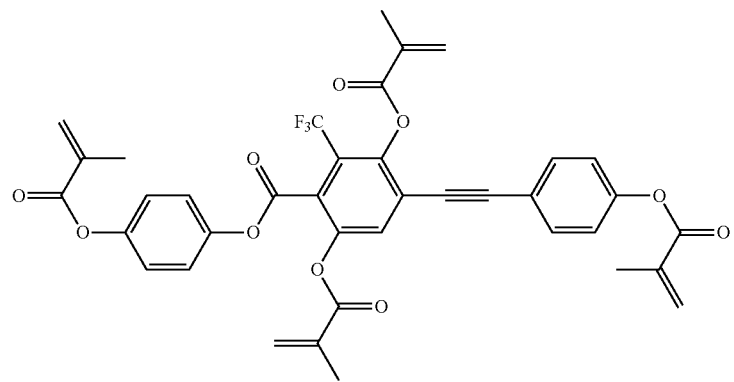

(1-497)
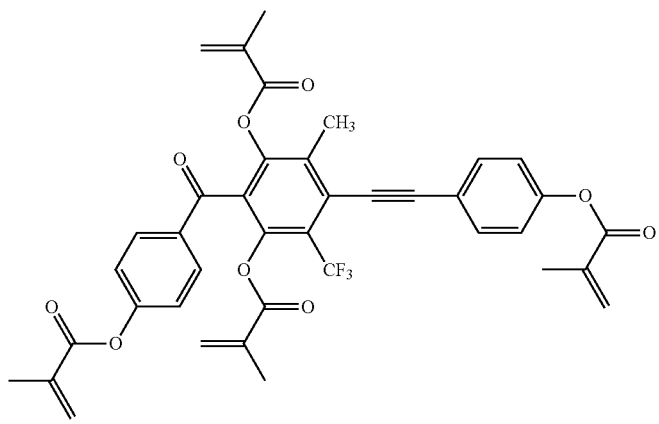
(1-498)
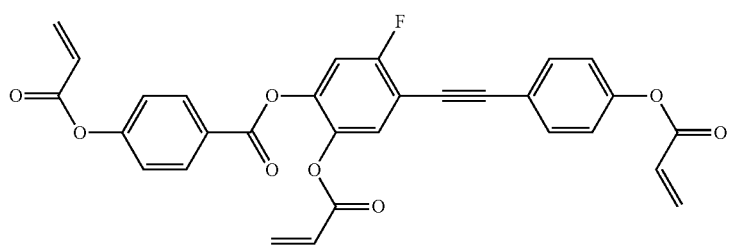
(1-499)
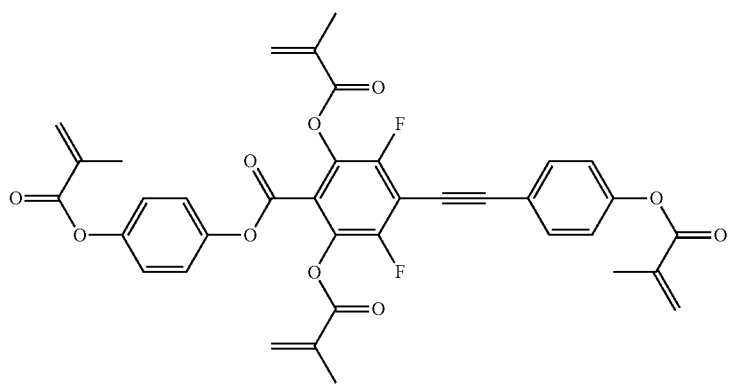
(1-500)
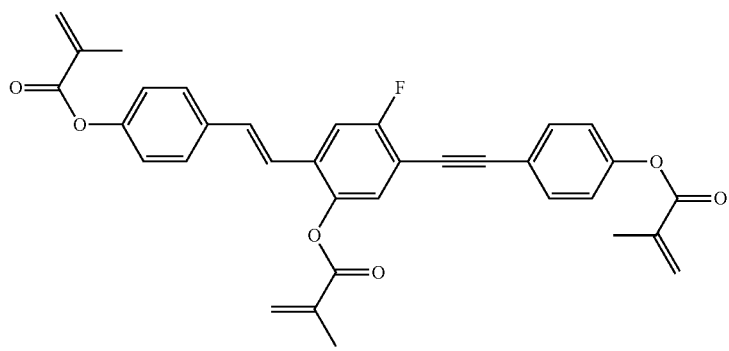

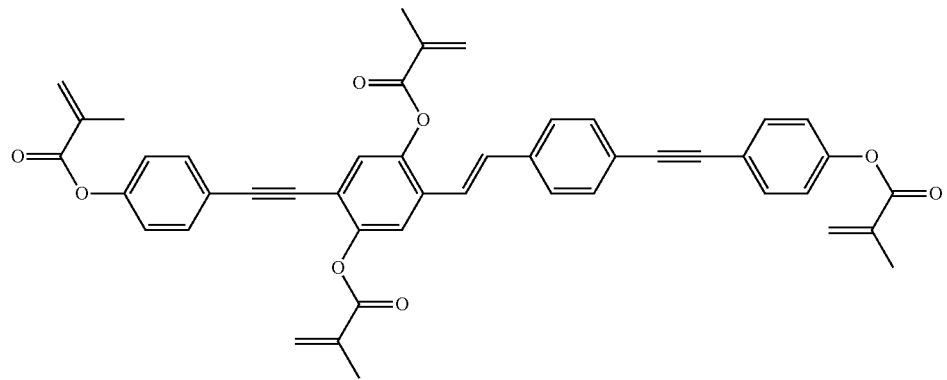
(1-501)
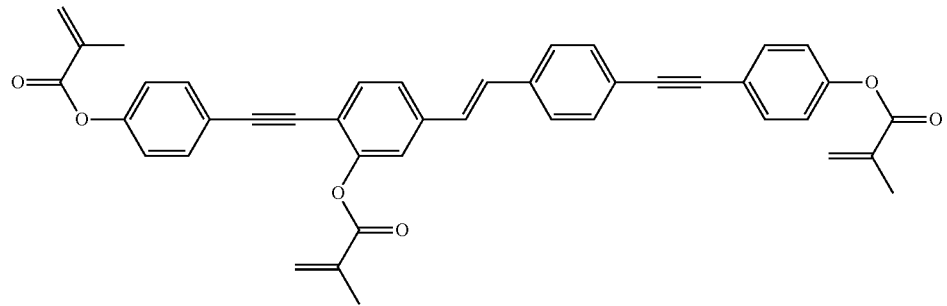
(1-502)
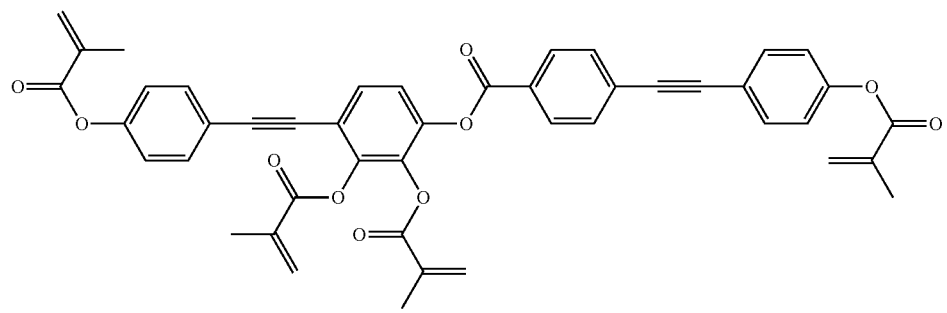
(1-503)
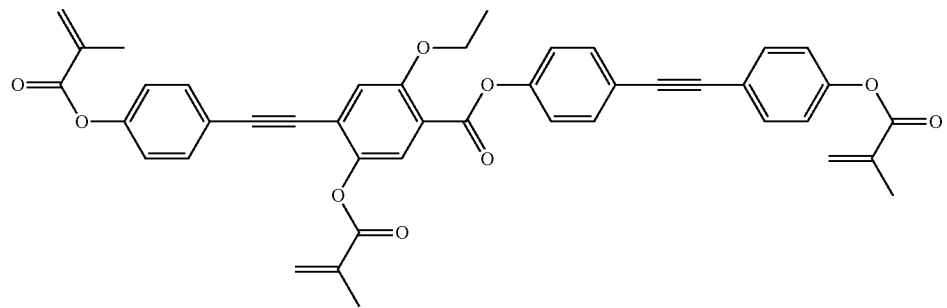
(1-504)

(1-505)
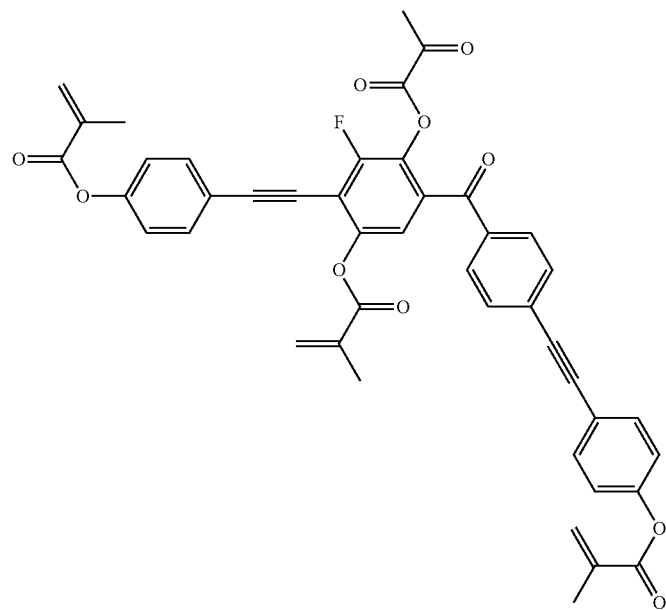
(1-506)
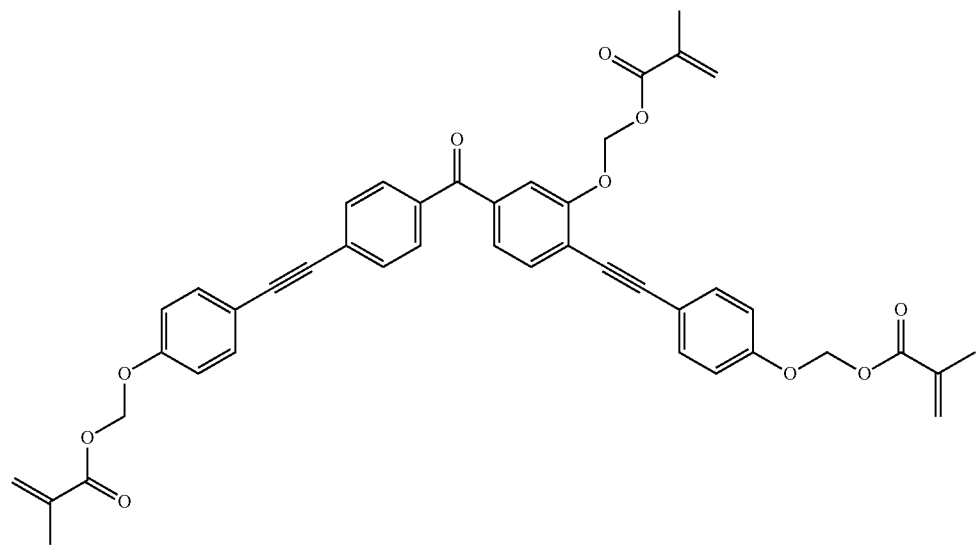
(1-507)
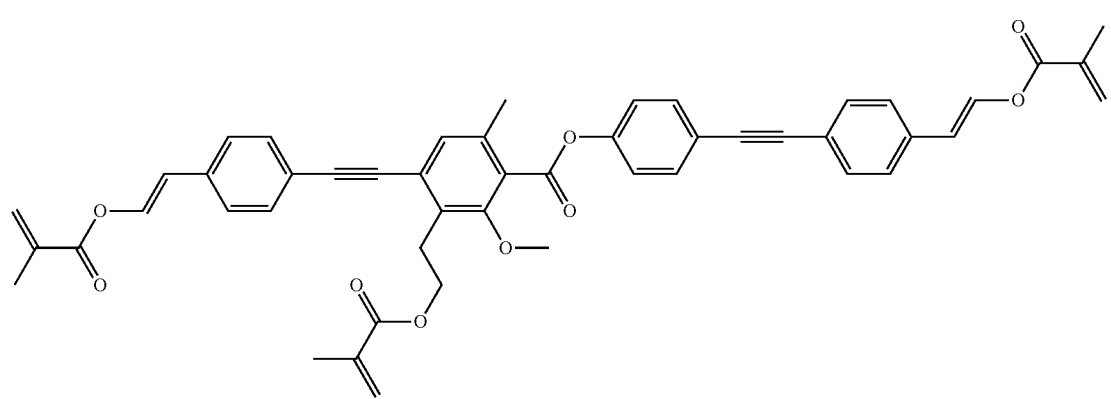

(1-508)
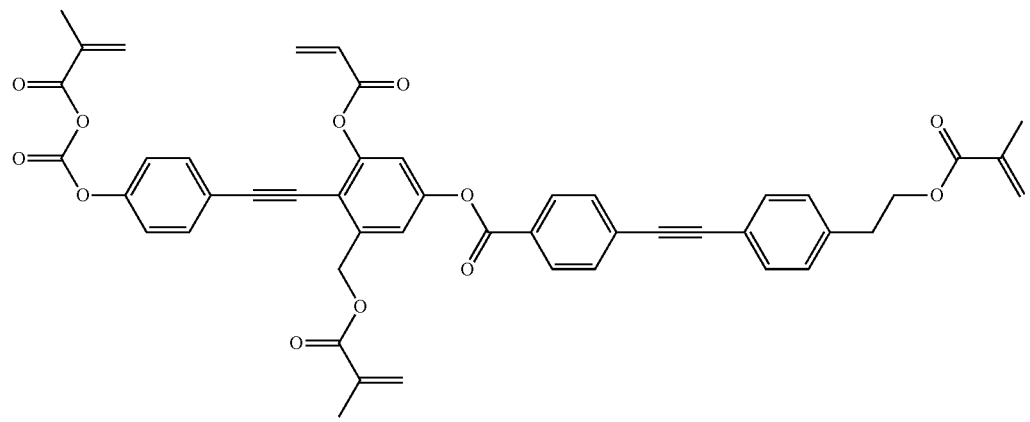
(1-509)
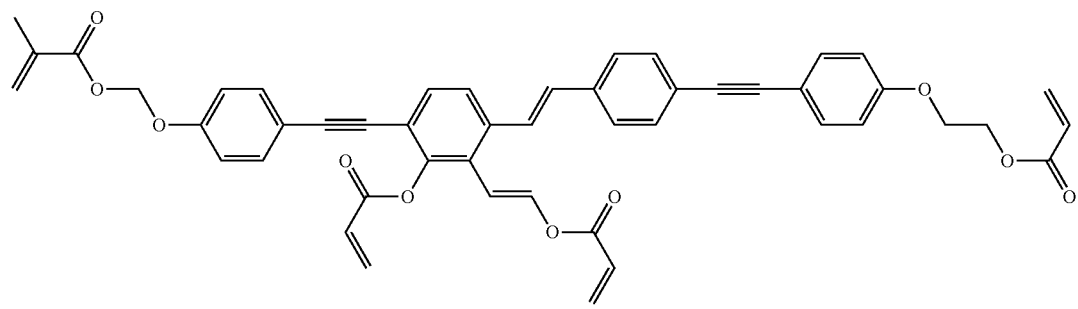
(1-510)
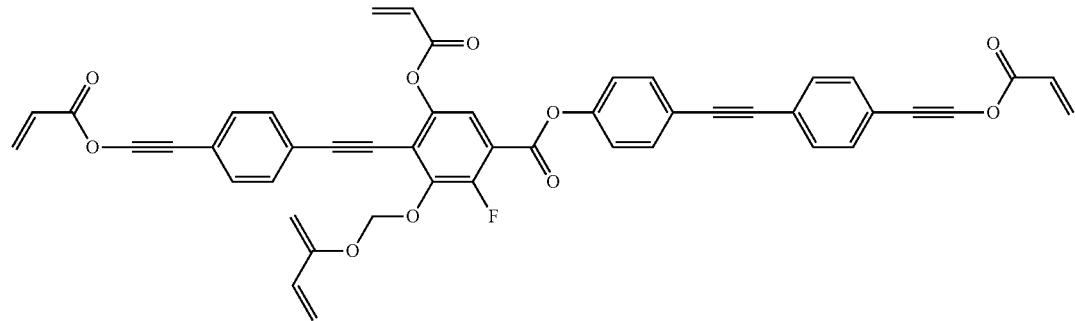
(1-511)
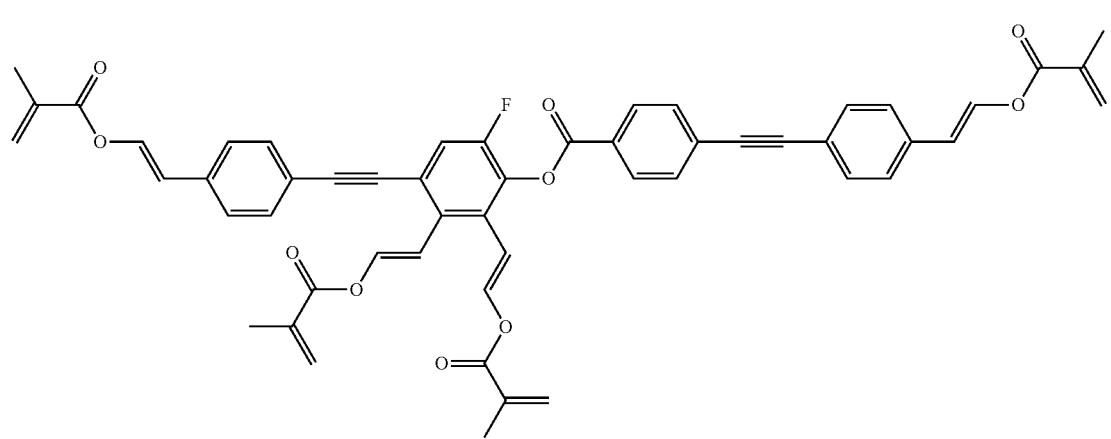

-continued
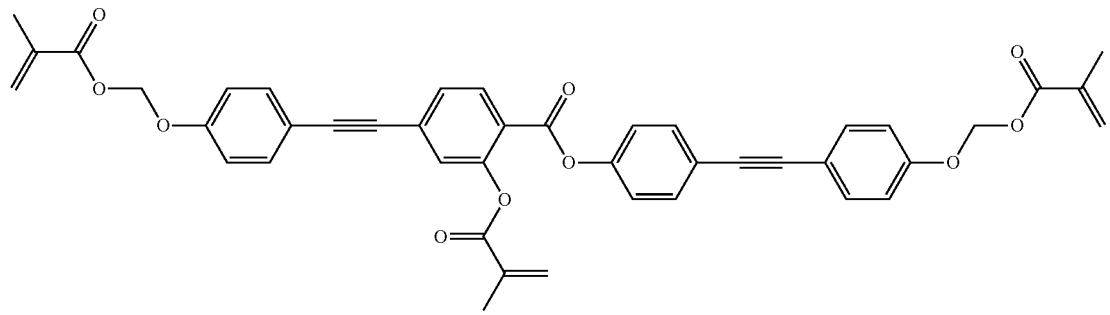
(1-512)
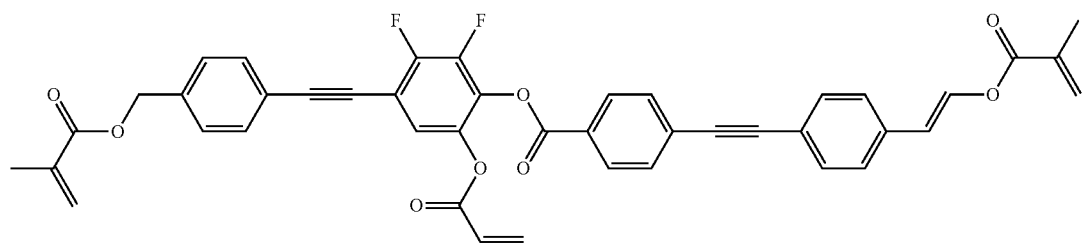
(1-513)
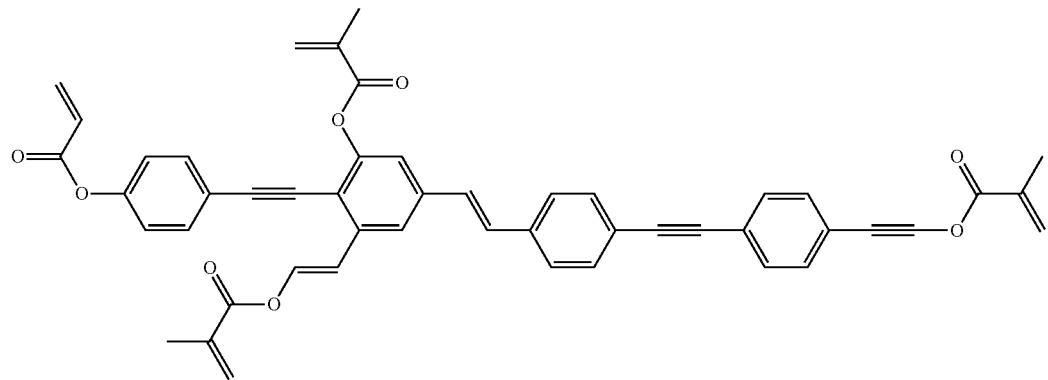
(1-514)
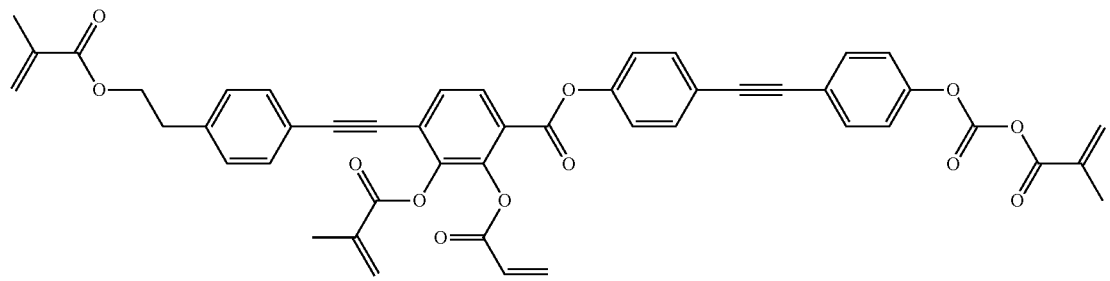
(1-515)
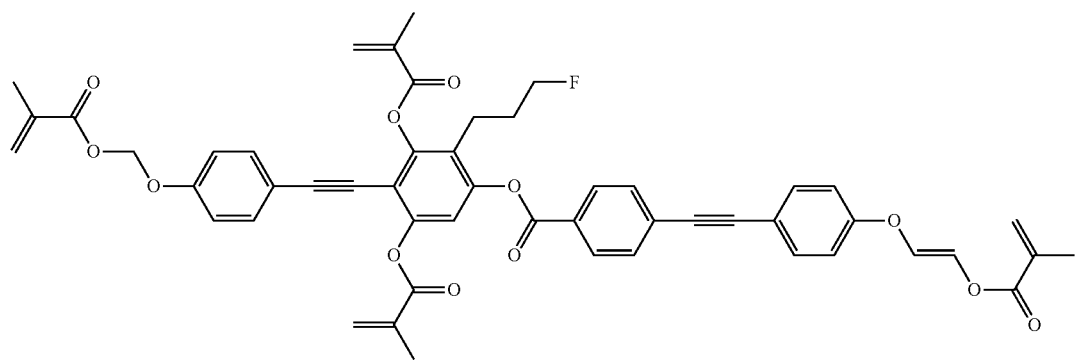
(1-516)

-continued
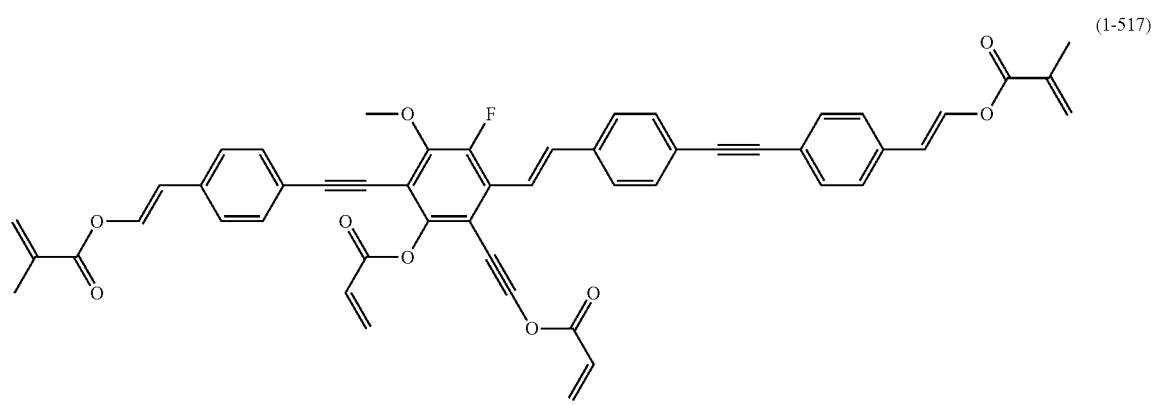
(1-517)
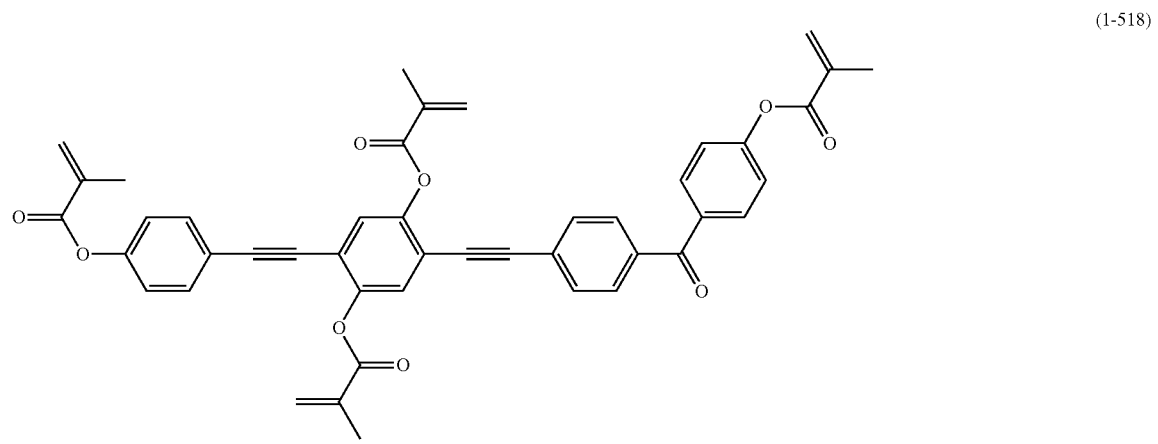
(1-518)
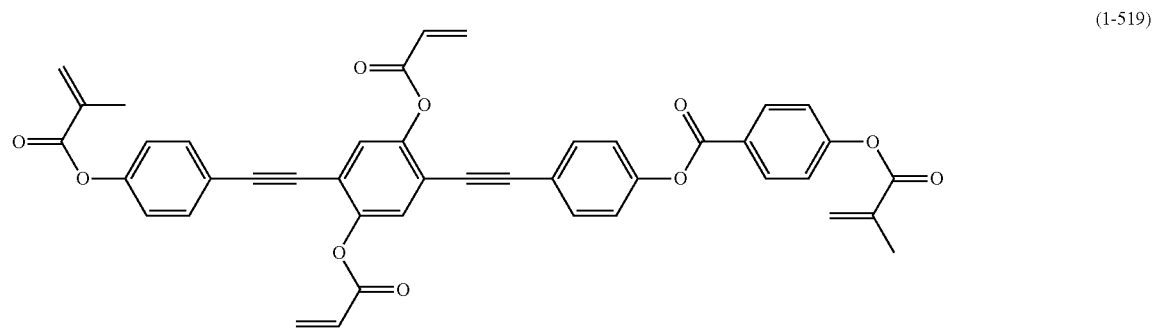
(1-519)
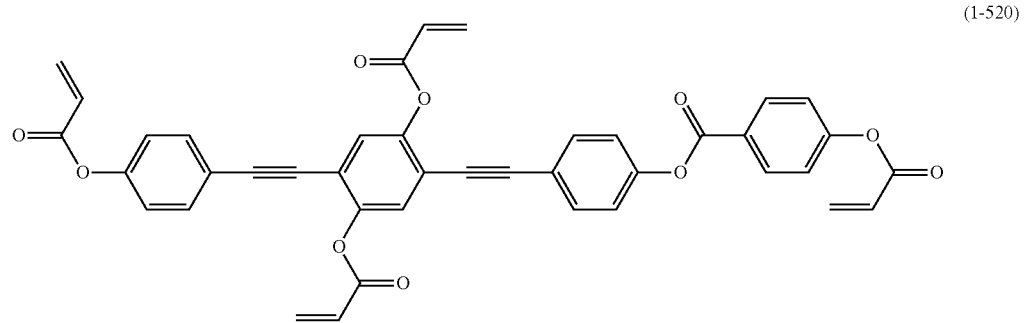
(1-520)

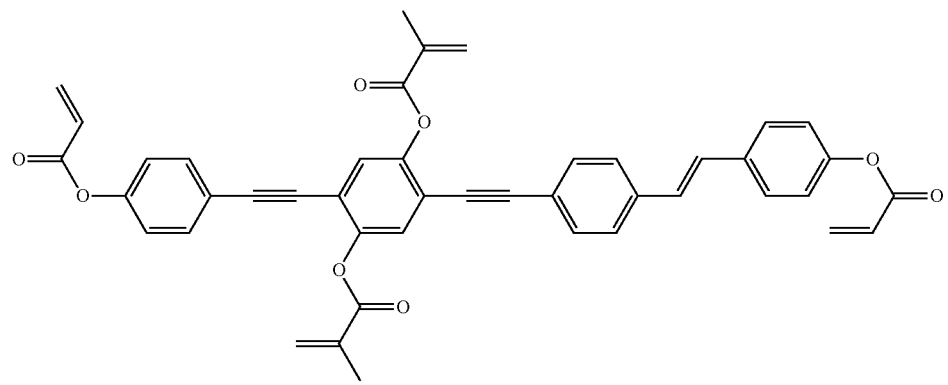
(1-521)
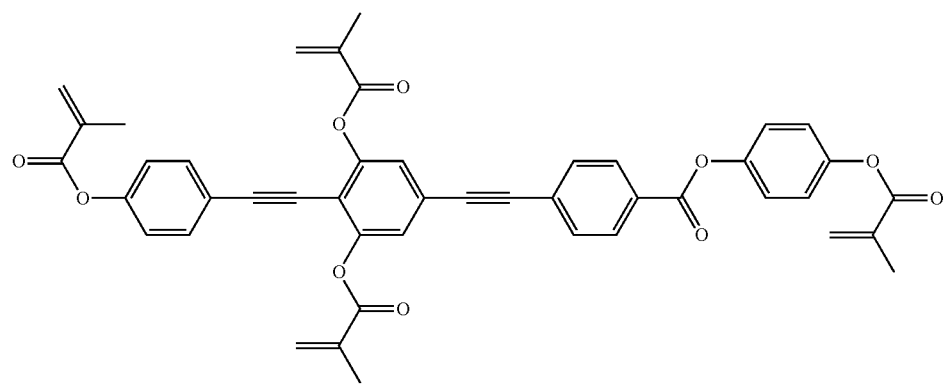
(1-522)
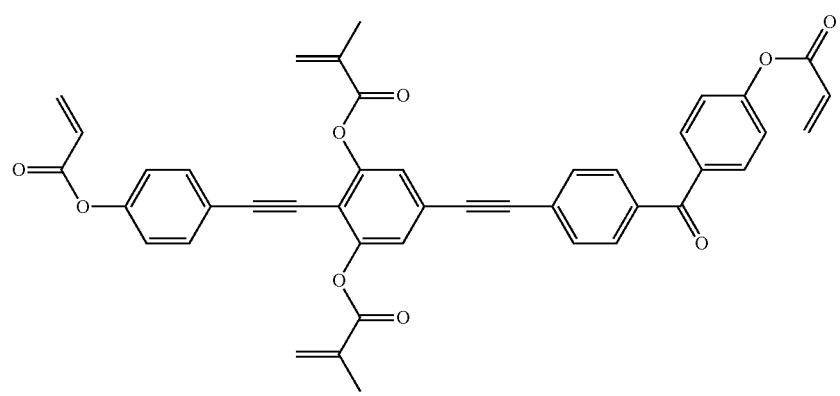
(1-523)
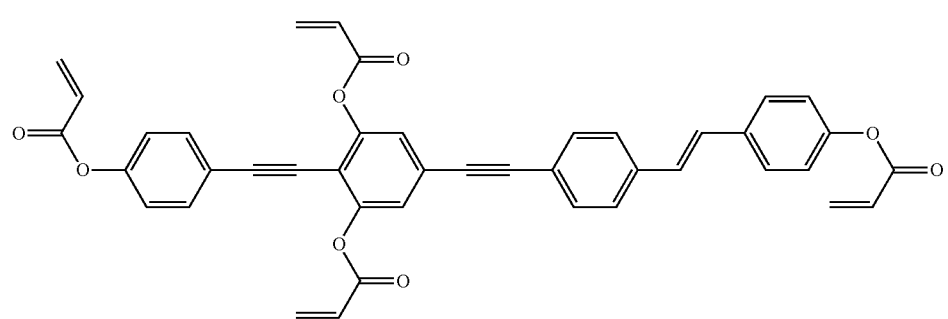
(1-524)

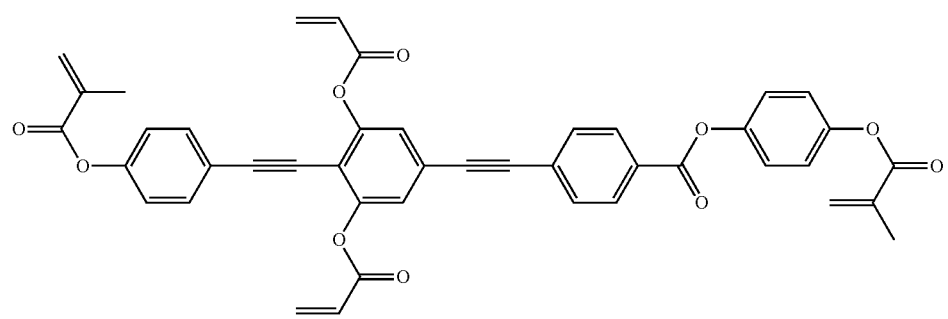
(1-525)
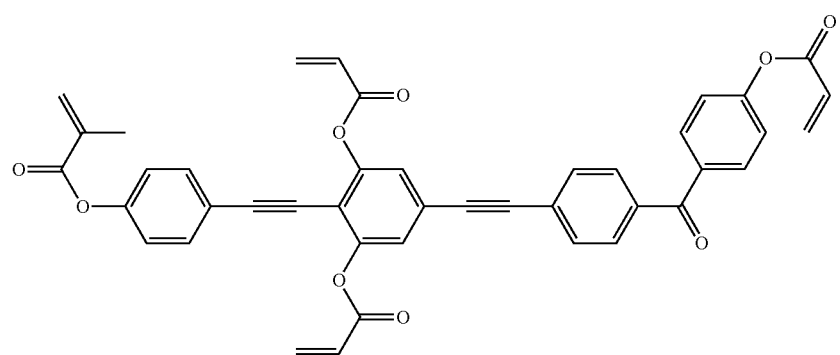
(1-526)
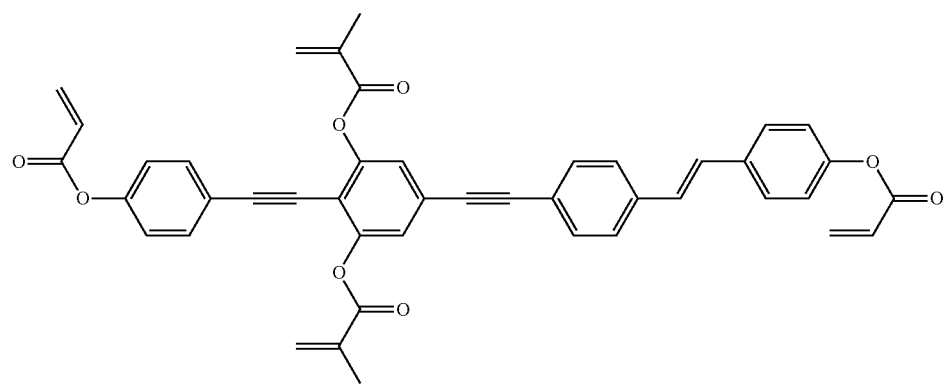
(1-527)
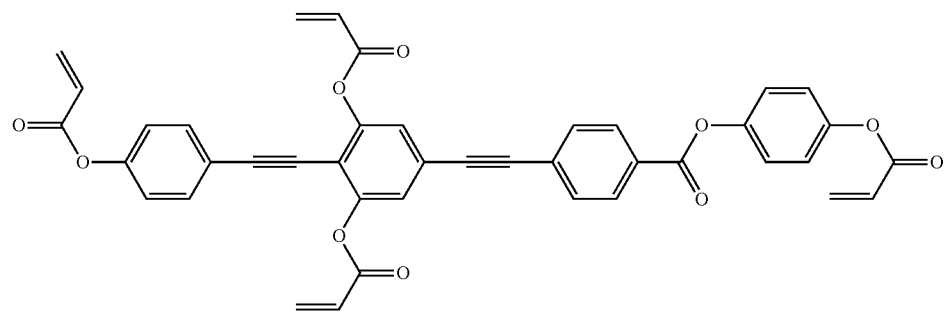
(1-528)

-continued
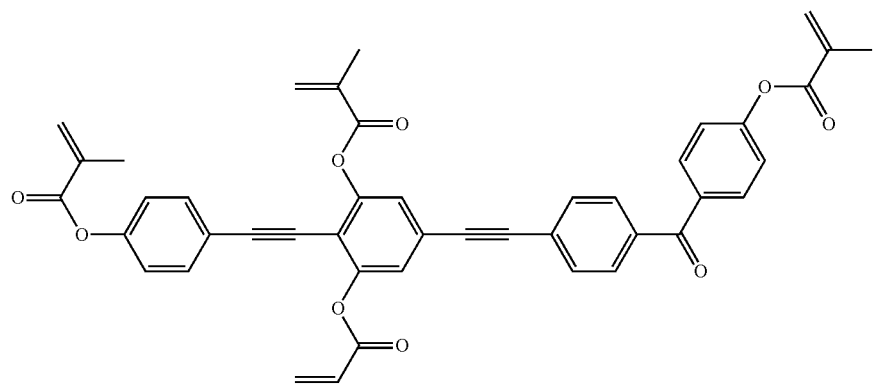
(1-529)
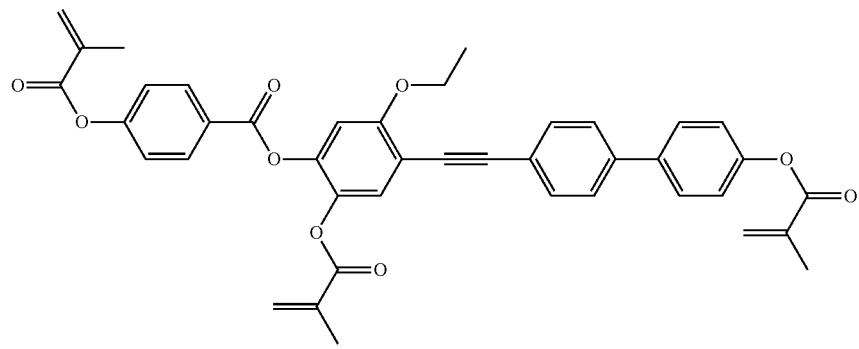
(1-530)
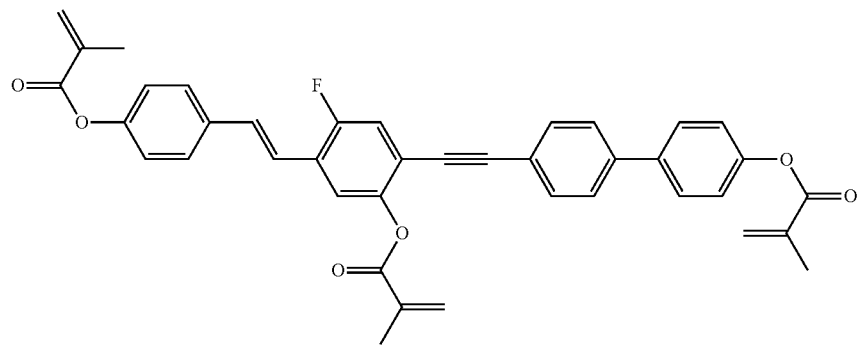
(1-531)
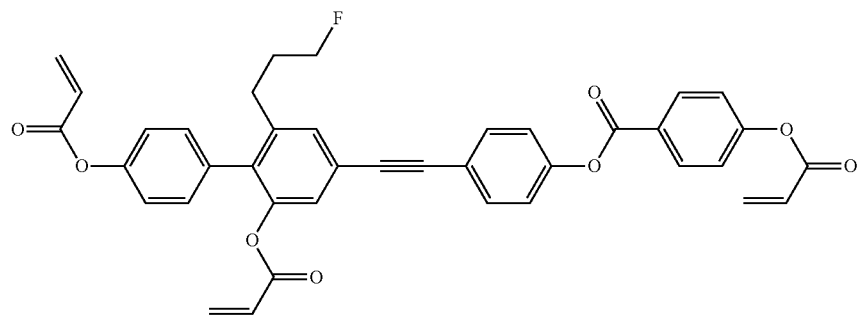
(1-532)

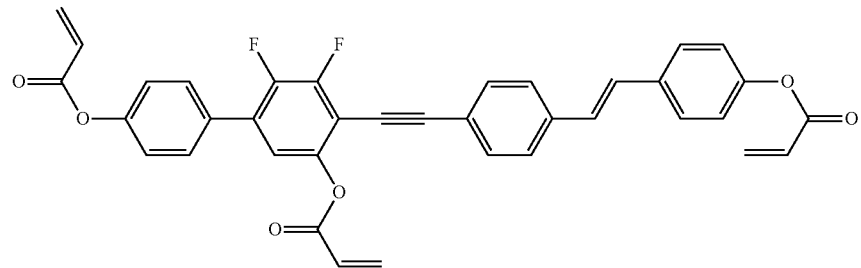
(1-533)
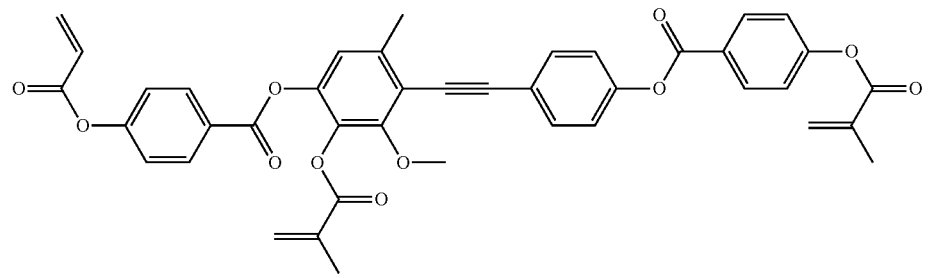
(1-534)
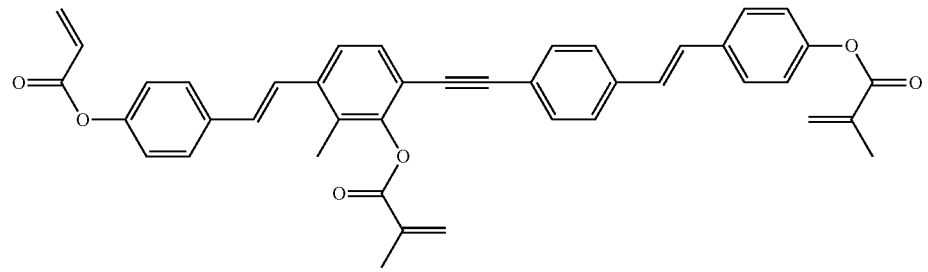
(1-535)
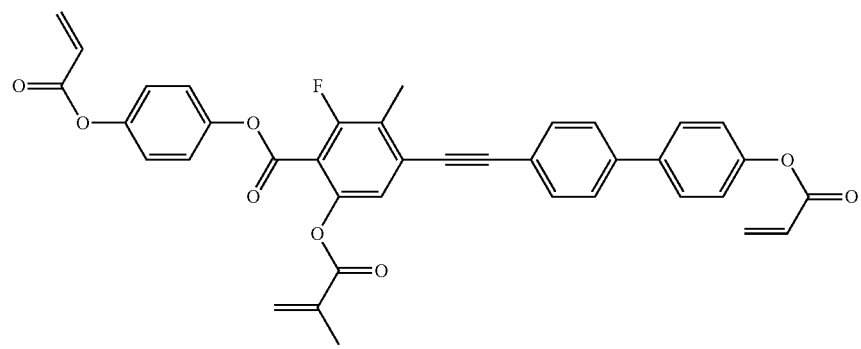
(1-536)
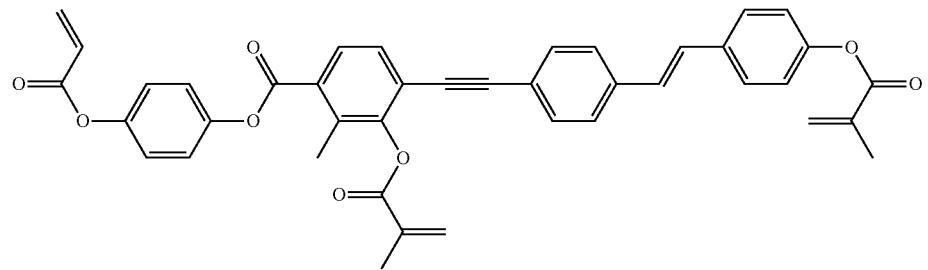
(1-537)

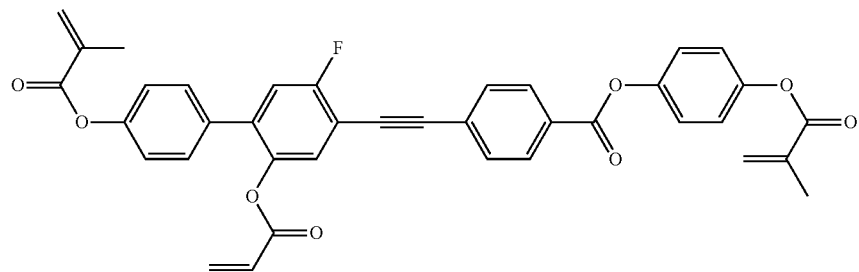
(1-538)
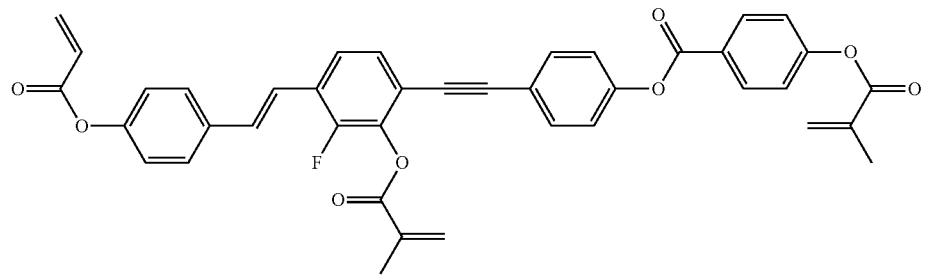
(1-539)
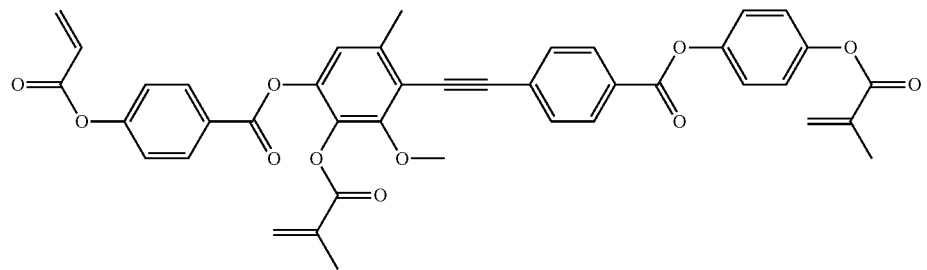
(1-540)
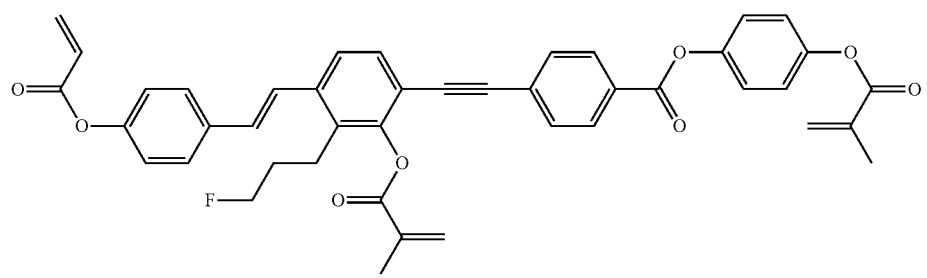
(1-541)
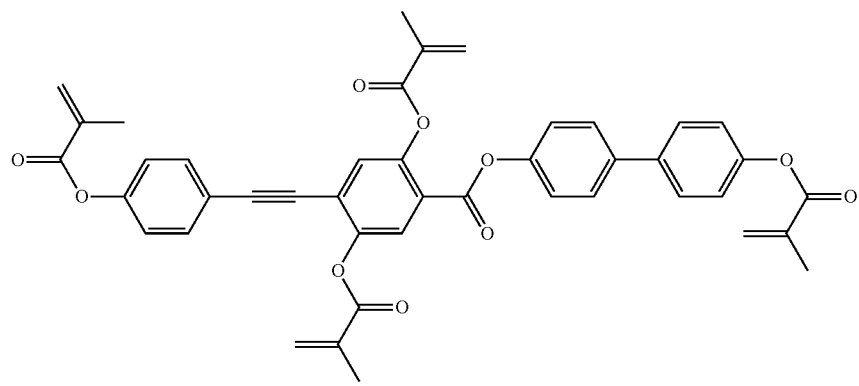
(1-542)

-continued
(1-543)
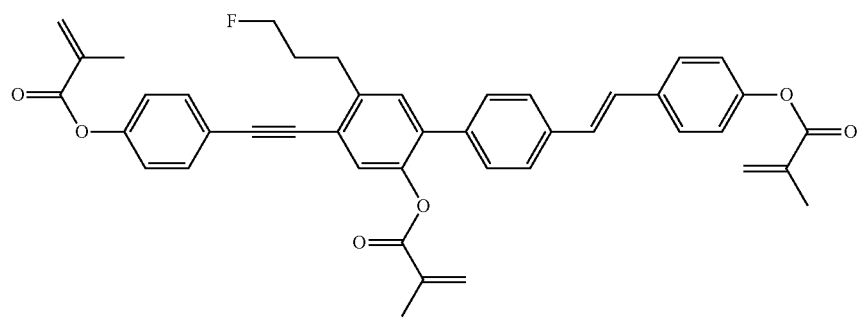
(1-544)
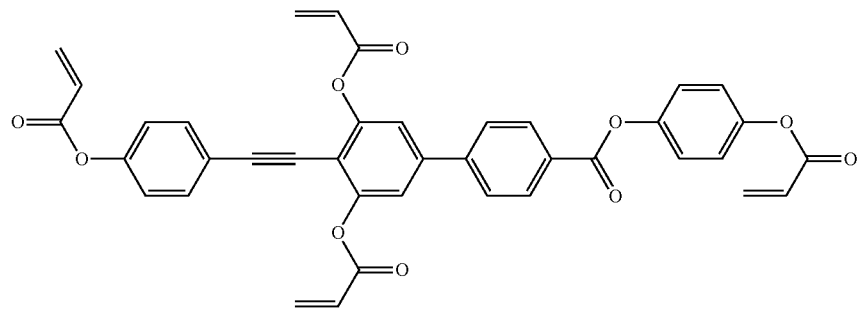
(1-545)
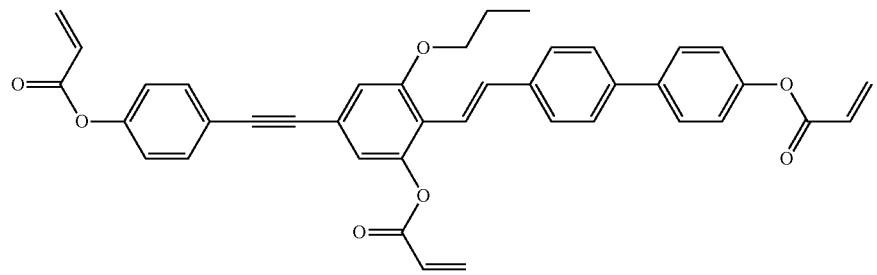
(1-546)
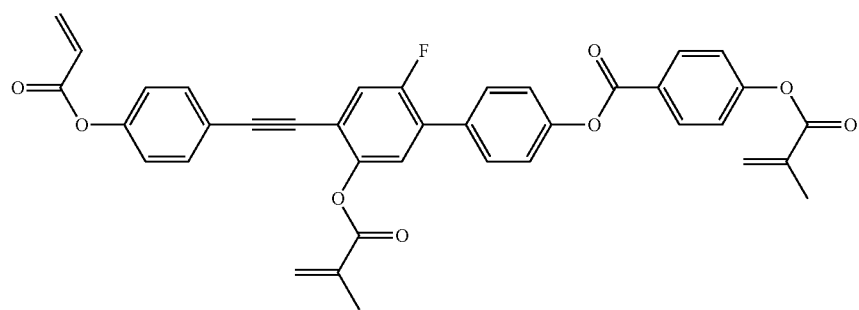
(1-547)
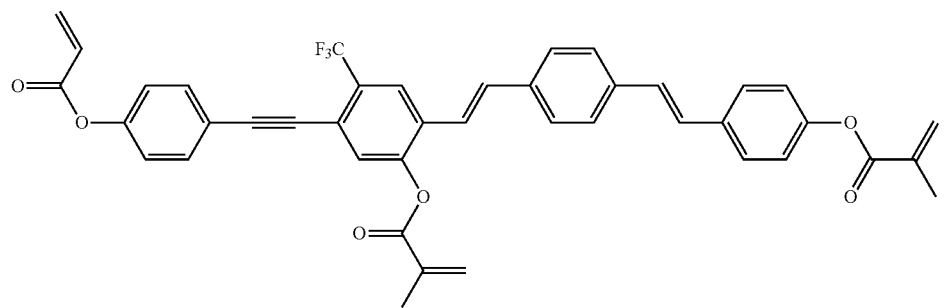

(1-548)
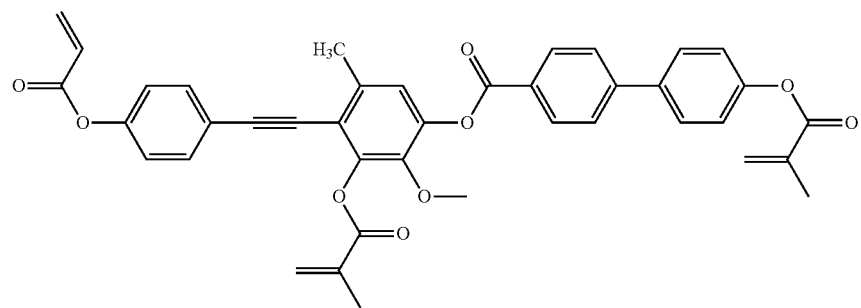
(1-549)
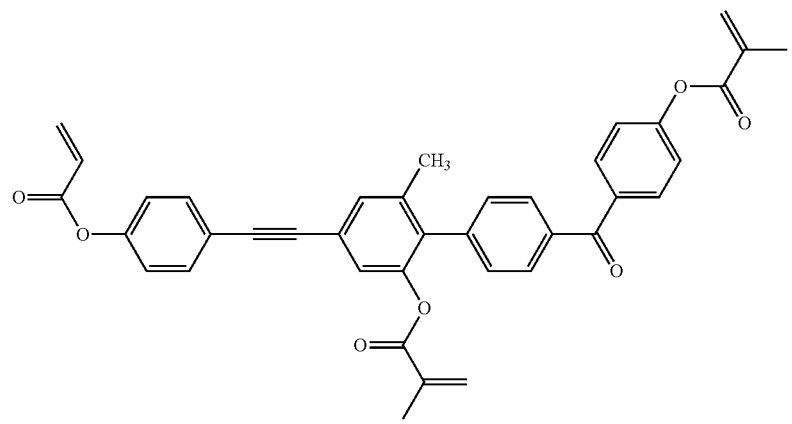
(1-550)
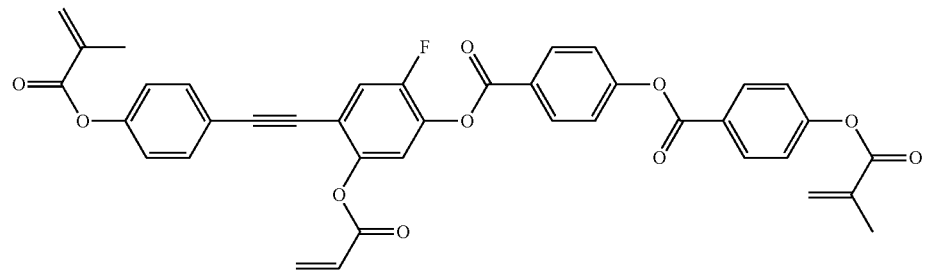
(1-551)
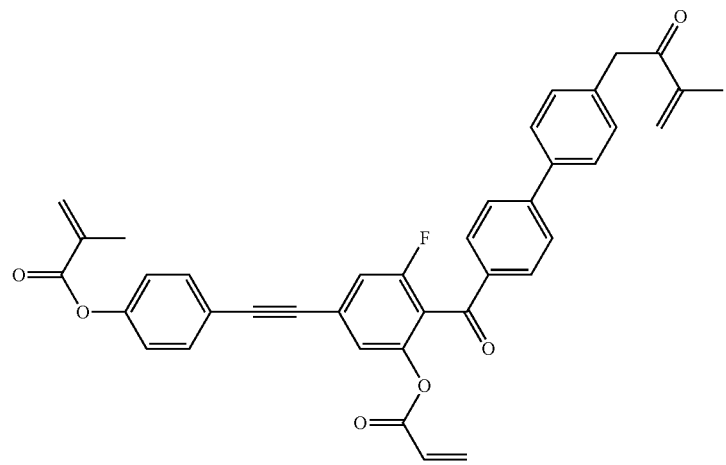

(1-552)
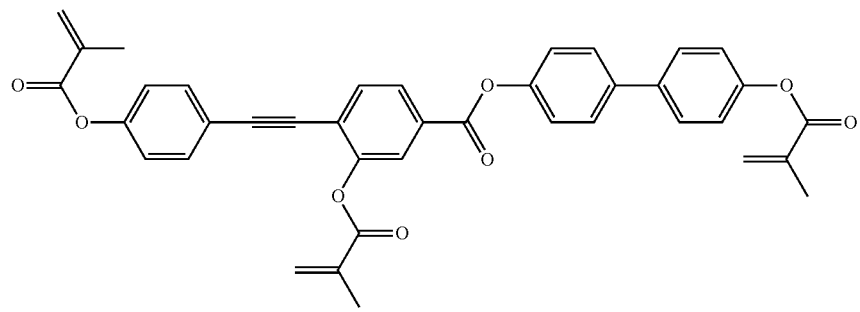
(1-553)
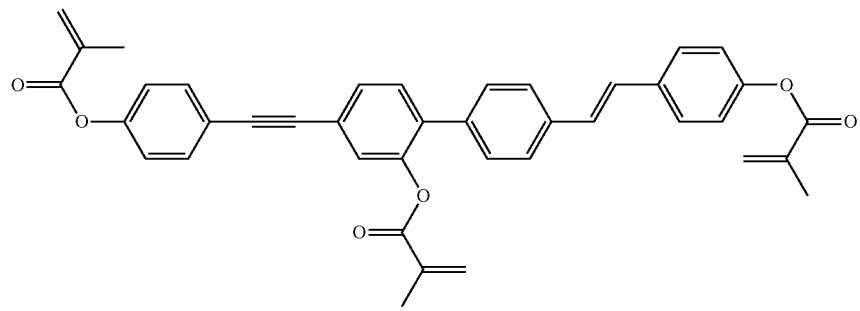
(1-554)
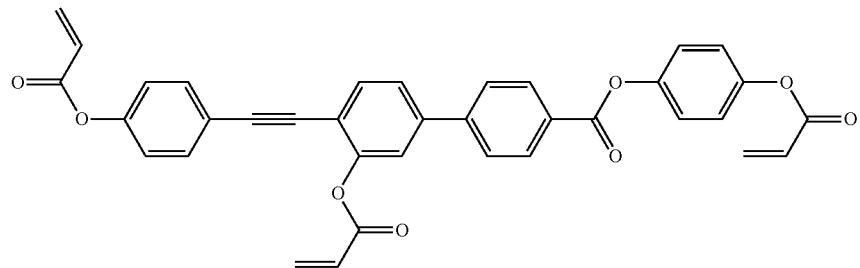
(1-555)
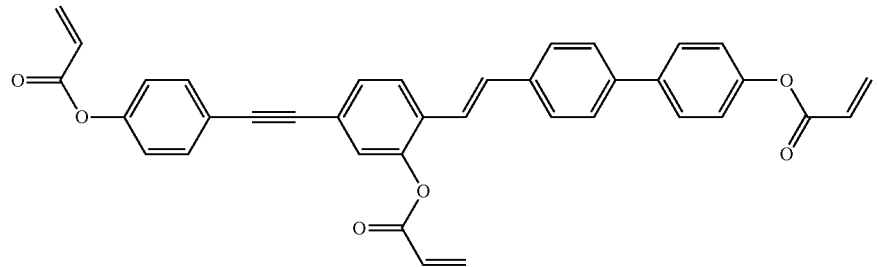
(1-556)
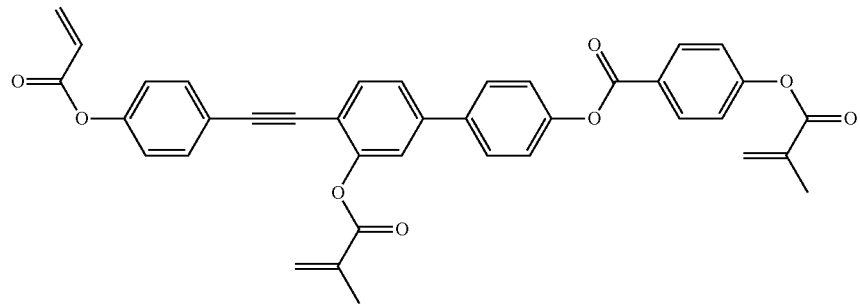

-continued
(1-557)
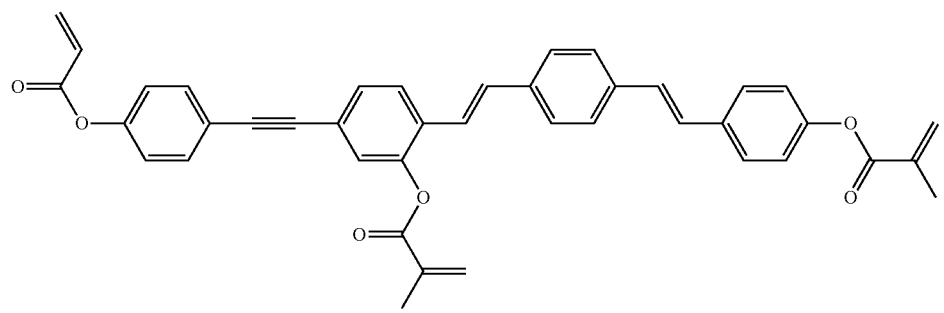
(1-558)
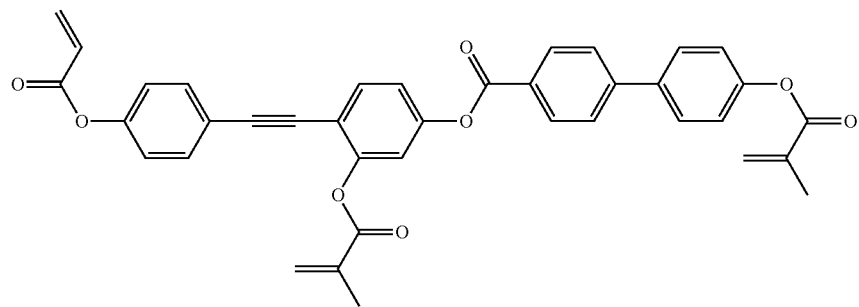
(1-559)
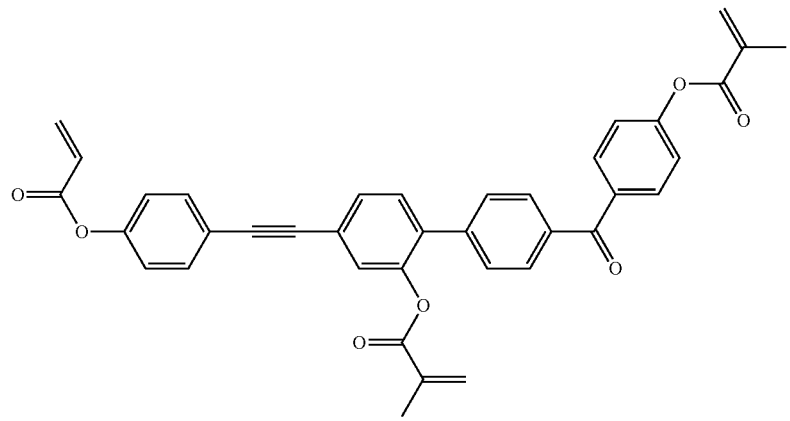
(1-560)
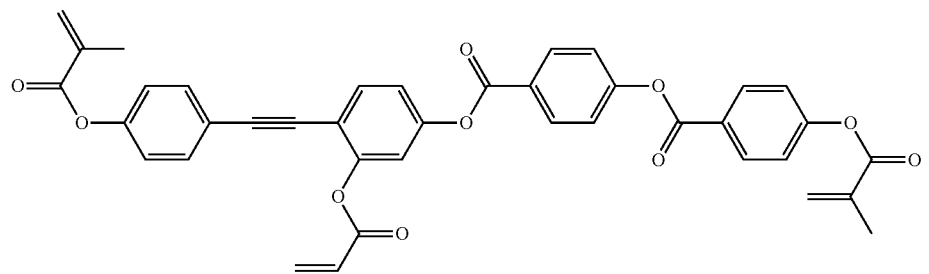

(1-561)
(1-562)
(1-563)
(1-564)
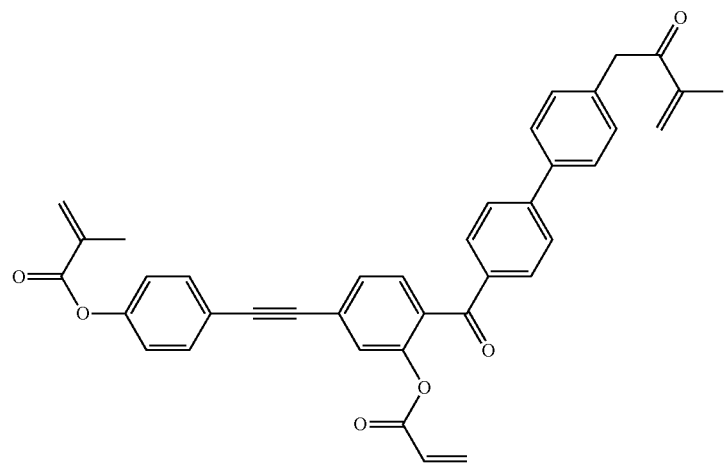

-continued
(1-565)
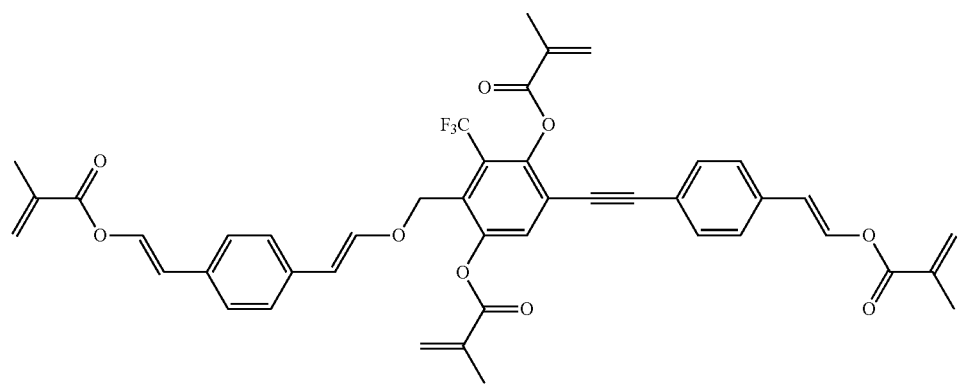
(1-566)
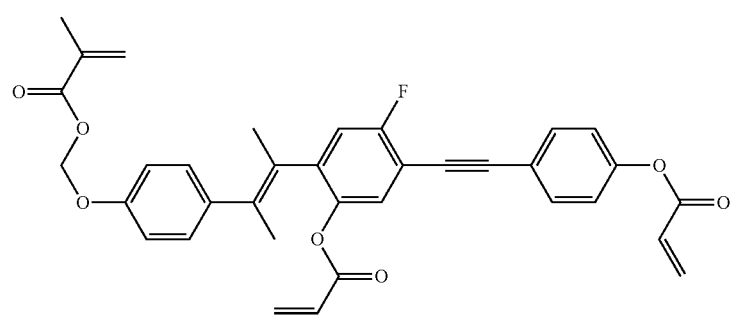
(1-567)
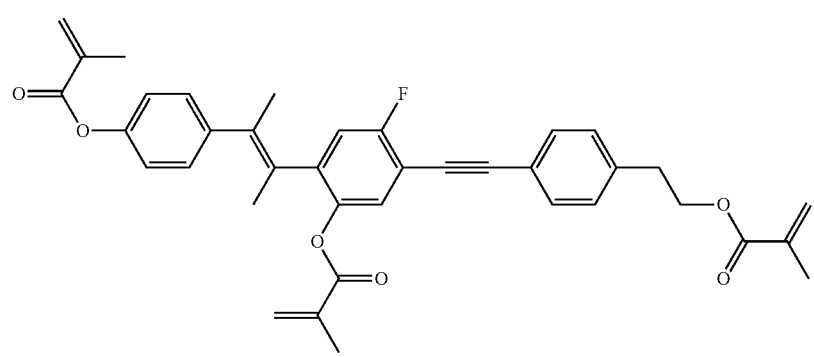
(1-568)
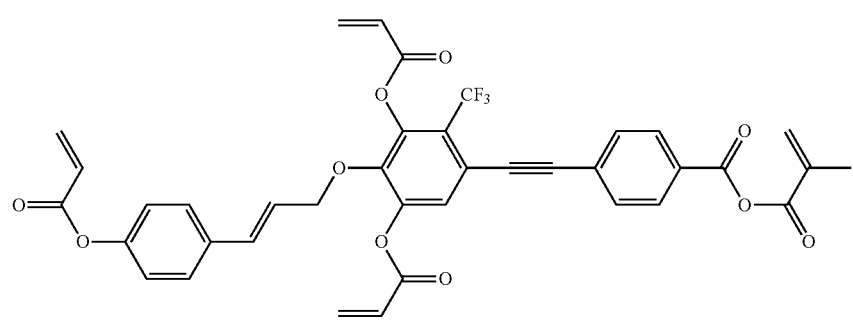

(1-569)
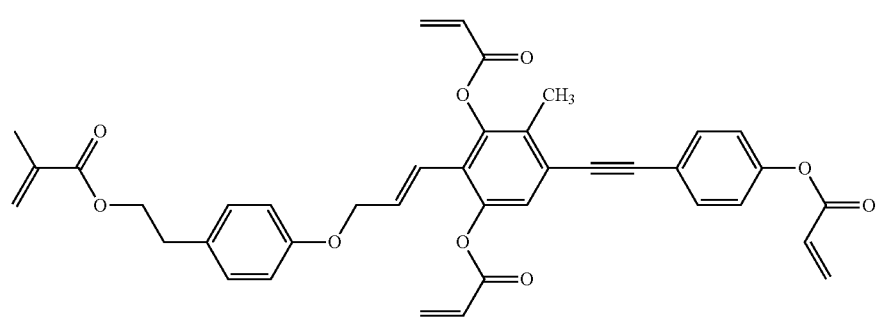
(1-570)
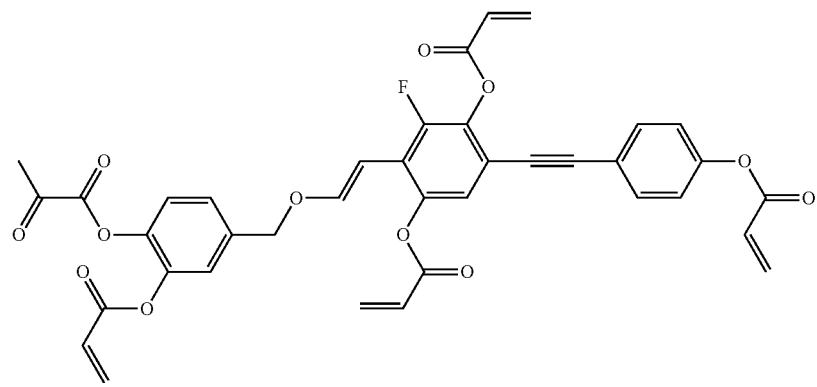
(1-571)
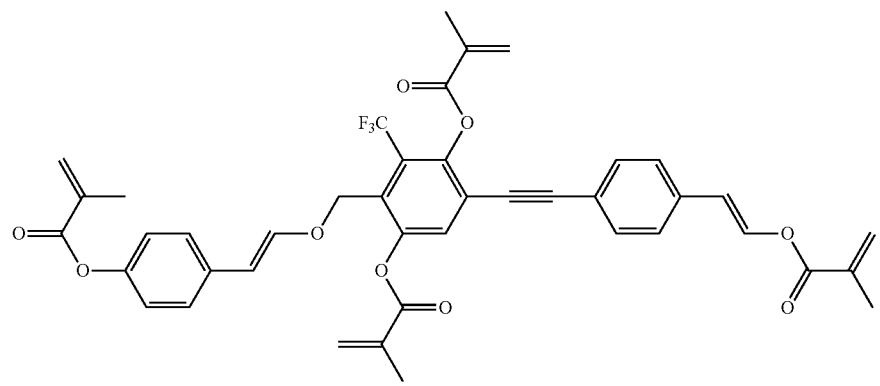
(1-572)
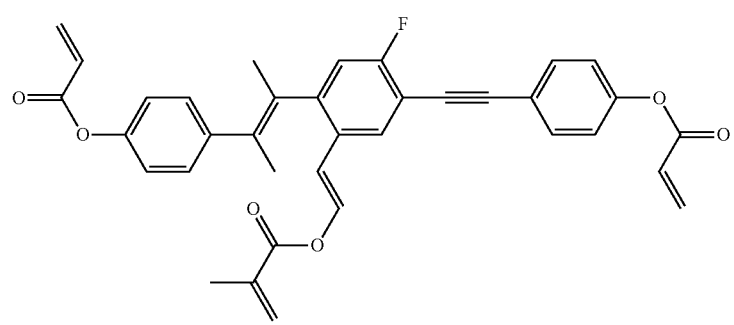

(1-573)
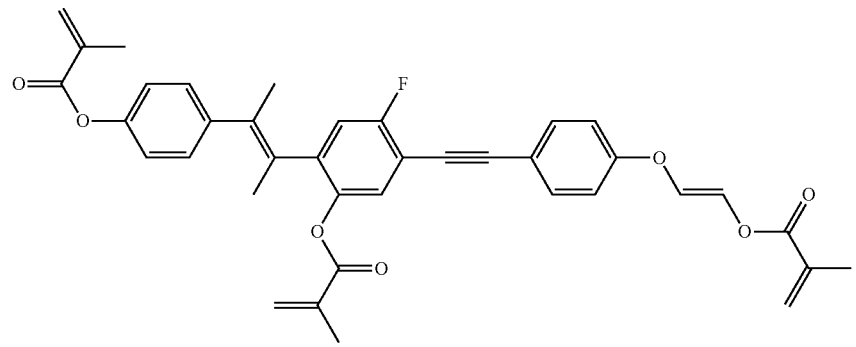
(1-574)
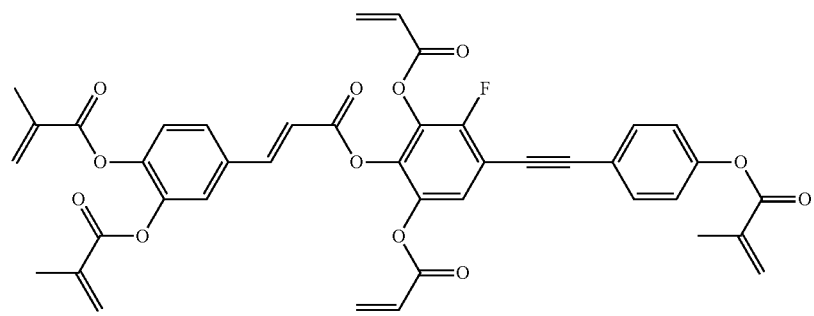
(1-575)
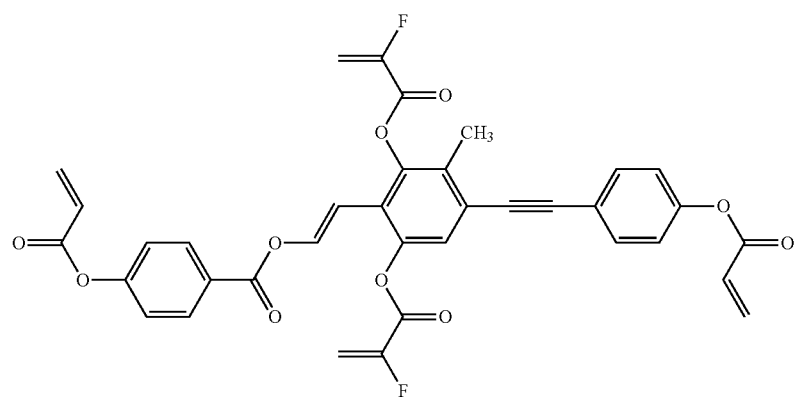
(1-576)
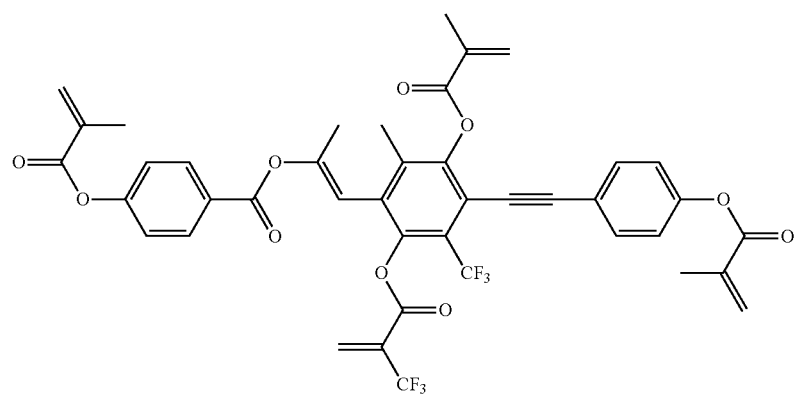

(1-577)
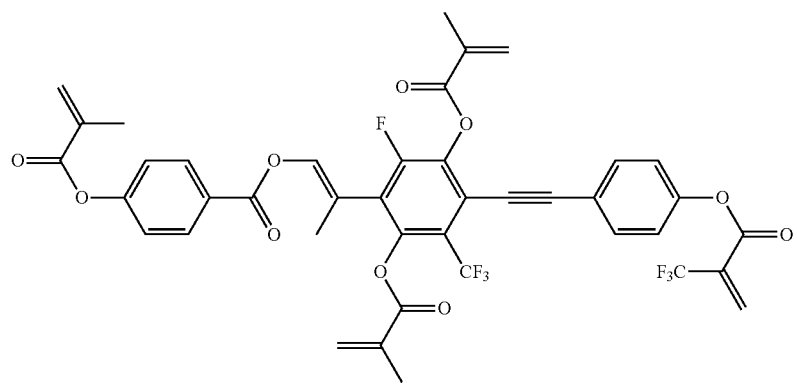
(1-578)
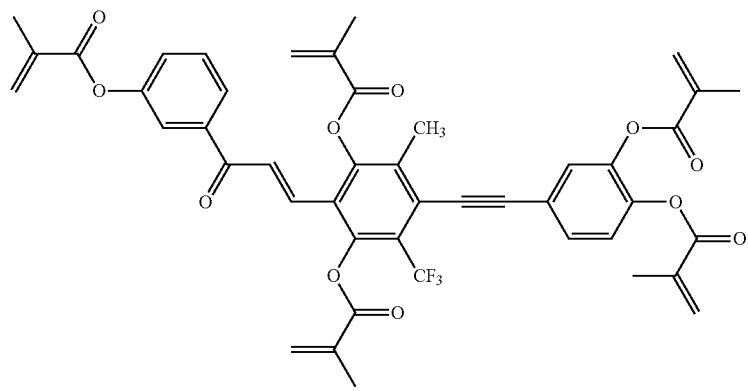
(1-579)
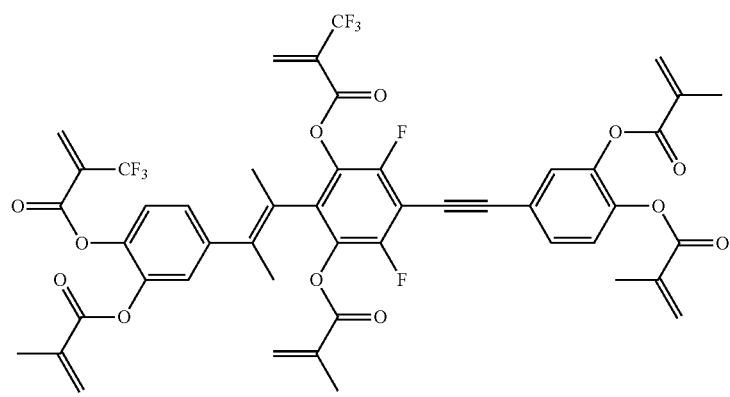
(1-580)
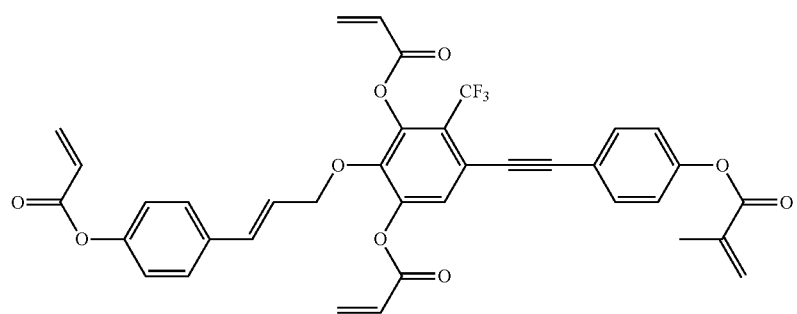

(1-581)
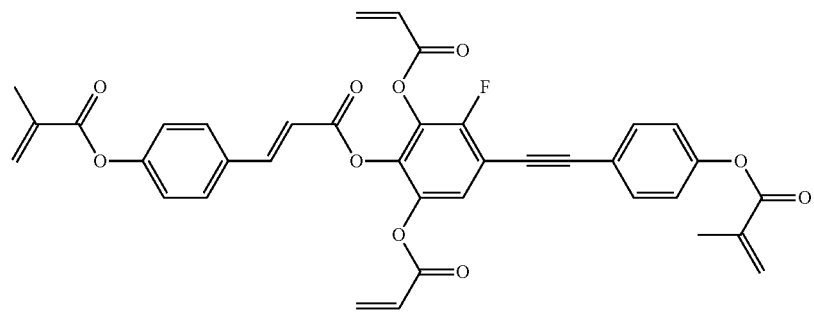
(1-582)
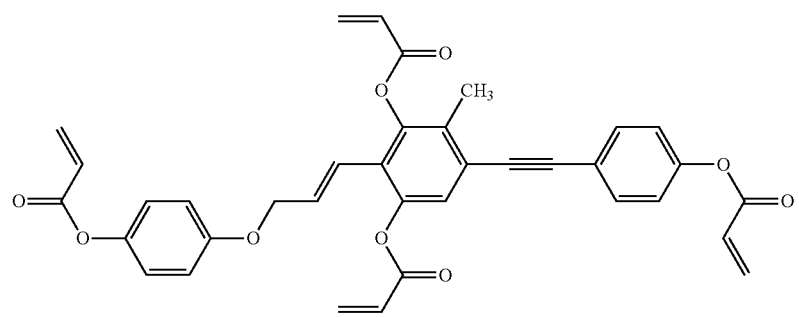
(1-583)
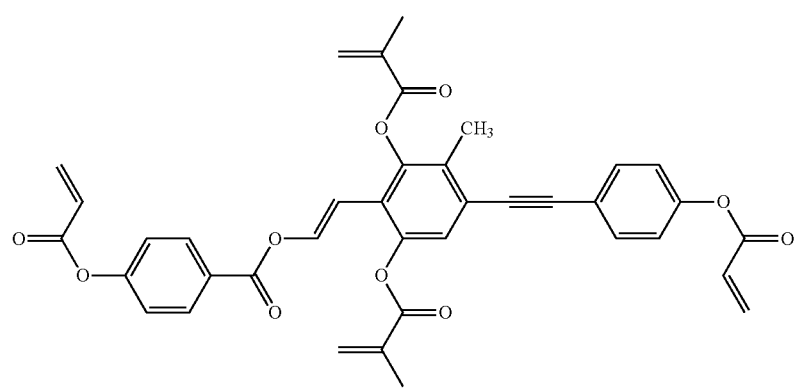
(1-584)
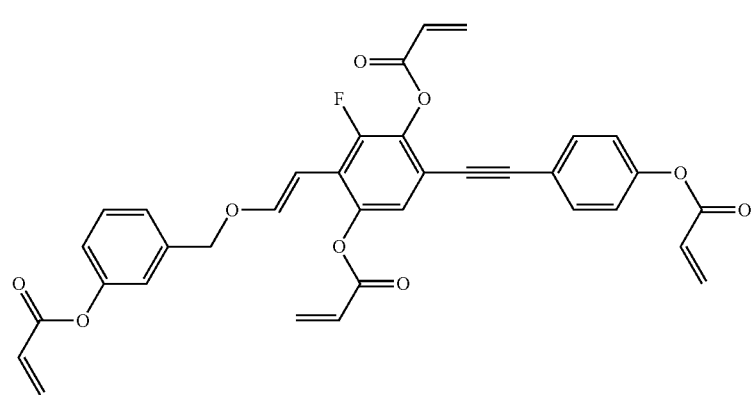

(1-585)
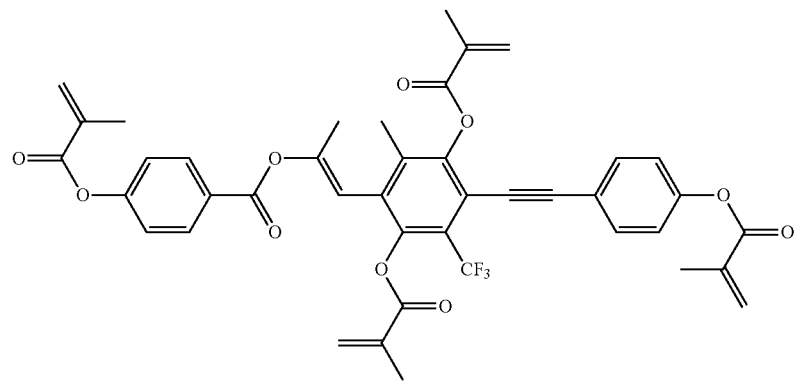
(1-586)
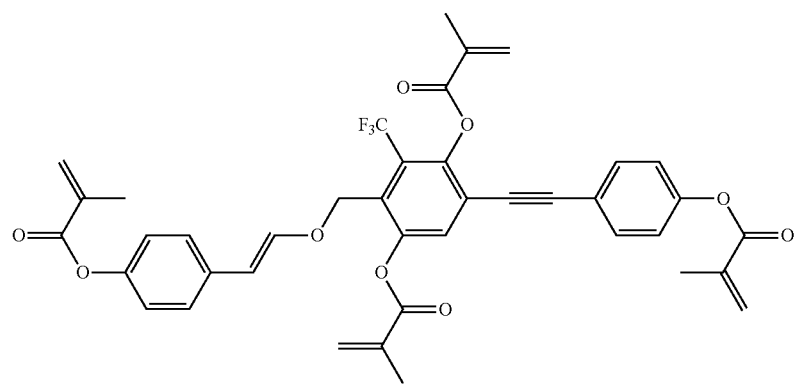
(1-587)
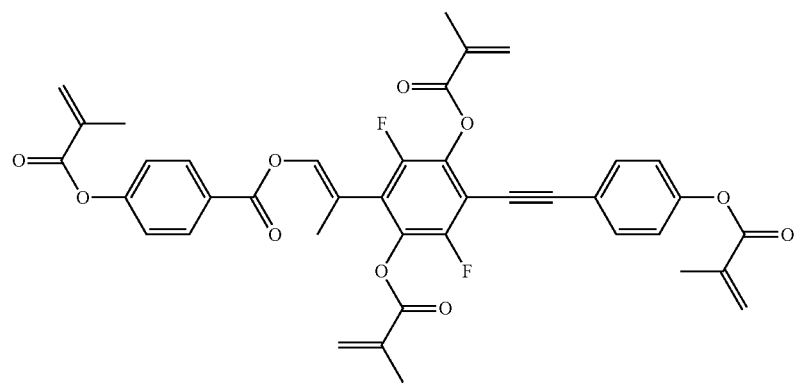
(1-588)
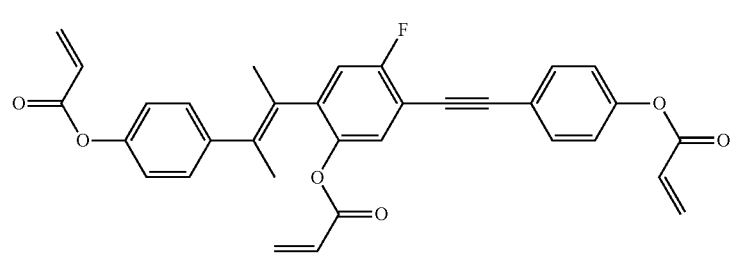

(1-589)
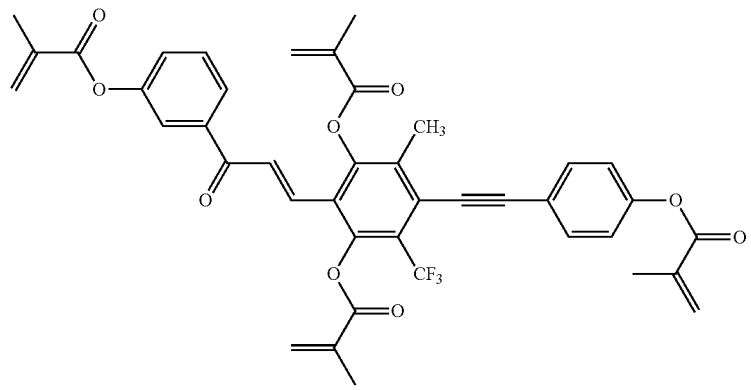
(1-590)
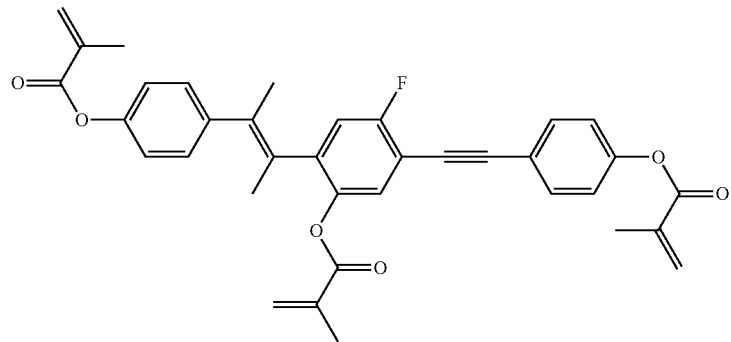
(1-591)
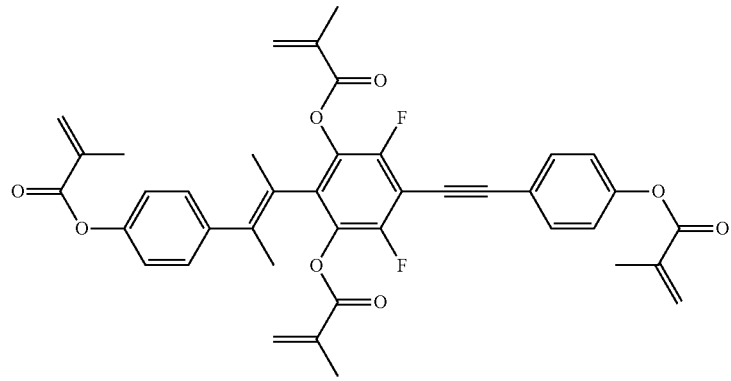
(1-592)
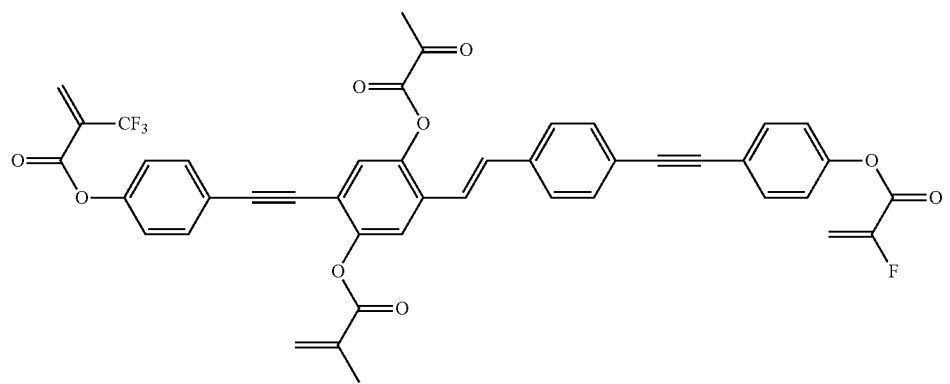

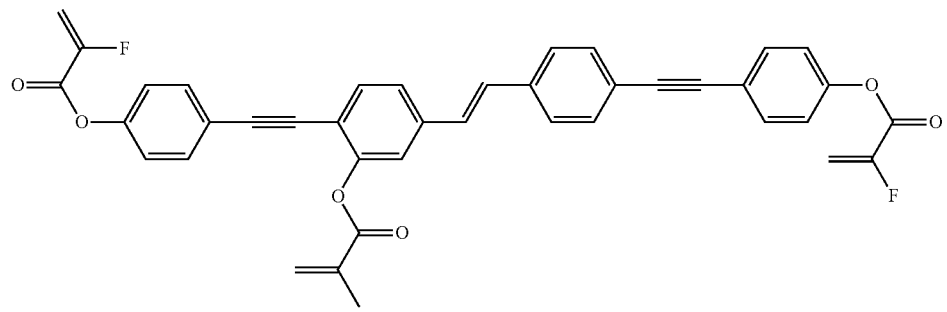
(1-593)
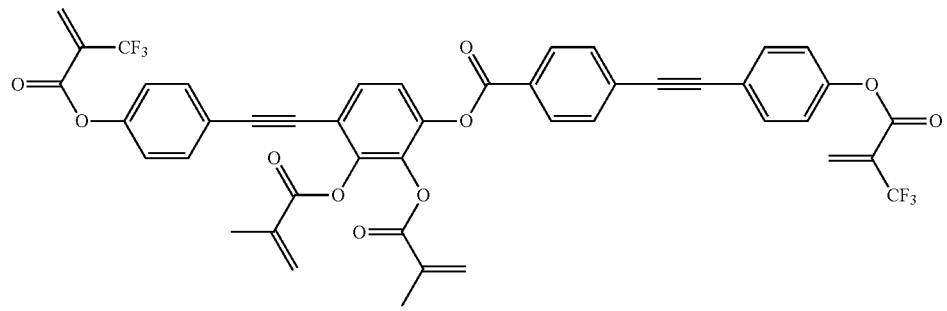
(1-594)
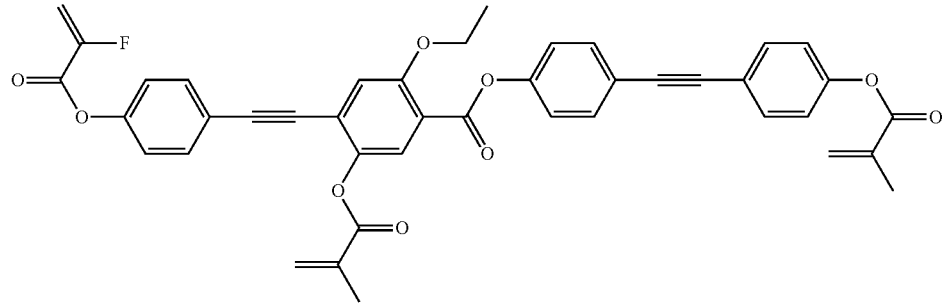
(1-595)
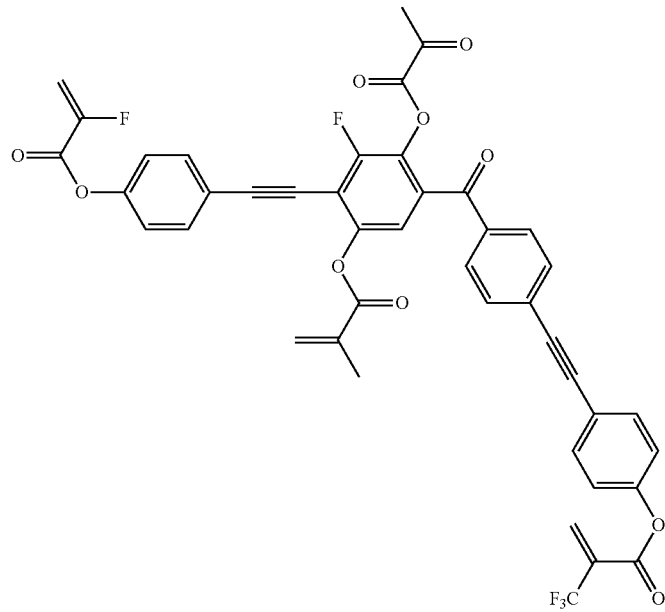
(1-596)

-continued
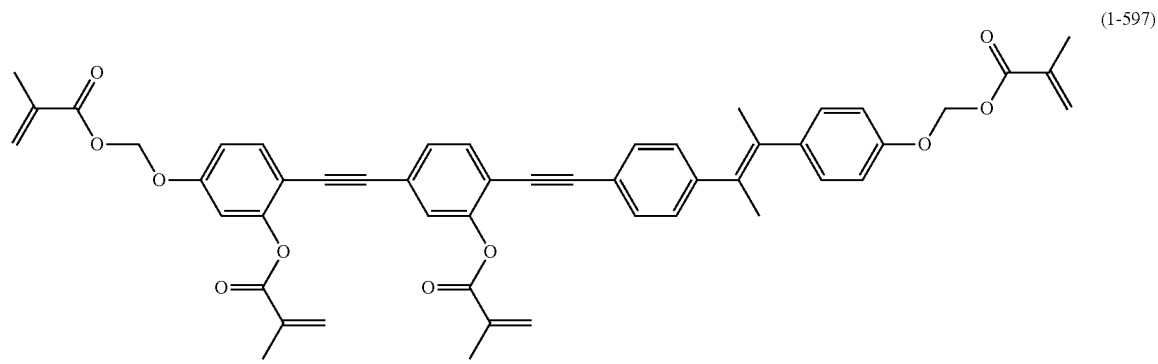
(1-597)
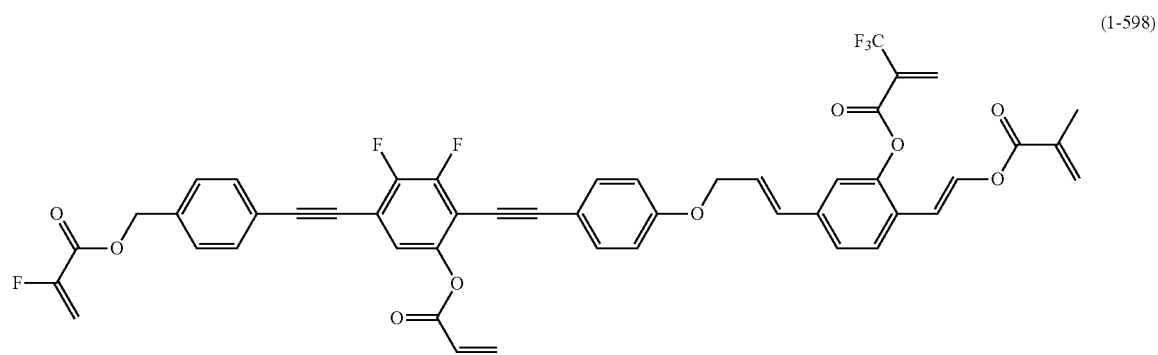
(1-598)
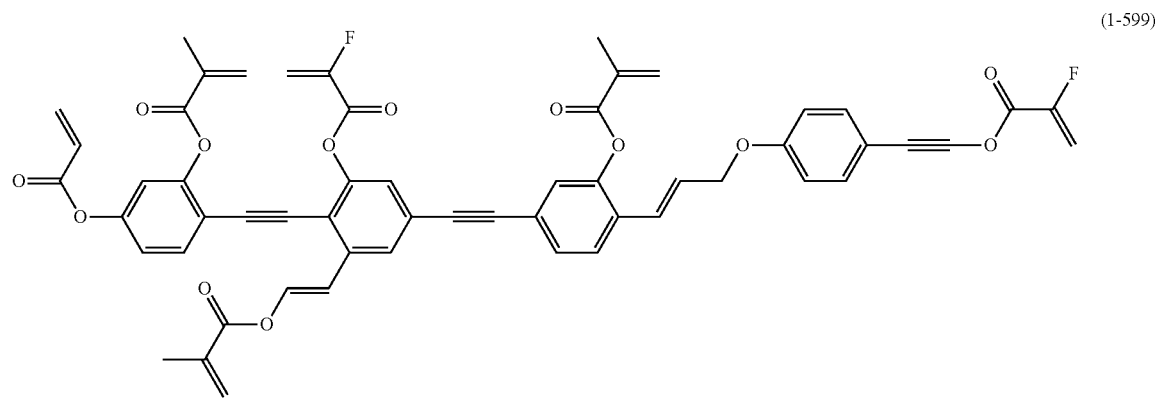
(1-599)
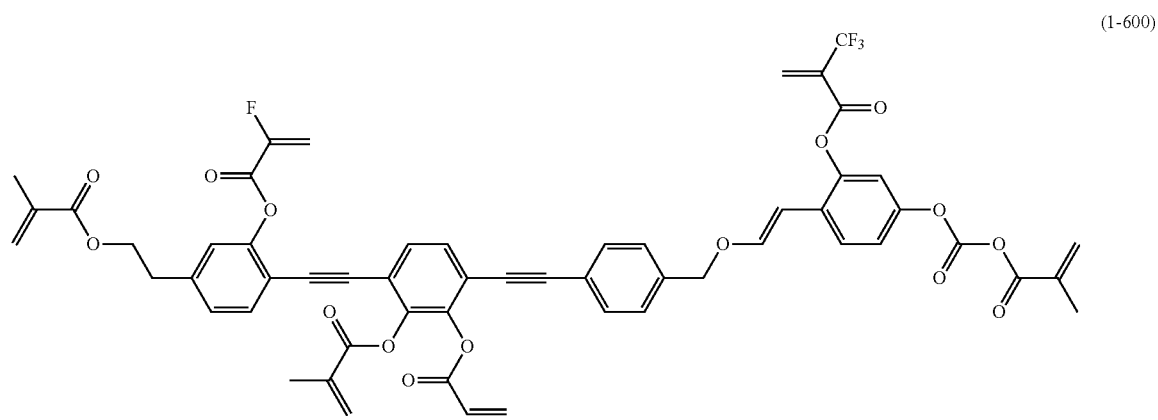
(1-600)

-continued
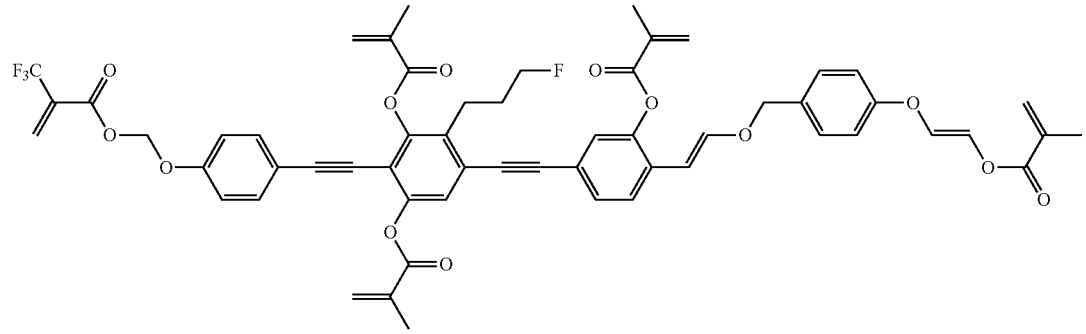
(1-601)
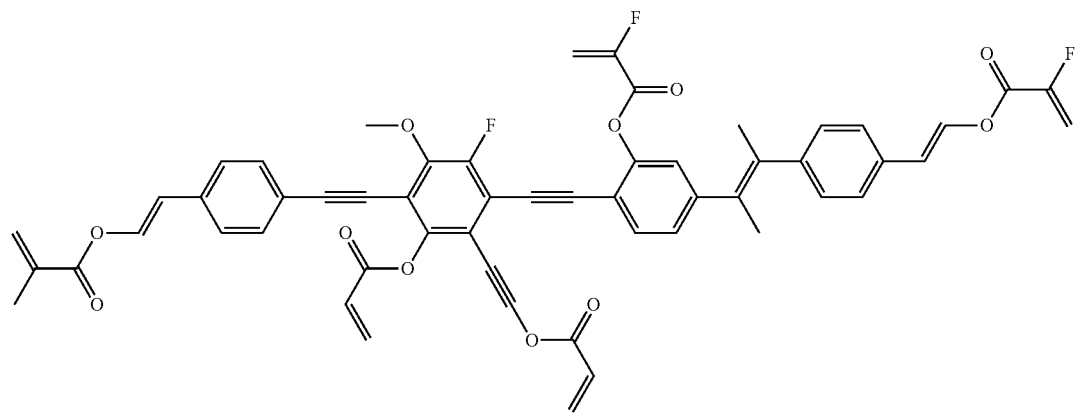
(1-602)
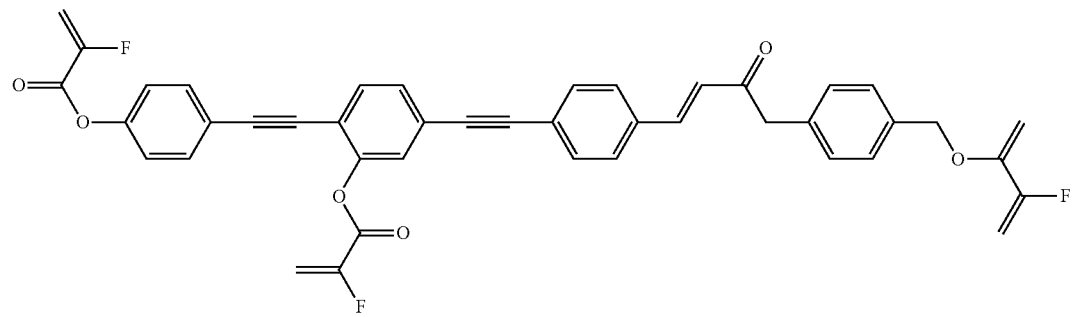
(1-603)
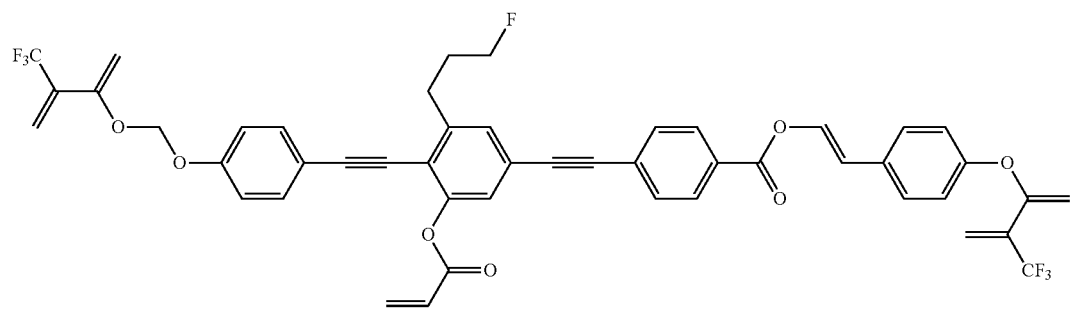
(1-604)

(1-605)
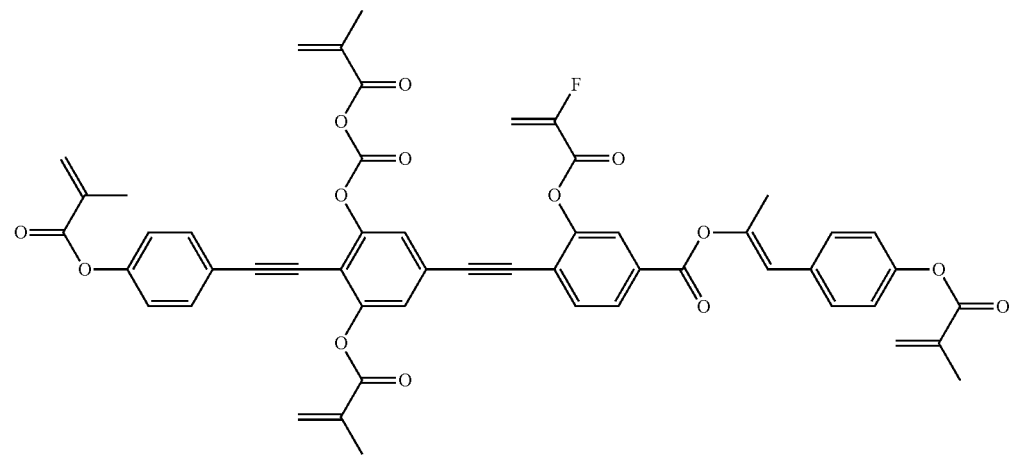
(1-606)
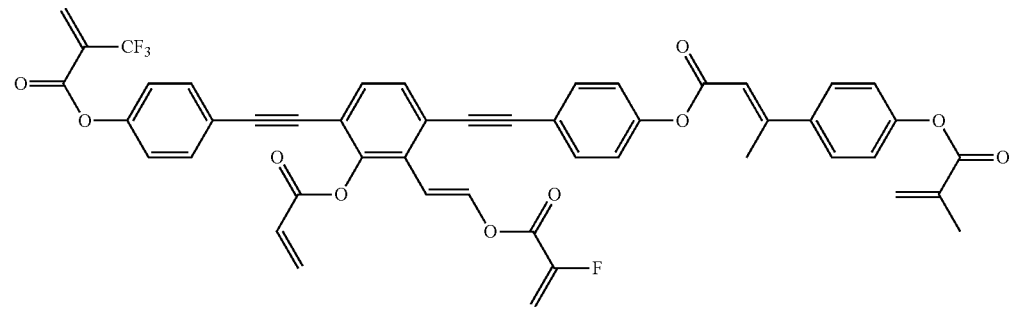
(1-607)
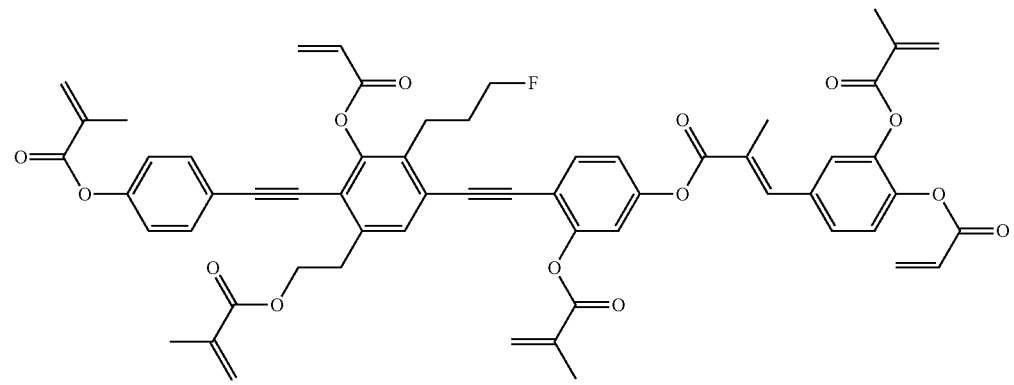
(1-608)
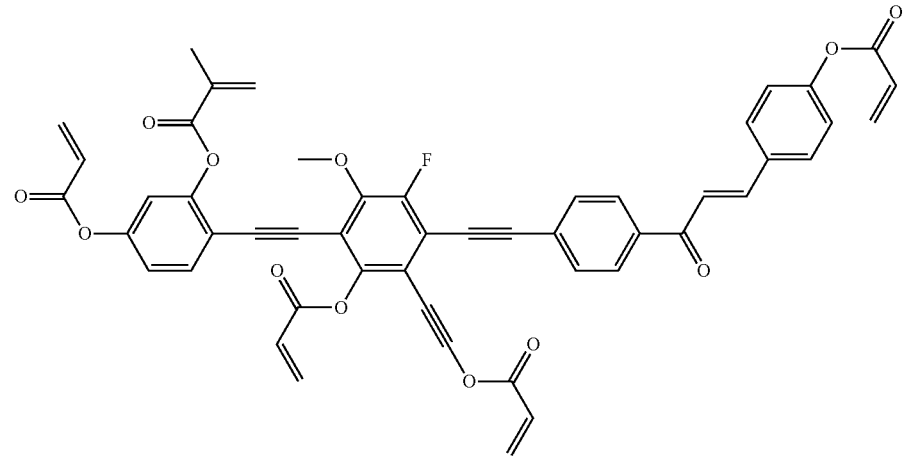

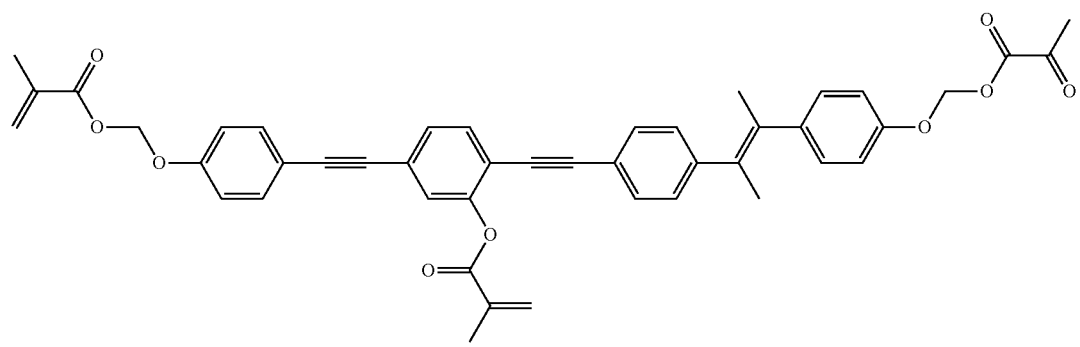
(1-609)
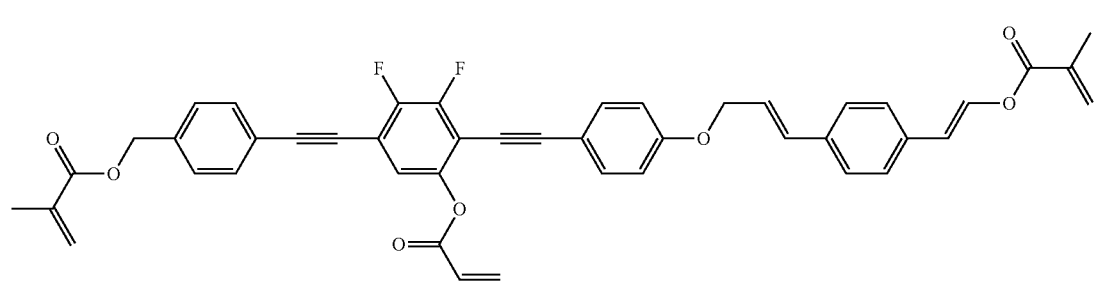
(1-610)
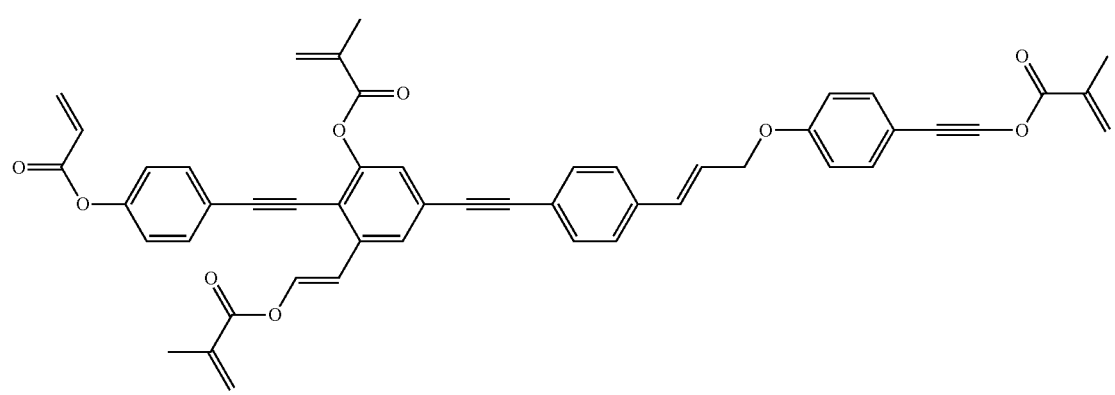
(1-611)
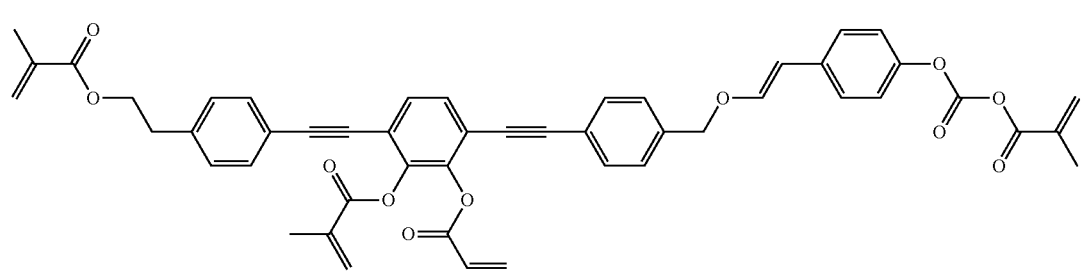
(1-612)
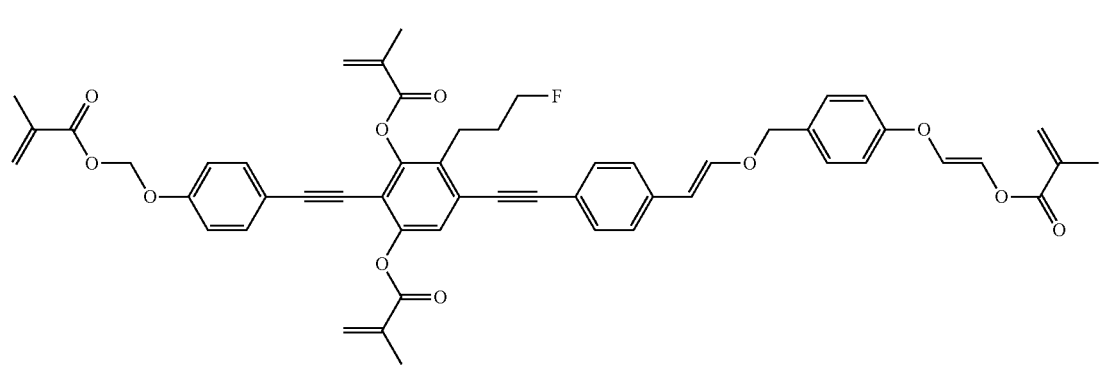
(1-613)

-continued
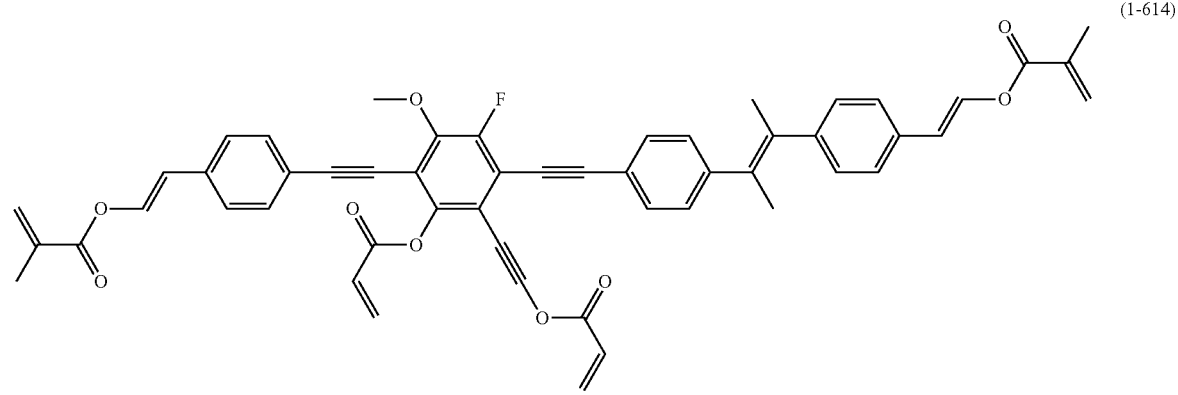
(1-614)
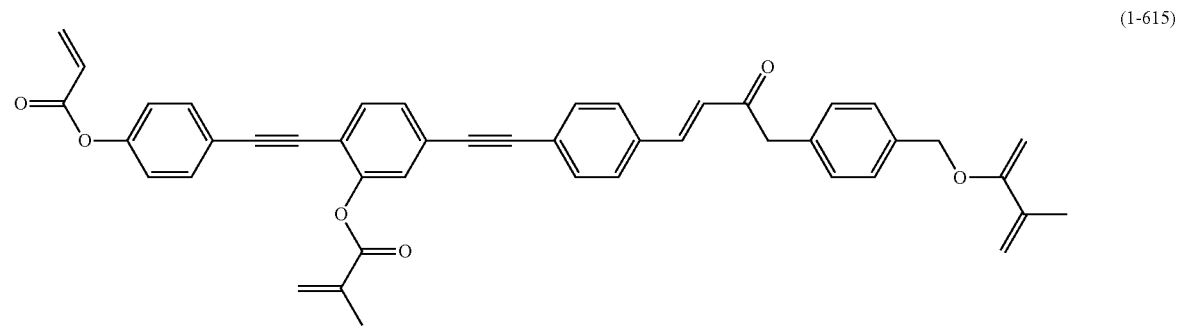
(1-615)
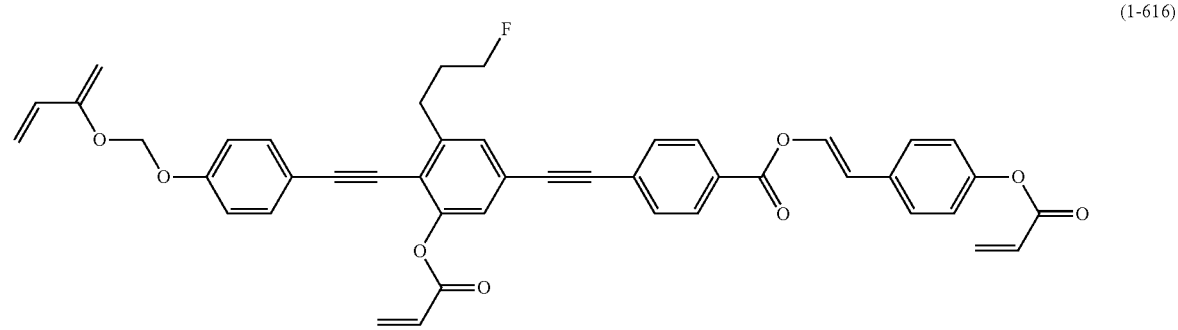
(1-616)
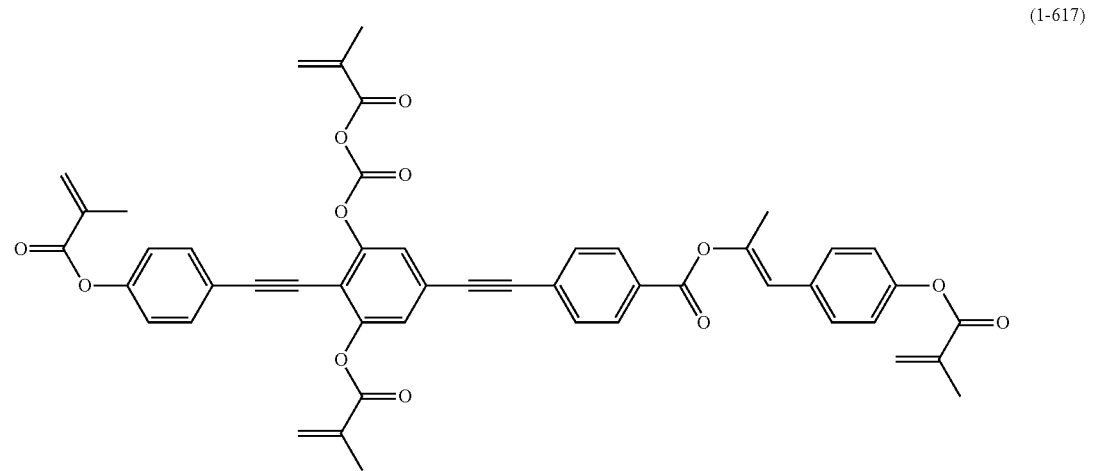
(1-617)

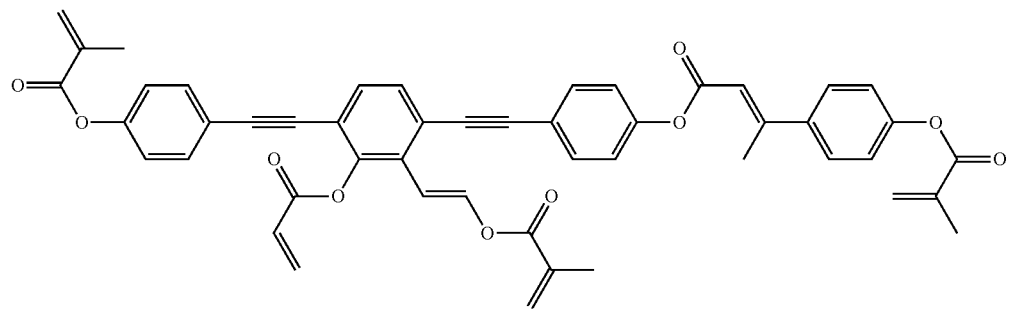
(1-618)
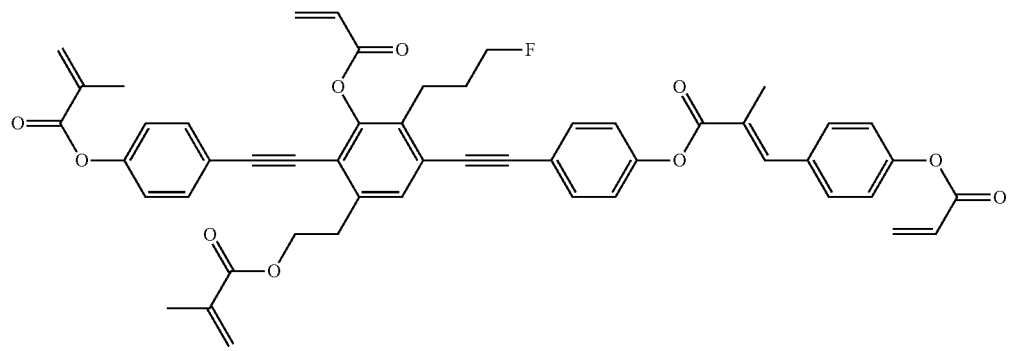
(1-619)
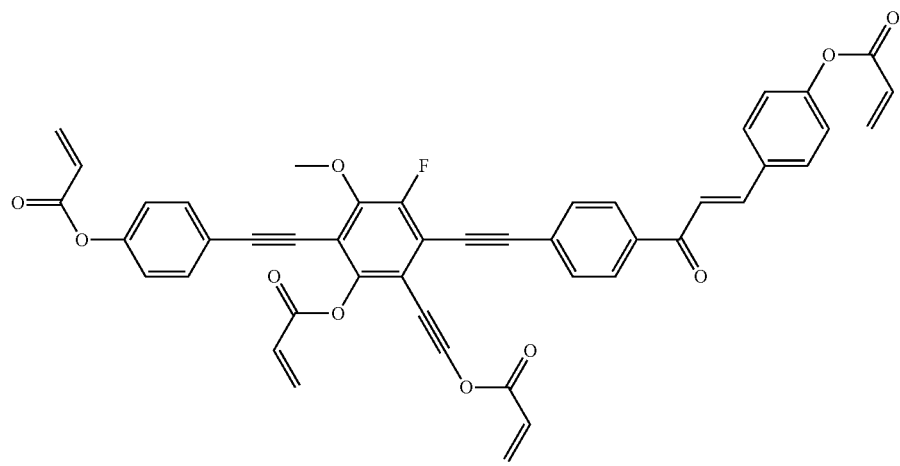
(1-620)
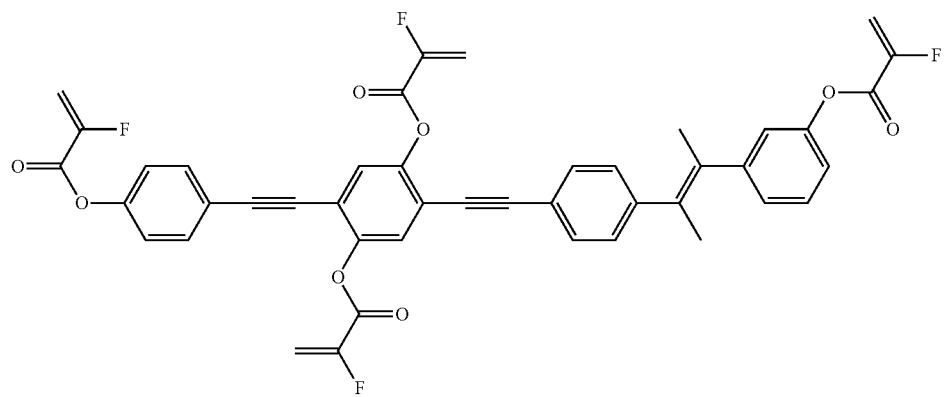
(1-621)

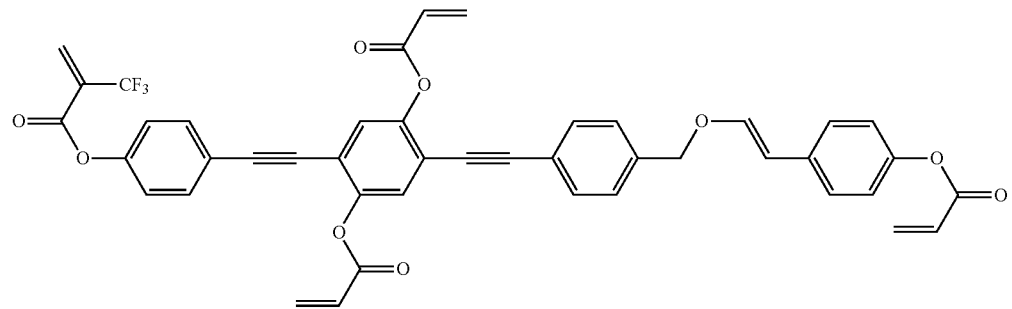
(1-622)
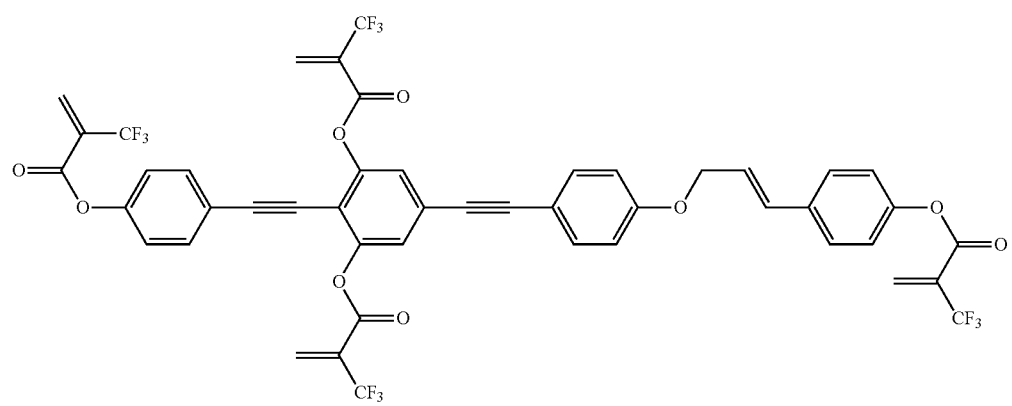
(1-623)
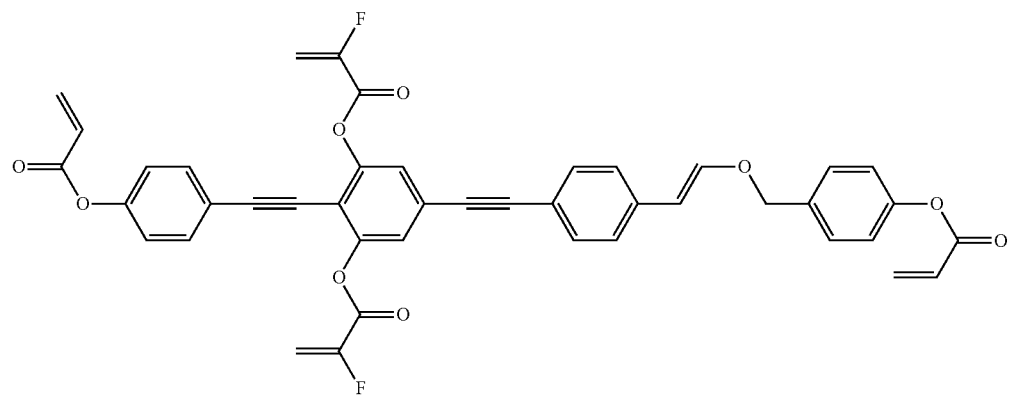
(1-624)
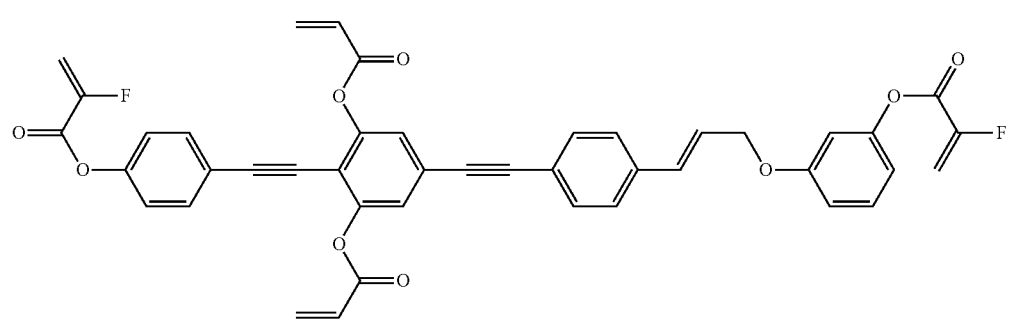
(1-625)

(1-626)
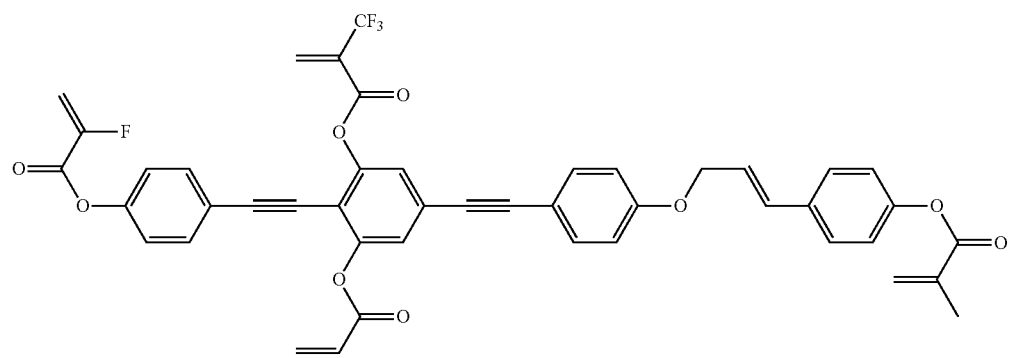
(1-627)
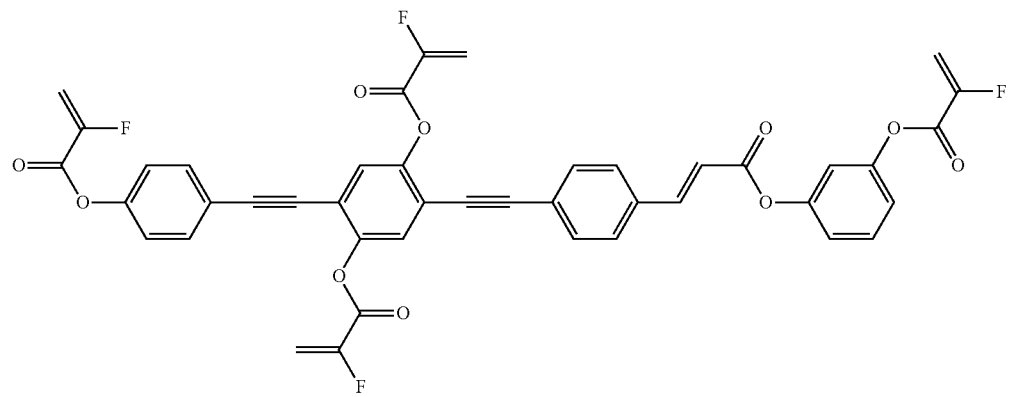
(1-628)
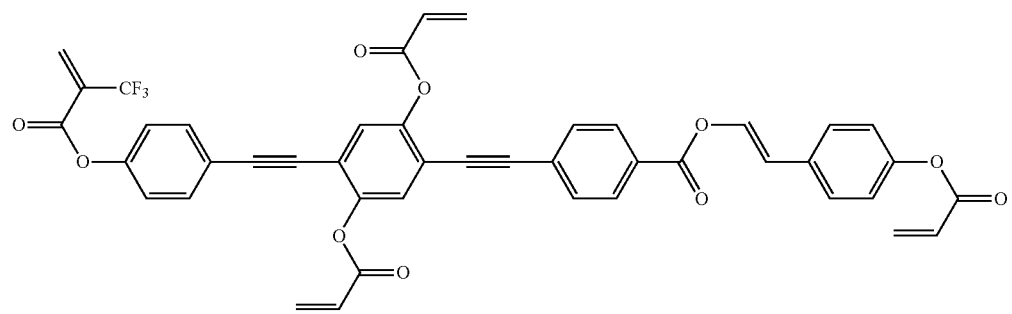
(1-629)
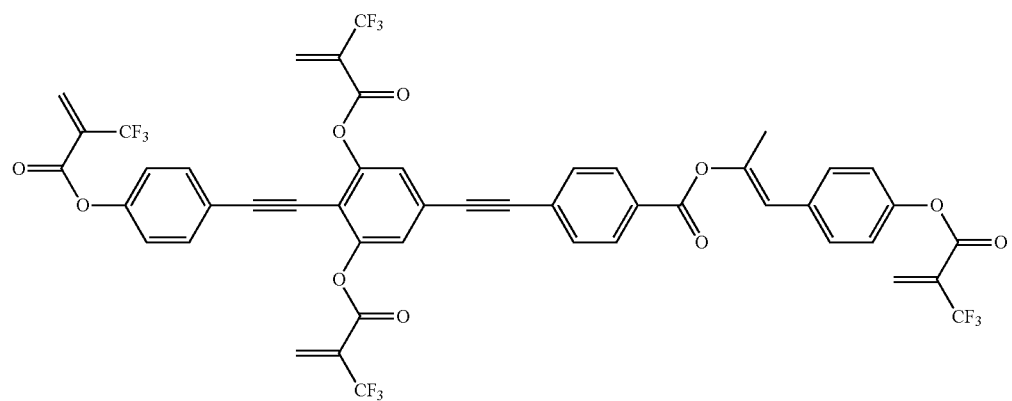

(1-630)
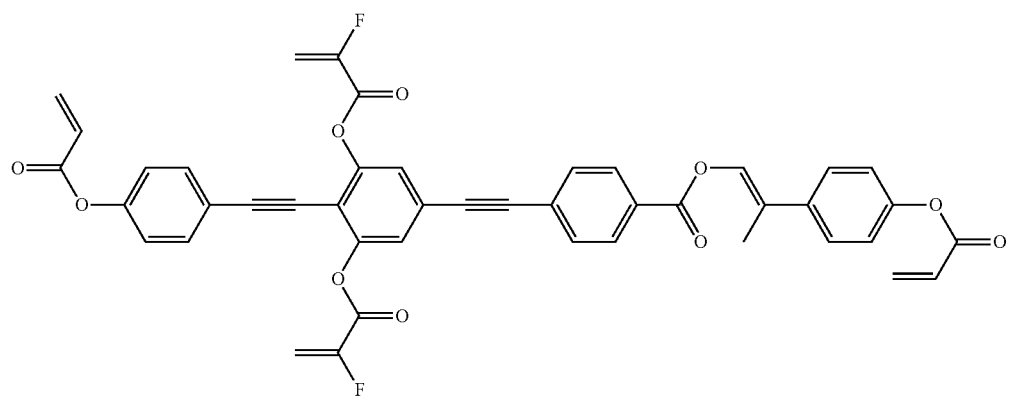
(1-631)
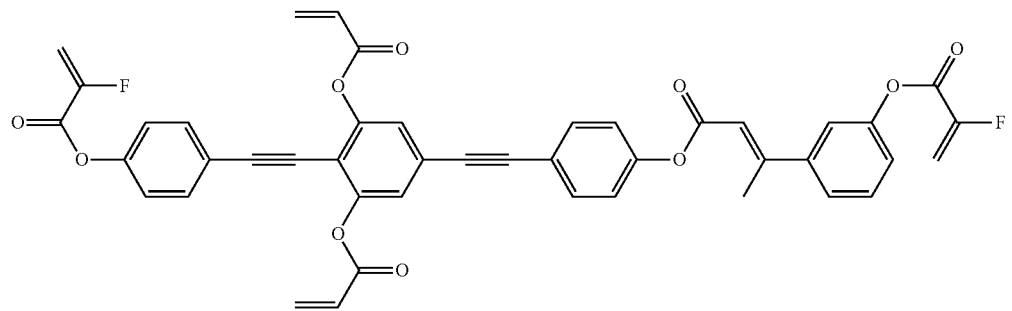
(1-632)
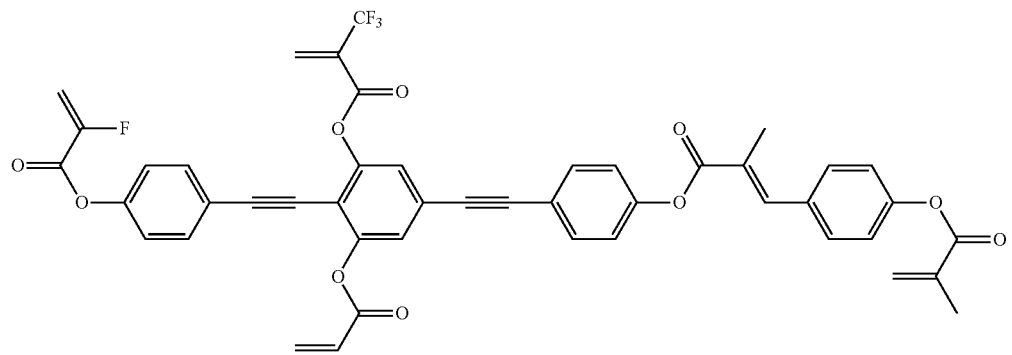
(1-633)
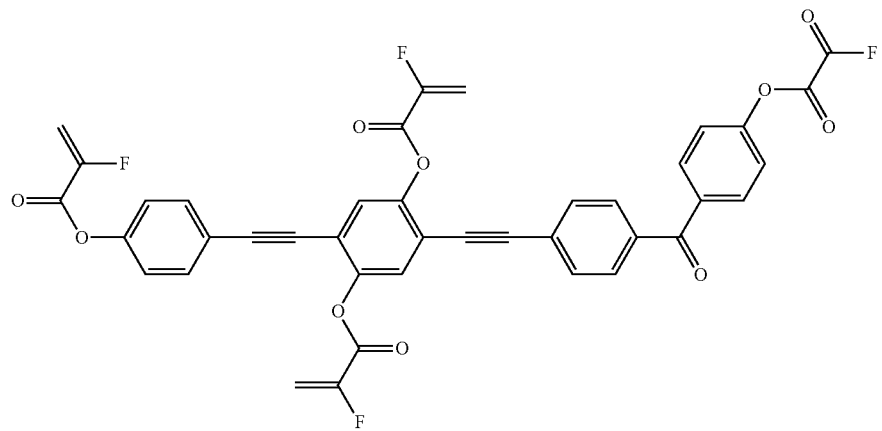

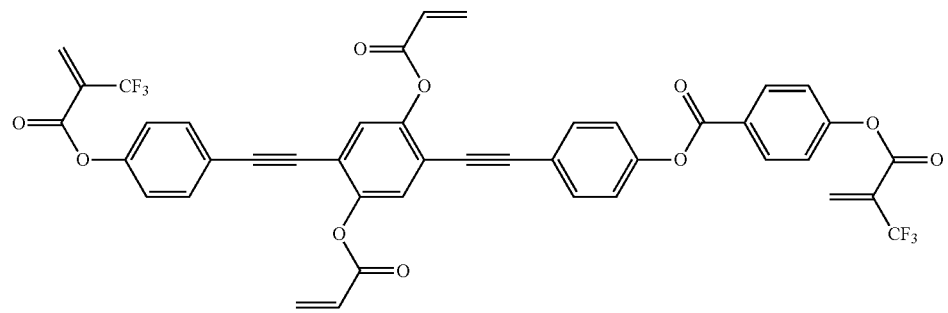
(1-634)
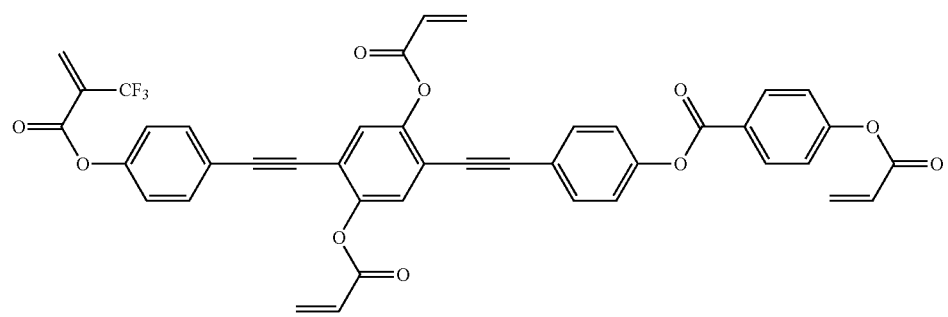
(1-635)
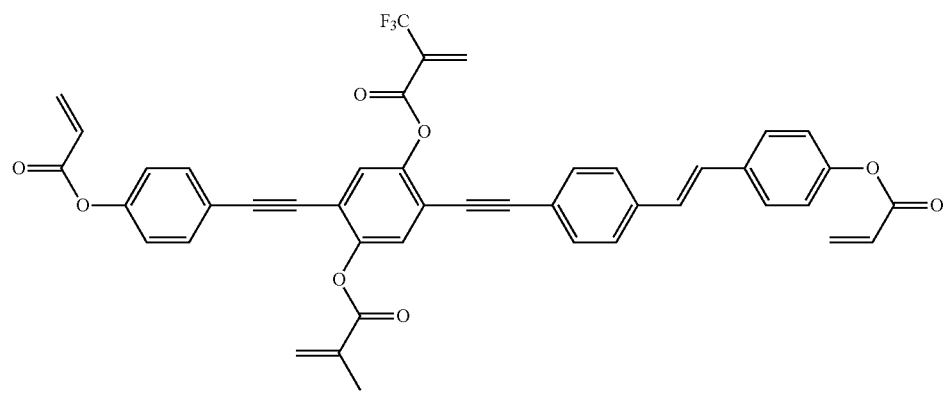
(1-636)
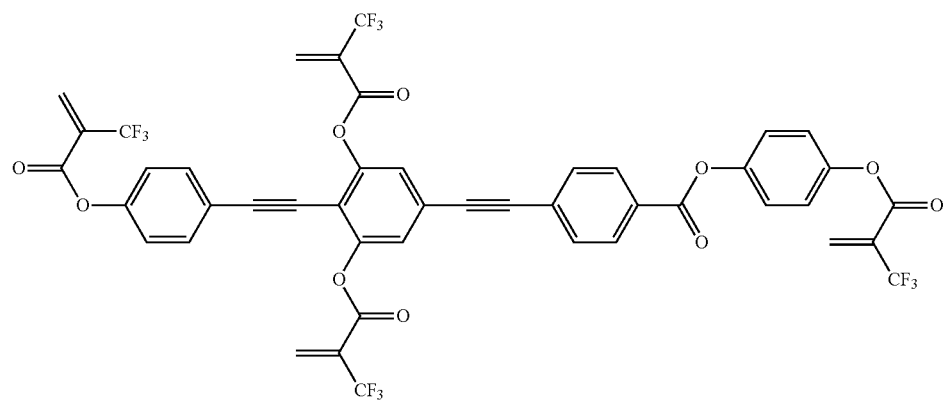
(1-637)

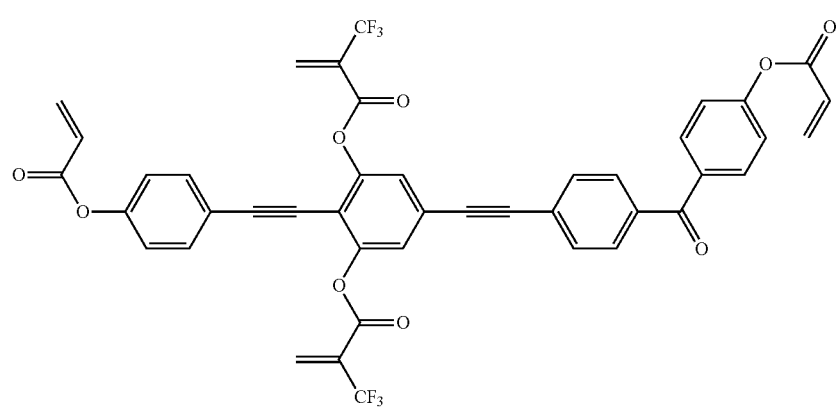
(1-638)
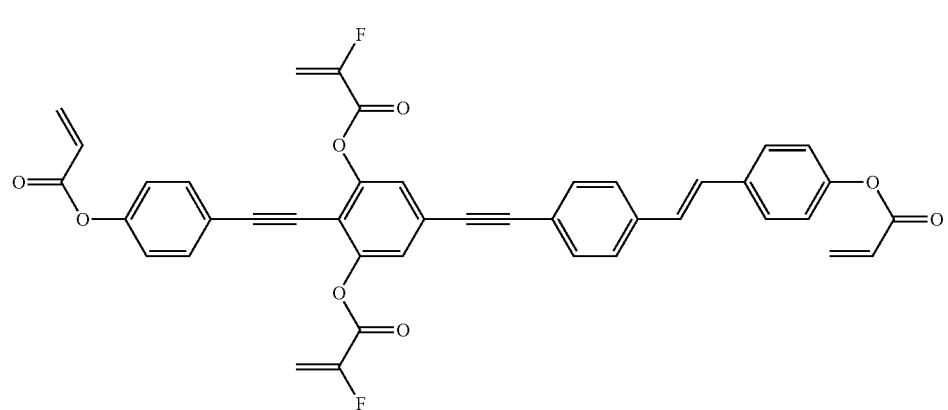
(1-639)
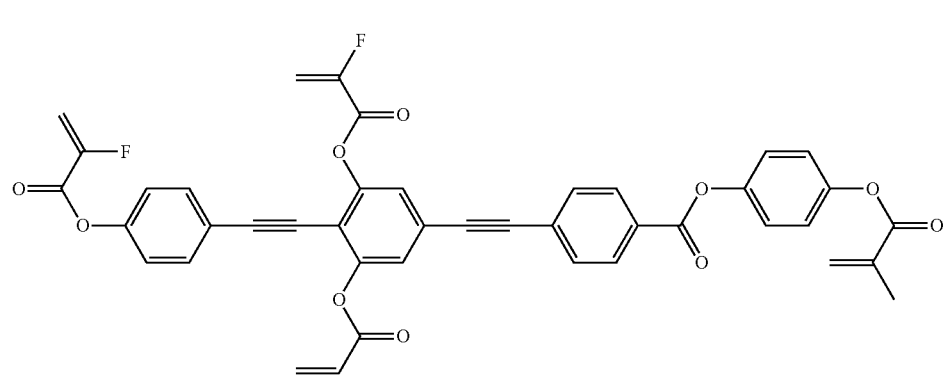
(1-640)
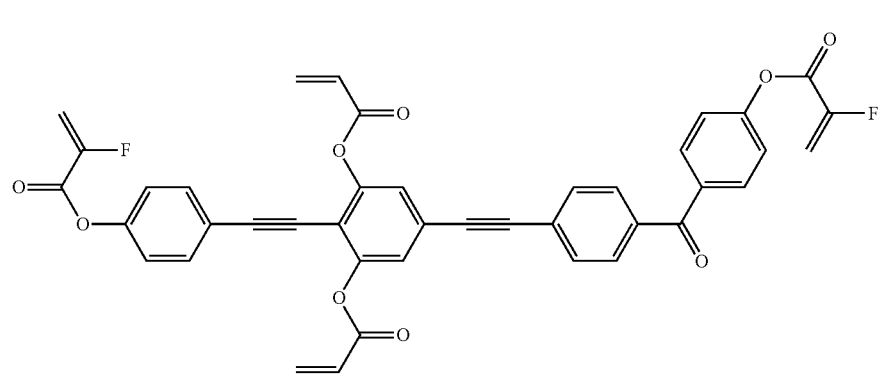
(1-641)

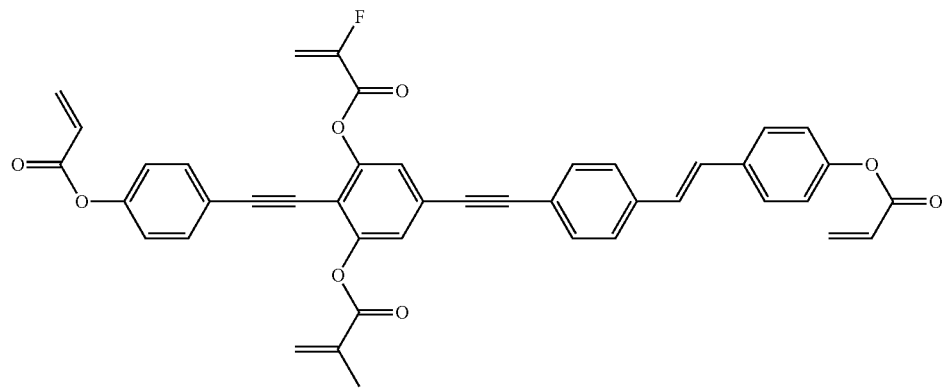
(1-642)
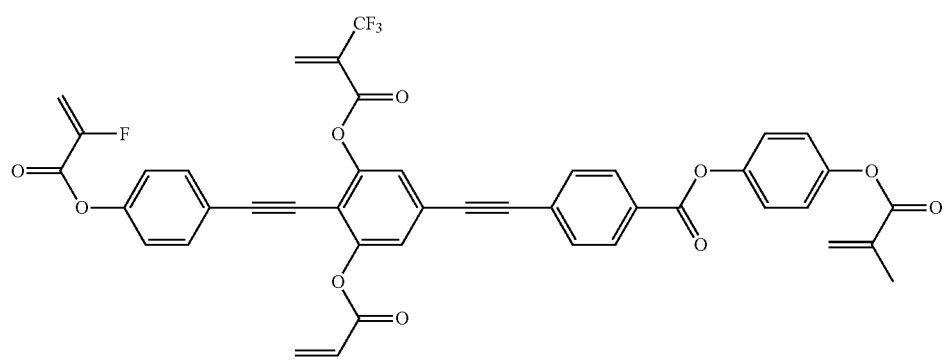
(1-643)
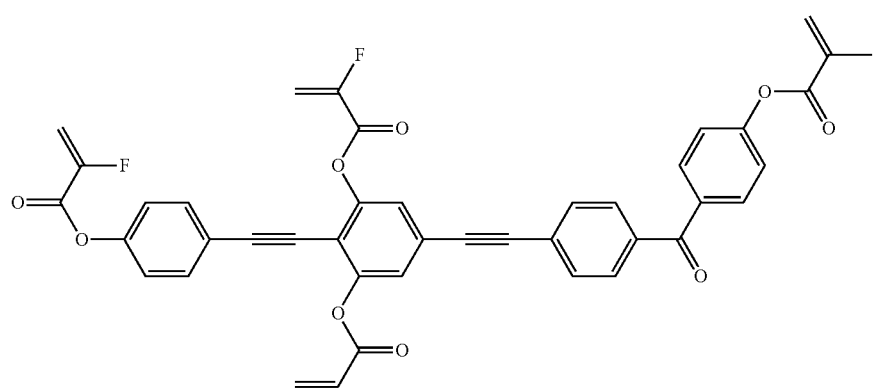
(1-644)
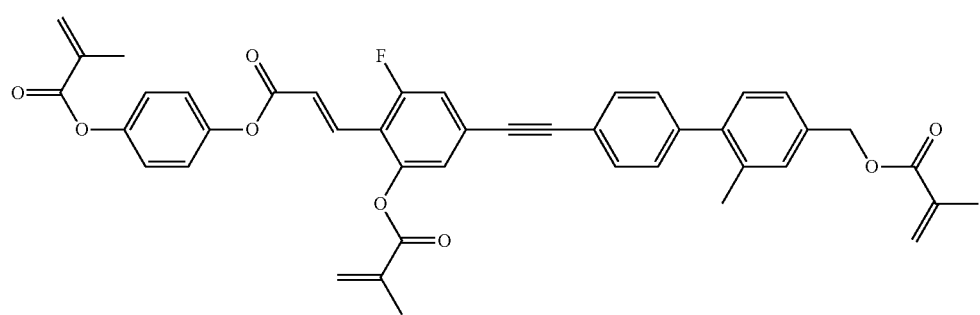
(1-645)

(1-646)
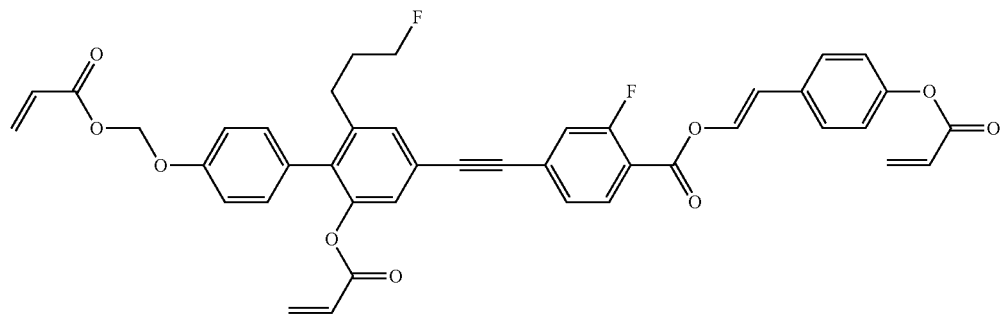
(1-647)
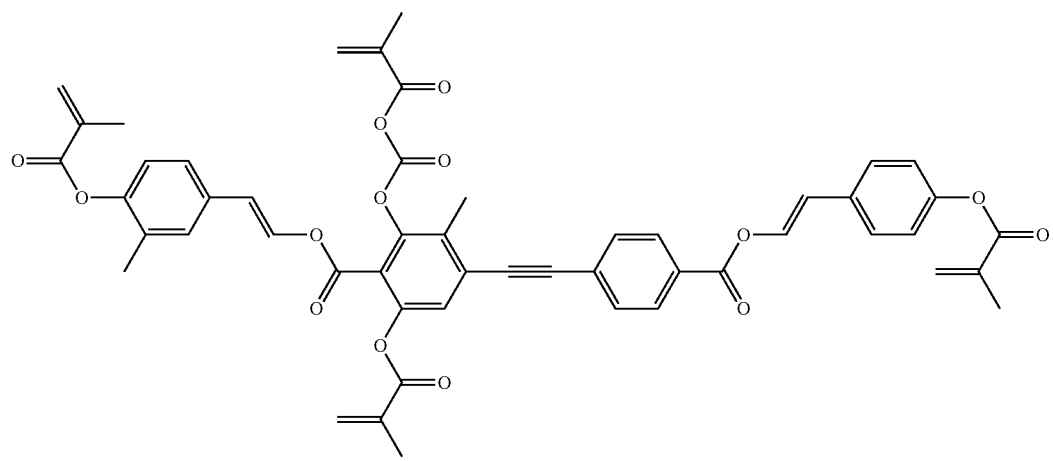
(1-648)
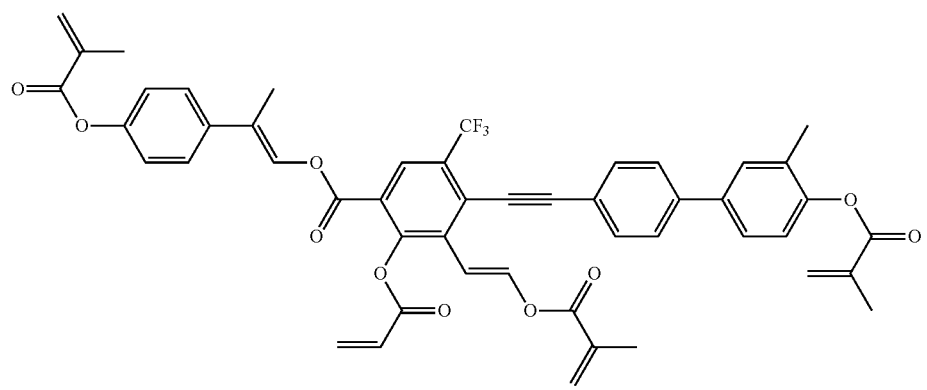
(1-649)
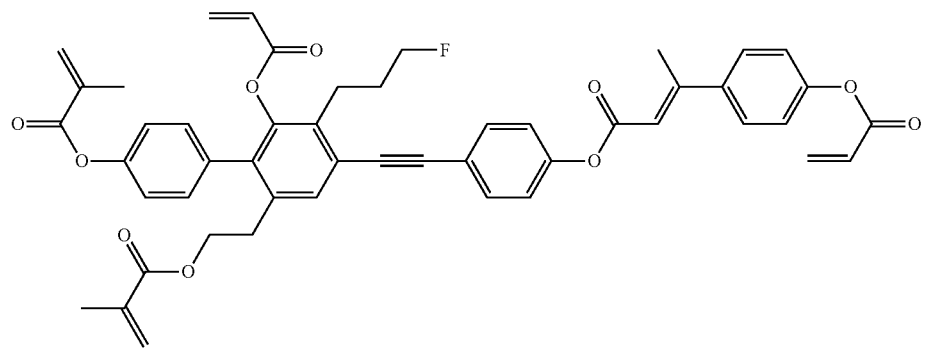

-continued
(1-650)
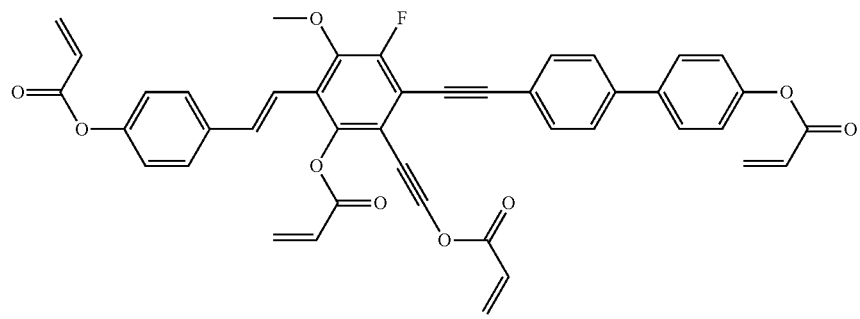
(1-651)
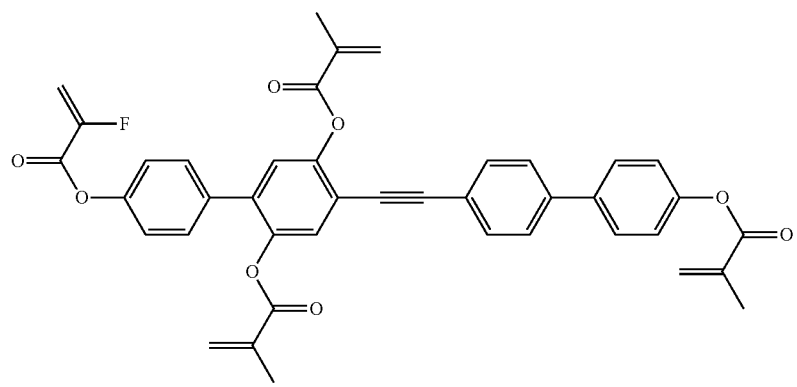
(1-652)
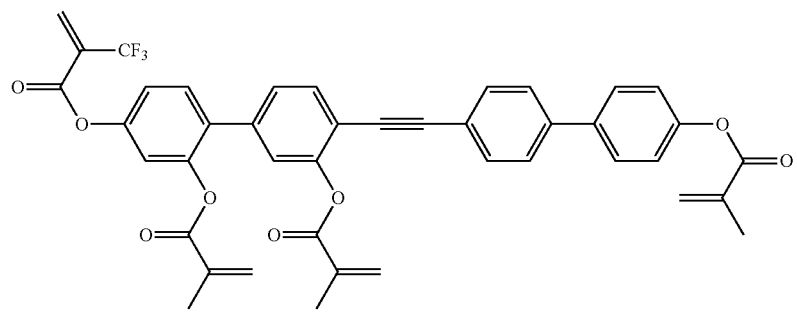
(1-653)
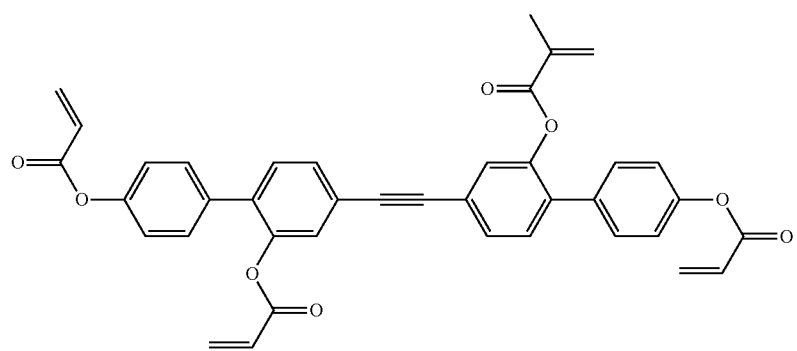

(1-654)
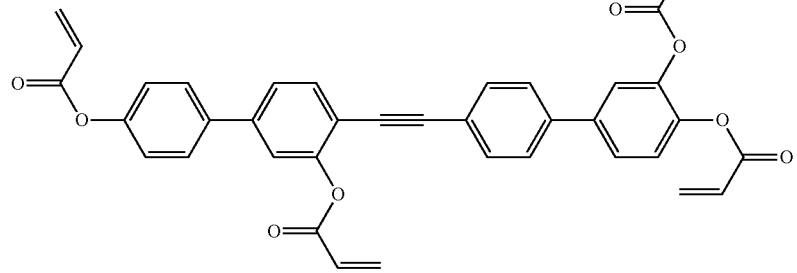
(1-655)
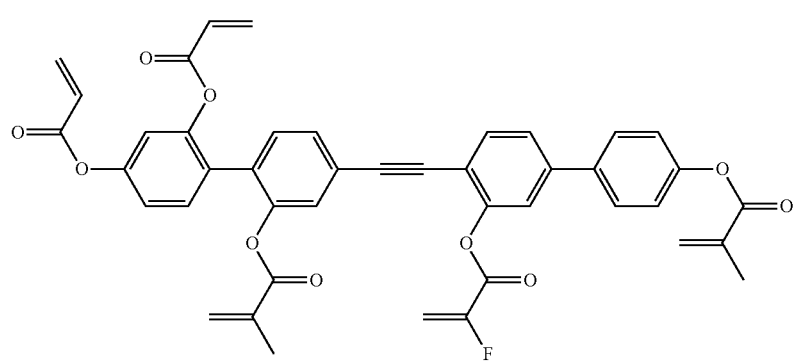
(1-656)
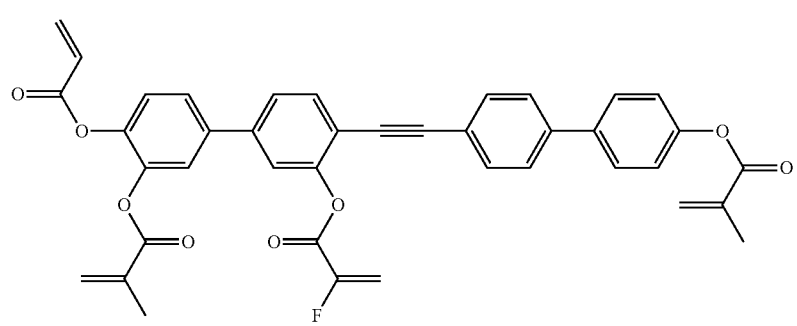
(1-657)
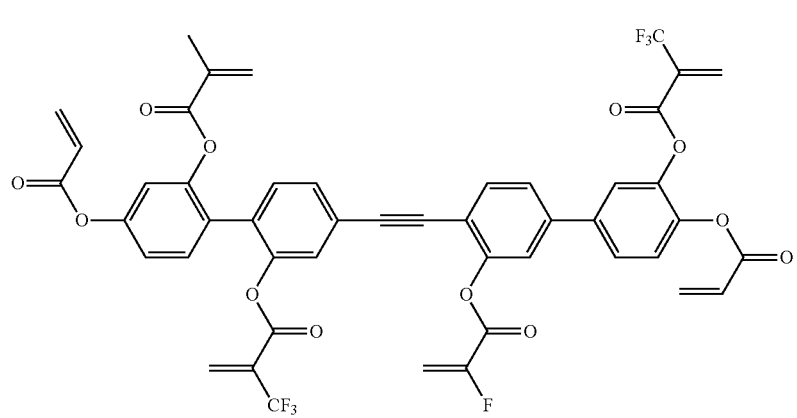

(1-658)
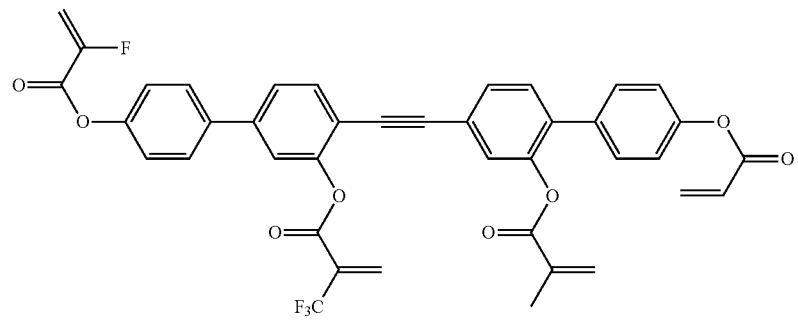
(1-659)
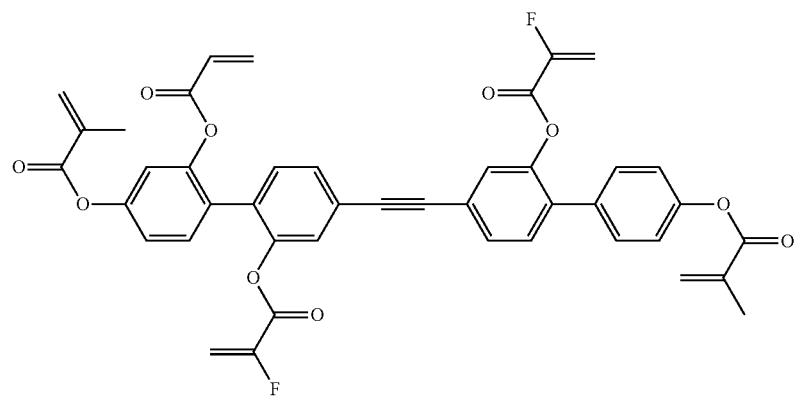
(1-660)
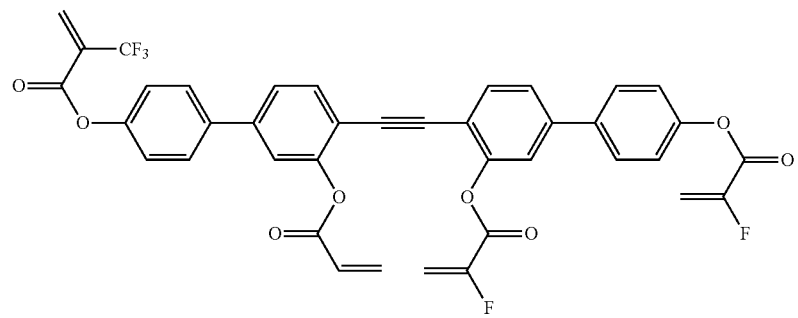
(1-661)
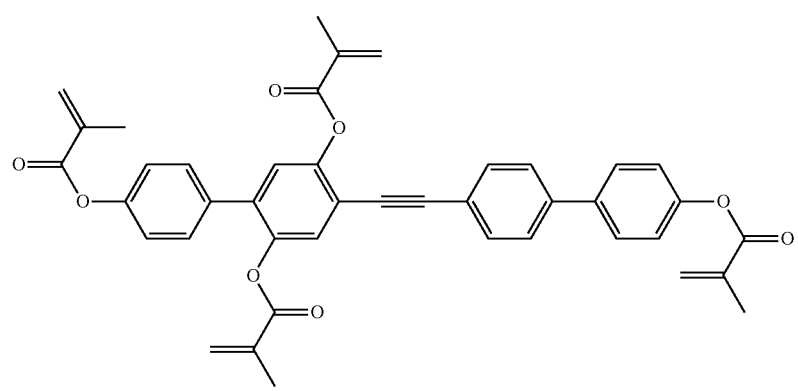

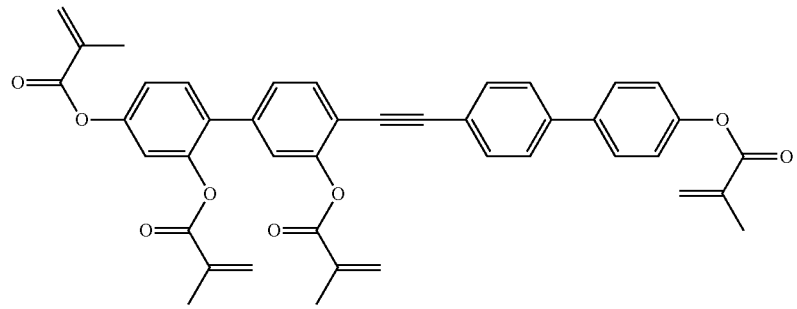
(1-662)
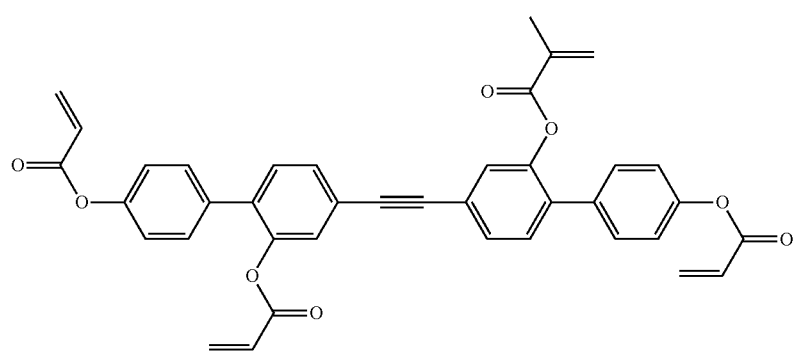
(1-663)
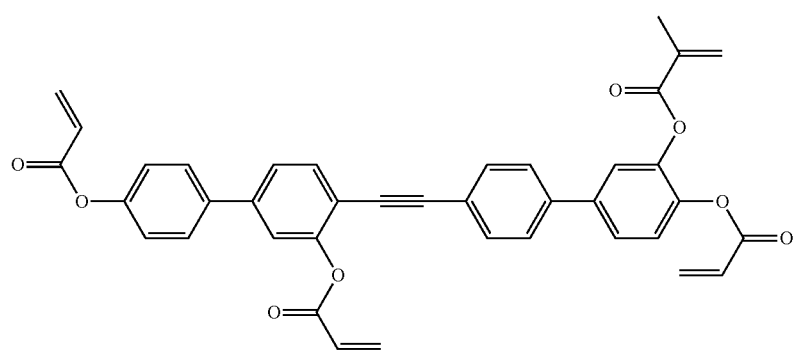
(1-664)
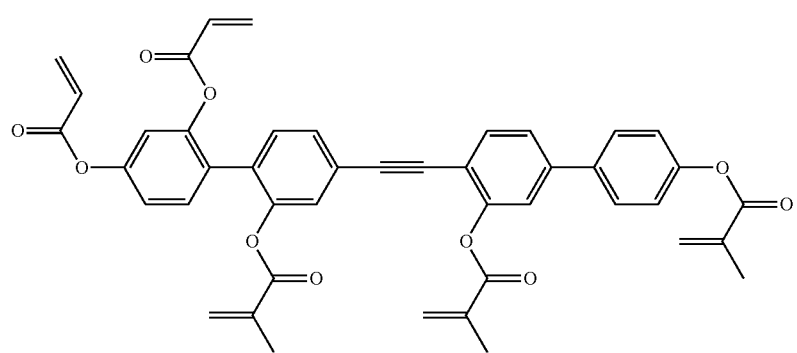
(1-665)

-continued
(1-666)
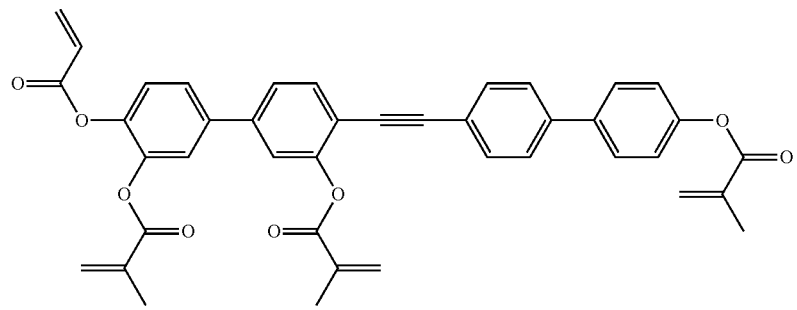
(1-667)
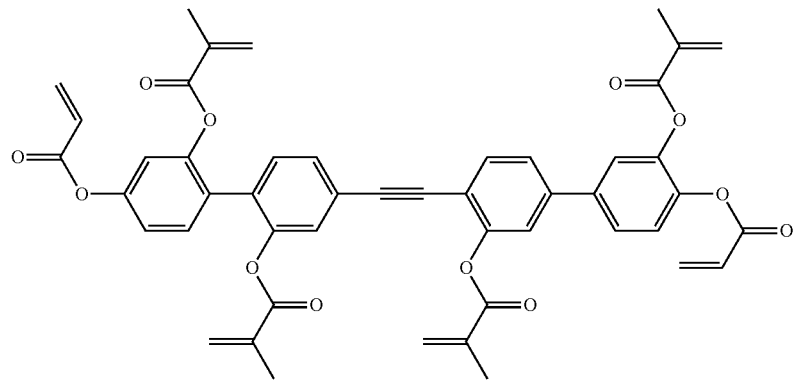
(1-668)
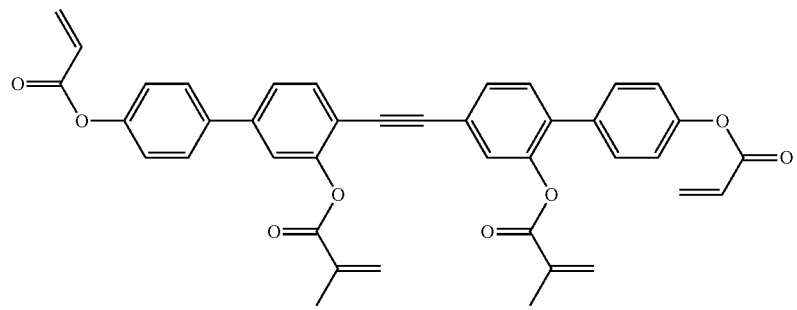
(1-669)
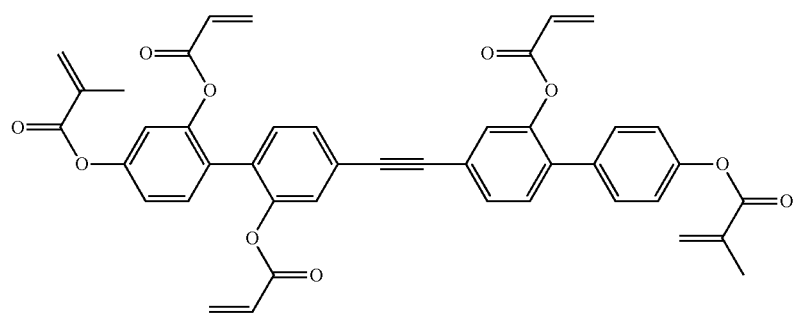
(1-670)
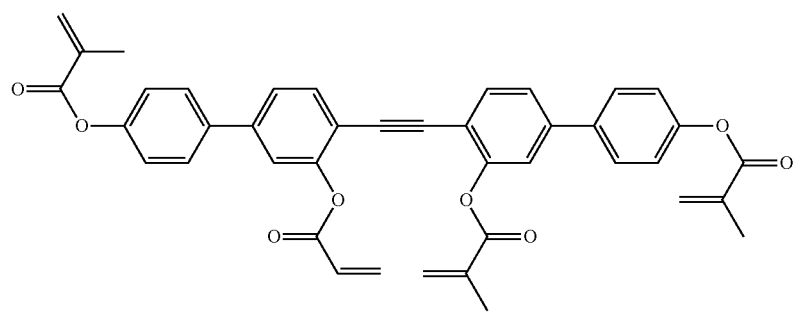

(1-671)
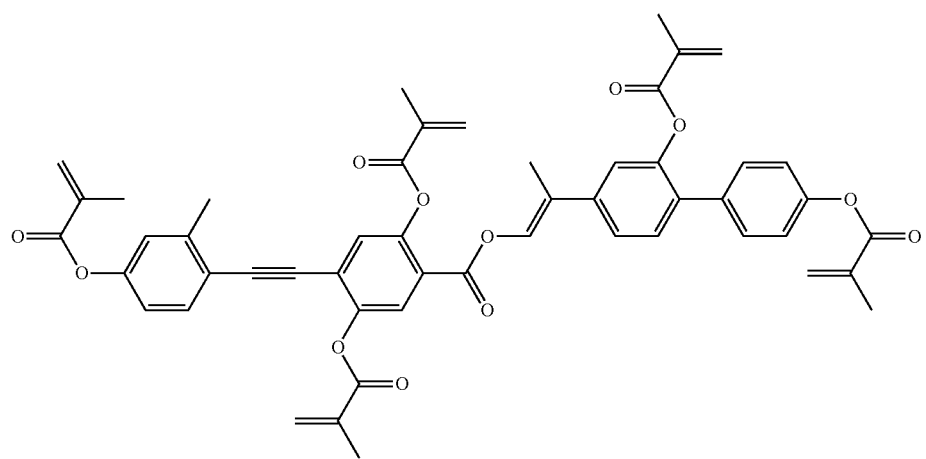
(1-672)
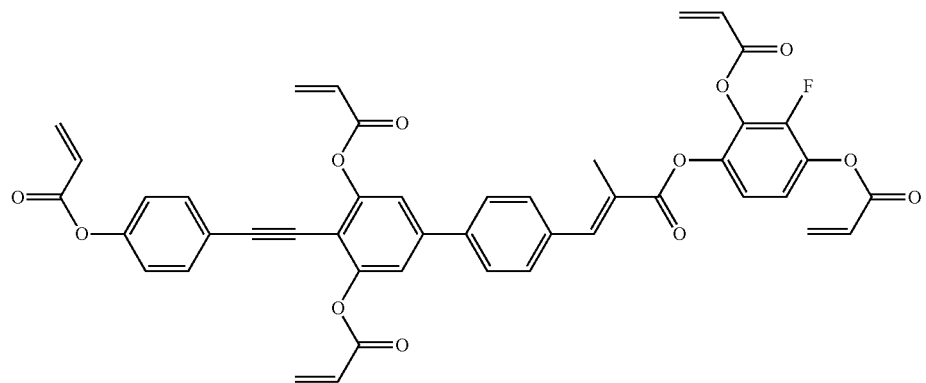
(1-673)
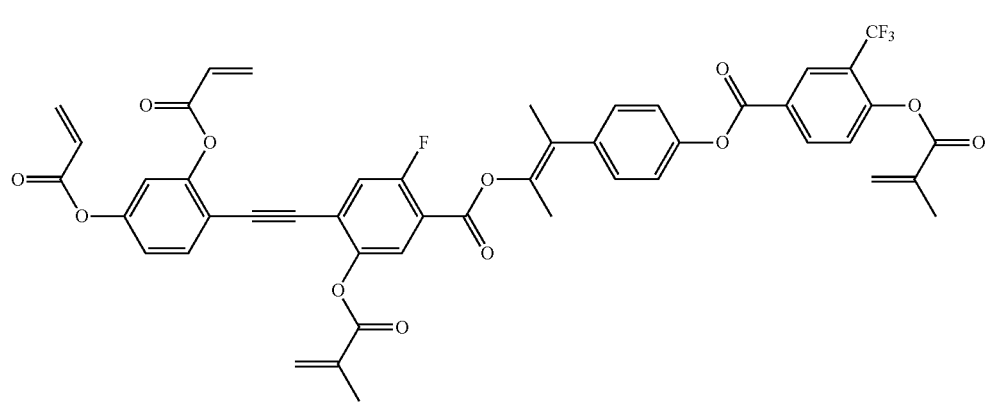

-continued
(1-674)
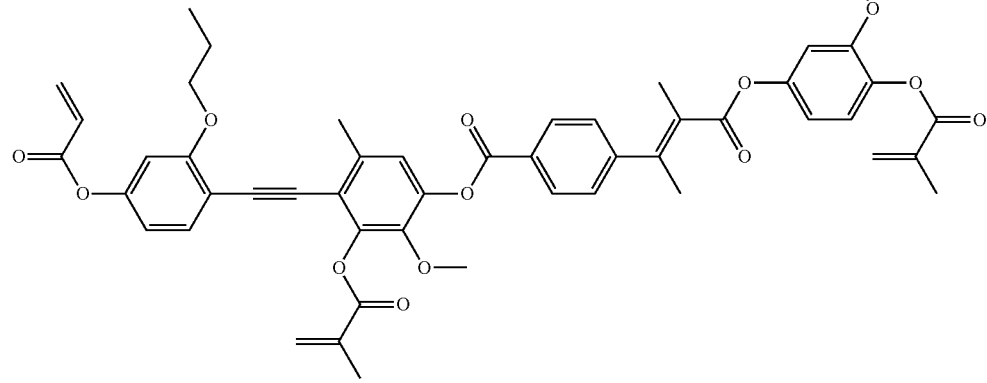
(1-675)
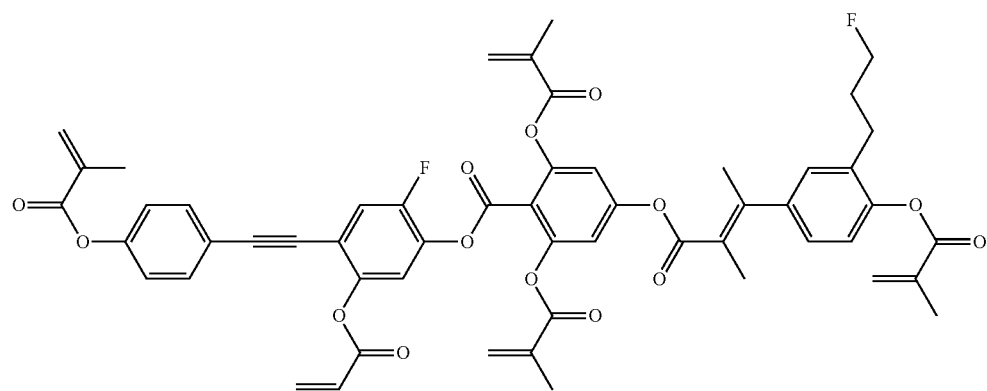
(1-676)
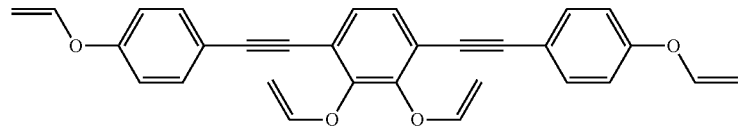
(1-677)
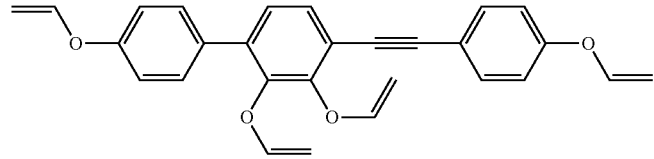
(1-678)
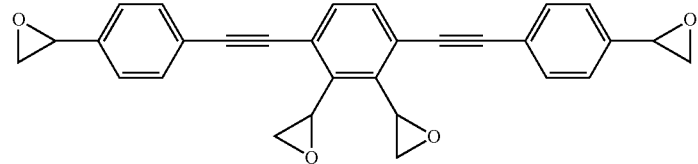
(1-679)
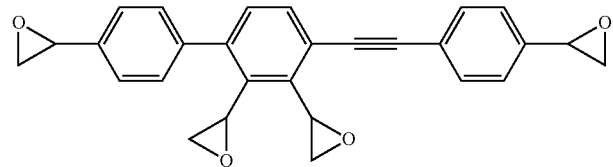

(1-680)
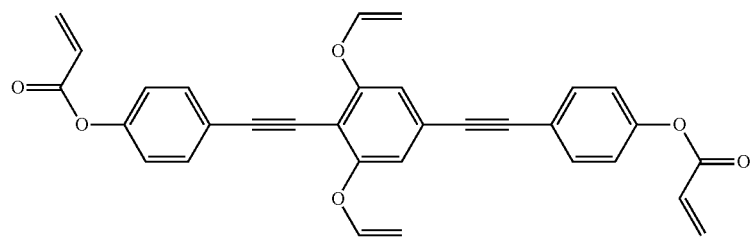
(1-681)
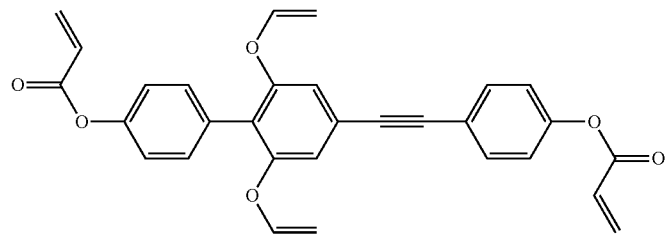
(1-682)
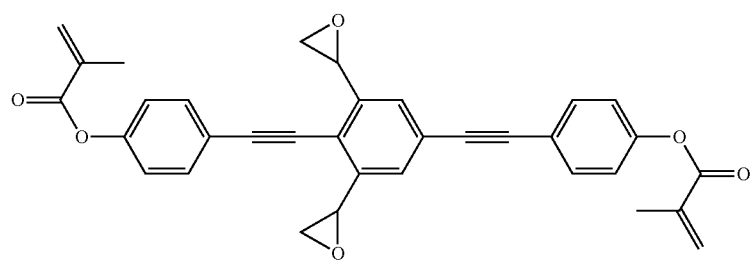
(1-683)
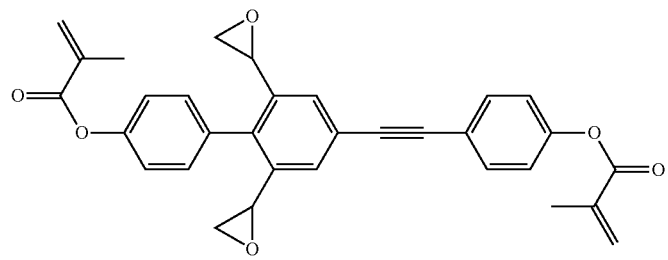
(1-684)
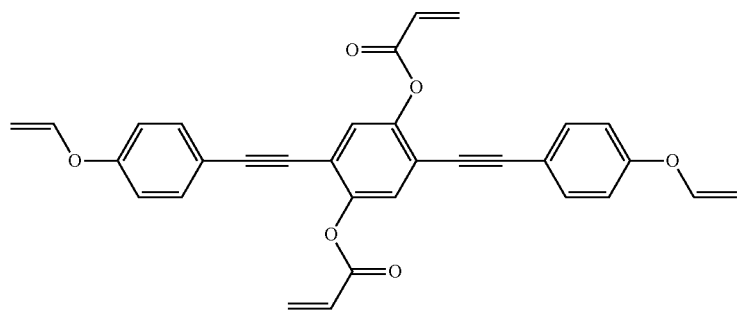
(1-685)
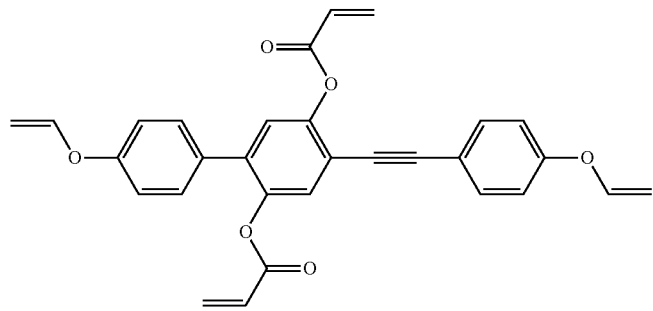

-continued
(1-686)
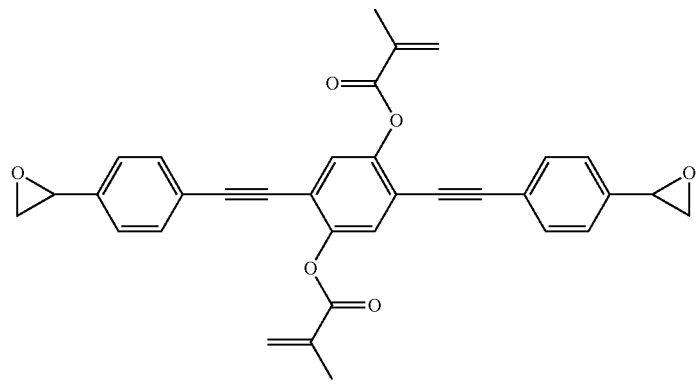
(1-687)
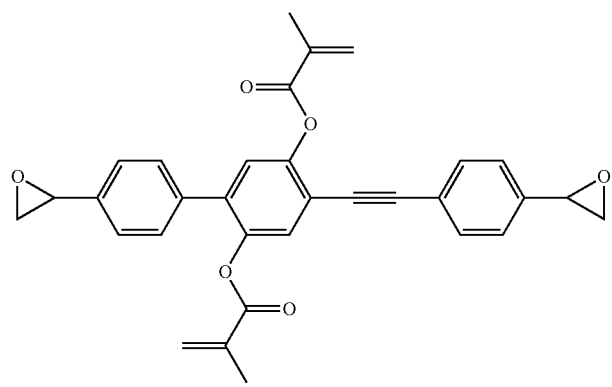
(1-688)
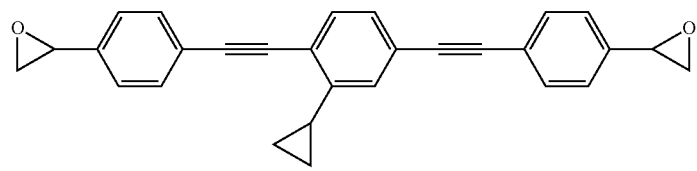
(1-689)
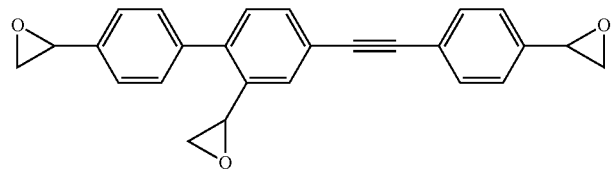
(1-690)
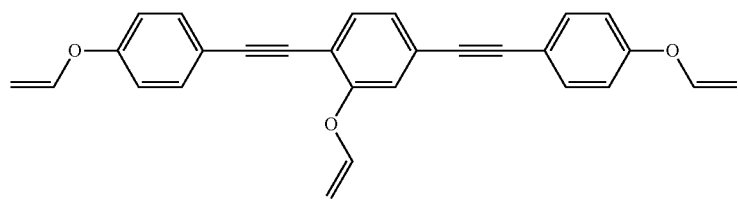
(1-691)
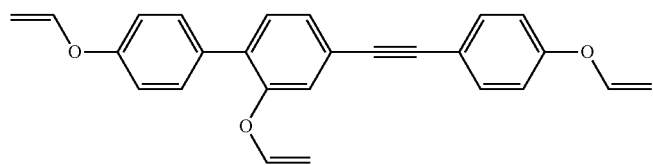

-continued

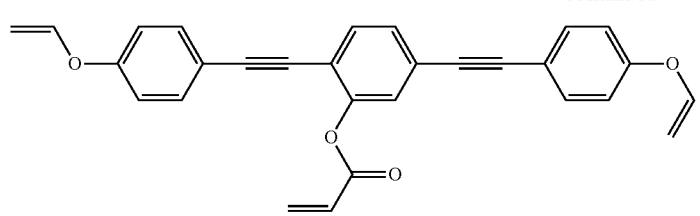
(1-692)

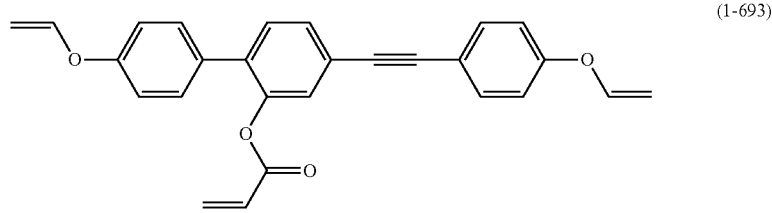
(1-693)

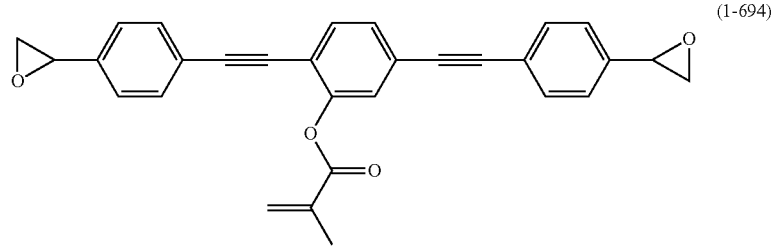
(1-694)

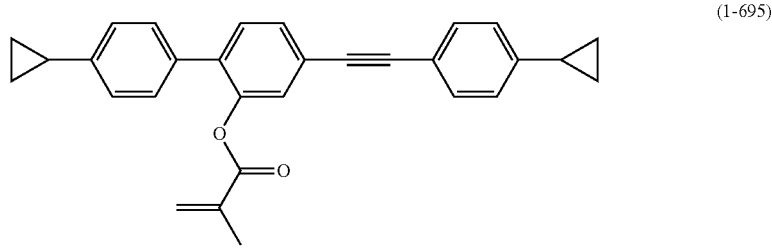
(1-695)

Comparative Example 1

For comparison, compound (R-1) was prepared according to the scheme described below.

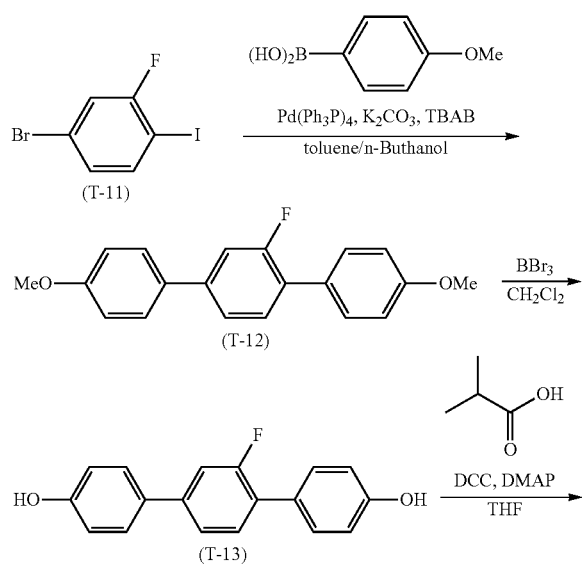

-continued

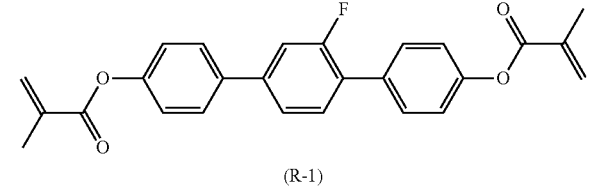
(R-1)

First Step: Synthesis of Compound (T-12)

A mixture of compound (T-11) (40.0 g), 4-methoxyphenylboronic acid (42.42 g), 5% Pd—C (1.2 g; made by N.E. Chemcat Corporation), tetrabutylammonium bromide (17.4 g), potassium carbonate (73.49 g) and a mixed solvent (360 mL; toluene: 2-propanol:water=1:1:1 in a volume ratio) was heated under reflux. After 32 hours, Pd—C in the resulting mixture was filtered off, and the filtrate was subjected to extraction with toluene. The resulting extract was washed with saturated brine, and concentrated and dried under reduced pressure. The resulting residue was purified by silica gel chromatography (toluene: ethyl acetate=19:1 in a volume ratio) to give a colorless crystal of compound (T-12; 3 g, yield; 7.2%).

Second Step: Synthesis of Compound (T-13)

Compound (T-12) (8.62 g) was dissolved into methylene chloride (100 mL), and then boron tribromide (70.0 mL; 1.0 mol/L of methylene chloride solution) was added dropwise thereto in the temperature range of −20° C. or lower, and the resulting mixture was stirred at room temperature overnight. The resulting reaction mixture was poured into ice water (100 mL) and subjected to extraction with methylene chloride (100 mL). The resulting extract was washed with saturated brine, dried and concentrated under reduced pressure. The resulting residue was purified by silica gel chromatography (ethyl acetate) to give a brown crystal of compound (T-13; 4.2 g, yield: 53.6%).

Third Step: Synthesis of Compound (R-1)

A reaction of compound (T-13) (4.0 g) was performed in a manner similar to the reaction in Example 1 to give a colorless crystal of comparative compound (R-1).

$^1$H-NMR (δ ppm; $CDCl_3$): 7.64-7.64 (m, 4H), 7.50 (dd, J=8.1, 8.0 Hz, 1H), 7.43 (dd, J=8.0, 1.7 Hz, 1H), 7.38 (dd, J=11.9, 1.7 Hz, 1H), 7.23 (d, J=8.5 Hz 2H×2), 6.38 (s, 1H×2), 5.79-5.78 (m, 1H×2), 2.09 (s, 3H×2). $^{19}$F-NMR (δ ppm; $CDCl_3$): −118.10 (dd, J=11.9, 8.1 Hz, 1F).

Physical properties of comparative compound (R-1) were as described below. Melting point: 179.11° C., polymerization starting temperature: 184.15° C.

Comparative Experiment

Reactivity in polymerization between compound (1-108) and comparative compound (R-1) was compared. The reactivity was evaluated by an amount of unreacted polymerizable compound.

Liquid crystal composition A described below was used in Comparative Experiment.

| | | |
|---|---|---|
| 3-H2B(2F,3F)-O2 | (9-4) | 18% |
| 5-H2B(2F,3F)-O2 | (9-4) | 17% |
| 3-HH1OCro(7F,8F)-5 | (13-6) | 6% |
| 3-HBB(2F,3F)-O2 | (10-7) | 10% |
| 4-HBB(2F,3F)-O2 | (10-7) | 6% |
| 5-HBB(2F,3F)-O2 | (10-7) | 6% |
| 2-HH-3 | (2-1) | 14% |
| 3-HH-4 | (2-1) | 8% |
| 3-HHB-1 | (3-1) | 5% |
| 3-HHB-3 | (3-1) | 6% |
| 3-HHB-O1 | (3-1) | 4% |

To the liquid crystal composition A, a polymerizable compound was added at a ratio of 0.3% by weight based on the weight of liquid crystal composition A. The resulting composition was irradiated with ultraviolet light at 75 mW/cm$^2$ for 200 seconds (15,000 mJ). A mercury-xenon lamp, EXECURE4000-D, made by HOYA CANDEO OPTRONICS Corporation was used for irradiation with ultraviolet light. An amount of polymerizable compound remained in the composition was measured by HPLC. The results obtained by irradiating the composition with ultraviolet light for 400 seconds (30,000 mJ) are also simultaneously summarized in Table 1. In a row of "unreacted matter," a ratio of the unreacted polymerizable compound to the polymerizable compound added was shown. An expression "2% or less" indicates that no detection was allowed for the unreacted polymerizable compound. Table 1 shows that the unreacted matter remained therein in comparative compound (R-1), but the compound of the invention was consumed by polymerization. Therefore, the compound of the invention can be concluded to be further excellent from a view point of high reactivity.

TABLE 1

Amount of unreacted polymerizable compound

| Polymerizable compound | Structural formula | Unreacted matter (% by weight) | |
|---|---|---|---|
| | | 15,000mJ | 30,000mJ |
| Compound (1-108) | | 15% | 2% or less |
| Comparative compound (R-1) | | 41% | 26% |

2. Example of Polymerizable Composition

Compounds described in Examples were expressed using symbols based on definitions in Table 2 below. In Table 2, a configuration of 1,4-cyclohexylene is trans. A parenthesized number next to a symbolized compound in Examples corresponds to the number of the compound. A symbol (-) means any other liquid crystal compound. A content (percentage) of a liquid crystal compound is expressed in terms of weight percent (% by weight) based on the weight of the liquid crystal composition. A ratio of an additive such as a polymerizable compound is expressed in terms of weight percent (% by weight) based on the weight of the liquid crystal composition in a manner similar to the ratio of the liquid crystal compounds. Values of physical properties of the liquid crystal composition were summarized in a last part. The physical properties were measured according to the methods described above, and measured values were directly described (without extrapolation).

TABLE 2

Method for Description of Compounds using Symbols
R—(A$_1$)—Z$_1$— . . . —Z$_n$—(A$_n$)—R'

| 1) Left-terminal Group R— | Symbol |
|---|---|
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |

| 2) Right-terminal Group —R' | Symbol |
|---|---|
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |

| 3) Bonding Group —Z$_n$— | Symbol |
|---|---|
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |

| 4) Ring Structure —A$_n$— | Symbol |
|---|---|
|  | H |
| 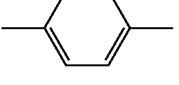 | B |
| 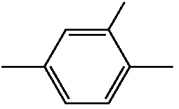 | B(F) |
| 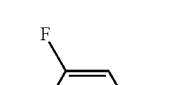 | B(2F) |

TABLE 2-continued

Method for Description of Compounds using Symbols
R—(A$_1$)—Z$_1$— . . . —Z$_n$—(A$_n$)—R'

| | |
|---|---|
| 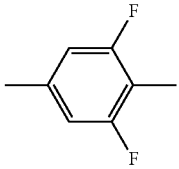 | B(F,F) |
| 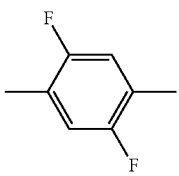 | B(2F,5F) |
| 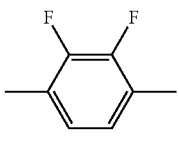 | B(2F,3F) |
| 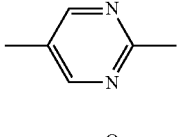 | Py |
| 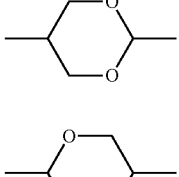 | G |
| 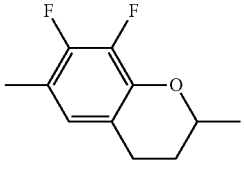 | Dh |
| 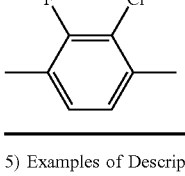 | Cro |
| 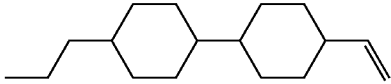 | B(2F,3CL) |

5) Examples of Description

Example 1 3-HH—V

TABLE 2-continued

Method for Description of Compounds using Symbols
$R-(A_1)-Z_1-\ldots-Z_n-(A_n)-R'$ Example 2  3-BB(F,F)XB(F,F)—F

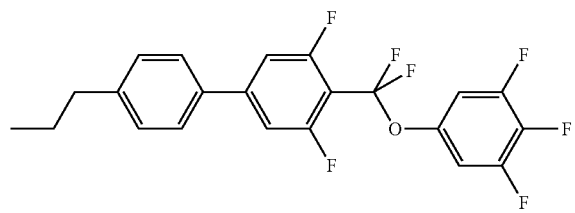 [SMILES: CCCc1ccc(-c2cc(F)c(C(F)(F)Oc3cc(F)c(F)c(F)c3)c(F)c2)cc1]

Example 3  3-HH-4

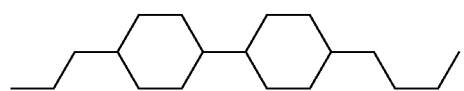

Example 4  3-HBB—(2F,3F)—O2

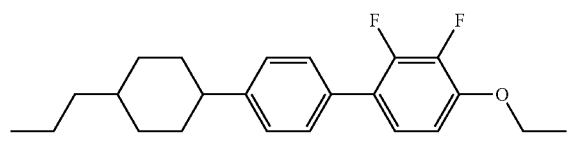 [SMILES: CCCC1CCC(c2ccc(-c3ccc(OCC)c(F)c3F)cc2)CC1]

Example 2

| | | |
|---|---|---|
| 3-HB-O2 | (2-5) | 10% |
| 5-HB-CL | (5-2) | 10% |
| 3-HBB(F,F)-F | (6-24) | 10% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 10% |
| 5-PyBB-F | (6-80) | 10% |
| 5-HBB(F)B-2 | (4-5) | 10% |
| 5-HBB(F)B-3 | (4-5) | 10% |

To the composition described above, compound (1-108) was added at a ratio of 0.2%.

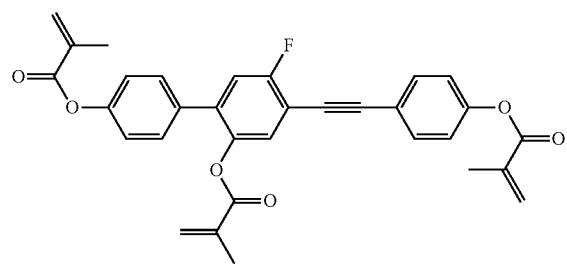

(1-108)

NI=100.8° C.; Δn=0.192; Δ∈=8.2; η=41.0 mPa·s.

Example 3

| | | |
|---|---|---|
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 5% |
| 5-HHEB-F | (6-10) | 5% |
| 2-HHB(F)-F | (6-2) | 5% |
| 3-HHB(F)-F | (6-2) | 7% |
| 5-HHB(F)-F | (6-2) | 7% |
| 3-HHB(F,F)-F | (6-3) | 5% |

To the composition described above, compound (1-108) was added at a ratio of 0.3%.
NI=103.7° C.; Δn=0.102; Δ∈=4.5; η=19.0 mPa·s.

Example 4

| | | |
|---|---|---|
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 10% |
| 3-HBB(F,F)-F | (6-24) | 19% |
| 5-HBB(F,F)-F | (6-24) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

To the composition described above, compound (1-108) was added at a ratio of 0.2%.
NI=98.8° C.; Δn=0.115; Δ∈=8.9; η=34.8 mPa·s.

Example 5

| | | |
|---|---|---|
| 5-HB-CL | (5-2) | 11% |
| 3-HH-4 | (2-1) | 8% |
| 3-HHB-1 | (3-1) | 5% |
| 3-HHB(F,F)-F | (6-3) | 8% |
| 3-HBB(F,F)-F | (6-3) | 20% |
| 5-HBB(F,F)-F | (6-3) | 15% |
| 3-HHEB(F,F)-F | (6-12) | 10% |
| 4-HHEB(F,F)-F | (6-12) | 3% |
| 5-HHEB(F,F)-F | (6-12) | 4% |
| 2-HBEB(F,F)-F | (6-39) | 5% |
| 3-HBEB(F,F)-F | (6-39) | 5% |
| 5-HBEB(F,F)-F | (6-39) | 3% |
| 3-HHBB(F,F)-F | (7-6) | 3% |

To the composition described above, compound (1-108) was added at a ratio of 0.1%.
NI=76.5° C.; Δn=0.101; Δ∈=9.0; η=21.9 mPa·s.

Example 6

| | | |
|---|---|---|
| 5-HB-CL | (5-2) | 3% |
| 7-HB(F)-F | (5-3) | 7% |
| 3-HH-4 | (2-1) | 11% |
| 3-HH-EMe | (2-2) | 23% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |

| 2-H2GB(F,F)-F | (6-106) | 4% |
| 3-H2GB(F,F)-F | (6-106) | 5% |
| 5-GHB(F,F)-F | (6-109) | 5% |

To the composition described above, Compound (1-108) was added at a ratio of 0.2%.
NI=79.9° C.; Δn=0.063; Δ∈=5.3; η=18.3 mPa·s.

Example 7

| 3-HB-O1 | (2-5) | 15% |
| 3-HH-4 | (2-1) | 5% |
| 3-HH-V | (2-1) | 10% |
| 3-HB(2F,3F)-O2 | (9-1) | 10% |
| 5-HB(2F,3F)-O2 | (9-1) | 10% |
| 2-HHB(2F,3F)-1 | (10-1) | 10% |
| 3-HHB(2F,3F)-1 | (10-1) | 10% |
| 3-HHB(2F,3F)-O2 | (10-1) | 12% |
| 5-HHB(2F,3F)-O2 | (10-1) | 12% |
| 3-HHB-1 | (6-1) | 6% |

To the composition described above, compound (1-108) was added at a ratio of 0.2%.
NI=84.5° C.; Δn=0.084; Δ∈=−2.9; η=31.7 mPa·s.

Example 8

| 3-HH-4 | (2-1) | 8% |
| 3-HH-V | (2-1) | 5% |
| 5-HB-O2 | (2-5) | 5% |
| 3-H2B(2F,3F)-O2 | (9-4) | 18% |
| 5-H2B(2F,3F)-O2 | (9-4) | 16% |
| 2-HHB(2F,3CL)-O2 | (10-12) | 2% |
| 3-HHB(2F,3CL)-O2 | (10-12) | 3% |
| 4-HHB(2F,3CL)-O2 | (10-12) | 2% |
| 5-HHB(2F,3CL)-O2 | (10-12) | 2% |
| 3-HBB(2F,3F)-O2 | (10-7) | 9% |
| 5-HBB(2F,3F)-O2 | (10-7) | 9% |
| V-HHB-1 | (3-1) | 6% |
| 3-HHB-3 | (3-1) | 6% |
| 3-HHEBH-3 | (4-6) | 3% |
| 3-HHEBH-4 | (4-6) | 3% |
| 3-HHEBH-5 | (4-6) | 3% |

To the composition described above, compound (1-108) was added at a ratio of 0.3%.
NI=93.9° C.; Δn=0.098; Δ∈=−3.5; η=26.3 mPa·s.

Example 9

| 2-HH-5 | (2-1) | 3% |
| 3-HH-4 | (2-1) | 15% |
| 3-HH-5 | (2-1) | 4% |
| 3-HB-O2 | (2-5) | 7% |
| 5-HB-O2 | (2-5) | 5% |
| 3-H2B(2F,3F)-O2 | (9-4) | 15% |
| 5-H2B(2F,3F)-O2 | (9-4) | 15% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 9% |
| 5-HBB(2F,3F)-O2 | (10-7) | 9% |
| 3-HHB-1 | (3-1) | 3% |
| 3-HHB-3 | (3-1) | 4% |
| 3-HHB-O1 | (3-1) | 3% |

To the composition described above, compound (1-108) was added at a ratio of 0.2%.
NI=76.3° C.; Δn=0.093; Δ∈=−4.0; η=19.5 mPa·s.

Example 10

| 2-HH-3 | (2-1) | 16% |
| 2-HH-5 | (2-1) | 5% |
| 3-HH-4 | (2-1) | 9% |
| 1-BB-3 | (2-8) | 9% |
| 3-HB-O2 | (2-5) | 2% |
| 3-BB(2F,3F)-O2 | (9-3) | 9% |
| 5-BB(2F,3F)-O2 | (9-3) | 6% |
| 2-HH1OB(2F,3F)-O2 | (10-5) | 13% |
| 3-HH1OB(2F,3F)-O2 | (10-5) | 21% |
| 3-HHB-1 | (3-1) | 5% |
| 3-HHB-O1 | (3-1) | 3% |
| 5-B(F)BB-2 | (3-8) | 2% |

To the composition described above, compound (1-108) was added at a ratio of 0.2%.
NI=75.1° C.; Δn=0.098; Δ∈=−3.2; η=15.5 mPa·s.

Example 11

| 2-HH-3 | (2-1) | 16% |
| 7-HB-1 | (2-5) | 10% |
| 5-HB-O2 | (2-5) | 8% |
| 3-HB(2F,3F)-O2 | (9-1) | 17% |
| 5-HB(2F,3F)-O2 | (9-1) | 16% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 2% |
| 3-HH1OCro(7F,8F)-5 | (13-6) | 5% |
| 3-HHB-1 | (3-1) | 4% |
| 5-HBB(F)B-2 | (4-5) | 6% |
| 5-HBB(F)B-3 | (4-5) | 10% |

To the composition described above, compound (1-108) was added at a ratio of 0.3%.
NI=72.7° C.; Δn=0.098; Δ∈=−2.5; η=21.2 mPa·s.

Example 12

| 3-HH-4 | (2-1) | 9% |
| 1-BB-3 | (2-8) | 10% |
| 3-HH-V | (2-1) | 20% |
| 3-BB(2F,3F)-O2 | (9-3) | 13% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 5-B(F)BB-2 | (3-8) | 6% |

To the composition described above, compound (1-108) was added at a ratio of 0.2%.
NI=76.7° C.; Δn=0.106; Δ∈=−3.0; η=15.9 mPa·s.

Example 13

| 1V2-BEB(F,F)-C | (8-15) | 8% |
| 3-HB-C | (8-1) | 20% |
| 2-BTB-1 | (2-10) | 10% |
| 5-HH-VFF | (2-1) | 26% |
| 3-HHB-1 | (3-1) | 4% |

-continued

| | | |
|---|---|---|
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 4% |
| 3-H2BTB-4 | (3-17) | 4% |

To the composition described above, compound (1-108) was added at a ratio of 0.1%.

NI=80.4° C.; Δn=0.134; Δ∈=8.1; η=13.7 mPa·s.

Example 14

| | | |
|---|---|---|
| 5-HB(F)B(F,F)XB(F,F)-F | (7-41) | 5% |
| 3-BB(F)B(F,F)XB(F,F)-F | (7-41) | 3% |
| 4-BB(F)B(F,F)XB(F,F)-F | (7-41) | 7% |
| 5-BB(F)B(F,F)XB(F,F)-F | (7-41) | 3% |
| 3-HH-V | (2-1) | 38% |
| 3-HH-V1 | (2-1) | 10% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 11% |
| 3-HHBB(F,F)-F | (7-6) | 3% |

To the composition described above, compound (1-108) was added at a ratio of 0.2%.

NI=82.9° C.; Δη=0.106; Δ∈=6.3; η=12.3 mPa·s.

Example 15

| | | |
|---|---|---|
| 3-GB(F)B(F,F)XB(F,F)-F | (7-57) | 5% |
| 5-HB(F)B(F,F)XB(F,F)-F | (7-41) | 4% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 5% |
| 3-HH-V | (2-1) | 37% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

To the composition described above, compound (1-108) was added at a ratio of 0.4%.

NI=83.4° C.; Δη=0.107; Δ∈=8.5; η=16.4 mPa·s.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal display device having a mode such as a PSA mode can be prepared by polymerizing a polymerizable composition containing polymerizable compound (1) and a liquid crystal composition. The device has a wide temperature range in which the device can be used, a short response time, a high voltage holding ratio, a low threshold voltage, a large contrast ratio and a long service life. Accordingly, compound (1) can be used for a liquid crystal projector, a liquid crystal television or the like. Compound (1) can be also used as a raw material of an optically anisotropic body.

What is claimed is:

1. A polymerizable composition, containing at least one compound selected from the group of compounds represented by formula (1) and at least one compound selected from the group of compounds represented by formulas (2) to (4):

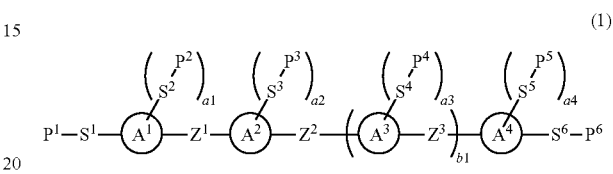

wherein, in formula (1), $P^1$, $P^2$, $P^3$, $P^4$, $P^5$ and $P^6$ are independently a polymerizable group;

$S^1$, $S^2$, $S^3$, $S^4$, $S^5$ and $S^6$ are independently a single bond or alkylene having 1 to 12 carbons, and in the alkylene, at least one of —$CH_2$— may be replaced by —O—, —COO— or —OCO—, at least one of —$CH_2CH_2$— may be replaced by —CH=CH—, and in the groups, at least one of hydrogen may be replaced by halogen;

a1, a3 and a4 are independently 0, 1, 2, 3 or 4, a2 is 1, 2, 3 or 4, a sum of a1, a2, a3 and a4 is 3 to 10, in which either or both of -$S^1$-$P^1$ and -$S^6$-$P^6$ may be hydrogen;

ring $A^1$, ring $A^2$, ring $A^3$ and ring $A^4$ are independently a divalent group derived from benzene, anthracene, pyrimidine or pyridine, and in the divalent group, at least one of hydrogen may be replaced by halogen, alkyl having 1 to 12 carbons, or alkyl having 1 to 12 carbons in which at least one of hydrogen is replaced by halogen, and ring $A^2$ and ring $A^3$ may be independently a divalent group derived from cyclohexane, cyclohexene, tetrahydropyran or dioxane;

$Z^1$, $Z^2$ and $Z^3$ are independently a single bond or alkylene having 1 to 12 carbons, and in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$), —C($CH_3$)=C($CH_3$)— or —C≡C—, and in the groups, at least one of hydrogen may be replaced by halogen, and at least one of $Z^1$, $Z^2$ and $Z^3$ is —C≡C—, wherein when the number of —C≡C— is two or more, or when at least one of $Z^1$, $Z^2$ and $Z^3$ is a single bond, —CH=CH—, —COO—, or —OCO—, $S^1$ and $S^6$ are single bonds; and b1 is 0 or 1;

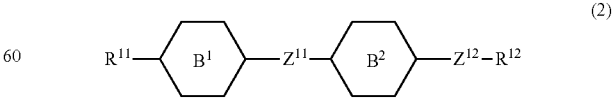

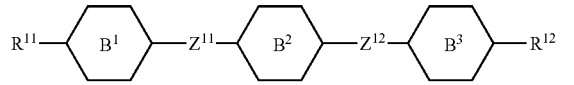

(4)

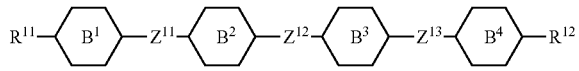

wherein, in formulas (2) to (4),
$R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —$CH_2CH_2$—, —CH=CH—, —C≡C— or —COO—.

2. The polymerizable composition according to claim 1, further containing at least one compound selected from the group of compounds represented by formulas (5) to (7):

(5)

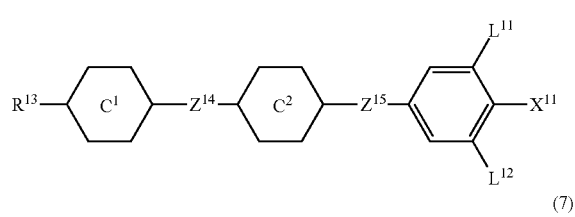

(6)

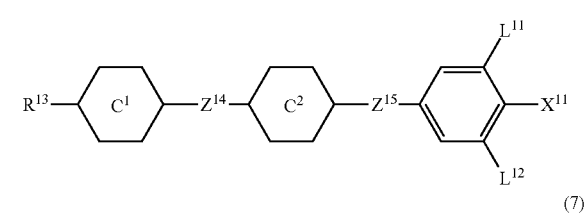

(7)

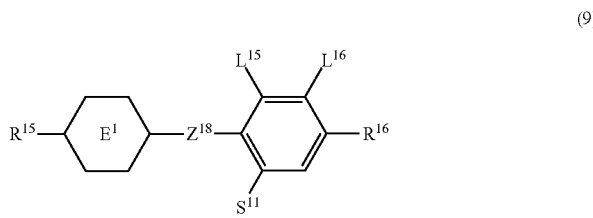

wherein, in formulas (5) to (7),
$R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
$Z^{14}$, $Z^{15}$ and $Z^{16}$ are independently a single bond, —$CH_2CH_2$—, —CH=CH—, —COO—, —$CF_2O$—, —$OCF_2$—, —$CH_2O$— or —$(CH_2)_4$—; and
$L^{11}$ and $L^{12}$ are independently hydrogen or fluorine.

3. The polymerizable composition according to claim 1, further containing at least one compound selected from the group of compounds represented by formula (8):

(8)

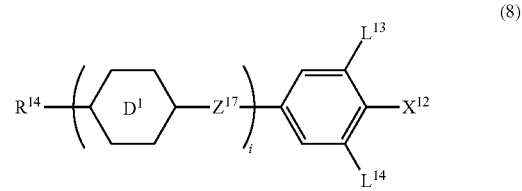

wherein, in formula (8),
$R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$X^{12}$ is —C≡N or —C≡C—C≡N;
ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
$Z^{17}$ is a single bond, —$CH_2CH_2$—, —C≡C—, —COO—, —$CF_2O$—, —$OCF_2$— or —$CH_2O$—;
$L^{13}$ and $L^{14}$ are independently hydrogen or fluorine; and
i is 1, 2, 3 or 4.

4. The polymerizable composition according to claim 1, further containing at least one compound selected from the group of compounds represented by formulas (9) to (15):

(9)

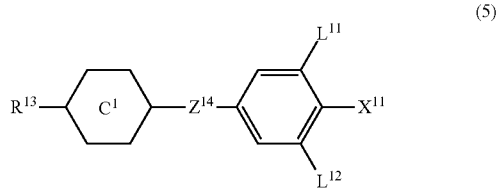

(10)

(11)

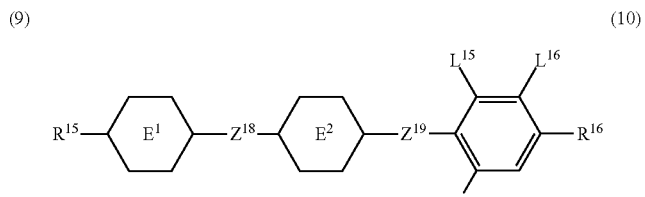

(12)

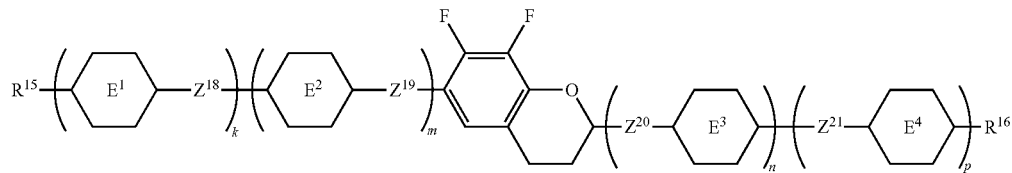
(13)

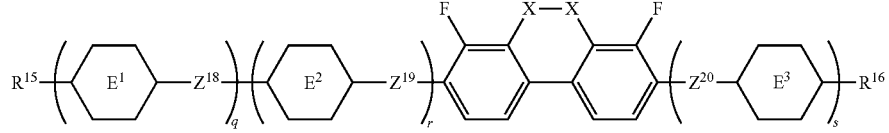
(14)

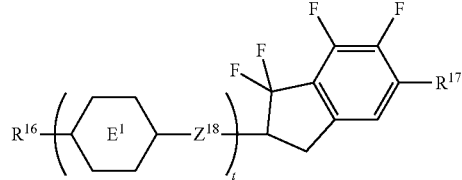
(15)

wherein, in formulas (9) to (15),
- $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
- $R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
- ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
- ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;
- $Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;
- $L^{15}$ and $L^{16}$ are independently fluorine or chlorine;
- $S^{11}$ is hydrogen or methyl;
- X is —CHF— or —$CF_2$—; and
- j, k, m, n, p, q, r and s are independently 0 or 1, a sum of k, m, n and p is 1 or 2, a sum of q, r and s is 0, 1, 2 or 3, and t is 1, 2 or 3.

5. A liquid crystal composite, formed by polymerization of the polymerizable composition according to claim 1.

6. A liquid crystal display device, including the polymerizable composition according to claim 1.

7. A polymerizable compound represented by formula (1-1):

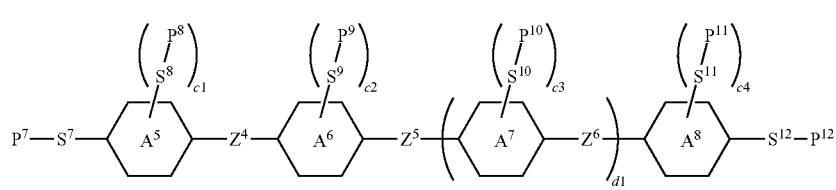
(1-1)

wherein, in formula (1-1),
- $P^7$, $P^8$, $P^9$, $P^{10}$, $P^{11}$ and $P^{12}$ are independently a polymerizable group;
- $S^7$, $S^8$, $S^9$, $S^{10}$, $S^{11}$ and $S^{12}$ are independently a single bond or alkylene having 1 to 6 carbons, and in the alkylene, one or two of —$CH_2$— may be replaced by —O—, —COO— or —OCO—, one or two of —$CH_2$—$CH_2$— may be replaced by —CH=CH—, and in the groups, at least one of hydrogen may be replaced by fluorine or chlorine;
- c1, c3, and c4 are independently 0, 1 or 2, c2 is 1 or 2, and a sum of c1, c2, c3 and c4 is 3 to 6;
- ring $A^5$, ring $A^6$, ring $A^7$ and ring $A^8$ are independently 1,4-phenylene, pyrimidine-2,5-diyl or pyridine-2,5-diyl, and in the rings, at least one of hydrogen may be replaced by fluorine, chlorine, alkyl having 1 to 12 carbons, or alkyl having 1 to 12 carbons in which at least one of hydrogen is replaced by fluorine or chlorine, ring $A^6$ and ring $A^7$ may be independently 1,4-cyclohexylene, 1,4-cyclohexenylene, tetrahydropyran-2,5-diyl or 1,3-dioxane-2,5-diyl;
- $Z^4$, $Z^5$ and $Z^6$ are independently a single bond or alkylene having 1 to 6 carbons, and in the alkylene, one or two of —$CH_2$— may be replaced by —O—, —CO—, —COO— or —OCO—, one or two of —$CH_2$—$CH_2$— may be replaced by —CH=CH—, —C($CH_3$)=CH—, —CH=C($CH_3$)—, —C($CH_3$)=C($CH_3$)— or —C≡C—, and in the groups, at least one of hydrogen may be replaced by fluorine or chlorine, and at least one of $Z^4$, $Z^5$ and $Z^6$ is —C≡C—, wherein when the number of —C≡C— is two or more, or when at least one of $Z^4$, $Z^5$ and $Z^6$ is a single bond, —CH=CH—, —COO—, or —OCO—, $S^7$ and $S^{12}$ are single bonds; and d1 is 0 or 1.

8. The polymerizable compound according to claim 7, represented by formula (1-2) or (1-3):

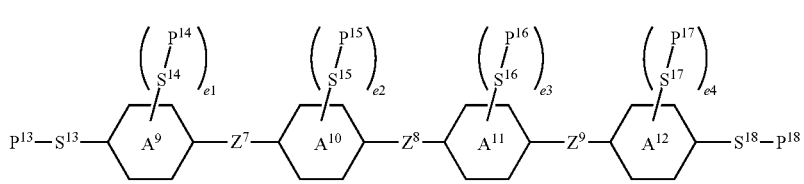

(1-2)

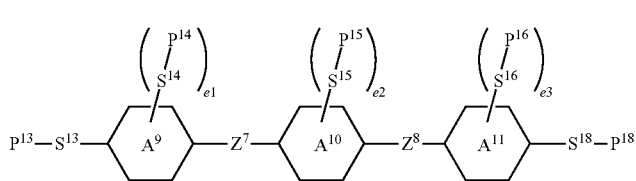

(1-3)

wherein, in formula (1-2) and formula (1-3),
- $P^{13}$, $P^{14}$, $P^{15}$, $P^{16}$, $P^{17}$ and $P^{18}$ are independently —OCO-($M^1$)C=CH($M^2$), vinyloxy or oxiranyl, in which $M^1$ and $M^2$ are independently hydrogen, fluorine, methyl or trifluoromethyl;
- $S^{13}$, $S^{14}$, $S^{15}$, $S^{16}$, $S^{17}$ and $S^{18}$ are independently a single bond or alkylene having 1 to 6 carbons, and in the alkylene, one of —$CH_2$— may be replaced by —O—, —COO— or —OCO—, one of —$CH_2$—$CH_2$— may be replaced by —CH=CH—, and in the groups, at least one of hydrogen may be replaced by fluorine or chlorine;
- e1, e3 and e4 are independently 0, 1 or 2, e2 is 1 or 2, and a sum of e1, e2, e3 and e4 is 3 to 6;
- ring $A^9$, ring $A^{10}$, ring $A^{11}$ and ring $A^{12}$ are independently 1,4-phenylene, pyrimidine-2,5-diyl or pyridine-2,5-diyl, and in the rings, at least one of hydrogen may be replaced by fluorine, chlorine, alkyl having 1 to 6 carbons, or alkyl having 1 to 6 carbons in which at least one of hydrogen is replaced by fluorine or chlorine;
- $Z^7$, $Z^8$ and $Z^9$ are independently a single bond, alkylene having 1 to 6 carbons, —CO—, —$CH_2$O—, —$OCH_2$—, —COO—, —OCO—, —CH=CH—, —C($CH_3$)=CH—, —CH=C($CH_3$)—, —C($CH_3$)=C($CH_3$)—, —C≡C—, —CO—CH=CH—, —CH=CH—CO—, —CH=CH—$CH_2$O—, —$OCH_2$—CH=CH—, —CH=CH—$OCH_2$—, —$CH_2$O—CH=CH—, —CH=CH—COO—, —OCO—CH=CH—, —CH=CH—OCO—, —COO—CH=CH—, —C($CH_3$)=CH—COO—, —OCO—CH=C($CH_3$)—, —C($CH_3$)=CH—OCO—, —COO—CH=C($CH_3$)—, —CH=C($CH_3$)—COO—, —OCO—($CH_3$)C=CH—, —CH=C($CH_3$)—OCO—, —COO—($CH_3$)C=CH—, —C($CH_3$)=C($CH_3$)—COO— or —OCO—C($CH_3$)=C($CH_3$)—, and in the groups, at least one of hydrogen may be replaced by fluorine or chlorine, in which, in formula (1-2), at least one of $Z^7$, $Z^8$ and $Z^9$ is —C≡C—, and in formula (1-3), at least one of $Z^7$ and $Z^8$ is —C≡C—, wherein when the number of —C≡C— is two or more, or when at least one of $Z^7$, $Z^8$ and $Z^9$ is a single bond, —CH=CH—, —COO—, or —OCO—, $S^{13}$ and $S^{18}$ are single bonds.

9. The polymerizable compound according to claim 7, represented by formulas (1-4) to (1-10):

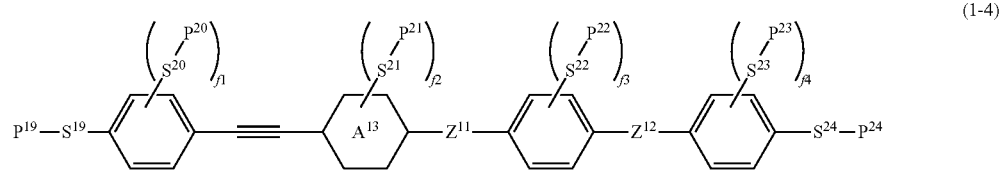

(1-4)

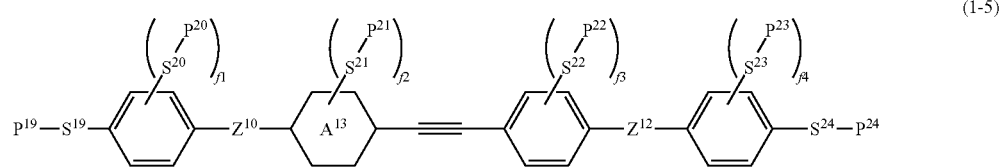

(1-5)

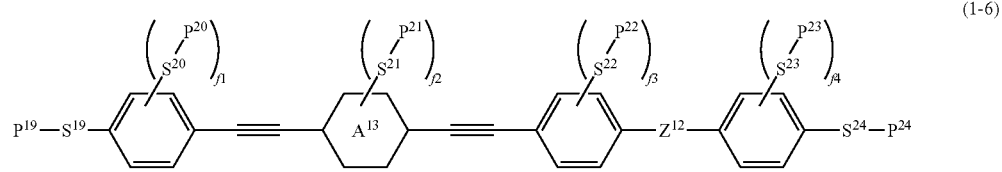

(1-6)

(1-7)
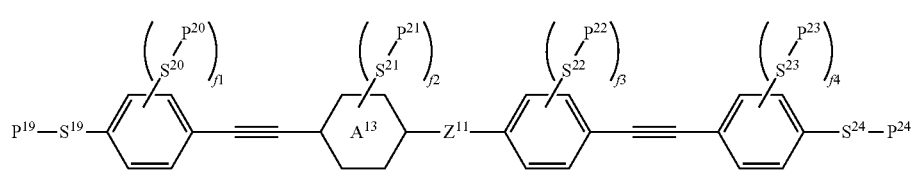

(1-8)
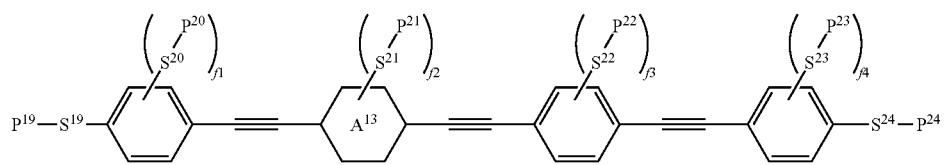

(1-9)
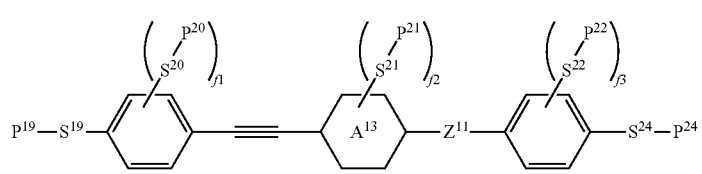

(1-10)
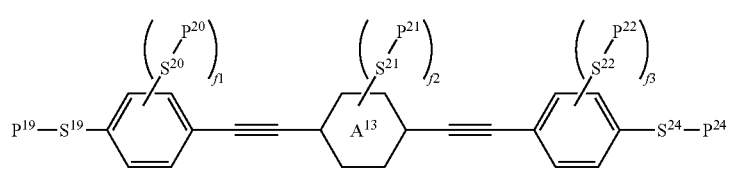

wherein, in formulas (1-4) to (1-10),
$P^{19}$, $P^{20}$, $P^{21}$, $P^{22}$, $P^{23}$ and $P^{24}$ are independently —OCO-$(M^1)C=CH(M^2)$, in which $M^1$ and $M^2$ are independently hydrogen, fluorine, methyl or trifluoromethyl;
$S^{19}$, $S^{20}$, $S^{21}$, $S^{22}$ and $S^{24}$ are independently a single bond or alkylene having 1 to 5 carbons, and in the alkylene, one of —$CH_2$— may be replaced by —O—, —COO— or —OCO—, and one of —$CH_2$—$CH_2$— may be replaced by —CH=CH—;
f1, f3, and f4 are independently 0, 1 or 2, f2 is 1 or 2, and a sum of f1, f2, f3 and f4 is 3 to 6;
ring $A^{13}$ is 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-chloro-3-fluoro-1,4-phenylene, 2-methyl-1,4-phenylene, 2-difluoromethyl-1,4-phenylene, 2-trifluoromethyl-1,4-phenylene, 2-ethyl-1,4-phenylene, 2-pentafluoroethyl 1,4-phenylene or 2-propyl-1,4-phenylene;
$Z^{10}$, $Z^{11}$ and $Z^{12}$ are independently a single bond, alkylene having 1 to 5 carbons, —CO—, —$CH_2O$—, —$OCH_2$—, —COO—, —OCO—, —CH=CH—, —C≡C—, —CH=CH—$CH_2O$—, —$OCH_2$—CH=CH—, —CH=CH—$OCH_2$—, —$CH_2O$—CH=CH—, —CH=CH—COO—, —OCO—CH=CH—, —CH=CH—OCO— or —COO—CH=CH—, and in the groups, at least one of hydrogen may be replaced by fluorine,
wherein when the number of —C≡C— is two or more, or when at least one of $Z^{10}$, $Z^{11}$ and $Z^{12}$ is a single bond, —CH=CH—, —COO—, or —OCO—, $S^{19}$ and $S^{24}$ are single bonds.

10. The polymerizable compound according to claim 7, represented by formulas (1-11) to (1-17):

(1-11)
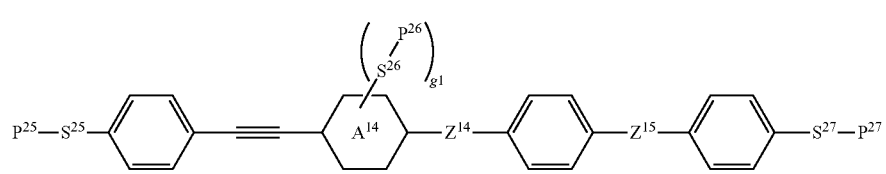

(1-12)
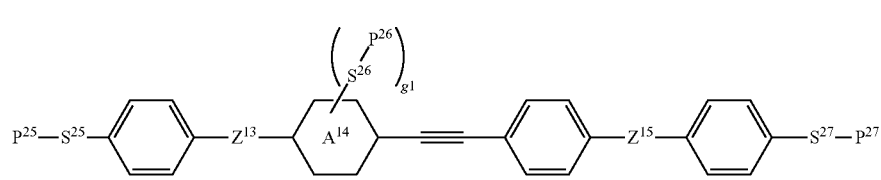

(1-13)
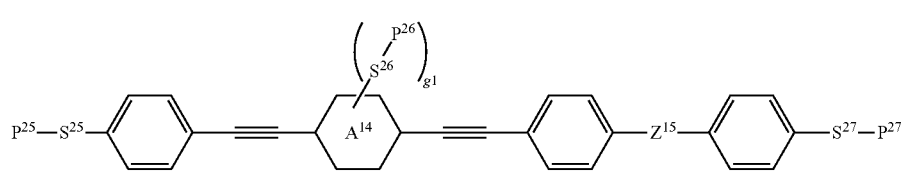

(1-14)
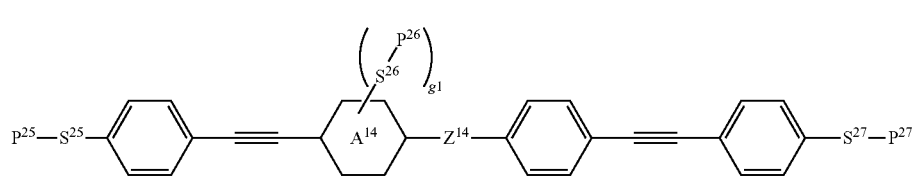

(1-15)
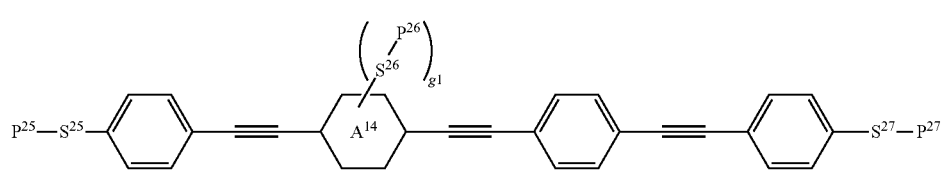

(1-16)
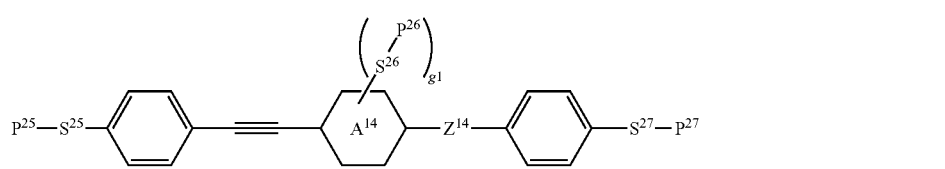

(1-17)
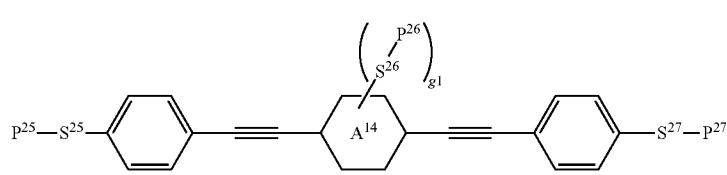

wherein, in formulas (1-11) to (1-17),
$P^{25}$, $P^{26}$ and $P^{27}$ are independently acryloyloxy or methacryloyloxy;
$S^{25}$, $S^{26}$ and $S^{27}$ are independently a single bond, —CH$_2$—, —CH$_2$O—, —OCH$_2$—, —COO—, —OCO—, —CH=CH—, —CH$_2$CH$_2$O—, —OCH$_2$CH$_2$—, —CH=CH—O— or —O—CH=CH—;
g1 is 1 or 2;
ring $A^{14}$ is 1,4-phenylene, 2-fluoro-1,4-phenylene, 2,5-difluoro-1,4-phenylene, 2,6-difluoro-1,4-phenylene, 2-chloro-1,4-phenylene, 2-methyl-1,4-phenylene, 2-ethyl-1,4-phenylene, 2-difluoromethyl-1,4-phenylene or 2-trifluoromethyl-1,4-phenylene; and
$Z^{13}$, $Z^{14}$ and $Z^{15}$ are independently a single bond, —CO—, —COO—, —OCO— or —CH=CH—,
wherein when the number of —C≡C— is two or more, or when at least one of $Z^{13}$, $Z^{14}$ and $Z^{15}$ is a single bond, —CH=CH—, —COO—, or —OCO—, $S^{25}$ and $S^{27}$ are single bonds.

11. The polymerizable compound according to claim 7, represented by formulas (1-18) to (1-24):

(1-18)
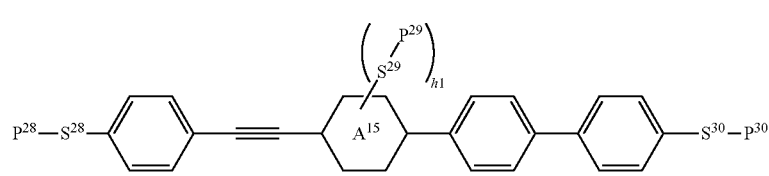

(1-19)

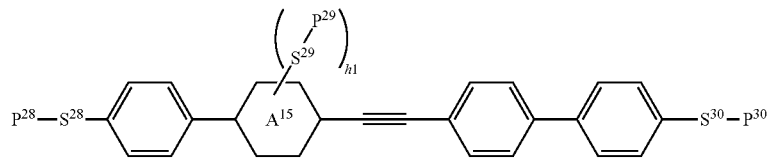

(1-20)

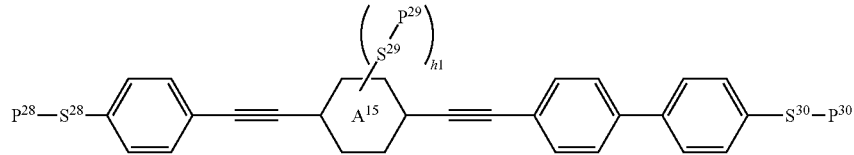

(1-21)

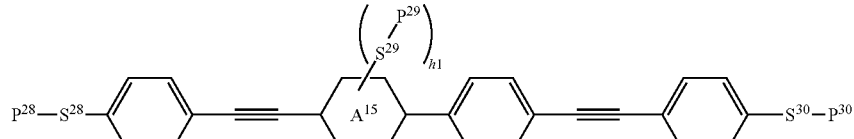

(1-22)

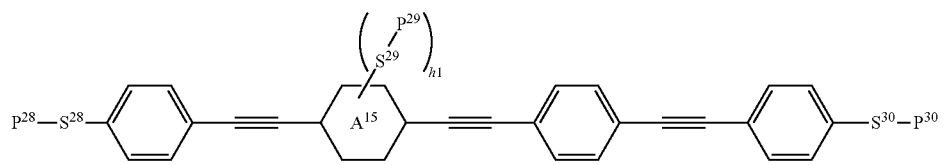

(1-23)

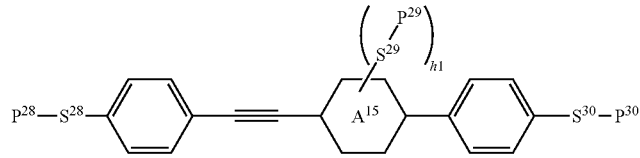

(1-24)

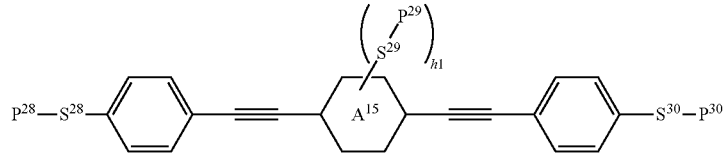

wherein, in formulas (1-18) to (1-24),
$P^{28}$, $P^{29}$ and $P^{30}$ are independently acryloyloxy or methacryloyloxy;
$S^{28}$ and $S^{30}$ are single bonds;
$S^{29}$ is a single bond, —CH$_2$—, —CH$_2$O—, —OCH$_2$—, —COO—, —OCO—, —CH=CH—, —CH$_2$CH$_2$O—, —OCH$_2$CH$_2$—, —CH=CH—O— or —O—CH=CH—;
h1 is 1 or 2; and
ring $A^{15}$ is 1,4-phenylene, 2-fluoro-1,4-phenylene, 2,5-difluoro-1,4-phenylene, 2-methyl-1,4-phenylene, 2-difluoromethyl-1,4-phenylene or 2-trifluoromethyl-1,4-phenylene.

12. The polymerizable compound according to claim 7, represented by formulas (1-25) or (1-26):

(1-25)

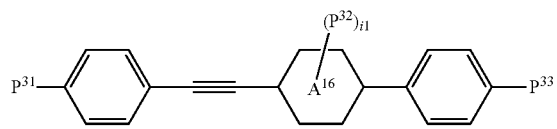

(1-26)

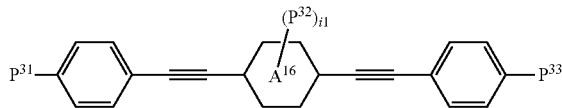

wherein, in formulas (1-25) and (1-26), $P^{31}$, $P^{32}$ and $P^{33}$ are independently acryloyloxy or methacryloyloxy; i1 is 1 or 2; and ring $A^{16}$ is 1,4-phenylene, 2-fluoro-1,4-phenylene, 2-methyl-1,4-phenylene or 2-trifluoromethyl-1,4-phenylene.

13. The polymerizable compound according to claim 7, represented by formula (1-27) or (1-28):

(1-27)

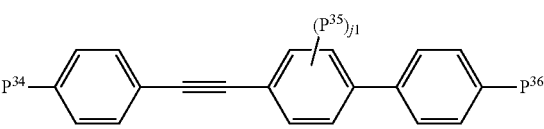

-continued
(1-28)
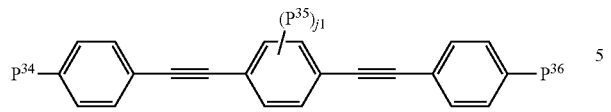
wherein, in formulas (1-27) and (1-28), $P^{34}$, $P^{35}$ and $P^{36}$ are independently acryloyloxy or methacryloyloxy; and j1 is 1 or 2.
14. The polymerizable composition, containing at least one compound selected from the group of compounds according to claim 7.
15. An optically anisotropic body, formed by polymerization of the polymerizable composition according to claim 14.
* * * * *